US008859250B2

(12) United States Patent
Schilling et al.

(10) Patent No.: US 8,859,250 B2
(45) Date of Patent: Oct. 14, 2014

(54) CRYSTAL STRUCTURE OF GLUTAMINYL CYCLASE

(71) Applicant: Probiodrug AG, Halle/Saale (DE)

(72) Inventors: Stephan Schilling, Halle/Saale (DE); Jens-Ulrich Rahfeld, Röblingen Am See (DE); Birgit Koch, Amsdorf (DE); Michael Wermann, Halle/Saale (DE); Christoph Parthier, Halle/Saale (DE); David Ruiz-Carillo, Halle/Saale (DE); Milton T. Stubbs, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 0 days.

(21) Appl. No.: 13/777,871

(22) Filed: Feb. 26, 2013

(65) Prior Publication Data

US 2013/0217090 A1   Aug. 22, 2013

Related U.S. Application Data

(62) Division of application No. 13/213,507, filed on Aug. 19, 2011, now Pat. No. 8,409,837.

(60) Provisional application No. 61/375,103, filed on Aug. 19, 2010.

(51) Int. Cl.
  *C12N 9/00* (2006.01)
  *G01N 31/00* (2006.01)
  *G06F 19/00* (2011.01)

(52) U.S. Cl.
  CPC ........ *C12M 9/104* (2013.01); *C12Y 203/02005* (2013.01); *G06F 19/706* (2013.01); *C07K 2299/00* (2013.01)
  USPC .............................................. 435/183; 436/4

(58) Field of Classification Search
  None
  See application file for complete search history.

(56) References Cited

U.S. PATENT DOCUMENTS

| | | | |
|---|---|---|---|
| 7,572,614 | B2 | 8/2009 | Wang et al. |
| 2007/0202586 | A1 | 8/2007 | Wang et al. |

FOREIGN PATENT DOCUMENTS

| | | |
|---|---|---|
| WO | WO 2005/039548 | 5/2005 |
| WO | WO 2008/034891 | 3/2008 |
| WO | WO 2008/087197 | 7/2008 |
| WO | WO 2010/026209 | 3/2010 |

OTHER PUBLICATIONS

Drenth, "Principles of Protein X-Ray Crystallography", 2nd Edition, 1999 Springer-Verlag New York Inc., Chapter 1, p. 1-21.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Moon et al., "A synergistic approach to protein crystallization: Combination of a fixed-arm carrier with surface entropy reduction", Protein Science, 2010, 19:901-913.*
Balbes, A Perspective of Modern Methods in Computer-Aided Drug Design, in Reviews in Computational Chemistry, 1994, pp. 337-380, vol. 5, Lipkowitz and Boyd, Eds., VCH, New York.
Bateman, Evidence for Essential Histidines in Human Pituitary Glutaminyl Cyclase, Biochemistry, 2001, pp. 11246-11250, vol. 40, No. 37.
Bockers, Glutaminyl-Cyclase Expression in the Bovine/Porcine Hypothalamus and Pituitary, Journal of Neuroendocrinology, 1995, pp. 445-453, vol. 7.
Böhm, The Computer Program LUDI: A New Method for the de novo design of enzyme inhibitors, Journal of Computer-Aided Molecular Design, 1992, pp. 61-78, vol. 6.
Bricogne, Bayesian Statistical Viewpoint on Structure Determination: Basic Concepts and Examples, Methods in Enzymology, 1997, pp. 361-423, vol. 276.
Brunger A T et al., Crystalography & NMR system: A New Software Suite for Macromolecular Structure Determination, Acta Cryst, 1998, pp. 905-921, vol. D54.
Buchholz, Inhibitors for Human Glutaminyl Cylase by Structure Based Design and Biosteric Replacement, Journal of Medicinal Chemistry, 2009, pp. 7069-7080, vol. 52.
Busby, An Enzyme(s) That Converts Glutaminyl-peptides into Pyroglutamyl-peptides: Presence in Pituitary, Brain, Adrenal Medulla, and Lymphocytes, The Journal of Biological Chemistry, 1987, pp. 8532-8536, vol. 262, No. 18.
Cohen, Molecular Modeling Software and Methods for Medicinal Chemistry, Journal of Medicinal Chemistry, 1990, pp. 883-894, vol. 33, No. 3.
Consalvo, A Rapid Flurometric Assay for N-Terminal Glutaminyl Cyclase Activity Using High-Performance Liquid Chromatography, Analytical Biochemistry, pp. 131-138, vol. 175, 1988.
Cudney, Protein Crystallization and Dumb Luck, The Rigaku Journal, 1999, pp. 1-7, vol. 16, No. 1.
Dahl, *Carica papaya* Glutamine Cyclotransferase Belongs to a Novel Plant Enzyme Subfamily: Cloning and Characterization of the Recombinant Enzyme, Protein Expression and Purification, 2000, pp. 27-36, vol. 20.
Eisen, Hook: A Program for Finding Novel Molecular Architectures that Satisfy the Chemical and Steric Requirements of a Macromolecule Binding Site, Proteins: Structure, Function, and Genetics, 1994, pp. 199-221, vol. 19.
El Moussaoui, Revisiting the enzymes stored in the laticifers of *Carica papaya* in the context of their possible participation in the plant defence mechanism, CMLS Cellular and Molecular Life Sciences, 2001, pp. 556-570, vol. 58.
Fischer, Identification of a mammalian glutaminyl cyclase converting glutaminyl into pyroglutamyl peptides, Proc. Natl. Acad. Sci. USA, 1987, pp. 3628-3632, vol. 84.
Gillet, Sprout: A Program for Structure Generation, Journal of Computer-Aided Molecular Design, 1993, pp. 127-153, vol. 7.
Gololobov, Substrate and Inhibitor Specificity of Glutamine Cyclotransferase (QC), Biol. Chem. Hoppe Seyler, pp. 395-398, vol. 377, 1996.

(Continued)

*Primary Examiner* — Suzanne M Noakes
(74) *Attorney, Agent, or Firm* — Dentons US LLP

(57) ABSTRACT

Novel crystal structures of human and murine glutaminyl cyclase (QC, EC 2.3.2.5), methods of preparing the crystals, as well as the use of said crystal structures for identifying inhibitors of human and murine glutaminyl cyclase.

13 Claims, 188 Drawing Sheets

(56) References Cited

OTHER PUBLICATIONS

Goodford, A Computational Procedure for Determining Energetically Favorable Binding Sites on Biologically Important Macromolecules, Journal of Medicinal Chemistry, 1985, pp. 849-857, vol. 28, No. 7.

Goodsell, Automated Docking of Substrates to Proteins by Simulated Annealing, Proteins: Structure, Function, and Genetics, 1990, pp. 195-202, vol. 8.

Guida, Software for Structure-Based Drug Design, Current Opinion in Structural Biology, 1994, pp. 777-781, vol. 4.

Hannig, Strategies for optimizing heterologous protein expression in *Escherichia coli*, TIBTECH, 1998, pp. 54-60, vol. 16.

Huang, Cloning, expression, characterization, and crystallization of a glutaminyl cyclase from human bone marrow: A single zinc metalloenzyme, Protein Expression & Purification, 2005, pp. 65-72, vol. 73.

Huang, Crystal structures of human glutaminyl cyclase, and enzyme responsible for protein N-terminal pyroglutamate formation, Proceedings of the National Academy of Sciences of the United States of America, 2005, pp. 13117-13122, vol. 102, No. 37.

Huang, A conserved hydrogen-bond network in the catalytic centre of animal glutaminyl cyclases is critical for catalysis, Biochem J., 2008, pp. 181-190, vol. 411.

Huang, Crystal structure and functional analysis of the glutaminyl cyclase from *Xanthomonas campestris*, J. Mol. Biol., 2010, pp. 374-388, vol. 401.

Johnson et al., Phylogenic Relationships from Three-dimensional Protein Structures, Methods in Enzymology, 1990, pp. 670-690, vol. 183.

Kuntz, A Geometric Approach to Macromolecule-Ligand Interactions, J. Mol. Biol., 1982, pp. 269-288, vol. 161.

Lattman, Use of the Rotation and Translation Functions, Methods in Enzymology, 1985, pp. 55-77, vol. 115.

Lauri, Caveat: A program to facilitate the design of organic molecules, Journal of Computer-Aided Molecular Design, 1994, pp. 51-66, vol. 8.

Martin, 3D Database Searching in Drug Design, Journal of Medicinal Chemistry, 1992, pp. 2145-2154, vol. 35, No. 12.

McPherson, Current approaches to macromolecular crystallization, Eur. J. Biochem., 1990, pp. 1-23, vol. 189.

Meng, Automated Docking with Grid-Based Energy Evaluation, Journal of Computational Chemistry, 1992, pp. 505-524, vol. 13, No. 4.

Messer, Enzymatic Cyclization of L-Glutamine and L-Glutaminyl Peptides, Nature, 1963, pp. 1299, vol. 197, No. 4874.

Miranker, Functionality Maps of Binding Sites: A Multiple Copy Simultaneous Search Method, Proteins: Structure, Function and Genetics, 1991, pp. 29-34, vol. 11.

Murshudov, Refinement of Macromolecular Structures by the Maximum-Likelihood Method, Acta Crystallographica, 1997, pp. 240-255.

Navia, Use of Structural Information in Drug Design, Current Opinions in Structural Biology, 1992, pp. 202-210, vol. 2.

Nishibata, Automatic Creation of Drug Candidate Structures Based on Receptor Structure. Starting Point for Artificial Lead Generation, Tetrahedron, 1991, pp. 8985-8990.

Pohl, Primary structure and functional expression of a glutaminyl cyclase, Proc. Natl. Acad. Sci. USA, 1991, pp. 10059-10063, vol. 88.

Rowland, Using X-ray crystallography in drug discovery, Current Opinion in Drug Discovery & Development, 2002, pp. 613-619, vol. 5.

Ruiz-Carrillo, Structures of Glycosylated Mammalian Glutaminyl Cyclases Reveal Conformational Variability near the Active Center, Biochemistry, 2011, pp. 6280-6288, vol. 50.

Song, Molecular cloning, sequence analysis and expression of human pituitary glutaminyl cyclase, Journal of Molecular Endocrinology, 1994, pp. 77-86, vol. 13.

Stephan, Mammalian glutaminyl cyclises and their isoenzymes have identical enzymatic characteristics, The FEBS Journal, 2009, pp. 6522-6536, vol. 276.

Tronrud, An Efficient General-Purpose Least-Squares Refinement Program for Macromolecular Structures, Acta Cryst., 1987, pp. 489-501.

Weber, Physical Principles of Protein Crystallization, Adv Protein Chem, 1991, pp. 1-36, vol. 41.

\* cited by examiner

```
        ATOM TYPE RES    #        x        y        z     Occ   B
ATOM       1   N   TRP A  36   -22.625  -35.504  -25.921  1.00 55.89    A  N
ATOM       2   CA  TRP A  36   -23.144  -36.590  -25.042  1.00 55.45    A  C
ATOM       3   CB  TRP A  36   -22.718  -37.179  -25.007  0.00 20.00       C
ATOM       4   CG  TRP A  36   -23.500  -38.118  -25.893  0.00 20.00       C
ATOM       5   CD1 TRP A  36   -24.840  -38.115  -26.101  0.00 20.00       C
ATOM       6   NE1 TRP A  36   -25.201  -39.127  -26.967  0.00 20.00       N
ATOM       7   CE2 TRP A  36   -24.074  -39.821  -27.319  0.00 20.00       C
ATOM       8   CD2 TRP A  36   -22.985  -39.220  -26.652  0.00 20.00       C
ATOM       9   CE3 TRP A  36   -21.712  -39.754  -26.836  0.00 20.00       C
ATOM      10   CZ3 TRP A  36   -21.565  -40.862  -27.685  0.00 20.00       C
ATOM      11   CH2 TRP A  36   -22.663  -41.434  -28.332  0.00 20.00       C
ATOM      12   CZ2 TRP A  36   -23.929  -40.927  -28.157  0.00 20.00       C
ATOM      13   C   TRP A  36   -23.748  -35.990  -23.779  1.00 56.28    A  C
ATOM      14   O   TRP A  36   -24.568  -35.058  -23.858  1.00 56.74    A  O
ATOM      15   N   PRO A  37   -23.343  -36.502  -22.598  1.00 56.69    A  N
ATOM      16   CA  PRO A  37   -24.108  -36.089  -21.409  1.00 56.71    A  C
ATOM      17   CB  PRO A  37   -24.351  -37.981  -21.742  0.00 20.00       C
ATOM      18   CG  PRO A  37   -23.002  -38.301  -22.393  0.00 20.00       C
ATOM      19   CD  PRO A  37   -22.340  -36.964  -22.745  0.00 20.00       C
ATOM      20   C   PRO A  37   -23.628  -36.520  -19.999  1.00 57.03    A  C
ATOM      21   O   PRO A  37   -22.560  -37.143  -19.831  1.00 57.42    A  O
ATOM      22   N   GLU A  38   -24.391  -36.102  -18.985  1.00 56.51    A  N
ATOM      23   CA  GLU A  38   -25.410  -35.067  -19.185  1.00 55.98    A  C
ATOM      24   CB  GLU A  38   -26.738  -35.669  -19.619  1.00 56.62    A  C
ATOM      25   CG  GLU A  38   -27.306  -34.892  -20.781  1.00 59.21    A  C
ATOM      26   CD  GLU A  38   -28.778  -34.703  -20.678  1.00 61.94    A  C
ATOM      27   OE1 GLU A  38   -29.402  -34.475  -21.737  1.00 62.25    A  O
ATOM      28   OE2 GLU A  38   -29.303  -34.785  -19.541  1.00 63.58    A  O
ATOM      29   C   GLU A  38   -25.599  -34.168  -17.972  1.00 54.76    A  C
ATOM      30   O   GLU A  38   -26.429  -33.254  -17.967  1.00 54.28    A  O
ATOM      31   N   GLU A  39   -24.810  -34.459  -16.948  1.00 53.99    A  N
ATOM      32   CA  GLU A  39   -24.652  -33.625  -15.767  1.00 53.61    A  C
ATOM      33   CB  GLU A  39   -23.511  -34.177  -14.917  1.00 53.91    A  C
ATOM      34   CG  GLU A  39   -23.868  -35.485  -14.219  1.00 56.92    A  C
ATOM      35   CD  GLU A  39   -22.727  -36.482  -14.225  1.00 60.01    A  C
ATOM      36   OE1 GLU A  39   -22.033  -36.567  -13.189  1.00 60.64    A  O
ATOM      37   OE2 GLU A  39   -22.519  -37.165  -15.268  1.00 63.06    A  O
ATOM      38   C   GLU A  39   -24.370  -32.167  -16.113  1.00 52.52    A  C
ATOM      39   O   GLU A  39   -24.879  -31.271  -15.448  1.00 52.35    A  O
ATOM      40   N   LYS A  40   -23.571  -31.946  -17.157  1.00 51.28    A  N
ATOM      41   CA  LYS A  40   -23.250  -30.609  -17.634  1.00 50.46    A  C
ATOM      42   CB  LYS A  40   -22.371  -30.695  -18.873  1.00 50.74    A  C
ATOM      43   CG  LYS A  40   -23.030  -31.401  -20.016  1.00 50.38    A  C
ATOM      44   CD  LYS A  40   -22.193  -31.350  -21.246  1.00 50.17    A  C
ATOM      45   CE  LYS A  40   -23.104  -31.367  -22.467  1.00 49.41    A  C
ATOM      46   NZ  LYS A  40   -22.319  -31.501  -23.690  1.00 51.70    A  N
ATOM      47   C   LYS A  40   -24.496  -29.770  -17.934  1.00 50.18    A  C
ATOM      48   O   LYS A  40   -24.517  -28.556  -17.678  1.00 49.22    A  O
ATOM      49   N   ASN A  41   -25.534  -30.433  -18.450  1.00 49.65    A  N
ATOM      50   CA  ASN A  41   -26.753  -29.757  -18.848  1.00 49.26    A  C
ATOM      51   CB  ASN A  41   -27.559  -30.656  -19.768  1.00 49.35    A  C
ATOM      52   CG  ASN A  41   -26.867  -30.885  -21.101  1.00 48.57    A  C
ATOM      53   OD1 ASN A  41   -26.188  -31.891  -21.299  1.00 47.48    A  O
ATOM      54   ND2 ASN A  41   -27.016  -29.935  -22.012  1.00 47.30    A  N
ATOM      55   C   ASN A  41   -27.592  -29.274  -17.675  1.00 49.68    A  C
ATOM      56   O   ASN A  41   -28.414  -28.369  -17.831  1.00 49.83    A  O
ATOM      57   N   TYR A  42   -27.344  -29.859  -16.500  1.00 49.72    A  N
ATOM      58   CA  TYR A  42   -28.084  -29.584  -15.263  1.00 49.59    A  C
ATOM      59   CB  TYR A  42   -28.683  -30.890  -14.722  1.00 50.43    A  C
ATOM      60   CG  TYR A  42   -29.808  -31.444  -15.571  1.00 53.94    A  C
ATOM      61   CD1 TYR A  42   -31.130  -31.394  -15.115  1.00 56.51    A  C
ATOM      62   CE1 TYR A  42   -32.172  -31.896  -15.882  1.00 59.43    A  C
ATOM      63   CZ  TYR A  42   -31.899  -32.452  -17.133  1.00 60.50    A  C
ATOM      64   OH  TYR A  42   -32.944  -32.946  -17.896  1.00 62.93    A  O
ATOM      65   CE2 TYR A  42   -30.588  -32.509  -17.617  1.00 59.15    A  C
ATOM      66   CD2 TYR A  42   -29.555  -32.009  -16.835  1.00 56.70    A  C
ATOM      67   C   TYR A  42   -27.214  -28.944  -14.181  1.00 48.56    A  C
ATOM      68   O   TYR A  42   -27.716  -28.541  -13.135  1.00 47.79    A  O
ATOM      69   N   HIS A  43   -25.905  -28.875  -14.427  1.00 47.78    A  N
```

FIGURE 1-1 (COORDINATES)

```
ATOM     70  CA  HIS A  43     -24.977 -28.257 -13.475  1.00 46.52      A  C
ATOM     71  CB  HIS A  43     -23.500 -28.372 -13.893  1.00 45.88      A  C
ATOM     72  CG  HIS A  43     -22.552 -27.829 -12.867  1.00 44.06      A  C
ATOM     73  ND1 HIS A  43     -22.061 -26.540 -12.916  1.00 44.15      A  N
ATOM     74  CE1 HIS A  43     -21.280 -26.332 -11.872  1.00 43.53      A  C
ATOM     75  NE2 HIS A  43     -21.267 -27.429 -11.134  1.00 43.10      A  N
ATOM     76  CD2 HIS A  43     -22.058 -28.377 -11.731  1.00 41.10      A  C
ATOM     77  C   HIS A  43     -25.334 -26.803 -13.270  1.00 46.55      A  C
ATOM     78  O   HIS A  43     -25.650 -26.082 -14.246  1.00 46.67      A  O
ATOM     79  N   GLN A  44     -25.235 -26.406 -11.994  1.00 45.81      A  N
ATOM     80  CA  GLN A  44     -25.653 -25.118 -11.459  1.00 45.63      A  C
ATOM     81  CB  GLN A  44     -26.856 -25.341 -10.511  1.00 45.93      A  C
ATOM     82  CG  GLN A  44     -28.144 -25.817 -11.205  1.00 45.00      A  C
ATOM     83  CD  GLN A  44     -28.745 -24.714 -12.046  1.00 46.37      A  C
ATOM     84  OE1 GLN A  44     -28.565 -23.538 -11.737  1.00 47.41      A  O
ATOM     85  NE2 GLN A  44     -29.443 -25.075 -13.119  1.00 44.57      A  N
ATOM     86  C   GLN A  44     -24.494 -24.475 -10.665  1.00 45.52      A  C
ATOM     87  O   GLN A  44     -23.781 -25.176  -9.928  1.00 45.33      A  O
ATOM     88  N   PRO A  45     -24.319 -23.136 -10.771  1.00 45.43      A  N
ATOM     89  CA  PRO A  45     -23.246 -22.495 -10.011  1.00 45.39      A  C
ATOM     90  CB  PRO A  45     -23.194 -21.098 -10.628  1.00 45.09      A  C
ATOM     91  CG  PRO A  45     -24.589 -20.820 -11.009  1.00 44.21      A  C
ATOM     92  CD  PRO A  45     -25.196 -22.133 -11.413  1.00 45.02      A  C
ATOM     93  C   PRO A  45     -23.621 -22.377  -8.533  1.00 45.73      A  C
ATOM     94  O   PRO A  45     -24.792 -22.246  -8.231  1.00 45.91      A  O
ATOM     95  N   ALA A  46     -22.651 -22.447  -7.626  1.00 46.21      A  N
ATOM     96  CA  ALA A  46     -22.878 -22.052  -6.234  1.00 46.26      A  C
ATOM     97  CB  ALA A  46     -21.990 -22.838  -5.290  1.00 45.98      A  C
ATOM     98  C   ALA A  46     -22.583 -20.551  -6.142  1.00 46.70      A  C
ATOM     99  O   ALA A  46     -21.418 -20.142  -6.031  1.00 47.03      A  O
ATOM    100  N   ILE A  47     -23.639 -19.742  -6.233  1.00 47.08      A  N
ATOM    101  CA  ILE A  47     -23.560 -18.261  -6.197  1.00 47.46      A  C
ATOM    102  CB  ILE A  47     -24.931 -17.613  -6.562  1.00 47.55      A  C
ATOM    103  CG1 ILE A  47     -25.495 -18.265  -7.839  1.00 47.78      A  C
ATOM    104  CD1 ILE A  47     -26.999 -18.193  -7.974  1.00 48.94      A  C
ATOM    105  CG2 ILE A  47     -24.767 -16.100  -6.788  1.00 47.89      A  C
ATOM    106  C   ILE A  47     -22.989 -17.682  -4.872  1.00 46.99      A  C
ATOM    107  O   ILE A  47     -23.418 -18.056  -3.786  1.00 47.54      A  O
ATOM    108  N   LEU A  48     -22.012 -16.785  -4.973  1.00 46.32      A  N
ATOM    109  CA  LEU A  48     -21.267 -16.320  -3.796  1.00 45.84      A  C
ATOM    110  CB  LEU A  48     -19.813 -16.013  -4.165  1.00 46.09      A  C
ATOM    111  CG  LEU A  48     -18.903 -17.160  -4.609  1.00 47.47      A  C
ATOM    112  CD1 LEU A  48     -17.715 -16.619  -5.438  1.00 48.59      A  C
ATOM    113  CD2 LEU A  48     -18.445 -18.022  -3.423  1.00 47.34      A  C
ATOM    114  C   LEU A  48     -21.866 -15.081  -3.175  1.00 45.26      A  C
ATOM    115  O   LEU A  48     -22.374 -14.212  -3.898  1.00 44.95      A  O
ATOM    116  N   ASN A  49     -21.760 -14.983  -1.845  1.00 44.53      A  N
ATOM    117  CA  ASN A  49     -22.271 -13.815  -1.120  1.00 44.39      A  C
ATOM    118  CB  ASN A  49     -22.533 -14.116   0.400  1.00 43.82      A  C
ATOM    119  CG  ASN A  49     -21.250 -14.380   1.218  1.00 41.78      A  C
ATOM    120  OD1 ASN A  49     -20.254 -13.653   1.108  1.00 38.26      A  O
ATOM    121  ND2 ASN A  49     -21.297 -15.399   2.071  1.00 38.92      A  N
ATOM    122  C   ASN A  49     -21.429 -12.545  -1.399  1.00 44.61      A  C
ATOM    123  O   ASN A  49     -20.294 -12.649  -1.874  1.00 44.46      A  O
ATOM    124  N   SER A  50     -22.002 -11.364  -1.138  1.00 44.73      A  N
ATOM    125  CA  SER A  50     -21.318 -10.056  -1.339  1.00 44.71      A  C
ATOM    126  CB  SER A  50     -22.197  -8.895  -0.848  1.00 44.64      A  C
ATOM    127  OG  SER A  50     -23.275  -8.689  -1.748  1.00 46.21      A  O
ATOM    128  C   SER A  50     -19.941  -9.925  -0.695  1.00 43.91      A  C
ATOM    129  O   SER A  50     -19.048  -9.269  -1.230  1.00 43.52      A  O
ATOM    130  N   SER A  51     -19.798 -10.538   0.468  1.00 43.57      A  N
ATOM    131  CA  SER A  51     -18.552 -10.552   1.190  1.00 43.25      A  C
ATOM    132  CB  SER A  51     -18.816 -11.115   2.593  1.00 43.41      A  C
ATOM    133  OG  SER A  51     -17.655 -11.062   3.393  1.00 43.26      A  O
ATOM    134  C   SER A  51     -17.488 -11.374   0.421  1.00 42.83      A  C
ATOM    135  O   SER A  51     -16.317 -10.994   0.337  1.00 43.34      A  O
ATOM    136  N   ALA A  52     -17.904 -12.488  -0.159  1.00 41.75      A  N
ATOM    137  CA  ALA A  52     -17.002 -13.319  -0.934  1.00 41.17      A  C
ATOM    138  CB  ALA A  52     -17.608 -14.716  -1.099  1.00 40.39      A  C
ATOM    139  C   ALA A  52     -16.634 -12.662  -2.309  1.00 41.42      A  C
```

FIGURE 1-2 (COORDINATES)

```
ATOM  140  O    ALA A  52     -15.507 -12.786  -2.803  1.00 40.74      A  O
ATOM  141  N    LEU A  53     -17.587 -11.952  -2.908  1.00 41.13      A  N
ATOM  142  CA   LEU A  53     -17.322 -11.133  -4.080  1.00 40.89      A  C
ATOM  143  CB   LEU A  53     -18.618 -10.413  -4.523  1.00 40.49      A  C
ATOM  144  CG   LEU A  53     -19.486 -10.956  -5.696  1.00 38.97      A  C
ATOM  145  CD1  LEU A  53     -19.190 -12.395  -6.074  1.00 35.91      A  C
ATOM  146  CD2  LEU A  53     -20.975 -10.768  -5.461  1.00 34.76      A  C
ATOM  147  C    LEU A  53     -16.145 -10.146  -3.863  1.00 41.27      A  C
ATOM  148  O    LEU A  53     -15.205 -10.080  -4.686  1.00 40.86      A  O
ATOM  149  N    ARG A  54     -16.188  -9.419  -2.745  1.00 41.07      A  N
ATOM  150  CA   ARG A  54     -15.254  -8.319  -2.488  1.00 41.50      A  C
ATOM  151  CB   ARG A  54     -15.669  -7.547  -1.206  1.00 41.98      A  C
ATOM  152  CG   ARG A  54     -15.106  -6.123  -1.028  1.00 43.25      A  C
ATOM  153  CD   ARG A  54     -15.929  -5.271   0.021  1.00 48.77      A  C
ATOM  154  NE   ARG A  54     -17.009  -4.454  -0.587  1.00 51.12      A  N
ATOM  155  CZ   ARG A  54     -18.333  -4.682  -0.495  1.00 51.86      A  C
ATOM  156  NH1  ARG A  54     -18.827  -5.715   0.198  1.00 50.89      A  N
ATOM  157  NH2  ARG A  54     -19.180  -3.865  -1.119  1.00 51.65      A  N
ATOM  158  C    ARG A  54     -13.852  -8.895  -2.369  1.00 41.04      A  C
ATOM  159  O    ARG A  54     -12.881  -8.336  -2.878  1.00 40.89      A  O
ATOM  160  N    GLN A  55     -13.780 -10.045  -1.709  1.00 41.05      A  N
ATOM  161  CA   GLN A  55     -12.551 -10.762  -1.462  1.00 41.00      A  C
ATOM  162  CB   GLN A  55     -12.909 -11.966  -0.608  1.00 41.57      A  C
ATOM  163  CG   GLN A  55     -11.784 -12.784  -0.050  1.00 44.17      A  C
ATOM  164  CD   GLN A  55     -12.320 -14.094   0.527  1.00 49.75      A  C
ATOM  165  OE1  GLN A  55     -13.419 -14.134   1.114  1.00 50.80      A  O
ATOM  166  NE2  GLN A  55     -11.554 -15.177   0.357  1.00 51.51      A  N
ATOM  167  C    GLN A  55     -11.919 -11.163  -2.808  1.00 40.55      A  C
ATOM  168  O    GLN A  55     -10.706 -11.050  -2.991  1.00 40.17      A  O
ATOM  169  N    ILE A  56     -12.763 -11.585  -3.750  1.00 39.88      A  N
ATOM  170  CA   ILE A  56     -12.319 -11.916  -5.093  1.00 39.48      A  C
ATOM  171  CB   ILE A  56     -13.390 -12.664  -5.929  1.00 39.50      A  C
ATOM  172  CG1  ILE A  56     -13.806 -13.978  -5.225  1.00 39.61      A  C
ATOM  173  CD1  ILE A  56     -12.677 -14.709  -4.473  1.00 35.37      A  C
ATOM  174  CG2  ILE A  56     -12.851 -12.921  -7.340  1.00 37.92      A  C
ATOM  175  C    ILE A  56     -11.857 -10.684  -5.850  1.00 39.08      A  C
ATOM  176  O    ILE A  56     -10.783 -10.702  -6.469  1.00 39.02      A  O
ATOM  177  N    ALA A  57     -12.659  -9.627  -5.801  1.00 37.88      A  N
ATOM  178  CA   ALA A  57     -12.250  -8.380  -6.400  1.00 37.85      A  C
ATOM  179  CB   ALA A  57     -13.297  -7.335  -6.187  1.00 37.53      A  C
ATOM  180  C    ALA A  57     -10.900  -7.915  -5.851  1.00 38.02      A  C
ATOM  181  O    ALA A  57     -10.072  -7.371  -6.582  1.00 38.35      A  O
ATOM  182  N    GLU A  58     -10.667  -8.178  -4.572  1.00 38.08      A  N
ATOM  183  CA   GLU A  58      -9.480  -7.703  -3.892  1.00 38.50      A  C
ATOM  184  CB   GLU A  58      -9.692  -7.713  -2.389  1.00 39.31      A  C
ATOM  185  CG   GLU A  58     -10.620  -6.654  -1.855  1.00 43.91      A  C
ATOM  186  CD   GLU A  58     -10.953  -6.908  -0.373  1.00 49.32      A  C
ATOM  187  OE1  GLU A  58     -10.014  -6.879   0.472  1.00 50.64      A  O
ATOM  188  OE2  GLU A  58     -12.148  -7.148  -0.065  1.00 51.28      A  O
ATOM  189  C    GLU A  58      -8.252  -8.540  -4.149  1.00 37.56      A  C
ATOM  190  O    GLU A  58      -7.152  -7.998  -4.206  1.00 38.05      A  O
ATOM  191  N    GLY A  59      -8.428  -9.855  -4.258  1.00 35.99      A  N
ATOM  192  CA   GLY A  59      -7.297 -10.764  -4.342  1.00 34.95      A  C
ATOM  193  C    GLY A  59      -6.697 -10.952  -5.736  1.00 34.43      A  C
ATOM  194  O    GLY A  59      -5.801 -11.772  -5.902  1.00 34.41      A  O
ATOM  195  N    THR A  60      -7.195 -10.214  -6.727  1.00 33.95      A  N
ATOM  196  CA   THR A  60      -6.558 -10.157  -8.056  1.00 33.44      A  C
ATOM  197  CB   THR A  60      -7.548 -10.407  -9.244  1.00 33.39      A  C
ATOM  198  OG1  THR A  60      -6.840 -10.316 -10.494  1.00 34.27      A  O
ATOM  199  CG2  THR A  60      -8.700  -9.391  -9.276  1.00 33.24      A  C
ATOM  200  C    THR A  60      -5.818  -8.827  -8.278  1.00 33.58      A  C
ATOM  201  O    THR A  60      -6.356  -7.752  -7.994  1.00 33.98      A  O
ATOM  202  N    SER A  61      -4.598  -8.913  -8.810  1.00 33.35      A  N
ATOM  203  CA   SER A  61      -3.762  -7.743  -9.092  1.00 32.73      A  C
ATOM  204  CB   SER A  61      -2.397  -7.944  -8.446  1.00 31.83      A  C
ATOM  205  OG   SER A  61      -1.461  -6.945  -8.814  1.00 31.55      A  O
ATOM  206  C    SER A  61      -3.608  -7.532 -10.610  1.00 32.70      A  C
ATOM  207  O    SER A  61      -3.012  -8.342 -11.294  1.00 32.76      A  O
ATOM  208  N    ILE A  62      -4.128  -6.441 -11.134  1.00 32.44      A  N
ATOM  209  CA   ILE A  62      -3.920  -6.179 -12.539  1.00 32.50      A  C
```

FIGURE 1-3 (COORDINATES)

```
ATOM   210  CB   ILE A  62      -4.832  -5.040 -13.051  1.00 32.27           A  C
ATOM   211  CG1  ILE A  62      -4.811  -4.948 -14.589  1.00 32.22           A  C
ATOM   212  CD1  ILE A  62      -5.092  -6.227 -15.323  1.00 27.48           A  C
ATOM   213  CG2  ILE A  62      -4.402  -3.702 -12.444  1.00 31.41           A  C
ATOM   214  C    ILE A  62      -2.421  -5.918 -12.821  1.00 33.01           A  C
ATOM   215  O    ILE A  62      -1.883  -6.402 -13.824  1.00 32.40           A  O
ATOM   216  N    SER A  63      -1.752  -5.175 -11.925  1.00 32.85           A  N
ATOM   217  CA   SER A  63      -0.315  -4.845 -12.068  1.00 32.81           A  C
ATOM   218  CB   SER A  63       0.148  -3.902 -10.940  1.00 33.34           A  C
ATOM   219  OG   SER A  63       0.061  -4.575  -9.671  1.00 35.90           A  O
ATOM   220  C    SER A  63       0.576  -6.083 -12.068  1.00 32.43           A  C
ATOM   221  O    SER A  63       1.598  -6.139 -12.764  1.00 32.20           A  O
ATOM   222  N    GLU A  64       0.206  -7.087 -11.290  1.00 32.37           A  N
ATOM   223  CA   GLU A  64       1.002  -8.308 -11.258  1.00 32.86           A  C
ATOM   224  CB   GLU A  64       0.549  -9.208 -10.129  1.00 32.97           A  C
ATOM   225  CG   GLU A  64       1.676  -9.896  -9.444  1.00 37.17           A  C
ATOM   226  CD   GLU A  64       2.174  -9.119  -8.227  1.00 42.56           A  C
ATOM   227  OE1  GLU A  64       3.130  -8.307  -8.378  1.00 44.23           A  O
ATOM   228  OE2  GLU A  64       1.600  -9.326  -7.124  1.00 44.50           A  O
ATOM   229  C    GLU A  64       0.855  -9.051 -12.619  1.00 32.80           A  C
ATOM   230  O    GLU A  64       1.811  -9.617 -13.140  1.00 31.84           A  O
ATOM   231  N    MET A  65      -0.349  -8.998 -13.179  1.00 31.60           A  N
ATOM   232  CA   MET A  65      -0.649  -9.703 -14.372  1.00 31.45           A  C
ATOM   233  CB   MET A  65      -2.170  -9.656 -14.678  1.00 30.56           A  C
ATOM   234  CG   MET A  65      -2.485 -10.441 -15.941  1.00 30.76           A  C
ATOM   235  SD   MET A  65      -3.994  -9.974 -16.806  1.00 28.80           A  S
ATOM   236  CE   MET A  65      -3.379  -8.601 -17.789  1.00 31.16           A  C
ATOM   237  C    MET A  65       0.162  -9.052 -15.482  1.00 30.82           A  C
ATOM   238  O    MET A  65       0.810  -9.728 -16.299  1.00 29.72           A  O
ATOM   239  N    TRP A  66       0.139  -7.728 -15.462  1.00 31.30           A  N
ATOM   240  CA   TRP A  66       0.760  -6.909 -16.491  1.00 31.89           A  C
ATOM   241  CB   TRP A  66       0.558  -5.425 -16.169  1.00 31.92           A  C
ATOM   242  CG   TRP A  66       0.438  -4.634 -17.402  1.00 30.21           A  C
ATOM   243  CD1  TRP A  66       1.455  -4.129 -18.147  1.00 28.12           A  C
ATOM   244  NE1  TRP A  66       0.955  -3.500 -19.260  1.00 26.34           A  N
ATOM   245  CE2  TRP A  66      -0.407  -3.579 -19.243  1.00 27.30           A  C
ATOM   246  CD2  TRP A  66      -0.768  -4.298 -18.077  1.00 27.28           A  C
ATOM   247  CE3  TRP A  66      -2.115  -4.556 -17.828  1.00 27.23           A  C
ATOM   248  CZ3  TRP A  66      -3.062  -4.076 -18.726  1.00 28.43           A  C
ATOM   249  CH2  TRP A  66      -2.670  -3.349 -19.899  1.00 30.70           A  C
ATOM   250  CZ2  TRP A  66      -1.356  -3.077 -20.160  1.00 27.06           A  C
ATOM   251  C    TRP A  66       2.252  -7.194 -16.656  1.00 32.22           A  C
ATOM   252  O    TRP A  66       2.757  -7.381 -17.774  1.00 32.68           A  O
ATOM   253  N    GLU A  67       2.938  -7.245 -15.520  1.00 32.78           A  N
ATOM   254  CA   GLU A  67       4.395  -7.262 -15.462  1.00 33.29           A  C
ATOM   255  CB   GLU A  67       4.825  -6.649 -14.131  1.00 33.71           A  C
ATOM   256  CG   GLU A  67       6.196  -6.054 -14.085  1.00 39.21           A  C
ATOM   257  CD   GLU A  67       6.501  -5.559 -12.673  1.00 44.87           A  C
ATOM   258  OE1  GLU A  67       7.179  -6.289 -11.896  1.00 44.41           A  O
ATOM   259  OE2  GLU A  67       6.001  -4.461 -12.327  1.00 47.56           A  O
ATOM   260  C    GLU A  67       4.911  -8.699 -15.555  1.00 31.88           A  C
ATOM   261  O    GLU A  67       5.902  -8.987 -16.247  1.00 32.48           A  O
ATOM   262  N    ASN A  68       4.232  -9.591 -14.848  1.00 29.56           A  N
ATOM   263  CA   ASN A  68       4.705 -10.951 -14.692  1.00 29.05           A  C
ATOM   264  CB   ASN A  68       4.533 -11.430 -13.231  1.00 29.02           A  C
ATOM   265  CG   ASN A  68       5.299 -10.569 -12.280  1.00 29.73           A  C
ATOM   266  OD1  ASN A  68       6.332 -10.052 -12.659  1.00 28.60           A  O
ATOM   267  ND2  ASN A  68       4.795 -10.386 -11.054  1.00 30.99           A  N
ATOM   268  C    ASN A  68       4.070 -11.940 -15.631  1.00 27.48           A  C
ATOM   269  O    ASN A  68       4.716 -12.904 -15.980  1.00 27.70           A  O
ATOM   270  N    ASP A  69       2.801 -11.727 -15.995  1.00 27.22           A  N
ATOM   271  CA   ASP A  69       2.078 -12.672 -16.848  1.00 26.60           A  C
ATOM   272  CB   ASP A  69       0.643 -12.970 -16.350  1.00 27.06           A  C
ATOM   273  CG   ASP A  69       0.589 -13.878 -15.110  1.00 29.69           A  C
ATOM   274  OD1  ASP A  69      -0.307 -13.656 -14.261  1.00 38.49           A  O
ATOM   275  OD2  ASP A  69       1.395 -14.819 -14.963  1.00 28.69           A  O
ATOM   276  C    ASP A  69       2.052 -12.138 -18.277  1.00 26.40           A  C
ATOM   277  O    ASP A  69       2.322 -12.881 -19.170  1.00 27.35           A  O
ATOM   278  N    LEU A  70       1.769 -10.850 -18.468  1.00 25.60           A  N
ATOM   279  CA   LEU A  70       1.465 -10.292 -19.788  1.00 26.00           A  C
```

FIGURE 1-4 (COORDINATES)

```
ATOM    280  CB  LEU A  70       0.334  -9.231 -19.707  1.00 25.73           A  C
ATOM    281  CG  LEU A  70       0.123  -8.260 -20.872  1.00 27.63           A  C
ATOM    282  CD1 LEU A  70      -0.254  -8.964 -22.209  1.00 24.63           A  C
ATOM    283  CD2 LEU A  70      -0.940  -7.245 -20.425  1.00 25.53           A  C
ATOM    284  C   LEU A  70       2.674  -9.787 -20.590  1.00 25.90           A  C
ATOM    285  O   LEU A  70       2.837 -10.161 -21.759  1.00 25.28           A  O
ATOM    286  N   GLN A  71       3.520  -8.953 -19.984  1.00 25.84           A  N
ATOM    287  CA  GLN A  71       4.652  -8.380 -20.732  1.00 26.49           A  C
ATOM    288  CB  GLN A  71       5.399  -7.312 -19.920  1.00 26.75           A  C
ATOM    289  CG  GLN A  71       4.690  -5.977 -20.003  1.00 30.02           A  C
ATOM    290  CD  GLN A  71       5.133  -4.990 -18.947  1.00 34.51           A  C
ATOM    291  OE1 GLN A  71       4.946  -3.786 -19.128  1.00 37.57           A  O
ATOM    292  NE2 GLN A  71       5.715  -5.482 -17.839  1.00 34.01           A  N
ATOM    293  C   GLN A  71       5.598  -9.424 -21.324  1.00 26.20           A  C
ATOM    294  O   GLN A  71       5.968  -9.317 -22.513  1.00 26.96           A  O
ATOM    295  N   PRO A  72       5.942 -10.477 -20.548  1.00 25.56           A  N
ATOM    296  CA  PRO A  72       6.816 -11.400 -21.272  1.00 24.95           A  C
ATOM    297  CB  PRO A  72       7.177 -12.431 -20.219  1.00 24.11           A  C
ATOM    298  CG  PRO A  72       7.005 -11.692 -18.907  1.00 25.07           A  C
ATOM    299  CD  PRO A  72       5.792 -10.864 -19.136  1.00 25.37           A  C
ATOM    300  C   PRO A  72       6.180 -12.071 -22.493  1.00 24.13           A  C
ATOM    301  O   PRO A  72       6.910 -12.661 -23.262  1.00 24.09           A  O
ATOM    302  N   LEU A  73       4.856 -11.968 -22.683  1.00 23.82           A  N
ATOM    303  CA  LEU A  73       4.187 -12.602 -23.876  1.00 23.96           A  C
ATOM    304  CB  LEU A  73       2.743 -12.938 -23.595  1.00 22.88           A  C
ATOM    305  CG  LEU A  73       2.194 -14.343 -23.458  1.00 25.41           A  C
ATOM    306  CD1 LEU A  73       3.264 -15.370 -23.374  1.00 23.36           A  C
ATOM    307  CD2 LEU A  73       1.127 -14.485 -22.288  1.00 32.94           A  C
ATOM    308  C   LEU A  73       4.162 -11.729 -25.095  1.00 24.58           A  C
ATOM    309  O   LEU A  73       3.848 -12.216 -26.189  1.00 25.25           A  O
ATOM    310  N   LEU A  74       4.387 -10.422 -24.910  1.00 25.38           A  N
ATOM    311  CA  LEU A  74       4.292  -9.438 -25.999  1.00 24.40           A  C
ATOM    312  CB  LEU A  74       4.010  -8.039 -25.434  1.00 24.65           A  C
ATOM    313  CG  LEU A  74       2.582  -7.915 -24.891  1.00 26.90           A  C
ATOM    314  CD1 LEU A  74       2.390  -6.607 -24.126  1.00 27.12           A  C
ATOM    315  CD2 LEU A  74       1.548  -8.092 -26.028  1.00 26.11           A  C
ATOM    316  C   LEU A  74       5.536  -9.479 -26.893  1.00 24.63           A  C
ATOM    317  O   LEU A  74       6.366  -8.540 -26.916  1.00 24.53           A  O
ATOM    318  N   ILE A  75       5.689 -10.607 -27.590  1.00 23.38           A  N
ATOM    319  CA  ILE A  75       6.834 -10.860 -28.428  1.00 21.63           A  C
ATOM    320  CB  ILE A  75       7.829 -11.797 -27.777  1.00 20.78           A  C
ATOM    321  CG1 ILE A  75       7.163 -13.112 -27.415  1.00 19.96           A  C
ATOM    322  CD1 ILE A  75       8.112 -14.099 -26.726  1.00 18.90           A  C
ATOM    323  CG2 ILE A  75       8.553 -11.127 -26.514  1.00 24.54           A  C
ATOM    324  C   ILE A  75       6.287 -11.524 -29.713  1.00 21.67           A  C
ATOM    325  O   ILE A  75       5.131 -12.034 -29.713  1.00 21.56           A  O
ATOM    326  N   GLU A  76       7.089 -11.528 -30.762  1.00 19.78           A  N
ATOM    327  CA  GLU A  76       6.678 -12.210 -31.972  1.00 21.61           A  C
ATOM    328  CB  GLU A  76       7.598 -11.895 -33.145  1.00 21.10           A  C
ATOM    329  CG  GLU A  76       7.012 -12.363 -34.504  1.00 25.67           A  C
ATOM    330  CD  GLU A  76       7.878 -11.996 -35.732  1.00 31.78           A  C
ATOM    331  OE1 GLU A  76       9.100 -11.913 -35.562  1.00 36.20           A  O
ATOM    332  OE2 GLU A  76       7.357 -11.804 -36.881  1.00 34.34           A  O
ATOM    333  C   GLU A  76       6.743 -13.707 -31.606  1.00 22.53           A  C
ATOM    334  O   GLU A  76       7.803 -14.235 -31.208  1.00 23.85           A  O
ATOM    335  N   ARG A  77       5.625 -14.412 -31.740  1.00 20.93           A  N
ATOM    336  CA  ARG A  77       5.603 -15.801 -31.326  1.00 17.70           A  C
ATOM    337  CB  ARG A  77       5.000 -15.930 -29.902  1.00 17.62           A  C
ATOM    338  CG  ARG A  77       3.757 -15.016 -29.681  1.00 15.40           A  C
ATOM    339  CD  ARG A  77       3.242 -14.996 -28.147  1.00  8.13           A  C
ATOM    340  NE  ARG A  77       1.888 -14.490 -28.152  1.00 12.21           A  N
ATOM    341  CZ  ARG A  77       1.512 -13.230 -28.425  1.00 17.64           A  C
ATOM    342  NH1 ARG A  77       2.400 -12.253 -28.717  1.00 19.74           A  N
ATOM    343  NH2 ARG A  77       0.211 -12.945 -28.417  1.00 15.07           A  N
ATOM    344  C   ARG A  77       4.771 -16.551 -32.325  1.00 17.97           A  C
ATOM    345  O   ARG A  77       3.957 -17.330 -31.940  1.00 16.88           A  O
ATOM    346  N   TYR A  78       4.973 -16.375 -33.646  1.00 17.84           A  N
ATOM    347  CA  TYR A  78       4.175 -17.207 -34.486  1.00 17.46           A  C
ATOM    348  CB  TYR A  78       4.174 -16.648 -35.908  1.00 19.35           A  C
ATOM    349  CG  TYR A  78       5.508 -16.652 -36.553  1.00 19.23           A  C
```

FIGURE 1-5 (COORDINATES)

```
ATOM    350  CD1 TYR A  78       6.288 -15.498 -36.592  1.00 18.80      A  C
ATOM    351  CE1 TYR A  78       7.529 -15.488 -37.255  1.00 21.36      A  C
ATOM    352  CZ  TYR A  78       8.014 -16.671 -37.814  1.00 24.69      A  C
ATOM    353  OH  TYR A  78       9.239 -16.695 -38.435  1.00 24.75      A  O
ATOM    354  CE2 TYR A  78       7.254 -17.852 -37.775  1.00 24.70      A  C
ATOM    355  CD2 TYR A  78       6.014 -17.841 -37.125  1.00 22.15      A  C
ATOM    356  C   TYR A  78       4.656 -18.676 -34.410  1.00 17.74      A  C
ATOM    357  O   TYR A  78       5.799 -18.939 -34.010  1.00 20.00      A  O
ATOM    358  N   PRO A  79       3.833 -19.644 -34.846  1.00 17.79      A  N
ATOM    359  CA  PRO A  79       4.191 -21.053 -34.645  1.00 17.59      A  C
ATOM    360  CB  PRO A  79       2.968 -21.819 -35.212  1.00 18.19      A  C
ATOM    361  CG  PRO A  79       1.897 -20.872 -35.175  1.00 15.18      A  C
ATOM    362  CD  PRO A  79       2.520 -19.530 -35.499  1.00 16.02      A  C
ATOM    363  C   PRO A  79       5.512 -21.599 -35.211  1.00 18.06      A  C
ATOM    364  O   PRO A  79       5.893 -21.383 -36.394  1.00 18.98      A  O
ATOM    365  N   GLY A  80       6.190 -22.347 -34.349  1.00 17.10      A  N
ATOM    366  CA  GLY A  80       7.545 -22.875 -34.599  1.00 16.54      A  C
ATOM    367  C   GLY A  80       8.746 -21.928 -34.507  1.00 15.62      A  C
ATOM    368  O   GLY A  80       9.873 -22.385 -34.567  1.00 15.13      A  O
ATOM    369  N   SER A  81       8.513 -20.616 -34.364  1.00 17.74      A  N
ATOM    370  CA  SER A  81       9.559 -19.537 -34.176  1.00 15.86      A  C
ATOM    371  CB  SER A  81       8.833 -18.147 -34.164  1.00 16.21      A  C
ATOM    372  OG  SER A  81       8.211 -17.949 -32.842  1.00 16.17      A  O
ATOM    373  C   SER A  81      10.169 -19.684 -32.745  1.00 16.01      A  C
ATOM    374  O   SER A  81       9.569 -20.315 -31.898  1.00 14.75      A  O
ATOM    375  N   PRO A  82      11.337 -19.043 -32.482  1.00 15.04      A  N
ATOM    376  CA  PRO A  82      11.972 -18.988 -31.156  1.00 14.87      A  C
ATOM    377  CB  PRO A  82      13.334 -18.334 -31.439  1.00 14.34      A  C
ATOM    378  CG  PRO A  82      13.619 -18.751 -33.073  1.00 13.48      A  C
ATOM    379  CD  PRO A  82      12.190 -18.493 -33.552  1.00 14.95      A  C
ATOM    380  C   PRO A  82      11.139 -18.234 -30.167  1.00 15.25      A  C
ATOM    381  O   PRO A  82      11.005 -18.629 -28.971  1.00 18.03      A  O
ATOM    382  N   GLY A  83      10.525 -17.154 -30.624  1.00 16.82      A  N
ATOM    383  CA  GLY A  83       9.449 -16.517 -29.843  1.00 14.91      A  C
ATOM    384  C   GLY A  83       8.325 -17.445 -29.371  1.00 14.99      A  C
ATOM    385  O   GLY A  83       7.874 -17.422 -28.129  1.00 14.73      A  O
ATOM    386  N   SER A  84       7.831 -18.280 -30.256  1.00 12.28      A  N
ATOM    387  CA  SER A  84       6.915 -19.387 -29.712  1.00 15.95      A  C
ATOM    388  CB  SER A  84       6.545 -20.398 -30.755  1.00 16.25      A  C
ATOM    389  OG  SER A  84       5.572 -21.282 -30.207  1.00 17.99      A  O
ATOM    390  C   SER A  84       7.471 -20.231 -28.520  1.00 19.22      A  C
ATOM    391  O   SER A  84       6.735 -20.534 -27.536  1.00 16.79      A  O
ATOM    392  N   TYR A  85       8.756 -20.646 -28.674  1.00 19.64      A  N
ATOM    393  CA  TYR A  85       9.427 -21.401 -27.658  1.00 19.53      A  C
ATOM    394  CB  TYR A  85      10.810 -21.758 -28.187  1.00 21.66      A  C
ATOM    395  CG  TYR A  85      11.654 -22.504 -27.232  1.00 21.82      A  C
ATOM    396  CD1 TYR A  85      11.724 -23.898 -27.287  1.00 26.65      A  C
ATOM    397  CE1 TYR A  85      12.538 -24.601 -26.386  1.00 26.98      A  C
ATOM    398  CZ  TYR A  85      13.275 -23.889 -25.472  1.00 27.96      A  C
ATOM    399  OH  TYR A  85      14.044 -24.544 -24.567  1.00 35.29      A  O
ATOM    400  CE2 TYR A  85      13.239 -22.515 -25.407  1.00 27.39      A  C
ATOM    401  CD2 TYR A  85      12.432 -21.825 -26.301  1.00 25.49      A  C
ATOM    402  C   TYR A  85       9.503 -20.651 -26.337  1.00 19.69      A  C
ATOM    403  O   TYR A  85       9.101 -21.181 -25.315  1.00 19.09      A  O
ATOM    404  N   ALA A  86      10.026 -19.415 -26.357  1.00 20.09      A  N
ATOM    405  CA  ALA A  86      10.037 -18.550 -25.179  1.00 18.71      A  C
ATOM    406  CB  ALA A  86      10.780 -17.232 -25.441  1.00 16.90      A  C
ATOM    407  C   ALA A  86       8.641 -18.290 -24.619  1.00 19.75      A  C
ATOM    408  O   ALA A  86       8.453 -18.338 -23.371  1.00 19.99      A  O
ATOM    409  N   ALA A  87       7.660 -17.971 -25.464  1.00 18.21      A  N
ATOM    410  CA  ALA A  87       6.279 -17.856 -24.913  1.00 20.36      A  C
ATOM    411  CB  ALA A  87       5.214 -17.474 -25.955  1.00 20.08      A  C
ATOM    412  C   ALA A  87       5.847 -19.140 -24.166  1.00 21.03      A  C
ATOM    413  O   ALA A  87       5.302 -19.070 -23.011  1.00 19.45      A  O
ATOM    414  N   ARG A  88       6.102 -20.290 -24.815  1.00 20.20      A  N
ATOM    415  CA  ARG A  88       5.689 -21.565 -24.238  1.00 21.14      A  C
ATOM    416  CB  ARG A  88       6.014 -22.714 -25.187  1.00 20.68      A  C
ATOM    417  CG  ARG A  88       5.697 -24.201 -24.767  1.00 22.32      A  C
ATOM    418  CD  ARG A  88       6.276 -25.200 -25.822  1.00 26.58      A  C
ATOM    419  NE  ARG A  88       6.119 -24.541 -27.098  1.00 29.38      A  N
```

FIGURE 1-6 (COORDINATES)

```
ATOM    420  CZ  ARG A  88       6.975 -24.512 -28.094  1.00 33.39           A  C
ATOM    421  NH1 ARG A  88       8.113 -25.183 -28.056  1.00 33.72           A  N
ATOM    422  NH2 ARG A  88       6.644 -23.808 -29.172  1.00 36.12           A  N
ATOM    423  C   ARG A  88       6.376 -21.763 -22.904  1.00 21.89           A  C
ATOM    424  O   ARG A  88       5.786 -22.275 -21.968  1.00 21.58           A  O
ATOM    425  N   GLN A  89       7.658 -21.413 -22.846  1.00 23.69           A  N
ATOM    426  CA  GLN A  89       8.439 -21.596 -21.629  1.00 25.01           A  C
ATOM    427  CB  GLN A  89       9.897 -21.326 -21.943  1.00 26.08           A  C
ATOM    428  CG  GLN A  89      10.845 -21.669 -20.795  1.00 32.59           A  C
ATOM    429  CD  GLN A  89      12.303 -21.492 -21.161  1.00 37.59           A  C
ATOM    430  OE1 GLN A  89      12.661 -21.315 -22.334  1.00 42.25           A  O
ATOM    431  NE2 GLN A  89      13.155 -21.557 -20.163  1.00 38.71           A  N
ATOM    432  C   GLN A  89       7.918 -20.687 -20.516  1.00 24.46           A  C
ATOM    433  O   GLN A  89       7.829 -21.100 -19.350  1.00 24.54           A  O
ATOM    434  N   HIS A  90       7.581 -19.441 -20.867  1.00 24.26           A  N
ATOM    435  CA  HIS A  90       6.950 -18.517 -19.916  1.00 24.24           A  C
ATOM    436  CB  HIS A  90       6.715 -17.155 -20.594  1.00 25.35           A  C
ATOM    437  CG  HIS A  90       5.797 -16.222 -19.849  1.00 23.63           A  C
ATOM    438  ND1 HIS A  90       6.079 -15.746 -18.580  1.00 22.99           A  N
ATOM    439  CE1 HIS A  90       5.108 -14.939 -18.181  1.00 22.29           A  C
ATOM    440  NE2 HIS A  90       4.223 -14.840 -19.164  1.00 24.21           A  N
ATOM    441  CD2 HIS A  90       4.642 -15.618 -20.227  1.00 22.32           A  C
ATOM    442  C   HIS A  90       5.639 -19.082 -19.345  1.00 23.83           A  C
ATOM    443  O   HIS A  90       5.437 -19.161 -18.085  1.00 22.65           A  O
ATOM    444  N   ILE A  91       4.749 -19.500 -20.239  1.00 22.65           A  N
ATOM    445  CA  ILE A  91       3.452 -20.050 -19.807  1.00 22.63           A  C
ATOM    446  CB  ILE A  91       2.547 -20.537 -21.004  1.00 23.21           A  C
ATOM    447  CG1 ILE A  91       1.959 -19.362 -21.813  1.00 21.87           A  C
ATOM    448  CD1 ILE A  91       1.862 -19.574 -23.408  1.00 23.59           A  C
ATOM    449  CG2 ILE A  91       1.406 -21.424 -20.496  1.00 20.95           A  C
ATOM    450  C   ILE A  91       3.706 -21.156 -18.735  1.00 24.79           A  C
ATOM    451  O   ILE A  91       3.168 -21.093 -17.576  1.00 23.53           A  O
ATOM    452  N   MET A  92       4.533 -22.142 -19.109  1.00 24.94           A  N
ATOM    453  CA  MET A  92       4.805 -23.299 -18.252  1.00 25.98           A  C
ATOM    454  CB  MET A  92       5.624 -24.352 -18.997  1.00 26.23           A  C
ATOM    455  CG  MET A  92       4.788 -25.072 -20.055  1.00 28.11           A  C
ATOM    456  SD  MET A  92       5.870 -25.956 -21.182  1.00 36.67           A  S
ATOM    457  CE  MET A  92       6.083 -27.456 -20.231  1.00 37.16           A  C
ATOM    458  C   MET A  92       5.441 -22.959 -16.905  1.00 26.65           A  C
ATOM    459  O   MET A  92       5.037 -23.513 -15.877  1.00 26.75           A  O
ATOM    460  N   GLN A  93       6.410 -22.041 -16.929  1.00 26.68           A  N
ATOM    461  CA  GLN A  93       7.049 -21.561 -15.730  1.00 28.16           A  C
ATOM    462  CB  GLN A  93       8.210 -20.640 -16.107  1.00 28.45           A  C
ATOM    463  CG  GLN A  93       9.523 -21.393 -16.180  1.00 32.15           A  C
ATOM    464  CD  GLN A  93      10.532 -20.791 -17.136  1.00 37.68           A  C
ATOM    465  OE1 GLN A  93      10.438 -19.616 -17.534  1.00 39.59           A  O
ATOM    466  NE2 GLN A  93      11.519 -21.593 -17.508  1.00 36.73           A  N
ATOM    467  C   GLN A  93       6.084 -20.885 -14.764  1.00 28.36           A  C
ATOM    468  O   GLN A  93       6.136 -21.143 -13.551  1.00 29.19           A  O
ATOM    469  N   ARG A  94       5.201 -20.022 -15.281  1.00 28.36           A  N
ATOM    470  CA  ARG A  94       4.229 -19.327 -14.428  1.00 28.96           A  C
ATOM    471  CB  ARG A  94       3.484 -18.170 -15.125  1.00 28.39           A  C
ATOM    472  CG  ARG A  94       4.388 -17.052 -15.659  1.00 30.03           A  C
ATOM    473  CD  ARG A  94       4.944 -16.072 -14.586  1.00 24.33           A  C
ATOM    474  NE  ARG A  94       3.837 -15.429 -13.914  1.00 28.48           A  N
ATOM    475  CZ  ARG A  94       3.869 -14.959 -12.659  1.00 28.23           A  C
ATOM    476  NH1 ARG A  94       4.973 -15.057 -11.941  1.00 25.11           A  N
ATOM    477  NH2 ARG A  94       2.780 -14.411 -12.140  1.00 25.40           A  N
ATOM    478  C   ARG A  94       3.224 -20.285 -13.848  1.00 29.49           A  C
ATOM    479  O   ARG A  94       2.834 -20.137 -12.659  1.00 29.54           A  O
ATOM    480  N   ILE A  95       2.780 -21.258 -14.636  1.00 29.34           A  N
ATOM    481  CA  ILE A  95       1.937 -22.255 -14.001  1.00 30.85           A  C
ATOM    482  CB  ILE A  95       0.712 -22.836 -14.861  1.00 31.26           A  C
ATOM    483  CG1 ILE A  95       0.526 -24.349 -14.671  1.00 30.97           A  C
ATOM    484  CD1 ILE A  95       1.718 -25.102 -14.827  1.00 32.98           A  C
ATOM    485  CG2 ILE A  95       0.654 -22.398 -16.334  1.00 31.77           A  C
ATOM    486  C   ILE A  95       2.663 -23.204 -12.993  1.00 31.45           A  C
ATOM    487  O   ILE A  95       2.092 -23.534 -11.929  1.00 31.21           A  O
ATOM    488  N   GLN A  96       3.909 -23.577 -13.296  1.00 31.50           A  N
ATOM    489  CA  GLN A  96       4.679 -24.493 -12.438  1.00 32.60           A  C
```

FIGURE 1-7 (COORDINATES)

```
ATOM  490  CB   GLN A  96      6.070 -24.739 -13.003  1.00 32.75      A  C
ATOM  491  CG   GLN A  96      6.312 -26.131 -13.506  1.00 36.58      A  C
ATOM  492  CD   GLN A  96      7.048 -26.152 -14.877  1.00 42.55      A  C
ATOM  493  OE1  GLN A  96      7.876 -25.271 -15.202  1.00 43.59      A  O
ATOM  494  NE2  GLN A  96      6.745 -27.163 -15.669  1.00 41.27      A  N
ATOM  495  C    GLN A  96      4.906 -23.916 -11.061  1.00 32.96      A  C
ATOM  496  O    GLN A  96      5.277 -24.626 -10.149  1.00 32.00      A  O
ATOM  497  N    ARG A  97      4.716 -22.612 -10.908  1.00 33.06      A  N
ATOM  498  CA   ARG A  97      5.210 -22.008  -9.718  1.00 33.18      A  C
ATOM  499  CB   ARG A  97      5.859 -20.653 -10.022  1.00 33.83      A  C
ATOM  500  CG   ARG A  97      5.046 -19.392  -9.834  1.00 35.84      A  C
ATOM  501  CD   ARG A  97      6.008 -18.208 -10.013  1.00 41.63      A  C
ATOM  502  NE   ARG A  97      5.577 -16.912  -9.454  1.00 48.93      A  N
ATOM  503  CZ   ARG A  97      4.332 -16.532  -9.111  1.00 50.97      A  C
ATOM  504  NH1  ARG A  97      3.278 -17.332  -9.236  1.00 50.55      A  N
ATOM  505  NH2  ARG A  97      4.140 -15.303  -8.626  1.00 53.89      A  N
ATOM  506  C    ARG A  97      4.134 -21.964  -8.661  1.00 32.46      A  C
ATOM  507  O    ARG A  97      4.416 -21.677  -7.559  1.00 31.84      A  O
ATOM  508  N    LEU A  98      2.909 -22.293  -9.045  1.00 32.48      A  N
ATOM  509  CA   LEU A  98      1.751 -22.273  -8.168  1.00 31.28      A  C
ATOM  510  CB   LEU A  98      0.490 -22.177  -9.025  1.00 31.20      A  C
ATOM  511  CG   LEU A  98      0.480 -21.032 -10.015  1.00 32.13      A  C
ATOM  512  CD1  LEU A  98     -0.665 -21.199 -11.027  1.00 29.81      A  C
ATOM  513  CD2  LEU A  98      0.456 -19.655  -9.308  1.00 30.49      A  C
ATOM  514  C    LEU A  98      1.656 -23.531  -7.334  1.00 30.91      A  C
ATOM  515  O    LEU A  98      2.168 -24.599  -7.736  1.00 30.84      A  O
ATOM  516  N    GLN A  99      0.951 -23.431  -6.197  1.00 29.83      A  N
ATOM  517  CA   GLN A  99      0.819 -24.577  -5.272  1.00 28.62      A  C
ATOM  518  CB   GLN A  99      0.396 -24.125  -3.857  1.00 28.58      A  C
ATOM  519  CG   GLN A  99      0.979 -22.786  -3.373  1.00 27.74      A  C
ATOM  520  CD   GLN A  99      0.649 -22.519  -1.862  1.00 31.16      A  C
ATOM  521  OE1  GLN A  99      1.547 -22.509  -1.013  1.00 32.36      A  O
ATOM  522  NE2  GLN A  99     -0.630 -22.296  -1.552  1.00 27.31      A  N
ATOM  523  C    GLN A  99     -0.192 -25.595  -5.815  1.00 27.54      A  C
ATOM  524  O    GLN A  99     -0.004 -26.816  -5.667  1.00 25.97      A  O
ATOM  525  N    ALA A 100     -1.274 -25.112  -6.436  1.00 26.73      A  N
ATOM  526  CA   ALA A 100     -2.194 -26.065  -7.042  1.00 27.70      A  C
ATOM  527  CB   ALA A 100     -3.414 -25.394  -7.720  1.00 27.57      A  C
ATOM  528  C    ALA A 100     -1.472 -27.101  -7.966  1.00 27.60      A  C
ATOM  529  O    ALA A 100     -0.369 -26.897  -8.479  1.00 27.03      A  O
ATOM  530  N    ASP A 101     -2.078 -28.256  -8.076  1.00 27.94      A  N
ATOM  531  CA   ASP A 101     -1.391 -29.360  -8.621  1.00 28.69      A  C
ATOM  532  CB   ASP A 101     -1.847 -30.615  -7.925  1.00 28.55      A  C
ATOM  533  CG   ASP A 101     -0.848 -31.719  -8.077  1.00 32.24      A  C
ATOM  534  OD1  ASP A 101      0.267 -31.434  -8.593  1.00 31.87      A  O
ATOM  535  OD2  ASP A 101     -1.172 -32.862  -7.666  1.00 37.91      A  O
ATOM  536  C    ASP A 101     -1.675 -29.463 -10.122  1.00 27.92      A  C
ATOM  537  O    ASP A 101     -2.304 -30.423 -10.569  1.00 28.67      A  O
ATOM  538  N    TRP A 102     -1.247 -28.462 -10.878  1.00 27.07      A  N
ATOM  539  CA   TRP A 102     -1.471 -28.494 -12.343  1.00 25.39      A  C
ATOM  540  CB   TRP A 102     -1.107 -27.176 -12.968  1.00 24.06      A  C
ATOM  541  CG   TRP A 102     -2.060 -26.092 -12.581  1.00 24.34      A  C
ATOM  542  CD1  TRP A 102     -1.882 -25.192 -11.583  1.00 23.48      A  C
ATOM  543  NE1  TRP A 102     -2.948 -24.349 -11.527  1.00 26.14      A  N
ATOM  544  CE2  TRP A 102     -3.857 -24.689 -12.496  1.00 24.31      A  C
ATOM  545  CD2  TRP A 102     -3.338 -25.797 -13.173  1.00 23.86      A  C
ATOM  546  CE3  TRP A 102     -4.093 -26.364 -14.219  1.00 26.12      A  C
ATOM  547  CZ3  TRP A 102     -5.343 -25.803 -14.534  1.00 23.70      A  C
ATOM  548  CH2  TRP A 102     -5.824 -24.690 -13.840  1.00 20.21      A  C
ATOM  549  CZ2  TRP A 102     -5.105 -24.117 -12.822  1.00 21.72      A  C
ATOM  550  C    TRP A 102     -0.625 -29.521 -12.993  1.00 26.00      A  C
ATOM  551  O    TRP A 102      0.585 -29.568 -12.737  1.00 25.05      A  O
ATOM  552  N    VAL A 103     -1.248 -30.321 -13.872  1.00 26.86      A  N
ATOM  553  CA   VAL A 103     -0.508 -31.285 -14.663  1.00 26.76      A  C
ATOM  554  CB   VAL A 103     -1.110 -32.739 -14.533  1.00 27.21      A  C
ATOM  555  CG1  VAL A 103     -0.315 -33.733 -15.322  1.00 27.14      A  C
ATOM  556  CG2  VAL A 103     -1.192 -33.207 -12.981  1.00 26.85      A  C
ATOM  557  C    VAL A 103     -0.371 -30.721 -16.100  1.00 27.00      A  C
ATOM  558  O    VAL A 103     -1.378 -30.407 -16.794  1.00 25.95      A  O
ATOM  559  N    LEU A 104      0.884 -30.564 -16.509  1.00 26.53      A  N
```

FIGURE 1-8 (COORDINATES)

```
ATOM  560  CA   LEU A 104      1.205 -29.898 -17.768  1.00 26.60      A  C
ATOM  561  CB   LEU A 104      2.417 -28.998 -17.601  1.00 26.42      A  C
ATOM  562  CG   LEU A 104      2.181 -27.629 -16.962  1.00 25.97      A  C
ATOM  563  CD1  LEU A 104      3.473 -26.961 -16.579  1.00 20.62      A  C
ATOM  564  CD2  LEU A 104      1.400 -26.776 -17.992  1.00 27.64      A  C
ATOM  565  C    LEU A 104      1.505 -30.906 -18.809  1.00 27.14      A  C
ATOM  566  O    LEU A 104      2.230 -31.854 -18.543  1.00 28.84      A  O
ATOM  567  N    GLU A 105      0.965 -30.719 -19.995  1.00 27.38      A  N
ATOM  568  CA   GLU A 105      1.198 -31.639 -21.093  1.00 28.09      A  C
ATOM  569  CB   GLU A 105      0.029 -32.621 -21.222  1.00 28.34      A  C
ATOM  570  CG   GLU A 105     -0.142 -33.108 -22.686  1.00 33.26      A  C
ATOM  571  CD   GLU A 105     -1.249 -34.154 -22.921  1.00 41.83      A  C
ATOM  572  OE1  GLU A 105     -1.913 -34.637 -21.957  1.00 47.36      A  O
ATOM  573  OE2  GLU A 105     -1.444 -34.511 -24.094  1.00 42.73      A  O
ATOM  574  C    GLU A 105      1.297 -30.851 -22.382  1.00 28.24      A  C
ATOM  575  O    GLU A 105      0.504 -29.962 -22.610  1.00 28.98      A  O
ATOM  576  N    ILE A 106      2.216 -31.217 -23.251  1.00 27.96      A  N
ATOM  577  CA   ILE A 106      2.478 -30.460 -24.442  1.00 28.38      A  C
ATOM  578  CB   ILE A 106      3.993 -30.051 -24.489  1.00 28.26      A  C
ATOM  579  CG1  ILE A 106      4.348 -29.239 -23.243  1.00 30.52      A  C
ATOM  580  CD1  ILE A 106      3.675 -27.880 -23.174  1.00 35.91      A  C
ATOM  581  CG2  ILE A 106      4.343 -29.295 -25.732  1.00 29.60      A  C
ATOM  582  C    ILE A 106      2.083 -31.308 -25.619  1.00 27.47      A  C
ATOM  583  O    ILE A 106      2.631 -32.342 -25.825  1.00 28.48      A  O
ATOM  584  N    ASP A 107      1.129 -30.863 -26.408  1.00 27.06      A  N
ATOM  585  CA   ASP A 107      0.690 -31.627 -27.561  1.00 25.63      A  C
ATOM  586  CB   ASP A 107     -0.871 -31.512 -27.676  1.00 25.65      A  C
ATOM  587  CG   ASP A 107     -1.455 -32.071 -29.003  1.00 29.68      A  C
ATOM  588  OD1  ASP A 107     -0.979 -33.106 -29.496  1.00 29.42      A  O
ATOM  589  OD2  ASP A 107     -2.440 -31.485 -29.550  1.00 28.16      A  O
ATOM  590  C    ASP A 107      1.472 -31.078 -28.759  1.00 24.76      A  C
ATOM  591  O    ASP A 107      1.031 -30.099 -29.366  1.00 24.97      A  O
ATOM  592  N    THR A 108      2.630 -31.674 -29.107  1.00 21.92      A  N
ATOM  593  CA   THR A 108      3.422 -31.126 -30.236  1.00 21.41      A  C
ATOM  594  CB   THR A 108      4.919 -31.085 -29.927  1.00 21.23      A  C
ATOM  595  OG1  THR A 108      5.143 -30.173 -28.854  1.00 27.08      A  O
ATOM  596  CG2  THR A 108      5.704 -30.578 -31.152  1.00 22.83      A  C
ATOM  597  C    THR A 108      3.209 -31.882 -31.534  1.00 18.72      A  C
ATOM  598  O    THR A 108      2.952 -33.036 -31.482  1.00 20.25      A  O
ATOM  599  N    PHE A 109      3.376 -31.304 -32.708  1.00 18.39      A  N
ATOM  600  CA   PHE A 109      3.045 -32.083 -33.904  1.00 16.22      A  C
ATOM  601  CB   PHE A 109      1.499 -32.434 -33.989  1.00 15.44      A  C
ATOM  602  CG   PHE A 109      0.561 -31.191 -34.021  1.00 15.13      A  C
ATOM  603  CD1  PHE A 109      0.109 -30.587 -32.818  1.00 10.47      A  C
ATOM  604  CE1  PHE A 109     -0.730 -29.452 -32.849  1.00  9.80      A  C
ATOM  605  CZ   PHE A 109     -1.165 -28.946 -34.171  1.00 13.21      A  C
ATOM  606  CE2  PHE A 109     -0.703 -29.525 -35.331  1.00  9.70      A  C
ATOM  607  CD2  PHE A 109      0.119 -30.670 -35.247  1.00 10.60      A  C
ATOM  608  C    PHE A 109      3.488 -31.331 -35.119  1.00 17.19      A  C
ATOM  609  O    PHE A 109      3.734 -30.152 -35.035  1.00 19.35      A  O
ATOM  610  N    LEU A 110      3.595 -32.010 -36.245  1.00 16.74      A  N
ATOM  611  CA   LEU A 110      3.946 -31.390 -37.543  1.00 19.38      A  C
ATOM  612  CB   LEU A 110      4.840 -32.299 -38.334  1.00 19.31      A  C
ATOM  613  CG   LEU A 110      6.238 -32.324 -37.731  1.00 24.74      A  C
ATOM  614  CD1  LEU A 110      7.125 -33.301 -38.528  1.00 27.88      A  C
ATOM  615  CD2  LEU A 110      6.824 -30.880 -37.746  1.00 26.02      A  C
ATOM  616  C    LEU A 110      2.727 -31.252 -38.361  1.00 19.90      A  C
ATOM  617  O    LEU A 110      1.929 -32.198 -38.454  1.00 18.83      A  O
ATOM  618  N    SER A 111      2.513 -30.083 -38.931  1.00 20.27      A  N
ATOM  619  CA   SER A 111      1.427 -30.044 -39.895  1.00 21.55      A  C
ATOM  620  CB   SER A 111      0.241 -29.380 -39.272  1.00 21.47      A  C
ATOM  621  OG   SER A 111     -0.853 -29.453 -40.126  1.00 25.64      A  O
ATOM  622  C    SER A 111      1.905 -29.376 -41.195  1.00 22.13      A  C
ATOM  623  O    SER A 111      2.813 -28.531 -41.179  1.00 22.44      A  O
ATOM  624  N    GLN A 112      1.317 -29.754 -42.312  1.00 22.04      A  N
ATOM  625  CA   GLN A 112      1.605 -29.061 -43.573  1.00 23.25      A  C
ATOM  626  CB   GLN A 112      0.883 -29.825 -44.673  1.00 23.40      A  C
ATOM  627  CG   GLN A 112      0.851 -29.176 -45.994  1.00 26.64      A  C
ATOM  628  CD   GLN A 112      2.005 -29.589 -46.770  1.00 33.66      A  C
ATOM  629  OE1  GLN A 112      1.913 -30.559 -47.517  1.00 39.87      A  O
```

FIGURE 1-9 (COORDINATES)

```
ATOM    630  NE2 GLN A 112      3.154 -28.915 -46.569  1.00 34.97      A   N
ATOM    631  C   GLN A 112      1.120 -27.575 -43.531  1.00 24.09      A   C
ATOM    632  O   GLN A 112     -0.040 -27.296 -43.181  1.00 24.96      A   O
ATOM    633  N   THR A 113      1.972 -26.614 -43.911  1.00 23.36      A   N
ATOM    634  CA  THR A 113      1.517 -25.226 -44.056  1.00 20.68      A   C
ATOM    635  CB  THR A 113      2.144 -24.310 -42.976  1.00 21.32      A   C
ATOM    636  OG1 THR A 113      3.484 -23.929 -43.376  1.00 19.94      A   O
ATOM    637  CG2 THR A 113      2.117 -24.957 -41.573  1.00 18.76      A   C
ATOM    638  C   THR A 113      1.834 -24.723 -45.504  1.00 20.52      A   C
ATOM    639  O   THR A 113      2.473 -25.456 -46.272  1.00 19.73      A   O
ATOM    640  N   PRO A 114      1.368 -23.502 -45.881  1.00 19.80      A   N
ATOM    641  CA  PRO A 114      1.786 -22.878 -47.144  1.00 19.43      A   C
ATOM    642  CB  PRO A 114      1.035 -21.533 -47.145  1.00 19.26      A   C
ATOM    643  CG  PRO A 114     -0.072 -21.697 -46.165  1.00 19.59      A   C
ATOM    644  CD  PRO A 114      0.561 -22.555 -45.087  1.00 20.54      A   C
ATOM    645  C   PRO A 114      3.331 -22.651 -47.192  1.00 19.68      A   C
ATOM    646  O   PRO A 114      3.906 -22.520 -48.318  1.00 17.57      A   O
ATOM    647  N   TYR A 115      3.980 -22.713 -46.007  1.00 18.15      A   N
ATOM    648  CA  TYR A 115      5.462 -22.709 -45.918  1.00 20.18      A   C
ATOM    649  CB  TYR A 115      5.961 -21.627 -44.919  1.00 21.23      A   C
ATOM    650  CG  TYR A 115      5.460 -20.255 -45.285  1.00 20.64      A   C
ATOM    651  CD1 TYR A 115      5.785 -19.723 -46.553  1.00 26.97      A   C
ATOM    652  CE1 TYR A 115      5.340 -18.498 -46.964  1.00 28.09      A   C
ATOM    653  CZ  TYR A 115      4.509 -17.771 -46.131  1.00 30.82      A   C
ATOM    654  OH  TYR A 115      4.126 -16.546 -46.631  1.00 30.86      A   O
ATOM    655  CE2 TYR A 115      4.112 -18.287 -44.857  1.00 22.71      A   C
ATOM    656  CD2 TYR A 115      4.610 -19.538 -44.452  1.00 17.31      A   C
ATOM    657  C   TYR A 115      6.085 -24.052 -45.562  1.00 20.77      A   C
ATOM    658  O   TYR A 115      7.151 -24.069 -44.918  1.00 20.94      A   O
ATOM    659  N   GLY A 116      5.409 -25.160 -45.953  1.00 20.42      A   N
ATOM    660  CA  GLY A 116      5.869 -26.531 -45.722  1.00 19.80      A   C
ATOM    661  C   GLY A 116      5.597 -26.974 -44.288  1.00 21.56      A   C
ATOM    662  O   GLY A 116      4.927 -26.280 -43.494  1.00 20.21      A   O
ATOM    663  N   TYR A 117      6.114 -28.144 -43.951  1.00 21.66      A   N
ATOM    664  CA  TYR A 117      5.812 -28.718 -42.665  1.00 22.08      A   C
ATOM    665  CB  TYR A 117      6.371 -30.146 -42.586  1.00 22.43      A   C
ATOM    666  CG  TYR A 117      5.500 -31.094 -43.344  1.00 22.56      A   C
ATOM    667  CD1 TYR A 117      5.714 -31.309 -44.711  1.00 24.72      A   C
ATOM    668  CE1 TYR A 117      4.899 -32.144 -45.410  1.00 23.81      A   C
ATOM    669  CZ  TYR A 117      3.837 -32.768 -44.776  1.00 26.15      A   C
ATOM    670  OH  TYR A 117      3.035 -33.593 -45.533  1.00 28.08      A   O
ATOM    671  CE2 TYR A 117      3.593 -32.576 -43.413  1.00 23.09      A   C
ATOM    672  CD2 TYR A 117      4.423 -31.736 -42.719  1.00 21.46      A   C
ATOM    673  C   TYR A 117      6.380 -27.847 -41.574  1.00 21.20      A   C
ATOM    674  O   TYR A 117      7.465 -27.335 -41.733  1.00 21.86      A   O
ATOM    675  N   ARG A 118      5.659 -27.692 -40.476  1.00 20.27      A   N
ATOM    676  CA  ARG A 118      6.128 -26.872 -39.392  1.00 19.92      A   C
ATOM    677  CB  ARG A 118      5.549 -25.441 -39.541  1.00 21.42      A   C
ATOM    678  CG  ARG A 118      6.258 -24.506 -40.644  1.00 21.45      A   C
ATOM    679  CD  ARG A 118      5.844 -22.978 -40.571  1.00 19.23      A   C
ATOM    680  NE  ARG A 118      6.436 -22.335 -39.348  1.00 21.41      A   N
ATOM    681  CZ  ARG A 118      7.717 -21.950 -39.273  1.00 16.91      A   C
ATOM    682  NH1 ARG A 118      8.524 -22.108 -40.359  1.00 10.25      A   N
ATOM    683  NH2 ARG A 118      8.162 -21.406 -38.151  1.00 15.72      A   N
ATOM    684  C   ARG A 118      5.661 -27.486 -38.124  1.00 20.29      A   C
ATOM    685  O   ARG A 118      4.776 -28.331 -38.160  1.00 20.94      A   O
ATOM    686  N   SER A 119      6.228 -27.076 -36.991  1.00 19.87      A   N
ATOM    687  CA  SER A 119      5.905 -27.677 -35.715  1.00 20.75      A   C
ATOM    688  CB  SER A 119      7.165 -27.871 -34.902  1.00 21.62      A   C
ATOM    689  OG  SER A 119      6.763 -28.291 -33.612  1.00 23.96      A   O
ATOM    690  C   SER A 119      4.988 -26.847 -34.847  1.00 20.19      A   C
ATOM    691  O   SER A 119      5.141 -25.628 -34.795  1.00 20.51      A   O
ATOM    692  N   PHE A 120      4.052 -27.484 -34.143  1.00 19.08      A   N
ATOM    693  CA  PHE A 120      3.057 -26.726 -33.363  1.00 18.00      A   C
ATOM    694  CB  PHE A 120      1.669 -26.782 -33.979  1.00 16.75      A   C
ATOM    695  CG  PHE A 120      1.565 -26.154 -35.401  1.00 14.00      A   C
ATOM    696  CD1 PHE A 120      0.932 -24.883 -35.573  1.00 10.76      A   C
ATOM    697  CE1 PHE A 120      0.810 -24.300 -36.855  1.00 12.13      A   C
ATOM    698  CZ  PHE A 120      1.293 -25.013 -37.982  1.00 11.47      A   C
ATOM    699  CE2 PHE A 120      1.869 -26.310 -37.805  1.00  7.26      A   C
```

FIGURE 1-10 (COORDINATES)

```
ATOM    700  CD2 PHE A 120       2.031 -26.820 -36.503  1.00  8.03      A  C
ATOM    701  C   PHE A 120       3.048 -27.328 -31.954  1.00 19.11      A  C
ATOM    702  O   PHE A 120       3.428 -28.491 -31.794  1.00 22.20      A  O
ATOM    703  N   SER A 121       2.567 -26.619 -30.947  1.00 17.58      A  N
ATOM    704  CA  SER A 121       2.671 -27.189 -29.555  1.00 17.96      A  C
ATOM    705  CB  SER A 121       3.960 -26.747 -28.862  1.00 17.05      A  C
ATOM    706  OG  SER A 121       5.108 -27.416 -29.361  1.00 21.70      A  O
ATOM    707  C   SER A 121       1.564 -26.551 -28.773  1.00 16.70      A  C
ATOM    708  O   SER A 121       1.739 -25.425 -28.405  1.00 16.24      A  O
ATOM    709  N   ASN A 122       0.423 -27.223 -28.572  1.00 17.07      A  N
ATOM    710  CA  ASN A 122      -0.612 -26.694 -27.709  1.00 17.03      A  C
ATOM    711  CB  ASN A 122      -1.937 -27.433 -27.896  1.00 17.87      A  C
ATOM    712  CG  ASN A 122      -2.486 -27.295 -29.314  1.00 18.91      A  C
ATOM    713  OD1 ASN A 122      -2.676 -26.197 -29.808  1.00 14.16      A  O
ATOM    714  ND2 ASN A 122      -2.788 -28.398 -29.931  1.00 20.73      A  N
ATOM    715  C   ASN A 122      -0.145 -26.973 -26.283  1.00 17.54      A  C
ATOM    716  O   ASN A 122       0.614 -27.904 -26.068  1.00 18.29      A  O
ATOM    717  N   ILE A 123      -0.595 -26.200 -25.316  1.00 17.76      A  N
ATOM    718  CA  ILE A 123      -0.120 -26.420 -23.927  1.00 18.45      A  C
ATOM    719  CB  ILE A 123       0.485 -25.152 -23.345  1.00 17.75      A  C
ATOM    720  CG1 ILE A 123       1.609 -24.626 -24.183  1.00 15.80      A  C
ATOM    721  CD1 ILE A 123       1.930 -23.067 -23.830  1.00 13.60      A  C
ATOM    722  CG2 ILE A 123       1.028 -25.343 -21.841  1.00 16.26      A  C
ATOM    723  C   ILE A 123      -1.372 -26.630 -23.164  1.00 19.80      A  C
ATOM    724  O   ILE A 123      -2.275 -25.770 -23.257  1.00 21.54      A  O
ATOM    725  N   ILE A 124      -1.473 -27.770 -22.469  1.00 21.13      A  N
ATOM    726  CA  ILE A 124      -2.632 -28.129 -21.647  1.00 21.04      A  C
ATOM    727  CB  ILE A 124      -3.322 -29.492 -22.077  1.00 20.66      A  C
ATOM    728  CG1 ILE A 124      -3.769 -29.496 -23.547  1.00 20.57      A  C
ATOM    729  CD1 ILE A 124      -2.670 -29.919 -24.524  1.00 23.06      A  C
ATOM    730  CG2 ILE A 124      -4.533 -29.818 -21.203  1.00 17.31      A  C
ATOM    731  C   ILE A 124      -2.193 -28.193 -20.171  1.00 22.39      A  C
ATOM    732  O   ILE A 124      -1.248 -28.890 -19.830  1.00 22.52      A  O
ATOM    733  N   SER A 125      -2.930 -27.509 -19.321  1.00 23.42      A  N
ATOM    734  CA  SER A 125      -2.659 -27.438 -17.872  1.00 25.35      A  C
ATOM    735  CB  SER A 125      -2.454 -25.969 -17.444  1.00 25.05      A  C
ATOM    736  OG  SER A 125      -1.971 -25.878 -16.097  1.00 28.29      A  O
ATOM    737  C   SER A 125      -3.897 -27.964 -17.192  1.00 25.69      A  C
ATOM    738  O   SER A 125      -4.934 -27.287 -17.224  1.00 27.29      A  O
ATOM    739  N   THR A 126      -3.822 -29.161 -16.617  1.00 26.21      A  N
ATOM    740  CA  THR A 126      -5.014 -29.758 -15.987  1.00 26.50      A  C
ATOM    741  CB  THR A 126      -5.406 -31.064 -16.680  1.00 26.27      A  C
ATOM    742  OG1 THR A 126      -5.497 -30.847 -18.108  1.00 25.41      A  O
ATOM    743  CG2 THR A 126      -6.726 -31.549 -16.132  1.00 25.51      A  C
ATOM    744  C   THR A 126      -4.881 -29.997 -14.470  1.00 27.00      A  C
ATOM    745  O   THR A 126      -3.902 -30.581 -14.012  1.00 27.56      A  O
ATOM    746  N   LEU A 127      -5.849 -29.516 -13.698  1.00 27.82      A  N
ATOM    747  CA  LEU A 127      -6.034 -30.048 -12.341  1.00 29.35      A  C
ATOM    748  CB  LEU A 127      -6.653 -29.023 -11.400  1.00 28.16      A  C
ATOM    749  CG  LEU A 127      -5.897 -27.688 -11.288  1.00 28.44      A  C
ATOM    750  CD1 LEU A 127      -6.688 -26.727 -10.453  1.00 28.33      A  C
ATOM    751  CD2 LEU A 127      -4.562 -27.907 -10.685  1.00 30.30      A  C
ATOM    752  C   LEU A 127      -6.895 -31.326 -12.434  1.00 30.88      A  C
ATOM    753  O   LEU A 127      -7.864 -31.386 -13.207  1.00 29.72      A  O
ATOM    754  N   ASN A 128      -6.514 -32.343 -11.651  1.00 32.04      A  N
ATOM    755  CA  ASN A 128      -7.298 -33.567 -11.512  1.00 33.22      A  C
ATOM    756  CB  ASN A 128      -8.635 -33.273 -10.819  1.00 33.02      A  C
ATOM    757  CG  ASN A 128      -8.444 -32.643  -9.423  1.00 35.63      A  C
ATOM    758  OD1 ASN A 128      -8.044 -33.320  -8.467  1.00 36.87      A  O
ATOM    759  ND2 ASN A 128      -8.728 -31.352  -9.311  1.00 34.43      A  N
ATOM    760  C   ASN A 128      -7.484 -34.219 -12.873  1.00 33.04      A  C
ATOM    761  O   ASN A 128      -8.590 -34.282 -13.393  1.00 33.53      A  O
ATOM    762  N   PRO A 129      -6.389 -34.706 -13.461  1.00 33.08      A  N
ATOM    763  CA  PRO A 129      -6.512 -35.123 -14.869  1.00 33.17      A  C
ATOM    764  CB  PRO A 129      -5.090 -35.568 -15.233  1.00 32.77      A  C
ATOM    765  CG  PRO A 129      -4.211 -35.044 -14.104  1.00 34.00      A  C
ATOM    766  CD  PRO A 129      -5.064 -35.014 -12.891  1.00 32.74      A  C
ATOM    767  C   PRO A 129      -7.501 -36.285 -15.060  1.00 33.42      A  C
ATOM    768  O   PRO A 129      -7.943 -36.548 -16.187  1.00 32.94      A  O
ATOM    769  N   THR A 130      -7.812 -36.985 -13.964  1.00 33.15      A  N
```

FIGURE 1-11 (COORDINATES)

```
ATOM    770  CA  THR A 130      -8.669 -38.146 -14.025  1.00 33.36           A    C
ATOM    771  CB  THR A 130      -8.114 -39.335 -13.214  1.00 33.78           A    C
ATOM    772  OG1 THR A 130      -8.025 -38.977 -11.820  1.00 35.48           A    O
ATOM    773  CG2 THR A 130      -6.738 -39.746 -13.740  1.00 32.63           A    C
ATOM    774  C   THR A 130     -10.120 -37.850 -13.654  1.00 33.74           A    C
ATOM    775  O   THR A 130     -10.990 -38.639 -14.003  1.00 34.80           A    O
ATOM    776  N   ALA A 131     -10.391 -36.735 -12.970  1.00 33.14           A    N
ATOM    777  CA  ALA A 131     -11.760 -36.232 -12.822  1.00 32.73           A    C
ATOM    778  CB  ALA A 131     -11.761 -34.762 -12.374  1.00 32.39           A    C
ATOM    779  C   ALA A 131     -12.519 -36.389 -14.143  1.00 33.09           A    C
ATOM    780  O   ALA A 131     -11.932 -36.230 -15.227  1.00 33.03           A    O
ATOM    781  N   ILE A 132     -13.813 -36.705 -14.049  1.00 33.25           A    N
ATOM    782  CA  ILE A 132     -14.627 -37.012 -15.226  1.00 33.71           A    C
ATOM    783  CB  ILE A 132     -16.077 -37.501 -14.888  1.00 34.11           A    C
ATOM    784  CG1 ILE A 132     -16.105 -38.550 -13.770  1.00 36.19           A    C
ATOM    785  CD1 ILE A 132     -17.528 -38.896 -13.265  1.00 39.57           A    C
ATOM    786  CG2 ILE A 132     -16.771 -38.007 -16.164  1.00 34.28           A    C
ATOM    787  C   ILE A 132     -14.826 -35.765 -16.051  1.00 33.04           A    C
ATOM    788  O   ILE A 132     -14.704 -35.801 -17.265  1.00 33.23           A    O
ATOM    789  N   ARG A 133     -15.225 -34.690 -15.366  1.00 32.31           A    N
ATOM    790  CA  ARG A 133     -15.596 -33.455 -16.023  1.00 30.37           A    C
ATOM    791  CB  ARG A 133     -16.990 -33.046 -15.572  1.00 29.66           A    C
ATOM    792  CG  ARG A 133     -18.001 -34.150 -15.810  1.00 28.56           A    C
ATOM    793  CD  ARG A 133     -19.290 -33.913 -15.092  1.00 26.56           A    C
ATOM    794  NE  ARG A 133     -19.739 -32.527 -15.130  1.00 27.47           A    N
ATOM    795  CZ  ARG A 133     -20.331 -31.928 -14.089  1.00 30.34           A    C
ATOM    796  NH1 ARG A 133     -20.503 -32.616 -12.981  1.00 27.92           A    N
ATOM    797  NH2 ARG A 133     -20.751 -30.662 -14.131  1.00 29.38           A    N
ATOM    798  C   ARG A 133     -14.606 -32.354 -15.719  1.00 30.20           A    C
ATOM    799  O   ARG A 133     -14.072 -32.237 -14.569  1.00 30.79           A    O
ATOM    800  N   HIS A 134     -14.392 -31.516 -16.723  1.00 28.97           A    N
ATOM    801  CA  HIS A 134     -13.616 -30.295 -16.540  1.00 28.32           A    C
ATOM    802  CB  HIS A 134     -12.175 -30.441 -17.026  1.00 26.99           A    C
ATOM    803  CG  HIS A 134     -11.314 -31.329 -16.167  1.00 27.50           A    C
ATOM    804  ND1 HIS A 134     -11.115 -32.673 -16.442  1.00 28.21           A    N
ATOM    805  CE1 HIS A 134     -10.305 -33.194 -15.536  1.00 25.40           A    C
ATOM    806  NE2 HIS A 134      -9.919 -32.227 -14.727  1.00 24.20           A    N
ATOM    807  CD2 HIS A 134     -10.545 -31.055 -15.088  1.00 24.00           A    C
ATOM    808  C   HIS A 134     -14.227 -29.074 -17.197  1.00 28.61           A    C
ATOM    809  O   HIS A 134     -14.691 -29.104 -18.353  1.00 28.61           A    O
ATOM    810  N   LEU A 135     -14.214 -27.989 -16.442  1.00 28.33           A    N
ATOM    811  CA  LEU A 135     -14.403 -26.671 -17.017  1.00 27.29           A    C
ATOM    812  CB  LEU A 135     -14.581 -25.653 -15.896  1.00 26.31           A    C
ATOM    813  CG  LEU A 135     -14.812 -24.161 -16.219  1.00 25.66           A    C
ATOM    814  CD1 LEU A 135     -15.921 -23.884 -17.280  1.00 22.14           A    C
ATOM    815  CD2 LEU A 135     -15.074 -23.426 -14.880  1.00 24.25           A    C
ATOM    816  C   LEU A 135     -13.136 -26.315 -17.790  1.00 26.17           A    C
ATOM    817  O   LEU A 135     -12.053 -26.369 -17.244  1.00 26.31           A    O
ATOM    818  N   VAL A 136     -13.273 -25.900 -19.041  1.00 24.82           A    N
ATOM    819  CA  VAL A 136     -12.075 -25.601 -19.850  1.00 22.90           A    C
ATOM    820  CB  VAL A 136     -12.090 -26.458 -21.121  1.00 23.99           A    C
ATOM    821  CG1 VAL A 136     -10.714 -26.388 -21.833  1.00 21.58           A    C
ATOM    822  CG2 VAL A 136     -12.522 -27.904 -20.769  1.00 21.97           A    C
ATOM    823  C   VAL A 136     -11.964 -24.095 -20.182  1.00 21.89           A    C
ATOM    824  O   VAL A 136     -12.903 -23.519 -20.742  1.00 21.26           A    O
ATOM    825  N   LEU A 137     -10.882 -23.449 -19.738  1.00 21.10           A    N
ATOM    826  CA  LEU A 137     -10.529 -22.100 -20.194  1.00 21.89           A    C
ATOM    827  CB  LEU A 137     -10.025 -21.258 -19.037  1.00 22.09           A    C
ATOM    828  CG  LEU A 137     -10.891 -21.110 -17.746  1.00 28.27           A    C
ATOM    829  CD1 LEU A 137     -10.398 -19.953 -16.878  1.00 27.51           A    C
ATOM    830  CD2 LEU A 137     -12.442 -20.929 -18.003  1.00 26.86           A    C
ATOM    831  C   LEU A 137      -9.462 -22.125 -21.363  1.00 21.14           A    C
ATOM    832  O   LEU A 137      -8.495 -22.854 -21.300  1.00 20.51           A    O
ATOM    833  N   ALA A 138      -9.642 -21.329 -22.407  1.00 21.06           A    N
ATOM    834  CA  ALA A 138      -8.725 -21.418 -23.551  1.00 22.04           A    C
ATOM    835  CB  ALA A 138      -9.260 -22.409 -24.588  1.00 20.91           A    C
ATOM    836  C   ALA A 138      -8.420 -20.047 -24.192  1.00 22.72           A    C
ATOM    837  O   ALA A 138      -9.291 -19.171 -24.247  1.00 23.33           A    O
ATOM    838  N   CYS A 139      -7.158 -19.839 -24.587  1.00 22.15           A    N
ATOM    839  CA  CYS A 139      -6.779 -18.717 -25.474  1.00 21.68           A    C
```

FIGURE 1-12 (COORDINATES)

```
ATOM    840  CB  CYS A 139      -5.931 -17.666 -24.732  1.00 21.20           A    C
ATOM    841  SG  CYS A 139      -4.303 -18.293 -24.147  1.00 27.27           A    S
ATOM    842  C   CYS A 139      -5.952 -19.356 -26.628  1.00 19.17           A    C
ATOM    843  O   CYS A 139      -5.552 -20.524 -26.528  1.00 18.76           A    O
ATOM    844  N   HIS A 140      -5.629 -18.610 -27.683  1.00 17.97           A    N
ATOM    845  CA  HIS A 140      -4.543 -19.066 -28.518  1.00 16.17           A    C
ATOM    846  CB  HIS A 140      -4.907 -18.966 -30.024  1.00 17.30           A    C
ATOM    847  CG  HIS A 140      -4.766 -17.602 -30.568  1.00 16.98           A    C
ATOM    848  ND1 HIS A 140      -3.542 -17.095 -30.936  1.00 16.52           A    N
ATOM    849  CE1 HIS A 140      -3.697 -15.847 -31.329  1.00 19.56           A    C
ATOM    850  NE2 HIS A 140      -4.963 -15.509 -31.193  1.00 15.13           A    N
ATOM    851  CD2 HIS A 140      -5.664 -16.593 -30.729  1.00 18.49           A    C
ATOM    852  C   HIS A 140      -3.327 -18.214 -28.166  1.00 15.63           A    C
ATOM    853  O   HIS A 140      -3.448 -16.985 -28.054  1.00 15.52           A    O
ATOM    854  N   TYR A 141      -2.161 -18.836 -28.032  1.00 15.46           A    N
ATOM    855  CA  TYR A 141      -0.911 -18.154 -27.591  1.00 15.14           A    C
ATOM    856  CB  TYR A 141      -0.162 -18.871 -26.414  1.00 14.94           A    C
ATOM    857  CG  TYR A 141       0.802 -20.068 -26.845  1.00 17.17           A    C
ATOM    858  CD1 TYR A 141       0.287 -21.363 -27.018  1.00 15.90           A    C
ATOM    859  CE1 TYR A 141       1.107 -22.455 -27.421  1.00 16.19           A    C
ATOM    860  CZ  TYR A 141       2.462 -22.230 -27.703  1.00 18.15           A    C
ATOM    861  OH  TYR A 141       3.210 -23.314 -28.126  1.00 16.55           A    O
ATOM    862  CE2 TYR A 141       3.032 -20.953 -27.570  1.00 12.83           A    C
ATOM    863  CD2 TYR A 141       2.204 -19.870 -27.119  1.00 14.55           A    C
ATOM    864  C   TYR A 141       0.032 -17.852 -28.735  1.00 14.21           A    C
ATOM    865  O   TYR A 141       1.025 -17.112 -28.536  1.00 14.61           A    O
ATOM    866  N   ASP A 142      -0.249 -18.354 -29.938  1.00 14.91           A    N
ATOM    867  CA  ASP A 142       0.490 -17.835 -31.097  1.00 14.30           A    C
ATOM    868  CB  ASP A 142       0.292 -18.738 -32.323  1.00 15.61           A    C
ATOM    869  CG  ASP A 142      -1.155 -18.759 -32.819  1.00 14.52           A    C
ATOM    870  OD1 ASP A 142      -1.999 -18.890 -31.929  1.00 12.39           A    O
ATOM    871  OD2 ASP A 142      -1.412 -18.697 -34.085  1.00 10.59           A    O
ATOM    872  C   ASP A 142       0.135 -16.371 -31.498  1.00 16.38           A    C
ATOM    873  O   ASP A 142      -0.904 -15.816 -31.057  1.00 16.59           A    O
ATOM    874  N   SER A 143       0.997 -15.790 -32.372  1.00 14.35           A    N
ATOM    875  CA  SER A 143       0.985 -14.440 -32.852  1.00 14.26           A    C
ATOM    876  CB  SER A 143       2.439 -13.965 -32.742  1.00 13.37           A    C
ATOM    877  OG  SER A 143       2.368 -12.677 -32.314  1.00 23.23           A    O
ATOM    878  C   SER A 143       0.818 -14.703 -34.402  1.00 13.72           A    C
ATOM    879  O   SER A 143       1.406 -15.607 -34.904  1.00 11.10           A    O
ATOM    880  N   LYS A 144       0.066 -13.912 -35.104  1.00 14.07           A    N
ATOM    881  CA  LYS A 144      -0.138 -14.136 -36.588  1.00 14.08           A    C
ATOM    882  CB  LYS A 144      -1.298 -13.278 -37.081  1.00 13.63           A    C
ATOM    883  CG  LYS A 144      -1.517 -13.310 -38.659  1.00 15.65           A    C
ATOM    884  CD  LYS A 144      -2.933 -12.649 -38.944  1.00 16.88           A    C
ATOM    885  CE  LYS A 144      -3.156 -12.643 -40.537  1.00 15.55           A    C
ATOM    886  NZ  LYS A 144      -3.186 -14.063 -40.981  1.00 20.04           A    N
ATOM    887  C   LYS A 144       1.145 -13.763 -37.287  1.00 15.62           A    C
ATOM    888  O   LYS A 144       1.769 -12.675 -37.075  1.00 16.49           A    O
ATOM    889  N   TYR A 145       1.622 -14.669 -38.102  1.00 18.46           A    N
ATOM    890  CA  TYR A 145       2.776 -14.328 -38.954  1.00 19.81           A    C
ATOM    891  CB  TYR A 145       3.236 -15.589 -39.694  1.00 18.26           A    C
ATOM    892  CG  TYR A 145       4.397 -15.389 -40.638  1.00 20.11           A    C
ATOM    893  CD1 TYR A 145       5.678 -15.194 -40.144  1.00 21.63           A    C
ATOM    894  CE1 TYR A 145       6.744 -14.998 -40.978  1.00 17.93           A    C
ATOM    895  CZ  TYR A 145       6.531 -14.992 -42.349  1.00 19.01           A    C
ATOM    896  OH  TYR A 145       7.609 -14.826 -43.112  1.00 19.54           A    O
ATOM    897  CE2 TYR A 145       5.289 -15.201 -42.910  1.00 19.50           A    C
ATOM    898  CD2 TYR A 145       4.209 -15.384 -42.047  1.00 22.97           A    C
ATOM    899  C   TYR A 145       2.487 -13.166 -39.915  1.00 21.41           A    C
ATOM    900  O   TYR A 145       1.630 -13.285 -40.762  1.00 22.70           A    O
ATOM    901  N   PHE A 146       3.270 -12.073 -39.859  1.00 24.47           A    N
ATOM    902  CA  PHE A 146       3.134 -10.995 -40.899  1.00 26.12           A    C
ATOM    903  CB  PHE A 146       2.603  -9.679 -40.306  1.00 25.51           A    C
ATOM    904  CG  PHE A 146       1.079  -9.691 -39.974  1.00 24.61           A    C
ATOM    905  CD1 PHE A 146       0.121  -9.578 -40.988  1.00 24.40           A    C
ATOM    906  CE1 PHE A 146      -1.224  -9.560 -40.698  1.00 21.20           A    C
ATOM    907  CZ  PHE A 146      -1.648  -9.632 -39.323  1.00 23.40           A    C
ATOM    908  CE2 PHE A 146      -0.720  -9.744 -38.322  1.00 21.73           A    C
ATOM    909  CD2 PHE A 146       0.640  -9.767 -38.645  1.00 21.50           A    C
```

FIGURE 1-13 (COORDINATES)

```
ATOM    910  C   PHE A 146       4.316 -10.722 -41.854  1.00 27.94           A  C
ATOM    911  O   PHE A 146       5.500 -10.817 -41.490  1.00 30.70           A  O
ATOM    912  N   ASN A 150       5.606  -3.387 -41.809  1.00 56.35           A  N
ATOM    913  CA  ASN A 150       5.759  -1.931 -41.838  1.00 56.26           A  C
ATOM    914  CB  ASN A 150       4.639  -1.247 -40.995  1.00 56.71           A  C
ATOM    915  CG  ASN A 150       3.558  -0.558 -41.863  1.00 57.42           A  C
ATOM    916  OD1 ASN A 150       3.585  -0.625 -43.098  1.00 59.07           A  O
ATOM    917  ND2 ASN A 150       2.627   0.127 -41.212  1.00 56.90           A  N
ATOM    918  C   ASN A 150       7.166  -1.458 -41.395  1.00 55.56           A  C
ATOM    919  O   ASN A 150       7.466  -0.258 -41.422  1.00 55.68           A  O
ATOM    920  N   ASN A 151       8.034  -2.416 -41.048  1.00 54.51           A  N
ATOM    921  CA  ASN A 151       9.197  -2.188 -40.150  1.00 52.59           A  C
ATOM    922  CB  ASN A 151      10.088  -1.020 -40.605  1.00 53.52           A  C
ATOM    923  CG  ASN A 151      11.557  -1.153 -40.120  1.00 55.10           A  C
ATOM    924  OD1 ASN A 151      12.162  -0.166 -39.697  1.00 55.68           A  O
ATOM    925  ND2 ASN A 151      12.121  -2.369 -40.194  1.00 55.31           A  N
ATOM    926  C   ASN A 151       8.700  -2.030 -38.691  1.00 50.62           A  C
ATOM    927  O   ASN A 151       9.203  -1.196 -37.901  1.00 51.17           A  O
ATOM    928  N   ARG A 152       7.680  -2.844 -38.385  1.00 46.95           A  N
ATOM    929  CA  ARG A 152       7.146  -3.063 -37.043  1.00 43.79           A  C
ATOM    930  CB  ARG A 152       5.904  -2.235 -36.841  1.00 44.47           A  C
ATOM    931  CG  ARG A 152       6.227  -0.947 -36.207  1.00 44.77           A  C
ATOM    932  CD  ARG A 152       5.139  -0.018 -36.496  1.00 45.95           A  C
ATOM    933  NE  ARG A 152       4.220   0.058 -35.372  1.00 46.19           A  N
ATOM    934  CZ  ARG A 152       2.985   0.526 -35.477  1.00 44.52           A  C
ATOM    935  NH1 ARG A 152       2.543   0.915 -36.672  1.00 41.82           A  N
ATOM    936  NH2 ARG A 152       2.202   0.583 -34.404  1.00 41.71           A  N
ATOM    937  C   ARG A 152       6.823  -4.528 -36.829  1.00 40.53           A  C
ATOM    938  O   ARG A 152       6.699  -5.288 -37.791  1.00 39.99           A  O
ATOM    939  N   VAL A 153       6.723  -4.938 -35.577  1.00 36.69           A  N
ATOM    940  CA  VAL A 153       6.460  -6.351 -35.309  1.00 33.98           A  C
ATOM    941  CB  VAL A 153       7.239  -6.901 -34.081  1.00 34.09           A  C
ATOM    942  CG1 VAL A 153       7.456  -8.391 -34.222  1.00 33.70           A  C
ATOM    943  CG2 VAL A 153       8.532  -6.164 -33.810  1.00 35.06           A  C
ATOM    944  C   VAL A 153       5.020  -6.474 -34.918  1.00 30.62           A  C
ATOM    945  O   VAL A 153       4.564  -5.666 -34.156  1.00 31.45           A  O
ATOM    946  N   PHE A 154       4.307  -7.493 -35.385  1.00 27.34           A  N
ATOM    947  CA  PHE A 154       2.968  -7.786 -34.852  1.00 23.86           A  C
ATOM    948  CB  PHE A 154       2.120  -8.569 -35.850  1.00 22.46           A  C
ATOM    949  CG  PHE A 154       0.695  -8.800 -35.372  1.00 21.17           A  C
ATOM    950  CD1 PHE A 154      -0.227  -7.740 -35.329  1.00 20.71           A  C
ATOM    951  CE1 PHE A 154      -1.558  -7.939 -34.886  1.00 22.16           A  C
ATOM    952  CZ  PHE A 154      -1.970  -9.205 -34.478  1.00 20.64           A  C
ATOM    953  CE2 PHE A 154      -1.035 -10.269 -34.511  1.00 19.95           A  C
ATOM    954  CD2 PHE A 154       0.270 -10.055 -34.946  1.00 18.54           A  C
ATOM    955  C   PHE A 154       3.066  -8.568 -33.545  1.00 23.33           A  C
ATOM    956  O   PHE A 154       3.669  -9.659 -33.536  1.00 24.25           A  O
ATOM    957  N   VAL A 155       2.484  -8.080 -32.449  1.00 23.00           A  N
ATOM    958  CA  VAL A 155       2.565  -8.871 -31.191  1.00 22.92           A  C
ATOM    959  CB  VAL A 155       3.323  -8.188 -30.043  1.00 23.74           A  C
ATOM    960  CG1 VAL A 155       4.823  -7.884 -30.432  1.00 24.62           A  C
ATOM    961  CG2 VAL A 155       2.575  -6.966 -29.513  1.00 21.04           A  C
ATOM    962  C   VAL A 155       1.247  -9.376 -30.641  1.00 24.63           A  C
ATOM    963  O   VAL A 155       1.246  -9.900 -29.481  1.00 25.46           A  O
ATOM    964  N   GLY A 156       0.152  -9.237 -31.425  1.00 24.25           A  N
ATOM    965  CA  GLY A 156      -1.221  -9.591 -30.999  1.00 23.33           A  C
ATOM    966  C   GLY A 156      -1.434  -9.419 -29.474  1.00 24.02           A  C
ATOM    967  O   GLY A 156      -1.489 -10.385 -28.693  1.00 24.40           A  O
ATOM    968  N   ALA A 157      -1.549  -8.177 -29.027  1.00 24.68           A  N
ATOM    969  CA  ALA A 157      -1.752  -7.910 -27.581  1.00 23.45           A  C
ATOM    970  CB  ALA A 157      -1.493  -6.424 -27.320  1.00 23.69           A  C
ATOM    971  C   ALA A 157      -3.176  -8.341 -27.080  1.00 23.31           A  C
ATOM    972  O   ALA A 157      -3.304  -9.006 -26.026  1.00 23.36           A  O
ATOM    973  N   THR A 158      -4.238  -7.955 -27.808  1.00 20.18           A  N
ATOM    974  CA  THR A 158      -5.578  -8.546 -27.579  1.00 18.17           A  C
ATOM    975  CB  THR A 158      -6.711  -7.721 -28.254  1.00 17.83           A  C
ATOM    976  OG1 THR A 158      -6.453  -7.652 -29.681  1.00 17.89           A  O
ATOM    977  CG2 THR A 158      -6.769  -6.301 -27.690  1.00 17.30           A  C
ATOM    978  C   THR A 158      -5.717  -9.986 -28.144  1.00 16.55           A  C
ATOM    979  O   THR A 158      -6.624 -10.712 -27.733  1.00 15.55           A  O
```

FIGURE 1-14 (COORDINATES)

```
ATOM    980  N   ASP A 159     -4.862 -10.342 -29.136  1.00 14.48      A  N
ATOM    981  CA  ASP A 159     -4.987 -11.469 -30.111  1.00 11.04      A  C
ATOM    982  CB  ASP A 159     -5.084 -10.794 -31.473  1.00 12.07      A  C
ATOM    983  CG  ASP A 159     -5.604 -11.703 -32.631  1.00  4.97      A  C
ATOM    984  OD1 ASP A 159     -5.471 -11.194 -33.838  1.00 19.86      A  O
ATOM    985  OD2 ASP A 159     -6.057 -12.860 -32.487  1.00  2.00      A  O
ATOM    986  C   ASP A 159     -3.642 -12.344 -30.002  1.00 12.60      A  C
ATOM    987  O   ASP A 159     -2.902 -12.547 -30.990  1.00  9.30      A  O
ATOM    988  N   SER A 160     -3.308 -12.868 -28.800  1.00  8.76      A  N
ATOM    989  CA  SER A 160     -4.220 -13.002 -27.735  1.00 12.64      A  C
ATOM    990  CB  SER A 160     -5.047 -14.321 -27.890  1.00 13.17      A  C
ATOM    991  OG  SER A 160     -6.412 -14.057 -28.254  1.00 17.60      A  O
ATOM    992  C   SER A 160     -3.416 -13.048 -26.439  1.00 13.24      A  C
ATOM    993  O   SER A 160     -3.751 -13.823 -25.575  1.00 16.51      A  O
ATOM    994  N   ALA A 161     -2.352 -12.253 -26.324  1.00 13.71      A  N
ATOM    995  CA  ALA A 161     -1.540 -12.269 -25.124  1.00 16.08      A  C
ATOM    996  CB  ALA A 161     -0.465 -11.150 -25.228  1.00 16.25      A  C
ATOM    997  C   ALA A 161     -2.360 -12.028 -23.887  1.00 15.98      A  C
ATOM    998  O   ALA A 161     -2.097 -12.583 -22.789  1.00 19.71      A  O
ATOM    999  N   VAL A 162     -3.294 -11.089 -24.021  1.00 18.00      A  N
ATOM   1000  CA  VAL A 162     -4.145 -10.676 -22.927  1.00 19.34      A  C
ATOM   1001  CB  VAL A 162     -4.871  -9.291 -23.211  1.00 19.92      A  C
ATOM   1002  CG1 VAL A 162     -6.084  -9.042 -22.206  1.00 19.84      A  C
ATOM   1003  CG2 VAL A 162     -3.873  -8.144 -23.176  1.00 18.33      A  C
ATOM   1004  C   VAL A 162     -5.067 -11.848 -22.523  1.00 20.46      A  C
ATOM   1005  O   VAL A 162     -5.054 -12.287 -21.319  1.00 20.51      A  O
ATOM   1006  N   PRO A 163     -5.807 -12.427 -23.499  1.00 19.31      A  N
ATOM   1007  CA  PRO A 163     -6.524 -13.621 -22.967  1.00 20.24      A  C
ATOM   1008  CB  PRO A 163     -7.207 -14.241 -24.176  1.00 20.56      A  C
ATOM   1009  CG  PRO A 163     -7.218 -13.190 -25.305  1.00 18.59      A  C
ATOM   1010  CD  PRO A 163     -6.231 -12.046 -24.879  1.00 20.25      A  C
ATOM   1011  C   PRO A 163     -5.627 -14.645 -22.181  1.00 21.53      A  C
ATOM   1012  O   PRO A 163     -6.024 -15.048 -21.065  1.00 22.37      A  O
ATOM   1013  N   CYS A 164     -4.415 -14.959 -22.660  1.00 21.58      A  N
ATOM   1014  CA  CYS A 164     -3.513 -15.926 -21.925  1.00 20.98      A  C
ATOM   1015  CB  CYS A 164     -2.286 -16.382 -22.728  1.00 21.61      A  C
ATOM   1016  SG  CYS A 164     -2.690 -16.874 -24.445  1.00 27.12      A  S
ATOM   1017  C   CYS A 164     -3.070 -15.459 -20.532  1.00 21.80      A  C
ATOM   1018  O   CYS A 164     -2.997 -16.282 -19.604  1.00 18.81      A  O
ATOM   1019  N   ALA A 165     -2.814 -14.144 -20.426  1.00 21.51      A  N
ATOM   1020  CA  ALA A 165     -2.339 -13.537 -19.224  1.00 21.72      A  C
ATOM   1021  CB  ALA A 165     -1.790 -12.110 -19.475  1.00 20.62      A  C
ATOM   1022  C   ALA A 165     -3.458 -13.538 -18.206  1.00 21.63      A  C
ATOM   1023  O   ALA A 165     -3.226 -13.859 -17.085  1.00 21.72      A  O
ATOM   1024  N   MET A 166     -4.672 -13.206 -18.632  1.00 22.08      A  N
ATOM   1025  CA  MET A 166     -5.880 -13.407 -17.790  1.00 22.38      A  C
ATOM   1026  CB  MET A 166     -7.162 -13.042 -18.566  1.00 21.83      A  C
ATOM   1027  CG  MET A 166     -7.276 -11.551 -18.933  1.00 20.60      A  C
ATOM   1028  SD  MET A 166     -8.603 -11.162 -20.083  1.00 24.78      A  S
ATOM   1029  CE  MET A 166     -9.907 -11.130 -18.888  1.00 25.06      A  C
ATOM   1030  C   MET A 166     -6.014 -14.818 -17.235  1.00 22.86      A  C
ATOM   1031  O   MET A 166     -6.238 -15.006 -16.036  1.00 22.95      A  O
ATOM   1032  N   MET A 167     -5.909 -15.812 -18.104  1.00 24.01      A  N
ATOM   1033  CA  MET A 167     -5.893 -17.231 -17.652  1.00 24.93      A  C
ATOM   1034  CB  MET A 167     -5.770 -18.216 -18.812  1.00 25.15      A  C
ATOM   1035  CG  MET A 167     -7.063 -18.334 -19.637  1.00 23.01      A  C
ATOM   1036  SD  MET A 167     -6.719 -18.818 -21.372  1.00 24.73      A  S
ATOM   1037  CE  MET A 167     -6.192 -20.516 -21.090  1.00 18.27      A  C
ATOM   1038  C   MET A 167     -4.781 -17.467 -16.622  1.00 25.42      A  C
ATOM   1039  O   MET A 167     -5.048 -18.027 -15.513  1.00 23.90      A  O
ATOM   1040  N   LEU A 168     -3.571 -16.997 -16.941  1.00 24.94      A  N
ATOM   1041  CA  LEU A 168     -2.485 -17.085 -15.949  1.00 25.76      A  C
ATOM   1042  CB  LEU A 168     -1.149 -16.620 -16.517  1.00 25.58      A  C
ATOM   1043  CG  LEU A 168     -0.453 -17.445 -17.622  1.00 25.94      A  C
ATOM   1044  CD1 LEU A 168      0.711 -16.618 -18.209  1.00 22.37      A  C
ATOM   1045  CD2 LEU A 168      0.098 -18.806 -17.129  1.00 20.30      A  C
ATOM   1046  C   LEU A 168     -2.789 -16.379 -14.620  1.00 26.33      A  C
ATOM   1047  O   LEU A 168     -2.499 -16.927 -13.532  1.00 26.01      A  O
ATOM   1048  N   GLU A 169     -3.360 -15.171 -14.698  1.00 25.86      A  N
ATOM   1049  CA  GLU A 169     -3.641 -14.410 -13.481  1.00 26.50      A  C
```

FIGURE 1-15 (COORDINATES)

```
ATOM   1050  CB   GLU A 169      -3.948 -12.941 -13.830  1.00 26.36           A  C
ATOM   1051  CG   GLU A 169      -4.723 -12.162 -12.753  1.00 27.63           A  C
ATOM   1052  CD   GLU A 169      -3.976 -12.025 -11.422  1.00 28.92           A  C
ATOM   1053  OE1  GLU A 169      -2.764 -12.346 -11.336  1.00 30.76           A  O
ATOM   1054  OE2  GLU A 169      -4.610 -11.582 -10.445  1.00 27.64           A  O
ATOM   1055  C    GLU A 169      -4.745 -15.081 -12.630  1.00 26.60           A  C
ATOM   1056  O    GLU A 169      -4.659 -15.174 -11.361  1.00 26.70           A  O
ATOM   1057  N    LEU A 170      -5.799 -15.542 -13.318  1.00 26.18           A  N
ATOM   1058  CA   LEU A 170      -6.798 -16.383 -12.672  1.00 26.08           A  C
ATOM   1059  CB   LEU A 170      -7.904 -16.820 -13.614  1.00 25.75           A  C
ATOM   1060  CG   LEU A 170      -8.977 -17.717 -12.991  1.00 26.44           A  C
ATOM   1061  CD1  LEU A 170     -10.336 -17.584 -13.675  1.00 26.95           A  C
ATOM   1062  CD2  LEU A 170      -8.509 -19.192 -13.039  1.00 28.31           A  C
ATOM   1063  C    LEU A 170      -6.181 -17.583 -11.906  1.00 25.86           A  C
ATOM   1064  O    LEU A 170      -6.515 -17.814 -10.728  1.00 25.21           A  O
ATOM   1065  N    ALA A 171      -5.295 -18.318 -12.553  1.00 24.71           A  N
ATOM   1066  CA   ALA A 171      -4.654 -19.444 -11.882  1.00 25.56           A  C
ATOM   1067  CB   ALA A 171      -3.714 -20.185 -12.855  1.00 25.26           A  C
ATOM   1068  C    ALA A 171      -3.919 -18.990 -10.576  1.00 26.67           A  C
ATOM   1069  O    ALA A 171      -3.997 -19.672  -9.517  1.00 25.94           A  O
ATOM   1070  N    ARG A 172      -3.274 -17.817 -10.643  1.00 26.70           A  N
ATOM   1071  CA   ARG A 172      -2.565 -17.298  -9.486  1.00 27.59           A  C
ATOM   1072  CB   ARG A 172      -1.517 -16.243  -9.894  1.00 28.07           A  C
ATOM   1073  CG   ARG A 172      -0.513 -15.833  -8.771  1.00 27.70           A  C
ATOM   1074  CD   ARG A 172      -0.057 -14.383  -8.963  1.00 27.83           A  C
ATOM   1075  NE   ARG A 172      -1.219 -13.480  -9.049  1.00 25.61           A  N
ATOM   1076  CZ   ARG A 172      -1.862 -12.969  -8.000  1.00 29.21           A  C
ATOM   1077  NH1  ARG A 172      -1.451 -13.217  -6.746  1.00 22.20           A  N
ATOM   1078  NH2  ARG A 172      -2.926 -12.199  -8.215  1.00 30.02           A  N
ATOM   1079  C    ARG A 172      -3.526 -16.771  -8.420  1.00 28.27           A  C
ATOM   1080  O    ARG A 172      -3.464 -17.214  -7.279  1.00 28.97           A  O
ATOM   1081  N    ALA A 173      -4.425 -15.859  -8.775  1.00 28.13           A  N
ATOM   1082  CA   ALA A 173      -5.384 -15.319  -7.792  1.00 28.25           A  C
ATOM   1083  CB   ALA A 173      -6.275 -14.287  -8.436  1.00 27.77           A  C
ATOM   1084  C    ALA A 173      -6.224 -16.373  -7.062  1.00 28.79           A  C
ATOM   1085  O    ALA A 173      -6.494 -16.259  -5.859  1.00 27.52           A  O
ATOM   1086  N    LEU A 174      -6.610 -17.425  -7.783  1.00 29.53           A  N
ATOM   1087  CA   LEU A 174      -7.402 -18.496  -7.166  1.00 28.98           A  C
ATOM   1088  CB   LEU A 174      -8.474 -18.970  -8.174  1.00 29.21           A  C
ATOM   1089  CG   LEU A 174      -9.339 -17.854  -8.840  1.00 29.43           A  C
ATOM   1090  CD1  LEU A 174     -10.360 -18.384  -9.880  1.00 24.75           A  C
ATOM   1091  CD2  LEU A 174     -10.017 -16.913  -7.802  1.00 24.79           A  C
ATOM   1092  C    LEU A 174      -6.550 -19.686  -6.656  1.00 29.10           A  C
ATOM   1093  O    LEU A 174      -7.107 -20.714  -6.260  1.00 29.48           A  O
ATOM   1094  N    ASP A 175      -5.225 -19.557  -6.652  1.00 28.23           A  N
ATOM   1095  CA   ASP A 175      -4.392 -20.685  -6.314  1.00 30.27           A  C
ATOM   1096  CB   ASP A 175      -2.905 -20.289  -6.204  1.00 30.17           A  C
ATOM   1097  CG   ASP A 175      -1.956 -21.497  -6.317  1.00 32.69           A  C
ATOM   1098  OD1  ASP A 175      -2.382 -22.577  -6.786  1.00 33.57           A  O
ATOM   1099  OD2  ASP A 175      -0.766 -21.370  -5.945  1.00 36.92           A  O
ATOM   1100  C    ASP A 175      -4.873 -21.380  -5.026  1.00 30.66           A  C
ATOM   1101  O    ASP A 175      -5.175 -22.570  -5.026  1.00 30.45           A  O
ATOM   1102  N    LYS A 176      -4.975 -20.641  -3.933  1.00 31.98           A  N
ATOM   1103  CA   LYS A 176      -5.343 -21.291  -2.683  1.00 33.12           A  C
ATOM   1104  CB   LYS A 176      -5.252 -20.329  -1.494  1.00 33.99           A  C
ATOM   1105  CG   LYS A 176      -3.990 -20.558  -0.640  1.00 36.73           A  C
ATOM   1106  CD   LYS A 176      -3.670 -19.386   0.311  1.00 39.84           A  C
ATOM   1107  CE   LYS A 176      -2.141 -19.162   0.407  1.00 40.05           A  C
ATOM   1108  NZ   LYS A 176      -1.752 -17.706   0.512  1.00 42.70           A  N
ATOM   1109  C    LYS A 176      -6.682 -22.020  -2.777  1.00 32.66           A  C
ATOM   1110  O    LYS A 176      -6.777 -23.246  -2.352  1.00 32.23           A  O
ATOM   1111  N    LYS A 177      -7.696 -21.395  -3.369  1.00 32.51           A  N
ATOM   1112  CA   LYS A 177      -8.964 -22.101  -3.529  1.00 33.32           A  C
ATOM   1113  CB   LYS A 177     -10.110 -21.178  -3.936  1.00 34.06           A  C
ATOM   1114  CG   LYS A 177     -10.145 -19.859  -3.145  1.00 36.56           A  C
ATOM   1115  CD   LYS A 177     -11.549 -19.248  -3.035  1.00 39.91           A  C
ATOM   1116  CE   LYS A 177     -11.470 -17.711  -2.836  1.00 41.02           A  C
ATOM   1117  NZ   LYS A 177     -12.708 -17.088  -2.248  1.00 41.90           A  N
ATOM   1118  C    LYS A 177      -8.852 -23.286  -4.491  1.00 33.44           A  C
ATOM   1119  O    LYS A 177      -9.449 -24.293  -4.244  1.00 32.98           A  O
```

FIGURE 1-16 (COORDINATES)

```
ATOM   1120  N   LEU A 178      -8.086 -23.179  -5.576  1.00 33.67           A N
ATOM   1121  CA  LEU A 178      -7.960 -24.297  -6.517  1.00 33.90           A C
ATOM   1122  CB  LEU A 178      -7.237 -23.868  -7.794  1.00 33.14           A C
ATOM   1123  CG  LEU A 178      -8.000 -22.903  -8.678  1.00 32.38           A C
ATOM   1124  CD1 LEU A 178      -7.045 -22.210  -9.623  1.00 28.82           A C
ATOM   1125  CD2 LEU A 178      -9.098 -23.660  -9.376  1.00 29.95           A C
ATOM   1126  C   LEU A 178      -7.205 -25.478  -5.899  1.00 34.78           A C
ATOM   1127  O   LEU A 178      -7.407 -26.634  -6.289  1.00 33.76           A O
ATOM   1128  N   LEU A 179      -6.322 -25.158  -4.951  1.00 35.84           A N
ATOM   1129  CA  LEU A 179      -5.526 -26.149  -4.227  1.00 37.01           A C
ATOM   1130  CB  LEU A 179      -4.494 -25.458  -3.307  1.00 36.88           A C
ATOM   1131  CG  LEU A 179      -3.541 -26.318  -2.463  1.00 36.76           A C
ATOM   1132  CD1 LEU A 179      -2.522 -27.127  -3.330  1.00 37.07           A C
ATOM   1133  CD2 LEU A 179      -2.831 -25.513  -1.346  1.00 34.60           A C
ATOM   1134  C   LEU A 179      -6.407 -27.136  -3.430  1.00 37.64           A C
ATOM   1135  O   LEU A 179      -6.014 -28.293  -3.253  1.00 38.53           A O
ATOM   1136  N   SER A 180      -7.584 -26.700  -2.975  1.00 37.54           A N
ATOM   1137  CA  SER A 180      -8.508 -27.577  -2.233  1.00 38.08           A C
ATOM   1138  CB  SER A 180      -9.623 -26.746  -1.604  1.00 38.08           A C
ATOM   1139  OG  SER A 180     -10.725 -26.630  -2.477  1.00 38.39           A O
ATOM   1140  C   SER A 180      -9.112 -28.765  -3.036  1.00 38.93           A C
ATOM   1141  O   SER A 180      -9.523 -29.783  -2.440  1.00 37.84           A O
ATOM   1142  N   LEU A 181      -9.151 -28.620  -4.376  1.00 38.98           A N
ATOM   1143  CA  LEU A 181      -9.606 -29.656  -5.306  1.00 39.21           A C
ATOM   1144  CB  LEU A 181      -9.669 -29.084  -6.716  1.00 39.11           A C
ATOM   1145  CG  LEU A 181     -10.793 -28.107  -6.966  1.00 39.74           A C
ATOM   1146  CD1 LEU A 181     -10.369 -27.131  -8.042  1.00 37.99           A C
ATOM   1147  CD2 LEU A 181     -12.031 -28.889  -7.351  1.00 39.69           A C
ATOM   1148  C   LEU A 181      -8.665 -30.844  -5.370  1.00 39.74           A C
ATOM   1149  O   LEU A 181      -8.958 -31.844  -6.032  1.00 39.00           A O
ATOM   1150  N   LYS A 182      -7.495 -30.711  -4.749  1.00 40.19           A N
ATOM   1151  CA  LYS A 182      -6.506 -31.782  -4.782  1.00 40.71           A C
ATOM   1152  CB  LYS A 182      -5.105 -31.231  -4.464  1.00 40.30           A C
ATOM   1153  CG  LYS A 182      -4.100 -32.313  -4.067  1.00 42.29           A C
ATOM   1154  CD  LYS A 182      -2.676 -31.829  -3.834  1.00 42.31           A C
ATOM   1155  CE  LYS A 182      -1.764 -33.063  -3.805  1.00 42.01           A C
ATOM   1156  NZ  LYS A 182      -0.422 -32.681  -3.347  1.00 42.31           A N
ATOM   1157  C   LYS A 182      -6.918 -32.963  -3.873  1.00 40.72           A C
ATOM   1158  O   LYS A 182      -7.524 -32.761  -2.805  1.00 41.92           A O
ATOM   1159  N   ASP A 190     -16.551 -33.914  -8.616  1.00 37.67           A N
ATOM   1160  CA  ASP A 190     -15.720 -34.604  -9.601  1.00 37.93           A C
ATOM   1161  CB  ASP A 190     -16.225 -36.001  -9.908  1.00 38.58           A C
ATOM   1162  CG  ASP A 190     -15.128 -36.848 -10.480  1.00 41.78           A C
ATOM   1163  OD1 ASP A 190     -15.380 -37.842 -11.202  1.00 43.13           A O
ATOM   1164  OD2 ASP A 190     -13.962 -36.458 -10.209  1.00 46.68           A O
ATOM   1165  C   ASP A 190     -15.553 -33.817 -10.915  1.00 36.98           A C
ATOM   1166  O   ASP A 190     -15.532 -34.341 -12.054  1.00 36.62           A O
ATOM   1167  N   LEU A 191     -15.439 -32.533 -10.711  1.00 35.23           A N
ATOM   1168  CA  LEU A 191     -15.399 -31.607 -11.774  1.00 34.51           A C
ATOM   1169  CB  LEU A 191     -16.707 -30.809 -11.782  1.00 34.44           A C
ATOM   1170  CG  LEU A 191     -16.803 -29.417 -12.376  1.00 32.98           A C
ATOM   1171  CD1 LEU A 191     -16.957 -29.441 -13.892  1.00 30.57           A C
ATOM   1172  CD2 LEU A 191     -18.020 -28.803 -11.697  1.00 33.91           A C
ATOM   1173  C   LEU A 191     -14.224 -30.778 -11.351  1.00 33.25           A C
ATOM   1174  O   LEU A 191     -14.080 -30.429 -10.180  1.00 32.39           A O
ATOM   1175  N   SER A 192     -13.336 -30.537 -12.289  1.00 32.33           A N
ATOM   1176  CA  SER A 192     -12.204 -29.684 -11.995  1.00 31.57           A C
ATOM   1177  CB  SER A 192     -10.977 -30.537 -11.681  1.00 31.44           A C
ATOM   1178  OG  SER A 192     -10.018 -29.761 -10.999  1.00 33.70           A O
ATOM   1179  C   SER A 192     -11.982 -28.707 -13.160  1.00 30.97           A C
ATOM   1180  O   SER A 192     -12.894 -28.512 -14.002  1.00 30.64           A O
ATOM   1181  N   LEU A 193     -10.780 -28.103 -13.183  1.00 29.77           A N
ATOM   1182  CA  LEU A 193     -10.400 -27.039 -14.108  1.00 27.37           A C
ATOM   1183  CB  LEU A 193      -9.963 -25.804 -13.307  1.00 27.15           A C
ATOM   1184  CG  LEU A 193      -9.702 -24.486 -14.072  1.00 27.87           A C
ATOM   1185  CD1 LEU A 193     -10.914 -24.022 -14.870  1.00 24.89           A C
ATOM   1186  CD2 LEU A 193      -9.233 -23.377 -13.140  1.00 26.21           A C
ATOM   1187  C   LEU A 193      -9.291 -27.456 -15.100  1.00 26.33           A C
ATOM   1188  O   LEU A 193      -8.348 -28.184 -14.745  1.00 25.63           A O
ATOM   1189  N   GLN A 194      -9.396 -26.984 -16.344  1.00 24.98           A N
```

FIGURE 1-17 (COORDINATES)

```
ATOM   1190  CA   GLN A 194      -8.352 -27.222 -17.328  1.00 23.27           A  C
ATOM   1191  CB   GLN A 194      -8.789 -28.273 -18.342  1.00 24.68           A  C
ATOM   1192  CG   GLN A 194      -7.708 -28.551 -19.450  1.00 23.25           A  C
ATOM   1193  CD   GLN A 194      -8.054 -29.771 -20.304  1.00 21.12           A  C
ATOM   1194  OE1  GLN A 194      -7.427 -30.837 -20.223  1.00 21.76           A  O
ATOM   1195  NE2  GLN A 194      -9.074 -29.617 -21.115  1.00 23.54           A  N
ATOM   1196  C    GLN A 194      -8.114 -25.901 -18.044  1.00 22.95           A  C
ATOM   1197  O    GLN A 194      -9.078 -25.206 -18.405  1.00 22.15           A  O
ATOM   1198  N    LEU A 195      -6.837 -25.538 -18.217  1.00 21.66           A  N
ATOM   1199  CA   LEU A 195      -6.488 -24.458 -19.151  1.00 21.56           A  C
ATOM   1200  CB   LEU A 195      -5.494 -23.475 -18.497  1.00 21.64           A  C
ATOM   1201  CG   LEU A 195      -5.824 -22.997 -17.060  1.00 23.01           A  C
ATOM   1202  CD1  LEU A 195      -4.597 -22.288 -16.459  1.00 20.52           A  C
ATOM   1203  CD2  LEU A 195      -7.041 -22.054 -17.114  1.00 21.60           A  C
ATOM   1204  C    LEU A 195      -5.905 -25.040 -20.441  1.00 20.96           A  C
ATOM   1205  O    LEU A 195      -5.085 -25.967 -20.356  1.00 22.21           A  O
ATOM   1206  N    ILE A 196      -6.326 -24.511 -21.602  1.00 20.12           A  N
ATOM   1207  CA   ILE A 196      -5.719 -24.800 -22.928  1.00 19.35           A  C
ATOM   1208  CB   ILE A 196      -6.747 -25.454 -23.890  1.00 19.32           A  C
ATOM   1209  CG1  ILE A 196      -7.235 -26.804 -23.366  1.00 20.48           A  C
ATOM   1210  CD1  ILE A 196      -8.347 -27.475 -24.230  1.00 20.28           A  C
ATOM   1211  CG2  ILE A 196      -6.115 -25.686 -25.316  1.00 18.92           A  C
ATOM   1212  C    ILE A 196      -5.138 -23.516 -23.606  1.00 19.09           A  C
ATOM   1213  O    ILE A 196      -5.839 -22.527 -23.782  1.00 20.79           A  O
ATOM   1214  N    PHE A 197      -3.862 -23.524 -23.961  1.00 18.14           A  N
ATOM   1215  CA   PHE A 197      -3.232 -22.485 -24.763  1.00 17.56           A  C
ATOM   1216  CB   PHE A 197      -1.940 -22.009 -24.123  1.00 18.14           A  C
ATOM   1217  CG   PHE A 197      -2.074 -21.620 -22.660  1.00 16.62           A  C
ATOM   1218  CD1  PHE A 197      -2.164 -20.287 -22.305  1.00 20.64           A  C
ATOM   1219  CE1  PHE A 197      -2.295 -19.879 -20.939  1.00 19.91           A  C
ATOM   1220  CZ   PHE A 197      -2.333 -20.840 -19.935  1.00 20.03           A  C
ATOM   1221  CE2  PHE A 197      -2.213 -22.189 -20.267  1.00 19.26           A  C
ATOM   1222  CD2  PHE A 197      -2.120 -22.572 -21.659  1.00 21.18           A  C
ATOM   1223  C    PHE A 197      -2.900 -23.086 -26.133  1.00 18.47           A  C
ATOM   1224  O    PHE A 197      -1.875 -23.762 -26.330  1.00 18.11           A  O
ATOM   1225  N    PHE A 198      -3.798 -22.843 -27.059  1.00 17.41           A  N
ATOM   1226  CA   PHE A 198      -3.693 -23.332 -28.445  1.00 15.96           A  C
ATOM   1227  CB   PHE A 198      -4.970 -22.993 -29.124  1.00 14.08           A  C
ATOM   1228  CG   PHE A 198      -6.121 -23.802 -28.695  1.00 13.41           A  C
ATOM   1229  CD1  PHE A 198      -6.096 -25.186 -28.784  1.00 15.05           A  C
ATOM   1230  CE1  PHE A 198      -7.230 -25.973 -28.436  1.00 14.78           A  C
ATOM   1231  CZ   PHE A 198      -8.426 -25.318 -27.991  1.00 16.94           A  C
ATOM   1232  CE2  PHE A 198      -8.448 -23.933 -27.910  1.00 17.15           A  C
ATOM   1233  CD2  PHE A 198      -7.300 -23.170 -28.306  1.00 16.32           A  C
ATOM   1234  C    PHE A 198      -2.591 -22.682 -29.258  1.00 15.98           A  C
ATOM   1235  O    PHE A 198      -2.472 -21.451 -29.341  1.00 16.98           A  O
ATOM   1236  N    ASP A 199      -1.827 -23.474 -29.964  1.00 15.10           A  N
ATOM   1237  CA   ASP A 199      -0.837 -22.897 -30.859  1.00 15.43           A  C
ATOM   1238  CB   ASP A 199       0.428 -23.806 -30.928  1.00 15.15           A  C
ATOM   1239  CG   ASP A 199       1.621 -23.134 -31.683  1.00 19.17           A  C
ATOM   1240  OD1  ASP A 199       1.436 -22.043 -32.259  1.00 19.11           A  O
ATOM   1241  OD2  ASP A 199       2.754 -23.687 -31.690  1.00 21.82           A  O
ATOM   1242  C    ASP A 199      -1.511 -22.848 -32.212  1.00 14.37           A  C
ATOM   1243  O    ASP A 199      -2.509 -23.523 -32.368  1.00 16.76           A  O
ATOM   1244  N    GLY A 200      -0.945 -22.140 -33.215  1.00 14.21           A  N
ATOM   1245  CA   GLY A 200      -1.441 -22.210 -34.580  1.00 13.13           A  C
ATOM   1246  C    GLY A 200      -2.920 -21.823 -34.877  1.00 15.80           A  C
ATOM   1247  O    GLY A 200      -3.430 -22.138 -35.974  1.00 14.79           A  O
ATOM   1248  N    GLU A 201      -3.628 -21.154 -33.949  1.00 14.95           A  N
ATOM   1249  CA   GLU A 201      -4.915 -20.510 -34.326  1.00 15.34           A  C
ATOM   1250  CB   GLU A 201      -5.388 -19.453 -33.365  1.00 14.30           A  C
ATOM   1251  CG   GLU A 201      -6.882 -19.217 -33.469  1.00 18.81           A  C
ATOM   1252  CD   GLU A 201      -7.281 -17.956 -34.192  1.00 23.88           A  C
ATOM   1253  OE1  GLU A 201      -6.419 -17.079 -34.273  1.00 21.17           A  O
ATOM   1254  OE2  GLU A 201      -8.477 -17.850 -34.662  1.00 29.13           A  O
ATOM   1255  C    GLU A 201      -4.938 -19.802 -35.701  1.00 15.08           A  C
ATOM   1256  O    GLU A 201      -5.900 -19.978 -36.404  1.00 15.27           A  O
ATOM   1257  N    GLU A 202      -3.980 -18.883 -35.953  1.00 14.95           A  N
ATOM   1258  CA   GLU A 202      -3.905 -18.032 -37.138  1.00 14.13           A  C
ATOM   1259  CB   GLU A 202      -2.888 -16.900 -36.813  1.00 14.71           A  C
```

FIGURE 1-18 (COORDINATES)

```
ATOM   1260  CG  GLU A 202      -3.300 -16.088 -35.471  1.00 12.16           A   C
ATOM   1261  CD  GLU A 202      -4.391 -14.989 -35.751  1.00 16.54           A   C
ATOM   1262  OE1 GLU A 202      -4.905 -14.941 -36.930  1.00 11.04           A   O
ATOM   1263  OE2 GLU A 202      -4.680 -14.122 -34.856  1.00  9.29           A   O
ATOM   1264  C   GLU A 202      -3.517 -18.680 -38.455  1.00 13.77           A   C
ATOM   1265  O   GLU A 202      -2.599 -19.542 -38.521  1.00 14.08           A   O
ATOM   1266  N   ALA A 203      -4.068 -18.164 -39.534  1.00 15.78           A   N
ATOM   1267  CA  ALA A 203      -3.549 -18.477 -40.886  1.00 17.32           A   C
ATOM   1268  CB  ALA A 203      -4.380 -17.814 -41.943  1.00 16.59           A   C
ATOM   1269  C   ALA A 203      -2.098 -18.056 -41.100  1.00 19.35           A   C
ATOM   1270  O   ALA A 203      -1.716 -16.953 -40.741  1.00 22.03           A   O
ATOM   1271  N   PHE A 204      -1.290 -18.904 -41.705  1.00 20.70           A   N
ATOM   1272  CA  PHE A 204       0.031 -18.480 -42.139  1.00 22.10           A   C
ATOM   1273  CB  PHE A 204       0.986 -19.684 -42.416  1.00 20.38           A   C
ATOM   1274  CG  PHE A 204       1.816 -20.057 -41.225  1.00 24.31           A   C
ATOM   1275  CD1 PHE A 204       1.411 -21.105 -40.363  1.00 25.09           A   C
ATOM   1276  CE1 PHE A 204       2.148 -21.410 -39.210  1.00 24.24           A   C
ATOM   1277  CZ  PHE A 204       3.290 -20.672 -38.896  1.00 25.25           A   C
ATOM   1278  CE2 PHE A 204       3.695 -19.628 -39.716  1.00 25.37           A   C
ATOM   1279  CD2 PHE A 204       2.964 -19.313 -40.890  1.00 22.38           A   C
ATOM   1280  C   PHE A 204      -0.079 -17.554 -43.366  1.00 23.05           A   C
ATOM   1281  O   PHE A 204       0.751 -16.655 -43.565  1.00 22.94           A   O
ATOM   1282  N   LEU A 205      -1.101 -17.750 -44.178  1.00 22.90           A   N
ATOM   1283  CA  LEU A 205      -1.170 -16.973 -45.459  1.00 24.12           A   C
ATOM   1284  CB  LEU A 205      -0.770 -17.816 -46.674  1.00 22.60           A   C
ATOM   1285  CG  LEU A 205      -0.884 -17.069 -48.014  1.00 25.79           A   C
ATOM   1286  CD1 LEU A 205       0.269 -16.086 -48.265  1.00 27.76           A   C
ATOM   1287  CD2 LEU A 205      -0.906 -18.024 -49.129  1.00 28.14           A   C
ATOM   1288  C   LEU A 205      -2.532 -16.278 -45.687  1.00 24.04           A   C
ATOM   1289  O   LEU A 205      -2.589 -15.076 -45.926  1.00 24.93           A   O
ATOM   1290  N   HIS A 206      -3.618 -17.037 -45.588  1.00 24.77           A   N
ATOM   1291  CA  HIS A 206      -4.910 -16.589 -46.022  1.00 26.66           A   C
ATOM   1292  CB  HIS A 206      -5.009 -16.648 -47.567  1.00 26.89           A   C
ATOM   1293  CG  HIS A 206      -6.310 -16.142 -48.127  1.00 29.58           A   C
ATOM   1294  ND1 HIS A 206      -7.542 -16.623 -47.735  1.00 33.72           A   N
ATOM   1295  CE1 HIS A 206      -8.499 -16.018 -48.415  1.00 28.26           A   C
ATOM   1296  NE2 HIS A 206      -7.933 -15.144 -49.226  1.00 32.98           A   N
ATOM   1297  CD2 HIS A 206      -6.567 -15.211 -49.079  1.00 32.33           A   C
ATOM   1298  C   HIS A 206      -5.825 -17.608 -45.370  1.00 27.12           A   C
ATOM   1299  O   HIS A 206      -5.650 -18.809 -45.578  1.00 26.23           A   O
ATOM   1300  N   TRP A 207      -6.794 -17.111 -44.595  1.00 27.00           A   N
ATOM   1301  CA  TRP A 207      -7.480 -17.916 -43.652  1.00 27.22           A   C
ATOM   1302  CB  TRP A 207      -8.281 -17.069 -42.657  1.00 25.79           A   C
ATOM   1303  CG  TRP A 207      -9.105 -17.902 -41.730  1.00 22.21           A   C
ATOM   1304  CD1 TRP A 207     -10.089 -18.804 -42.080  1.00 16.08           A   C
ATOM   1305  NE1 TRP A 207     -10.603 -19.404 -40.896  1.00 20.66           A   N
ATOM   1306  CE2 TRP A 207      -9.981 -18.868 -39.794  1.00 16.12           A   C
ATOM   1307  CD2 TRP A 207      -9.012 -17.946 -40.259  1.00 18.45           A   C
ATOM   1308  CE3 TRP A 207      -8.221 -17.282 -39.317  1.00 22.96           A   C
ATOM   1309  CZ3 TRP A 207      -8.414 -17.552 -37.928  1.00 17.70           A   C
ATOM   1310  CH2 TRP A 207      -9.384 -18.470 -37.512  1.00 18.00           A   C
ATOM   1311  CZ2 TRP A 207     -10.175 -19.133 -38.416  1.00 18.92           A   C
ATOM   1312  C   TRP A 207      -8.426 -18.865 -44.322  1.00 28.21           A   C
ATOM   1313  O   TRP A 207      -9.503 -18.469 -44.744  1.00 29.57           A   O
ATOM   1314  N   SER A 208      -8.067 -20.138 -44.315  1.00 27.98           A   N
ATOM   1315  CA  SER A 208      -8.951 -21.172 -44.877  1.00 28.37           A   C
ATOM   1316  CB  SER A 208      -8.446 -21.607 -46.281  1.00 27.61           A   C
ATOM   1317  OG  SER A 208      -7.206 -22.318 -46.148  1.00 30.57           A   O
ATOM   1318  C   SER A 208      -9.129 -22.338 -43.890  1.00 28.22           A   C
ATOM   1319  O   SER A 208      -8.485 -22.343 -42.767  1.00 27.11           A   O
ATOM   1320  N   PRO A 209     -10.050 -23.290 -44.240  1.00 27.70           A   N
ATOM   1321  CA  PRO A 209     -10.241 -24.513 -43.429  1.00 27.95           A   C
ATOM   1322  CB  PRO A 209     -11.135 -25.386 -44.347  1.00 28.30           A   C
ATOM   1323  CG  PRO A 209     -12.025 -24.351 -45.041  1.00 26.73           A   C
ATOM   1324  CD  PRO A 209     -11.053 -23.208 -45.326  1.00 28.45           A   C
ATOM   1325  C   PRO A 209      -8.917 -25.202 -43.081  1.00 26.30           A   C
ATOM   1326  O   PRO A 209      -8.704 -25.581 -41.929  1.00 26.22           A   O
ATOM   1327  N   GLN A 210      -8.014 -25.252 -44.047  1.00 25.84           A   N
ATOM   1328  CA  GLN A 210      -6.700 -25.920 -43.903  1.00 26.36           A   C
ATOM   1329  CB  GLN A 210      -6.250 -26.508 -45.262  1.00 27.44           A   C
```

FIGURE 1-19 (COORDINATES)

```
ATOM   1330  CG   GLN A 210      -7.246  -27.522  -45.815  1.00  30.49           A  C
ATOM   1331  CD   GLN A 210      -6.960  -27.882  -47.260  1.00  37.43           A  C
ATOM   1332  OE1  GLN A 210      -6.203  -28.824  -47.539  1.00  40.42           A  O
ATOM   1333  NE2  GLN A 210      -7.584  -27.157  -48.189  1.00  37.27           A  N
ATOM   1334  C    GLN A 210      -5.594  -25.003  -43.415  1.00  25.12           A  C
ATOM   1335  O    GLN A 210      -4.588  -25.458  -42.869  1.00  25.78           A  O
ATOM   1336  N    ASP A 211      -5.766  -23.715  -43.617  1.00  23.72           A  N
ATOM   1337  CA   ASP A 211      -4.769  -22.740  -43.172  1.00  22.45           A  C
ATOM   1338  CB   ASP A 211      -4.246  -21.884  -44.357  1.00  22.16           A  C
ATOM   1339  CG   ASP A 211      -3.119  -20.928  -43.919  1.00  24.81           A  C
ATOM   1340  OD1  ASP A 211      -2.762  -20.045  -44.694  1.00  18.05           A  O
ATOM   1341  OD2  ASP A 211      -2.633  -21.042  -42.761  1.00  23.64           A  O
ATOM   1342  C    ASP A 211      -5.380  -21.896  -42.078  1.00  21.58           A  C
ATOM   1343  O    ASP A 211      -5.790  -20.736  -42.337  1.00  22.81           A  O
ATOM   1344  N    SER A 212      -5.474  -22.504  -40.877  1.00  20.44           A  N
ATOM   1345  CA   SER A 212      -5.918  -21.887  -39.623  1.00  19.63           A  C
ATOM   1346  CB   SER A 212      -7.197  -21.006  -39.833  1.00  21.24           A  C
ATOM   1347  OG   SER A 212      -8.390  -21.755  -40.196  1.00  17.73           A  O
ATOM   1348  C    SER A 212      -6.213  -22.963  -38.613  1.00  18.56           A  C
ATOM   1349  O    SER A 212      -6.379  -24.104  -38.969  1.00  19.43           A  O
ATOM   1350  N    LEU A 213      -6.294  -22.597  -37.325  1.00  19.30           A  N
ATOM   1351  CA   LEU A 213      -6.774  -23.485  -36.276  1.00  18.97           A  C
ATOM   1352  CB   LEU A 213      -8.259  -23.842  -36.525  1.00  19.79           A  C
ATOM   1353  CG   LEU A 213      -9.220  -22.648  -36.696  1.00  20.05           A  C
ATOM   1354  CD1  LEU A 213     -10.673  -23.186  -36.725  1.00  20.44           A  C
ATOM   1355  CD2  LEU A 213      -9.036  -21.653  -35.524  1.00  11.28           A  C
ATOM   1356  C    LEU A 213      -6.008  -24.800  -36.185  1.00  18.58           A  C
ATOM   1357  O    LEU A 213      -6.614  -25.868  -35.965  1.00  19.42           A  O
ATOM   1358  N    TYR A 214      -4.706  -24.749  -36.395  1.00  16.97           A  N
ATOM   1359  CA   TYR A 214      -3.887  -25.987  -36.566  1.00  17.88           A  C
ATOM   1360  CB   TYR A 214      -2.418  -25.637  -36.964  1.00  14.86           A  C
ATOM   1361  CG   TYR A 214      -2.213  -25.108  -38.421  1.00  15.37           A  C
ATOM   1362  CD1  TYR A 214      -1.980  -25.980  -39.479  1.00  15.69           A  C
ATOM   1363  CE1  TYR A 214      -1.775  -25.481  -40.857  1.00  17.73           A  C
ATOM   1364  CZ   TYR A 214      -1.781  -24.106  -41.093  1.00  13.56           A  C
ATOM   1365  OH   TYR A 214      -1.574  -23.643  -42.379  1.00  19.43           A  O
ATOM   1366  CE2  TYR A 214      -2.016  -23.241  -40.054  1.00  15.93           A  C
ATOM   1367  CD2  TYR A 214      -2.209  -23.741  -38.704  1.00  14.91           A  C
ATOM   1368  C    TYR A 214      -3.943  -26.665  -35.220  1.00  17.84           A  C
ATOM   1369  O    TYR A 214      -4.269  -27.839  -35.119  1.00  19.11           A  O
ATOM   1370  N    GLY A 215      -3.624  -25.892  -34.178  1.00  17.92           A  N
ATOM   1371  CA   GLY A 215      -3.583  -26.373  -32.739  1.00  16.84           A  C
ATOM   1372  C    GLY A 215      -4.906  -26.990  -32.359  1.00  16.92           A  C
ATOM   1373  O    GLY A 215      -4.943  -28.155  -31.990  1.00  14.93           A  O
ATOM   1374  N    SER A 216      -6.007  -26.209  -32.471  1.00  18.22           A  N
ATOM   1375  CA   SER A 216      -7.282  -26.602  -31.898  1.00  17.81           A  C
ATOM   1376  CB   SER A 216      -8.320  -25.442  -31.922  1.00  18.18           A  C
ATOM   1377  OG   SER A 216      -8.377  -24.822  -33.220  1.00  21.35           A  O
ATOM   1378  C    SER A 216      -7.836  -27.791  -32.640  1.00  18.59           A  C
ATOM   1379  O    SER A 216      -8.389  -28.682  -32.001  1.00  18.48           A  O
ATOM   1380  N    ARG A 217      -7.731  -27.782  -33.981  1.00  15.12           A  N
ATOM   1381  CA   ARG A 217      -8.213  -28.887  -34.763  1.00  15.90           A  C
ATOM   1382  CB   ARG A 217      -8.050  -28.553  -36.290  1.00  15.46           A  C
ATOM   1383  CG   ARG A 217      -9.062  -27.527  -36.809  1.00  15.95           A  C
ATOM   1384  CD   ARG A 217      -8.935  -27.395  -38.395  1.00  19.49           A  C
ATOM   1385  NE   ARG A 217      -7.675  -26.788  -38.875  1.00  22.29           A  N
ATOM   1386  CZ   ARG A 217      -6.700  -27.483  -39.488  1.00  25.37           A  C
ATOM   1387  NH1  ARG A 217      -6.854  -28.782  -39.666  1.00  23.24           A  N
ATOM   1388  NH2  ARG A 217      -5.592  -26.896  -39.974  1.00  22.49           A  N
ATOM   1389  C    ARG A 217      -7.479  -30.228  -34.530  1.00  16.33           A  C
ATOM   1390  O    ARG A 217      -8.087  -31.315  -34.569  1.00  15.22           A  O
ATOM   1391  N    HIS A 218      -6.158  -30.166  -34.402  1.00  16.33           A  N
ATOM   1392  CA   HIS A 218      -5.410  -31.329  -33.963  1.00  16.61           A  C
ATOM   1393  CB   HIS A 218      -3.909  -30.987  -33.998  1.00  15.59           A  C
ATOM   1394  CG   HIS A 218      -3.027  -32.086  -33.462  1.00  16.23           A  C
ATOM   1395  ND1  HIS A 218      -2.751  -32.245  -32.098  1.00  15.55           A  N
ATOM   1396  CE1  HIS A 218      -1.946  -33.293  -31.948  1.00  15.43           A  C
ATOM   1397  NE2  HIS A 218      -1.722  -33.828  -33.145  1.00  16.60           A  N
ATOM   1398  CD2  HIS A 218      -2.410  -33.102  -34.101  1.00   9.17           A  C
ATOM   1399  C    HIS A 218      -5.787  -31.717  -32.499  1.00  16.78           A  C
```

FIGURE 1-20 (COORDINATES)

```
ATOM   1400  O   HIS A 218      -5.817 -32.904 -32.131  1.00 17.82          A  O
ATOM   1401  N   LEU A 219      -5.994 -30.761 -31.631  1.00 16.08          A  N
ATOM   1402  CA  LEU A 219      -6.271 -31.217 -30.207  1.00 14.72          A  C
ATOM   1403  CB  LEU A 219      -6.091 -30.120 -29.256  1.00 12.68          A  C
ATOM   1404  CG  LEU A 219      -6.322 -30.542 -27.734  1.00  9.93          A  C
ATOM   1405  CD1 LEU A 219      -5.350 -31.607 -27.258  1.00 11.30          A  C
ATOM   1406  CD2 LEU A 219      -6.085 -29.336 -27.020  1.00  9.50          A  C
ATOM   1407  C   LEU A 219      -7.713 -31.782 -30.009  1.00 18.08          A  C
ATOM   1408  O   LEU A 219      -7.939 -32.745 -29.238  1.00 20.70          A  O
ATOM   1409  N   ALA A 220      -8.703 -31.155 -30.643  1.00 18.16          A  N
ATOM   1410  CA  ALA A 220     -10.075 -31.642 -30.553  1.00 17.45          A  C
ATOM   1411  CB  ALA A 220     -11.019 -30.771 -31.379  1.00 15.66          A  C
ATOM   1412  C   ALA A 220     -10.103 -33.091 -31.053  1.00 18.35          A  C
ATOM   1413  O   ALA A 220     -10.714 -33.915 -30.394  1.00 19.20          A  O
ATOM   1414  N   ALA A 221      -9.442 -33.392 -32.194  1.00 17.41          A  N
ATOM   1415  CA  ALA A 221      -9.326 -34.771 -32.695  1.00 18.90          A  C
ATOM   1416  CB  ALA A 221      -8.701 -34.833 -34.196  1.00 16.62          A  C
ATOM   1417  C   ALA A 221      -8.563 -35.734 -31.757  1.00 18.16          A  C
ATOM   1418  O   ALA A 221      -8.949 -36.892 -31.576  1.00 17.75          A  O
ATOM   1419  N   LYS A 222      -7.458 -35.287 -31.200  1.00 19.44          A  N
ATOM   1420  CA  LYS A 222      -6.746 -36.117 -30.179  1.00 21.36          A  C
ATOM   1421  CB  LYS A 222      -5.536 -35.407 -29.551  1.00 21.80          A  C
ATOM   1422  CG  LYS A 222      -4.461 -36.302 -28.987  1.00 24.53          A  C
ATOM   1423  CD  LYS A 222      -3.713 -35.577 -27.855  1.00 28.27          A  C
ATOM   1424  CE  LYS A 222      -4.618 -35.603 -26.597  1.00 37.13          A  C
ATOM   1425  NZ  LYS A 222      -3.925 -35.730 -25.272  1.00 33.57          A  N
ATOM   1426  C   LYS A 222      -7.737 -36.437 -29.086  1.00 19.60          A  C
ATOM   1427  O   LYS A 222      -7.939 -37.588 -28.757  1.00 19.77          A  O
ATOM   1428  N   MET A 223      -8.405 -35.421 -28.594  1.00 20.05          A  N
ATOM   1429  CA  MET A 223      -9.279 -35.586 -27.401  1.00 19.53          A  C
ATOM   1430  CB  MET A 223      -9.711 -34.222 -26.925  1.00 19.59          A  C
ATOM   1431  CG  MET A 223      -8.605 -33.458 -26.143  1.00 20.23          A  C
ATOM   1432  SD  MET A 223      -9.202 -31.875 -25.490  1.00 20.90          A  S
ATOM   1433  CE  MET A 223      -9.644 -32.312 -23.788  1.00 21.82          A  C
ATOM   1434  C   MET A 223     -10.542 -36.470 -27.701  1.00 19.97          A  C
ATOM   1435  O   MET A 223     -11.137 -37.071 -26.784  1.00 19.25          A  O
ATOM   1436  N   ALA A 224     -10.891 -36.576 -28.999  1.00 18.18          A  N
ATOM   1437  CA  ALA A 224     -12.120 -37.197 -29.435  1.00 18.85          A  C
ATOM   1438  CB  ALA A 224     -12.576 -36.609 -30.810  1.00 18.17          A  C
ATOM   1439  C   ALA A 224     -11.853 -38.671 -29.603  1.00 19.34          A  C
ATOM   1440  O   ALA A 224     -12.781 -39.495 -29.632  1.00 20.10          A  O
ATOM   1441  N   SER A 225     -10.583 -39.034 -29.726  1.00 19.77          A  N
ATOM   1442  CA  SER A 225     -10.265 -40.437 -29.830  1.00 20.49          A  C
ATOM   1443  CB  SER A 225      -9.537 -40.743 -31.110  1.00 19.16          A  C
ATOM   1444  OG  SER A 225      -8.527 -39.793 -31.256  1.00 23.93          A  O
ATOM   1445  C   SER A 225      -9.461 -40.924 -28.665  1.00 21.07          A  C
ATOM   1446  O   SER A 225      -8.873 -41.983 -28.768  1.00 23.43          A  O
ATOM   1447  N   THR A 226      -9.499 -40.237 -27.538  1.00 21.22          A  N
ATOM   1448  CA  THR A 226      -8.729 -40.656 -26.378  1.00 22.42          A  C
ATOM   1449  CB  THR A 226      -7.773 -39.552 -25.880  1.00 22.53          A  C
ATOM   1450  OG1 THR A 226      -6.847 -39.261 -26.926  1.00 18.81          A  O
ATOM   1451  CG2 THR A 226      -6.998 -39.968 -24.597  1.00 17.57          A  C
ATOM   1452  C   THR A 226      -9.707 -40.933 -25.295  1.00 24.48          A  C
ATOM   1453  O   THR A 226     -10.445 -40.045 -24.930  1.00 24.78          A  O
ATOM   1454  N   PRO A 227      -9.738 -42.172 -24.791  1.00 26.35          A  N
ATOM   1455  CA  PRO A 227     -10.766 -42.582 -23.833  1.00 27.42          A  C
ATOM   1456  CB  PRO A 227     -10.499 -44.089 -23.657  1.00 28.28          A  C
ATOM   1457  CG  PRO A 227      -9.829 -44.524 -24.965  1.00 27.91          A  C
ATOM   1458  CD  PRO A 227      -8.886 -43.307 -25.196  1.00 27.43          A  C
ATOM   1459  C   PRO A 227     -10.612 -41.840 -22.519  1.00 28.77          A  C
ATOM   1460  O   PRO A 227      -9.491 -41.537 -22.150  1.00 28.61          A  O
ATOM   1461  N   HIS A 228     -11.740 -41.495 -21.881  1.00 30.04          A  N
ATOM   1462  CA  HIS A 228     -11.779 -40.707 -20.659  1.00 31.32          A  C
ATOM   1463  CB  HIS A 228     -11.751 -39.169 -20.897  1.00 31.75          A  C
ATOM   1464  CG  HIS A 228     -11.504 -38.381 -19.639  1.00 31.29          A  C
ATOM   1465  ND1 HIS A 228     -10.290 -38.403 -18.983  1.00 32.71          A  N
ATOM   1466  CE1 HIS A 228     -10.362 -37.679 -17.880  1.00 30.21          A  C
ATOM   1467  NE2 HIS A 228     -11.587 -37.194 -17.788  1.00 32.26          A  N
ATOM   1468  CD2 HIS A 228     -12.325 -37.631 -18.871  1.00 31.09          A  C
ATOM   1469  C   HIS A 228     -13.057 -41.049 -19.879  1.00 32.52          A  C
```

FIGURE 1-21 (COORDINATES)

```
ATOM   1470  O   HIS A 228     -14.127 -41.186 -20.499  1.00 32.01      A  O
ATOM   1471  N   PRO A 229     -12.932 -41.223 -18.541  1.00 32.92      A  N
ATOM   1472  CA  PRO A 229     -11.660 -41.373 -17.796  1.00 34.49      A  C
ATOM   1473  CB  PRO A 229     -12.126 -41.618 -16.355  1.00 34.17      A  C
ATOM   1474  CG  PRO A 229     -13.380 -40.780 -16.279  1.00 33.25      A  C
ATOM   1475  CD  PRO A 229     -14.064 -40.989 -17.622  1.00 33.53      A  C
ATOM   1476  C   PRO A 229     -10.774 -42.534 -18.273  1.00 36.15      A  C
ATOM   1477  O   PRO A 229     -11.235 -43.367 -19.064  1.00 36.04      A  O
ATOM   1478  N   PRO A 230      -9.489 -42.576 -17.833  1.00 37.64      A  N
ATOM   1479  CA  PRO A 230      -8.599 -43.587 -18.425  1.00 38.37      A  C
ATOM   1480  CB  PRO A 230      -7.237 -43.291 -17.792  1.00 38.62      A  C
ATOM   1481  CG  PRO A 230      -7.298 -41.841 -17.494  1.00 38.75      A  C
ATOM   1482  CD  PRO A 230      -8.726 -41.646 -16.979  1.00 38.28      A  C
ATOM   1483  C   PRO A 230      -9.071 -44.990 -18.095  1.00 38.85      A  C
ATOM   1484  O   PRO A 230      -9.494 -45.259 -16.956  1.00 38.50      A  O
ATOM   1485  N   GLY A 231      -9.037 -45.844 -19.112  1.00 38.56      A  N
ATOM   1486  CA  GLY A 231      -9.639 -47.147 -19.036  1.00 39.93      A  C
ATOM   1487  C   GLY A 231     -11.153 -47.192 -19.115  1.00 40.44      A  C
ATOM   1488  O   GLY A 231     -11.732 -48.205 -18.792  1.00 41.47      A  O
ATOM   1489  N   ALA A 232     -11.819 -46.122 -19.538  1.00 41.21      A  N
ATOM   1490  CA  ALA A 232     -13.272 -46.213 -19.796  1.00 41.06      A  C
ATOM   1491  CB  ALA A 232     -13.989 -44.913 -19.463  1.00 41.19      A  C
ATOM   1492  C   ALA A 232     -13.557 -46.634 -21.232  1.00 40.98      A  C
ATOM   1493  O   ALA A 232     -12.707 -46.524 -22.123  1.00 40.58      A  O
ATOM   1494  N   ARG A 233     -14.763 -47.137 -21.441  1.00 41.39      A  N
ATOM   1495  CA  ARG A 233     -15.202 -47.513 -22.763  1.00 41.78      A  C
ATOM   1496  CB  ARG A 233     -15.560 -49.010 -22.837  1.00 42.83      A  C
ATOM   1497  CG  ARG A 233     -16.544 -49.508 -21.770  1.00 47.27      A  C
ATOM   1498  CD  ARG A 233     -17.650 -50.386 -22.400  1.00 55.12      A  C
ATOM   1499  NE  ARG A 233     -17.214 -51.754 -22.697  1.00 59.12      A  N
ATOM   1500  CZ  ARG A 233     -17.589 -52.818 -21.993  1.00 61.46      A  C
ATOM   1501  NH1 ARG A 233     -18.420 -52.678 -20.958  1.00 62.69      A  N
ATOM   1502  NH2 ARG A 233     -17.134 -54.025 -22.321  1.00 63.35      A  N
ATOM   1503  C   ARG A 233     -16.366 -46.626 -23.226  1.00 40.87      A  C
ATOM   1504  O   ARG A 233     -17.263 -46.319 -22.444  1.00 39.91      A  O
ATOM   1505  N   GLY A 234     -16.343 -46.236 -24.507  1.00 39.94      A  N
ATOM   1506  CA  GLY A 234     -17.427 -45.470 -25.091  1.00 38.58      A  C
ATOM   1507  C   GLY A 234     -17.348 -43.949 -24.937  1.00 38.06      A  C
ATOM   1508  O   GLY A 234     -17.900 -43.259 -25.785  1.00 38.40      A  O
ATOM   1509  N   THR A 235     -16.670 -43.431 -23.891  1.00 36.50      A  N
ATOM   1510  CA  THR A 235     -16.507 -41.966 -23.624  1.00 34.82      A  C
ATOM   1511  CB  THR A 235     -17.008 -41.574 -22.207  1.00 35.31      A  C
ATOM   1512  OG1 THR A 235     -16.394 -42.429 -21.235  1.00 35.99      A  O
ATOM   1513  CG2 THR A 235     -18.537 -41.651 -22.098  1.00 34.81      A  C
ATOM   1514  C   THR A 235     -15.072 -41.396 -23.753  1.00 33.12      A  C
ATOM   1515  O   THR A 235     -14.115 -41.956 -23.217  1.00 33.23      A  O
ATOM   1516  N   SER A 236     -14.939 -40.247 -24.411  1.00 31.13      A  N
ATOM   1517  CA  SER A 236     -13.617 -39.691 -24.772  1.00 29.29      A  C
ATOM   1518  CB  SER A 236     -13.591 -39.259 -26.248  1.00 29.53      A  C
ATOM   1519  OG  SER A 236     -14.406 -38.110 -26.386  1.00 27.18      A  O
ATOM   1520  C   SER A 236     -13.329 -38.471 -23.930  1.00 29.07      A  C
ATOM   1521  O   SER A 236     -14.194 -37.971 -23.214  1.00 26.61      A  O
ATOM   1522  N   GLN A 237     -12.114 -37.946 -24.071  1.00 29.21      A  N
ATOM   1523  CA  GLN A 237     -11.775 -36.690 -23.443  1.00 29.19      A  C
ATOM   1524  CB  GLN A 237     -10.342 -36.388 -23.732  1.00 30.15      A  C
ATOM   1525  CG  GLN A 237      -9.386 -37.002 -22.749  1.00 30.38      A  C
ATOM   1526  CD  GLN A 237      -7.972 -36.762 -23.198  1.00 34.23      A  C
ATOM   1527  OE1 GLN A 237      -7.734 -36.331 -24.345  1.00 32.59      A  O
ATOM   1528  NE2 GLN A 237      -7.013 -37.074 -22.326  1.00 31.85      A  N
ATOM   1529  C   GLN A 237     -12.715 -35.489 -23.788  1.00 29.79      A  C
ATOM   1530  O   GLN A 237     -13.031 -34.701 -22.910  1.00 28.90      A  O
ATOM   1531  N   LEU A 238     -13.160 -35.345 -25.039  1.00 30.58      A  N
ATOM   1532  CA  LEU A 238     -14.132 -34.272 -25.372  1.00 31.74      A  C
ATOM   1533  CB  LEU A 238     -14.660 -34.399 -26.804  1.00 32.36      A  C
ATOM   1534  CG  LEU A 238     -13.912 -34.105 -28.085  1.00 31.72      A  C
ATOM   1535  CD1 LEU A 238     -14.924 -34.177 -29.214  1.00 38.23      A  C
ATOM   1536  CD2 LEU A 238     -13.318 -32.756 -28.125  1.00 34.12      A  C
ATOM   1537  C   LEU A 238     -15.341 -34.336 -24.463  1.00 32.50      A  C
ATOM   1538  O   LEU A 238     -15.832 -33.338 -23.981  1.00 33.91      A  O
ATOM   1539  N   HIS A 239     -15.837 -35.535 -24.260  1.00 33.22      A  N
```

FIGURE 1-22 (COORDINATES)

```
ATOM   1540  CA   HIS A 239     -17.006 -35.769 -23.466  1.00 33.92      A  C
ATOM   1541  CB   HIS A 239     -17.399 -37.252 -23.572  1.00 34.82      A  C
ATOM   1542  CG   HIS A 239     -18.863 -37.461 -23.577  1.00 38.69      A  C
ATOM   1543  ND1  HIS A 239     -19.576 -37.732 -22.424  1.00 44.82      A  N
ATOM   1544  CE1  HIS A 239     -20.861 -37.821 -22.720  1.00 46.59      A  C
ATOM   1545  NE2  HIS A 239     -21.006 -37.603 -24.020  1.00 45.75      A  N
ATOM   1546  CD2  HIS A 239     -19.771 -37.357 -24.573  1.00 43.15      A  C
ATOM   1547  C    HIS A 239     -16.861 -35.326 -22.008  1.00 33.53      A  C
ATOM   1548  O    HIS A 239     -17.841 -35.015 -21.357  1.00 34.32      A  O
ATOM   1549  N    GLY A 240     -15.648 -35.264 -21.493  1.00 32.83      A  N
ATOM   1550  CA   GLY A 240     -15.434 -34.764 -20.127  1.00 31.55      A  C
ATOM   1551  C    GLY A 240     -15.384 -33.237 -20.109  1.00 31.02      A  C
ATOM   1552  O    GLY A 240     -15.244 -32.614 -19.023  1.00 28.98      A  O
ATOM   1553  N    MET A 241     -15.503 -32.643 -21.307  1.00 29.04      A  N
ATOM   1554  CA   MET A 241     -15.512 -31.161 -21.445  1.00 30.48      A  C
ATOM   1555  CB   MET A 241     -15.044 -30.682 -22.868  1.00 31.07      A  C
ATOM   1556  CG   MET A 241     -13.532 -30.723 -23.125  1.00 32.26      A  C
ATOM   1557  SD   MET A 241     -13.110 -30.166 -24.802  1.00 33.73      A  S
ATOM   1558  CE   MET A 241     -12.728 -28.466 -24.450  1.00 33.58      A  C
ATOM   1559  C    MET A 241     -16.896 -30.539 -21.146  1.00 29.06      A  C
ATOM   1560  O    MET A 241     -17.691 -30.372 -22.084  1.00 27.59      A  O
ATOM   1561  N    ASP A 242     -17.158 -30.193 -19.870  1.00 28.24      A  N
ATOM   1562  CA   ASP A 242     -18.429 -29.560 -19.448  1.00 28.05      A  C
ATOM   1563  CB   ASP A 242     -18.333 -28.997 -18.022  1.00 27.86      A  C
ATOM   1564  CG   ASP A 242     -19.096 -29.810 -17.019  1.00 30.39      A  C
ATOM   1565  OD1  ASP A 242     -19.360 -31.018 -17.268  1.00 32.14      A  O
ATOM   1566  OD2  ASP A 242     -19.418 -29.237 -15.953  1.00 34.14      A  O
ATOM   1567  C    ASP A 242     -18.837 -28.393 -20.306  1.00 28.00      A  C
ATOM   1568  O    ASP A 242     -20.008 -28.283 -20.683  1.00 28.94      A  O
ATOM   1569  N    LEU A 243     -17.857 -27.515 -20.559  1.00 26.95      A  N
ATOM   1570  CA   LEU A 243     -18.019 -26.197 -21.185  1.00 25.18      A  C
ATOM   1571  CB   LEU A 243     -18.750 -25.219 -20.230  1.00 25.11      A  C
ATOM   1572  CG   LEU A 243     -18.879 -23.741 -20.623  1.00 24.03      A  C
ATOM   1573  CD1  LEU A 243     -20.047 -23.535 -21.574  1.00 22.20      A  C
ATOM   1574  CD2  LEU A 243     -19.081 -22.860 -19.406  1.00 23.93      A  C
ATOM   1575  C    LEU A 243     -16.621 -25.610 -21.602  1.00 24.56      A  C
ATOM   1576  O    LEU A 243     -15.671 -25.532 -20.792  1.00 22.94      A  O
ATOM   1577  N    LEU A 244     -16.517 -25.211 -22.869  1.00 22.56      A  N
ATOM   1578  CA   LEU A 244     -15.314 -24.508 -23.323  1.00 22.07      A  C
ATOM   1579  CB   LEU A 244     -14.858 -25.041 -24.696  1.00 20.12      A  C
ATOM   1580  CG   LEU A 244     -13.683 -24.318 -25.371  1.00 21.72      A  C
ATOM   1581  CD1  LEU A 244     -12.315 -24.586 -24.716  1.00 22.33      A  C
ATOM   1582  CD2  LEU A 244     -13.669 -24.693 -26.916  1.00 19.04      A  C
ATOM   1583  C    LEU A 244     -15.537 -22.983 -23.370  1.00 20.53      A  C
ATOM   1584  O    LEU A 244     -16.431 -22.487 -24.059  1.00 22.63      A  O
ATOM   1585  N    VAL A 245     -14.673 -22.258 -22.701  1.00 18.57      A  N
ATOM   1586  CA   VAL A 245     -14.793 -20.818 -22.525  1.00 17.89      A  C
ATOM   1587  CB   VAL A 245     -14.710 -20.434 -20.973  1.00 18.64      A  C
ATOM   1588  CG1  VAL A 245     -14.931 -18.952 -20.768  1.00 18.71      A  C
ATOM   1589  CG2  VAL A 245     -15.735 -21.199 -20.174  1.00 13.23      A  C
ATOM   1590  C    VAL A 245     -13.597 -20.247 -23.196  1.00 18.45      A  C
ATOM   1591  O    VAL A 245     -12.550 -20.269 -22.628  1.00 19.44      A  O
ATOM   1592  N    LEU A 246     -13.736 -19.829 -24.456  1.00 19.14      A  N
ATOM   1593  CA   LEU A 246     -12.659 -19.384 -25.256  1.00 17.79      A  C
ATOM   1594  CB   LEU A 246     -13.000 -19.801 -26.712  1.00 17.31      A  C
ATOM   1595  CG   LEU A 246     -12.078 -19.333 -27.821  1.00 16.72      A  C
ATOM   1596  CD1  LEU A 246     -10.640 -19.808 -27.572  1.00 17.53      A  C
ATOM   1597  CD2  LEU A 246     -12.562 -19.873 -29.188  1.00 17.73      A  C
ATOM   1598  C    LEU A 246     -12.548 -17.843 -25.106  1.00 18.99      A  C
ATOM   1599  O    LEU A 246     -13.488 -17.127 -25.496  1.00 20.29      A  O
ATOM   1600  N    LEU A 247     -11.450 -17.310 -24.539  1.00 17.85      A  N
ATOM   1601  CA   LEU A 247     -11.187 -15.852 -24.552  1.00 18.25      A  C
ATOM   1602  CB   LEU A 247     -10.320 -15.460 -23.377  1.00 18.33      A  C
ATOM   1603  CG   LEU A 247     -10.976 -15.557 -22.009  1.00 19.72      A  C
ATOM   1604  CD1  LEU A 247     -11.466 -16.997 -21.776  1.00 21.48      A  C
ATOM   1605  CD2  LEU A 247      -9.986 -15.138 -20.950  1.00 26.06      A  C
ATOM   1606  C    LEU A 247     -10.404 -15.511 -25.815  1.00 19.57      A  C
ATOM   1607  O    LEU A 247      -9.401 -16.126 -26.082  1.00 20.49      A  O
ATOM   1608  N    ASP A 248     -10.837 -14.539 -26.592  1.00 20.22      A  N
ATOM   1609  CA   ASP A 248     -10.051 -14.092 -27.794  1.00 21.61      A  C
```

FIGURE 1-23 (COORDINATES)

```
ATOM   1610  CB  ASP A 248     -10.388 -14.990 -28.971  1.00 18.51      A  C
ATOM   1611  CG  ASP A 248      -9.523 -14.751 -30.192  1.00 20.73      A  C
ATOM   1612  OD1 ASP A 248      -8.466 -14.106 -30.169  1.00 21.68      A  O
ATOM   1613  OD2 ASP A 248      -9.881 -15.296 -31.234  1.00 15.43      A  O
ATOM   1614  C   ASP A 248     -10.340 -12.582 -28.019  1.00 21.47      A  C
ATOM   1615  O   ASP A 248     -11.383 -12.075 -27.620  1.00 22.25      A  O
ATOM   1616  N   LEU A 249      -9.342 -11.842 -28.516  1.00 22.66      A  N
ATOM   1617  CA  LEU A 249      -9.478 -10.442 -28.870  1.00 20.39      A  C
ATOM   1618  CB  LEU A 249     -10.474 -10.302 -30.040  1.00 21.31      A  C
ATOM   1619  CG  LEU A 249     -10.079 -11.195 -31.247  1.00 21.62      A  C
ATOM   1620  CD1 LEU A 249     -11.054 -10.943 -32.454  1.00 19.97      A  C
ATOM   1621  CD2 LEU A 249      -8.684 -10.885 -31.682  1.00 15.35      A  C
ATOM   1622  C   LEU A 249      -9.907  -9.628 -27.641  1.00 19.89      A  C
ATOM   1623  O   LEU A 249     -10.721  -8.784 -27.765  1.00 18.85      A  O
ATOM   1624  N   ILE A 250      -9.361  -9.892 -26.453  1.00 19.54      A  N
ATOM   1625  CA  ILE A 250      -9.744  -9.129 -25.298  1.00 19.35      A  C
ATOM   1626  CB  ILE A 250     -10.052 -10.061 -24.075  1.00 20.44      A  C
ATOM   1627  CG1 ILE A 250     -11.257 -11.001 -24.406  1.00 21.77      A  C
ATOM   1628  CD1 ILE A 250     -11.679 -11.893 -23.234  1.00 23.07      A  C
ATOM   1629  CG2 ILE A 250     -10.235  -9.246 -22.763  1.00 14.72      A  C
ATOM   1630  C   ILE A 250      -8.637  -8.096 -24.951  1.00 21.48      A  C
ATOM   1631  O   ILE A 250      -7.422  -8.401 -25.019  1.00 20.16      A  O
ATOM   1632  N   GLY A 251      -9.067  -6.891 -24.534  1.00 22.95      A  N
ATOM   1633  CA  GLY A 251      -8.137  -5.885 -23.962  1.00 24.05      A  C
ATOM   1634  C   GLY A 251      -8.351  -4.450 -24.398  1.00 25.08      A  C
ATOM   1635  O   GLY A 251      -7.787  -3.501 -23.812  1.00 25.51      A  O
ATOM   1636  N   ALA A 252      -9.161  -4.305 -25.441  1.00 26.19      A  N
ATOM   1637  CA  ALA A 252      -9.532  -3.024 -25.971  1.00 26.31      A  C
ATOM   1638  CB  ALA A 252     -10.027  -3.159 -27.444  1.00 26.12      A  C
ATOM   1639  C   ALA A 252     -10.604  -2.392 -25.071  1.00 27.15      A  C
ATOM   1640  O   ALA A 252     -11.379  -3.123 -24.400  1.00 27.37      A  O
ATOM   1641  N   PRO A 253     -10.642  -1.032 -25.048  1.00 27.30      A  N
ATOM   1642  CA  PRO A 253     -11.673  -0.262 -24.345  1.00 27.13      A  C
ATOM   1643  CB  PRO A 253     -11.333   1.195 -24.730  1.00 27.15      A  C
ATOM   1644  CG  PRO A 253     -10.453   1.058 -26.032  1.00 27.38      A  C
ATOM   1645  CD  PRO A 253      -9.659  -0.151 -25.731  1.00 26.66      A  C
ATOM   1646  C   PRO A 253     -13.037  -0.617 -24.891  1.00 26.79      A  C
ATOM   1647  O   PRO A 253     -13.176  -0.875 -26.080  1.00 27.50      A  O
ATOM   1648  N   ASN A 254     -14.027  -0.629 -24.024  1.00 27.18      A  N
ATOM   1649  CA  ASN A 254     -15.468  -0.732 -24.376  1.00 28.92      A  C
ATOM   1650  CB  ASN A 254     -16.018   0.590 -24.994  1.00 29.15      A  C
ATOM   1651  CG  ASN A 254     -15.674   1.840 -24.163  1.00 30.30      A  C
ATOM   1652  OD1 ASN A 254     -16.039   1.969 -22.981  1.00 33.00      A  O
ATOM   1653  ND2 ASN A 254     -14.994   2.775 -24.796  1.00 29.47      A  N
ATOM   1654  C   ASN A 254     -15.864  -1.894 -25.279  1.00 29.20      A  C
ATOM   1655  O   ASN A 254     -16.581  -1.653 -26.283  1.00 28.23      A  O
ATOM   1656  N   PRO A 255     -15.421  -3.144 -24.934  1.00 28.98      A  N
ATOM   1657  CA  PRO A 255     -15.791  -4.341 -25.707  1.00 28.72      A  C
ATOM   1658  CB  PRO A 255     -14.919  -5.437 -25.101  1.00 27.41      A  C
ATOM   1659  CG  PRO A 255     -14.778  -5.064 -23.700  1.00 29.62      A  C
ATOM   1660  CD  PRO A 255     -14.686  -3.518 -23.707  1.00 29.84      A  C
ATOM   1661  C   PRO A 255     -17.262  -4.712 -25.511  1.00 29.23      A  C
ATOM   1662  O   PRO A 255     -17.807  -4.582 -24.377  1.00 29.31      A  O
ATOM   1663  N   THR A 256     -17.894  -5.171 -26.590  1.00 28.64      A  N
ATOM   1664  CA  THR A 256     -19.241  -5.737 -26.464  1.00 29.73      A  C
ATOM   1665  CB  THR A 256     -20.335  -4.899 -27.179  1.00 28.92      A  C
ATOM   1666  OG1 THR A 256     -19.957  -4.654 -28.547  1.00 31.27      A  O
ATOM   1667  CG2 THR A 256     -20.537  -3.579 -26.446  1.00 29.61      A  C
ATOM   1668  C   THR A 256     -19.280  -7.188 -26.918  1.00 29.54      A  C
ATOM   1669  O   THR A 256     -19.057  -7.495 -28.095  1.00 29.82      A  O
ATOM   1670  N   PHE A 257     -19.561  -8.057 -25.957  1.00 30.06      A  N
ATOM   1671  CA  PHE A 257     -19.598  -9.493 -26.154  1.00 31.58      A  C
ATOM   1672  CB  PHE A 257     -18.993 -10.223 -24.940  1.00 31.68      A  C
ATOM   1673  CG  PHE A 257     -17.510 -10.015 -24.753  1.00 34.12      A  C
ATOM   1674  CD1 PHE A 257     -16.586 -10.618 -25.609  1.00 34.78      A  C
ATOM   1675  CE1 PHE A 257     -15.220 -10.436 -25.429  1.00 34.20      A  C
ATOM   1676  CZ  PHE A 257     -14.747  -9.691 -24.360  1.00 35.77      A  C
ATOM   1677  CE2 PHE A 257     -15.630  -9.103 -23.479  1.00 36.53      A  C
ATOM   1678  CD2 PHE A 257     -17.025  -9.264 -23.678  1.00 37.30      A  C
ATOM   1679  C   PHE A 257     -21.038  -9.966 -26.297  1.00 31.27      A  C
```

FIGURE 1-24 (COORDINATES)

```
ATOM   1680  O    PHE A 257     -21.788  -9.941 -25.320  1.00 31.80      A  O
ATOM   1681  N    PRO A 258     -21.416 -10.410 -27.498  1.00 31.38      A  N
ATOM   1682  CA   PRO A 258     -22.713 -11.035 -27.775  1.00 31.94      A  C
ATOM   1683  CB   PRO A 258     -22.644 -11.336 -29.288  1.00 32.28      A  C
ATOM   1684  CG   PRO A 258     -21.550 -10.496 -29.808  1.00 31.52      A  C
ATOM   1685  CD   PRO A 258     -20.574 -10.345 -28.709  1.00 31.10      A  C
ATOM   1686  C    PRO A 258     -22.947 -12.367 -27.062  1.00 32.09      A  C
ATOM   1687  O    PRO A 258     -22.021 -13.006 -26.574  1.00 32.07      A  O
ATOM   1688  N    ASN A 259     -24.194 -12.806 -27.046  1.00 32.21      A  N
ATOM   1689  CA   ASN A 259     -24.511 -14.127 -26.562  1.00 32.94      A  C
ATOM   1690  CB   ASN A 259     -25.773 -14.125 -25.703  1.00 33.36      A  C
ATOM   1691  CG   ASN A 259     -26.063 -15.485 -25.074  1.00 35.37      A  C
ATOM   1692  OD1  ASN A 259     -27.078 -15.656 -24.418  1.00 40.17      A  O
ATOM   1693  ND2  ASN A 259     -25.167 -16.432 -25.240  1.00 35.01      A  N
ATOM   1694  C    ASN A 259     -24.701 -15.016 -27.775  1.00 32.56      A  C
ATOM   1695  O    ASN A 259     -25.771 -15.005 -28.385  1.00 32.75      A  O
ATOM   1696  N    PHE A 260     -23.662 -15.802 -28.078  1.00 31.37      A  N
ATOM   1697  CA   PHE A 260     -23.530 -16.560 -29.328  1.00 29.95      A  C
ATOM   1698  CB   PHE A 260     -22.035 -16.877 -29.587  1.00 28.64      A  C
ATOM   1699  CG   PHE A 260     -21.209 -15.684 -30.007  1.00 27.32      A  C
ATOM   1700  CD1  PHE A 260     -20.334 -15.074 -29.101  1.00 26.43      A  C
ATOM   1701  CE1  PHE A 260     -19.528 -13.982 -29.500  1.00 24.07      A  C
ATOM   1702  CZ   PHE A 260     -19.613 -13.455 -30.830  1.00 20.38      A  C
ATOM   1703  CE2  PHE A 260     -20.466 -14.052 -31.736  1.00 20.04      A  C
ATOM   1704  CD2  PHE A 260     -21.272 -15.178 -31.325  1.00 23.47      A  C
ATOM   1705  C    PHE A 260     -24.320 -17.853 -29.419  1.00 29.27      A  C
ATOM   1706  O    PHE A 260     -24.793 -18.205 -30.486  1.00 29.15      A  O
ATOM   1707  N    PHE A 261     -24.443 -18.589 -28.317  1.00 30.00      A  N
ATOM   1708  CA   PHE A 261     -24.935 -19.984 -28.419  1.00 30.48      A  C
ATOM   1709  CB   PHE A 261     -23.777 -21.006 -28.263  1.00 29.52      A  C
ATOM   1710  CG   PHE A 261     -22.687 -20.821 -29.274  1.00 25.53      A  C
ATOM   1711  CD1  PHE A 261     -22.951 -21.007 -30.639  1.00 23.63      A  C
ATOM   1712  CE1  PHE A 261     -21.975 -20.815 -31.588  1.00 19.52      A  C
ATOM   1713  CZ   PHE A 261     -20.698 -20.407 -31.192  1.00 20.03      A  C
ATOM   1714  CE2  PHE A 261     -20.404 -20.231 -29.865  1.00 20.45      A  C
ATOM   1715  CD2  PHE A 261     -21.420 -20.421 -28.890  1.00 22.50      A  C
ATOM   1716  C    PHE A 261     -26.056 -20.273 -27.444  1.00 32.12      A  C
ATOM   1717  O    PHE A 261     -25.885 -20.081 -26.230  1.00 31.89      A  O
ATOM   1718  N    PRO A 262     -27.224 -20.696 -27.977  1.00 33.76      A  N
ATOM   1719  CA   PRO A 262     -28.313 -21.103 -27.079  1.00 34.95      A  C
ATOM   1720  CB   PRO A 262     -29.312 -21.821 -28.022  1.00 34.75      A  C
ATOM   1721  CG   PRO A 262     -29.126 -21.131 -29.332  1.00 34.47      A  C
ATOM   1722  CD   PRO A 262     -27.661 -20.653 -29.394  1.00 33.88      A  C
ATOM   1723  C    PRO A 262     -27.793 -22.038 -25.978  1.00 35.65      A  C
ATOM   1724  O    PRO A 262     -28.072 -21.795 -24.809  1.00 35.94      A  O
ATOM   1725  N    ASN A 263     -27.003 -23.056 -26.327  1.00 36.14      A  N
ATOM   1726  CA   ASN A 263     -26.637 -24.066 -25.316  1.00 38.00      A  C
ATOM   1727  CB   ASN A 263     -26.324 -25.443 -25.942  1.00 38.09      A  C
ATOM   1728  CG   ASN A 263     -25.000 -25.480 -26.681  1.00 40.65      A  C
ATOM   1729  OD1  ASN A 263     -24.388 -24.446 -26.937  1.00 45.96      A  O
ATOM   1730  ND2  ASN A 263     -24.555 -26.688 -27.052  1.00 43.41      A  N
ATOM   1731  C    ASN A 263     -25.578 -23.628 -24.275  1.00 37.83      A  C
ATOM   1732  O    ASN A 263     -25.085 -24.438 -23.463  1.00 38.66      A  O
ATOM   1733  N    SER A 264     -25.223 -22.347 -24.329  1.00 37.31      A  N
ATOM   1734  CA   SER A 264     -24.424 -21.705 -23.293  1.00 35.68      A  C
ATOM   1735  CB   SER A 264     -23.014 -21.392 -23.813  1.00 36.20      A  C
ATOM   1736  OG   SER A 264     -23.019 -20.575 -24.990  1.00 36.15      A  O
ATOM   1737  C    SER A 264     -25.109 -20.430 -22.847  1.00 34.44      A  C
ATOM   1738  O    SER A 264     -24.565 -19.712 -22.025  1.00 34.88      A  O
ATOM   1739  N    ALA A 265     -26.287 -20.126 -23.382  1.00 32.75      A  N
ATOM   1740  CA   ALA A 265     -26.965 -18.892 -22.977  1.00 33.45      A  C
ATOM   1741  CB   ALA A 265     -28.279 -18.639 -23.749  1.00 32.87      A  C
ATOM   1742  C    ALA A 265     -27.167 -18.721 -21.463  1.00 33.27      A  C
ATOM   1743  O    ALA A 265     -27.155 -17.596 -20.977  1.00 34.92      A  O
ATOM   1744  N    ARG A 266     -27.332 -19.792 -20.701  1.00 32.80      A  N
ATOM   1745  CA   ARG A 266     -27.585 -19.588 -19.270  1.00 32.87      A  C
ATOM   1746  CB   ARG A 266     -28.352 -20.778 -18.644  1.00 32.85      A  C
ATOM   1747  CG   ARG A 266     -27.508 -22.049 -18.419  1.00 32.84      A  C
ATOM   1748  CD   ARG A 266     -28.329 -23.327 -18.197  1.00 28.71      A  C
ATOM   1749  NE   ARG A 266     -27.442 -24.485 -18.257  1.00 25.33      A  N
```

FIGURE 1-25 (COORDINATES)

```
ATOM   1750  CZ  ARG A 266     -26.848 -25.048 -17.212  1.00 29.76           A  C
ATOM   1751  NH1 ARG A 266     -27.048 -24.604 -15.958  1.00 30.05           A  N
ATOM   1752  NH2 ARG A 266     -26.064 -26.086 -17.426  1.00 31.33           A  N
ATOM   1753  C   ARG A 266     -26.266 -19.275 -18.545  1.00 33.16           A  C
ATOM   1754  O   ARG A 266     -26.255 -18.636 -17.465  1.00 32.79           A  O
ATOM   1755  N   TRP A 267     -25.157 -19.732 -19.161  1.00 32.60           A  N
ATOM   1756  CA  TRP A 267     -23.818 -19.391 -18.702  1.00 31.83           A  C
ATOM   1757  CB  TRP A 267     -22.766 -20.431 -19.188  1.00 31.06           A  C
ATOM   1758  CG  TRP A 267     -23.040 -21.734 -18.475  1.00 31.53           A  C
ATOM   1759  CD1 TRP A 267     -23.418 -22.957 -19.047  1.00 27.68           A  C
ATOM   1760  NE1 TRP A 267     -23.656 -23.881 -18.028  1.00 28.99           A  N
ATOM   1761  CE2 TRP A 267     -23.452 -23.284 -16.798  1.00 29.28           A  C
ATOM   1762  CD2 TRP A 267     -23.077 -21.933 -17.031  1.00 28.01           A  C
ATOM   1763  CE3 TRP A 267     -22.833 -21.100 -15.925  1.00 30.49           A  C
ATOM   1764  CZ3 TRP A 267     -22.953 -21.644 -14.597  1.00 30.34           A  C
ATOM   1765  CH2 TRP A 267     -23.314 -22.994 -14.402  1.00 29.66           A  C
ATOM   1766  CZ2 TRP A 267     -23.565 -23.829 -15.477  1.00 29.77           A  C
ATOM   1767  C   TRP A 267     -23.490 -17.913 -18.985  1.00 31.64           A  C
ATOM   1768  O   TRP A 267     -23.005 -17.198 -18.088  1.00 30.80           A  O
ATOM   1769  N   PHE A 268     -23.814 -17.452 -20.192  1.00 31.18           A  N
ATOM   1770  CA  PHE A 268     -23.714 -16.019 -20.551  1.00 32.59           A  C
ATOM   1771  CB  PHE A 268     -24.205 -15.787 -21.980  1.00 31.87           A  C
ATOM   1772  CG  PHE A 268     -23.983 -14.401 -22.474  1.00 33.22           A  C
ATOM   1773  CD1 PHE A 268     -22.843 -14.086 -23.233  1.00 34.40           A  C
ATOM   1774  CE1 PHE A 268     -22.623 -12.780 -23.707  1.00 32.94           A  C
ATOM   1775  CZ  PHE A 268     -23.550 -11.780 -23.437  1.00 34.62           A  C
ATOM   1776  CE2 PHE A 268     -24.707 -12.077 -22.666  1.00 34.49           A  C
ATOM   1777  CD2 PHE A 268     -24.908 -13.387 -22.194  1.00 34.29           A  C
ATOM   1778  C   PHE A 268     -24.482 -15.096 -19.608  1.00 33.38           A  C
ATOM   1779  O   PHE A 268     -24.022 -13.977 -19.312  1.00 33.26           A  O
ATOM   1780  N   GLU A 269     -25.663 -15.567 -19.187  1.00 34.14           A  N
ATOM   1781  CA  GLU A 269     -26.492 -14.912 -18.162  1.00 35.22           A  C
ATOM   1782  CB  GLU A 269     -27.751 -15.720 -17.908  1.00 36.21           A  C
ATOM   1783  CG  GLU A 269     -28.921 -15.394 -18.801  1.00 40.30           A  C
ATOM   1784  CD  GLU A 269     -30.167 -16.180 -18.389  1.00 47.67           A  C
ATOM   1785  OE1 GLU A 269     -30.323 -16.557 -17.176  1.00 48.38           A  O
ATOM   1786  OE2 GLU A 269     -31.001 -16.402 -19.291  1.00 50.18           A  O
ATOM   1787  C   GLU A 269     -25.791 -14.749 -16.832  1.00 34.51           A  C
ATOM   1788  O   GLU A 269     -25.863 -13.700 -16.203  1.00 34.53           A  O
ATOM   1789  N   ARG A 270     -25.128 -15.802 -16.385  1.00 34.73           A  N
ATOM   1790  CA  ARG A 270     -24.327 -15.726 -15.170  1.00 34.56           A  C
ATOM   1791  CB  ARG A 270     -23.692 -17.074 -14.888  1.00 34.19           A  C
ATOM   1792  CG  ARG A 270     -24.701 -18.167 -14.555  1.00 35.69           A  C
ATOM   1793  CD  ARG A 270     -25.614 -17.756 -13.364  1.00 32.76           A  C
ATOM   1794  NE  ARG A 270     -24.814 -17.365 -12.213  1.00 31.87           A  N
ATOM   1795  CZ  ARG A 270     -25.094 -16.361 -11.385  1.00 33.74           A  C
ATOM   1796  NH1 ARG A 270     -26.164 -15.608 -11.571  1.00 35.54           A  N
ATOM   1797  NH2 ARG A 270     -24.284 -16.093 -10.371  1.00 33.15           A  N
ATOM   1798  C   ARG A 270     -23.263 -14.612 -15.256  1.00 35.04           A  C
ATOM   1799  O   ARG A 270     -23.029 -13.896 -14.262  1.00 35.14           A  O
ATOM   1800  N   LEU A 271     -22.641 -14.449 -16.438  1.00 34.36           A  N
ATOM   1801  CA  LEU A 271     -21.670 -13.379 -16.646  1.00 34.50           A  C
ATOM   1802  CB  LEU A 271     -20.985 -13.472 -18.037  1.00 33.12           A  C
ATOM   1803  CG  LEU A 271     -19.941 -14.573 -18.294  1.00 32.10           A  C
ATOM   1804  CD1 LEU A 271     -19.397 -14.559 -19.777  1.00 30.65           A  C
ATOM   1805  CD2 LEU A 271     -18.763 -14.543 -17.337  1.00 27.02           A  C
ATOM   1806  C   LEU A 271     -22.378 -12.024 -16.461  1.00 35.22           A  C
ATOM   1807  O   LEU A 271     -21.798 -11.079 -15.891  1.00 34.91           A  O
ATOM   1808  N   GLN A 272     -23.616 -11.942 -16.967  1.00 35.68           A  N
ATOM   1809  CA  GLN A 272     -24.436 -10.727 -16.862  1.00 36.37           A  C
ATOM   1810  CB  GLN A 272     -25.692 -10.831 -17.706  1.00 36.26           A  C
ATOM   1811  CG  GLN A 272     -25.404 -10.795 -19.179  1.00 37.16           A  C
ATOM   1812  CD  GLN A 272     -26.649 -10.603 -20.007  1.00 38.59           A  C
ATOM   1813  OE1 GLN A 272     -26.673  -9.801 -20.965  1.00 38.93           A  O
ATOM   1814  NE2 GLN A 272     -27.679 -11.377 -19.688  1.00 36.77           A  N
ATOM   1815  C   GLN A 272     -24.800 -10.414 -15.419  1.00 36.40           A  C
ATOM   1816  O   GLN A 272     -24.704  -9.259 -14.984  1.00 37.51           A  O
ATOM   1817  N   ALA A 273     -25.173 -11.447 -14.678  1.00 36.39           A  N
ATOM   1818  CA  ALA A 273     -25.531 -11.320 -13.270  1.00 36.03           A  C
ATOM   1819  CB  ALA A 273     -26.016 -12.625 -12.755  1.00 35.65           A  C
```

FIGURE 1-26 (COORDINATES)

```
ATOM   1820  C   ALA A 273     -24.320 -10.853 -12.489  1.00 36.34      A    C
ATOM   1821  O   ALA A 273     -24.427  -9.956 -11.644  1.00 36.84      A    O
ATOM   1822  N   ILE A 274     -23.165 -11.451 -12.806  1.00 37.05      A    N
ATOM   1823  CA  ILE A 274     -21.878 -11.164 -12.153  1.00 36.40      A    C
ATOM   1824  CB  ILE A 274     -20.796 -12.221 -12.537  1.00 36.35      A    C
ATOM   1825  CG1 ILE A 274     -21.228 -13.624 -12.122  1.00 35.23      A    C
ATOM   1826  CD1 ILE A 274     -20.420 -14.733 -12.787  1.00 32.13      A    C
ATOM   1827  CG2 ILE A 274     -19.427 -11.877 -11.908  1.00 36.13      A    C
ATOM   1828  C   ILE A 274     -21.347  -9.746 -12.435  1.00 36.23      A    C
ATOM   1829  O   ILE A 274     -20.915  -9.042 -11.503  1.00 36.49      A    O
ATOM   1830  N   GLU A 275     -21.349  -9.342 -13.703  1.00 36.04      A    N
ATOM   1831  CA  GLU A 275     -20.931  -7.991 -14.079  1.00 35.96      A    C
ATOM   1832  CB  GLU A 275     -21.150  -7.734 -15.578  1.00 34.99      A    C
ATOM   1833  CG  GLU A 275     -20.636  -6.390 -16.110  1.00 32.85      A    C
ATOM   1834  CD  GLU A 275     -20.749  -6.285 -17.645  1.00 33.19      A    C
ATOM   1835  OE1 GLU A 275     -21.289  -7.206 -18.263  1.00 30.63      A    O
ATOM   1836  OE2 GLU A 275     -20.301  -5.292 -18.248  1.00 32.22      A    O
ATOM   1837  C   GLU A 275     -21.782  -7.039 -13.261  1.00 36.66      A    C
ATOM   1838  O   GLU A 275     -21.247  -6.116 -12.633  1.00 36.65      A    O
ATOM   1839  N   HIS A 276     -23.094  -7.311 -13.258  1.00 37.06      A    N
ATOM   1840  CA  HIS A 276     -24.088  -6.506 -12.560  1.00 38.62      A    C
ATOM   1841  CB  HIS A 276     -25.496  -7.076 -12.745  1.00 39.16      A    C
ATOM   1842  CG  HIS A 276     -26.562  -6.217 -12.134  1.00 42.07      A    C
ATOM   1843  ND1 HIS A 276     -27.211  -5.224 -12.840  1.00 44.18      A    N
ATOM   1844  CE1 HIS A 276     -28.071  -4.610 -12.047  1.00 43.40      A    C
ATOM   1845  NE2 HIS A 276     -27.990  -5.159 -10.846  1.00 46.55      A    N
ATOM   1846  CD2 HIS A 276     -27.052  -6.164 -10.870  1.00 42.79      A    C
ATOM   1847  C   HIS A 276     -23.819  -6.347 -11.058  1.00 38.66      A    C
ATOM   1848  O   HIS A 276     -23.842  -5.234 -10.529  1.00 38.28      A    O
ATOM   1849  N   GLU A 277     -23.587  -7.458 -10.380  1.00 38.74      A    N
ATOM   1850  CA  GLU A 277     -23.280  -7.401  -8.972  1.00 40.06      A    C
ATOM   1851  CB  GLU A 277     -23.472  -8.771  -8.327  1.00 40.47      A    C
ATOM   1852  CG  GLU A 277     -23.536  -8.742  -6.803  1.00 42.32      A    C
ATOM   1853  CD  GLU A 277     -24.706  -7.954  -6.251  1.00 43.90      A    C
ATOM   1854  OE1 GLU A 277     -24.872  -7.990  -5.009  1.00 45.66      A    O
ATOM   1855  OE2 GLU A 277     -25.445  -7.307  -7.044  1.00 44.14      A    O
ATOM   1856  C   GLU A 277     -21.896  -6.830  -8.651  1.00 40.30      A    C
ATOM   1857  O   GLU A 277     -21.700  -6.173  -7.615  1.00 40.29      A    O
ATOM   1858  N   LEU A 278     -20.920  -7.038  -9.511  1.00 40.14      A    N
ATOM   1859  CA  LEU A 278     -19.643  -6.471  -9.146  1.00 40.82      A    C
ATOM   1860  CB  LEU A 278     -18.499  -7.049  -9.986  1.00 40.79      A    C
ATOM   1861  CG  LEU A 278     -18.032  -8.482  -9.665  1.00 41.11      A    C
ATOM   1862  CD1 LEU A 278     -17.045  -8.912 -10.728  1.00 40.58      A    C
ATOM   1863  CD2 LEU A 278     -17.406  -8.671  -8.242  1.00 40.13      A    C
ATOM   1864  C   LEU A 278     -19.761  -4.949  -9.237  1.00 40.96      A    C
ATOM   1865  O   LEU A 278     -19.225  -4.204  -8.395  1.00 40.51      A    O
ATOM   1866  N   HIS A 279     -20.521  -4.514 -10.237  1.00 41.28      A    N
ATOM   1867  CA  HIS A 279     -20.744  -3.102 -10.492  1.00 42.19      A    C
ATOM   1868  CB  HIS A 279     -21.564  -2.930 -11.775  1.00 41.79      A    C
ATOM   1869  CG  HIS A 279     -22.027  -1.528 -11.998  1.00 43.11      A    C
ATOM   1870  ND1 HIS A 279     -21.230  -0.567 -12.580  1.00 43.63      A    N
ATOM   1871  CE1 HIS A 279     -21.896   0.574 -12.641  1.00 43.37      A    C
ATOM   1872  NE2 HIS A 279     -23.089   0.392 -12.104  1.00 42.12      A    N
ATOM   1873  CD2 HIS A 279     -23.193  -0.911 -11.682  1.00 43.90      A    C
ATOM   1874  C   HIS A 279     -21.405  -2.373  -9.300  1.00 42.21      A    C
ATOM   1875  O   HIS A 279     -20.949  -1.331  -8.875  1.00 42.15      A    O
ATOM   1876  N   GLU A 280     -22.467  -2.950  -8.761  1.00 43.02      A    N
ATOM   1877  CA  GLU A 280     -23.182  -2.367  -7.608  1.00 43.72      A    C
ATOM   1878  CB  GLU A 280     -24.427  -3.187  -7.240  1.00 43.72      A    C
ATOM   1879  CG  GLU A 280     -25.440  -3.379  -8.337  1.00 44.52      A    C
ATOM   1880  CD  GLU A 280     -26.383  -2.224  -8.451  1.00 46.68      A    C
ATOM   1881  OE1 GLU A 280     -27.558  -2.379  -8.027  1.00 48.70      A    O
ATOM   1882  OE2 GLU A 280     -25.944  -1.162  -8.941  1.00 46.11      A    O
ATOM   1883  C   GLU A 280     -22.322  -2.296  -6.360  1.00 43.48      A    C
ATOM   1884  O   GLU A 280     -22.493  -1.405  -5.542  1.00 43.58      A    O
ATOM   1885  N   LEU A 281     -21.427  -3.259  -6.189  1.00 43.13      A    N
ATOM   1886  CA  LEU A 281     -20.709  -3.352  -4.942  1.00 42.59      A    C
ATOM   1887  CB  LEU A 281     -20.318  -4.799  -4.629  1.00 42.25      A    C
ATOM   1888  CG  LEU A 281     -21.442  -5.783  -4.238  1.00 42.20      A    C
ATOM   1889  CD1 LEU A 281     -20.901  -7.190  -4.191  1.00 41.77      A    C
```

FIGURE 1-27 (COORDINATES)

```
ATOM   1890  CD2 LEU A 281     -22.120   -5.454   -2.890  1.00 41.83      A  C
ATOM   1891  C   LEU A 281     -19.524   -2.412   -5.023  1.00 42.63      A  C
ATOM   1892  O   LEU A 281     -18.692   -2.362   -4.112  1.00 42.90      A  O
ATOM   1893  N   GLY A 282     -19.504   -1.631   -6.107  1.00 42.59      A  N
ATOM   1894  CA  GLY A 282     -18.418   -0.708   -6.429  1.00 42.28      A  C
ATOM   1895  C   GLY A 282     -17.065   -1.389   -6.620  1.00 42.54      A  C
ATOM   1896  O   GLY A 282     -16.015   -0.763   -6.408  1.00 42.15      A  O
ATOM   1897  N   LEU A 283     -17.088   -2.665   -7.023  1.00 42.64      A  N
ATOM   1898  CA  LEU A 283     -15.866   -3.475   -7.219  1.00 42.41      A  C
ATOM   1899  CB  LEU A 283     -16.120   -4.931   -6.812  1.00 42.07      A  C
ATOM   1900  CG  LEU A 283     -16.650   -5.132   -5.376  1.00 40.30      A  C
ATOM   1901  CD1 LEU A 283     -17.121   -6.540   -5.166  1.00 37.32      A  C
ATOM   1902  CD2 LEU A 283     -15.605   -4.765   -4.341  1.00 39.60      A  C
ATOM   1903  C   LEU A 283     -15.271   -3.402   -8.636  1.00 43.03      A  C
ATOM   1904  O   LEU A 283     -14.141   -3.854   -8.861  1.00 44.09      A  O
ATOM   1905  N   LEU A 284     -16.022   -2.862   -9.592  1.00 42.91      A  N
ATOM   1906  CA  LEU A 284     -15.480   -2.580  -10.921  1.00 42.96      A  C
ATOM   1907  CB  LEU A 284     -16.553   -2.779  -12.002  1.00 42.21      A  C
ATOM   1908  CG  LEU A 284     -17.214   -4.168  -12.083  1.00 40.61      A  C
ATOM   1909  CD1 LEU A 284     -18.224   -4.216  -13.211  1.00 37.76      A  C
ATOM   1910  CD2 LEU A 284     -16.187   -5.290  -12.242  1.00 35.67      A  C
ATOM   1911  C   LEU A 284     -14.895   -1.156  -10.973  1.00 43.97      A  C
ATOM   1912  O   LEU A 284     -15.111   -0.354  -10.058  1.00 44.56      A  O
ATOM   1913  N   LYS A 285     -14.151   -0.851  -12.031  1.00 44.81      A  N
ATOM   1914  CA  LYS A 285     -13.523    0.451  -12.205  1.00 45.87      A  C
ATOM   1915  CB  LYS A 285     -12.006    0.340  -12.053  1.00 45.88      A  C
ATOM   1916  CG  LYS A 285     -11.523   -0.249  -10.728  1.00 47.31      A  C
ATOM   1917  CD  LYS A 285      -9.999   -0.342  -10.694  1.00 50.27      A  C
ATOM   1918  CE  LYS A 285      -9.448   -0.310   -9.262  1.00 51.65      A  C
ATOM   1919  NZ  LYS A 285      -7.944   -0.299   -9.259  1.00 51.61      A  N
ATOM   1920  C   LYS A 285     -13.862    1.020  -13.580  1.00 46.33      A  C
ATOM   1921  O   LYS A 285     -13.855    0.285  -14.571  1.00 46.71      A  O
ATOM   1922  N   ASP A 286     -14.145    2.325  -13.630  1.00 46.79      A  N
ATOM   1923  CA  ASP A 286     -14.564    3.038  -14.856  1.00 47.53      A  C
ATOM   1924  CB  ASP A 286     -13.384    3.268  -15.822  1.00 47.52      A  C
ATOM   1925  CG  ASP A 286     -12.322    4.188  -15.251  1.00 49.52      A  C
ATOM   1926  OD1 ASP A 286     -12.701    5.171  -14.589  1.00 51.26      A  O
ATOM   1927  OD2 ASP A 286     -11.107    3.935  -15.460  1.00 51.83      A  O
ATOM   1928  C   ASP A 286     -15.674    2.311  -15.595  1.00 47.57      A  C
ATOM   1929  O   ASP A 286     -15.684    2.277  -16.828  1.00 47.56      A  O
ATOM   1930  N   HIS A 287     -16.603    1.732  -14.846  1.00 47.91      A  N
ATOM   1931  CA  HIS A 287     -17.593    0.840  -15.430  1.00 48.57      A  C
ATOM   1932  CB  HIS A 287     -17.587   -0.512  -14.700  1.00 48.30      A  C
ATOM   1933  CG  HIS A 287     -18.548   -1.522  -15.262  1.00 49.41      A  C
ATOM   1934  ND1 HIS A 287     -19.777   -1.784  -14.689  1.00 49.84      A  N
ATOM   1935  CE1 HIS A 287     -20.400   -2.717  -15.390  1.00 49.58      A  C
ATOM   1936  NE2 HIS A 287     -19.619   -3.072  -16.396  1.00 49.38      A  N
ATOM   1937  CD2 HIS A 287     -18.458   -2.335  -16.345  1.00 48.29      A  C
ATOM   1938  C   HIS A 287     -19.001    1.441  -15.440  1.00 49.32      A  C
ATOM   1939  O   HIS A 287     -19.550    1.821  -14.388  1.00 49.12      A  O
ATOM   1940  N   SER A 288     -19.585    1.498  -16.638  1.00 49.93      A  N
ATOM   1941  CA  SER A 288     -20.960    1.965  -16.812  1.00 50.26      A  C
ATOM   1942  CB  SER A 288     -21.040    2.970  -17.962  1.00 50.28      A  C
ATOM   1943  OG  SER A 288     -22.370    3.090  -18.428  1.00 50.56      A  O
ATOM   1944  C   SER A 288     -21.935    0.806  -17.059  1.00 50.42      A  C
ATOM   1945  O   SER A 288     -21.623   -0.132  -17.792  1.00 49.96      A  O
ATOM   1946  N   LEU A 289     -23.112    0.883  -16.436  1.00 50.41      A  N
ATOM   1947  CA  LEU A 289     -24.189   -0.048  -16.740  1.00 50.31      A  C
ATOM   1948  CB  LEU A 289     -25.351    0.116  -15.756  1.00 50.43      A  C
ATOM   1949  CG  LEU A 289     -25.305   -0.657  -14.432  1.00 50.94      A  C
ATOM   1950  CD1 LEU A 289     -26.656   -0.613  -13.776  1.00 50.28      A  C
ATOM   1951  CD2 LEU A 289     -24.848   -2.126  -14.614  1.00 51.81      A  C
ATOM   1952  C   LEU A 289     -24.670    0.119  -18.187  1.00 49.78      A  C
ATOM   1953  O   LEU A 289     -25.039   -0.845  -18.858  1.00 49.87      A  O
ATOM   1954  N   GLU A 290     -24.632    1.342  -18.679  1.00 49.39      A  N
ATOM   1955  CA  GLU A 290     -25.125    1.592  -20.025  1.00 49.59      A  C
ATOM   1956  CB  GLU A 290     -25.568    3.052  -20.229  1.00 50.11      A  C
ATOM   1957  CG  GLU A 290     -26.905    3.416  -19.527  1.00 50.60      A  C
ATOM   1958  CD  GLU A 290     -26.750    3.698  -18.009  1.00 53.11      A  C
ATOM   1959  OE1 GLU A 290     -27.636    3.275  -17.230  1.00 55.42      A  O
```

FIGURE 1-28 (COORDINATES)

```
ATOM   1960  OE2 GLU A 290     -25.753   4.331 -17.584  1.00 51.92      A  O
ATOM   1961  C   GLU A 290     -24.104   1.153 -21.047  1.00 48.73      A  C
ATOM   1962  O   GLU A 290     -24.466   0.756 -22.136  1.00 49.20      A  O
ATOM   1963  N   GLY A 291     -22.829   1.218 -20.690  1.00 48.12      A  N
ATOM   1964  CA  GLY A 291     -21.782   0.590 -21.492  1.00 46.61      A  C
ATOM   1965  C   GLY A 291     -21.351  -0.758 -20.913  1.00 45.75      A  C
ATOM   1966  O   GLY A 291     -20.201  -0.928 -20.515  1.00 45.22      A  O
ATOM   1967  N   ARG A 292     -22.253  -1.733 -20.845  1.00 44.88      A  N
ATOM   1968  CA  ARG A 292     -21.833  -3.025 -20.275  1.00 45.21      A  C
ATOM   1969  CB  ARG A 292     -22.878  -3.680 -19.340  1.00 45.47      A  C
ATOM   1970  CG  ARG A 292     -24.318  -3.821 -19.868  1.00 49.45      A  C
ATOM   1971  CD  ARG A 292     -24.954  -5.164 -19.435  1.00 54.48      A  C
ATOM   1972  NE  ARG A 292     -25.402  -5.190 -18.032  1.00 59.61      A  N
ATOM   1973  CZ  ARG A 292     -25.252  -6.232 -17.200  1.00 62.09      A  C
ATOM   1974  NH1 ARG A 292     -24.630  -7.344 -17.597  1.00 62.91      A  N
ATOM   1975  NH2 ARG A 292     -25.702  -6.152 -15.951  1.00 63.40      A  N
ATOM   1976  C   ARG A 292     -21.207  -3.994 -21.310  1.00 43.73      A  C
ATOM   1977  O   ARG A 292     -21.494  -3.928 -22.503  1.00 43.96      A  O
ATOM   1978  N   TYR A 293     -20.311  -4.847 -20.834  1.00 42.77      A  N
ATOM   1979  CA  TYR A 293     -19.555  -5.788 -21.686  1.00 41.34      A  C
ATOM   1980  CB  TYR A 293     -18.413  -6.418 -20.884  1.00 39.89      A  C
ATOM   1981  CG  TYR A 293     -17.508  -5.424 -20.215  1.00 35.54      A  C
ATOM   1982  CD1 TYR A 293     -17.159  -4.241 -20.856  1.00 32.70      A  C
ATOM   1983  CE1 TYR A 293     -16.310  -3.295 -20.240  1.00 32.65      A  C
ATOM   1984  CZ  TYR A 293     -15.809  -3.551 -18.977  1.00 33.08      A  C
ATOM   1985  OH  TYR A 293     -14.962  -2.636 -18.388  1.00 31.32      A  O
ATOM   1986  CE2 TYR A 293     -16.142  -4.746 -18.305  1.00 33.65      A  C
ATOM   1987  CD2 TYR A 293     -16.999  -5.670 -18.937  1.00 34.10      A  C
ATOM   1988  C   TYR A 293     -20.448  -6.881 -22.224  1.00 41.42      A  C
ATOM   1989  O   TYR A 293     -20.404  -7.202 -23.415  1.00 40.95      A  O
ATOM   1990  N   PHE A 294     -21.261  -7.412 -21.316  1.00 42.18      A  N
ATOM   1991  CA  PHE A 294     -22.134  -8.553 -21.551  1.00 44.12      A  C
ATOM   1992  CB  PHE A 294     -21.927  -9.586 -20.445  1.00 43.09      A  C
ATOM   1993  CG  PHE A 294     -20.520 -10.128 -20.398  1.00 42.77      A  C
ATOM   1994  CD1 PHE A 294     -20.061 -10.998 -21.381  1.00 41.03      A  C
ATOM   1995  CE1 PHE A 294     -18.766 -11.494 -21.346  1.00 42.21      A  C
ATOM   1996  CZ  PHE A 294     -17.886 -11.118 -20.324  1.00 42.81      A  C
ATOM   1997  CE2 PHE A 294     -18.316 -10.240 -19.351  1.00 42.66      A  C
ATOM   1998  CD2 PHE A 294     -19.641  -9.744 -19.390  1.00 43.40      A  C
ATOM   1999  C   PHE A 294     -23.610  -8.169 -21.734  1.00 45.81      A  C
ATOM   2000  O   PHE A 294     -24.401  -8.112 -20.799  1.00 46.13      A  O
ATOM   2001  N   GLN A 295     -23.947  -7.951 -22.991  1.00 48.41      A  N
ATOM   2002  CA  GLN A 295     -25.211  -7.399 -23.417  1.00 50.88      A  C
ATOM   2003  CB  GLN A 295     -24.936  -6.492 -24.614  1.00 51.70      A  C
ATOM   2004  CG  GLN A 295     -23.986  -7.129 -25.671  1.00 54.79      A  C
ATOM   2005  CD  GLN A 295     -23.796  -6.250 -26.903  1.00 59.07      A  C
ATOM   2006  OE1 GLN A 295     -23.641  -6.748 -28.031  1.00 60.52      A  O
ATOM   2007  NE2 GLN A 295     -23.822  -4.931 -26.694  1.00 60.96      A  N
ATOM   2008  C   GLN A 295     -26.201  -8.472 -23.841  1.00 51.61      A  C
ATOM   2009  O   GLN A 295     -25.826  -9.518 -24.371  1.00 51.82      A  O
ATOM   2010  N   ASN A 296     -27.474  -8.186 -23.619  1.00 52.95      A  N
ATOM   2011  CA  ASN A 296     -28.555  -8.981 -24.183  1.00 54.41      A  C
ATOM   2012  CB  ASN A 296     -29.900  -8.511 -23.632  1.00 54.49      A  C
ATOM   2013  CG  ASN A 296     -30.262  -9.184 -22.338  1.00 56.18      A  C
ATOM   2014  OD1 ASN A 296     -31.192  -8.758 -21.645  1.00 58.08      A  O
ATOM   2015  ND2 ASN A 296     -29.541 -10.256 -22.000  1.00 58.60      A  N
ATOM   2016  C   ASN A 296     -28.606  -8.931 -25.708  1.00 54.81      A  C
ATOM   2017  O   ASN A 296     -29.662  -8.647 -26.283  1.00 55.22      A  O
ATOM   2018  N   TYR A 297     -27.473  -9.183 -26.357  1.00 54.97      A  N
ATOM   2019  CA  TYR A 297     -27.445  -9.271 -27.804  1.00 55.30      A  C
ATOM   2020  CB  TYR A 297     -26.464  -8.261 -28.416  1.00 55.76      A  C
ATOM   2021  CG  TYR A 297     -26.535  -8.217 -29.937  1.00 58.66      A  C
ATOM   2022  CD1 TYR A 297     -27.777  -8.279 -30.602  1.00 62.04      A  C
ATOM   2023  CE1 TYR A 297     -27.871  -8.242 -32.020  1.00 63.84      A  C
ATOM   2024  CZ  TYR A 297     -26.707  -8.135 -32.781  1.00 64.70      A  C
ATOM   2025  OH  TYR A 297     -26.803  -8.102 -34.165  1.00 64.60      A  O
ATOM   2026  CE2 TYR A 297     -25.452  -8.071 -32.137  1.00 63.60      A  C
ATOM   2027  CD2 TYR A 297     -25.377  -8.101 -30.717  1.00 60.97      A  C
ATOM   2028  C   TYR A 297     -27.101 -10.685 -28.253  1.00 54.97      A  C
ATOM   2029  O   TYR A 297     -26.226 -11.332 -27.700  1.00 54.53      A  O
```

FIGURE 1-29 (COORDINATES)

```
ATOM   2030  N    SER A 298     -27.813 -11.162 -29.258  1.00 54.78      A  N
ATOM   2031  CA   SER A 298     -27.464 -12.404 -29.910  1.00 54.59      A  C
ATOM   2032  CB   SER A 298     -28.691 -13.301 -30.037  1.00 54.82      A  C
ATOM   2033  OG   SER A 298     -29.793 -12.562 -30.529  1.00 56.61      A  O
ATOM   2034  C    SER A 298     -26.846 -12.078 -31.272  1.00 53.99      A  C
ATOM   2035  O    SER A 298     -27.126 -11.032 -31.860  1.00 54.23      A  O
ATOM   2036  N    TYR A 299     -26.001 -12.971 -31.770  1.00 52.56      A  N
ATOM   2037  CA   TYR A 299     -25.202 -12.660 -32.929  1.00 51.34      A  C
ATOM   2038  CB   TYR A 299     -23.710 -12.929 -32.644  1.00 51.26      A  C
ATOM   2039  CG   TYR A 299     -22.834 -12.649 -33.841  1.00 51.06      A  C
ATOM   2040  CD1  TYR A 299     -22.532 -11.341 -34.212  1.00 51.91      A  C
ATOM   2041  CE1  TYR A 299     -21.749 -11.071 -35.328  1.00 51.75      A  C
ATOM   2042  CZ   TYR A 299     -21.263 -12.119 -36.084  1.00 51.47      A  C
ATOM   2043  OH   TYR A 299     -20.483 -11.852 -37.176  1.00 51.18      A  O
ATOM   2044  CE2  TYR A 299     -21.536 -13.429 -35.734  1.00 51.69      A  C
ATOM   2045  CD2  TYR A 299     -22.325 -13.689 -34.618  1.00 51.61      A  C
ATOM   2046  C    TYR A 299     -25.680 -13.384 -34.187  1.00 50.73      A  C
ATOM   2047  O    TYR A 299     -25.959 -14.577 -34.155  1.00 50.73      A  O
ATOM   2048  N    GLY A 300     -25.746 -12.660 -35.299  1.00 49.86      A  N
ATOM   2049  CA   GLY A 300     -26.196 -13.223 -36.565  1.00 49.07      A  C
ATOM   2050  C    GLY A 300     -25.344 -14.347 -37.122  1.00 48.64      A  C
ATOM   2051  O    GLY A 300     -25.679 -14.892 -38.188  1.00 49.18      A  O
ATOM   2052  N    GLY A 301     -24.249 -14.686 -36.418  1.00 47.80      A  N
ATOM   2053  CA   GLY A 301     -23.320 -15.831 -36.739  1.00 45.42      A  C
ATOM   2054  C    GLY A 301     -22.513 -15.518 -37.987  1.00 43.78      A  C
ATOM   2055  O    GLY A 301     -22.810 -14.498 -38.649  1.00 44.56      A  O
ATOM   2056  N    VAL A 302     -21.483 -16.305 -38.329  1.00 40.97      A  N
ATOM   2057  CA   VAL A 302     -20.833 -17.328 -37.501  1.00 38.17      A  C
ATOM   2058  CB   VAL A 302     -21.021 -18.780 -38.095  1.00 38.42      A  C
ATOM   2059  CG1  VAL A 302     -22.060 -18.794 -39.220  1.00 38.43      A  C
ATOM   2060  CG2  VAL A 302     -19.729 -19.392 -38.601  1.00 36.69      A  C
ATOM   2061  C    VAL A 302     -19.343 -16.944 -37.471  1.00 35.69      A  C
ATOM   2062  O    VAL A 302     -18.799 -16.549 -38.491  1.00 35.11      A  O
ATOM   2063  N    ILE A 303     -18.684 -17.060 -36.327  1.00 33.06      A  N
ATOM   2064  CA   ILE A 303     -17.251 -16.699 -36.238  1.00 31.34      A  C
ATOM   2065  CB   ILE A 303     -16.959 -15.875 -34.940  1.00 31.69      A  C
ATOM   2066  CG1  ILE A 303     -17.718 -14.564 -34.954  1.00 29.92      A  C
ATOM   2067  CD1  ILE A 303     -17.651 -13.869 -33.650  1.00 36.68      A  C
ATOM   2068  CG2  ILE A 303     -15.425 -15.575 -34.801  1.00 30.04      A  C
ATOM   2069  C    ILE A 303     -16.316 -17.918 -36.198  1.00 29.97      A  C
ATOM   2070  O    ILE A 303     -16.462 -18.756 -35.317  1.00 29.33      A  O
ATOM   2071  N    GLN A 304     -15.341 -17.989 -37.109  1.00 28.96      A  N
ATOM   2072  CA   GLN A 304     -14.250 -18.998 -37.044  1.00 27.80      A  C
ATOM   2073  CB   GLN A 304     -13.474 -19.056 -38.378  1.00 28.05      A  C
ATOM   2074  CG   GLN A 304     -14.276 -19.535 -39.603  1.00 29.76      A  C
ATOM   2075  CD   GLN A 304     -14.957 -20.882 -39.367  1.00 34.80      A  C
ATOM   2076  OE1  GLN A 304     -14.333 -21.852 -38.895  1.00 34.46      A  O
ATOM   2077  NE2  GLN A 304     -16.257 -20.949 -39.691  1.00 37.66      A  N
ATOM   2078  C    GLN A 304     -13.240 -18.712 -35.913  1.00 27.55      A  C
ATOM   2079  O    GLN A 304     -12.700 -17.610 -35.805  1.00 27.78      A  O
ATOM   2080  N    ASP A 305     -12.951 -19.723 -35.100  1.00 26.36      A  N
ATOM   2081  CA   ASP A 305     -11.974 -19.614 -34.026  1.00 24.94      A  C
ATOM   2082  CB   ASP A 305     -12.519 -18.707 -32.904  1.00 25.55      A  C
ATOM   2083  CG   ASP A 305     -11.402 -18.060 -32.042  1.00 24.13      A  C
ATOM   2084  OD1  ASP A 305     -10.205 -18.430 -32.136  1.00 26.01      A  O
ATOM   2085  OD2  ASP A 305     -11.744 -17.167 -31.254  1.00 21.83      A  O
ATOM   2086  C    ASP A 305     -11.682 -21.032 -33.512  1.00 23.57      A  C
ATOM   2087  O    ASP A 305     -12.248 -22.001 -34.000  1.00 21.96      A  O
ATOM   2088  N    ASP A 306     -10.813 -21.136 -32.500  1.00 22.77      A  N
ATOM   2089  CA   ASP A 306     -10.428 -22.410 -31.885  1.00 21.16      A  C
ATOM   2090  CB   ASP A 306      -9.356 -22.197 -30.808  1.00 21.49      A  C
ATOM   2091  CG   ASP A 306      -8.000 -21.771 -31.413  1.00 19.35      A  C
ATOM   2092  OD1  ASP A 306      -7.626 -22.260 -32.501  1.00 23.81      A  O
ATOM   2093  OD2  ASP A 306      -7.341 -20.886 -30.830  1.00 26.96      A  O
ATOM   2094  C    ASP A 306     -11.544 -23.296 -31.369  1.00 20.42      A  C
ATOM   2095  O    ASP A 306     -11.348 -24.488 -31.191  1.00 19.47      A  O
ATOM   2096  N    HIS A 307     -12.732 -22.734 -31.187  1.00 20.41      A  N
ATOM   2097  CA   HIS A 307     -13.892 -23.508 -30.658  1.00 21.17      A  C
ATOM   2098  CB   HIS A 307     -14.935 -22.556 -30.075  1.00 21.95      A  C
ATOM   2099  CG   HIS A 307     -15.653 -21.736 -31.118  1.00 22.13      A  C
```

FIGURE 1-30 (COORDINATES)

```
ATOM   2100  ND1 HIS A 307     -15.037 -20.736 -31.849  1.00 18.66      A    N
ATOM   2101  CE1 HIS A 307     -15.911 -20.201 -32.679  1.00 20.94      A    C
ATOM   2102  NE2 HIS A 307     -17.067 -20.823 -32.527  1.00 20.36      A    N
ATOM   2103  CD2 HIS A 307     -16.940 -21.766 -31.536  1.00 21.91      A    C
ATOM   2104  C   HIS A 307     -14.539 -24.308 -31.751  1.00 19.11      A    C
ATOM   2105  O   HIS A 307     -15.160 -25.300 -31.492  1.00 21.27      A    O
ATOM   2106  N   ILE A 308     -14.367 -23.887 -32.988  1.00 19.30      A    N
ATOM   2107  CA  ILE A 308     -14.952 -24.560 -34.119  1.00 17.14      A    C
ATOM   2108  CB  ILE A 308     -14.457 -23.948 -35.463  1.00 17.49      A    C
ATOM   2109  CG1 ILE A 308     -15.101 -22.588 -35.671  1.00 19.61      A    C
ATOM   2110  CD1 ILE A 308     -16.744 -22.626 -35.734  1.00 17.42      A    C
ATOM   2111  CG2 ILE A 308     -14.825 -24.885 -36.669  1.00 18.64      A    C
ATOM   2112  C   ILE A 308     -14.824 -26.086 -34.071  1.00 17.84      A    C
ATOM   2113  O   ILE A 308     -15.853 -26.773 -34.142  1.00 18.50      A    O
ATOM   2114  N   PRO A 309     -13.569 -26.659 -33.994  1.00 17.34      A    N
ATOM   2115  CA  PRO A 309     -13.500 -28.158 -34.012  1.00 16.74      A    C
ATOM   2116  CB  PRO A 309     -11.980 -28.468 -34.079  1.00 17.06      A    C
ATOM   2117  CG  PRO A 309     -11.257 -27.142 -33.971  1.00 15.67      A    C
ATOM   2118  CD  PRO A 309     -12.245 -26.013 -34.087  1.00 15.06      A    C
ATOM   2119  C   PRO A 309     -14.073 -28.849 -32.748  1.00 16.84      A    C
ATOM   2120  O   PRO A 309     -14.410 -30.063 -32.790  1.00 17.45      A    O
ATOM   2121  N   PHE A 310     -14.125 -28.131 -31.629  1.00 18.25      A    N
ATOM   2122  CA  PHE A 310     -14.849 -28.601 -30.402  1.00 18.43      A    C
ATOM   2123  CB  PHE A 310     -14.331 -27.828 -29.207  1.00 18.40      A    C
ATOM   2124  CG  PHE A 310     -12.911 -28.129 -28.904  1.00 21.49      A    C
ATOM   2125  CD1 PHE A 310     -11.901 -27.306 -29.386  1.00 20.22      A    C
ATOM   2126  CE1 PHE A 310     -10.567 -27.610 -29.169  1.00 17.26      A    C
ATOM   2127  CZ  PHE A 310     -10.246 -28.724 -28.488  1.00 19.21      A    C
ATOM   2128  CE2 PHE A 310     -11.277 -29.584 -27.990  1.00 19.58      A    C
ATOM   2129  CD2 PHE A 310     -12.576 -29.288 -28.212  1.00 19.82      A    C
ATOM   2130  C   PHE A 310     -16.403 -28.489 -30.478  1.00 18.55      A    C
ATOM   2131  O   PHE A 310     -17.113 -29.474 -30.318  1.00 17.38      A    O
ATOM   2132  N   LEU A 311     -16.903 -27.281 -30.751  1.00 20.07      A    N
ATOM   2133  CA  LEU A 311     -18.355 -27.063 -30.984  1.00 21.69      A    C
ATOM   2134  CB  LEU A 311     -18.638 -25.639 -31.478  1.00 22.10      A    C
ATOM   2135  CG  LEU A 311     -20.087 -25.149 -31.633  1.00 21.76      A    C
ATOM   2136  CD1 LEU A 311     -20.493 -24.540 -30.320  1.00 14.28      A    C
ATOM   2137  CD2 LEU A 311     -20.245 -24.102 -32.760  1.00 17.57      A    C
ATOM   2138  C   LEU A 311     -18.963 -28.080 -31.976  1.00 22.25      A    C
ATOM   2139  O   LEU A 311     -19.933 -28.748 -31.638  1.00 21.41      A    O
ATOM   2140  N   ARG A 312     -18.382 -28.203 -33.180  1.00 22.29      A    N
ATOM   2141  CA  ARG A 312     -18.930 -29.085 -34.203  1.00 21.55      A    C
ATOM   2142  CB  ARG A 312     -18.269 -28.822 -35.573  1.00 20.09      A    C
ATOM   2143  CG  ARG A 312     -16.877 -29.426 -35.678  1.00 19.53      A    C
ATOM   2144  CD  ARG A 312     -16.270 -29.097 -37.111  1.00 16.59      A    C
ATOM   2145  NE  ARG A 312     -14.948 -29.698 -37.284  1.00 11.54      A    N
ATOM   2146  CZ  ARG A 312     -14.757 -30.974 -37.583  1.00 13.62      A    C
ATOM   2147  NH1 ARG A 312     -13.542 -31.436 -37.723  1.00 16.14      A    N
ATOM   2148  NH2 ARG A 312     -15.800 -31.785 -37.746  1.00 18.16      A    N
ATOM   2149  C   ARG A 312     -18.808 -30.594 -33.825  1.00 22.11      A    C
ATOM   2150  O   ARG A 312     -19.322 -31.430 -34.509  1.00 22.75      A    O
ATOM   2151  N   ARG A 313     -18.153 -30.931 -32.714  1.00 23.59      A    N
ATOM   2152  CA  ARG A 313     -18.215 -32.312 -32.166  1.00 23.32      A    C
ATOM   2153  CB  ARG A 313     -16.800 -32.871 -31.851  1.00 22.43      A    C
ATOM   2154  CG  ARG A 313     -15.938 -33.269 -33.052  1.00 19.78      A    C
ATOM   2155  CD  ARG A 313     -14.507 -33.786 -32.577  1.00 12.69      A    C
ATOM   2156  NE  ARG A 313     -13.620 -34.158 -33.668  1.00 19.23      A    N
ATOM   2157  CZ  ARG A 313     -12.896 -33.354 -34.430  1.00 21.38      A    C
ATOM   2158  NH1 ARG A 313     -12.987 -32.029 -34.314  1.00 22.91      A    N
ATOM   2159  NH2 ARG A 313     -12.126 -33.887 -35.378  1.00 20.95      A    N
ATOM   2160  C   ARG A 313     -19.124 -32.353 -30.899  1.00 24.14      A    C
ATOM   2161  O   ARG A 313     -19.077 -33.319 -30.118  1.00 23.95      A    O
ATOM   2162  N   GLY A 314     -19.908 -31.294 -30.675  1.00 23.38      A    N
ATOM   2163  CA  GLY A 314     -20.878 -31.298 -29.611  1.00 23.28      A    C
ATOM   2164  C   GLY A 314     -20.462 -30.745 -28.256  1.00 24.57      A    C
ATOM   2165  O   GLY A 314     -21.283 -30.721 -27.348  1.00 24.40      A    O
ATOM   2166  N   VAL A 315     -19.234 -30.228 -28.111  1.00 24.76      A    N
ATOM   2167  CA  VAL A 315     -18.841 -29.552 -26.857  1.00 24.77      A    C
ATOM   2168  CB  VAL A 315     -17.329 -29.262 -26.868  1.00 24.84      A    C
ATOM   2169  CG1 VAL A 315     -16.886 -28.570 -25.591  1.00 23.72      A    C
```

FIGURE 1-31 (COORDINATES)

```
ATOM  2170  CG2 VAL A 315     -16.547 -30.541 -27.069  1.00 26.29      A  C
ATOM  2171  C   VAL A 315     -19.605 -28.211 -26.692  1.00 24.75      A  C
ATOM  2172  O   VAL A 315     -19.604 -27.417 -27.632  1.00 26.20      A  O
ATOM  2173  N   PRO A 316     -20.229 -27.936 -25.516  1.00 25.36      A  N
ATOM  2174  CA  PRO A 316     -20.800 -26.572 -25.374  1.00 25.38      A  C
ATOM  2175  CB  PRO A 316     -21.520 -26.589 -23.982  1.00 24.57      A  C
ATOM  2176  CG  PRO A 316     -21.390 -27.932 -23.460  1.00 26.03      A  C
ATOM  2177  CD  PRO A 316     -20.324 -28.692 -24.247  1.00 25.04      A  C
ATOM  2178  C   PRO A 316     -19.693 -25.503 -25.368  1.00 25.01      A  C
ATOM  2179  O   PRO A 316     -18.604 -25.748 -24.817  1.00 26.03      A  O
ATOM  2180  N   VAL A 317     -19.994 -24.335 -25.924  1.00 24.26      A  N
ATOM  2181  CA  VAL A 317     -19.052 -23.217 -26.004  1.00 24.10      A  C
ATOM  2182  CB  VAL A 317     -18.480 -23.028 -27.463  1.00 23.71      A  C
ATOM  2183  CG1 VAL A 317     -17.495 -21.822 -27.484  1.00 24.96      A  C
ATOM  2184  CG2 VAL A 317     -17.774 -24.302 -27.944  1.00 21.08      A  C
ATOM  2185  C   VAL A 317     -19.624 -21.884 -25.539  1.00 24.89      A  C
ATOM  2186  O   VAL A 317     -20.720 -21.457 -25.981  1.00 25.02      A  O
ATOM  2187  N   LEU A 318     -18.833 -21.213 -24.683  1.00 25.20      A  N
ATOM  2188  CA  LEU A 318     -19.074 -19.851 -24.181  1.00 24.57      A  C
ATOM  2189  CB  LEU A 318     -19.033 -19.815 -22.637  1.00 24.46      A  C
ATOM  2190  CG  LEU A 318     -19.265 -18.496 -21.866  1.00 25.00      A  C
ATOM  2191  CD1 LEU A 318     -20.624 -17.876 -22.187  1.00 24.20      A  C
ATOM  2192  CD2 LEU A 318     -19.182 -18.758 -20.372  1.00 27.12      A  C
ATOM  2193  C   LEU A 318     -17.948 -19.009 -24.795  1.00 24.60      A  C
ATOM  2194  O   LEU A 318     -16.798 -19.099 -24.397  1.00 25.40      A  O
ATOM  2195  N   HIS A 319     -18.266 -18.207 -25.786  1.00 23.96      A  N
ATOM  2196  CA  HIS A 319     -17.210 -17.637 -26.598  1.00 24.26      A  C
ATOM  2197  CB  HIS A 319     -17.565 -17.831 -28.071  1.00 23.33      A  C
ATOM  2198  CG  HIS A 319     -16.425 -17.603 -29.000  1.00 23.97      A  C
ATOM  2199  ND1 HIS A 319     -16.579 -17.626 -30.373  1.00 19.50      A  N
ATOM  2200  CE1 HIS A 319     -15.408 -17.388 -30.943  1.00 22.39      A  C
ATOM  2201  NE2 HIS A 319     -14.506 -17.207 -29.990  1.00 20.23      A  N
ATOM  2202  CD2 HIS A 319     -15.113 -17.333 -28.764  1.00 23.14      A  C
ATOM  2203  C   HIS A 319     -17.026 -16.164 -26.261  1.00 24.03      A  C
ATOM  2204  O   HIS A 319     -17.797 -15.343 -26.721  1.00 24.52      A  O
ATOM  2205  N   LEU A 320     -16.013 -15.854 -25.445  1.00 23.26      A  N
ATOM  2206  CA  LEU A 320     -15.658 -14.494 -25.071  1.00 22.00      A  C
ATOM  2207  CB  LEU A 320     -15.004 -14.487 -23.666  1.00 21.58      A  C
ATOM  2208  CG  LEU A 320     -15.735 -15.316 -22.562  1.00 22.76      A  C
ATOM  2209  CD1 LEU A 320     -15.232 -15.029 -21.108  1.00 22.18      A  C
ATOM  2210  CD2 LEU A 320     -17.226 -15.187 -22.573  1.00 22.99      A  C
ATOM  2211  C   LEU A 320     -14.776 -13.825 -26.149  1.00 21.66      A  C
ATOM  2212  O   LEU A 320     -13.593 -13.522 -25.933  1.00 20.48      A  O
ATOM  2213  N   ILE A 321     -15.357 -13.645 -27.342  1.00 22.04      A  N
ATOM  2214  CA  ILE A 321     -14.822 -12.747 -28.362  1.00 21.12      A  C
ATOM  2215  CB  ILE A 321     -14.583 -13.533 -29.690  1.00 22.07      A  C
ATOM  2216  CG1 ILE A 321     -13.769 -12.733 -30.702  1.00 16.85      A  C
ATOM  2217  CD1 ILE A 321     -13.356 -13.587 -31.861  1.00 18.37      A  C
ATOM  2218  CG2 ILE A 321     -15.901 -14.001 -30.307  1.00 18.12      A  C
ATOM  2219  C   ILE A 321     -15.865 -11.585 -28.573  1.00 23.16      A  C
ATOM  2220  O   ILE A 321     -17.091 -11.856 -28.728  1.00 23.59      A  O
ATOM  2221  N   PRO A 322     -15.413 -10.299 -28.564  1.00 22.80      A  N
ATOM  2222  CA  PRO A 322     -16.341  -9.188 -28.765  1.00 22.80      A  C
ATOM  2223  CB  PRO A 322     -15.497  -7.940 -28.456  1.00 22.99      A  C
ATOM  2224  CG  PRO A 322     -14.081  -8.426 -28.204  1.00 23.57      A  C
ATOM  2225  CD  PRO A 322     -14.012  -9.863 -28.600  1.00 22.62      A  C
ATOM  2226  C   PRO A 322     -16.745  -9.078 -30.218  1.00 24.41      A  C
ATOM  2227  O   PRO A 322     -16.039  -9.588 -31.112  1.00 23.58      A  O
ATOM  2228  N   SER A 323     -17.881  -8.415 -30.428  1.00 25.49      A  N
ATOM  2229  CA  SER A 323     -18.311  -7.992 -31.730  1.00 27.70      A  C
ATOM  2230  CB  SER A 323     -19.413  -8.881 -32.304  1.00 28.13      A  C
ATOM  2231  OG  SER A 323     -19.546  -8.622 -33.700  1.00 29.91      A  O
ATOM  2232  C   SER A 323     -18.826  -6.593 -31.464  1.00 28.58      A  C
ATOM  2233  O   SER A 323     -19.659  -6.412 -30.548  1.00 30.12      A  O
ATOM  2234  N   PRO A 324     -18.286  -5.589 -32.200  1.00 27.88      A  N
ATOM  2235  CA  PRO A 324     -17.296  -5.795 -33.277  1.00 26.96      A  C
ATOM  2236  CB  PRO A 324     -17.343  -4.475 -34.050  1.00 27.44      A  C
ATOM  2237  CG  PRO A 324     -17.571  -3.463 -32.962  1.00 27.98      A  C
ATOM  2238  CD  PRO A 324     -18.471  -4.155 -31.903  1.00 28.18      A  C
ATOM  2239  C   PRO A 324     -15.883  -6.087 -32.727  1.00 25.56      A  C
```

FIGURE 1-32 (COORDINATES)

```
ATOM   2240  O   PRO A 324     -15.649  -5.946 -31.508  1.00 24.25      A  O
ATOM   2241  N   PHE A 325     -14.988  -6.541 -33.602  1.00 24.05      A  N
ATOM   2242  CA  PHE A 325     -13.600  -6.832 -33.223  1.00 25.58      A  C
ATOM   2243  CB  PHE A 325     -12.796  -7.463 -34.386  1.00 25.02      A  C
ATOM   2244  CG  PHE A 325     -13.047  -8.945 -34.612  1.00 25.55      A  C
ATOM   2245  CD1 PHE A 325     -14.119  -9.607 -34.026  1.00 26.74      A  C
ATOM   2246  CE1 PHE A 325     -14.350 -10.967 -34.290  1.00 25.37      A  C
ATOM   2247  CZ  PHE A 325     -13.530 -11.656 -35.132  1.00 24.75      A  C
ATOM   2248  CE2 PHE A 325     -12.466 -11.007 -35.734  1.00 27.18      A  C
ATOM   2249  CD2 PHE A 325     -12.237  -9.653 -35.482  1.00 25.46      A  C
ATOM   2250  C   PHE A 325     -12.936  -5.488 -32.868  1.00 25.31      A  C
ATOM   2251  O   PHE A 325     -13.313  -4.474 -33.423  1.00 25.73      A  O
ATOM   2252  N   PRO A 326     -11.930  -5.492 -31.979  1.00 24.38      A  N
ATOM   2253  CA  PRO A 326     -11.169  -4.262 -31.657  1.00 23.07      A  C
ATOM   2254  CB  PRO A 326      -9.991  -4.783 -30.868  1.00 23.16      A  C
ATOM   2255  CG  PRO A 326     -10.536  -6.106 -30.221  1.00 23.62      A  C
ATOM   2256  CD  PRO A 326     -11.470  -6.671 -31.230  1.00 24.13      A  C
ATOM   2257  C   PRO A 326     -10.696  -3.531 -32.947  1.00 22.89      A  C
ATOM   2258  O   PRO A 326     -10.437  -4.165 -33.948  1.00 21.34      A  O
ATOM   2259  N   GLU A 327     -10.647  -2.185 -32.875  1.00 22.22      A  N
ATOM   2260  CA  GLU A 327     -10.128  -1.304 -33.882  1.00 19.62      A  C
ATOM   2261  CB  GLU A 327     -10.047   0.129 -33.274  1.00 19.75      A  C
ATOM   2262  CG  GLU A 327      -9.410   1.159 -34.182  1.00 14.97      A  C
ATOM   2263  CD  GLU A 327     -10.100   1.217 -35.573  1.00 19.17      A  C
ATOM   2264  OE1 GLU A 327     -11.347   1.054 -35.584  1.00 22.08      A  O
ATOM   2265  OE2 GLU A 327      -9.426   1.419 -36.638  1.00 16.30      A  O
ATOM   2266  C   GLU A 327      -8.750  -1.788 -34.379  1.00 19.78      A  C
ATOM   2267  O   GLU A 327      -8.419  -1.760 -35.599  1.00 18.80      A  O
ATOM   2268  N   VAL A 328      -7.935  -2.226 -33.446  1.00 18.68      A  N
ATOM   2269  CA  VAL A 328      -6.571  -2.640 -33.849  1.00 18.98      A  C
ATOM   2270  CB  VAL A 328      -5.618  -2.650 -32.625  1.00 19.95      A  C
ATOM   2271  CG1 VAL A 328      -5.429  -1.256 -32.082  1.00 17.97      A  C
ATOM   2272  CG2 VAL A 328      -6.121  -3.659 -31.548  1.00 16.36      A  C
ATOM   2273  C   VAL A 328      -6.419  -4.045 -34.429  1.00 19.21      A  C
ATOM   2274  O   VAL A 328      -5.293  -4.469 -34.668  1.00 19.63      A  O
ATOM   2275  N   TRP A 329      -7.512  -4.794 -34.616  1.00 18.91      A  N
ATOM   2276  CA  TRP A 329      -7.416  -6.224 -34.947  1.00 17.80      A  C
ATOM   2277  CB  TRP A 329      -8.838  -6.819 -35.015  1.00 16.68      A  C
ATOM   2278  CG  TRP A 329      -8.910  -8.254 -35.432  1.00 19.15      A  C
ATOM   2279  CD1 TRP A 329      -8.799  -9.373 -34.610  1.00 18.58      A  C
ATOM   2280  NE1 TRP A 329      -8.981 -10.520 -35.357  1.00 20.26      A  N
ATOM   2281  CE2 TRP A 329      -9.146 -10.191 -36.689  1.00 18.22      A  C
ATOM   2282  CD2 TRP A 329      -9.121  -8.765 -36.781  1.00 18.65      A  C
ATOM   2283  CE3 TRP A 329      -9.297  -8.159 -38.040  1.00 22.18      A  C
ATOM   2284  CZ3 TRP A 329      -9.515  -8.973 -39.176  1.00 19.00      A  C
ATOM   2285  CH2 TRP A 329      -9.525 -10.419 -39.057  1.00 20.44      A  C
ATOM   2286  CZ2 TRP A 329      -9.349 -11.031 -37.826  1.00 18.94      A  C
ATOM   2287  C   TRP A 329      -6.656  -6.466 -36.249  1.00 17.98      A  C
ATOM   2288  O   TRP A 329      -6.998  -5.839 -37.282  1.00 19.07      A  O
ATOM   2289  N   HIS A 330      -5.643  -7.371 -36.199  1.00 17.66      A  N
ATOM   2290  CA  HIS A 330      -4.758  -7.713 -37.357  1.00 16.47      A  C
ATOM   2291  CB  HIS A 330      -5.443  -8.623 -38.401  1.00 13.88      A  C
ATOM   2292  CG  HIS A 330      -5.663 -10.080 -37.990  1.00 14.24      A  C
ATOM   2293  ND1 HIS A 330      -6.033 -11.028 -38.930  1.00 11.59      A  N
ATOM   2294  CE1 HIS A 330      -6.194 -12.209 -38.329  1.00 18.52      A  C
ATOM   2295  NE2 HIS A 330      -5.898 -12.090 -37.036  1.00  2.00      A  N
ATOM   2296  CD2 HIS A 330      -5.591 -10.755 -36.789  1.00  5.87      A  C
ATOM   2297  C   HIS A 330      -4.057  -6.464 -37.978  1.00 15.96      A  C
ATOM   2298  O   HIS A 330      -3.858  -6.298 -39.229  1.00 16.54      A  O
ATOM   2299  N   THR A 331      -3.617  -5.611 -37.074  1.00 16.01      A  N
ATOM   2300  CA  THR A 331      -2.800  -4.431 -37.381  1.00 16.42      A  C
ATOM   2301  CB  THR A 331      -3.737  -3.148 -37.218  1.00 16.06      A  C
ATOM   2302  OG1 THR A 331      -3.367  -2.183 -38.173  1.00 25.36      A  O
ATOM   2303  CG2 THR A 331      -3.621  -2.525 -35.829  1.00 11.64      A  C
ATOM   2304  C   THR A 331      -1.633  -4.283 -36.408  1.00 18.09      A  C
ATOM   2305  O   THR A 331      -1.733  -4.663 -35.200  1.00 17.67      A  O
ATOM   2306  N   MET A 332      -0.591  -3.591 -36.864  1.00 19.52      A  N
ATOM   2307  CA  MET A 332       0.609  -3.454 -36.078  1.00 19.44      A  C
ATOM   2308  CB  MET A 332       1.663  -2.681 -36.824  1.00 19.44      A  C
ATOM   2309  CG  MET A 332       2.248  -3.533 -37.938  1.00 25.50      A  C
```

FIGURE 1-33 (COORDINATES)

```
ATOM   2310  SD  MET A 332       2.910  -5.115 -37.281  1.00 32.49           A    S
ATOM   2311  CE  MET A 332       3.260  -5.824 -38.895  1.00 29.79           A    C
ATOM   2312  C   MET A 332       0.357  -2.760 -34.780  1.00 19.59           A    C
ATOM   2313  O   MET A 332       1.186  -2.828 -33.922  1.00 18.61           A    O
ATOM   2314  N   ASP A 333      -0.797  -2.077 -34.691  1.00 20.40           A    N
ATOM   2315  CA  ASP A 333      -1.212  -1.324 -33.548  1.00 19.29           A    C
ATOM   2316  CB  ASP A 333      -2.139  -0.163 -33.902  1.00 20.00           A    C
ATOM   2317  CG  ASP A 333      -1.461   0.897 -34.721  1.00 19.67           A    C
ATOM   2318  OD1 ASP A 333      -0.539   1.512 -34.206  1.00 19.64           A    O
ATOM   2319  OD2 ASP A 333      -1.843   1.116 -35.898  1.00 23.45           A    O
ATOM   2320  C   ASP A 333      -1.832  -2.183 -32.470  1.00 21.36           A    C
ATOM   2321  O   ASP A 333      -2.183  -1.635 -31.396  1.00 20.07           A    O
ATOM   2322  N   ASP A 334      -1.951  -3.516 -32.708  1.00 21.25           A    N
ATOM   2323  CA  ASP A 334      -2.433  -4.351 -31.621  1.00 22.34           A    C
ATOM   2324  CB  ASP A 334      -2.974  -5.696 -32.124  1.00 21.93           A    C
ATOM   2325  CG  ASP A 334      -3.696  -6.474 -31.037  1.00 25.31           A    C
ATOM   2326  OD1 ASP A 334      -3.663  -6.003 -29.869  1.00 27.88           A    O
ATOM   2327  OD2 ASP A 334      -4.345  -7.524 -31.337  1.00 24.93           A    O
ATOM   2328  C   ASP A 334      -1.314  -4.565 -30.588  1.00 22.67           A    C
ATOM   2329  O   ASP A 334      -0.703  -5.672 -30.570  1.00 23.71           A    O
ATOM   2330  N   ASN A 335      -1.043  -3.538 -29.764  1.00 21.00           A    N
ATOM   2331  CA  ASN A 335       0.169  -3.492 -28.917  1.00 20.64           A    C
ATOM   2332  CB  ASN A 335       1.188  -2.492 -29.435  1.00 19.06           A    C
ATOM   2333  CG  ASN A 335       0.622  -1.040 -29.487  1.00 19.44           A    C
ATOM   2334  OD1 ASN A 335      -0.273  -0.679 -28.712  1.00 21.43           A    O
ATOM   2335  ND2 ASN A 335       1.106  -0.239 -30.435  1.00 21.40           A    N
ATOM   2336  C   ASN A 335      -0.180  -3.154 -27.460  1.00 21.29           A    C
ATOM   2337  O   ASN A 335      -1.343  -2.962 -27.112  1.00 21.28           A    O
ATOM   2338  N   GLU A 336       0.816  -3.071 -26.616  1.00 22.48           A    N
ATOM   2339  CA  GLU A 336       0.543  -2.808 -25.204  1.00 25.15           A    C
ATOM   2340  CB  GLU A 336       1.829  -2.835 -24.409  1.00 24.42           A    C
ATOM   2341  CG  GLU A 336       1.568  -2.830 -22.894  1.00 28.41           A    C
ATOM   2342  CD  GLU A 336       2.861  -2.829 -22.074  1.00 32.55           A    C
ATOM   2343  OE1 GLU A 336       3.951  -3.119 -22.632  1.00 33.84           A    O
ATOM   2344  OE2 GLU A 336       2.783  -2.533 -20.877  1.00 33.28           A    O
ATOM   2345  C   GLU A 336      -0.148  -1.425 -25.040  1.00 27.05           A    C
ATOM   2346  O   GLU A 336      -1.079  -1.315 -24.234  1.00 26.45           A    O
ATOM   2347  N   GLU A 337       0.291  -0.417 -25.836  1.00 28.89           A    N
ATOM   2348  CA  GLU A 337      -0.139   1.003 -25.756  1.00 31.09           A    C
ATOM   2349  CB  GLU A 337       0.482   1.825 -26.933  1.00 31.66           A    C
ATOM   2350  CG  GLU A 337       0.799   3.293 -26.585  1.00 38.45           A    C
ATOM   2351  CD  GLU A 337       1.004   4.256 -27.808  1.00 47.28           A    C
ATOM   2352  OE1 GLU A 337       0.479   5.401 -27.749  1.00 49.09           A    O
ATOM   2353  OE2 GLU A 337       1.689   3.900 -28.818  1.00 50.95           A    O
ATOM   2354  C   GLU A 337      -1.657   1.137 -25.799  1.00 30.72           A    C
ATOM   2355  O   GLU A 337      -2.238   1.959 -25.109  1.00 30.98           A    O
ATOM   2356  N   ASN A 338      -2.299   0.288 -26.610  1.00 30.31           A    N
ATOM   2357  CA  ASN A 338      -3.724   0.410 -26.951  1.00 28.79           A    C
ATOM   2358  CB  ASN A 338      -3.926   0.174 -28.434  1.00 28.46           A    C
ATOM   2359  CG  ASN A 338      -3.329   1.288 -29.253  1.00 30.52           A    C
ATOM   2360  OD1 ASN A 338      -2.539   1.065 -30.158  1.00 34.33           A    O
ATOM   2361  ND2 ASN A 338      -3.666   2.517 -28.891  1.00 31.59           A    N
ATOM   2362  C   ASN A 338      -4.642  -0.444 -26.101  1.00 28.46           A    C
ATOM   2363  O   ASN A 338      -5.851  -0.596 -26.351  1.00 27.63           A    O
ATOM   2364  N   LEU A 339      -4.065  -0.952 -25.034  1.00 28.10           A    N
ATOM   2365  CA  LEU A 339      -4.800  -1.846 -24.202  1.00 28.13           A    C
ATOM   2366  CB  LEU A 339      -3.890  -2.921 -23.594  1.00 27.88           A    C
ATOM   2367  CG  LEU A 339      -3.236  -4.039 -24.382  1.00 26.66           A    C
ATOM   2368  CD1 LEU A 339      -2.400  -4.801 -23.374  1.00 22.70           A    C
ATOM   2369  CD2 LEU A 339      -4.298  -4.948 -25.030  1.00 25.87           A    C
ATOM   2370  C   LEU A 339      -5.317  -0.981 -23.115  1.00 27.86           A    C
ATOM   2371  O   LEU A 339      -4.692   0.028 -22.769  1.00 27.56           A    O
ATOM   2372  N   ASP A 340      -6.405  -1.440 -22.521  1.00 27.81           A    N
ATOM   2373  CA  ASP A 340      -7.026  -0.717 -21.443  1.00 27.34           A    C
ATOM   2374  CB  ASP A 340      -8.453  -0.358 -21.841  1.00 26.78           A    C
ATOM   2375  CG  ASP A 340      -9.074   0.535 -20.849  1.00 27.22           A    C
ATOM   2376  OD1 ASP A 340      -9.924   0.024 -20.114  1.00 30.30           A    O
ATOM   2377  OD2 ASP A 340      -8.632   1.706 -20.727  1.00 25.65           A    O
ATOM   2378  C   ASP A 340      -6.984  -1.422 -20.087  1.00 27.34           A    C
ATOM   2379  O   ASP A 340      -7.609  -2.438 -19.877  1.00 26.82           A    O
```

FIGURE 1-34 (COORDINATES)

```
ATOM   2380  N   GLU A 341      -6.230  -0.850 -19.161  1.00 28.94           A  N
ATOM   2381  CA  GLU A 341      -5.997  -1.441 -17.882  1.00 29.64           A  C
ATOM   2382  CB  GLU A 341      -5.155  -0.485 -17.028  1.00 29.91           A  C
ATOM   2383  CG  GLU A 341      -5.197  -0.948 -15.597  1.00 35.43           A  C
ATOM   2384  CD  GLU A 341      -4.405  -0.107 -14.644  1.00 41.23           A  C
ATOM   2385  OE1 GLU A 341      -3.464   0.577 -15.098  1.00 44.06           A  O
ATOM   2386  OE2 GLU A 341      -4.713  -0.167 -13.426  1.00 44.05           A  O
ATOM   2387  C   GLU A 341      -7.283  -1.849 -17.123  1.00 29.35           A  C
ATOM   2388  O   GLU A 341      -7.450  -3.016 -16.706  1.00 29.46           A  O
ATOM   2389  N   SER A 342      -8.187  -0.887 -16.939  1.00 29.63           A  N
ATOM   2390  CA  SER A 342      -9.393  -1.091 -16.130  1.00 29.12           A  C
ATOM   2391  CB  SER A 342     -10.114   0.232 -15.892  1.00 28.87           A  C
ATOM   2392  OG  SER A 342      -9.177   1.125 -15.335  1.00 33.43           A  O
ATOM   2393  C   SER A 342     -10.356  -2.111 -16.724  1.00 28.16           A  C
ATOM   2394  O   SER A 342     -10.944  -2.867 -15.979  1.00 27.26           A  O
ATOM   2395  N   THR A 343     -10.532  -2.103 -18.050  1.00 27.60           A  N
ATOM   2396  CA  THR A 343     -11.378  -3.078 -18.737  1.00 27.44           A  C
ATOM   2397  CB  THR A 343     -11.276  -2.876 -20.283  1.00 27.29           A  C
ATOM   2398  OG1 THR A 343     -11.692  -1.547 -20.626  1.00 27.78           A  O
ATOM   2399  CG2 THR A 343     -12.144  -3.898 -21.019  1.00 26.57           A  C
ATOM   2400  C   THR A 343     -10.909  -4.523 -18.402  1.00 27.63           A  C
ATOM   2401  O   THR A 343     -11.702  -5.428 -18.081  1.00 26.48           A  O
ATOM   2402  N   ILE A 344      -9.597  -4.719 -18.502  1.00 27.28           A  N
ATOM   2403  CA  ILE A 344      -9.027  -6.002 -18.228  1.00 27.62           A  C
ATOM   2404  CB  ILE A 344      -7.594  -6.131 -18.724  1.00 27.52           A  C
ATOM   2405  CG1 ILE A 344      -7.517  -5.840 -20.224  1.00 27.09           A  C
ATOM   2406  CD1 ILE A 344      -6.034  -5.572 -20.682  1.00 24.03           A  C
ATOM   2407  CG2 ILE A 344      -7.097  -7.567 -18.432  1.00 27.82           A  C
ATOM   2408  C   ILE A 344      -9.056  -6.320 -16.742  1.00 27.31           A  C
ATOM   2409  O   ILE A 344      -9.344  -7.448 -16.373  1.00 27.21           A  O
ATOM   2410  N   ASP A 345      -8.730  -5.366 -15.892  1.00 27.18           A  N
ATOM   2411  CA  ASP A 345      -8.879  -5.641 -14.470  1.00 27.92           A  C
ATOM   2412  CB  ASP A 345      -8.483  -4.434 -13.638  1.00 27.03           A  C
ATOM   2413  CG  ASP A 345      -8.466  -4.723 -12.150  1.00 30.10           A  C
ATOM   2414  OD1 ASP A 345      -8.079  -5.835 -11.694  1.00 30.38           A  O
ATOM   2415  OD2 ASP A 345      -8.864  -3.796 -11.403  1.00 36.23           A  O
ATOM   2416  C   ASP A 345     -10.330  -6.067 -14.242  1.00 28.32           A  C
ATOM   2417  O   ASP A 345     -10.591  -7.057 -13.562  1.00 28.08           A  O
ATOM   2418  N   ASN A 346     -11.277  -5.357 -14.864  1.00 28.83           A  N
ATOM   2419  CA  ASN A 346     -12.690  -5.657 -14.666  1.00 29.47           A  C
ATOM   2420  CB  ASN A 346     -13.623  -4.669 -15.394  1.00 29.54           A  C
ATOM   2421  CG  ASN A 346     -13.693  -3.285 -14.742  1.00 31.88           A  C
ATOM   2422  OD1 ASN A 346     -13.221  -3.055 -13.613  1.00 32.00           A  O
ATOM   2423  ND2 ASN A 346     -14.310  -2.350 -15.464  1.00 32.46           A  N
ATOM   2424  C   ASN A 346     -13.025  -7.081 -15.132  1.00 29.51           A  C
ATOM   2425  O   ASN A 346     -13.564  -7.858 -14.358  1.00 30.20           A  O
ATOM   2426  N   LEU A 347     -12.733  -7.409 -16.396  1.00 28.31           A  N
ATOM   2427  CA  LEU A 347     -13.021  -8.751 -16.912  1.00 27.81           A  C
ATOM   2428  CB  LEU A 347     -12.669  -8.869 -18.427  1.00 26.23           A  C
ATOM   2429  CG  LEU A 347     -13.531  -7.998 -19.368  1.00 24.10           A  C
ATOM   2430  CD1 LEU A 347     -12.845  -7.700 -20.713  1.00 19.54           A  C
ATOM   2431  CD2 LEU A 347     -14.896  -8.641 -19.609  1.00 22.28           A  C
ATOM   2432  C   LEU A 347     -12.381  -9.870 -16.076  1.00 26.76           A  C
ATOM   2433  O   LEU A 347     -12.941 -10.925 -15.947  1.00 26.92           A  O
ATOM   2434  N   ASN A 348     -11.197  -9.634 -15.523  1.00 27.16           A  N
ATOM   2435  CA  ASN A 348     -10.524 -10.639 -14.672  1.00 27.16           A  C
ATOM   2436  CB  ASN A 348      -9.170 -10.122 -14.154  1.00 26.85           A  C
ATOM   2437  CG  ASN A 348      -8.014 -10.328 -15.157  1.00 28.08           A  C
ATOM   2438  OD1 ASN A 348      -8.139 -11.088 -16.131  1.00 25.25           A  O
ATOM   2439  ND2 ASN A 348      -6.864  -9.662 -14.894  1.00 27.18           A  N
ATOM   2440  C   ASN A 348     -11.389 -11.070 -13.482  1.00 26.96           A  C
ATOM   2441  O   ASN A 348     -11.454 -12.257 -13.153  1.00 26.19           A  O
ATOM   2442  N   LYS A 349     -12.059 -10.092 -12.866  1.00 28.04           A  N
ATOM   2443  CA  LYS A 349     -12.824 -10.309 -11.641  1.00 29.07           A  C
ATOM   2444  CB  LYS A 349     -13.114  -8.985 -10.934  1.00 28.43           A  C
ATOM   2445  CG  LYS A 349     -11.867  -8.189 -10.635  1.00 30.05           A  C
ATOM   2446  CD  LYS A 349     -12.212  -6.759 -10.196  1.00 31.87           A  C
ATOM   2447  CE  LYS A 349     -11.200  -6.276  -9.158  1.00 28.89           A  C
ATOM   2448  NZ  LYS A 349     -11.203  -4.828  -9.077  1.00 31.58           A  N
ATOM   2449  C   LYS A 349     -14.129 -11.024 -11.999  1.00 29.34           A  C
```

FIGURE 1-35 (COORDINATES)

```
ATOM   2450  O    LYS A 349     -14.559 -11.921 -11.284  1.00 30.05      A    O
ATOM   2451  N    ILE A 350     -14.749 -10.612 -13.112  1.00 29.65      A    N
ATOM   2452  CA   ILE A 350     -15.957 -11.278 -13.637  1.00 28.36      A    C
ATOM   2453  CB   ILE A 350     -16.480 -10.598 -14.902  1.00 27.50      A    C
ATOM   2454  CG1  ILE A 350     -16.896  -9.167 -14.564  1.00 27.78      A    C
ATOM   2455  CD1  ILE A 350     -17.450  -8.315 -15.765  1.00 29.72      A    C
ATOM   2456  CG2  ILE A 350     -17.646 -11.374 -15.490  1.00 28.68      A    C
ATOM   2457  C    ILE A 350     -15.617 -12.740 -13.878  1.00 27.96      A    C
ATOM   2458  O    ILE A 350     -16.247 -13.645 -13.296  1.00 29.96      A    O
ATOM   2459  N    LEU A 351     -14.561 -12.965 -14.653  1.00 27.06      A    N
ATOM   2460  CA   LEU A 351     -14.118 -14.303 -14.997  1.00 25.88      A    C
ATOM   2461  CB   LEU A 351     -12.972 -14.229 -16.026  1.00 25.71      A    C
ATOM   2462  CG   LEU A 351     -12.421 -15.637 -16.321  1.00 24.86      A    C
ATOM   2463  CD1  LEU A 351     -13.394 -16.359 -17.219  1.00 23.66      A    C
ATOM   2464  CD2  LEU A 351     -11.015 -15.599 -16.876  1.00 23.71      A    C
ATOM   2465  C    LEU A 351     -13.725 -15.155 -13.781  1.00 25.62      A    C
ATOM   2466  O    LEU A 351     -14.096 -16.318 -13.692  1.00 25.27      A    O
ATOM   2467  N    GLN A 352     -13.003 -14.574 -12.836  1.00 25.92      A    N
ATOM   2468  CA   GLN A 352     -12.619 -15.313 -11.630  1.00 27.44      A    C
ATOM   2469  CB   GLN A 352     -11.651 -14.489 -10.798  1.00 27.76      A    C
ATOM   2470  CG   GLN A 352     -10.243 -14.504 -11.414  1.00 29.73      A    C
ATOM   2471  CD   GLN A 352      -9.285 -13.444 -10.858  1.00 31.13      A    C
ATOM   2472  OE1  GLN A 352      -9.272 -13.136  -9.643  1.00 30.07      A    O
ATOM   2473  NE2  GLN A 352      -8.457 -12.889 -11.752  1.00 28.40      A    N
ATOM   2474  C    GLN A 352     -13.830 -15.780 -10.789  1.00 27.84      A    C
ATOM   2475  O    GLN A 352     -13.872 -16.932 -10.294  1.00 26.99      A    O
ATOM   2476  N    VAL A 353     -14.824 -14.891 -10.681  1.00 28.46      A    N
ATOM   2477  CA   VAL A 353     -16.066 -15.168  -9.950  1.00 28.16      A    C
ATOM   2478  CB   VAL A 353     -16.932 -13.863  -9.800  1.00 28.42      A    C
ATOM   2479  CG1  VAL A 353     -18.347 -14.180  -9.431  1.00 27.46      A    C
ATOM   2480  CG2  VAL A 353     -16.326 -12.926  -8.736  1.00 27.22      A    C
ATOM   2481  C    VAL A 353     -16.825 -16.281 -10.685  1.00 28.86      A    C
ATOM   2482  O    VAL A 353     -17.213 -17.282 -10.078  1.00 28.88      A    O
ATOM   2483  N    PHE A 354     -16.972 -16.130 -12.017  1.00 28.81      A    N
ATOM   2484  CA   PHE A 354     -17.617 -17.145 -12.857  1.00 27.75      A    C
ATOM   2485  CB   PHE A 354     -17.396 -16.803 -14.341  1.00 27.60      A    C
ATOM   2486  CG   PHE A 354     -18.099 -17.730 -15.267  1.00 27.45      A    C
ATOM   2487  CD1  PHE A 354     -19.382 -17.466 -15.688  1.00 24.94      A    C
ATOM   2488  CE1  PHE A 354     -20.017 -18.358 -16.546  1.00 28.99      A    C
ATOM   2489  CZ   PHE A 354     -19.370 -19.559 -16.958  1.00 24.07      A    C
ATOM   2490  CE2  PHE A 354     -18.132 -19.822 -16.529  1.00 23.86      A    C
ATOM   2491  CD2  PHE A 354     -17.477 -18.910 -15.692  1.00 26.44      A    C
ATOM   2492  C    PHE A 354     -17.055 -18.516 -12.573  1.00 27.86      A    C
ATOM   2493  O    PHE A 354     -17.786 -19.505 -12.447  1.00 29.13      A    O
ATOM   2494  N    VAL A 355     -15.743 -18.574 -12.467  1.00 27.48      A    N
ATOM   2495  CA   VAL A 355     -15.043 -19.840 -12.333  1.00 27.77      A    C
ATOM   2496  CB   VAL A 355     -13.574 -19.701 -12.776  1.00 28.45      A    C
ATOM   2497  CG1  VAL A 355     -12.665 -20.840 -12.227  1.00 27.16      A    C
ATOM   2498  CG2  VAL A 355     -13.525 -19.557 -14.314  1.00 23.46      A    C
ATOM   2499  C    VAL A 355     -15.204 -20.431 -10.951  1.00 29.13      A    C
ATOM   2500  O    VAL A 355     -15.572 -21.599 -10.835  1.00 30.29      A    O
ATOM   2501  N    LEU A 356     -14.991 -19.645  -9.896  1.00 29.64      A    N
ATOM   2502  CA   LEU A 356     -15.340 -20.147  -8.548  1.00 30.44      A    C
ATOM   2503  CB   LEU A 356     -15.077 -19.077  -7.507  1.00 30.31      A    C
ATOM   2504  CG   LEU A 356     -13.599 -18.712  -7.438  1.00 31.81      A    C
ATOM   2505  CD1  LEU A 356     -13.417 -17.516  -6.506  1.00 34.35      A    C
ATOM   2506  CD2  LEU A 356     -12.754 -19.912  -7.010  1.00 31.17      A    C
ATOM   2507  C    LEU A 356     -16.784 -20.667  -8.383  1.00 30.40      A    C
ATOM   2508  O    LEU A 356     -17.021 -21.695  -7.743  1.00 30.95      A    O
ATOM   2509  N    GLU A 357     -17.738 -19.960  -8.968  1.00 30.42      A    N
ATOM   2510  CA   GLU A 357     -19.138 -20.304  -8.815  1.00 31.55      A    C
ATOM   2511  CB   GLU A 357     -20.021 -19.133  -9.293  1.00 31.68      A    C
ATOM   2512  CG   GLU A 357     -20.030 -17.968  -8.281  1.00 32.66      A    C
ATOM   2513  CD   GLU A 357     -21.121 -16.919  -8.546  1.00 36.65      A    C
ATOM   2514  OE1  GLU A 357     -21.643 -16.841  -9.706  1.00 36.94      A    O
ATOM   2515  OE2  GLU A 357     -21.446 -16.168  -7.581  1.00 35.86      A    O
ATOM   2516  C    GLU A 357     -19.468 -21.623  -9.522  1.00 31.59      A    C
ATOM   2517  O    GLU A 357     -20.163 -22.497  -8.980  1.00 32.53      A    O
ATOM   2518  N    TYR A 358     -18.911 -21.781 -10.719  1.00 31.36      A    N
ATOM   2519  CA   TYR A 358     -19.069 -22.996 -11.491  1.00 30.15      A    C
```

FIGURE 1-36 (COORDINATES)

```
ATOM   2520  CB  TYR A 358     -18.327 -22.838 -12.810  1.00 29.53      A  C
ATOM   2521  CG  TYR A 358     -18.788 -23.811 -13.807  1.00 26.85      A  C
ATOM   2522  CD1 TYR A 358     -19.633 -23.416 -14.839  1.00 25.31      A  C
ATOM   2523  CE1 TYR A 358     -20.061 -24.313 -15.795  1.00 25.79      A  C
ATOM   2524  CZ  TYR A 358     -19.677 -25.646 -15.697  1.00 28.54      A  C
ATOM   2525  OH  TYR A 358     -20.128 -26.565 -16.611  1.00 29.36      A  O
ATOM   2526  CE2 TYR A 358     -18.846 -26.061 -14.652  1.00 30.30      A  C
ATOM   2527  CD2 TYR A 358     -18.412 -25.138 -13.715  1.00 25.51      A  C
ATOM   2528  C   TYR A 358     -18.525 -24.207 -10.750  1.00 30.26      A  C
ATOM   2529  O   TYR A 358     -19.146 -25.263 -10.727  1.00 29.96      A  O
ATOM   2530  N   LEU A 359     -17.349 -24.032 -10.166  1.00 30.52      A  N
ATOM   2531  CA  LEU A 359     -16.655 -25.080  -9.432  1.00 31.83      A  C
ATOM   2532  CB  LEU A 359     -15.137 -24.781  -9.408  1.00 32.30      A  C
ATOM   2533  CG  LEU A 359     -14.049 -25.297 -10.404  1.00 33.62      A  C
ATOM   2534  CD1 LEU A 359     -14.592 -25.767 -11.730  1.00 32.60      A  C
ATOM   2535  CD2 LEU A 359     -12.937 -24.273 -10.603  1.00 31.67      A  C
ATOM   2536  C   LEU A 359     -17.143 -25.153  -7.981  1.00 32.40      A  C
ATOM   2537  O   LEU A 359     -16.590 -25.920  -7.193  1.00 32.28      A  O
ATOM   2538  N   HIS A 360     -18.142 -24.353  -7.620  1.00 32.80      A  N
ATOM   2539  CA  HIS A 360     -18.586 -24.303  -6.218  1.00 34.83      A  C
ATOM   2540  CB  HIS A 360     -19.422 -25.544  -5.845  1.00 35.04      A  C
ATOM   2541  CG  HIS A 360     -20.590 -25.812  -6.755  1.00 36.15      A  C
ATOM   2542  ND1 HIS A 360     -21.716 -26.486  -6.328  1.00 36.53      A  N
ATOM   2543  CE1 HIS A 360     -22.576 -26.590  -7.325  1.00 38.78      A  C
ATOM   2544  NE2 HIS A 360     -22.049 -26.011  -8.394  1.00 39.78      A  N
ATOM   2545  CD2 HIS A 360     -20.802 -25.516  -8.063  1.00 38.21      A  C
ATOM   2546  C   HIS A 360     -17.374 -24.245  -5.297  1.00 34.88      A  C
ATOM   2547  O   HIS A 360     -17.206 -25.108  -4.449  1.00 35.08      A  O
ATOM   2548  N   LEU A 361     -16.509 -23.260  -5.500  1.00 36.08      A  N
ATOM   2549  CA  LEU A 361     -15.371 -23.048  -4.589  1.00 37.43      A  C
ATOM   2550  CB  LEU A 361     -14.031 -23.215  -5.302  1.00 37.14      A  C
ATOM   2551  CG  LEU A 361     -13.632 -24.645  -5.666  1.00 39.13      A  C
ATOM   2552  CD1 LEU A 361     -12.378 -24.535  -6.530  1.00 38.50      A  C
ATOM   2553  CD2 LEU A 361     -13.431 -25.582  -4.429  1.00 38.67      A  C
ATOM   2554  C   LEU A 361     -15.413 -21.699  -3.883  1.00 37.66      A  C
ATOM   2555  O   LEU A 361     -14.514 -21.381  -3.074  1.00 37.47      A  O
ATOM   2556  OXT LEU A 361     -16.340 -20.910  -4.128  1.00 38.56      A  O
ATOM   2557  ZN  ZN  B   1      -5.979 -12.699 -34.883  1.00 12.86      B  ZN
ATOM   2558  N3  IMD C   1      -7.492 -13.735 -34.851  1.00  4.57      C  N
ATOM   2559  C4  IMD C   1      -8.076 -13.947 -33.521  1.00  9.49      C  C
ATOM   2560  C5  IMD C   1      -9.389 -14.467 -33.712  1.00 10.21      C  C
ATOM   2561  C2  IMD C   1      -8.450 -14.092 -35.759  1.00  6.46      C  C
ATOM   2562  N1  IMD C   1      -9.552 -14.532 -35.123  1.00 11.44      C  N
ATOM   2563  O   HOH S   1      10.163 -19.797 -37.050  0.50  2.00      S  O
ATOM   2564  O   HOH S   2      -2.322 -13.026 -33.337  1.00  7.65      S  O
ATOM   2565  O   HOH S   3      -9.780   0.679 -38.949  1.00 16.60      S  O
ATOM   2566  O   HOH S   4      -0.613 -14.277 -41.749  1.00 15.36      S  O
ATOM   2567  O   HOH S   5      -8.574 -18.557 -29.677  1.00 15.35      S  O
ATOM   2568  O   HOH S   6      -5.367  -8.375 -33.666  1.00 20.26      S  O
ATOM   2569  O   HOH S   7       3.693 -12.326 -35.010  1.00 20.53      S  O
ATOM   2570  O   HOH S   8      -5.395 -23.620 -33.328  1.00 22.13      S  O
ATOM   2571  O   HOH S   9      -5.180 -15.242 -39.266  1.00  5.65      S  O
ATOM   2572  O   HOH S  10      -0.540 -18.980 -36.626  1.00 26.09      S  O
ATOM   2573  O   HOH S  11     -18.787 -17.256 -31.546  1.00 23.66      S  O
ATOM   2574  O   HOH S  12      -1.360 -15.164 -28.679  1.00 16.27      S  O
ATOM   2575  O   HOH S  13       8.416 -25.452 -37.296  1.00 13.14      S  O
ATOM   2576  O   HOH S  14      -2.752 -31.451 -18.951  1.00 21.12      S  O
ATOM   2577  O   HOH S  15       5.139 -23.501 -32.058  1.00 21.86      S  O
ATOM   2578  O   HOH S  16     -11.127  -4.018 -36.370  1.00 19.95      S  O
ATOM   2579  O   HOH S  17      -8.447  -1.688 -30.362  1.00 21.00      S  O
ATOM   2580  O   HOH S  18       0.320 -16.974 -38.750  1.00 24.72      S  O
ATOM   2581  O   HOH S  19     -11.208  -1.154 -30.100  1.00 24.06      S  O
ATOM   2582  O   HOH S  20      -4.401   0.574 -19.655  1.00 39.30      S  O
ATOM   2583  O   HOH S  21      -6.670  -2.333 -28.231  1.00 18.68      S  O
ATOM   2584  O   HOH S  22      -9.461 -24.584 -39.851  1.00 26.76      S  O
ATOM   2585  O   HOH S  23      -0.616   2.343 -31.647  1.00 32.84      S  O
ATOM   2586  O   HOH S  24      -0.797  -2.336 -39.427  1.00 27.06      S  O
ATOM   2587  O   HOH S  25      -7.521 -16.719 -28.049  1.00 29.65      S  O
ATOM   2588  O   HOH S  26     -13.621  -0.678 -35.766  1.00 39.59      S  O
ATOM   2589  O   HOH S  27       9.494 -22.759 -31.774  1.00 18.91      S  O
```

FIGURE 1-37 (COORDINATES)

```
ATOM   2590  O   HOH S  28      -4.766 -35.427 -33.531  1.00 34.31           S    O
ATOM   2591  O   HOH S  29     -19.919 -17.820 -33.837  1.00 19.19           S    O
ATOM   2592  O   HOH S  30     -15.488  -6.621 -36.091  1.00 21.88           S    O
ATOM   2593  O   HOH S  31       0.379 -15.122  -5.765  1.00 33.51           S    O
ATOM   2594  O   HOH S  32      -0.386 -31.995 -42.453  1.00 18.74           S    O
ATOM   2595  O   HOH S  33     -22.450 -26.542 -17.726  1.00 18.28           S    O
ATOM   2596  O   HOH S  34      -9.260 -12.948  -6.978  1.00 32.10           S    O
ATOM   2597  O   HOH S  35     -21.388 -27.952 -29.356  1.00 37.90           S    O
ATOM   2598  O   HOH S  36       3.356 -34.921 -35.995  1.00 26.91           S    O
ATOM   2599  O   HOH S  37       3.367 -26.490  -8.904  1.00 40.13           S    O
ATOM   2600  O   HOH S  38     -22.764 -13.796  -7.352  1.00 38.94           S    O
ATOM   2601  O   HOH S  39      -7.056 -36.788 -11.053  1.00 30.86           S    O
ATOM   2602  O   HOH S  40      10.492 -10.745 -37.316  0.50 25.46           S    O
ATOM   2603  O   HOH S  41       4.090 -33.294 -22.535  1.00 24.41           S    O
ATOM   2604  O   HOH S  42      -7.127 -13.902 -40.593  1.00 20.92           S    O
ATOM   2605  O   HOH S  43      -6.224  -5.536  -9.952  1.00 40.65           S    O
ATOM   2606  O   HOH S  44      -4.276  -6.380 -41.798  1.00 42.30           S    O
ATOM   2607  O   HOH S  45       6.156 -26.579 -31.815  1.00 41.90           S    O
ATOM   2608  O   HOH S  46     -26.358 -23.331 -28.619  1.00 43.36           S    O
ATOM   2609  O   HOH S  47      -6.363 -10.529 -41.440  1.00 26.60           S    O
ATOM   2610  O   HOH S  48       2.345 -10.176  -4.693  1.00 44.34           S    O
ATOM   2611  O   HOH S  49     -20.318 -14.756 -25.450  1.00 31.15           S    O
ATOM   2612  O   HOH S  50     -18.722 -20.017 -34.604  1.00 26.19           S    O
ATOM   2613  O   HOH S  51       8.037 -28.872 -46.187  1.00 34.69           S    O
ATOM   2614  O   HOH S  52      -8.281 -13.594 -14.397  1.00 26.42           S    O
ATOM   2615  O   HOH S  53     -23.400 -18.173 -25.402  1.00 22.65           S    O
ATOM   2616  O   HOH S  54      -0.435 -12.738 -11.767  1.00 33.27           S    O
ATOM   2617  O   HOH S  55       2.326 -14.552 -44.769  1.00 38.74           S    O
ATOM   2618  O   HOH S  56       0.405 -16.476 -13.132  1.00 24.71           S    O
ATOM   2619  O   HOH S  57      -4.340 -32.084 -10.228  1.00 30.30           S    O
ATOM   2620  O   HOH S  58       8.375  -8.121 -17.806  1.00 37.24           S    O
ATOM   2621  O   HOH S  59      10.442 -17.514 -21.945  1.00 32.93           S    O
ATOM   2622  O   HOH S  60      10.466 -15.230 -41.923  1.00 31.43           S    O
ATOM   2623  O   HOH S  61     -22.125 -26.726 -20.527  1.00 22.42           S    O
ATOM   2624  O   HOH S  63      -3.542 -22.293  -9.265  1.00 25.42           S    O
ATOM   2625  O   HOH S  64     -18.705 -33.030 -18.889  1.00 28.90           S    O
ATOM   2626  O   HOH S  65       1.323  -5.693 -32.605  1.00 24.51           S    O
ATOM   2627  O   HOH S  68       3.196 -33.709 -47.909  1.00 44.67           S    O
ATOM   2628  O   HOH S  69      -3.198 -20.486 -47.339  1.00 30.85           S    O
ATOM   2629  O   HOH S  70      -7.403 -43.007 -21.851  1.00 44.23           S    O
ATOM   2630  O   HOH S  71      -8.242 -45.320 -21.379  1.00 39.10           S    O
ATOM   2631  O   HOH S  72      -7.235 -33.558 -21.592  1.00 39.47           S    O
ATOM   2632  O   HOH S  74     -24.066 -16.679 -32.258  1.00 41.34           S    O
ATOM   2633  O   HOH S  75       4.789  -3.749 -25.273  1.00 41.21           S    O
ATOM   2634  O   HOH S  76       1.778 -25.884 -10.498  1.00 35.48           S    O
ATOM   2635  O   HOH S  78       3.275 -26.624 -47.974  1.00 37.58           S    O
ATOM   2636  O   HOH S  79       9.849 -26.401 -41.824  1.00 28.06           S    O
ATOM   2637  O   HOH S  80       8.707 -23.114 -42.801  1.00 34.63           S    O
ATOM   2638  O   HOH S  81     -12.750 -34.076 -18.338  1.00 16.55           S    O
ATOM   2639  O   HOH S  83      -1.822   0.523 -22.119  1.00 37.34           S    O
ATOM   2640  O   HOH S  84     -26.428 -15.172 -31.099  1.00 48.18           S    O
ATOM   2641  O   HOH S  85      -6.857  -8.091 -12.208  1.00 28.06           S    O
ATOM   2642  O   HOH S  86      -4.311 -27.870 -42.486  1.00 33.92           S    O
ATOM   2643  O   HOH S  87     -11.396  -6.032 -26.727  1.00 21.01           S    O
ATOM   2644  O   HOH S  88     -20.166 -19.735 -13.223  1.00 38.08           S    O
ATOM   2645  O   HOH S  90      -1.591  -4.339 -41.542  1.00 46.30           S    O
ATOM   2646  O   HOH S  91       7.578 -15.392 -12.712  1.00 41.49           S    O
ATOM   2647  O   HOH S  92     -18.289  -0.912  -9.423  1.00 25.60           S    O
ATOM   2648  O   HOH S  93       9.476 -27.418 -28.347  1.00 40.27           S    O
ATOM   2649  O   HOH S  94     -11.594  -5.864 -24.191  1.00 28.47           S    O
ATOM   2650  O   HOH S  96      -5.862 -35.008 -19.174  1.00 37.12           S    O
ATOM   2651  O   HOH S  97      -2.811  -3.564  -9.405  1.00 29.74           S    O
ATOM   2652  O   HOH S 100     -10.220 -29.774  -0.004  1.00 25.18           S    O
ATOM   2653  O   HOH S 101       4.983 -11.753 -37.292  1.00 31.79           S    O
ATOM   2654  O   HOH S 102       3.362 -20.239 -30.747  1.00 21.70           S    O
ATOM   2655  O   HOH S 103      -3.633 -13.572 -43.515  1.00 27.62           S    O
ATOM   2656  O   HOH S 104      -5.807 -14.283 -43.504  1.00 20.89           S    O
ATOM   2657  O   HOH S 105      -0.107 -32.088 -47.048  1.00 43.34           S    O
ATOM   2658  O   HOH S 106       2.648 -17.795 -11.634  1.00 33.99           S    O
ATOM   2659  O   HOH S 107      -0.652 -13.565 -44.192  1.00 37.05           S    O
```

FIGURE 1-38 (COORDINATES)

```
ATOM   2660  O   HOH S 109     -3.987  -3.434 -28.331  1.00 28.07      S    O
ATOM   2661  O   HOH S 110    -22.549 -17.677 -34.467  1.00 37.97      S    O
ATOM   2662  O   HOH S 111     -8.930 -24.789 -47.305  1.00 37.08      S    O
ATOM   2663  O   HOH S 112      7.780 -13.719 -15.257  1.00 38.93      S    O
ATOM   2664  O   HOH S 113    -13.677  -4.251 -35.916  1.00 29.69      S    O
ATOM   2665  O   HOH S 114     -6.113 -29.730 -42.848  1.00 29.80      S    O
ATOM   2666  O   HOH S 115      3.761  -3.877 -27.641  1.00 30.49      S    O
ATOM   2667  O   HOH S 116    -25.527   0.696 -24.561  1.00 32.73      S    O
ATOM   2668  O   HOH S 119    -16.342  -4.946 -29.136  1.00 26.68      S    O
ATOM   2669  O   HOH S 120     -4.342 -36.380 -22.918  1.00 37.92      S    O
ATOM   2670  O   HOH S 121    -13.940  -0.538 -21.689  1.00 24.48      S    O
ATOM   2671  O   HOH S 122     -7.512   1.862 -17.978  1.00 26.89      S    O
ATOM   2672  O   HOH S 123    -13.309  -1.816 -28.784  1.00 24.34      S    O
ATOM   2673  O   HOH S 124    -28.752 -28.026 -20.533  1.00 45.04      S    O
ATOM   2674  O   HOH S 128    -16.385  -1.908 -28.768  1.00 38.23      S    O
ATOM   2675  O   HOH S 131    -11.977 -34.044 -20.759  1.00 25.72      S    O
ATOM   2676  O   HOH S 132      5.219 -32.924 -26.727  1.00 56.31      S    O
ATOM   2677  O   HOH S 134    -13.086 -39.517 -32.457  1.00 37.78      S    O
ATOM   2678  O   HOH S 135     10.771 -10.387 -34.826  1.00 41.35      S    O
ATOM   2679  O   HOH S 137    -14.594  -1.440 -31.089  1.00 35.10      S    O
ATOM   2680  O   HOH S 139     10.434 -14.448 -39.473  1.00 39.17      S    O
ATOM   2681  O   HOH S 141      2.962 -31.153 -14.872  1.00 33.76      S    O
ATOM   2682  O   HOH S 142     -8.972  -3.583  -8.705  1.00 31.73      S    O
ATOM   2683  O   HOH S 144      1.352 -34.408 -29.387  1.00 41.97      S    O
ATOM   2684  O   HOH S 145     -8.360 -36.747  -8.736  1.00 35.53      S    O
ATOM   2685  O   HOH S 146      8.293 -21.514 -12.119  1.00 42.43      S    O
ATOM   2686  O   HOH S 147      9.107 -26.670 -26.018  1.00 37.32      S    O
ATOM   2687  O   HOH S 148    -20.884 -17.274 -26.290  1.00 23.37      S    O
ATOM   2688  O   HOH S 149    -19.419 -33.943 -27.007  1.00 36.17      S    O
ATOM   2689  O   HOH S 150    -14.103  -1.726 -33.444  1.00 27.47      S    O
ATOM   2690  O   HOH S 151    -22.691  -6.802 -31.939  1.00 38.96      S    O
ATOM   2691  O   HOH S 152    -27.608  -9.688 -10.974  1.00 34.86      S    O
ATOM   2692  O   HOH S 153      2.565 -16.208  -6.251  1.00 47.19      S    O
ATOM   2693  O   HOH S 154     -7.082   2.012 -25.632  1.00 41.87      S    O
ATOM   2694  O   HOH S 155     -7.901 -18.928 -49.467  1.00 46.28      S    O
ATOM   2695  O   HOH S 156    -22.910  -0.951  -2.721  1.00 41.85      S    O
ATOM   2696  O   HOH S 157    -26.364 -25.584 -20.224  1.00 31.94      S    O
ATOM   2697  O   HOH S 158      7.933 -11.554 -39.603  1.00 43.14      S    O
ATOM   2698  O   HOH S 159      5.566  -9.179 -37.412  1.00 29.42      S    O
ATOM   2699  O   HOH S 160    -23.496 -29.716 -28.136  1.00 46.88      S    O
ATOM   2700  O   HOH S 161     -6.480 -24.497  -0.089  1.00 45.57      S    O
ATOM   2701  O   HOH S 162      4.459 -22.875 -50.899  1.00 47.57      S    O
ATOM   2702  O   HOH S 163    -25.462 -19.879 -32.688  1.00 46.37      S    O
ATOM   2703  O   HOH S 164      9.468  -9.782 -30.577  1.00 32.83      S    O
ATOM   2704  O   HOH S 165    -13.744 -20.451  -0.569  1.00 48.50      S    O
ATOM   2705  O   HOH S 166    -11.024 -16.272 -44.565  1.00 40.77      S    O
ATOM   2706  O   HOH S 167    -22.121 -35.823 -29.227  1.00 30.43      S    O
ATOM   2707  O   HOH S 180    -12.717 -28.246 -37.271  1.00 27.80      S    O
ATOM   2708  O   HOH S 181     -0.656  -5.429  -6.750  1.00 42.16      S    O
ATOM   2709  O   HOH S 182     -4.433   2.908 -23.900  1.00 42.57      S    O
ATOM   2710  O   HOH S 183      2.284 -12.122 -10.397  1.00 28.67      S    O
ATOM   2711  O   HOH S 184     -7.889 -10.619  -1.313  1.00 32.41      S    O
ATOM   2712  O   HOH S 185    -17.105  -9.101 -35.658  1.00 48.16      S    O
ATOM   2713  O   HOH S 186    -17.719 -18.626 -40.720  1.00 50.26      S    O
ATOM   2714  O   HOH S 187     -6.733  -5.284 -40.156  1.00 27.69      S    O
ATOM   2715  O   HOH S 188    -21.274 -33.844 -18.162  1.00 35.01      S    O
ATOM   2716  O   HOH S 189     -4.338 -38.680 -26.219  1.00 44.73      S    O
ATOM   2717  O   HOH S 190    -15.715   2.975 -20.136  1.00 36.82      S    O
ATOM   2718  O   HOH S 191      3.267   2.414 -32.232  1.00 39.09      S    O
ATOM   2719  O   HOH S 192      5.649 -10.467  -7.780  1.00 47.22      S    O
ATOM   2720  O   HOH S 193      7.369 -32.268 -24.958  1.00 39.77      S    O
ATOM   2721  O   HOH S 194     -5.850 -30.267 -45.620  1.00 37.49      S    O
ATOM   2722  O   HOH S 195    -20.860 -36.549 -17.515  1.00 52.54      S    O
ATOM   2723  O   HOH S 196     11.085 -18.047 -19.205  1.00 38.86      S    O
ATOM   2724  O   HOH S 197     -2.267 -34.871 -10.249  1.00 39.43      S    O
ATOM   2725  O   HOH S 198    -17.831 -55.990 -21.052  1.00 43.90      S    O
ATOM   2726  O   HOH S 199    -12.116 -15.086 -37.404  1.00 39.98      S    O
ATOM   2727  O   HOH S 200    -24.116 -17.525  -1.402  1.00 47.77      S    O
ATOM   2728  O   HOH S 201    -16.916 -56.875 -23.195  1.00 42.16      S    O
ATOM   2729  O   HOH S 202    -14.464 -15.610 -38.828  1.00 36.99      S    O

ATOM   2730  O   HOH S 203    -14.695 -28.735  -5.295  1.00 42.08      S    O
```

FIGURE 1-39 (COORDINATES)

```
HEADER     ----                                           XX-XXX-XX   xxxx
COMPND     ---
REMARK   3
REMARK   3 REFINEMENT.
REMARK   3   PROGRAM     : REFMAC 5.5.0109
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :    2.08
REMARK   3   RESOLUTION RANGE LOW  (ANGSTROMS) :   32.65
REMARK   3   DATA CUTOFF            (SIGMA(F)) : NONE
REMARK   3   COMPLETENESS FOR RANGE        (%) :  100.00
REMARK   3   NUMBER OF REFLECTIONS             :   21106
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.21246
REMARK   3   R VALUE            (WORKING SET) : 0.20973
REMARK   3   FREE R VALUE                     : 0.26419
REMARK   3   FREE R VALUE TEST SET SIZE   (%) : 5.0
REMARK   3   FREE R VALUE TEST SET COUNT      : 1111
REMARK   3
REMARK   3  FIT IN THE HIGHEST RESOLUTION BIN.
REMARK   3   TOTAL NUMBER OF BINS USED            :      20
REMARK   3   BIN RESOLUTION RANGE HIGH            :   2.080
REMARK   3   BIN RESOLUTION RANGE LOW             :   2.134
REMARK   3   REFLECTION IN BIN    (WORKING SET) :    1558
REMARK   3   BIN COMPLETENESS (WORKING+TEST) (%) :  100.00
REMARK   3   BIN R VALUE           (WORKING SET) :   0.352
REMARK   3   BIN FREE R VALUE SET COUNT          :      82
REMARK   3   BIN FREE R VALUE                    :   0.370
REMARK   3
REMARK   3  NUMBER OF NON-HYDROGEN ATOMS USED IN REFINEMENT.
REMARK   3   ALL ATOMS                :    2717
REMARK   3
REMARK   3  B VALUES.
REMARK   3   FROM WILSON PLOT         (A**2) : NULL
REMARK   3   MEAN B VALUE      (OVERALL, A**2) :  29.641
REMARK   3   OVERALL ANISOTROPIC B VALUE.
REMARK   3    B11 (A**2) :   -0.36
REMARK   3    B22 (A**2) :   -3.01
REMARK   3    B33 (A**2) :    4.29
REMARK   3    B12 (A**2) :    0.00
REMARK   3    B13 (A**2) :    1.70
REMARK   3    B23 (A**2) :    0.00
REMARK   3
REMARK   3  ESTIMATED OVERALL COORDINATE ERROR.
REMARK   3   ESU BASED ON R VALUE                    (A):   0.229
REMARK   3   ESU BASED ON FREE R VALUE               (A):   0.201
REMARK   3   ESU BASED ON MAXIMUM LIKELIHOOD         (A):   0.166
REMARK   3   ESU FOR B VALUES BASED ON MAXIMUM LIKELIHOOD (A**2):  14.688
REMARK   3
REMARK   3 CORRELATION COEFFICIENTS.
REMARK   3   CORRELATION COEFFICIENT FO-FC      :  0.949
REMARK   3   CORRELATION COEFFICIENT FO-FC FREE :  0.912
REMARK   3
REMARK   3  RMS DEVIATIONS FROM IDEAL VALUES        COUNT    RMS    WEIGHT
REMARK   3   BOND LENGTHS REFINED ATOMS       (A):  2618 ; 0.022 ; 0.021
REMARK   3   BOND ANGLES REFINED ATOMS   (DEGREES):  3558 ; 1.915 ; 1.959
REMARK   3   TORSION ANGLES, PERIOD 1    (DEGREES):   313 ; 7.090 ; 5.000
REMARK   3   TORSION ANGLES, PERIOD 2    (DEGREES):   131 ;34.901 ;23.969
REMARK   3   TORSION ANGLES, PERIOD 3    (DEGREES):   424 ;17.377 ;15.000
REMARK   3   TORSION ANGLES, PERIOD 4    (DEGREES):    16 ;24.299 ;15.000
REMARK   3   CHIRAL-CENTER RESTRAINTS       (A**3):   383 ; 0.137 ; 0.200
REMARK   3   GENERAL PLANES REFINED ATOMS     (A):  2034 ; 0.009 ; 0.021
REMARK   3
REMARK   3  ISOTROPIC THERMAL FACTOR RESTRAINTS.    COUNT    RMS    WEIGHT
```

FIGURE 1-40 (REMARKS)

```
REMARK   3   MAIN-CHAIN BOND REFINED ATOMS   (A**2):   1580 ; 0.999 ; 1.500
REMARK   3   MAIN-CHAIN ANGLE REFINED ATOMS  (A**2):   2547 ; 1.700 ; 2.000
REMARK   3   SIDE-CHAIN BOND REFINED ATOMS   (A**2):   1038 ; 2.886 ; 3.000
REMARK   3   SIDE-CHAIN ANGLE REFINED ATOMS  (A**2):   1011 ; 4.235 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  :    1
REMARK   3   ATOM RECORD CONTAINS RESIDUAL B FACTORS ONLY
REMARK   3
REMARK   3   TLS GROUP :    1
REMARK   3    NUMBER OF COMPONENTS GROUP :    1
REMARK   3    COMPONENTS        C SSSEQI    TO  C SSSEQI
REMARK   3    RESIDUE RANGE :        -1              -1
REMARK   3    ORIGIN FOR THE GROUP (A):   -9.1188 -18.3713 -23.0124
REMARK   3    T TENSOR
REMARK   3      T11:   0.0656 T22:   0.0568
REMARK   3      T33:   0.0262 T12:   0.0051
REMARK   3      T13:   0.0093 T23:  -0.0153
REMARK   3    L TENSOR
REMARK   3      L11:   0.5223 L22:   0.6783
REMARK   3      L33:   0.4028 L12:   0.1735
REMARK   3      L13:  -0.0599 L23:   0.1461
REMARK   3    S TENSOR
REMARK   3      S11:   0.0060 S12:  -0.0320 S13:   0.0755
REMARK   3      S21:   0.0781 S22:  -0.0405 S23:   0.1120
REMARK   3      S31:   0.0290 S32:  -0.0138 S33:   0.0345
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.20
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3   HYDROGENS HAVE BEEN ADDED IN THE RIDING POSITIONS
REMARK   3   U VALUES      : RESIDUAL ONLY
REMARK   3
SSBOND   1 CYS A  139    CYS A  164
CISPEP   1 PRO A   37    GLU A   38                          0.00
LINKR            PHE A  146                 ASN A  150                   gap
CISPEP   2 ASP A  159    SER A  160                          0.00
LINKR            LYS A  182                 ASP A  190                   gap
CISPEP   3 HIS A  228    PRO A  229                          0.00
CISPEP   4 GLY A  301    VAL A  302                          0.00
CISPEP   5 SER A  323    PRO A  324                          0.00
CRYST1   82.640   63.908   77.539  90.00 105.71  90.00 C 1 2 1
SCALE1      0.012101  0.000000  0.003404       0.00000
SCALE2      0.000000  0.015647  0.000000       0.00000
SCALE3      0.000000  0.000000  0.013397       0.00000
```

FIGURE 1-41 (REMARKS)

```
     ATOM TYPE RES   #       x       y       z     Occ   B
ATOM   1   N   ALA A  36    5.761 -34.825 -44.213 1.00 37.12    N
ATOM   2   CA  ALA A  36    5.064 -34.974 -42.910 1.00 36.64    C
ATOM   3   CB  ALA A  36    5.785 -35.986 -42.056 1.00 37.39    C
ATOM   4   C   ALA A  36    5.035 -33.596 -42.237 1.00 36.54    C
ATOM   5   O   ALA A  36    6.085 -32.941 -42.110 1.00 35.88    O
ATOM   6   N   TRP A  37    3.837 -33.148 -41.851 1.00 35.57    N
ATOM   7   CA  TRP A  37    3.662 -31.782 -41.315 1.00 35.58    C
ATOM   8   CB  TRP A  37    2.201 -31.397 -41.235 1.00 34.64    C
ATOM   9   CG  TRP A  37    1.399 -32.127 -40.180 1.00 33.33    C
ATOM  10   CD1 TRP A  37    0.564 -33.180 -40.386 1.00 31.95    C
ATOM  11   NE1 TRP A  37   -0.025 -33.554 -39.207 1.00 31.48    N
ATOM  12   CE2 TRP A  37    0.429 -32.746 -38.193 1.00 30.65    C
ATOM  13   CD2 TRP A  37    1.321 -31.820 -38.768 1.00 30.15    C
ATOM  14   CE3 TRP A  37    1.923 -30.854 -37.942 1.00 28.53    C
ATOM  15   CZ3 TRP A  37    1.630 -30.853 -36.580 1.00 27.36    C
ATOM  16   CH2 TRP A  37    0.720 -31.780 -36.032 1.00 27.77    C
ATOM  17   CZ2 TRP A  37    0.113 -32.739 -36.820 1.00 30.30    C
ATOM  18   C   TRP A  37    4.265 -31.624 -39.922 1.00 35.50    C
ATOM  19   O   TRP A  37    4.630 -30.513 -39.516 1.00 34.90    O
ATOM  20   N   THR A  38    4.317 -32.743 -39.200 1.00 35.72    N
ATOM  21   CA  THR A  38    4.888 -32.821 -37.857 1.00 36.00    C
ATOM  22   CB  THR A  38    4.751 -34.229 -37.283 1.00 35.91    C
ATOM  23   OG1 THR A  38    5.230 -35.178 -38.244 1.00 36.51    O
ATOM  24   CG2 THR A  38    3.317 -34.532 -36.975 1.00 35.49    C
ATOM  25   C   THR A  38    6.359 -32.460 -37.887 1.00 36.10    C
ATOM  26   O   THR A  38    6.915 -32.031 -36.891 1.00 37.44    O
ATOM  27   N   GLN A  39    6.970 -32.604 -39.054 1.00 36.16    N
ATOM  28   CA  GLN A  39    8.383 -32.356 -39.256 1.00 35.84    C
ATOM  29   CB  GLN A  39    8.856 -33.291 -40.387 1.00 36.59    C
ATOM  30   CG  GLN A  39   10.343 -33.488 -40.572 1.00 39.95    C
ATOM  31   CD  GLN A  39   11.093 -33.866 -39.301 1.00 43.37    C
ATOM  32   OE1 GLN A  39   10.586 -34.599 -38.448 1.00 44.80    O
ATOM  33   NE2 GLN A  39   12.327 -33.372 -39.182 1.00 46.36    N
ATOM  34   C   GLN A  39    8.649 -30.872 -39.570 1.00 34.93    C
ATOM  35   O   GLN A  39    9.788 -30.428 -39.575 1.00 35.23    O
ATOM  36   N   GLU A  40    7.597 -30.093 -39.807 1.00 34.39    N
ATOM  37   CA  GLU A  40    7.757 -28.671 -40.174 1.00 33.34    C
ATOM  38   CB  GLU A  40    6.416 -28.060 -40.580 1.00 33.26    C
ATOM  39   CG  GLU A  40    5.961 -28.498 -41.969 1.00 33.72    C
ATOM  40   CD  GLU A  40    4.509 -28.161 -42.265 1.00 36.21    C
ATOM  41   OE1 GLU A  40    3.960 -27.191 -41.672 1.00 35.05    O
ATOM  42   OE2 GLU A  40    3.925 -28.877 -43.116 1.00 37.46    O
ATOM  43   C   GLU A  40    8.411 -27.812 -39.086 1.00 32.83    C
ATOM  44   O   GLU A  40    9.187 -26.897 -39.388 1.00 31.85    O
ATOM  45   N   LYS A  41    8.115 -28.132 -37.823 1.00 32.58    N
ATOM  46   CA  LYS A  41    8.673 -27.379 -36.697 1.00 32.38    C
ATOM  47   CB  LYS A  41    8.182 -27.910 -35.361 1.00 31.90    C
ATOM  48   CG  LYS A  41    8.499 -29.378 -35.062 1.00 32.06    C
ATOM  49   CD  LYS A  41    7.747 -29.781 -33.833 1.00 34.40    C
ATOM  50   CE  LYS A  41    7.583 -31.275 -33.708 1.00 35.64    C
ATOM  51   NZ  LYS A  41    8.884 -31.876 -33.414 1.00 37.29    N
ATOM  52   C   LYS A  41   10.177 -27.438 -36.745 1.00 32.71    C
ATOM  53   O   LYS A  41   10.854 -26.487 -36.357 1.00 31.68    O
ATOM  54   N   ASN A  42   10.693 -28.556 -37.255 1.00 33.04    N
ATOM  55   CA  ASN A  42   12.130 -28.783 -37.305 1.00 33.78    C
ATOM  56   CB  ASN A  42   12.428 -30.273 -37.526 1.00 34.12    C
ATOM  57   CG  ASN A  42   11.837 -31.135 -36.432 1.00 35.37    C
ATOM  58   OD1 ASN A  42   11.061 -32.044 -36.701 1.00 37.72    O
ATOM  59   ND2 ASN A  42   12.160 -30.808 -35.173 1.00 37.12    N
ATOM  60   C   ASN A  42   12.836 -27.911 -38.316 1.00 33.69    C
ATOM  61   O   ASN A  42   14.041 -27.690 -38.219 1.00 34.74    O
ATOM  62   N   HIS A  43   12.089 -27.377 -39.270 1.00 33.15    N
ATOM  63   CA  HIS A  43   12.708 -26.564 -40.299 1.00 33.06    C
ATOM  64   CB  HIS A  43   12.532 -27.245 -41.666 1.00 34.20    C
ATOM  65   CG  HIS A  43   12.904 -28.697 -41.654 1.00 36.59    C
ATOM  66   ND1 HIS A  43   14.128 -29.147 -41.201 1.00 39.94    N
ATOM  67   CE1 HIS A  43   14.171 -30.466 -41.289 1.00 39.84    C
ATOM  68   NE2 HIS A  43   13.018 -30.886 -41.781 1.00 40.93    N
ATOM  69   CD2 HIS A  43   12.204 -29.802 -42.008 1.00 38.59    C
```

FIGURE 2-1 (COORDINATES)

```
ATOM    70  C   HIS A  43      12.160 -25.160 -40.290  1.00 31.76           C
ATOM    71  O   HIS A  43      12.529 -24.326 -41.122  1.00 32.09           O
ATOM    72  N   HIS A  44      11.285 -24.888 -39.320  1.00 30.40           N
ATOM    73  CA  HIS A  44      10.587 -23.615 -39.273  1.00 28.58           C
ATOM    74  CB  HIS A  44       9.539 -23.600 -38.162  1.00 27.65           C
ATOM    75  CG  HIS A  44       8.770 -22.320 -38.100  1.00 27.24           C
ATOM    76  ND1 HIS A  44       7.820 -21.976 -39.039  1.00 25.05           N
ATOM    77  CE1 HIS A  44       7.318 -20.791 -38.737  1.00 26.02           C
ATOM    78  NE2 HIS A  44       7.911 -20.354 -37.638  1.00 26.16           N
ATOM    79  CD2 HIS A  44       8.829 -21.288 -37.225  1.00 26.94           C
ATOM    80  C   HIS A  44      11.585 -22.510 -39.048  1.00 27.73           C
ATOM    81  O   HIS A  44      12.431 -22.610 -38.193  1.00 28.40           O
ATOM    82  N   GLN A  45      11.480 -21.452 -39.828  1.00 27.58           N
ATOM    83  CA  GLN A  45      12.396 -20.353 -39.712  1.00 27.96           C
ATOM    84  CB  GLN A  45      13.107 -20.127 -41.055  1.00 29.15           C
ATOM    85  CG  GLN A  45      13.878 -21.352 -41.554  1.00 30.39           C
ATOM    86  CD  GLN A  45      14.953 -21.781 -40.587  1.00 32.92           C
ATOM    87  OE1 GLN A  45      15.523 -20.961 -39.879  1.00 35.25           O
ATOM    88  NE2 GLN A  45      15.222 -23.085 -40.537  1.00 36.37           N
ATOM    89  C   GLN A  45      11.632 -19.115 -39.298  1.00 27.72           C
ATOM    90  O   GLN A  45      10.480 -18.949 -39.696  1.00 26.65           O
ATOM    91  N   PRO A  46      12.269 -18.234 -38.494  1.00 27.59           N
ATOM    92  CA  PRO A  46      11.556 -17.031 -38.086  1.00 27.52           C
ATOM    93  CB  PRO A  46      12.359 -16.543 -36.889  1.00 26.77           C
ATOM    94  CG  PRO A  46      13.759 -16.960 -37.208  1.00 27.48           C
ATOM    95  CD  PRO A  46      13.632 -18.287 -37.931  1.00 27.12           C
ATOM    96  C   PRO A  46      11.593 -15.991 -39.192  1.00 28.58           C
ATOM    97  O   PRO A  46      12.566 -15.935 -39.984  1.00 28.93           O
ATOM    98  N   ALA A  47      10.561 -15.169 -39.261  1.00 28.16           N
ATOM    99  CA  ALA A  47      10.572 -14.107 -40.245  1.00 29.73           C
ATOM   100  CB  ALA A  47       9.205 -13.941 -40.884  1.00 29.80           C
ATOM   101  C   ALA A  47      10.965 -12.886 -39.478  1.00 30.12           C
ATOM   102  O   ALA A  47      10.156 -12.374 -38.700  1.00 31.76           O
ATOM   103  N   HIS A  48      12.207 -12.437 -39.681  1.00 30.18           N
ATOM   104  CA  HIS A  48      12.814 -11.335 -38.919  1.00 30.62           C
ATOM   105  CB  HIS A  48      14.290 -11.127 -39.305  1.00 30.93           C
ATOM   106  CG  HIS A  48      15.173 -12.295 -38.992  1.00 30.76           C
ATOM   107  ND1 HIS A  48      16.540 -12.177 -38.880  1.00 32.41           N
ATOM   108  CE1 HIS A  48      17.061 -13.360 -38.604  1.00 31.73           C
ATOM   109  NE2 HIS A  48      16.080 -14.241 -38.540  1.00 31.05           N
ATOM   110  CD2 HIS A  48      14.890 -13.602 -38.778  1.00 30.87           C
ATOM   111  C   HIS A  48      12.099 -10.023 -39.099  1.00 30.81           C
ATOM   112  O   HIS A  48      11.625  -9.710 -40.193  1.00 30.45           O
ATOM   113  N   LEU A  49      12.024  -9.267 -38.006  1.00 30.96           N
ATOM   114  CA  LEU A  49      11.459  -7.929 -38.018  1.00 31.56           C
ATOM   115  CB  LEU A  49      10.868  -7.592 -36.642  1.00 30.97           C
ATOM   116  CG  LEU A  49       9.654  -8.372 -36.133  1.00 29.08           C
ATOM   117  CD1 LEU A  49       9.102  -7.702 -34.881  1.00 25.06           C
ATOM   118  CD2 LEU A  49       8.578  -8.468 -37.193  1.00 29.61           C
ATOM   119  C   LEU A  49      12.543  -6.923 -38.322  1.00 32.93           C
ATOM   120  O   LEU A  49      13.619  -6.979 -37.726  1.00 33.65           O
ATOM   121  N   ASN A  50      12.263  -5.992 -39.229  1.00 34.32           N
ATOM   122  CA  ASN A  50      13.141  -4.835 -39.442  1.00 35.23           C
ATOM   123  CB  ASN A  50      12.793  -4.103 -40.749  1.00 35.71           C
ATOM   124  CG  ASN A  50      11.346  -3.584 -40.773  1.00 38.53           C
ATOM   125  OD1 ASN A  50      10.848  -3.066 -39.765  1.00 40.15           O
ATOM   126  ND2 ASN A  50      10.661  -3.737 -41.919  1.00 39.74           N
ATOM   127  C   ASN A  50      13.087  -3.868 -38.262  1.00 35.24           C
ATOM   128  O   ASN A  50      12.237  -3.982 -37.374  1.00 35.77           O
ATOM   129  N   SER A  51      14.007  -2.915 -38.273  1.00 35.27           N
ATOM   130  CA  SER A  51      14.164  -1.900 -37.239  1.00 35.02           C
ATOM   131  CB  SER A  51      15.179  -0.889 -37.754  1.00 35.54           C
ATOM   132  OG  SER A  51      15.761  -0.173 -36.693  1.00 35.79           O
ATOM   133  C   SER A  51      12.848  -1.197 -36.853  1.00 35.18           C
ATOM   134  O   SER A  51      12.593  -0.873 -35.674  1.00 34.43           O
ATOM   135  N   SER A  52      12.021  -0.971 -37.869  1.00 34.58           N
ATOM   136  CA  SER A  52      10.763  -0.267 -37.728  1.00 34.64           C
ATOM   137  CB  SER A  52      10.262   0.095 -39.124  1.00 34.39           C
ATOM   138  OG  SER A  52       9.272   1.107 -39.081  1.00 37.19           O
ATOM   139  C   SER A  52       9.718  -1.119 -36.991  1.00 33.22           C
```

FIGURE 2-2 (COORDINATES)

```
ATOM    140  O   SER A  52       9.009  -0.640 -36.101  1.00 33.80           O
ATOM    141  N   SER A  53       9.625  -2.379 -37.390  1.00 31.91           N
ATOM    142  CA  SER A  53       8.701  -3.335 -36.801  1.00 30.58           C
ATOM    143  CB  SER A  53       8.613  -4.569 -37.681  1.00 31.28           C
ATOM    144  OG  SER A  53       8.350  -4.181 -39.027  1.00 33.00           O
ATOM    145  C   SER A  53       9.155  -3.682 -35.374  1.00 28.93           C
ATOM    146  O   SER A  53       8.332  -3.957 -34.505  1.00 28.78           O
ATOM    147  N   LEU A  54      10.466  -3.635 -35.137  1.00 27.39           N
ATOM    148  CA  LEU A  54      11.002  -3.827 -33.809  1.00 25.54           C
ATOM    149  CB  LEU A  54      12.523  -3.969 -33.829  1.00 25.45           C
ATOM    150  CG  LEU A  54      13.042  -5.261 -34.433  1.00 23.58           C
ATOM    151  CD1 LEU A  54      14.523  -5.065 -34.622  1.00 23.31           C
ATOM    152  CD2 LEU A  54      12.786  -6.458 -33.494  1.00 22.88           C
ATOM    153  C   LEU A  54      10.602  -2.661 -32.925  1.00 25.66           C
ATOM    154  O   LEU A  54      10.164  -2.876 -31.795  1.00 24.57           O
ATOM    155  N   GLN A  55      10.727  -1.429 -33.441  1.00 25.68           N
ATOM    156  CA  GLN A  55      10.345  -0.252 -32.662  1.00 26.46           C
ATOM    157  CB  GLN A  55      10.731   1.065 -33.358  1.00 27.79           C
ATOM    158  CG  GLN A  55      10.773   2.251 -32.361  1.00 32.74           C
ATOM    159  CD  GLN A  55      11.408   3.540 -32.899  1.00 39.76           C
ATOM    160  OE1 GLN A  55      12.583   3.563 -33.297  1.00 43.88           O
ATOM    161  NE2 GLN A  55      10.643   4.634 -32.857  1.00 40.70           N
ATOM    162  C   GLN A  55       8.848  -0.286 -32.308  1.00 25.34           C
ATOM    163  O   GLN A  55       8.483   0.039 -31.176  1.00 24.46           O
ATOM    164  N   GLN A  56       8.020  -0.663 -33.283  1.00 24.39           N
ATOM    165  CA  GLN A  56       6.582  -0.963 -33.085  1.00 25.01           C
ATOM    166  CB  GLN A  56       5.941  -1.566 -34.352  1.00 25.59           C
ATOM    167  CG  GLN A  56       4.448  -2.056 -34.218  1.00 29.85           C
ATOM    168  CD  GLN A  56       3.783  -2.349 -35.585  1.00 36.49           C
ATOM    169  OE1 GLN A  56       4.446  -2.804 -36.543  1.00 37.39           O
ATOM    170  NE2 GLN A  56       2.471  -2.090 -35.676  1.00 36.62           N
ATOM    171  C   GLN A  56       6.392  -1.924 -31.923  1.00 23.01           C
ATOM    172  O   GLN A  56       5.601  -1.659 -31.015  1.00 22.63           O
ATOM    173  N   VAL A  57       7.079  -3.057 -31.966  1.00 20.54           N
ATOM    174  CA  VAL A  57       6.917  -4.016 -30.877  1.00 19.73           C
ATOM    175  CB  VAL A  57       7.616  -5.359 -31.136  1.00 19.94           C
ATOM    176  CG1 VAL A  57       7.490  -6.242 -29.906  1.00 20.76           C
ATOM    177  CG2 VAL A  57       7.006  -6.033 -32.367  1.00 20.08           C
ATOM    178  C   VAL A  57       7.367  -3.387 -29.561  1.00 17.87           C
ATOM    179  O   VAL A  57       6.652  -3.438 -28.589  1.00 16.91           O
ATOM    180  N   ALA A  58       8.527  -2.743 -29.534  1.00 16.53           N
ATOM    181  CA  ALA A  58       8.954  -2.143 -28.286  1.00 16.57           C
ATOM    182  CB  ALA A  58      10.306  -1.484 -28.431  1.00 17.10           C
ATOM    183  C   ALA A  58       7.912  -1.127 -27.767  1.00 15.97           C
ATOM    184  O   ALA A  58       7.657  -1.090 -26.588  1.00 16.74           O
ATOM    185  N   GLU A  59       7.302  -0.348 -28.662  1.00 15.36           N
ATOM    186  CA  GLU A  59       6.347   0.713 -28.292  1.00 16.46           C
ATOM    187  CB  GLU A  59       6.056   1.639 -29.484  1.00 16.74           C
ATOM    188  CG  GLU A  59       7.061   2.735 -29.674  1.00 23.93           C
ATOM    189  CD  GLU A  59       6.979   3.362 -31.083  1.00 25.50           C
ATOM    190  OE1 GLU A  59       6.019   3.066 -31.846  1.00 28.68           O
ATOM    191  OE2 GLU A  59       7.883   4.159 -31.412  1.00 32.54           O
ATOM    192  C   GLU A  59       5.015   0.167 -27.867  1.00 14.93           C
ATOM    193  O   GLU A  59       4.298   0.807 -27.116  1.00 14.81           O
ATOM    194  N   GLY A  60       4.700  -1.029 -28.342  1.00 14.76           N
ATOM    195  CA  GLY A  60       3.366  -1.540 -28.202  1.00 13.61           C
ATOM    196  C   GLY A  60       3.124  -2.295 -26.908  1.00 14.10           C
ATOM    197  O   GLY A  60       2.017  -2.726 -26.662  1.00 13.73           O
ATOM    198  N   THR A  61       4.157  -2.483 -26.093  1.00 14.32           N
ATOM    199  CA  THR A  61       3.983  -3.158 -24.807  1.00 14.02           C
ATOM    200  CB  THR A  61       4.991  -4.352 -24.651  1.00 14.67           C
ATOM    201  OG1 THR A  61       4.762  -5.053 -23.399  1.00 14.11           O
ATOM    202  CG2 THR A  61       6.405  -3.893 -24.747  1.00 13.04           C
ATOM    203  C   THR A  61       4.130  -2.109 -23.713  1.00 15.01           C
ATOM    204  O   THR A  61       4.967  -1.200 -23.813  1.00 15.31           O
ATOM    205  N   SER A  62       3.313  -2.229 -22.673  1.00 14.36           N
ATOM    206  CA  SER A  62       3.343  -1.305 -21.571  1.00 14.86           C
ATOM    207  CB  SER A  62       2.005  -0.556 -21.461  1.00 14.40           C
ATOM    208  OG  SER A  62       1.990   0.167 -20.223  1.00 16.65           O
ATOM    209  C   SER A  62       3.544  -2.111 -20.299  1.00 14.22           C
```

FIGURE 2-3 (COORDINATES)

```
ATOM    210  O    SER A  62       2.658  -2.856 -19.888  1.00 12.99           O
ATOM    211  N    ILE A  63       4.694  -1.918 -19.654  1.00 15.13           N
ATOM    212  CA   ILE A  63       4.990  -2.615 -18.426  1.00 16.30           C
ATOM    213  CB   ILE A  63       6.499  -2.444 -18.021  1.00 17.10           C
ATOM    214  CG1  ILE A  63       6.868  -3.371 -16.850  1.00 15.31           C
ATOM    215  CD1  ILE A  63       6.779  -4.863 -17.216  1.00 14.41           C
ATOM    216  CG2  ILE A  63       6.809  -0.987 -17.668  1.00 17.36           C
ATOM    217  C    ILE A  63       4.005  -2.232 -17.316  1.00 16.55           C
ATOM    218  O    ILE A  63       3.589  -3.086 -16.536  1.00 16.26           O
ATOM    219  N    SER A  64       3.582  -0.957 -17.292  1.00 15.87           N
ATOM    220  CA   SER A  64       2.741  -0.471 -16.215  1.00 17.36           C
ATOM    221  CB   SER A  64       2.810   1.061 -16.128  1.00 17.74           C
ATOM    222  OG   SER A  64       2.348   1.622 -17.346  1.00 22.43           O
ATOM    223  C    SER A  64       1.291  -0.962 -16.372  1.00 15.86           C
ATOM    224  O    SER A  64       0.596  -1.240 -15.378  1.00 16.31           O
ATOM    225  N    GLU A  65       0.843  -1.098 -17.611  1.00 15.30           N
ATOM    226  CA   GLU A  65      -0.467  -1.669 -17.882  1.00 14.57           C
ATOM    227  CB   GLU A  65      -0.902  -1.455 -19.330  1.00 15.23           C
ATOM    228  CG   GLU A  65      -1.265   0.008 -19.630  1.00 17.50           C
ATOM    229  CD   GLU A  65      -1.784   0.239 -21.058  1.00 25.08           C
ATOM    230  OE1  GLU A  65      -1.311  -0.433 -21.990  1.00 27.27           O
ATOM    231  OE2  GLU A  65      -2.666   1.103 -21.236  1.00 27.72           O
ATOM    232  C    GLU A  65      -0.388  -3.158 -17.558  1.00 14.39           C
ATOM    233  O    GLU A  65      -1.260  -3.675 -16.874  1.00 13.95           O
ATOM    234  N    MET A  66       0.685  -3.837 -17.982  1.00 13.45           N
ATOM    235  CA   MET A  66       0.792  -5.241 -17.543  1.00 13.34           C
ATOM    236  CB   MET A  66       2.066  -5.899 -18.039  1.00 14.02           C
ATOM    237  CG   MET A  66       2.121  -7.384 -17.578  1.00 11.95           C
ATOM    238  SD   MET A  66       3.840  -7.912 -17.592  1.00 17.26           S
ATOM    239  CE   MET A  66       4.360  -7.350 -15.995  1.00 17.37           C
ATOM    240  C    MET A  66       0.744  -5.304 -16.013  1.00 13.83           C
ATOM    241  O    MET A  66       0.042  -6.119 -15.430  1.00 13.80           O
ATOM    242  N    TRP A  67       1.521  -4.438 -15.379  1.00 13.63           N
ATOM    243  CA   TRP A  67       1.645  -4.480 -13.941  1.00 15.86           C
ATOM    244  CB   TRP A  67       2.514  -3.348 -13.464  1.00 13.35           C
ATOM    245  CG   TRP A  67       3.302  -3.699 -12.243  1.00 16.15           C
ATOM    246  CD1  TRP A  67       2.889  -3.640 -10.960  1.00 16.55           C
ATOM    247  NE1  TRP A  67       3.919  -4.025 -10.109  1.00 18.28           N
ATOM    248  CE2  TRP A  67       5.011  -4.354 -10.869  1.00 17.76           C
ATOM    249  CD2  TRP A  67       4.663  -4.153 -12.216  1.00 15.44           C
ATOM    250  CE3  TRP A  67       5.609  -4.426 -13.209  1.00 18.73           C
ATOM    251  CZ3  TRP A  67       6.861  -4.887 -12.826  1.00 19.01           C
ATOM    252  CH2  TRP A  67       7.188  -5.049 -11.481  1.00 19.83           C
ATOM    253  CZ2  TRP A  67       6.276  -4.796 -10.483  1.00 19.32           C
ATOM    254  C    TRP A  67       0.280  -4.334 -13.308  1.00 15.78           C
ATOM    255  O    TRP A  67      -0.090  -5.112 -12.452  1.00 17.24           O
ATOM    256  N    GLN A  68      -0.434  -3.286 -13.692  1.00 17.24           N
ATOM    257  CA   GLN A  68      -1.705  -2.991 -13.071  1.00 17.07           C
ATOM    258  CB   GLN A  68      -2.195  -1.591 -13.462  1.00 17.79           C
ATOM    259  CG   GLN A  68      -3.255  -1.012 -12.510  1.00 22.82           C
ATOM    260  CD   GLN A  68      -2.812  -1.029 -11.042  1.00 26.41           C
ATOM    261  OE1  GLN A  68      -3.594  -1.363 -10.150  1.00 32.13           O
ATOM    262  NE2  GLN A  68      -1.559  -0.698 -10.793  1.00 29.28           N
ATOM    263  C    GLN A  68      -2.746  -4.028 -13.430  1.00 16.64           C
ATOM    264  O    GLN A  68      -3.437  -4.555 -12.557  1.00 17.00           O
ATOM    265  N    ASN A  69      -2.835  -4.379 -14.701  1.00 15.46           N
ATOM    266  CA   ASN A  69      -3.964  -5.160 -15.165  1.00 16.06           C
ATOM    267  CB   ASN A  69      -4.452  -4.647 -16.506  1.00 15.60           C
ATOM    268  CG   ASN A  69      -4.762  -3.171 -16.456  1.00 19.56           C
ATOM    269  OD1  ASN A  69      -5.298  -2.695 -15.458  1.00 18.72           O
ATOM    270  ND2  ASN A  69      -4.378  -2.441 -17.500  1.00 19.10           N
ATOM    271  C    ASN A  69      -3.741  -6.635 -15.261  1.00 14.80           C
ATOM    272  O    ASN A  69      -4.683  -7.402 -15.180  1.00 15.87           O
ATOM    273  N    ASP A  70      -2.501  -7.048 -15.450  1.00 15.29           N
ATOM    274  CA   ASP A  70      -2.234  -8.471 -15.625  1.00 15.59           C
ATOM    275  CB   ASP A  70      -1.383  -8.718 -16.869  1.00 15.89           C
ATOM    276  CG   ASP A  70      -2.177  -8.540 -18.141  1.00 17.90           C
ATOM    277  OD1  ASP A  70      -3.296  -9.071 -18.192  1.00 19.62           O
ATOM    278  OD2  ASP A  70      -1.689  -7.890 -19.079  1.00 22.94           O
ATOM    279  C    ASP A  70      -1.558  -9.080 -14.429  1.00 15.05           C
```

FIGURE 2-4 (COORDINATES)

```
ATOM    280  O   ASP A  70      -1.878 -10.185 -14.021  1.00 15.83           O
ATOM    281  N   LEU A  71      -0.584  -8.368 -13.898  1.00 14.67           N
ATOM    282  CA  LEU A  71       0.260  -8.927 -12.862  1.00 14.89           C
ATOM    283  CB  LEU A  71       1.617  -8.257 -12.912  1.00 14.51           C
ATOM    284  CG  LEU A  71       2.520  -8.604 -11.723  1.00 14.88           C
ATOM    285  CD1 LEU A  71       2.837 -10.122 -11.711  1.00 13.77           C
ATOM    286  CD2 LEU A  71       3.767  -7.745 -11.788  1.00 18.77           C
ATOM    287  C   LEU A  71      -0.338  -8.813 -11.456  1.00 15.48           C
ATOM    288  O   LEU A  71      -0.499  -9.828 -10.736  1.00 14.62           O
ATOM    289  N   ARG A  72      -0.681  -7.593 -11.062  1.00 15.33           N
ATOM    290  CA  ARG A  72      -1.176  -7.366  -9.681  1.00 15.61           C
ATOM    291  CB  ARG A  72      -1.541  -5.899  -9.474  1.00 16.75           C
ATOM    292  CG  ARG A  72      -0.324  -5.110  -9.149  1.00 15.23           C
ATOM    293  CD  ARG A  72      -0.583  -3.639  -9.147  1.00 21.30           C
ATOM    294  NE  ARG A  72       0.583  -3.007  -8.547  1.00 21.71           N
ATOM    295  CZ  ARG A  72       0.689  -1.721  -8.272  1.00 23.13           C
ATOM    296  NH1 ARG A  72      -0.335  -0.916  -8.514  1.00 24.46           N
ATOM    297  NH2 ARG A  72       1.807  -1.270  -7.707  1.00 24.04           N
ATOM    298  C   ARG A  72      -2.338  -8.264  -9.237  1.00 16.52           C
ATOM    299  O   ARG A  72      -2.301  -8.792  -8.111  1.00 16.39           O
ATOM    300  N   PRO A  73      -3.343  -8.496 -10.116  1.00 16.08           N
ATOM    301  CA  PRO A  73      -4.394  -9.408  -9.675  1.00 15.81           C
ATOM    302  CB  PRO A  73      -5.399  -9.385 -10.844  1.00 16.44           C
ATOM    303  CG  PRO A  73      -5.144  -8.013 -11.509  1.00 15.12           C
ATOM    304  CD  PRO A  73      -3.629  -7.954 -11.459  1.00 15.30           C
ATOM    305  C   PRO A  73      -3.898 -10.858  -9.455  1.00 16.34           C
ATOM    306  O   PRO A  73      -4.594 -11.630  -8.832  1.00 15.92           O
ATOM    307  N   LEU A  74      -2.728 -11.213  -9.995  1.00 15.74           N
ATOM    308  CA  LEU A  74      -2.097 -12.517  -9.749  1.00 14.83           C
ATOM    309  CB  LEU A  74      -1.180 -12.910 -10.915  1.00 13.34           C
ATOM    310  CG  LEU A  74      -1.895 -13.230 -12.200  1.00 15.08           C
ATOM    311  CD1 LEU A  74      -0.869 -13.479 -13.284  1.00 15.85           C
ATOM    312  CD2 LEU A  74      -2.781 -14.448 -12.020  1.00 19.54           C
ATOM    313  C   LEU A  74      -1.240 -12.566  -8.503  1.00 15.44           C
ATOM    314  O   LEU A  74      -0.867 -13.675  -8.087  1.00 16.56           O
ATOM    315  N   LEU A  75      -0.905 -11.416  -7.921  1.00 15.52           N
ATOM    316  CA  LEU A  75      -0.015 -11.384  -6.733  1.00 15.36           C
ATOM    317  CB  LEU A  75       0.778 -10.093  -6.682  1.00 16.05           C
ATOM    318  CG  LEU A  75       1.687  -9.946  -7.917  1.00 14.83           C
ATOM    319  CD1 LEU A  75       2.132  -8.494  -8.085  1.00 15.87           C
ATOM    320  CD2 LEU A  75       2.865 -10.885  -7.703  1.00 18.28           C
ATOM    321  C   LEU A  75      -0.753 -11.729  -5.421  1.00 15.90           C
ATOM    322  O   LEU A  75      -0.818 -10.981  -4.444  1.00 15.13           O
ATOM    323  N   ILE A  76      -1.293 -12.929  -5.437  1.00 15.79           N
ATOM    324  CA  ILE A  76      -2.124 -13.415  -4.363  1.00 15.67           C
ATOM    325  CB  ILE A  76      -3.610 -13.350  -4.728  1.00 15.92           C
ATOM    326  CG1 ILE A  76      -3.879 -14.115  -6.029  1.00 14.68           C
ATOM    327  CD1 ILE A  76      -5.331 -14.255  -6.450  1.00 18.73           C
ATOM    328  CG2 ILE A  76      -4.085 -11.872  -4.827  1.00 18.73           C
ATOM    329  C   ILE A  76      -1.714 -14.855  -4.155  1.00 16.17           C
ATOM    330  O   ILE A  76      -1.195 -15.534  -5.063  1.00 16.64           O
ATOM    331  N   GLU A  77      -2.014 -15.373  -2.983  1.00 14.73           N
ATOM    332  CA  GLU A  77      -1.764 -16.766  -2.773  1.00 15.91           C
ATOM    333  CB  GLU A  77      -1.990 -17.088  -1.305  1.00 15.14           C
ATOM    334  CG  GLU A  77      -1.805 -18.546  -0.964  1.00 18.50           C
ATOM    335  CD  GLU A  77      -1.995 -18.767   0.508  1.00 22.40           C
ATOM    336  OE1 GLU A  77      -2.946 -18.187   1.079  1.00 21.97           O
ATOM    337  OE2 GLU A  77      -1.184 -19.505   1.077  1.00 23.32           O
ATOM    338  C   GLU A  77      -2.685 -17.547  -3.688  1.00 14.31           C
ATOM    339  O   GLU A  77      -3.905 -17.339  -3.720  1.00 15.22           O
ATOM    340  N   ARG A  78      -2.118 -18.437  -4.487  1.00 14.35           N
ATOM    341  CA  ARG A  78      -2.906 -19.149  -5.441  1.00 13.93           C
ATOM    342  CB  ARG A  78      -2.897 -18.417  -6.813  1.00 14.40           C
ATOM    343  CG  ARG A  78      -1.452 -18.192  -7.319  1.00  9.79           C
ATOM    344  CD  ARG A  78      -1.378 -17.079  -8.435  1.00 10.34           C
ATOM    345  NE  ARG A  78      -0.003 -17.056  -8.938  1.00 11.66           N
ATOM    346  CZ  ARG A  78       1.001 -16.477  -8.285  1.00 12.83           C
ATOM    347  NH1 ARG A  78       0.777 -15.815  -7.133  1.00  8.54           N
ATOM    348  NH2 ARG A  78       2.245 -16.567  -8.741  1.00  8.82           N
ATOM    349  C   ARG A  78      -2.355 -20.560  -5.572  1.00 14.20           C
```

FIGURE 2-5 (COORDINATES)

```
ATOM   350  O    ARG A  78      -2.179 -21.075  -6.654  1.00 11.91           O
ATOM   351  N    TYR A  79      -2.052 -21.208  -4.454  1.00 14.62           N
ATOM   352  CA   TYR A  79      -1.675 -22.611  -4.591  1.00 15.82           C
ATOM   353  CB   TYR A  79      -1.050 -23.124  -3.327  1.00 14.55           C
ATOM   354  CG   TYR A  79      -1.924 -23.140  -2.112  1.00 15.41           C
ATOM   355  CD1  TYR A  79      -1.947 -22.053  -1.227  1.00 16.49           C
ATOM   356  CE1  TYR A  79      -2.706 -22.098  -0.067  1.00 18.82           C
ATOM   357  CZ   TYR A  79      -3.449 -23.219   0.224  1.00 16.91           C
ATOM   358  OH   TYR A  79      -4.182 -23.275   1.414  1.00 16.84           O
ATOM   359  CE2  TYR A  79      -3.458 -24.297  -0.651  1.00 15.86           C
ATOM   360  CD2  TYR A  79      -2.689 -24.260  -1.805  1.00 15.46           C
ATOM   361  C    TYR A  79      -2.941 -23.377  -4.960  1.00 15.65           C
ATOM   362  O    TYR A  79      -4.028 -22.854  -4.761  1.00 15.39           O
ATOM   363  N    PRO A  80      -2.804 -24.589  -5.536  1.00 16.07           N
ATOM   364  CA   PRO A  80      -4.009 -25.252  -6.045  1.00 16.62           C
ATOM   365  CB   PRO A  80      -3.491 -26.611  -6.567  1.00 15.76           C
ATOM   366  CG   PRO A  80      -2.064 -26.359  -6.869  1.00 17.10           C
ATOM   367  CD   PRO A  80      -1.592 -25.388  -5.803  1.00 15.98           C
ATOM   368  C    PRO A  80      -5.103 -25.459  -5.002  1.00 16.47           C
ATOM   369  O    PRO A  80      -4.838 -25.901  -3.874  1.00 15.64           O
ATOM   370  N    GLY A  81      -6.334 -25.144  -5.401  1.00 16.45           N
ATOM   371  CA   GLY A  81      -7.476 -25.244  -4.493  1.00 16.17           C
ATOM   372  C    GLY A  81      -7.680 -24.033  -3.599  1.00 15.73           C
ATOM   373  O    GLY A  81      -8.738 -23.872  -3.023  1.00 15.73           O
ATOM   374  N    SER A  82      -6.690 -23.159  -3.506  1.00 15.23           N
ATOM   375  CA   SER A  82      -6.874 -21.940  -2.766  1.00 15.75           C
ATOM   376  CB   SER A  82      -5.523 -21.251  -2.551  1.00 15.58           C
ATOM   377  OG   SER A  82      -5.069 -20.725  -3.785  1.00 14.29           O
ATOM   378  C    SER A  82      -7.892 -21.030  -3.487  1.00 16.44           C
ATOM   379  O    SER A  82      -8.082 -21.152  -4.697  1.00 17.30           O
ATOM   380  N    PRO A  83      -8.552 -20.116  -2.737  1.00 17.72           N
ATOM   381  CA   PRO A  83      -9.419 -19.083  -3.329  1.00 17.62           C
ATOM   382  CB   PRO A  83      -9.699 -18.132  -2.146  1.00 17.69           C
ATOM   383  CG   PRO A  83      -9.503 -18.975  -0.937  1.00 18.41           C
ATOM   384  CD   PRO A  83      -8.502 -20.027  -1.262  1.00 17.47           C
ATOM   385  C    PRO A  83      -8.697 -18.328  -4.443  1.00 17.60           C
ATOM   386  O    PRO A  83      -9.289 -18.034  -5.479  1.00 17.60           O
ATOM   387  N    GLY A  84      -7.414 -18.060  -4.210  1.00 17.13           N
ATOM   388  CA   GLY A  84      -6.592 -17.322  -5.106  1.00 16.68           C
ATOM   389  C    GLY A  84      -6.381 -18.078  -6.394  1.00 16.65           C
ATOM   390  O    GLY A  84      -6.219 -17.450  -7.425  1.00 17.30           O
ATOM   391  N    SER A  85      -6.385 -19.411  -6.345  1.00 15.66           N
ATOM   392  CA   SER A  85      -6.252 -20.234  -7.543  1.00 15.67           C
ATOM   393  CB   SER A  85      -6.184 -21.733  -7.166  1.00 16.55           C
ATOM   394  OG   SER A  85      -6.258 -22.581  -8.304  1.00 17.15           O
ATOM   395  C    SER A  85      -7.407 -19.949  -8.519  1.00 16.29           C
ATOM   396  O    SER A  85      -7.221 -19.747  -9.723  1.00 14.14           O
ATOM   397  N    TYR A  86      -8.607 -19.931  -7.977  1.00 16.63           N
ATOM   398  CA   TYR A  86      -9.785 -19.577  -8.742  1.00 17.32           C
ATOM   399  CB   TYR A  86     -11.032 -19.800  -7.878  1.00 18.92           C
ATOM   400  CG   TYR A  86     -12.281 -19.322  -8.555  1.00 21.53           C
ATOM   401  CD1  TYR A  86     -12.955 -20.135  -9.462  1.00 25.86           C
ATOM   402  CE1  TYR A  86     -14.112 -19.682 -10.121  1.00 27.02           C
ATOM   403  CZ   TYR A  86     -14.588 -18.410  -9.863  1.00 27.45           C
ATOM   404  OH   TYR A  86     -15.725 -17.972 -10.508  1.00 28.44           O
ATOM   405  CE2  TYR A  86     -13.939 -17.584  -8.961  1.00 25.26           C
ATOM   406  CD2  TYR A  86     -12.783 -18.038  -8.313  1.00 25.00           C
ATOM   407  C    TYR A  86      -9.723 -18.142  -9.281  1.00 17.11           C
ATOM   408  O    TYR A  86     -10.001 -17.921 -10.457  1.00 17.60           O
ATOM   409  N    SER A  87      -9.370 -17.181  -8.422  1.00 16.99           N
ATOM   410  CA   SER A  87      -9.321 -15.763  -8.807  1.00 17.11           C
ATOM   411  CB   SER A  87      -8.889 -14.929  -7.628  1.00 17.30           C
ATOM   412  OG   SER A  87      -9.927 -15.008  -6.629  1.00 24.96           O
ATOM   413  C    SER A  87      -8.303 -15.610  -9.913  1.00 14.46           C
ATOM   414  O    SER A  87      -8.534 -14.965 -10.905  1.00 14.86           O
ATOM   415  N    ALA A  88      -7.193 -16.297  -9.747  1.00 14.13           N
ATOM   416  CA   ALA A  88      -6.095 -16.185 -10.678  1.00 13.63           C
ATOM   417  CB   ALA A  88      -4.877 -16.898 -10.132  1.00 12.68           C
ATOM   418  C    ALA A  88      -6.540 -16.758 -12.024  1.00 13.92           C
ATOM   419  O    ALA A  88      -6.309 -16.138 -13.052  1.00 13.58           O
```

FIGURE 2-6 (COORDINATES)

```
ATOM   420  N   ARG A  89      -7.183 -17.927 -12.003  1.00 13.41           N
ATOM   421  CA  ARG A  89      -7.651 -18.596 -13.191  1.00 13.14           C
ATOM   422  CB  ARG A  89      -8.211 -19.961 -12.821  1.00 13.92           C
ATOM   423  CG  ARG A  89      -8.751 -20.768 -14.020  1.00 15.00           C
ATOM   424  CD  ARG A  89      -8.852 -22.235 -13.597  1.00 17.26           C
ATOM   425  NE  ARG A  89      -9.753 -22.410 -12.468  1.00 14.94           N
ATOM   426  CZ  ARG A  89      -9.388 -22.649 -11.210  1.00 15.41           C
ATOM   427  NH1 ARG A  89      -8.110 -22.674 -10.853  1.00 16.25           N
ATOM   428  NH2 ARG A  89     -10.333 -22.810 -10.276  1.00 18.83           N
ATOM   429  C   ARG A  89      -8.682 -17.726 -13.925  1.00 13.53           C
ATOM   430  O   ARG A  89      -8.574 -17.486 -15.135  1.00 13.64           O
ATOM   431  N   GLN A  90      -9.643 -17.206 -13.181  1.00 13.67           N
ATOM   432  CA  GLN A  90     -10.636 -16.289 -13.740  1.00 14.23           C
ATOM   433  CB  GLN A  90     -11.643 -15.887 -12.653  1.00 15.75           C
ATOM   434  CG  GLN A  90     -12.480 -17.104 -12.183  1.00 20.17           C
ATOM   435  CD  GLN A  90     -13.125 -17.842 -13.376  1.00 26.23           C
ATOM   436  OE1 GLN A  90     -13.654 -17.210 -14.311  1.00 31.43           O
ATOM   437  NE2 GLN A  90     -13.063 -19.177 -13.360  1.00 30.89           N
ATOM   438  C   GLN A  90      -9.993 -15.041 -14.359  1.00 13.46           C
ATOM   439  O   GLN A  90     -10.380 -14.618 -15.435  1.00 12.41           O
ATOM   440  N   HIS A  91      -9.037 -14.457 -13.650  1.00 12.61           N
ATOM   441  CA  HIS A  91      -8.345 -13.299 -14.131  1.00 12.73           C
ATOM   442  CB  HIS A  91      -7.321 -12.883 -13.110  1.00 12.62           C
ATOM   443  CG  HIS A  91      -6.292 -11.933 -13.628  1.00 13.82           C
ATOM   444  ND1 HIS A  91      -6.602 -10.656 -14.057  1.00 14.71           N
ATOM   445  CE1 HIS A  91      -5.495 -10.050 -14.442  1.00 15.61           C
ATOM   446  NE2 HIS A  91      -4.472 -10.864 -14.233  1.00 13.94           N
ATOM   447  CD2 HIS A  91      -4.944 -12.054 -13.734  1.00 14.36           C
ATOM   448  C   HIS A  91      -7.663 -13.606 -15.449  1.00 12.85           C
ATOM   449  O   HIS A  91      -7.868 -12.909 -16.456  1.00 11.50           O
ATOM   450  N   ILE A  92      -6.848 -14.650 -15.448  1.00 12.73           N
ATOM   451  CA  ILE A  92      -6.165 -15.056 -16.687  1.00 12.81           C
ATOM   452  CB  ILE A  92      -5.391 -16.383 -16.500  1.00 11.97           C
ATOM   453  CG1 ILE A  92      -4.212 -16.156 -15.546  1.00 13.61           C
ATOM   454  CD1 ILE A  92      -3.587 -17.448 -15.020  1.00 10.03           C
ATOM   455  CG2 ILE A  92      -4.949 -16.990 -17.898  1.00 12.22           C
ATOM   456  C   ILE A  92      -7.150 -15.191 -17.818  1.00 12.73           C
ATOM   457  O   ILE A  92      -6.974 -14.642 -18.885  1.00 12.07           O
ATOM   458  N   MET A  93      -8.236 -15.916 -17.581  1.00 12.88           N
ATOM   459  CA  MET A  93      -9.173 -16.144 -18.635  1.00 14.08           C
ATOM   460  CB  MET A  93     -10.166 -17.232 -18.224  1.00 13.96           C
ATOM   461  CG  MET A  93      -9.435 -18.531 -18.034  1.00 17.00           C
ATOM   462  SD  MET A  93     -10.547 -19.866 -17.710  1.00 23.60           S
ATOM   463  CE  MET A  93     -11.229 -19.362 -16.171  1.00 15.35           C
ATOM   464  C   MET A  93      -9.883 -14.868 -19.058  1.00 13.86           C
ATOM   465  O   MET A  93     -10.107 -14.633 -20.253  1.00 13.85           O
ATOM   466  N   GLN A  94     -10.234 -14.050 -18.087  1.00 15.36           N
ATOM   467  CA  GLN A  94     -10.861 -12.746 -18.396  1.00 16.31           C
ATOM   468  CB  GLN A  94     -11.171 -11.993 -17.109  1.00 16.72           C
ATOM   469  CG  GLN A  94     -11.906 -10.590 -17.250  1.00 19.96           C
ATOM   470  CD  GLN A  94     -10.985  -9.348 -17.547  1.00 25.57           C
ATOM   471  OE1 GLN A  94      -9.808  -9.281 -17.138  1.00 27.66           O
ATOM   472  NE2 GLN A  94     -11.553  -8.358 -18.249  1.00 25.98           N
ATOM   473  C   GLN A  94      -9.943 -11.922 -19.284  1.00 16.50           C
ATOM   474  O   GLN A  94     -10.396 -11.346 -20.282  1.00 16.78           O
ATOM   475  N   ARG A  95      -8.666 -11.872 -18.917  1.00 16.25           N
ATOM   476  CA  ARG A  95      -7.724 -11.055 -19.646  1.00 15.19           C
ATOM   477  CB  ARG A  95      -6.346 -10.967 -18.940  1.00 13.32           C
ATOM   478  CG  ARG A  95      -6.425 -10.222 -17.590  1.00 13.25           C
ATOM   479  CD  ARG A  95      -6.815  -8.744 -17.783  1.00 11.84           C
ATOM   480  NE  ARG A  95      -5.735  -8.080 -18.512  1.00 12.76           N
ATOM   481  CZ  ARG A  95      -5.783  -6.839 -18.956  1.00 15.99           C
ATOM   482  NH1 ARG A  95      -6.884  -6.106 -18.756  1.00 17.10           N
ATOM   483  NH2 ARG A  95      -4.745  -6.347 -19.606  1.00 18.37           N
ATOM   484  C   ARG A  95      -7.576 -11.546 -21.060  1.00 15.36           C
ATOM   485  O   ARG A  95      -7.378 -10.751 -21.974  1.00 16.56           O
ATOM   486  N   ILE A  96      -7.659 -12.854 -21.257  1.00 14.45           N
ATOM   487  CA  ILE A  96      -7.529 -13.375 -22.584  1.00 14.41           C
ATOM   488  CB  ILE A  96      -7.285 -14.896 -22.565  1.00 13.44           C
ATOM   489  CG1 ILE A  96      -5.839 -15.141 -22.106  1.00 16.10           C
```

FIGURE 2-7 (COORDINATES)

```
ATOM    490  CD1 ILE A  96      -5.604 -16.431 -21.442  1.00 19.40           C
ATOM    491  CG2 ILE A  96      -7.358 -15.424 -23.953  1.00 13.06           C
ATOM    492  C   ILE A  96      -8.779 -13.078 -23.375  1.00 15.82           C
ATOM    493  O   ILE A  96      -8.700 -12.665 -24.541  1.00 16.29           O
ATOM    494  N   GLN A  97      -9.918 -13.322 -22.737  1.00 15.53           N
ATOM    495  CA  GLN A  97     -11.215 -13.242 -23.389  1.00 16.87           C
ATOM    496  CB  GLN A  97     -12.288 -13.819 -22.445  1.00 17.50           C
ATOM    497  CG  GLN A  97     -12.320 -15.383 -22.525  1.00 22.26           C
ATOM    498  CD  GLN A  97     -12.806 -16.076 -21.239  1.00 29.13           C
ATOM    499  OE1 GLN A  97     -12.936 -15.438 -20.179  1.00 34.46           O
ATOM    500  NE2 GLN A  97     -13.068 -17.398 -21.324  1.00 30.04           N
ATOM    501  C   GLN A  97     -11.551 -11.817 -23.825  1.00 16.02           C
ATOM    502  O   GLN A  97     -12.280 -11.638 -24.783  1.00 17.08           O
ATOM    503  N   ARG A  98     -11.042 -10.822 -23.114  1.00 15.64           N
ATOM    504  CA  ARG A  98     -11.306  -9.421 -23.452  1.00 15.96           C
ATOM    505  CB  ARG A  98     -10.901  -8.488 -22.304  1.00 15.06           C
ATOM    506  CG  ARG A  98      -9.373  -8.458 -22.051  1.00 14.19           C
ATOM    507  CD  ARG A  98      -8.980  -7.449 -21.004  1.00 18.53           C
ATOM    508  NE  ARG A  98      -9.247  -6.104 -21.517  1.00 20.20           N
ATOM    509  CZ  ARG A  98      -8.394  -5.422 -22.270  1.00 23.97           C
ATOM    510  NH1 ARG A  98      -7.199  -5.943 -22.547  1.00 19.19           N
ATOM    511  NH2 ARG A  98      -8.727  -4.220 -22.745  1.00 23.68           N
ATOM    512  C   ARG A  98     -10.573  -8.997 -24.718  1.00 16.61           C
ATOM    513  O   ARG A  98     -10.810  -7.904 -25.246  1.00 16.83           O
ATOM    514  N   LEU A  99      -9.667  -9.838 -25.204  1.00 16.77           N
ATOM    515  CA  LEU A  99      -8.863  -9.492 -26.380  1.00 16.94           C
ATOM    516  CB  LEU A  99      -7.549 -10.283 -26.390  1.00 15.86           C
ATOM    517  CG  LEU A  99      -6.681  -9.869 -25.194  1.00 13.45           C
ATOM    518  CD1 LEU A  99      -5.453 -10.809 -25.167  1.00  9.09           C
ATOM    519  CD2 LEU A  99      -6.293  -8.366 -25.290  1.00 15.25           C
ATOM    520  C   LEU A  99      -9.604  -9.713 -27.672  1.00 17.28           C
ATOM    521  O   LEU A  99     -10.615 -10.416 -27.721  1.00 18.18           O
ATOM    522  N   GLN A 100      -9.119  -9.094 -28.736  1.00 17.41           N
ATOM    523  CA  GLN A 100      -9.798  -9.230 -30.015  1.00 17.34           C
ATOM    524  CB  GLN A 100      -9.501  -8.052 -30.988  1.00 18.72           C
ATOM    525  CG  GLN A 100      -9.927  -6.714 -30.435  1.00 19.98           C
ATOM    526  CD  GLN A 100     -11.399  -6.684 -30.077  1.00 23.20           C
ATOM    527  OE1 GLN A 100     -12.250  -7.079 -30.874  1.00 25.87           O
ATOM    528  NE2 GLN A 100     -11.703  -6.262 -28.859  1.00 25.31           N
ATOM    529  C   GLN A 100      -9.480 -10.514 -30.689  1.00 16.94           C
ATOM    530  O   GLN A 100     -10.364 -11.079 -31.340  1.00 15.87           O
ATOM    531  N   ALA A 101      -8.233 -10.994 -30.572  1.00 15.70           N
ATOM    532  CA  ALA A 101      -7.884 -12.278 -31.150  1.00 15.91           C
ATOM    533  CB  ALA A 101      -6.431 -12.655 -30.891  1.00 16.01           C
ATOM    534  C   ALA A 101      -8.817 -13.338 -30.610  1.00 16.81           C
ATOM    535  O   ALA A 101      -9.295 -13.242 -29.489  1.00 16.90           O
ATOM    536  N   GLU A 102      -9.029 -14.351 -31.421  1.00 18.49           N
ATOM    537  CA  GLU A 102     -10.100 -15.301 -31.203  1.00 19.51           C
ATOM    538  CB  GLU A 102     -10.629 -15.771 -32.542  1.00 21.02           C
ATOM    539  CG  GLU A 102     -11.011 -14.591 -33.441  1.00 24.60           C
ATOM    540  CD  GLU A 102     -11.818 -15.015 -34.646  1.00 31.32           C
ATOM    541  OE1 GLU A 102     -11.688 -16.183 -35.087  1.00 31.11           O
ATOM    542  OE2 GLU A 102     -12.597 -14.176 -35.140  1.00 34.01           O
ATOM    543  C   GLU A 102      -9.567 -16.457 -30.385  1.00 18.31           C
ATOM    544  O   GLU A 102      -9.574 -17.595 -30.810  1.00 19.04           O
ATOM    545  N   TRP A 103      -9.095 -16.118 -29.197  1.00 18.21           N
ATOM    546  CA  TRP A 103      -8.539 -17.079 -28.280  1.00 16.95           C
ATOM    547  CB  TRP A 103      -8.028 -16.363 -27.076  1.00 16.88           C
ATOM    548  CG  TRP A 103      -6.793 -15.630 -27.331  1.00 14.97           C
ATOM    549  CD1 TRP A 103      -6.654 -14.299 -27.534  1.00 15.18           C
ATOM    550  NE1 TRP A 103      -5.326 -13.995 -27.704  1.00 14.20           N
ATOM    551  CE2 TRP A 103      -4.593 -15.153 -27.651  1.00 11.65           C
ATOM    552  CD2 TRP A 103      -5.485 -16.197 -27.378  1.00 13.61           C
ATOM    553  CE3 TRP A 103      -4.990 -17.510 -27.262  1.00 13.38           C
ATOM    554  CZ3 TRP A 103      -3.614 -17.727 -27.361  1.00 12.30           C
ATOM    555  CH2 TRP A 103      -2.749 -16.655 -27.608  1.00 11.16           C
ATOM    556  CZ2 TRP A 103      -3.212 -15.351 -27.717  1.00 12.95           C
ATOM    557  C   TRP A 103      -9.633 -18.004 -27.851  1.00 16.74           C
ATOM    558  O   TRP A 103     -10.721 -17.572 -27.493  1.00 17.93           O
ATOM    559  N   VAL A 104      -9.350 -19.281 -27.923  1.00 16.36           N
```

FIGURE 2-8 (COORDINATES)

```
ATOM    560  CA   VAL A 104     -10.271 -20.273 -27.437  1.00 17.86           C
ATOM    561  CB   VAL A 104     -10.381 -21.447 -28.424  1.00 18.11           C
ATOM    562  CG1  VAL A 104     -11.191 -22.607 -27.788  1.00 19.33           C
ATOM    563  CG2  VAL A 104     -10.999 -20.949 -29.736  1.00 18.64           C
ATOM    564  C    VAL A 104      -9.691 -20.694 -26.094  1.00 17.80           C
ATOM    565  O    VAL A 104      -8.578 -21.206 -26.036  1.00 16.30           O
ATOM    566  N    VAL A 105     -10.435 -20.440 -25.029  1.00 18.36           N
ATOM    567  CA   VAL A 105      -9.953 -20.717 -23.697  1.00 18.84           C
ATOM    568  CB   VAL A 105     -10.259 -19.607 -22.733  1.00 19.75           C
ATOM    569  CG1  VAL A 105      -9.784 -19.974 -21.347  1.00 21.34           C
ATOM    570  CG2  VAL A 105      -9.596 -18.307 -23.176  1.00 20.92           C
ATOM    571  C    VAL A 105     -10.562 -22.005 -23.208  1.00 19.60           C
ATOM    572  O    VAL A 105     -11.761 -22.242 -23.392  1.00 19.73           O
ATOM    573  N    GLU A 106      -9.722 -22.882 -22.664  1.00 19.01           N
ATOM    574  CA   GLU A 106     -10.178 -24.146 -22.095  1.00 19.78           C
ATOM    575  CB   GLU A 106      -9.666 -25.318 -22.895  1.00 20.53           C
ATOM    576  CG   GLU A 106     -10.087 -25.375 -24.311  1.00 25.72           C
ATOM    577  CD   GLU A 106      -9.345 -26.442 -25.063  1.00 31.46           C
ATOM    578  OE1  GLU A 106     -10.030 -27.380 -25.515  1.00 38.32           O
ATOM    579  OE2  GLU A 106      -8.083 -26.364 -25.200  1.00 34.46           O
ATOM    580  C    GLU A 106      -9.518 -24.275 -20.757  1.00 19.83           C
ATOM    581  O    GLU A 106      -8.388 -23.842 -20.592  1.00 19.47           O
ATOM    582  N    VAL A 107     -10.211 -24.903 -19.814  1.00 19.74           N
ATOM    583  CA   VAL A 107      -9.609 -25.248 -18.531  1.00 21.19           C
ATOM    584  CB   VAL A 107     -10.432 -24.693 -17.388  1.00 21.58           C
ATOM    585  CG1  VAL A 107      -9.784 -24.999 -16.078  1.00 21.14           C
ATOM    586  CG2  VAL A 107     -10.608 -23.178 -17.568  1.00 24.12           C
ATOM    587  C    VAL A 107      -9.560 -26.772 -18.464  1.00 22.08           C
ATOM    588  O    VAL A 107     -10.579 -27.421 -18.669  1.00 23.19           O
ATOM    589  N    ASP A 108      -8.359 -27.321 -18.268  1.00 21.07           N
ATOM    590  CA   ASP A 108      -8.146 -28.723 -18.083  1.00 20.83           C
ATOM    591  CB   ASP A 108      -6.820 -29.107 -18.722  1.00 21.07           C
ATOM    592  CG   ASP A 108      -6.330 -30.428 -18.276  1.00 23.02           C
ATOM    593  OD1  ASP A 108      -7.157 -31.375 -18.204  1.00 20.71           O
ATOM    594  OD2  ASP A 108      -5.122 -30.533 -17.975  1.00 19.30           O
ATOM    595  C    ASP A 108      -8.130 -28.988 -16.573  1.00 19.89           C
ATOM    596  O    ASP A 108      -7.075 -28.850 -15.932  1.00 16.82           O
ATOM    597  N    THR A 109      -9.301 -29.343 -16.023  1.00 19.49           N
ATOM    598  CA   THR A 109      -9.467 -29.570 -14.590  1.00 18.73           C
ATOM    599  CB   THR A 109     -10.746 -28.923 -14.023  1.00 19.42           C
ATOM    600  OG1  THR A 109     -10.686 -27.509 -14.235  1.00 19.69           O
ATOM    601  CG2  THR A 109     -10.884 -29.184 -12.489  1.00 18.10           C
ATOM    602  C    THR A 109      -9.494 -31.066 -14.303  1.00 18.44           C
ATOM    603  O    THR A 109     -10.157 -31.828 -15.006  1.00 17.19           O
ATOM    604  N    PHE A 110      -8.789 -31.477 -13.257  1.00 17.82           N
ATOM    605  CA   PHE A 110      -8.646 -32.901 -12.930  1.00 18.40           C
ATOM    606  CB   PHE A 110      -7.565 -33.562 -13.767  1.00 17.07           C
ATOM    607  CG   PHE A 110      -6.256 -32.859 -13.661  1.00 17.98           C
ATOM    608  CD1  PHE A 110      -5.275 -33.305 -12.770  1.00 14.66           C
ATOM    609  CE1  PHE A 110      -4.058 -32.624 -12.639  1.00 14.51           C
ATOM    610  CZ   PHE A 110      -3.843 -31.471 -13.386  1.00 15.03           C
ATOM    611  CE2  PHE A 110      -4.815 -31.011 -14.269  1.00 15.81           C
ATOM    612  CD2  PHE A 110      -6.031 -31.696 -14.388  1.00 17.88           C
ATOM    613  C    PHE A 110      -8.190 -32.944 -11.499  1.00 19.02           C
ATOM    614  O    PHE A 110      -7.784 -31.929 -10.934  1.00 19.56           O
ATOM    615  N    LEU A 111      -8.268 -34.139 -10.931  1.00 19.27           N
ATOM    616  CA   LEU A 111      -7.809 -34.405  -9.594  1.00 19.35           C
ATOM    617  CB   LEU A 111      -8.883 -35.152  -8.800  1.00 19.77           C
ATOM    618  CG   LEU A 111     -10.260 -34.511  -8.711  1.00 21.12           C
ATOM    619  CD1  LEU A 111     -11.232 -35.511  -8.007  1.00 24.40           C
ATOM    620  CD2  LEU A 111     -10.161 -33.242  -7.926  1.00 22.07           C
ATOM    621  C    LEU A 111      -6.575 -35.279  -9.682  1.00 19.09           C
ATOM    622  O    LEU A 111      -6.478 -36.193 -10.500  1.00 19.63           O
ATOM    623  N    SER A 112      -5.632 -35.008  -8.804  1.00 19.32           N
ATOM    624  CA   SER A 112      -4.444 -35.790  -8.818  1.00 18.69           C
ATOM    625  CB   SER A 112      -3.367 -35.087  -9.637  1.00 19.06           C
ATOM    626  OG   SER A 112      -2.303 -35.958  -9.916  1.00 23.88           O
ATOM    627  C    SER A 112      -4.057 -35.900  -7.383  1.00 18.39           C
ATOM    628  O    SER A 112      -4.291 -34.972  -6.576  1.00 16.65           O
ATOM    629  N    ARG A 113      -3.447 -37.030  -7.059  1.00 16.99           N
```

FIGURE 2-9 (COORDINATES)

```
ATOM    630  CA   ARG A 113      -3.014 -37.255  -5.703  1.00 18.53           C
ATOM    631  CB   ARG A 113      -2.828 -38.753  -5.470  1.00 19.09           C
ATOM    632  CG   ARG A 113      -2.110 -39.111  -4.226  1.00 23.33           C
ATOM    633  CD   ARG A 113      -2.409 -40.539  -3.770  1.00 29.73           C
ATOM    634  NE   ARG A 113      -3.350 -40.453  -2.659  1.00 35.31           N
ATOM    635  CZ   ARG A 113      -3.012 -40.056  -1.431  1.00 39.56           C
ATOM    636  NH1  ARG A 113      -3.937 -39.981  -0.472  1.00 40.22           N
ATOM    637  NH2  ARG A 113      -1.744 -39.728  -1.156  1.00 42.78           N
ATOM    638  C    ARG A 113      -1.754 -36.483  -5.406  1.00 17.50           C
ATOM    639  O    ARG A 113      -0.763 -36.568  -6.139  1.00 17.81           O
ATOM    640  N    THR A 114      -1.816 -35.708  -4.333  1.00 17.01           N
ATOM    641  CA   THR A 114      -0.688 -34.978  -3.833  1.00 16.09           C
ATOM    642  CB   THR A 114      -1.075 -33.514  -3.577  1.00 16.59           C
ATOM    643  OG1  THR A 114      -1.842 -33.446  -2.358  1.00 15.72           O
ATOM    644  CG2  THR A 114      -1.896 -32.933  -4.764  1.00 13.72           C
ATOM    645  C    THR A 114      -0.330 -35.537  -2.444  1.00 17.90           C
ATOM    646  O    THR A 114      -1.102 -36.326  -1.899  1.00 17.16           O
ATOM    647  N    PRO A 115       0.786 -35.067  -1.835  1.00 17.76           N
ATOM    648  CA   PRO A 115       1.027 -35.548  -0.460  1.00 19.32           C
ATOM    649  CB   PRO A 115       2.304 -34.806  -0.043  1.00 18.74           C
ATOM    650  CG   PRO A 115       3.013 -34.603  -1.294  1.00 18.90           C
ATOM    651  CD   PRO A 115       1.985 -34.424  -2.387  1.00 17.14           C
ATOM    652  C    PRO A 115      -0.099 -35.251   0.528  1.00 20.03           C
ATOM    653  O    PRO A 115      -0.124 -35.832   1.604  1.00 21.62           O
ATOM    654  N    TYR A 116      -1.031 -34.371   0.172  1.00 20.62           N
ATOM    655  CA   TYR A 116      -2.097 -33.978   1.089  1.00 21.19           C
ATOM    656  CB   TYR A 116      -2.311 -32.452   1.075  1.00 20.97           C
ATOM    657  CG   TYR A 116      -1.202 -31.708   1.749  1.00 22.32           C
ATOM    658  CD1  TYR A 116      -1.156 -31.623   3.135  1.00 27.66           C
ATOM    659  CE1  TYR A 116      -0.126 -30.943   3.779  1.00 28.68           C
ATOM    660  CZ   TYR A 116       0.872 -30.346   3.018  1.00 26.79           C
ATOM    661  OH   TYR A 116       1.901 -29.676   3.658  1.00 29.90           O
ATOM    662  CE2  TYR A 116       0.834 -30.414   1.644  1.00 22.31           C
ATOM    663  CD2  TYR A 116      -0.194 -31.085   1.014  1.00 19.30           C
ATOM    664  C    TYR A 116      -3.370 -34.688   0.731  1.00 21.40           C
ATOM    665  O    TYR A 116      -4.427 -34.440   1.341  1.00 22.10           O
ATOM    666  N    GLY A 117      -3.280 -35.587  -0.244  1.00 21.03           N
ATOM    667  CA   GLY A 117      -4.469 -36.238  -0.724  1.00 20.56           C
ATOM    668  C    GLY A 117      -4.816 -35.763  -2.117  1.00 21.33           C
ATOM    669  O    GLY A 117      -4.014 -35.081  -2.763  1.00 21.54           O
ATOM    670  N    TYR A 118      -6.003 -36.129  -2.598  1.00 20.67           N
ATOM    671  CA   TYR A 118      -6.392 -35.721  -3.930  1.00 20.08           C
ATOM    672  CB   TYR A 118      -7.522 -36.592  -4.475  1.00 21.99           C
ATOM    673  CG   TYR A 118      -7.003 -37.840  -5.210  1.00 23.20           C
ATOM    674  CD1  TYR A 118      -6.899 -37.849  -6.577  1.00 25.36           C
ATOM    675  CE1  TYR A 118      -6.422 -38.962  -7.277  1.00 27.72           C
ATOM    676  CZ   TYR A 118      -6.030 -40.090  -6.597  1.00 27.83           C
ATOM    677  OH   TYR A 118      -5.575 -41.163  -7.340  1.00 32.73           O
ATOM    678  CE2  TYR A 118      -6.120 -40.130  -5.215  1.00 28.09           C
ATOM    679  CD2  TYR A 118      -6.597 -38.996  -4.522  1.00 27.50           C
ATOM    680  C    TYR A 118      -6.725 -34.233  -3.915  1.00 18.52           C
ATOM    681  O    TYR A 118      -7.294 -33.718  -2.964  1.00 17.49           O
ATOM    682  N    ARG A 119      -6.280 -33.542  -4.960  1.00 18.01           N
ATOM    683  CA   ARG A 119      -6.518 -32.117  -5.088  1.00 16.60           C
ATOM    684  CB   ARG A 119      -5.257 -31.316  -4.748  1.00 15.64           C
ATOM    685  CG   ARG A 119      -4.849 -31.297  -3.297  1.00 16.58           C
ATOM    686  CD   ARG A 119      -5.901 -30.660  -2.454  1.00 14.85           C
ATOM    687  NE   ARG A 119      -5.487 -30.635  -1.064  1.00 17.05           N
ATOM    688  CZ   ARG A 119      -5.854 -31.554  -0.182  1.00 17.50           C
ATOM    689  NH1  ARG A 119      -6.636 -32.556  -0.568  1.00 20.09           N
ATOM    690  NH2  ARG A 119      -5.447 -31.463   1.071  1.00 18.72           N
ATOM    691  C    ARG A 119      -6.922 -31.836  -6.521  1.00 16.13           C
ATOM    692  O    ARG A 119      -6.547 -32.558  -7.452  1.00 15.40           O
ATOM    693  N    SER A 120      -7.685 -30.767  -6.687  1.00 15.07           N
ATOM    694  CA   SER A 120      -8.099 -30.368  -7.989  1.00 14.33           C
ATOM    695  CB   SER A 120      -9.429 -29.656  -7.873  1.00 15.29           C
ATOM    696  OG   SER A 120      -9.904 -29.450  -9.164  1.00 16.24           O
ATOM    697  C    SER A 120      -7.074 -29.411  -8.600  1.00 14.77           C
ATOM    698  O    SER A 120      -6.514 -28.570  -7.880  1.00 15.29           O
ATOM    699  N    PHE A 121      -6.827 -29.576  -9.898  1.00 14.73           N
```

FIGURE 2-10 (COORDINATES)

```
ATOM   700  CA   PHE A 121      -5.981 -28.646 -10.620  1.00 14.41           C
ATOM   701  CB   PHE A 121      -4.673 -29.294 -11.000  1.00 13.64           C
ATOM   702  CG   PHE A 121      -3.907 -29.850  -9.841  1.00 15.35           C
ATOM   703  CD1  PHE A 121      -2.890 -29.113  -9.268  1.00 14.12           C
ATOM   704  CE1  PHE A 121      -2.151 -29.618  -8.175  1.00 15.26           C
ATOM   705  CZ   PHE A 121      -2.477 -30.863  -7.652  1.00 16.02           C
ATOM   706  CE2  PHE A 121      -3.515 -31.618  -8.227  1.00 14.76           C
ATOM   707  CD2  PHE A 121      -4.225 -31.107  -9.309  1.00 14.85           C
ATOM   708  C    PHE A 121      -6.707 -28.205 -11.878  1.00 14.27           C
ATOM   709  O    PHE A 121      -7.489 -28.958 -12.459  1.00 14.58           O
ATOM   710  N    SER A 122      -6.417 -26.997 -12.348  1.00 14.21           N
ATOM   711  CA   SER A 122      -6.995 -26.585 -13.612  1.00 14.43           C
ATOM   712  CB   SER A 122      -8.127 -25.602 -13.351  1.00 14.36           C
ATOM   713  OG   SER A 122      -9.158 -26.212 -12.601  1.00 17.96           O
ATOM   714  C    SER A 122      -5.931 -25.912 -14.420  1.00 13.64           C
ATOM   715  O    SER A 122      -5.566 -24.792 -14.110  1.00 13.50           O
ATOM   716  N    ASN A 123      -5.413 -26.603 -15.416  1.00 12.30           N
ATOM   717  CA   ASN A 123      -4.579 -25.937 -16.386  1.00 12.34           C
ATOM   718  CB   ASN A 123      -3.948 -26.911 -17.336  1.00 12.11           C
ATOM   719  CG   ASN A 123      -3.036 -27.891 -16.647  1.00 11.71           C
ATOM   720  OD1  ASN A 123      -3.113 -29.118 -16.880  1.00 17.12           O
ATOM   721  ND2  ASN A 123      -2.199 -27.393 -15.791  1.00  8.95           N
ATOM   722  C    ASN A 123      -5.468 -25.011 -17.179  1.00 13.22           C
ATOM   723  O    ASN A 123      -6.641 -25.321 -17.432  1.00 14.20           O
ATOM   724  N    ILE A 124      -4.901 -23.890 -17.591  1.00 11.94           N
ATOM   725  CA   ILE A 124      -5.629 -23.027 -18.529  1.00 12.51           C
ATOM   726  CB   ILE A 124      -5.666 -21.604 -18.025  1.00 11.20           C
ATOM   727  CG1  ILE A 124      -6.151 -21.583 -16.579  1.00 12.38           C
ATOM   728  CD1  ILE A 124      -5.939 -20.279 -16.004  1.00 11.72           C
ATOM   729  CG2  ILE A 124      -6.529 -20.707 -18.925  1.00 13.13           C
ATOM   730  C    ILE A 124      -4.915 -23.067 -19.866  1.00 12.45           C
ATOM   731  O    ILE A 124      -3.722 -22.858 -19.949  1.00 12.92           O
ATOM   732  N    ILE A 125      -5.667 -23.345 -20.906  1.00 13.04           N
ATOM   733  CA   ILE A 125      -5.105 -23.397 -22.226  1.00 12.69           C
ATOM   734  CB   ILE A 125      -5.214 -24.770 -22.866  1.00 13.75           C
ATOM   735  CG1  ILE A 125      -4.590 -25.838 -21.968  1.00 13.00           C
ATOM   736  CD1  ILE A 125      -5.540 -26.468 -20.990  1.00 16.08           C
ATOM   737  CG2  ILE A 125      -4.512 -24.735 -24.267  1.00 13.17           C
ATOM   738  C    ILE A 125      -5.844 -22.378 -23.073  1.00 13.18           C
ATOM   739  O    ILE A 125      -7.061 -22.420 -23.170  1.00 12.54           O
ATOM   740  N    SER A 126      -5.090 -21.494 -23.704  1.00 13.25           N
ATOM   741  CA   SER A 126      -5.691 -20.446 -24.538  1.00 13.37           C
ATOM   742  CB   SER A 126      -5.211 -19.073 -24.036  1.00 13.47           C
ATOM   743  OG   SER A 126      -6.044 -18.087 -24.603  1.00 20.70           O
ATOM   744  C    SER A 126      -5.130 -20.675 -25.900  1.00 12.12           C
ATOM   745  O    SER A 126      -3.926 -20.678 -26.047  1.00 11.71           O
ATOM   746  N    THR A 127      -5.976 -20.891 -26.905  1.00 13.73           N
ATOM   747  CA   THR A 127      -5.474 -21.282 -28.221  1.00 14.41           C
ATOM   748  CB   THR A 127      -5.791 -22.758 -28.525  1.00 14.75           C
ATOM   749  OG1  THR A 127      -5.393 -23.584 -27.425  1.00 15.97           O
ATOM   750  CG2  THR A 127      -5.139 -23.184 -29.790  1.00 13.90           C
ATOM   751  C    THR A 127      -6.050 -20.437 -29.332  1.00 15.25           C
ATOM   752  O    THR A 127      -7.270 -20.255 -29.416  1.00 16.26           O
ATOM   753  N    LEU A 128      -5.170 -19.913 -30.173  1.00 15.76           N
ATOM   754  CA   LEU A 128      -5.573 -19.248 -31.371  1.00 16.09           C
ATOM   755  CB   LEU A 128      -4.629 -18.103 -31.737  1.00 16.91           C
ATOM   756  CG   LEU A 128      -4.770 -16.810 -30.904  1.00 13.98           C
ATOM   757  CD1  LEU A 128      -3.705 -15.802 -31.281  1.00 13.59           C
ATOM   758  CD2  LEU A 128      -6.201 -16.199 -31.009  1.00 16.78           C
ATOM   759  C    LEU A 128      -5.571 -20.269 -32.476  1.00 16.78           C
ATOM   760  O    LEU A 128      -4.626 -21.051 -32.627  1.00 17.36           O
ATOM   761  N    ASN A 129      -6.655 -20.292 -33.242  1.00 17.68           N
ATOM   762  CA   ASN A 129      -6.752 -21.236 -34.361  1.00 18.42           C
ATOM   763  CB   ASN A 129      -5.705 -20.880 -35.421  1.00 19.55           C
ATOM   764  CG   ASN A 129      -5.753 -19.392 -35.817  1.00 20.76           C
ATOM   765  OD1  ASN A 129      -6.568 -18.980 -36.648  1.00 26.31           O
ATOM   766  ND2  ASN A 129      -4.896 -18.599 -35.232  1.00 16.06           N
ATOM   767  C    ASN A 129      -6.586 -22.680 -33.858  1.00 18.54           C
ATOM   768  O    ASN A 129      -5.622 -23.344 -34.175  1.00 17.92           O
ATOM   769  N    PRO A 130      -7.519 -23.144 -33.024  1.00 19.89           N
```

FIGURE 2-11 (COORDINATES)

```
ATOM    770  CA  PRO A 130      -7.365 -24.472 -32.463  1.00 21.07           C
ATOM    771  CB  PRO A 130      -8.662 -24.683 -31.661  1.00 20.55           C
ATOM    772  CG  PRO A 130      -9.554 -23.557 -32.012  1.00 21.69           C
ATOM    773  CD  PRO A 130      -8.663 -22.438 -32.419  1.00 19.79           C
ATOM    774  C   PRO A 130      -7.217 -25.527 -33.548  1.00 21.70           C
ATOM    775  O   PRO A 130      -6.603 -26.529 -33.286  1.00 22.78           O
ATOM    776  N   GLU A 131      -7.736 -25.266 -34.758  1.00 22.84           N
ATOM    777  CA  GLU A 131      -7.676 -26.187 -35.903  1.00 24.22           C
ATOM    778  CB  GLU A 131      -8.708 -25.777 -36.980  1.00 24.97           C
ATOM    779  CG  GLU A 131      -8.393 -24.464 -37.763  1.00 29.76           C
ATOM    780  CD  GLU A 131      -8.589 -23.134 -36.970  1.00 33.37           C
ATOM    781  OE1 GLU A 131      -9.182 -23.142 -35.866  1.00 36.38           O
ATOM    782  OE2 GLU A 131      -8.157 -22.068 -37.487  1.00 35.40           O
ATOM    783  C   GLU A 131      -6.296 -26.240 -36.543  1.00 24.32           C
ATOM    784  O   GLU A 131      -5.958 -27.182 -37.268  1.00 24.58           O
ATOM    785  N   ALA A 132      -5.491 -25.214 -36.303  1.00 23.31           N
ATOM    786  CA  ALA A 132      -4.163 -25.192 -36.902  1.00 22.43           C
ATOM    787  CB  ALA A 132      -3.462 -23.897 -36.587  1.00 22.41           C
ATOM    788  C   ALA A 132      -3.361 -26.405 -36.413  1.00 21.89           C
ATOM    789  O   ALA A 132      -3.383 -26.751 -35.232  1.00 21.09           O
ATOM    790  N   LYS A 133      -2.692 -27.069 -37.337  1.00 21.07           N
ATOM    791  CA  LYS A 133      -1.957 -28.259 -36.995  1.00 21.52           C
ATOM    792  CB  LYS A 133      -1.374 -28.902 -38.234  1.00 22.05           C
ATOM    793  CG  LYS A 133      -2.446 -29.562 -39.105  1.00 23.56           C
ATOM    794  CD  LYS A 133      -1.823 -30.504 -40.131  1.00 26.86           C
ATOM    795  CE  LYS A 133      -0.882 -29.751 -41.062  1.00 27.88           C
ATOM    796  NZ  LYS A 133      -1.530 -28.606 -41.789  1.00 31.60           N
ATOM    797  C   LYS A 133      -0.870 -27.923 -35.985  1.00 20.89           C
ATOM    798  O   LYS A 133      -0.667 -28.674 -35.055  1.00 21.05           O
ATOM    799  N   ARG A 134      -0.230 -26.769 -36.165  1.00 19.63           N
ATOM    800  CA  ARG A 134       0.908 -26.345 -35.341  1.00 19.12           C
ATOM    801  CB  ARG A 134       2.115 -26.047 -36.212  1.00 18.90           C
ATOM    802  CG  ARG A 134       2.545 -27.242 -37.058  1.00 23.09           C
ATOM    803  CD  ARG A 134       3.418 -26.795 -38.201  1.00 22.46           C
ATOM    804  NE  ARG A 134       4.516 -25.946 -37.778  1.00 25.19           N
ATOM    805  CZ  ARG A 134       5.181 -25.127 -38.581  1.00 26.99           C
ATOM    806  NH1 ARG A 134       4.849 -25.047 -39.872  1.00 28.12           N
ATOM    807  NH2 ARG A 134       6.155 -24.357 -38.099  1.00 27.44           N
ATOM    808  C   ARG A 134       0.618 -25.128 -34.479  1.00 17.46           C
ATOM    809  O   ARG A 134      -0.067 -24.176 -34.873  1.00 18.48           O
ATOM    810  N   HIS A 135       1.165 -25.152 -33.272  1.00 17.24           N
ATOM    811  CA  HIS A 135       1.164 -23.963 -32.426  1.00 15.72           C
ATOM    812  CB  HIS A 135       0.105 -24.098 -31.335  1.00 15.20           C
ATOM    813  CG  HIS A 135      -1.280 -24.005 -31.858  1.00 16.57           C
ATOM    814  ND1 HIS A 135      -1.892 -25.050 -32.506  1.00 17.11           N
ATOM    815  CE1 HIS A 135      -3.096 -24.673 -32.900  1.00 15.30           C
ATOM    816  NE2 HIS A 135      -3.283 -23.417 -32.535  1.00 15.71           N
ATOM    817  CD2 HIS A 135      -2.167 -22.979 -31.867  1.00 17.36           C
ATOM    818  C   HIS A 135       2.496 -23.788 -31.775  1.00 14.30           C
ATOM    819  O   HIS A 135       3.109 -24.756 -31.329  1.00 15.28           O
ATOM    820  N   LEU A 136       2.955 -22.543 -31.764  1.00 14.37           N
ATOM    821  CA  LEU A 136       3.993 -22.101 -30.872  1.00 13.32           C
ATOM    822  CB  LEU A 136       4.477 -20.716 -31.275  1.00 13.50           C
ATOM    823  CG  LEU A 136       5.461 -20.059 -30.320  1.00 14.60           C
ATOM    824  CD1 LEU A 136       6.758 -20.921 -30.207  1.00 11.46           C
ATOM    825  CD2 LEU A 136       5.715 -18.666 -30.763  1.00 12.90           C
ATOM    826  C   LEU A 136       3.265 -22.040 -29.546  1.00 12.69           C
ATOM    827  O   LEU A 136       2.123 -21.595 -29.474  1.00 11.55           O
ATOM    828  N   VAL A 137       3.898 -22.564 -28.505  1.00 11.16           N
ATOM    829  CA  VAL A 137       3.233 -22.555 -27.214  1.00 11.46           C
ATOM    830  CB  VAL A 137       3.009 -23.966 -26.725  1.00 10.25           C
ATOM    831  CG1 VAL A 137       2.133 -23.929 -25.426  1.00 12.95           C
ATOM    832  CG2 VAL A 137       2.446 -24.813 -27.799  1.00 13.38           C
ATOM    833  C   VAL A 137       4.094 -21.780 -26.222  1.00 11.06           C
ATOM    834  O   VAL A 137       5.288 -22.028 -26.099  1.00 11.18           O
ATOM    835  N   LEU A 138       3.460 -20.852 -25.520  1.00 10.09           N
ATOM    836  CA  LEU A 138       4.088 -20.095 -24.476  1.00 11.46           C
ATOM    837  CB  LEU A 138       3.891 -18.611 -24.685  1.00 12.57           C
ATOM    838  CG  LEU A 138       5.134 -17.897 -25.220  1.00 18.81           C
ATOM    839  CD1 LEU A 138       5.494 -18.406 -26.622  1.00 17.42           C
```

FIGURE 2-12 (COORDINATES)

```
ATOM    840  CD2 LEU A 138       4.887 -16.359 -25.167  1.00 22.71           C
ATOM    841  C   LEU A 138       3.410 -20.538 -23.212  1.00 10.97           C
ATOM    842  O   LEU A 138       2.211 -20.769 -23.181  1.00 11.30           O
ATOM    843  N   ALA A 139       4.192 -20.703 -22.165  1.00  9.82           N
ATOM    844  CA  ALA A 139       3.614 -21.296 -20.981  1.00  8.89           C
ATOM    845  CB  ALA A 139       3.747 -22.839 -20.988  1.00  9.42           C
ATOM    846  C   ALA A 139       4.223 -20.724 -19.754  1.00  8.46           C
ATOM    847  O   ALA A 139       5.377 -20.299 -19.751  1.00  7.69           O
ATOM    848  N   CYS A 140       3.421 -20.720 -18.698  1.00  9.11           N
ATOM    849  CA  CYS A 140       3.923 -20.458 -17.365  1.00  9.93           C
ATOM    850  CB  CYS A 140       3.653 -18.994 -16.953  1.00  9.83           C
ATOM    851  SG  CYS A 140       1.920 -18.699 -16.827  1.00 15.53           S
ATOM    852  C   CYS A 140       3.139 -21.402 -16.438  1.00  9.59           C
ATOM    853  O   CYS A 140       2.207 -22.118 -16.873  1.00 10.24           O
ATOM    854  N   HIS A 141       3.466 -21.354 -15.150  1.00  9.87           N
ATOM    855  CA  HIS A 141       2.591 -22.008 -14.189  1.00 10.34           C
ATOM    856  CB  HIS A 141       3.302 -23.028 -13.270  1.00  8.84           C
ATOM    857  CG  HIS A 141       4.127 -22.409 -12.171  1.00 10.34           C
ATOM    858  ND1 HIS A 141       5.495 -22.204 -12.265  1.00 13.19           N
ATOM    859  CE1 HIS A 141       5.932 -21.668 -11.135  1.00 10.19           C
ATOM    860  NE2 HIS A 141       4.908 -21.559 -10.308  1.00 13.48           N
ATOM    861  CD2 HIS A 141       3.773 -21.995 -10.936  1.00  8.84           C
ATOM    862  C   HIS A 141       1.970 -20.899 -13.406  1.00 10.12           C
ATOM    863  O   HIS A 141       2.647 -19.942 -13.038  1.00 10.97           O
ATOM    864  N   TYR A 142       0.680 -21.012 -13.166  1.00 10.70           N
ATOM    865  CA  TYR A 142      -0.021 -19.919 -12.525  1.00 10.23           C
ATOM    866  CB  TYR A 142      -1.314 -19.532 -13.285  1.00 10.66           C
ATOM    867  CG  TYR A 142      -2.495 -20.397 -12.998  1.00 11.84           C
ATOM    868  CD1 TYR A 142      -3.427 -20.062 -11.993  1.00 13.47           C
ATOM    869  CE1 TYR A 142      -4.536 -20.861 -11.752  1.00 13.38           C
ATOM    870  CZ  TYR A 142      -4.691 -22.019 -12.527  1.00 14.83           C
ATOM    871  OH  TYR A 142      -5.763 -22.857 -12.355  1.00 15.04           O
ATOM    872  CE2 TYR A 142      -3.767 -22.360 -13.513  1.00 12.55           C
ATOM    873  CD2 TYR A 142      -2.697 -21.541 -13.748  1.00 12.94           C
ATOM    874  C   TYR A 142      -0.289 -20.215 -11.066  1.00 10.58           C
ATOM    875  O   TYR A 142      -0.741 -19.362 -10.360  1.00 11.15           O
ATOM    876  N   ASP A 143       0.012 -21.432 -10.602  1.00  9.69           N
ATOM    877  CA  ASP A 143      -0.134 -21.732  -9.204  1.00 10.43           C
ATOM    878  CB  ASP A 143      -0.105 -23.243  -8.966  1.00  9.16           C
ATOM    879  CG  ASP A 143       1.209 -23.881  -9.418  1.00 11.01           C
ATOM    880  OD1 ASP A 143       1.562 -23.727 -10.591  1.00 13.12           O
ATOM    881  OD2 ASP A 143       1.848 -24.607  -8.626  1.00 10.45           O
ATOM    882  C   ASP A 143       0.991 -21.110  -8.451  1.00 10.30           C
ATOM    883  O   ASP A 143       2.044 -20.864  -9.003  1.00 10.80           O
ATOM    884  N   SER A 144       0.801 -20.893  -7.160  1.00 11.57           N
ATOM    885  CA  SER A 144       1.918 -20.448  -6.365  1.00 11.76           C
ATOM    886  CB  SER A 144       1.655 -19.124  -5.644  1.00 12.08           C
ATOM    887  OG  SER A 144       0.537 -19.229  -4.768  1.00 13.10           O
ATOM    888  C   SER A 144       2.137 -21.561  -5.370  1.00 11.83           C
ATOM    889  O   SER A 144       1.220 -22.261  -5.021  1.00 12.18           O
ATOM    890  N   LYS A 145       3.366 -21.694  -4.926  1.00 11.59           N
ATOM    891  CA  LYS A 145       3.750 -22.802  -4.087  1.00 11.05           C
ATOM    892  CB  LYS A 145       5.265 -22.792  -3.936  1.00 10.44           C
ATOM    893  CG  LYS A 145       5.816 -23.932  -3.070  1.00  9.44           C
ATOM    894  CD  LYS A 145       7.340 -24.040  -3.181  1.00 10.34           C
ATOM    895  CE  LYS A 145       7.902 -25.221  -2.310  1.00 11.93           C
ATOM    896  NZ  LYS A 145       7.256 -26.517  -2.782  1.00 14.05           N
ATOM    897  C   LYS A 145       3.078 -22.700  -2.741  1.00 12.28           C
ATOM    898  O   LYS A 145       3.097 -21.674  -2.088  1.00 13.37           O
ATOM    899  N   TYR A 146       2.478 -23.803  -2.315  1.00 13.75           N
ATOM    900  CA  TYR A 146       1.915 -23.855  -0.999  1.00 13.91           C
ATOM    901  CB  TYR A 146       1.070 -25.116  -0.823  1.00 14.18           C
ATOM    902  CG  TYR A 146       0.668 -25.269   0.620  1.00 14.71           C
ATOM    903  CD1 TYR A 146      -0.305 -24.425   1.193  1.00 12.49           C
ATOM    904  CE1 TYR A 146      -0.634 -24.542   2.513  1.00 15.68           C
ATOM    905  CZ  TYR A 146      -0.001 -25.498   3.280  1.00 15.59           C
ATOM    906  OH  TYR A 146      -0.317 -25.641   4.613  1.00 17.73           O
ATOM    907  CE2 TYR A 146       0.948 -26.325   2.755  1.00 16.37           C
ATOM    908  CD2 TYR A 146       1.288 -26.205   1.420  1.00 16.91           C
ATOM    909  C   TYR A 146       2.991 -23.813   0.070  1.00 14.59           C
```

FIGURE 2-13 (COORDINATES)

```
ATOM    910  O    TYR A 146       3.960 -24.585   0.054  1.00 15.06           O
ATOM    911  N    PHE A 147       2.820 -22.897   1.009  1.00 14.90           N
ATOM    912  CA   PHE A 147       3.550 -22.969   2.233  1.00 16.62           C
ATOM    913  CB   PHE A 147       4.528 -21.831   2.342  1.00 16.96           C
ATOM    914  CG   PHE A 147       5.666 -21.948   1.381  1.00 16.98           C
ATOM    915  CD1  PHE A 147       6.747 -22.765   1.677  1.00 17.54           C
ATOM    916  CE1  PHE A 147       7.808 -22.895   0.779  1.00 19.53           C
ATOM    917  CZ   PHE A 147       7.779 -22.181  -0.402  1.00 16.26           C
ATOM    918  CE2  PHE A 147       6.680 -21.399  -0.733  1.00 14.36           C
ATOM    919  CD2  PHE A 147       5.621 -21.284   0.161  1.00 16.76           C
ATOM    920  C    PHE A 147       2.540 -22.869   3.354  1.00 17.50           C
ATOM    921  O    PHE A 147       1.599 -22.100   3.262  1.00 17.34           O
ATOM    922  N    PRO A 148       2.778 -23.618   4.429  1.00 18.46           N
ATOM    923  CA   PRO A 148       1.915 -23.490   5.606  1.00 18.91           C
ATOM    924  CB   PRO A 148       2.685 -24.269   6.689  1.00 18.75           C
ATOM    925  CG   PRO A 148       3.380 -25.342   5.903  1.00 20.92           C
ATOM    926  CD   PRO A 148       3.832 -24.630   4.618  1.00 19.22           C
ATOM    927  C    PRO A 148       1.775 -22.039   5.991  1.00 18.55           C
ATOM    928  O    PRO A 148       2.775 -21.308   6.081  1.00 18.88           O
ATOM    929  N    ARG A 149       0.524 -21.624   6.157  1.00 18.44           N
ATOM    930  CA   ARG A 149       0.215 -20.293   6.599  1.00 17.71           C
ATOM    931  CB   ARG A 149      -1.288 -20.035   6.416  1.00 17.68           C
ATOM    932  CG   ARG A 149      -1.679 -18.606   6.589  1.00 16.31           C
ATOM    933  CD   ARG A 149      -0.963 -17.688   5.552  1.00 15.66           C
ATOM    934  NE   ARG A 149      -1.357 -16.301   5.748  1.00 17.10           N
ATOM    935  CZ   ARG A 149      -2.514 -15.799   5.323  1.00 18.46           C
ATOM    936  NH1  ARG A 149      -2.795 -14.528   5.559  1.00 15.90           N
ATOM    937  NH2  ARG A 149      -3.387 -16.562   4.647  1.00 18.12           N
ATOM    938  C    ARG A 149       0.603 -20.140   8.060  1.00 18.86           C
ATOM    939  O    ARG A 149      -0.215 -20.391   8.943  1.00 18.33           O
ATOM    940  N    TRP A 150       1.839 -19.717   8.310  1.00 18.98           N
ATOM    941  CA   TRP A 150       2.304 -19.592   9.679  1.00 19.70           C
ATOM    942  CB   TRP A 150       3.682 -20.238   9.844  1.00 20.46           C
ATOM    943  CG   TRP A 150       4.729 -19.601   9.027  1.00 21.32           C
ATOM    944  CD1  TRP A 150       5.046 -19.862   7.703  1.00 25.08           C
ATOM    945  NE1  TRP A 150       6.100 -19.050   7.311  1.00 23.33           N
ATOM    946  CE2  TRP A 150       6.497 -18.286   8.386  1.00 22.86           C
ATOM    947  CD2  TRP A 150       5.655 -18.612   9.481  1.00 23.92           C
ATOM    948  CE3  TRP A 150       5.850 -17.958  10.709  1.00 22.79           C
ATOM    949  CZ3  TRP A 150       6.877 -17.000  10.808  1.00 27.39           C
ATOM    950  CH2  TRP A 150       7.709 -16.711   9.701  1.00 24.93           C
ATOM    951  CZ2  TRP A 150       7.531 -17.342   8.490  1.00 23.67           C
ATOM    952  C    TRP A 150       2.276 -18.199  10.249  1.00 19.45           C
ATOM    953  O    TRP A 150       2.423 -18.026  11.450  1.00 20.75           O
ATOM    954  N    ASP A 151       2.080 -17.193   9.394  1.00 19.23           N
ATOM    955  CA   ASP A 151       1.964 -15.802   9.850  1.00 20.32           C
ATOM    956  CB   ASP A 151       3.338 -15.104  10.028  1.00 19.64           C
ATOM    957  CG   ASP A 151       4.103 -14.865   8.709  1.00 22.21           C
ATOM    958  OD1  ASP A 151       3.655 -15.250   7.616  1.00 21.89           O
ATOM    959  OD2  ASP A 151       5.195 -14.251   8.778  1.00 26.17           O
ATOM    960  C    ASP A 151       1.054 -15.102   8.839  1.00 18.91           C
ATOM    961  O    ASP A 151       0.434 -15.775   8.025  1.00 19.30           O
ATOM    962  N    SER A 152       0.957 -13.794   8.902  1.00 18.45           N
ATOM    963  CA   SER A 152       0.050 -13.066   8.027  1.00 18.81           C
ATOM    964  CB   SER A 152       0.004 -11.606   8.443  1.00 19.10           C
ATOM    965  OG   SER A 152       1.244 -10.966   8.209  1.00 23.24           O
ATOM    966  C    SER A 152       0.443 -13.097   6.567  1.00 17.41           C
ATOM    967  O    SER A 152      -0.386 -12.867   5.703  1.00 17.20           O
ATOM    968  N    ARG A 153       1.732 -13.301   6.302  1.00 17.32           N
ATOM    969  CA   ARG A 153       2.246 -13.218   4.929  1.00 16.52           C
ATOM    970  CB   ARG A 153       3.762 -13.097   4.944  1.00 16.63           C
ATOM    971  CG   ARG A 153       4.214 -11.794   5.467  1.00 18.61           C
ATOM    972  CD   ARG A 153       5.732 -11.787   5.687  1.00 21.58           C
ATOM    973  NE   ARG A 153       6.169 -12.896   6.546  1.00 23.13           N
ATOM    974  CZ   ARG A 153       7.401 -13.404   6.561  1.00 25.54           C
ATOM    975  NH1  ARG A 153       8.355 -12.916   5.745  1.00 21.81           N
ATOM    976  NH2  ARG A 153       7.675 -14.410   7.378  1.00 25.78           N
ATOM    977  C    ARG A 153       1.872 -14.441   4.160  1.00 16.70           C
ATOM    978  O    ARG A 153       1.631 -15.488   4.731  1.00 15.62           O
ATOM    979  N    VAL A 154       1.811 -14.288   2.839  1.00 16.05           N
```

FIGURE 2-14 (COORDINATES)

```
ATOM    980  CA  VAL A 154       1.596 -15.399   1.970  1.00 16.73           C
ATOM    981  CB  VAL A 154       0.198 -15.438   1.368  1.00 16.31           C
ATOM    982  CG1 VAL A 154      -0.796 -15.859   2.449  1.00 18.95           C
ATOM    983  CG2 VAL A 154      -0.185 -14.091   0.753  1.00 18.78           C
ATOM    984  C   VAL A 154       2.594 -15.346   0.868  1.00 15.73           C
ATOM    985  O   VAL A 154       3.088 -14.288   0.503  1.00 16.00           O
ATOM    986  N   PHE A 155       2.917 -16.522   0.380  1.00 16.24           N
ATOM    987  CA  PHE A 155       3.825 -16.640  -0.728  1.00 15.26           C
ATOM    988  CB  PHE A 155       4.467 -18.008  -0.753  1.00 14.86           C
ATOM    989  CG  PHE A 155       5.352 -18.202  -1.923  1.00 15.28           C
ATOM    990  CD1 PHE A 155       6.600 -17.573  -1.974  1.00 15.20           C
ATOM    991  CE1 PHE A 155       7.431 -17.740  -3.071  1.00 12.17           C
ATOM    992  CZ  PHE A 155       7.000 -18.489  -4.152  1.00 11.33           C
ATOM    993  CE2 PHE A 155       5.783 -19.094  -4.117  1.00 12.02           C
ATOM    994  CD2 PHE A 155       4.935 -18.943  -3.010  1.00 11.99           C
ATOM    995  C   PHE A 155       3.029 -16.434  -2.003  1.00 14.97           C
ATOM    996  O   PHE A 155       2.075 -17.170  -2.300  1.00 14.11           O
ATOM    997  N   VAL A 156       3.424 -15.431  -2.762  1.00 14.06           N
ATOM    998  CA  VAL A 156       2.699 -15.155  -3.983  1.00 12.87           C
ATOM    999  CB  VAL A 156       2.236 -13.681  -4.031  1.00 12.26           C
ATOM   1000  CG1 VAL A 156       1.254 -13.390  -2.855  1.00 12.17           C
ATOM   1001  CG2 VAL A 156       3.430 -12.745  -3.991  1.00 13.23           C
ATOM   1002  C   VAL A 156       3.525 -15.435  -5.232  1.00 12.22           C
ATOM   1003  O   VAL A 156       3.023 -15.221  -6.328  1.00 13.21           O
ATOM   1004  N   GLY A 157       4.776 -15.862  -5.064  1.00 12.06           N
ATOM   1005  CA  GLY A 157       5.631 -16.217  -6.217  1.00 11.59           C
ATOM   1006  C   GLY A 157       5.524 -15.214  -7.349  1.00 10.84           C
ATOM   1007  O   GLY A 157       5.047 -15.543  -8.453  1.00 11.77           O
ATOM   1008  N   ALA A 158       5.961 -13.996  -7.059  1.00 10.47           N
ATOM   1009  CA  ALA A 158       5.901 -12.902  -8.054  1.00 11.33           C
ATOM   1010  CB  ALA A 158       6.429 -11.613  -7.471  1.00 10.65           C
ATOM   1011  C   ALA A 158       6.695 -13.301  -9.261  1.00 11.01           C
ATOM   1012  O   ALA A 158       6.229 -13.172 -10.386  1.00 11.98           O
ATOM   1013  N   THR A 159       7.888 -13.854  -9.063  1.00 10.94           N
ATOM   1014  CA  THR A 159       8.657 -14.290 -10.241  1.00 10.68           C
ATOM   1015  CB  THR A 159      10.144 -14.347  -9.967  1.00 11.86           C
ATOM   1016  OG1 THR A 159      10.406 -15.345  -8.971  1.00 13.22           O
ATOM   1017  CG2 THR A 159      10.651 -13.030  -9.563  1.00 11.44           C
ATOM   1018  C   THR A 159       8.286 -15.681 -10.675  1.00 10.22           C
ATOM   1019  O   THR A 159       8.646 -16.134 -11.758  1.00  9.32           O
ATOM   1020  N   ASP A 160       7.561 -16.349  -9.786  1.00 10.93           N
ATOM   1021  CA  ASP A 160       7.400 -17.753  -9.843  1.00 11.09           C
ATOM   1022  CB  ASP A 160       8.290 -18.301  -8.730  1.00 11.11           C
ATOM   1023  CG  ASP A 160       8.279 -19.797  -8.647  1.00 11.17           C
ATOM   1024  OD1 ASP A 160       7.818 -20.464  -9.565  1.00  8.20           O
ATOM   1025  OD2 ASP A 160       8.751 -20.309  -7.620  1.00 12.08           O
ATOM   1026  C   ASP A 160       5.945 -18.115  -9.619  1.00 10.29           C
ATOM   1027  O   ASP A 160       5.593 -18.647  -8.583  1.00 10.56           O
ATOM   1028  N   SER A 161       5.071 -17.844 -10.578  1.00 11.12           N
ATOM   1029  CA  SER A 161       5.411 -17.306 -11.855  1.00 11.08           C
ATOM   1030  CB  SER A 161       5.449 -18.424 -12.885  1.00 10.60           C
ATOM   1031  OG  SER A 161       6.721 -19.029 -12.768  1.00 13.36           O
ATOM   1032  C   SER A 161       4.366 -16.277 -12.253  1.00 11.40           C
ATOM   1033  O   SER A 161       3.913 -16.249 -13.390  1.00  9.68           O
ATOM   1034  N   ALA A 162       4.001 -15.427 -11.303  1.00 10.20           N
ATOM   1035  CA  ALA A 162       3.006 -14.414 -11.615  1.00 10.66           C
ATOM   1036  CB  ALA A 162       2.736 -13.559 -10.405  1.00  9.51           C
ATOM   1037  C   ALA A 162       3.481 -13.560 -12.794  1.00 10.75           C
ATOM   1038  O   ALA A 162       2.704 -13.282 -13.730  1.00 11.03           O
ATOM   1039  N   VAL A 163       4.753 -13.139 -12.722  1.00  9.37           N
ATOM   1040  CA  VAL A 163       5.333 -12.300 -13.775  1.00 10.30           C
ATOM   1041  CB  VAL A 163       6.708 -11.795 -13.402  1.00  9.56           C
ATOM   1042  CG1 VAL A 163       7.433 -11.266 -14.693  1.00 10.38           C
ATOM   1043  CG2 VAL A 163       6.570 -10.646 -12.351  1.00 10.46           C
ATOM   1044  C   VAL A 163       5.307 -13.045 -15.106  1.00 10.36           C
ATOM   1045  O   VAL A 163       4.748 -12.513 -16.096  1.00 10.69           O
ATOM   1046  N   PRO A 164       5.890 -14.272 -15.173  1.00 10.72           N
ATOM   1047  CA  PRO A 164       5.742 -15.014 -16.459  1.00 10.99           C
ATOM   1048  CB  PRO A 164       6.259 -16.402 -16.114  1.00 10.08           C
ATOM   1049  CG  PRO A 164       7.344 -16.104 -15.148  1.00 10.89           C
```

FIGURE 2-15 (COORDINATES)

```
ATOM   1050  CD  PRO A 164       6.858 -14.966 -14.295  1.00  8.93           C
ATOM   1051  C   PRO A 164       4.324 -15.088 -17.010  1.00 11.50           C
ATOM   1052  O   PRO A 164       4.114 -14.910 -18.214  1.00 11.22           O
ATOM   1053  N   CYS A 165       3.363 -15.364 -16.154  1.00 12.58           N
ATOM   1054  CA  CYS A 165       1.970 -15.403 -16.608  1.00 11.77           C
ATOM   1055  CB  CYS A 165       1.065 -15.900 -15.504  1.00 12.47           C
ATOM   1056  SG  CYS A 165       1.547 -17.640 -15.075  1.00 15.37           S
ATOM   1057  C   CYS A 165       1.505 -14.033 -17.081  1.00 11.11           C
ATOM   1058  O   CYS A 165       0.853 -13.932 -18.112  1.00 13.13           O
ATOM   1059  N   ALA A 166       1.846 -12.995 -16.329  1.00 11.31           N
ATOM   1060  CA  ALA A 166       1.428 -11.626 -16.649  1.00 10.77           C
ATOM   1061  CB  ALA A 166       1.889 -10.688 -15.554  1.00 11.20           C
ATOM   1062  C   ALA A 166       2.079 -11.242 -17.992  1.00 10.96           C
ATOM   1063  O   ALA A 166       1.487 -10.557 -18.838  1.00 11.61           O
ATOM   1064  N   MET A 167       3.277 -11.764 -18.204  1.00  9.69           N
ATOM   1065  CA  MET A 167       4.007 -11.517 -19.441  1.00 10.29           C
ATOM   1066  CB  MET A 167       5.441 -12.027 -19.324  1.00 10.55           C
ATOM   1067  CG  MET A 167       6.241 -11.239 -18.370  1.00  9.42           C
ATOM   1068  SD  MET A 167       7.872 -11.979 -18.167  1.00 13.14           S
ATOM   1069  CE  MET A 167       8.588 -11.606 -19.735  1.00 13.36           C
ATOM   1070  C   MET A 167       3.332 -12.120 -20.618  1.00 10.35           C
ATOM   1071  O   MET A 167       3.257 -11.491 -21.694  1.00  9.46           O
ATOM   1072  N   MET A 168       2.825 -13.329 -20.447  1.00 10.08           N
ATOM   1073  CA  MET A 168       2.053 -13.993 -21.474  1.00  9.19           C
ATOM   1074  CB  MET A 168       1.717 -15.392 -21.053  1.00 10.37           C
ATOM   1075  CG  MET A 168       2.976 -16.222 -21.075  1.00 10.82           C
ATOM   1076  SD  MET A 168       2.767 -17.750 -20.168  1.00 14.29           S
ATOM   1077  CE  MET A 168       1.266 -18.499 -20.822  1.00  9.08           C
ATOM   1078  C   MET A 168       0.775 -13.204 -21.750  1.00  9.35           C
ATOM   1079  O   MET A 168       0.424 -13.010 -22.888  1.00  8.39           O
ATOM   1080  N   LEU A 169       0.114 -12.747 -20.696  1.00  9.10           N
ATOM   1081  CA  LEU A 169      -1.078 -11.959 -20.876  1.00 10.61           C
ATOM   1082  CB  LEU A 169      -1.701 -11.598 -19.538  1.00  9.17           C
ATOM   1083  CG  LEU A 169      -2.274 -12.852 -18.862  1.00 10.41           C
ATOM   1084  CD1 LEU A 169      -2.715 -12.581 -17.447  1.00 12.53           C
ATOM   1085  CD2 LEU A 169      -3.406 -13.489 -19.720  1.00 10.62           C
ATOM   1086  C   LEU A 169      -0.752 -10.659 -21.619  1.00 10.57           C
ATOM   1087  O   LEU A 169      -1.532 -10.217 -22.475  1.00 10.76           O
ATOM   1088  N   GLU A 170       0.362 -10.055 -21.231  1.00 10.32           N
ATOM   1089  CA  GLU A 170       0.765  -8.776 -21.811  1.00 11.28           C
ATOM   1090  CB  GLU A 170       1.960  -8.187 -21.052  1.00 10.86           C
ATOM   1091  CG  GLU A 170       2.650  -6.993 -21.751  1.00 12.70           C
ATOM   1092  CD  GLU A 170       1.727  -5.879 -22.210  1.00 16.31           C
ATOM   1093  OE1 GLU A 170       0.586  -5.698 -21.682  1.00 13.11           O
ATOM   1094  OE2 GLU A 170       2.177  -5.122 -23.103  1.00 18.43           O
ATOM   1095  C   GLU A 170       1.086  -9.049 -23.280  1.00 11.15           C
ATOM   1096  O   GLU A 170       0.741  -8.264 -24.166  1.00 10.77           O
ATOM   1097  N   LEU A 171       1.731 -10.180 -23.546  1.00 11.45           N
ATOM   1098  CA  LEU A 171       2.077 -10.484 -24.909  1.00 12.86           C
ATOM   1099  CB  LEU A 171       2.799 -11.827 -24.980  1.00 12.72           C
ATOM   1100  CG  LEU A 171       3.176 -12.259 -26.402  1.00 12.89           C
ATOM   1101  CD1 LEU A 171       4.583 -12.822 -26.318  1.00 11.53           C
ATOM   1102  CD2 LEU A 171       2.194 -13.314 -27.025  1.00 10.86           C
ATOM   1103  C   LEU A 171       0.811 -10.581 -25.728  1.00 12.73           C
ATOM   1104  O   LEU A 171       0.732 -10.087 -26.871  1.00 12.98           O
ATOM   1105  N   ALA A 172      -0.149 -11.333 -25.192  1.00 12.06           N
ATOM   1106  CA  ALA A 172      -1.381 -11.549 -25.915  1.00 12.79           C
ATOM   1107  CB  ALA A 172      -2.341 -12.456 -25.123  1.00 12.19           C
ATOM   1108  C   ALA A 172      -2.044 -10.225 -26.215  1.00 12.79           C
ATOM   1109  O   ALA A 172      -2.600 -10.051 -27.313  1.00 14.94           O
ATOM   1110  N   ARG A 173      -2.050  -9.334 -25.225  1.00 13.10           N
ATOM   1111  CA  ARG A 173      -2.605  -7.983 -25.380  1.00 13.16           C
ATOM   1112  CB  ARG A 173      -2.632  -7.262 -24.035  1.00 13.46           C
ATOM   1113  CG  ARG A 173      -3.334  -5.854 -24.073  1.00 13.73           C
ATOM   1114  CD  ARG A 173      -2.767  -4.931 -22.992  1.00 19.28           C
ATOM   1115  NE  ARG A 173      -1.373  -4.558 -23.258  1.00 15.97           N
ATOM   1116  CZ  ARG A 173      -0.994  -3.673 -24.178  1.00 21.80           C
ATOM   1117  NH1 ARG A 173      -1.912  -3.024 -24.924  1.00 17.34           N
ATOM   1118  NH2 ARG A 173       0.309  -3.422 -24.347  1.00 19.26           N
ATOM   1119  C   ARG A 173      -1.790  -7.117 -26.350  1.00 13.52           C
```

FIGURE 2-16 (COORDINATES)

```
ATOM   1120  O   ARG A 173      -2.344  -6.559 -27.285  1.00 12.90           O
ATOM   1121  N   ALA A 174      -0.490  -6.949 -26.072  1.00 14.01           N
ATOM   1122  CA  ALA A 174       0.379  -6.128 -26.931  1.00 13.93           C
ATOM   1123  CB  ALA A 174       1.833  -6.190 -26.491  1.00 13.31           C
ATOM   1124  C   ALA A 174       0.264  -6.535 -28.384  1.00 14.01           C
ATOM   1125  O   ALA A 174       0.239  -5.655 -29.272  1.00 14.38           O
ATOM   1126  N   LEU A 175       0.216  -7.843 -28.640  1.00 12.77           N
ATOM   1127  CA  LEU A 175       0.246  -8.393 -29.995  1.00 13.18           C
ATOM   1128  CB  LEU A 175       1.074  -9.664 -30.047  1.00 12.46           C
ATOM   1129  CG  LEU A 175       2.526  -9.501 -29.593  1.00 13.81           C
ATOM   1130  CD1 LEU A 175       3.257 -10.830 -29.764  1.00 14.51           C
ATOM   1131  CD2 LEU A 175       3.260  -8.290 -30.268  1.00 14.78           C
ATOM   1132  C   LEU A 175      -1.141  -8.689 -30.536  1.00 13.72           C
ATOM   1133  O   LEU A 175      -1.280  -9.320 -31.577  1.00 14.97           O
ATOM   1134  N   ASP A 176      -2.151  -8.210 -29.824  1.00 14.56           N
ATOM   1135  CA  ASP A 176      -3.506  -8.637 -30.103  1.00 15.63           C
ATOM   1136  CB  ASP A 176      -4.482  -7.920 -29.217  1.00 14.22           C
ATOM   1137  CG  ASP A 176      -5.884  -8.498 -29.332  1.00 16.93           C
ATOM   1138  OD1 ASP A 176      -6.024  -9.711 -29.479  1.00 17.01           O
ATOM   1139  OD2 ASP A 176      -6.842  -7.728 -29.323  1.00 14.30           O
ATOM   1140  C   ASP A 176      -3.890  -8.465 -31.569  1.00 16.38           C
ATOM   1141  O   ASP A 176      -4.418  -9.398 -32.197  1.00 17.13           O
ATOM   1142  N   LYS A 177      -3.578  -7.293 -32.117  1.00 16.64           N
ATOM   1143  CA  LYS A 177      -4.032  -6.973 -33.470  1.00 18.26           C
ATOM   1144  CB  LYS A 177      -3.737  -5.517 -33.809  1.00 18.62           C
ATOM   1145  CG  LYS A 177      -4.093  -5.143 -35.252  1.00 21.64           C
ATOM   1146  CD  LYS A 177      -3.658  -3.712 -35.564  1.00 27.82           C
ATOM   1147  CE  LYS A 177      -4.357  -3.172 -36.796  1.00 32.29           C
ATOM   1148  NZ  LYS A 177      -3.868  -1.760 -36.987  1.00 36.02           N
ATOM   1149  C   LYS A 177      -3.384  -7.924 -34.462  1.00 18.69           C
ATOM   1150  O   LYS A 177      -4.056  -8.524 -35.271  1.00 18.57           O
ATOM   1151  N   LYS A 178      -2.063  -8.072 -34.378  1.00 18.27           N
ATOM   1152  CA  LYS A 178      -1.378  -9.020 -35.233  1.00 18.40           C
ATOM   1153  CB  LYS A 178       0.133  -8.907 -35.035  1.00 17.83           C
ATOM   1154  CG  LYS A 178       0.685  -7.679 -35.712  1.00 20.07           C
ATOM   1155  CD  LYS A 178       1.962  -7.223 -35.095  1.00 27.02           C
ATOM   1156  CE  LYS A 178       2.522  -5.977 -35.822  1.00 29.61           C
ATOM   1157  NZ  LYS A 178       3.885  -5.624 -35.284  1.00 34.05           N
ATOM   1158  C   LYS A 178      -1.828 -10.449 -35.023  1.00 18.20           C
ATOM   1159  O   LYS A 178      -1.983 -11.198 -35.983  1.00 19.66           O
ATOM   1160  N   LEU A 179      -1.992 -10.861 -33.768  1.00 18.55           N
ATOM   1161  CA  LEU A 179      -2.449 -12.215 -33.484  1.00 18.56           C
ATOM   1162  CB  LEU A 179      -2.441 -12.501 -31.984  1.00 17.90           C
ATOM   1163  CG  LEU A 179      -1.057 -12.537 -31.321  1.00 17.08           C
ATOM   1164  CD1 LEU A 179      -1.205 -12.684 -29.789  1.00 12.65           C
ATOM   1165  CD2 LEU A 179      -0.255 -13.689 -31.888  1.00 19.14           C
ATOM   1166  C   LEU A 179      -3.848 -12.388 -34.014  1.00 19.80           C
ATOM   1167  O   LEU A 179      -4.156 -13.435 -34.551  1.00 19.14           O
ATOM   1168  N   HIS A 180      -4.674 -11.336 -33.898  1.00 21.68           N
ATOM   1169  CA  HIS A 180      -6.048 -11.383 -34.430  1.00 23.22           C
ATOM   1170  CB  HIS A 180      -6.794 -10.079 -34.180  1.00 22.96           C
ATOM   1171  CG  HIS A 180      -8.275 -10.184 -34.405  1.00 25.91           C
ATOM   1172  ND1 HIS A 180      -8.871 -11.316 -34.922  1.00 28.08           N
ATOM   1173  CE1 HIS A 180     -10.175 -11.124 -35.007  1.00 26.77           C
ATOM   1174  NE2 HIS A 180     -10.443  -9.914 -34.566  1.00 25.93           N
ATOM   1175  CD2 HIS A 180      -9.273  -9.301 -34.190  1.00 26.38           C
ATOM   1176  C   HIS A 180      -6.058 -11.745 -35.912  1.00 24.46           C
ATOM   1177  O   HIS A 180      -6.901 -12.524 -36.370  1.00 25.06           O
ATOM   1178  N   SER A 181      -5.079 -11.217 -36.639  1.00 25.60           N
ATOM   1179  CA  SER A 181      -4.982 -11.385 -38.081  1.00 26.71           C
ATOM   1180  CB  SER A 181      -3.916 -10.443 -38.644  1.00 26.02           C
ATOM   1181  OG  SER A 181      -2.620 -10.976 -38.439  1.00 24.18           O
ATOM   1182  C   SER A 181      -4.677 -12.837 -38.491  1.00 28.53           C
ATOM   1183  O   SER A 181      -4.859 -13.203 -39.650  1.00 28.77           O
ATOM   1184  N   LEU A 182      -4.233 -13.657 -37.534  1.00 30.19           N
ATOM   1185  CA  LEU A 182      -4.067 -15.094 -37.752  1.00 31.86           C
ATOM   1186  CB  LEU A 182      -3.420 -15.754 -36.527  1.00 31.11           C
ATOM   1187  CG  LEU A 182      -1.938 -15.503 -36.238  1.00 28.62           C
ATOM   1188  CD1 LEU A 182      -1.581 -16.001 -34.833  1.00 25.92           C
ATOM   1189  CD2 LEU A 182      -1.088 -16.175 -37.281  1.00 24.31           C
```

FIGURE 2-17 (COORDINATES)

```
ATOM   1190  C   LEU A 182      -5.383 -15.832 -38.052  1.00 33.81           C
ATOM   1191  O   LEU A 182      -5.344 -16.979 -38.467  1.00 34.41           O
ATOM   1192  N   LYS A 183      -6.534 -15.196 -37.819  1.00 36.23           N
ATOM   1193  CA  LYS A 183      -7.817 -15.829 -38.173  1.00 38.88           C
ATOM   1194  CB  LYS A 183      -9.028 -15.082 -37.586  1.00 38.78           C
ATOM   1195  CG  LYS A 183      -9.296 -13.700 -38.157  1.00 40.02           C
ATOM   1196  CD  LYS A 183     -10.607 -13.141 -37.605  1.00 42.93           C
ATOM   1197  CE  LYS A 183     -10.957 -11.769 -38.199  1.00 43.56           C
ATOM   1198  NZ  LYS A 183     -11.102 -11.816 -39.677  1.00 44.57           N
ATOM   1199  C   LYS A 183      -7.944 -16.007 -39.688  1.00 40.21           C
ATOM   1200  O   LYS A 183      -8.641 -16.909 -40.154  1.00 41.08           O
ATOM   1201  N   ASP A 184      -7.243 -15.154 -40.438  1.00 42.06           N
ATOM   1202  CA  ASP A 184      -7.247 -15.182 -41.903  1.00 42.97           C
ATOM   1203  CB  ASP A 184      -7.031 -13.772 -42.482  1.00 43.72           C
ATOM   1204  CG  ASP A 184      -7.934 -12.711 -41.838  1.00 44.78           C
ATOM   1205  OD1 ASP A 184      -9.183 -12.831 -41.957  1.00 46.98           O
ATOM   1206  OD2 ASP A 184      -7.392 -11.757 -41.222  1.00 44.08           O
ATOM   1207  C   ASP A 184      -6.147 -16.110 -42.399  1.00 43.29           C
ATOM   1208  O   ASP A 184      -6.422 -17.161 -42.994  1.00 43.95           O
ATOM   1209  N   PRO A 190       2.694 -21.486 -43.207  1.00 31.95           N
ATOM   1210  CA  PRO A 190       2.541 -22.585 -42.264  1.00 31.41           C
ATOM   1211  CB  PRO A 190       3.708 -22.381 -41.285  1.00 31.34           C
ATOM   1212  CG  PRO A 190       4.239 -20.963 -41.565  1.00 32.38           C
ATOM   1213  CD  PRO A 190       4.007 -20.840 -43.057  1.00 32.86           C
ATOM   1214  C   PRO A 190       1.209 -22.505 -41.527  1.00 30.33           C
ATOM   1215  O   PRO A 190       0.723 -21.405 -41.190  1.00 30.53           O
ATOM   1216  N   ASP A 191       0.628 -23.683 -41.317  1.00 28.26           N
ATOM   1217  CA  ASP A 191      -0.603 -23.851 -40.592  1.00 25.99           C
ATOM   1218  CB  ASP A 191      -1.176 -25.219 -40.927  1.00 26.29           C
ATOM   1219  CG  ASP A 191      -2.494 -25.457 -40.263  1.00 27.98           C
ATOM   1220  OD1 ASP A 191      -3.141 -24.469 -39.896  1.00 33.95           O
ATOM   1221  OD2 ASP A 191      -2.882 -26.621 -40.080  1.00 28.22           O
ATOM   1222  C   ASP A 191      -0.210 -23.765 -39.107  1.00 23.69           C
ATOM   1223  O   ASP A 191      -0.062 -24.775 -38.430  1.00 22.81           O
ATOM   1224  N   LEU A 192      -0.002 -22.540 -38.645  1.00 21.73           N
ATOM   1225  CA  LEU A 192       0.716 -22.318 -37.397  1.00 19.16           C
ATOM   1226  CB  LEU A 192       2.212 -22.316 -37.696  1.00 19.61           C
ATOM   1227  CG  LEU A 192       3.106 -21.581 -36.555  1.00 18.73           C
ATOM   1228  CD1 LEU A 192       3.278 -22.606 -35.469  1.00 19.35           C
ATOM   1229  CD2 LEU A 192       4.442 -21.109 -37.109  1.00 17.43           C
ATOM   1230  C   LEU A 192       0.144 -21.125 -36.660  1.00 18.42           C
ATOM   1231  O   LEU A 192      -0.016 -20.019 -37.211  1.00 18.35           O
ATOM   1232  N   SER A 193      -0.146 -21.335 -35.380  1.00 15.91           N
ATOM   1233  CA  SER A 193      -0.648 -20.253 -34.600  1.00 13.79           C
ATOM   1234  CB  SER A 193      -2.165 -20.250 -34.585  1.00 13.82           C
ATOM   1235  OG  SER A 193      -2.590 -18.995 -34.079  1.00 16.65           O
ATOM   1236  C   SER A 193      -0.052 -20.337 -33.194  1.00 12.52           C
ATOM   1237  O   SER A 193       1.001 -20.913 -33.022  1.00 14.11           O
ATOM   1238  N   LEU A 194      -0.707 -19.702 -32.248  1.00 11.69           N
ATOM   1239  CA  LEU A 194      -0.163 -19.502 -30.952  1.00 11.76           C
ATOM   1240  CB  LEU A 194      -0.003 -17.990 -30.692  1.00 11.18           C
ATOM   1241  CG  LEU A 194       0.677 -17.641 -29.365  1.00 11.84           C
ATOM   1242  CD1 LEU A 194       2.142 -18.103 -29.299  1.00 12.30           C
ATOM   1243  CD2 LEU A 194       0.565 -16.125 -29.157  1.00 10.80           C
ATOM   1244  C   LEU A 194      -1.036 -20.113 -29.910  1.00 12.21           C
ATOM   1245  O   LEU A 194      -2.254 -19.961 -29.932  1.00 11.77           O
ATOM   1246  N   GLN A 195      -0.396 -20.739 -28.922  1.00 11.31           N
ATOM   1247  CA  GLN A 195      -1.145 -21.215 -27.766  1.00 11.95           C
ATOM   1248  CB  GLN A 195      -1.192 -22.723 -27.801  1.00 10.04           C
ATOM   1249  CG  GLN A 195      -2.037 -23.357 -26.737  1.00 13.84           C
ATOM   1250  CD  GLN A 195      -2.087 -24.850 -26.949  1.00 17.69           C
ATOM   1251  OE1 GLN A 195      -3.123 -25.400 -27.302  1.00 19.42           O
ATOM   1252  NE2 GLN A 195      -0.954 -25.496 -26.809  1.00 16.54           N
ATOM   1253  C   GLN A 195      -0.420 -20.746 -26.530  1.00 11.71           C
ATOM   1254  O   GLN A 195       0.805 -20.630 -26.543  1.00 11.80           O
ATOM   1255  N   LEU A 196      -1.204 -20.458 -25.495  1.00 11.49           N
ATOM   1256  CA  LEU A 196      -0.687 -20.135 -24.160  1.00 11.35           C
ATOM   1257  CB  LEU A 196      -1.226 -18.805 -23.670  1.00 11.94           C
ATOM   1258  CG  LEU A 196      -1.026 -17.607 -24.618  1.00 12.87           C
ATOM   1259  CD1 LEU A 196      -1.646 -16.394 -23.975  1.00 12.13           C
```

FIGURE 2-18 (COORDINATES)

```
ATOM   1260  CD2 LEU A 196       0.429 -17.368 -24.864  1.00 10.86           C
ATOM   1261  C   LEU A 196      -1.199 -21.203 -23.237  1.00 11.86           C
ATOM   1262  O   LEU A 196      -2.356 -21.611 -23.340  1.00 11.49           O
ATOM   1263  N   ILE A 197      -0.331 -21.651 -22.338  1.00 10.91           N
ATOM   1264  CA  ILE A 197      -0.737 -22.608 -21.321  1.00 11.20           C
ATOM   1265  CB  ILE A 197      -0.056 -23.986 -21.491  1.00 11.70           C
ATOM   1266  CG1 ILE A 197      -0.498 -24.674 -22.810  1.00 15.21           C
ATOM   1267  CD1 ILE A 197       0.271 -25.992 -23.131  1.00 16.71           C
ATOM   1268  CG2 ILE A 197      -0.432 -24.877 -20.363  1.00 11.83           C
ATOM   1269  C   ILE A 197      -0.329 -22.023 -19.986  1.00 10.47           C
ATOM   1270  O   ILE A 197       0.817 -21.680 -19.799  1.00  9.90           O
ATOM   1271  N   PHE A 198      -1.274 -21.955 -19.064  1.00 10.47           N
ATOM   1272  CA  PHE A 198      -1.000 -21.559 -17.692  1.00 10.76           C
ATOM   1273  CB  PHE A 198      -1.951 -20.457 -17.266  1.00 11.03           C
ATOM   1274  CG  PHE A 198      -1.946 -19.286 -18.181  1.00 11.98           C
ATOM   1275  CD1 PHE A 198      -1.278 -18.129 -17.817  1.00 11.53           C
ATOM   1276  CE1 PHE A 198      -1.246 -17.018 -18.669  1.00 12.69           C
ATOM   1277  CZ  PHE A 198      -1.917 -17.071 -19.907  1.00  8.70           C
ATOM   1278  CE2 PHE A 198      -2.589 -18.219 -20.262  1.00 11.29           C
ATOM   1279  CD2 PHE A 198      -2.612 -19.327 -19.412  1.00 11.57           C
ATOM   1280  C   PHE A 198      -1.188 -22.808 -16.882  1.00 11.12           C
ATOM   1281  O   PHE A 198      -2.324 -23.235 -16.632  1.00 11.96           O
ATOM   1282  N   PHE A 199      -0.066 -23.426 -16.520  1.00  9.95           N
ATOM   1283  CA  PHE A 199      -0.147 -24.728 -15.831  1.00 10.36           C
ATOM   1284  CB  PHE A 199       1.191 -25.461 -15.821  1.00  9.15           C
ATOM   1285  CG  PHE A 199       1.627 -25.920 -17.179  1.00 10.55           C
ATOM   1286  CD1 PHE A 199       0.953 -26.947 -17.811  1.00 11.08           C
ATOM   1287  CE1 PHE A 199       1.385 -27.394 -19.051  1.00 16.01           C
ATOM   1288  CZ  PHE A 199       2.458 -26.765 -19.677  1.00 14.41           C
ATOM   1289  CE2 PHE A 199       3.131 -25.721 -19.071  1.00 12.76           C
ATOM   1290  CD2 PHE A 199       2.723 -25.319 -17.802  1.00 11.71           C
ATOM   1291  C   PHE A 199      -0.525 -24.472 -14.421  1.00 10.01           C
ATOM   1292  O   PHE A 199      -0.048 -23.518 -13.790  1.00  9.32           O
ATOM   1293  N   ASP A 200      -1.352 -25.362 -13.897  1.00 10.18           N
ATOM   1294  CA  ASP A 200      -1.619 -25.333 -12.484  1.00 11.37           C
ATOM   1295  CB  ASP A 200      -3.061 -25.760 -12.270  1.00 12.05           C
ATOM   1296  CG  ASP A 200      -3.557 -25.441 -10.906  1.00 13.23           C
ATOM   1297  OD1 ASP A 200      -2.793 -24.900 -10.060  1.00 13.20           O
ATOM   1298  OD2 ASP A 200      -4.757 -25.703 -10.684  1.00 12.84           O
ATOM   1299  C   ASP A 200      -0.708 -26.398 -11.886  1.00 11.02           C
ATOM   1300  O   ASP A 200      -0.243 -27.251 -12.612  1.00 11.43           O
ATOM   1301  N   GLY A 201      -0.488 -26.328 -10.572  1.00 11.07           N
ATOM   1302  CA  GLY A 201       0.175 -27.404  -9.836  1.00 11.95           C
ATOM   1303  C   GLY A 201       1.591 -27.693 -10.318  1.00 11.84           C
ATOM   1304  O   GLY A 201       2.055 -28.806 -10.195  1.00 12.38           O
ATOM   1305  N   GLU A 202       2.288 -26.717 -10.863  1.00 10.77           N
ATOM   1306  CA  GLU A 202       3.723 -26.923 -11.128  1.00 11.32           C
ATOM   1307  CB  GLU A 202       4.334 -25.682 -11.729  1.00 10.71           C
ATOM   1308  CG  GLU A 202       5.757 -25.822 -12.206  1.00 11.40           C
ATOM   1309  CD  GLU A 202       6.807 -25.430 -11.193  1.00 15.37           C
ATOM   1310  OE1 GLU A 202       6.463 -25.149 -10.039  1.00 14.07           O
ATOM   1311  OE2 GLU A 202       7.999 -25.415 -11.560  1.00 15.69           O
ATOM   1312  C   GLU A 202       4.467 -27.286  -9.829  1.00 11.23           C
ATOM   1313  O   GLU A 202       5.299 -28.208  -9.781  1.00 12.72           O
ATOM   1314  N   GLU A 203       4.152 -26.540  -8.772  1.00 12.13           N
ATOM   1315  CA  GLU A 203       4.870 -26.640  -7.520  1.00 12.32           C
ATOM   1316  CB  GLU A 203       4.604 -25.411  -6.669  1.00 11.80           C
ATOM   1317  CG  GLU A 203       5.018 -24.079  -7.356  1.00 12.32           C
ATOM   1318  CD  GLU A 203       6.503 -23.776  -7.243  1.00 12.05           C
ATOM   1319  OE1 GLU A 203       7.317 -24.673  -6.925  1.00 10.69           O
ATOM   1320  OE2 GLU A 203       6.886 -22.633  -7.546  1.00 12.52           O
ATOM   1321  C   GLU A 203       4.517 -27.875  -6.702  1.00 13.29           C
ATOM   1322  O   GLU A 203       3.347 -28.301  -6.642  1.00 12.19           O
ATOM   1323  N   ALA A 204       5.549 -28.432  -6.078  1.00 14.33           N
ATOM   1324  CA  ALA A 204       5.379 -29.437  -5.041  1.00 15.10           C
ATOM   1325  CB  ALA A 204       6.749 -29.809  -4.452  1.00 14.64           C
ATOM   1326  C   ALA A 204       4.505 -28.883  -3.926  1.00 16.30           C
ATOM   1327  O   ALA A 204       4.581 -27.692  -3.588  1.00 16.85           O
ATOM   1328  N   PHE A 205       3.689 -29.754  -3.358  1.00 16.95           N
ATOM   1329  CA  PHE A 205       2.957 -29.453  -2.152  1.00 17.77           C
```

FIGURE 2-19 (COORDINATES)

```
ATOM   1330  CB  PHE A 205       1.694 -30.314  -2.030  1.00 18.24           C
ATOM   1331  CG  PHE A 205       0.572 -29.803  -2.842  1.00 16.93           C
ATOM   1332  CD1 PHE A 205       0.547 -30.050  -4.204  1.00 18.00           C
ATOM   1333  CE1 PHE A 205      -0.471 -29.589  -4.999  1.00 18.92           C
ATOM   1334  CZ  PHE A 205      -1.501 -28.865  -4.427  1.00 21.74           C
ATOM   1335  CE2 PHE A 205      -1.489 -28.561  -3.057  1.00 16.85           C
ATOM   1336  CD2 PHE A 205      -0.455 -29.057  -2.261  1.00 19.53           C
ATOM   1337  C   PHE A 205       3.804 -29.611  -0.922  1.00 19.42           C
ATOM   1338  O   PHE A 205       3.592 -28.903   0.065  1.00 19.83           O
ATOM   1339  N   HIS A 206       4.757 -30.529  -0.967  1.00 22.24           N
ATOM   1340  CA  HIS A 206       5.511 -30.813   0.236  1.00 25.10           C
ATOM   1341  CB  HIS A 206       5.143 -32.163   0.835  1.00 25.75           C
ATOM   1342  CG  HIS A 206       5.748 -32.381   2.189  1.00 31.69           C
ATOM   1343  ND1 HIS A 206       6.886 -33.137   2.387  1.00 36.15           N
ATOM   1344  CE1 HIS A 206       7.203 -33.123   3.670  1.00 37.41           C
ATOM   1345  NE2 HIS A 206       6.317 -32.383   4.311  1.00 37.75           N
ATOM   1346  CD2 HIS A 206       5.400 -31.899   3.405  1.00 36.24           C
ATOM   1347  C   HIS A 206       6.999 -30.740  -0.006  1.00 25.94           C
ATOM   1348  O   HIS A 206       7.688 -29.924   0.611  1.00 27.92           O
ATOM   1349  N   HIS A 207       7.488 -31.597  -0.892  1.00 26.22           N
ATOM   1350  CA  HIS A 207       8.900 -31.688  -1.201  1.00 26.80           C
ATOM   1351  CB  HIS A 207       9.577 -32.773  -0.347  1.00 27.57           C
ATOM   1352  CG  HIS A 207      11.053 -32.903  -0.588  1.00 31.26           C
ATOM   1353  ND1 HIS A 207      11.596 -33.920  -1.353  1.00 35.09           N
ATOM   1354  CE1 HIS A 207      12.910 -33.785  -1.394  1.00 35.34           C
ATOM   1355  NE2 HIS A 207      13.246 -32.735  -0.662  1.00 37.24           N
ATOM   1356  CD2 HIS A 207      12.101 -32.164  -0.148  1.00 35.55           C
ATOM   1357  C   HIS A 207       9.008 -32.024  -2.673  1.00 25.16           C
ATOM   1358  O   HIS A 207       8.411 -33.013  -3.128  1.00 24.53           O
ATOM   1359  N   TRP A 208       9.734 -31.194  -3.415  1.00 24.08           N
ATOM   1360  CA  TRP A 208       9.792 -31.361  -4.859  1.00 23.67           C
ATOM   1361  CB  TRP A 208      10.732 -30.347  -5.519  1.00 24.20           C
ATOM   1362  CG  TRP A 208      10.750 -30.462  -7.009  1.00 22.12           C
ATOM   1363  CD1 TRP A 208      11.479 -31.336  -7.767  1.00 25.04           C
ATOM   1364  NE1 TRP A 208      11.202 -31.153  -9.103  1.00 24.57           N
ATOM   1365  CE2 TRP A 208      10.289 -30.129  -9.227  1.00 22.89           C
ATOM   1366  CD2 TRP A 208       9.976 -29.683  -7.929  1.00 22.92           C
ATOM   1367  CE3 TRP A 208       9.065 -28.630  -7.777  1.00 23.81           C
ATOM   1368  CZ3 TRP A 208       8.476 -28.079  -8.914  1.00 20.72           C
ATOM   1369  CH2 TRP A 208       8.803 -28.538 -10.189  1.00 21.54           C
ATOM   1370  CZ2 TRP A 208       9.709 -29.570 -10.369  1.00 23.37           C
ATOM   1371  C   TRP A 208      10.258 -32.766  -5.166  1.00 23.40           C
ATOM   1372  O   TRP A 208      11.296 -33.214  -4.653  1.00 24.34           O
ATOM   1373  N   SER A 209       9.497 -33.458  -5.997  1.00 23.32           N
ATOM   1374  CA  SER A 209       9.825 -34.813  -6.410  1.00 22.91           C
ATOM   1375  CB  SER A 209       9.462 -35.795  -5.299  1.00 23.07           C
ATOM   1376  OG  SER A 209       8.077 -36.066  -5.310  1.00 22.38           O
ATOM   1377  C   SER A 209       9.023 -35.120  -7.659  1.00 22.99           C
ATOM   1378  O   SER A 209       8.087 -34.376  -7.971  1.00 22.09           O
ATOM   1379  N   PRO A 210       9.360 -36.215  -8.390  1.00 23.03           N
ATOM   1380  CA  PRO A 210       8.543 -36.440  -9.592  1.00 22.83           C
ATOM   1381  CB  PRO A 210       9.186 -37.674 -10.253  1.00 24.12           C
ATOM   1382  CG  PRO A 210      10.547 -37.783  -9.693  1.00 23.14           C
ATOM   1383  CD  PRO A 210      10.461 -37.200  -8.274  1.00 23.92           C
ATOM   1384  C   PRO A 210       7.084 -36.713  -9.253  1.00 22.07           C
ATOM   1385  O   PRO A 210       6.216 -36.396 -10.038  1.00 22.35           O
ATOM   1386  N   GLN A 211       6.813 -37.294  -8.089  1.00 21.44           N
ATOM   1387  CA  GLN A 211       5.424 -37.508  -7.651  1.00 21.86           C
ATOM   1388  CB  GLN A 211       5.352 -38.588  -6.559  1.00 22.82           C
ATOM   1389  CG  GLN A 211       5.358 -40.019  -7.115  1.00 27.80           C
ATOM   1390  CD  GLN A 211       5.305 -41.108  -6.040  1.00 33.78           C
ATOM   1391  OE1 GLN A 211       4.918 -40.870  -4.885  1.00 35.16           O
ATOM   1392  NE2 GLN A 211       5.688 -42.335  -6.436  1.00 37.30           N
ATOM   1393  C   GLN A 211       4.784 -36.225  -7.137  1.00 20.21           C
ATOM   1394  O   GLN A 211       3.576 -36.051  -7.205  1.00 22.42           O
ATOM   1395  N   ASP A 212       5.600 -35.331  -6.615  1.00 18.88           N
ATOM   1396  CA  ASP A 212       5.072 -34.126  -6.018  1.00 17.12           C
ATOM   1397  CB  ASP A 212       5.394 -34.083  -4.516  1.00 17.40           C
ATOM   1398  CG  ASP A 212       4.718 -32.886  -3.798  1.00 15.80           C
ATOM   1399  OD1 ASP A 212       3.745 -32.323  -4.347  1.00 17.31           O
```

FIGURE 2-20 (COORDINATES)

```
ATOM   1400  OD2 ASP A 212       5.130 -32.578  -2.674  1.00 17.00           O
ATOM   1401  C   ASP A 212       5.620 -32.908  -6.776  1.00 16.58           C
ATOM   1402  O   ASP A 212       6.468 -32.193  -6.304  1.00 16.94           O
ATOM   1403  N   SER A 213       5.120 -32.715  -7.986  1.00 15.85           N
ATOM   1404  CA  SER A 213       5.464 -31.565  -8.810  1.00 13.94           C
ATOM   1405  CB  SER A 213       6.973 -31.423  -9.038  1.00 13.33           C
ATOM   1406  OG  SER A 213       7.421 -32.526  -9.765  1.00 14.15           O
ATOM   1407  C   SER A 213       4.811 -31.783 -10.134  1.00 12.81           C
ATOM   1408  O   SER A 213       4.414 -32.906 -10.466  1.00 15.49           O
ATOM   1409  N   LEU A 214       4.622 -30.697 -10.869  1.00 11.65           N
ATOM   1410  CA  LEU A 214       4.273 -30.778 -12.269  1.00 10.93           C
ATOM   1411  CB  LEU A 214       5.340 -31.542 -13.065  1.00 10.99           C
ATOM   1412  CG  LEU A 214       6.766 -31.015 -12.880  1.00 10.90           C
ATOM   1413  CD1 LEU A 214       7.728 -31.734 -13.834  1.00 11.62           C
ATOM   1414  CD2 LEU A 214       6.840 -29.475 -13.082  1.00 11.22           C
ATOM   1415  C   LEU A 214       2.956 -31.459 -12.458  1.00 11.43           C
ATOM   1416  O   LEU A 214       2.785 -32.188 -13.398  1.00 12.77           O
ATOM   1417  N   TYR A 215       2.048 -31.274 -11.515  1.00 12.23           N
ATOM   1418  CA  TYR A 215       0.773 -31.948 -11.610  1.00 13.09           C
ATOM   1419  CB  TYR A 215      -0.090 -31.548 -10.450  1.00 12.51           C
ATOM   1420  CG  TYR A 215       0.423 -32.070  -9.145  1.00 14.14           C
ATOM   1421  CD1 TYR A 215       0.152 -33.365  -8.741  1.00 16.57           C
ATOM   1422  CE1 TYR A 215       0.628 -33.833  -7.537  1.00 13.83           C
ATOM   1423  CZ  TYR A 215       1.397 -33.002  -6.736  1.00 15.20           C
ATOM   1424  OH  TYR A 215       1.843 -33.449  -5.540  1.00 15.72           O
ATOM   1425  CE2 TYR A 215       1.699 -31.701  -7.122  1.00 14.51           C
ATOM   1426  CD2 TYR A 215       1.190 -31.249  -8.318  1.00 14.18           C
ATOM   1427  C   TYR A 215       0.044 -31.544 -12.850  1.00 12.39           C
ATOM   1428  O   TYR A 215      -0.506 -32.392 -13.519  1.00 14.01           O
ATOM   1429  N   GLY A 216      -0.033 -30.233 -13.107  1.00 12.40           N
ATOM   1430  CA  GLY A 216      -0.762 -29.758 -14.273  1.00 11.90           C
ATOM   1431  C   GLY A 216      -0.101 -30.114 -15.566  1.00 12.74           C
ATOM   1432  O   GLY A 216      -0.762 -30.565 -16.493  1.00 12.34           O
ATOM   1433  N   SER A 217       1.227 -29.949 -15.647  1.00 12.78           N
ATOM   1434  CA  SER A 217       1.927 -30.253 -16.892  1.00 12.48           C
ATOM   1435  CB  SER A 217       3.341 -29.677 -16.914  1.00 12.16           C
ATOM   1436  OG  SER A 217       3.985 -30.006 -15.713  1.00 13.46           O
ATOM   1437  C   SER A 217       1.986 -31.749 -17.147  1.00 11.89           C
ATOM   1438  O   SER A 217       1.890 -32.163 -18.292  1.00 12.64           O
ATOM   1439  N   ARG A 218       2.115 -32.560 -16.098  1.00 12.40           N
ATOM   1440  CA  ARG A 218       2.101 -34.011 -16.334  1.00 13.29           C
ATOM   1441  CB  ARG A 218       2.370 -34.805 -15.073  1.00 13.15           C
ATOM   1442  CG  ARG A 218       3.882 -34.836 -14.771  1.00 14.30           C
ATOM   1443  CD  ARG A 218       4.191 -35.690 -13.560  1.00 14.53           C
ATOM   1444  NE  ARG A 218       3.751 -35.090 -12.304  1.00 15.40           N
ATOM   1445  CZ  ARG A 218       2.739 -35.525 -11.576  1.00 15.91           C
ATOM   1446  NH1 ARG A 218       2.011 -36.557 -11.999  1.00 19.83           N
ATOM   1447  NH2 ARG A 218       2.447 -34.938 -10.425  1.00 14.15           N
ATOM   1448  C   ARG A 218       0.767 -34.388 -16.879  1.00 13.28           C
ATOM   1449  O   ARG A 218       0.681 -35.175 -17.849  1.00 15.25           O
ATOM   1450  N   HIS A 219      -0.264 -33.804 -16.294  1.00 11.81           N
ATOM   1451  CA  HIS A 219      -1.601 -34.148 -16.707  1.00 13.49           C
ATOM   1452  CB  HIS A 219      -2.647 -33.558 -15.773  1.00 11.92           C
ATOM   1453  CG  HIS A 219      -4.031 -33.965 -16.164  1.00 14.91           C
ATOM   1454  ND1 HIS A 219      -4.788 -33.255 -17.070  1.00 17.96           N
ATOM   1455  CE1 HIS A 219      -5.935 -33.883 -17.261  1.00 20.57           C
ATOM   1456  NE2 HIS A 219      -5.932 -34.989 -16.538  1.00 19.74           N
ATOM   1457  CD2 HIS A 219      -4.748 -35.071 -15.854  1.00 16.93           C
ATOM   1458  C   HIS A 219      -1.856 -33.712 -18.142  1.00 13.85           C
ATOM   1459  O   HIS A 219      -2.348 -34.493 -19.008  1.00 14.22           O
ATOM   1460  N   LEU A 220      -1.499 -32.460 -18.431  1.00 14.02           N
ATOM   1461  CA  LEU A 220      -1.790 -31.927 -19.747  1.00 14.50           C
ATOM   1462  CB  LEU A 220      -1.582 -30.408 -19.789  1.00 13.46           C
ATOM   1463  CG  LEU A 220      -2.100 -29.678 -21.040  1.00 14.23           C
ATOM   1464  CD1 LEU A 220      -3.551 -29.954 -21.366  1.00 13.53           C
ATOM   1465  CD2 LEU A 220      -1.834 -28.179 -20.831  1.00 11.08           C
ATOM   1466  C   LEU A 220      -0.985 -32.583 -20.847  1.00 14.45           C
ATOM   1467  O   LEU A 220      -1.488 -32.745 -21.951  1.00 15.55           O
ATOM   1468  N   ALA A 221       0.279 -32.887 -20.586  1.00 14.98           N
ATOM   1469  CA  ALA A 221       1.114 -33.564 -21.585  1.00 16.31           C
```

FIGURE 2-21 (COORDINATES)

```
ATOM   1470  CB  ALA A 221       2.533 -33.758 -21.060  1.00 15.00           C
ATOM   1471  C   ALA A 221       0.498 -34.915 -21.945  1.00 17.33           C
ATOM   1472  O   ALA A 221       0.522 -35.362 -23.111  1.00 17.55           O
ATOM   1473  N   GLN A 222      -0.055 -35.558 -20.929  1.00 19.18           N
ATOM   1474  CA  GLN A 222      -0.672 -36.879 -21.087  1.00 20.90           C
ATOM   1475  CB  GLN A 222      -0.979 -37.445 -19.696  1.00 21.41           C
ATOM   1476  CG  GLN A 222      -1.895 -38.668 -19.675  1.00 26.53           C
ATOM   1477  CD  GLN A 222      -1.108 -39.912 -19.675  1.00 34.83           C
ATOM   1478  OE1 GLN A 222      -0.453 -40.259 -20.684  1.00 39.29           O
ATOM   1479  NE2 GLN A 222      -1.115 -40.603 -18.535  1.00 35.07           N
ATOM   1480  C   GLN A 222      -1.952 -36.704 -21.935  1.00 20.99           C
ATOM   1481  O   GLN A 222      -2.227 -37.459 -22.885  1.00 21.18           O
ATOM   1482  N   LYS A 223      -2.725 -35.692 -21.580  1.00 20.70           N
ATOM   1483  CA  LYS A 223      -3.961 -35.368 -22.244  1.00 20.86           C
ATOM   1484  CB  LYS A 223      -4.677 -34.221 -21.517  1.00 21.26           C
ATOM   1485  CG  LYS A 223      -6.086 -33.933 -22.028  1.00 21.58           C
ATOM   1486  CD  LYS A 223      -6.597 -32.683 -21.360  1.00 22.75           C
ATOM   1487  CE  LYS A 223      -7.908 -32.224 -21.954  1.00 29.68           C
ATOM   1488  NZ  LYS A 223      -9.030 -32.937 -21.322  1.00 33.57           N
ATOM   1489  C   LYS A 223      -3.718 -35.054 -23.715  1.00 21.92           C
ATOM   1490  O   LYS A 223      -4.427 -35.583 -24.569  1.00 21.63           O
ATOM   1491  N   MET A 224      -2.718 -34.217 -24.010  1.00 21.27           N
ATOM   1492  CA  MET A 224      -2.401 -33.849 -25.383  1.00 21.99           C
ATOM   1493  CB  MET A 224      -1.418 -32.674 -25.443  1.00 20.89           C
ATOM   1494  CG  MET A 224      -2.046 -31.381 -24.951  1.00 20.69           C
ATOM   1495  SD  MET A 224      -0.820 -30.072 -24.949  1.00 18.63           S
ATOM   1496  CE  MET A 224      -1.844 -28.587 -24.698  1.00 24.80           C
ATOM   1497  C   MET A 224      -1.859 -35.047 -26.150  1.00 23.42           C
ATOM   1498  O   MET A 224      -2.031 -35.127 -27.366  1.00 23.20           O
ATOM   1499  N   ALA A 225      -1.225 -35.977 -25.434  1.00 24.25           N
ATOM   1500  CA  ALA A 225      -0.751 -37.202 -26.067  1.00 27.38           C
ATOM   1501  CB  ALA A 225       0.230 -37.945 -25.160  1.00 26.09           C
ATOM   1502  C   ALA A 225      -1.919 -38.098 -26.466  1.00 28.19           C
ATOM   1503  O   ALA A 225      -1.811 -38.836 -27.422  1.00 29.52           O
ATOM   1504  N   SER A 226      -3.022 -38.041 -25.717  1.00 29.31           N
ATOM   1505  CA  SER A 226      -4.233 -38.805 -26.010  1.00 31.26           C
ATOM   1506  CB  SER A 226      -4.878 -39.332 -24.714  1.00 30.94           C
ATOM   1507  OG  SER A 226      -3.961 -40.135 -23.988  1.00 33.79           O
ATOM   1508  C   SER A 226      -5.252 -37.923 -26.721  1.00 31.82           C
ATOM   1509  O   SER A 226      -6.476 -38.132 -26.603  1.00 33.23           O
ATOM   1510  N   SER A 227      -4.768 -36.908 -27.426  1.00 31.26           N
ATOM   1511  CA  SER A 227      -5.670 -36.035 -28.137  1.00 30.88           C
ATOM   1512  CB  SER A 227      -5.687 -34.664 -27.498  1.00 30.56           C
ATOM   1513  OG  SER A 227      -6.318 -34.746 -26.244  1.00 31.23           O
ATOM   1514  C   SER A 227      -5.229 -35.957 -29.583  1.00 30.55           C
ATOM   1515  O   SER A 227      -4.326 -35.198 -29.906  1.00 29.80           O
ATOM   1516  N   PRO A 228      -5.864 -36.752 -30.467  1.00 30.37           N
ATOM   1517  CA  PRO A 228      -5.382 -36.684 -31.838  1.00 29.61           C
ATOM   1518  CB  PRO A 228      -6.303 -37.646 -32.594  1.00 29.93           C
ATOM   1519  CG  PRO A 228      -7.088 -38.385 -31.535  1.00 30.63           C
ATOM   1520  CD  PRO A 228      -7.144 -37.479 -30.367  1.00 31.53           C
ATOM   1521  C   PRO A 228      -5.518 -35.261 -32.382  1.00 28.15           C
ATOM   1522  O   PRO A 228      -6.453 -34.518 -32.026  1.00 27.11           O
ATOM   1523  N   HIS A 229      -4.562 -34.898 -33.222  1.00 27.90           N
ATOM   1524  CA  HIS A 229      -4.526 -33.585 -33.814  1.00 28.27           C
ATOM   1525  CB  HIS A 229      -3.829 -32.616 -32.864  1.00 27.39           C
ATOM   1526  CG  HIS A 229      -3.960 -31.192 -33.288  1.00 26.45           C
ATOM   1527  ND1 HIS A 229      -5.122 -30.479 -33.118  1.00 22.79           N
ATOM   1528  CE1 HIS A 229      -4.959 -29.260 -33.602  1.00 23.26           C
ATOM   1529  NE2 HIS A 229      -3.739 -29.170 -34.100  1.00 25.11           N
ATOM   1530  CD2 HIS A 229      -3.088 -30.363 -33.906  1.00 23.75           C
ATOM   1531  C   HIS A 229      -3.813 -33.596 -35.160  1.00 28.54           C
ATOM   1532  O   HIS A 229      -2.695 -34.037 -35.241  1.00 29.25           O
ATOM   1533  N   PRO A 230      -4.457 -33.094 -36.227  1.00 29.93           N
ATOM   1534  CA  PRO A 230      -5.803 -32.522 -36.275  1.00 30.90           C
ATOM   1535  CB  PRO A 230      -5.984 -32.139 -37.753  1.00 30.69           C
ATOM   1536  CG  PRO A 230      -4.646 -32.069 -38.332  1.00 30.31           C
ATOM   1537  CD  PRO A 230      -3.754 -32.967 -37.519  1.00 29.22           C
ATOM   1538  C   PRO A 230      -6.859 -33.535 -35.892  1.00 32.50           C
ATOM   1539  O   PRO A 230      -6.596 -34.746 -35.957  1.00 32.18           O
```

FIGURE 2-22 (COORDINATES)

```
ATOM   1540  N    PRO A 231      -8.046 -33.062 -35.478  1.00 33.91           N
ATOM   1541  CA   PRO A 231      -9.099 -34.034 -35.160  1.00 35.17           C
ATOM   1542  CB   PRO A 231     -10.321 -33.148 -34.923  1.00 35.58           C
ATOM   1543  CG   PRO A 231      -9.746 -31.814 -34.515  1.00 34.52           C
ATOM   1544  CD   PRO A 231      -8.521 -31.667 -35.343  1.00 34.53           C
ATOM   1545  C    PRO A 231      -9.353 -35.017 -36.324  1.00 35.78           C
ATOM   1546  O    PRO A 231      -9.580 -34.577 -37.457  1.00 36.20           O
ATOM   1547  N    GLY A 232      -9.279 -36.323 -36.044  1.00 36.66           N
ATOM   1548  CA   GLY A 232      -9.523 -37.380 -37.055  1.00 37.10           C
ATOM   1549  C    GLY A 232      -8.262 -37.738 -37.823  1.00 37.11           C
ATOM   1550  O    GLY A 232      -8.281 -38.462 -38.843  1.00 36.89           O
ATOM   1551  N    SER A 233      -7.155 -37.179 -37.343  1.00 36.15           N
ATOM   1552  CA   SER A 233      -5.838 -37.618 -37.726  1.00 35.64           C
ATOM   1553  CB   SER A 233      -4.826 -36.654 -37.117  1.00 35.53           C
ATOM   1554  OG   SER A 233      -3.659 -36.612 -37.905  1.00 39.00           O
ATOM   1555  C    SER A 233      -5.688 -38.990 -37.074  1.00 34.69           C
ATOM   1556  O    SER A 233      -6.315 -39.240 -36.041  1.00 34.39           O
ATOM   1557  N    ARG A 234      -4.876 -39.876 -37.639  1.00 33.28           N
ATOM   1558  CA   ARG A 234      -4.750 -41.211 -37.017  1.00 32.01           C
ATOM   1559  CB   ARG A 234      -4.516 -42.287 -38.075  1.00 32.52           C
ATOM   1560  CG   ARG A 234      -5.716 -43.172 -38.277  1.00 34.21           C
ATOM   1561  CD   ARG A 234      -6.797 -42.527 -39.060  1.00 35.59           C
ATOM   1562  NE   ARG A 234      -7.525 -43.581 -39.735  1.00 35.38           N
ATOM   1563  CZ   ARG A 234      -8.612 -44.163 -39.251  1.00 33.36           C
ATOM   1564  NH1  ARG A 234      -9.134 -43.767 -38.088  1.00 32.40           N
ATOM   1565  NH2  ARG A 234      -9.179 -45.125 -39.947  1.00 30.30           N
ATOM   1566  C    ARG A 234      -3.678 -41.315 -35.948  1.00 30.29           C
ATOM   1567  O    ARG A 234      -3.923 -41.800 -34.826  1.00 29.92           O
ATOM   1568  N    GLY A 235      -2.487 -40.874 -36.324  1.00 28.88           N
ATOM   1569  CA   GLY A 235      -1.315 -41.102 -35.530  1.00 27.51           C
ATOM   1570  C    GLY A 235      -0.678 -39.855 -34.971  1.00 26.37           C
ATOM   1571  O    GLY A 235       0.422 -39.922 -34.437  1.00 26.31           O
ATOM   1572  N    THR A 236      -1.340 -38.714 -35.123  1.00 26.19           N
ATOM   1573  CA   THR A 236      -0.753 -37.443 -34.650  1.00 24.82           C
ATOM   1574  CB   THR A 236      -0.562 -36.399 -35.770  1.00 24.93           C
ATOM   1575  OG1  THR A 236      -1.812 -36.184 -36.446  1.00 26.10           O
ATOM   1576  CG2  THR A 236       0.496 -36.841 -36.760  1.00 27.12           C
ATOM   1577  C    THR A 236      -1.628 -36.905 -33.530  1.00 24.26           C
ATOM   1578  O    THR A 236      -2.852 -37.083 -33.530  1.00 24.08           O
ATOM   1579  N    ASN A 237      -0.991 -36.270 -32.542  1.00 23.38           N
ATOM   1580  CA   ASN A 237      -1.731 -35.760 -31.404  1.00 22.25           C
ATOM   1581  CB   ASN A 237      -1.440 -36.609 -30.159  1.00 21.74           C
ATOM   1582  CG   ASN A 237       0.039 -36.766 -29.895  1.00 24.29           C
ATOM   1583  OD1  ASN A 237       0.832 -35.870 -30.190  1.00 26.38           O
ATOM   1584  ND2  ASN A 237       0.435 -37.923 -29.325  1.00 26.13           N
ATOM   1585  C    ASN A 237      -1.338 -34.303 -31.191  1.00 20.12           C
ATOM   1586  O    ASN A 237      -0.487 -33.786 -31.887  1.00 19.26           O
ATOM   1587  N    GLN A 238      -1.931 -33.681 -30.195  1.00 20.13           N
ATOM   1588  CA   GLN A 238      -1.648 -32.285 -29.881  1.00 19.97           C
ATOM   1589  CB   GLN A 238      -2.570 -31.810 -28.798  1.00 20.28           C
ATOM   1590  CG   GLN A 238      -4.008 -31.693 -29.301  1.00 22.76           C
ATOM   1591  CD   GLN A 238      -4.966 -31.381 -28.190  1.00 26.77           C
ATOM   1592  OE1  GLN A 238      -4.628 -31.495 -27.006  1.00 30.03           O
ATOM   1593  NE2  GLN A 238      -6.184 -31.004 -28.552  1.00 24.72           N
ATOM   1594  C    GLN A 238      -0.187 -32.047 -29.526  1.00 19.67           C
ATOM   1595  O    GLN A 238       0.344 -30.964 -29.759  1.00 18.71           O
ATOM   1596  N    LEU A 239       0.493 -33.059 -29.004  1.00 19.33           N
ATOM   1597  CA   LEU A 239       1.912 -32.889 -28.726  1.00 19.93           C
ATOM   1598  CB   LEU A 239       2.466 -34.073 -27.955  1.00 19.88           C
ATOM   1599  CG   LEU A 239       2.004 -34.310 -26.516  1.00 22.14           C
ATOM   1600  CD1  LEU A 239       2.726 -35.538 -26.044  1.00 24.40           C
ATOM   1601  CD2  LEU A 239       2.324 -33.129 -25.596  1.00 22.08           C
ATOM   1602  C    LEU A 239       2.701 -32.657 -29.999  1.00 19.80           C
ATOM   1603  O    LEU A 239       3.618 -31.839 -30.049  1.00 20.11           O
ATOM   1604  N    ASP A 240       2.332 -33.387 -31.048  1.00 20.41           N
ATOM   1605  CA   ASP A 240       2.905 -33.202 -32.370  1.00 19.85           C
ATOM   1606  CB   ASP A 240       2.255 -34.186 -33.325  1.00 20.46           C
ATOM   1607  CG   ASP A 240       2.743 -35.608 -33.084  1.00 23.46           C
ATOM   1608  OD1  ASP A 240       3.975 -35.780 -33.023  1.00 26.53           O
ATOM   1609  OD2  ASP A 240       1.898 -36.508 -32.912  1.00 23.92           O
```

FIGURE 2-23 (COORDINATES)

```
ATOM   1610  C   ASP A 240       2.694 -31.807 -32.872  1.00 20.03           C
ATOM   1611  O   ASP A 240       3.543 -31.256 -33.520  1.00 20.62           O
ATOM   1612  N   GLY A 241       1.558 -31.238 -32.520  1.00 20.94           N
ATOM   1613  CA  GLY A 241       1.198 -29.884 -32.900  1.00 20.27           C
ATOM   1614  C   GLY A 241       2.012 -28.818 -32.207  1.00 20.71           C
ATOM   1615  O   GLY A 241       1.989 -27.663 -32.613  1.00 20.18           O
ATOM   1616  N   MET A 242       2.729 -29.199 -31.147  1.00 20.15           N
ATOM   1617  CA  MET A 242       3.515 -28.231 -30.403  1.00 19.99           C
ATOM   1618  CB  MET A 242       3.715 -28.705 -28.965  1.00 20.54           C
ATOM   1619  CG  MET A 242       2.439 -28.817 -28.222  1.00 21.31           C
ATOM   1620  SD  MET A 242       2.776 -29.312 -26.510  1.00 22.51           S
ATOM   1621  CE  MET A 242       3.534 -27.842 -25.852  1.00 18.77           C
ATOM   1622  C   MET A 242       4.815 -28.017 -31.115  1.00 19.86           C
ATOM   1623  O   MET A 242       5.720 -28.854 -31.067  1.00 19.94           O
ATOM   1624  N   ASP A 243       4.899 -26.900 -31.821  1.00 18.68           N
ATOM   1625  CA  ASP A 243       6.100 -26.556 -32.563  1.00 18.07           C
ATOM   1626  CB  ASP A 243       5.897 -25.231 -33.255  1.00 17.75           C
ATOM   1627  CG  ASP A 243       5.825 -25.383 -34.750  1.00 18.89           C
ATOM   1628  OD1 ASP A 243       5.258 -26.395 -35.171  1.00 18.38           O
ATOM   1629  OD2 ASP A 243       6.335 -24.510 -35.468  1.00 19.68           O
ATOM   1630  C   ASP A 243       7.265 -26.383 -31.625  1.00 18.10           C
ATOM   1631  O   ASP A 243       8.392 -26.812 -31.892  1.00 17.22           O
ATOM   1632  N   LEU A 244       6.962 -25.676 -30.543  1.00 16.02           N
ATOM   1633  CA  LEU A 244       7.949 -25.229 -29.621  1.00 16.06           C
ATOM   1634  CB  LEU A 244       8.687 -24.037 -30.198  1.00 14.93           C
ATOM   1635  CG  LEU A 244       9.752 -23.385 -29.320  1.00 16.66           C
ATOM   1636  CD1 LEU A 244      10.862 -24.422 -29.001  1.00 17.75           C
ATOM   1637  CD2 LEU A 244      10.301 -22.138 -30.010  1.00 15.31           C
ATOM   1638  C   LEU A 244       7.176 -24.851 -28.384  1.00 15.41           C
ATOM   1639  O   LEU A 244       6.123 -24.208 -28.468  1.00 15.89           O
ATOM   1640  N   LEU A 245       7.659 -25.341 -27.247  1.00 15.58           N
ATOM   1641  CA  LEU A 245       7.119 -24.954 -25.970  1.00 14.14           C
ATOM   1642  CB  LEU A 245       6.837 -26.178 -25.054  1.00 13.44           C
ATOM   1643  CG  LEU A 245       6.474 -25.798 -23.604  1.00 12.53           C
ATOM   1644  CD1 LEU A 245       5.121 -25.007 -23.585  1.00 11.06           C
ATOM   1645  CD2 LEU A 245       6.440 -26.994 -22.608  1.00 12.84           C
ATOM   1646  C   LEU A 245       8.118 -24.007 -25.344  1.00 14.38           C
ATOM   1647  O   LEU A 245       9.237 -24.413 -24.973  1.00 14.72           O
ATOM   1648  N   VAL A 246       7.711 -22.747 -25.211  1.00 12.41           N
ATOM   1649  CA  VAL A 246       8.554 -21.736 -24.597  1.00 12.68           C
ATOM   1650  CB  VAL A 246       8.536 -20.411 -25.395  1.00 13.04           C
ATOM   1651  CG1 VAL A 246       9.502 -19.383 -24.788  1.00 13.06           C
ATOM   1652  CG2 VAL A 246       8.862 -20.710 -26.853  1.00 11.75           C
ATOM   1653  C   VAL A 246       7.998 -21.524 -23.205  1.00 12.70           C
ATOM   1654  O   VAL A 246       6.925 -20.946 -23.020  1.00 13.00           O
ATOM   1655  N   LEU A 247       8.741 -22.023 -22.232  1.00 12.11           N
ATOM   1656  CA  LEU A 247       8.261 -22.059 -20.859  1.00 12.07           C
ATOM   1657  CB  LEU A 247       8.499 -23.423 -20.218  1.00 11.86           C
ATOM   1658  CG  LEU A 247       8.085 -23.477 -18.738  1.00 11.41           C
ATOM   1659  CD1 LEU A 247       6.557 -23.255 -18.608  1.00 12.03           C
ATOM   1660  CD2 LEU A 247       8.506 -24.816 -18.078  1.00 10.19           C
ATOM   1661  C   LEU A 247       8.973 -20.997 -20.080  1.00 11.97           C
ATOM   1662  O   LEU A 247      10.203 -21.021 -19.967  1.00 11.57           O
ATOM   1663  N   LEU A 248       8.201 -20.054 -19.555  1.00 10.29           N
ATOM   1664  CA  LEU A 248       8.778 -18.910 -18.873  1.00 10.68           C
ATOM   1665  CB  LEU A 248       7.976 -17.624 -19.127  1.00 10.32           C
ATOM   1666  CG  LEU A 248       7.992 -16.958 -20.508  1.00 13.68           C
ATOM   1667  CD1 LEU A 248       7.100 -15.695 -20.459  1.00 16.86           C
ATOM   1668  CD2 LEU A 248       7.499 -17.919 -21.535  1.00 22.52           C
ATOM   1669  C   LEU A 248       8.644 -19.222 -17.415  1.00 10.30           C
ATOM   1670  O   LEU A 248       7.553 -19.558 -16.951  1.00 10.91           O
ATOM   1671  N   ASP A 249       9.737 -19.058 -16.678  1.00 10.16           N
ATOM   1672  CA  ASP A 249       9.670 -19.297 -15.250  1.00 10.28           C
ATOM   1673  CB  ASP A 249       9.871 -20.790 -14.945  1.00  9.98           C
ATOM   1674  CG  ASP A 249       9.334 -21.208 -13.583  1.00  9.76           C
ATOM   1675  OD1 ASP A 249       8.993 -20.387 -12.731  1.00 11.93           O
ATOM   1676  OD2 ASP A 249       9.283 -22.439 -13.340  1.00 12.07           O
ATOM   1677  C   ASP A 249      10.711 -18.434 -14.540  1.00 10.84           C
ATOM   1678  O   ASP A 249      11.771 -18.183 -15.066  1.00 10.67           O
ATOM   1679  N   LEU A 250      10.381 -17.965 -13.343  1.00 10.11           N
```

FIGURE 2-24 (COORDINATES)

```
ATOM   1680  CA   LEU A 250      11.363 -17.260 -12.523  1.00 10.88           C
ATOM   1681  CB   LEU A 250      12.543 -18.148 -12.150  1.00 12.36           C
ATOM   1682  CG   LEU A 250      12.153 -19.460 -11.460  1.00 11.25           C
ATOM   1683  CD1  LEU A 250      13.399 -20.080 -10.878  1.00 13.92           C
ATOM   1684  CD2  LEU A 250      11.156 -19.179 -10.371  1.00 12.32           C
ATOM   1685  C    LEU A 250      11.858 -16.030 -13.243  1.00 12.12           C
ATOM   1686  O    LEU A 250      13.072 -15.786 -13.367  1.00 12.76           O
ATOM   1687  N    ILE A 251      10.909 -15.228 -13.685  1.00  9.93           N
ATOM   1688  CA   ILE A 251      11.253 -13.987 -14.338  1.00 10.98           C
ATOM   1689  CB   ILE A 251      10.663 -13.907 -15.764  1.00 10.92           C
ATOM   1690  CG1  ILE A 251      11.180 -15.101 -16.625  1.00 10.10           C
ATOM   1691  CD1  ILE A 251      10.622 -15.211 -18.055  1.00 13.38           C
ATOM   1692  CG2  ILE A 251      10.918 -12.529 -16.321  1.00  9.06           C
ATOM   1693  C    ILE A 251      10.703 -12.860 -13.507  1.00 12.27           C
ATOM   1694  O    ILE A 251       9.567 -12.922 -13.041  1.00 11.60           O
ATOM   1695  N    GLY A 252      11.524 -11.826 -13.308  1.00 11.51           N
ATOM   1696  CA   GLY A 252      11.080 -10.628 -12.672  1.00 13.35           C
ATOM   1697  C    GLY A 252      12.166 -10.043 -11.789  1.00 14.15           C
ATOM   1698  O    GLY A 252      12.088  -8.887 -11.404  1.00 15.41           O
ATOM   1699  N    ALA A 253      13.139 -10.865 -11.410  1.00 15.25           N
ATOM   1700  CA   ALA A 253      14.326 -10.391 -10.701  1.00 16.87           C
ATOM   1701  CB   ALA A 253      15.152 -11.565 -10.143  1.00 16.45           C
ATOM   1702  C    ALA A 253      15.203  -9.559 -11.638  1.00 18.81           C
ATOM   1703  O    ALA A 253      15.160  -9.702 -12.863  1.00 18.78           O
ATOM   1704  N    ALA A 254      15.981  -8.669 -11.038  1.00 19.75           N
ATOM   1705  CA   ALA A 254      17.004  -7.942 -11.755  1.00 21.24           C
ATOM   1706  CB   ALA A 254      17.638  -6.912 -10.822  1.00 20.94           C
ATOM   1707  C    ALA A 254      18.066  -8.946 -12.216  1.00 22.07           C
ATOM   1708  O    ALA A 254      18.329  -9.955 -11.547  1.00 23.75           O
ATOM   1709  N    ASN A 255      18.626  -8.684 -13.385  1.00 22.55           N
ATOM   1710  CA   ASN A 255      19.763  -9.440 -13.901  1.00 22.90           C
ATOM   1711  CB   ASN A 255      21.027  -8.963 -13.184  1.00 24.23           C
ATOM   1712  CG   ASN A 255      21.118  -7.428 -13.193  1.00 27.44           C
ATOM   1713  OD1  ASN A 255      21.168  -6.792 -14.276  1.00 32.25           O
ATOM   1714  ND2  ASN A 255      21.067  -6.827 -12.006  1.00 30.06           N
ATOM   1715  C    ASN A 255      19.617 -10.958 -13.942  1.00 21.68           C
ATOM   1716  O    ASN A 255      20.500 -11.698 -13.498  1.00 21.78           O
ATOM   1717  N    PRO A 256      18.505 -11.425 -14.528  1.00 20.61           N
ATOM   1718  CA   PRO A 256      18.346 -12.826 -14.812  1.00 19.75           C
ATOM   1719  CB   PRO A 256      16.923 -12.899 -15.345  1.00 19.43           C
ATOM   1720  CG   PRO A 256      16.767 -11.575 -16.066  1.00 17.76           C
ATOM   1721  CD   PRO A 256      17.411 -10.622 -15.121  1.00 19.85           C
ATOM   1722  C    PRO A 256      19.321 -13.235 -15.925  1.00 19.60           C
ATOM   1723  O    PRO A 256      19.735 -12.407 -16.770  1.00 20.40           O
ATOM   1724  N    THR A 257      19.647 -14.512 -15.941  1.00 18.74           N
ATOM   1725  CA   THR A 257      20.355 -15.099 -17.041  1.00 20.00           C
ATOM   1726  CB   THR A 257      21.872 -15.317 -16.731  1.00 20.69           C
ATOM   1727  OG1  THR A 257      22.010 -16.109 -15.552  1.00 26.79           O
ATOM   1728  CG2  THR A 257      22.549 -14.022 -16.451  1.00 20.88           C
ATOM   1729  C    THR A 257      19.617 -16.391 -17.315  1.00 18.46           C
ATOM   1730  O    THR A 257      19.279 -17.129 -16.391  1.00 18.38           O
ATOM   1731  N    PHE A 258      19.313 -16.595 -18.587  1.00 16.93           N
ATOM   1732  CA   PHE A 258      18.560 -17.720 -19.107  1.00 17.52           C
ATOM   1733  CB   PHE A 258      17.463 -17.206 -20.053  1.00 16.40           C
ATOM   1734  CG   PHE A 258      16.516 -16.316 -19.373  1.00 17.04           C
ATOM   1735  CD1  PHE A 258      15.495 -16.858 -18.610  1.00 14.75           C
ATOM   1736  CE1  PHE A 258      14.624 -16.053 -17.923  1.00 16.35           C
ATOM   1737  CZ   PHE A 258      14.764 -14.683 -17.987  1.00 18.59           C
ATOM   1738  CE2  PHE A 258      15.813 -14.130 -18.725  1.00 19.14           C
ATOM   1739  CD2  PHE A 258      16.679 -14.950 -19.409  1.00 16.46           C
ATOM   1740  C    PHE A 258      19.491 -18.635 -19.873  1.00 18.63           C
ATOM   1741  O    PHE A 258      19.931 -18.278 -20.963  1.00 18.13           O
ATOM   1742  N    PRO A 259      19.745 -19.835 -19.321  1.00 19.61           N
ATOM   1743  CA   PRO A 259      20.618 -20.791 -19.975  1.00 20.17           C
ATOM   1744  CB   PRO A 259      20.737 -21.910 -18.941  1.00 20.81           C
ATOM   1745  CG   PRO A 259      20.366 -21.266 -17.636  1.00 19.97           C
ATOM   1746  CD   PRO A 259      19.247 -20.371 -18.041  1.00 19.18           C
ATOM   1747  C    PRO A 259      19.962 -21.354 -21.216  1.00 20.55           C
ATOM   1748  O    PRO A 259      18.722 -21.372 -21.342  1.00 20.07           O
ATOM   1749  N    ASN A 260      20.815 -21.826 -22.114  1.00 20.60           N
```

FIGURE 2-25 (COORDINATES)

```
ATOM   1750  CA  ASN A 260      20.392 -22.562 -23.272  1.00 21.13           C
ATOM   1751  CB  ASN A 260      21.308 -22.197 -24.422  1.00 21.44           C
ATOM   1752  CG  ASN A 260      20.828 -22.741 -25.742  1.00 22.27           C
ATOM   1753  OD1 ASN A 260      19.731 -23.303 -25.856  1.00 24.22           O
ATOM   1754  ND2 ASN A 260      21.653 -22.569 -26.756  1.00 23.99           N
ATOM   1755  C   ASN A 260      20.464 -24.053 -22.972  1.00 21.83           C
ATOM   1756  O   ASN A 260      21.531 -24.649 -22.962  1.00 23.27           O
ATOM   1757  N   PHE A 261      19.324 -24.681 -22.774  1.00 21.98           N
ATOM   1758  CA  PHE A 261      19.316 -26.016 -22.242  1.00 21.90           C
ATOM   1759  CB  PHE A 261      18.039 -26.234 -21.435  1.00 21.16           C
ATOM   1760  CG  PHE A 261      17.980 -25.446 -20.171  1.00 20.16           C
ATOM   1761  CD1 PHE A 261      17.196 -24.305 -20.099  1.00 17.43           C
ATOM   1762  CE1 PHE A 261      17.120 -23.567 -18.901  1.00 15.84           C
ATOM   1763  CZ  PHE A 261      17.856 -23.974 -17.770  1.00 17.35           C
ATOM   1764  CE2 PHE A 261      18.634 -25.154 -17.830  1.00 15.30           C
ATOM   1765  CD2 PHE A 261      18.690 -25.872 -19.031  1.00 19.63           C
ATOM   1766  C   PHE A 261      19.400 -27.091 -23.304  1.00 22.92           C
ATOM   1767  O   PHE A 261      19.863 -28.206 -23.027  1.00 23.55           O
ATOM   1768  N   PHE A 262      18.890 -26.802 -24.498  1.00 22.50           N
ATOM   1769  CA  PHE A 262      18.616 -27.879 -25.432  1.00 22.76           C
ATOM   1770  CB  PHE A 262      17.120 -28.151 -25.540  1.00 22.77           C
ATOM   1771  CG  PHE A 262      16.466 -28.349 -24.222  1.00 21.91           C
ATOM   1772  CD1 PHE A 262      16.732 -29.488 -23.480  1.00 19.00           C
ATOM   1773  CE1 PHE A 262      16.138 -29.687 -22.252  1.00 22.51           C
ATOM   1774  CZ  PHE A 262      15.266 -28.730 -21.742  1.00 19.12           C
ATOM   1775  CE2 PHE A 262      15.013 -27.575 -22.456  1.00 18.66           C
ATOM   1776  CD2 PHE A 262      15.604 -27.395 -23.711  1.00 22.48           C
ATOM   1777  C   PHE A 262      19.197 -27.648 -26.793  1.00 23.78           C
ATOM   1778  O   PHE A 262      18.871 -26.630 -27.426  1.00 24.04           O
ATOM   1779  N   PRO A 263      20.063 -28.591 -27.242  1.00 24.03           N
ATOM   1780  CA  PRO A 263      20.578 -28.559 -28.609  1.00 24.85           C
ATOM   1781  CB  PRO A 263      21.189 -29.959 -28.793  1.00 24.19           C
ATOM   1782  CG  PRO A 263      21.566 -30.403 -27.450  1.00 25.38           C
ATOM   1783  CD  PRO A 263      20.556 -29.778 -26.497  1.00 24.54           C
ATOM   1784  C   PRO A 263      19.453 -28.353 -29.607  1.00 24.33           C
ATOM   1785  O   PRO A 263      19.564 -27.489 -30.471  1.00 25.67           O
ATOM   1786  N   LYS A 264      18.382 -29.122 -29.459  1.00 24.50           N
ATOM   1787  CA  LYS A 264      17.204 -29.046 -30.316  1.00 24.11           C
ATOM   1788  CB  LYS A 264      16.080 -29.891 -29.745  1.00 24.81           C
ATOM   1789  CG  LYS A 264      14.859 -29.999 -30.660  1.00 26.72           C
ATOM   1790  CD  LYS A 264      13.730 -30.817 -30.033  1.00 27.71           C
ATOM   1791  CE  LYS A 264      13.983 -32.305 -30.015  1.00 29.75           C
ATOM   1792  NZ  LYS A 264      12.701 -33.077 -29.858  1.00 27.15           N
ATOM   1793  C   LYS A 264      16.682 -27.635 -30.593  1.00 24.09           C
ATOM   1794  O   LYS A 264      16.296 -27.321 -31.712  1.00 24.40           O
ATOM   1795  N   THR A 265      16.648 -26.779 -29.588  1.00 23.51           N
ATOM   1796  CA  THR A 265      16.084 -25.439 -29.792  1.00 21.87           C
ATOM   1797  CB  THR A 265      14.928 -25.200 -28.789  1.00 22.03           C
ATOM   1798  OG1 THR A 265      15.412 -25.506 -27.486  1.00 20.98           O
ATOM   1799  CG2 THR A 265      13.799 -26.127 -29.089  1.00 20.23           C
ATOM   1800  C   THR A 265      17.120 -24.346 -29.667  1.00 22.13           C
ATOM   1801  O   THR A 265      16.776 -23.151 -29.536  1.00 21.47           O
ATOM   1802  N   THR A 266      18.404 -24.714 -29.748  1.00 21.20           N
ATOM   1803  CA  THR A 266      19.435 -23.696 -29.631  1.00 20.95           C
ATOM   1804  CB  THR A 266      20.830 -24.299 -29.754  1.00 22.03           C
ATOM   1805  OG1 THR A 266      20.996 -25.245 -28.685  1.00 28.03           O
ATOM   1806  CG2 THR A 266      21.845 -23.228 -29.607  1.00 20.39           C
ATOM   1807  C   THR A 266      19.246 -22.551 -30.624  1.00 19.57           C
ATOM   1808  O   THR A 266      19.513 -21.405 -30.300  1.00 19.03           O
ATOM   1809  N   ARG A 267      18.752 -22.854 -31.820  1.00 19.50           N
ATOM   1810  CA  ARG A 267      18.581 -21.800 -32.841  1.00 19.95           C
ATOM   1811  CB  ARG A 267      18.160 -22.395 -34.173  1.00 19.42           C
ATOM   1812  CG  ARG A 267      16.856 -23.162 -34.176  1.00 20.60           C
ATOM   1813  CD  ARG A 267      16.813 -24.069 -35.381  1.00 22.43           C
ATOM   1814  NE  ARG A 267      15.514 -24.689 -35.585  1.00 27.87           N
ATOM   1815  CZ  ARG A 267      14.562 -24.187 -36.374  1.00 30.59           C
ATOM   1816  NH1 ARG A 267      14.762 -23.050 -37.018  1.00 28.71           N
ATOM   1817  NH2 ARG A 267      13.400 -24.830 -36.511  1.00 32.24           N
ATOM   1818  C   ARG A 267      17.557 -20.772 -32.399  1.00 19.77           C
ATOM   1819  O   ARG A 267      17.666 -19.588 -32.698  1.00 18.29           O
```

FIGURE 2-26 (COORDINATES)

```
ATOM   1820  N    TRP A 268      16.563 -21.257 -31.660  1.00 19.03           N
ATOM   1821  CA   TRP A 268      15.582 -20.362 -31.082  1.00 18.82           C
ATOM   1822  CB   TRP A 268      14.351 -21.160 -30.697  1.00 18.00           C
ATOM   1823  CG   TRP A 268      13.711 -21.765 -31.917  1.00 18.68           C
ATOM   1824  CD1  TRP A 268      13.552 -23.075 -32.193  1.00 20.23           C
ATOM   1825  NE1  TRP A 268      12.951 -23.236 -33.432  1.00 21.85           N
ATOM   1826  CE2  TRP A 268      12.708 -21.998 -33.951  1.00 18.14           C
ATOM   1827  CD2  TRP A 268      13.185 -21.053 -33.029  1.00 18.22           C
ATOM   1828  CE3  TRP A 268      13.065 -19.693 -33.333  1.00 16.27           C
ATOM   1829  CZ3  TRP A 268      12.464 -19.328 -34.520  1.00 17.41           C
ATOM   1830  CH2  TRP A 268      12.006 -20.290 -35.419  1.00 15.87           C
ATOM   1831  CZ2  TRP A 268      12.114 -21.629 -35.155  1.00 19.12           C
ATOM   1832  C    TRP A 268      16.174 -19.620 -29.899  1.00 19.08           C
ATOM   1833  O    TRP A 268      15.885 -18.448 -29.685  1.00 18.78           O
ATOM   1834  N    PHE A 269      17.032 -20.270 -29.135  1.00 17.42           N
ATOM   1835  CA   PHE A 269      17.714 -19.525 -28.090  1.00 18.15           C
ATOM   1836  CB   PHE A 269      18.562 -20.455 -27.232  1.00 19.14           C
ATOM   1837  CG   PHE A 269      19.262 -19.744 -26.128  1.00 17.90           C
ATOM   1838  CD1  PHE A 269      18.659 -19.602 -24.895  1.00 16.58           C
ATOM   1839  CE1  PHE A 269      19.296 -18.936 -23.851  1.00 19.19           C
ATOM   1840  CZ   PHE A 269      20.564 -18.364 -24.059  1.00 18.12           C
ATOM   1841  CE2  PHE A 269      21.172 -18.482 -25.306  1.00 19.68           C
ATOM   1842  CD2  PHE A 269      20.526 -19.180 -26.341  1.00 18.15           C
ATOM   1843  C    PHE A 269      18.539 -18.393 -28.694  1.00 18.06           C
ATOM   1844  O    PHE A 269      18.545 -17.259 -28.210  1.00 18.62           O
ATOM   1845  N    ASN A 270      19.219 -18.716 -29.780  1.00 19.05           N
ATOM   1846  CA   ASN A 270      20.017 -17.764 -30.551  1.00 19.84           C
ATOM   1847  CB   ASN A 270      20.666 -18.516 -31.715  1.00 20.81           C
ATOM   1848  CG   ASN A 270      21.756 -19.497 -31.263  1.00 24.37           C
ATOM   1849  OD1  ASN A 270      22.181 -20.355 -32.054  1.00 28.39           O
ATOM   1850  ND2  ASN A 270      22.228 -19.361 -30.014  1.00 23.28           N
ATOM   1851  C    ASN A 270      19.179 -16.593 -31.067  1.00 19.05           C
ATOM   1852  O    ASN A 270      19.645 -15.475 -31.140  1.00 18.79           O
ATOM   1853  N    ARG A 271      17.930 -16.869 -31.429  1.00 19.05           N
ATOM   1854  CA   ARG A 271      17.023 -15.819 -31.842  1.00 17.57           C
ATOM   1855  CB   ARG A 271      15.690 -16.399 -32.353  1.00 17.65           C
ATOM   1856  CG   ARG A 271      15.785 -17.091 -33.735  1.00 18.94           C
ATOM   1857  CD   ARG A 271      16.485 -16.179 -34.767  1.00 19.74           C
ATOM   1858  NE   ARG A 271      15.826 -14.865 -34.851  1.00 21.05           N
ATOM   1859  CZ   ARG A 271      16.392 -13.703 -35.193  1.00 24.64           C
ATOM   1860  NH1  ARG A 271      17.673 -13.627 -35.539  1.00 25.88           N
ATOM   1861  NH2  ARG A 271      15.661 -12.594 -35.196  1.00 22.56           N
ATOM   1862  C    ARG A 271      16.786 -14.912 -30.666  1.00 16.82           C
ATOM   1863  O    ARG A 271      16.856 -13.716 -30.812  1.00 16.15           O
ATOM   1864  N    LEU A 272      16.522 -15.452 -29.476  1.00 16.37           N
ATOM   1865  CA   LEU A 272      16.393 -14.540 -28.323  1.00 16.18           C
ATOM   1866  CB   LEU A 272      16.089 -15.288 -27.002  1.00 15.60           C
ATOM   1867  CG   LEU A 272      14.721 -15.961 -27.064  1.00 15.98           C
ATOM   1868  CD1  LEU A 272      14.583 -17.055 -26.003  1.00 14.64           C
ATOM   1869  CD2  LEU A 272      13.577 -14.937 -26.990  1.00 17.40           C
ATOM   1870  C    LEU A 272      17.633 -13.665 -28.151  1.00 16.68           C
ATOM   1871  O    LEU A 272      17.538 -12.463 -27.896  1.00 16.46           O
ATOM   1872  N    GLN A 273      18.815 -14.274 -28.243  1.00 17.66           N
ATOM   1873  CA   GLN A 273      20.058 -13.505 -28.147  1.00 18.45           C
ATOM   1874  CB   GLN A 273      21.243 -14.436 -28.404  1.00 19.16           C
ATOM   1875  CG   GLN A 273      21.345 -15.515 -27.359  1.00 22.36           C
ATOM   1876  CD   GLN A 273      22.650 -16.292 -27.490  1.00 26.98           C
ATOM   1877  OE1  GLN A 273      22.763 -17.208 -28.316  1.00 32.09           O
ATOM   1878  NE2  GLN A 273      23.631 -15.923 -26.685  1.00 27.93           N
ATOM   1879  C    GLN A 273      20.112 -12.353 -29.143  1.00 17.46           C
ATOM   1880  O    GLN A 273      20.372 -11.197 -28.773  1.00 17.26           O
ATOM   1881  N    ALA A 274      19.853 -12.695 -30.401  1.00 17.51           N
ATOM   1882  CA   ALA A 274      19.862 -11.739 -31.516  1.00 17.56           C
ATOM   1883  CB   ALA A 274      19.507 -12.472 -32.823  1.00 17.60           C
ATOM   1884  C    ALA A 274      18.870 -10.609 -31.236  1.00 17.34           C
ATOM   1885  O    ALA A 274      19.187  -9.425 -31.373  1.00 17.20           O
ATOM   1886  N    ILE A 275      17.667 -10.994 -30.774  1.00 17.45           N
ATOM   1887  CA   ILE A 275      16.630 -10.018 -30.460  1.00 16.41           C
ATOM   1888  CB   ILE A 275      15.273 -10.703 -30.196  1.00 16.76           C
ATOM   1889  CG1  ILE A 275      14.721 -11.313 -31.492  1.00 15.00           C
```

FIGURE 2-27 (COORDINATES)

```
ATOM   1890  CD1 ILE A 275      13.737 -12.482 -31.309  1.00 12.53           C
ATOM   1891  CG2 ILE A 275      14.254  -9.703 -29.604  1.00 16.80           C
ATOM   1892  C   ILE A 275      17.058  -9.098 -29.321  1.00 17.49           C
ATOM   1893  O   ILE A 275      16.901  -7.902 -29.411  1.00 17.23           O
ATOM   1894  N   GLU A 276      17.565  -9.661 -28.228  1.00 16.06           N
ATOM   1895  CA  GLU A 276      18.073  -8.861 -27.123  1.00 15.95           C
ATOM   1896  CB  GLU A 276      18.752  -9.787 -26.089  1.00 14.70           C
ATOM   1897  CG  GLU A 276      19.385  -9.000 -24.941  1.00 15.73           C
ATOM   1898  CD  GLU A 276      19.976  -9.879 -23.880  1.00 11.11           C
ATOM   1899  OE1 GLU A 276      20.057 -11.094 -24.074  1.00 17.22           O
ATOM   1900  OE2 GLU A 276      20.339  -9.333 -22.844  1.00 15.84           O
ATOM   1901  C   GLU A 276      19.101  -7.851 -27.614  1.00 16.17           C
ATOM   1902  O   GLU A 276      19.059  -6.671 -27.286  1.00 15.93           O
ATOM   1903  N   LYS A 277      19.991  -8.351 -28.451  1.00 17.87           N
ATOM   1904  CA  LYS A 277      21.084  -7.549 -28.977  1.00 19.00           C
ATOM   1905  CB  LYS A 277      22.058  -8.451 -29.721  1.00 19.55           C
ATOM   1906  CG  LYS A 277      23.226  -7.642 -30.263  1.00 24.12           C
ATOM   1907  CD  LYS A 277      24.323  -8.521 -30.805  1.00 28.87           C
ATOM   1908  CE  LYS A 277      25.302  -7.660 -31.559  1.00 33.22           C
ATOM   1909  NZ  LYS A 277      24.817  -7.472 -32.963  1.00 35.49           N
ATOM   1910  C   LYS A 277      20.553  -6.400 -29.864  1.00 18.91           C
ATOM   1911  O   LYS A 277      20.876  -5.225 -29.616  1.00 19.01           O
ATOM   1912  N   GLU A 278      19.713  -6.735 -30.843  1.00 18.90           N
ATOM   1913  CA  GLU A 278      19.211  -5.746 -31.791  1.00 20.20           C
ATOM   1914  CB  GLU A 278      18.555  -6.431 -32.989  1.00 20.85           C
ATOM   1915  CG  GLU A 278      17.207  -6.990 -32.685  1.00 20.88           C
ATOM   1916  CD  GLU A 278      16.661  -7.877 -33.767  1.00 27.04           C
ATOM   1917  OE1 GLU A 278      17.407  -8.215 -34.712  1.00 29.18           O
ATOM   1918  OE2 GLU A 278      15.468  -8.252 -33.659  1.00 28.72           O
ATOM   1919  C   GLU A 278      18.281  -4.785 -31.068  1.00 20.53           C
ATOM   1920  O   GLU A 278      18.358  -3.579 -31.260  1.00 19.84           O
ATOM   1921  N   LEU A 279      17.437  -5.290 -30.147  1.00 20.11           N
ATOM   1922  CA  LEU A 279      16.653  -4.354 -29.400  1.00 19.56           C
ATOM   1923  CB  LEU A 279      15.630  -5.042 -28.484  1.00 19.90           C
ATOM   1924  CG  LEU A 279      14.490  -5.737 -29.211  1.00 19.30           C
ATOM   1925  CD1 LEU A 279      13.628  -6.462 -28.177  1.00 19.31           C
ATOM   1926  CD2 LEU A 279      13.655  -4.765 -30.027  1.00 21.74           C
ATOM   1927  C   LEU A 279      17.572  -3.457 -28.607  1.00 19.95           C
ATOM   1928  O   LEU A 279      17.369  -2.243 -28.557  1.00 20.20           O
ATOM   1929  N   TYR A 280      18.612  -4.035 -28.015  1.00 19.70           N
ATOM   1930  CA  TYR A 280      19.534  -3.213 -27.241  1.00 20.58           C
ATOM   1931  CB  TYR A 280      20.735  -3.997 -26.700  1.00 20.18           C
ATOM   1932  CG  TYR A 280      21.711  -3.036 -26.056  1.00 21.97           C
ATOM   1933  CD1 TYR A 280      21.330  -2.303 -24.946  1.00 23.21           C
ATOM   1934  CE1 TYR A 280      22.175  -1.376 -24.379  1.00 25.76           C
ATOM   1935  CZ  TYR A 280      23.425  -1.164 -24.948  1.00 26.30           C
ATOM   1936  OH  TYR A 280      24.251  -0.243 -24.357  1.00 27.03           O
ATOM   1937  CE2 TYR A 280      23.821  -1.845 -26.072  1.00 25.22           C
ATOM   1938  CD2 TYR A 280      22.962  -2.782 -26.630  1.00 26.24           C
ATOM   1939  C   TYR A 280      20.076  -2.111 -28.146  1.00 21.20           C
ATOM   1940  O   TYR A 280      20.098  -0.940 -27.756  1.00 21.76           O
ATOM   1941  N   GLU A 281      20.512  -2.511 -29.341  1.00 22.27           N
ATOM   1942  CA  GLU A 281      21.264  -1.601 -30.219  1.00 24.34           C
ATOM   1943  CB  GLU A 281      21.827  -2.312 -31.418  1.00 25.19           C
ATOM   1944  CG  GLU A 281      22.817  -3.426 -31.104  1.00 28.25           C
ATOM   1945  CD  GLU A 281      23.072  -4.296 -32.331  1.00 34.31           C
ATOM   1946  OE1 GLU A 281      22.157  -4.461 -33.204  1.00 36.88           O
ATOM   1947  OE2 GLU A 281      24.198  -4.814 -32.431  1.00 34.72           O
ATOM   1948  C   GLU A 281      20.377  -0.481 -30.716  1.00 24.81           C
ATOM   1949  O   GLU A 281      20.858   0.623 -30.978  1.00 24.61           O
ATOM   1950  N   LEU A 282      19.086  -0.773 -30.834  1.00 24.56           N
ATOM   1951  CA  LEU A 282      18.125   0.202 -31.321  1.00 25.11           C
ATOM   1952  CB  LEU A 282      16.958  -0.512 -31.995  1.00 25.39           C
ATOM   1953  CG  LEU A 282      17.133  -1.278 -33.313  1.00 27.30           C
ATOM   1954  CD1 LEU A 282      15.868  -2.031 -33.608  1.00 29.69           C
ATOM   1955  CD2 LEU A 282      18.309  -2.261 -33.353  1.00 32.48           C
ATOM   1956  C   LEU A 282      17.669   1.125 -30.200  1.00 23.91           C
ATOM   1957  O   LEU A 282      16.840   2.026 -30.422  1.00 24.60           O
ATOM   1958  N   GLY A 283      18.209   0.916 -29.001  1.00 22.85           N
ATOM   1959  CA  GLY A 283      17.904   1.747 -27.835  1.00 22.51           C
```

FIGURE 2-28 (COORDINATES)

```
ATOM   1960  C    GLY A 283      16.453   1.505 -27.420  1.00 22.60           C
ATOM   1961  O    GLY A 283      15.761   2.416 -26.982  1.00 22.96           O
ATOM   1962  N    LEU A 284      16.007   0.269 -27.583  1.00 22.44           N
ATOM   1963  CA   LEU A 284      14.629  -0.113 -27.310  1.00 21.12           C
ATOM   1964  CB   LEU A 284      14.041  -0.854 -28.499  1.00 21.20           C
ATOM   1965  CG   LEU A 284      14.005  -0.007 -29.753  1.00 20.05           C
ATOM   1966  CD1  LEU A 284      13.608  -0.856 -30.904  1.00 20.19           C
ATOM   1967  CD2  LEU A 284      13.042   1.144 -29.571  1.00 22.28           C
ATOM   1968  C    LEU A 284      14.479  -0.944 -26.043  1.00 21.56           C
ATOM   1969  O    LEU A 284      13.376  -1.365 -25.719  1.00 21.57           O
ATOM   1970  N    LEU A 285      15.581  -1.163 -25.336  1.00 20.61           N
ATOM   1971  CA   LEU A 285      15.530  -1.753 -24.027  1.00 19.99           C
ATOM   1972  CB   LEU A 285      16.554  -2.860 -23.906  1.00 20.19           C
ATOM   1973  CG   LEU A 285      16.443  -3.976 -24.921  1.00 18.14           C
ATOM   1974  CD1  LEU A 285      17.362  -5.103 -24.484  1.00 18.69           C
ATOM   1975  CD2  LEU A 285      14.999  -4.457 -25.002  1.00 18.16           C
ATOM   1976  C    LEU A 285      15.801  -0.673 -23.007  1.00 21.64           C
ATOM   1977  O    LEU A 285      16.221   0.437 -23.363  1.00 21.69           O
ATOM   1978  N    LYS A 286      15.570  -0.981 -21.741  1.00 20.80           N
ATOM   1979  CA   LYS A 286      15.802  -0.014 -20.718  1.00 22.15           C
ATOM   1980  CB   LYS A 286      14.500   0.588 -20.180  1.00 21.63           C
ATOM   1981  CG   LYS A 286      13.662   1.330 -21.204  1.00 24.11           C
ATOM   1982  CD   LYS A 286      12.247   1.563 -20.606  1.00 29.87           C
ATOM   1983  CE   LYS A 286      11.495   2.762 -21.167  1.00 31.14           C
ATOM   1984  NZ   LYS A 286      11.340   2.744 -22.644  1.00 31.82           N
ATOM   1985  C    LYS A 286      16.633  -0.610 -19.606  1.00 22.81           C
ATOM   1986  O    LYS A 286      16.493  -1.778 -19.242  1.00 22.36           O
ATOM   1987  N    ASP A 287      17.511   0.230 -19.067  1.00 23.07           N
ATOM   1988  CA   ASP A 287      18.399  -0.126 -17.980  1.00 24.18           C
ATOM   1989  CB   ASP A 287      17.670  -0.008 -16.661  1.00 25.33           C
ATOM   1990  CG   ASP A 287      17.285   1.416 -16.375  1.00 30.49           C
ATOM   1991  OD1  ASP A 287      18.171   2.306 -16.535  1.00 36.97           O
ATOM   1992  OD2  ASP A 287      16.109   1.650 -16.039  1.00 34.43           O
ATOM   1993  C    ASP A 287      19.055  -1.469 -18.149  1.00 23.09           C
ATOM   1994  O    ASP A 287      19.160  -2.255 -17.215  1.00 22.69           O
ATOM   1995  N    HIS A 288      19.517  -1.716 -19.357  1.00 23.12           N
ATOM   1996  CA   HIS A 288      20.094  -2.996 -19.675  1.00 22.74           C
ATOM   1997  CB   HIS A 288      19.004  -3.991 -20.080  1.00 21.93           C
ATOM   1998  CG   HIS A 288      19.539  -5.364 -20.316  1.00 21.32           C
ATOM   1999  ND1  HIS A 288      19.554  -5.956 -21.561  1.00 21.40           N
ATOM   2000  CE1  HIS A 288      20.133  -7.139 -21.473  1.00 17.37           C
ATOM   2001  NE2  HIS A 288      20.489  -7.335 -20.213  1.00 21.71           N
ATOM   2002  CD2  HIS A 288      20.151  -6.231 -19.476  1.00 19.04           C
ATOM   2003  C    HIS A 288      21.084  -2.864 -20.801  1.00 22.92           C
ATOM   2004  O    HIS A 288      20.721  -2.538 -21.939  1.00 22.94           O
ATOM   2005  N    SER A 289      22.336  -3.149 -20.481  1.00 23.22           N
ATOM   2006  CA   SER A 289      23.369  -3.259 -21.495  1.00 23.51           C
ATOM   2007  CB   SER A 289      24.673  -2.674 -20.963  1.00 23.13           C
ATOM   2008  OG   SER A 289      25.225  -3.553 -20.001  1.00 25.92           O
ATOM   2009  C    SER A 289      23.561  -4.739 -21.830  1.00 23.67           C
ATOM   2010  O    SER A 289      22.952  -5.627 -21.197  1.00 23.95           O
ATOM   2011  N    LEU A 290      24.411  -5.014 -22.815  1.00 23.29           N
ATOM   2012  CA   LEU A 290      24.748  -6.385 -23.113  1.00 22.52           C
ATOM   2013  CB   LEU A 290      24.976  -6.568 -24.608  1.00 22.60           C
ATOM   2014  CG   LEU A 290      23.750  -6.079 -25.412  1.00 24.18           C
ATOM   2015  CD1  LEU A 290      23.955  -6.214 -26.916  1.00 26.13           C
ATOM   2016  CD2  LEU A 290      22.479  -6.794 -24.959  1.00 21.69           C
ATOM   2017  C    LEU A 290      25.952  -6.846 -22.289  1.00 22.52           C
ATOM   2018  O    LEU A 290      26.567  -7.853 -22.616  1.00 21.99           O
ATOM   2019  N    GLU A 291      26.270  -6.108 -21.232  1.00 22.29           N
ATOM   2020  CA   GLU A 291      27.383  -6.463 -20.355  1.00 23.24           C
ATOM   2021  CB   GLU A 291      27.587  -5.388 -19.286  1.00 23.60           C
ATOM   2022  CG   GLU A 291      28.433  -4.219 -19.806  1.00 23.36           C
ATOM   2023  CD   GLU A 291      29.737  -4.737 -20.421  1.00 28.27           C
ATOM   2024  OE1  GLU A 291      30.408  -5.580 -19.787  1.00 31.41           O
ATOM   2025  OE2  GLU A 291      30.068  -4.348 -21.541  1.00 26.64           O
ATOM   2026  C    GLU A 291      27.092  -7.812 -19.696  1.00 24.11           C
ATOM   2027  O    GLU A 291      27.979  -8.643 -19.493  1.00 24.43           O
ATOM   2028  N    ARG A 292      25.823  -7.992 -19.364  1.00 24.56           N
ATOM   2029  CA   ARG A 292      25.324  -9.222 -18.783  1.00 24.73           C
```

FIGURE 2-29 (COORDINATES)

```
ATOM   2030  CB  ARG A 292      25.036  -9.028 -17.298  1.00 26.31           C
ATOM   2031  CG  ARG A 292      26.274  -8.732 -16.433  1.00 29.41           C
ATOM   2032  CD  ARG A 292      25.856  -8.607 -14.966  1.00 36.66           C
ATOM   2033  NE  ARG A 292      25.139  -7.357 -14.658  1.00 40.77           N
ATOM   2034  CZ  ARG A 292      24.631  -7.057 -13.455  1.00 41.93           C
ATOM   2035  NH1 ARG A 292      24.738  -7.910 -12.437  1.00 39.73           N
ATOM   2036  NH2 ARG A 292      24.006  -5.898 -13.263  1.00 42.70           N
ATOM   2037  C   ARG A 292      24.048  -9.579 -19.522  1.00 23.92           C
ATOM   2038  O   ARG A 292      22.954  -9.372 -19.001  1.00 24.06           O
ATOM   2039  N   LYS A 293      24.203 -10.096 -20.736  1.00 22.38           N
ATOM   2040  CA  LYS A 293      23.090 -10.434 -21.599  1.00 22.92           C
ATOM   2041  CB  LYS A 293      23.595 -11.164 -22.853  1.00 23.15           C
ATOM   2042  CG  LYS A 293      24.265 -10.268 -23.904  1.00 24.68           C
ATOM   2043  CD  LYS A 293      24.790 -11.125 -25.081  1.00 28.08           C
ATOM   2044  CE  LYS A 293      26.127 -11.789 -24.726  1.00 28.38           C
ATOM   2045  NZ  LYS A 293      26.856 -12.276 -25.935  1.00 33.95           N
ATOM   2046  C   LYS A 293      22.131 -11.345 -20.839  1.00 22.39           C
ATOM   2047  O   LYS A 293      22.561 -12.158 -20.025  1.00 21.57           O
ATOM   2048  N   TYR A 294      20.832 -11.182 -21.071  1.00 20.33           N
ATOM   2049  CA  TYR A 294      19.877 -12.109 -20.494  1.00 20.81           C
ATOM   2050  CB  TYR A 294      18.452 -11.702 -20.873  1.00 20.79           C
ATOM   2051  CG  TYR A 294      18.062 -10.387 -20.338  1.00 16.88           C
ATOM   2052  CD1 TYR A 294      18.363 -10.038 -19.032  1.00 18.93           C
ATOM   2053  CE1 TYR A 294      17.994  -8.841 -18.523  1.00 20.90           C
ATOM   2054  CZ  TYR A 294      17.257  -7.956 -19.301  1.00 21.55           C
ATOM   2055  OH  TYR A 294      16.902  -6.752 -18.773  1.00 21.88           O
ATOM   2056  CE2 TYR A 294      16.911  -8.275 -20.587  1.00 21.74           C
ATOM   2057  CD2 TYR A 294      17.323  -9.491 -21.115  1.00 18.53           C
ATOM   2058  C   TYR A 294      20.103 -13.484 -21.048  1.00 21.01           C
ATOM   2059  O   TYR A 294      20.013 -14.463 -20.320  1.00 22.01           O
ATOM   2060  N   PHE A 295      20.351 -13.550 -22.351  1.00 21.26           N
ATOM   2061  CA  PHE A 295      20.499 -14.802 -23.035  1.00 22.71           C
ATOM   2062  CB  PHE A 295      19.638 -14.849 -24.275  1.00 21.87           C
ATOM   2063  CG  PHE A 295      18.217 -14.623 -23.939  1.00 20.13           C
ATOM   2064  CD1 PHE A 295      17.493 -15.634 -23.345  1.00 18.79           C
ATOM   2065  CE1 PHE A 295      16.189 -15.418 -22.943  1.00 19.42           C
ATOM   2066  CZ  PHE A 295      15.614 -14.183 -23.149  1.00 19.03           C
ATOM   2067  CE2 PHE A 295      16.332 -13.137 -23.704  1.00 17.52           C
ATOM   2068  CD2 PHE A 295      17.644 -13.364 -24.098  1.00 19.52           C
ATOM   2069  C   PHE A 295      21.956 -15.065 -23.283  1.00 24.16           C
ATOM   2070  O   PHE A 295      22.532 -14.676 -24.296  1.00 23.75           O
ATOM   2071  N   GLN A 296      22.495 -15.732 -22.280  1.00 26.78           N
ATOM   2072  CA  GLN A 296      23.876 -16.124 -22.212  1.00 29.86           C
ATOM   2073  CB  GLN A 296      24.480 -15.780 -20.853  1.00 29.94           C
ATOM   2074  CG  GLN A 296      24.694 -14.295 -20.591  1.00 31.56           C
ATOM   2075  CD  GLN A 296      26.009 -13.733 -21.153  1.00 34.46           C
ATOM   2076  OE1 GLN A 296      26.301 -13.854 -22.344  1.00 34.03           O
ATOM   2077  NE2 GLN A 296      26.791 -13.084 -20.286  1.00 35.85           N
ATOM   2078  C   GLN A 296      23.854 -17.614 -22.390  1.00 30.77           C
ATOM   2079  O   GLN A 296      23.155 -18.356 -21.656  1.00 31.12           O
ATOM   2080  N   ASN A 297      24.585 -18.034 -23.406  1.00 31.63           N
ATOM   2081  CA  ASN A 297      24.815 -19.424 -23.645  1.00 33.03           C
ATOM   2082  CB  ASN A 297      24.715 -19.691 -25.144  1.00 32.67           C
ATOM   2083  CG  ASN A 297      24.777 -21.151 -25.470  1.00 34.17           C
ATOM   2084  OD1 ASN A 297      25.383 -21.955 -24.734  1.00 37.58           O
ATOM   2085  ND2 ASN A 297      24.168 -21.520 -26.573  1.00 36.16           N
ATOM   2086  C   ASN A 297      26.203 -19.799 -23.094  1.00 33.56           C
ATOM   2087  O   ASN A 297      27.218 -19.512 -23.727  1.00 32.92           O
ATOM   2088  N   PHE A 298      26.216 -20.417 -21.905  1.00 34.83           N
ATOM   2089  CA  PHE A 298      27.412 -20.954 -21.274  1.00 35.61           C
ATOM   2090  CB  PHE A 298      27.340 -20.849 -19.756  1.00 37.57           C
ATOM   2091  CG  PHE A 298      26.990 -19.493 -19.220  1.00 41.36           C
ATOM   2092  CD1 PHE A 298      25.673 -19.219 -18.808  1.00 45.52           C
ATOM   2093  CE1 PHE A 298      25.334 -17.979 -18.258  1.00 46.94           C
ATOM   2094  CZ  PHE A 298      26.326 -16.995 -18.112  1.00 48.29           C
ATOM   2095  CE2 PHE A 298      27.652 -17.277 -18.499  1.00 45.98           C
ATOM   2096  CD2 PHE A 298      27.973 -18.527 -19.040  1.00 43.26           C
ATOM   2097  C   PHE A 298      27.499 -22.451 -21.566  1.00 35.42           C
ATOM   2098  O   PHE A 298      28.018 -23.239 -20.738  1.00 34.83           O
ATOM   2099  N   GLY A 299      26.998 -22.851 -22.729  1.00 34.73           N
```

FIGURE 2-30 (COORDINATES)

```
ATOM   2100  CA  GLY A 299      26.896 -24.264 -23.057  1.00 34.14           C
ATOM   2101  C   GLY A 299      25.571 -24.819 -22.586  1.00 33.86           C
ATOM   2102  O   GLY A 299      24.872 -24.201 -21.778  1.00 33.76           O
ATOM   2103  N   TYR A 300      25.217 -25.999 -23.075  1.00 33.59           N
ATOM   2104  CA  TYR A 300      23.958 -26.589 -22.693  1.00 33.21           C
ATOM   2105  CB  TYR A 300      23.708 -27.896 -23.445  1.00 33.77           C
ATOM   2106  CG  TYR A 300      23.595 -27.614 -24.921  1.00 35.33           C
ATOM   2107  CD1 TYR A 300      22.650 -26.713 -25.384  1.00 36.10           C
ATOM   2108  CE1 TYR A 300      22.554 -26.408 -26.715  1.00 39.85           C
ATOM   2109  CZ  TYR A 300      23.412 -27.012 -27.634  1.00 40.32           C
ATOM   2110  OH  TYR A 300      23.287 -26.696 -28.979  1.00 43.23           O
ATOM   2111  CE2 TYR A 300      24.365 -27.906 -27.208  1.00 38.85           C
ATOM   2112  CD2 TYR A 300      24.463 -28.199 -25.846  1.00 37.47           C
ATOM   2113  C   TYR A 300      23.840 -26.705 -21.181  1.00 32.66           C
ATOM   2114  O   TYR A 300      24.593 -27.454 -20.544  1.00 32.28           O
ATOM   2115  N   GLY A 301      22.920 -25.891 -20.627  1.00 31.51           N
ATOM   2116  CA  GLY A 301      22.547 -25.922 -19.218  1.00 28.99           C
ATOM   2117  C   GLY A 301      22.117 -27.312 -18.758  1.00 27.67           C
ATOM   2118  O   GLY A 301      21.613 -28.094 -19.527  1.00 28.40           O
ATOM   2119  N   ASN A 302      22.394 -27.636 -17.505  1.00 26.85           N
ATOM   2120  CA  ASN A 302      21.884 -28.830 -16.881  1.00 24.38           C
ATOM   2121  CB  ASN A 302      22.567 -29.040 -15.564  1.00 25.43           C
ATOM   2122  CG  ASN A 302      24.005 -29.494 -15.730  1.00 28.03           C
ATOM   2123  OD1 ASN A 302      24.316 -30.307 -16.606  1.00 32.57           O
ATOM   2124  ND2 ASN A 302      24.888 -28.965 -14.895  1.00 31.75           N
ATOM   2125  C   ASN A 302      20.406 -28.591 -16.650  1.00 22.71           C
ATOM   2126  O   ASN A 302      20.009 -27.584 -16.055  1.00 21.52           O
ATOM   2127  N   ILE A 303      19.603 -29.505 -17.180  1.00 20.98           N
ATOM   2128  CA  ILE A 303      18.147 -29.394 -17.170  1.00 19.34           C
ATOM   2129  CB  ILE A 303      17.509 -30.685 -17.698  1.00 19.55           C
ATOM   2130  CG1 ILE A 303      16.010 -30.487 -17.934  1.00 22.46           C
ATOM   2131  CD1 ILE A 303      15.416 -31.537 -18.865  1.00 25.65           C
ATOM   2132  CG2 ILE A 303      17.746 -31.881 -16.733  1.00 22.54           C
ATOM   2133  C   ILE A 303      17.637 -29.117 -15.778  1.00 17.86           C
ATOM   2134  O   ILE A 303      18.139 -29.719 -14.810  1.00 15.67           O
ATOM   2135  N   ILE A 304      16.659 -28.203 -15.673  1.00 15.46           N
ATOM   2136  CA  ILE A 304      15.997 -27.896 -14.416  1.00 14.09           C
ATOM   2137  CB  ILE A 304      15.954 -26.397 -14.152  1.00 14.29           C
ATOM   2138  CG1 ILE A 304      17.397 -25.834 -14.065  1.00 14.09           C
ATOM   2139  CD1 ILE A 304      17.508 -24.314 -14.090  1.00 11.85           C
ATOM   2140  CG2 ILE A 304      15.163 -26.148 -12.849  1.00 15.56           C
ATOM   2141  C   ILE A 304      14.571 -28.408 -14.553  1.00 13.22           C
ATOM   2142  O   ILE A 304      13.920 -28.084 -15.538  1.00 13.35           O
ATOM   2143  N   GLN A 305      14.116 -29.233 -13.624  1.00 12.60           N
ATOM   2144  CA  GLN A 305      12.753 -29.763 -13.700  1.00 13.62           C
ATOM   2145  CB  GLN A 305      12.463 -30.748 -12.556  1.00 14.13           C
ATOM   2146  CG  GLN A 305      13.379 -31.988 -12.557  1.00 17.25           C
ATOM   2147  CD  GLN A 305      13.330 -32.790 -13.851  1.00 21.89           C
ATOM   2148  OE1 GLN A 305      12.278 -33.319 -14.231  1.00 25.35           O
ATOM   2149  NE2 GLN A 305      14.487 -32.924 -14.513  1.00 26.02           N
ATOM   2150  C   GLN A 305      11.758 -28.615 -13.627  1.00 11.83           C
ATOM   2151  O   GLN A 305      11.927 -27.648 -12.876  1.00 13.27           O
ATOM   2152  N   ASP A 306      10.741 -28.727 -14.454  1.00 11.85           N
ATOM   2153  CA  ASP A 306       9.726 -27.682 -14.584  1.00 11.50           C
ATOM   2154  CB  ASP A 306      10.332 -26.385 -15.185  1.00 10.22           C
ATOM   2155  CG  ASP A 306       9.576 -25.162 -14.814  1.00  7.51           C
ATOM   2156  OD1 ASP A 306       8.474 -25.278 -14.271  1.00 10.66           O
ATOM   2157  OD2 ASP A 306      10.071 -24.058 -15.054  1.00 10.79           O
ATOM   2158  C   ASP A 306       8.652 -28.255 -15.508  1.00 10.88           C
ATOM   2159  O   ASP A 306       8.727 -29.402 -15.976  1.00 10.81           O
ATOM   2160  N   ASP A 307       7.635 -27.443 -15.757  1.00 12.12           N
ATOM   2161  CA  ASP A 307       6.487 -27.896 -16.517  1.00 11.73           C
ATOM   2162  CB  ASP A 307       5.496 -26.749 -16.639  1.00 12.62           C
ATOM   2163  CG  ASP A 307       4.739 -26.533 -15.361  1.00 12.19           C
ATOM   2164  OD1 ASP A 307       4.343 -27.528 -14.691  1.00 14.65           O
ATOM   2165  OD2 ASP A 307       4.542 -25.363 -15.048  1.00 12.64           O
ATOM   2166  C   ASP A 307       6.814 -28.368 -17.908  1.00 10.89           C
ATOM   2167  O   ASP A 307       5.977 -28.987 -18.512  1.00 10.73           O
ATOM   2168  N   HIS A 308       7.993 -28.047 -18.448  1.00 11.30           N
ATOM   2169  CA  HIS A 308       8.344 -28.546 -19.790  1.00 12.26           C
```

FIGURE 2-31 (COORDINATES)

```
ATOM  2170  CB   HIS A 308       9.526 -27.763 -20.343  1.00 13.27           C
ATOM  2171  CG   HIS A 308      10.780 -27.930 -19.532  1.00 13.16           C
ATOM  2172  ND1  HIS A 308      10.797 -27.803 -18.152  1.00 14.33           N
ATOM  2173  CE1  HIS A 308      12.031 -27.980 -17.712  1.00 14.60           C
ATOM  2174  NE2  HIS A 308      12.809 -28.234 -18.749  1.00 14.31           N
ATOM  2175  CD2  HIS A 308      12.053 -28.198 -19.899  1.00 13.75           C
ATOM  2176  C    HIS A 308       8.698 -30.040 -19.816  1.00 13.96           C
ATOM  2177  O    HIS A 308       8.646 -30.701 -20.863  1.00 14.06           O
ATOM  2178  N    ILE A 309       9.069 -30.570 -18.672  1.00 14.72           N
ATOM  2179  CA   ILE A 309       9.607 -31.941 -18.633  1.00 15.54           C
ATOM  2180  CB   ILE A 309       9.993 -32.335 -17.193  1.00 15.30           C
ATOM  2181  CG1  ILE A 309      11.221 -31.520 -16.755  1.00 18.06           C
ATOM  2182  CD1  ILE A 309      12.447 -31.650 -17.651  1.00 17.96           C
ATOM  2183  CG2  ILE A 309      10.204 -33.866 -17.070  1.00 16.43           C
ATOM  2184  C    ILE A 309       8.665 -32.981 -19.233  1.00 15.42           C
ATOM  2185  O    ILE A 309       9.104 -33.772 -20.077  1.00 15.30           O
ATOM  2186  N    PRO A 310       7.374 -33.012 -18.783  1.00 15.16           N
ATOM  2187  CA   PRO A 310       6.441 -33.991 -19.357  1.00 15.35           C
ATOM  2188  CB   PRO A 310       5.102 -33.611 -18.727  1.00 14.44           C
ATOM  2189  CG   PRO A 310       5.439 -32.899 -17.496  1.00 14.26           C
ATOM  2190  CD   PRO A 310       6.697 -32.147 -17.802  1.00 14.26           C
ATOM  2191  C    PRO A 310       6.345 -33.845 -20.867  1.00 15.27           C
ATOM  2192  O    PRO A 310       6.064 -34.814 -21.535  1.00 16.31           O
ATOM  2193  N    PHE A 311       6.505 -32.625 -21.383  1.00 15.55           N
ATOM  2194  CA   PHE A 311       6.498 -32.391 -22.831  1.00 15.35           C
ATOM  2195  CB   PHE A 311       6.166 -30.944 -23.114  1.00 13.86           C
ATOM  2196  CG   PHE A 311       4.827 -30.583 -22.658  1.00 12.54           C
ATOM  2197  CD1  PHE A 311       4.622 -30.117 -21.365  1.00 10.01           C
ATOM  2198  CE1  PHE A 311       3.355 -29.782 -20.950  1.00 11.94           C
ATOM  2199  CZ   PHE A 311       2.288 -29.932 -21.803  1.00 14.28           C
ATOM  2200  CE2  PHE A 311       2.465 -30.432 -23.066  1.00 13.67           C
ATOM  2201  CD2  PHE A 311       3.740 -30.747 -23.497  1.00 11.24           C
ATOM  2202  C    PHE A 311       7.799 -32.769 -23.493  1.00 16.00           C
ATOM  2203  O    PHE A 311       7.827 -33.370 -24.568  1.00 16.71           O
ATOM  2204  N    LEU A 312       8.885 -32.403 -22.856  1.00 18.07           N
ATOM  2205  CA   LEU A 312      10.207 -32.705 -23.393  1.00 19.31           C
ATOM  2206  CB   LEU A 312      11.251 -32.133 -22.452  1.00 19.33           C
ATOM  2207  CG   LEU A 312      12.704 -32.201 -22.920  1.00 19.95           C
ATOM  2208  CD1  LEU A 312      13.036 -31.071 -23.904  1.00 18.61           C
ATOM  2209  CD2  LEU A 312      13.514 -32.107 -21.651  1.00 18.05           C
ATOM  2210  C    LEU A 312      10.372 -34.217 -23.524  1.00 21.25           C
ATOM  2211  O    LEU A 312      10.917 -34.717 -24.525  1.00 20.59           O
ATOM  2212  N    ARG A 313       9.895 -34.919 -22.498  1.00 23.35           N
ATOM  2213  CA   ARG A 313       9.844 -36.374 -22.400  1.00 25.37           C
ATOM  2214  CB   ARG A 313       8.929 -36.690 -21.219  1.00 25.91           C
ATOM  2215  CG   ARG A 313       8.986 -38.049 -20.594  1.00 31.23           C
ATOM  2216  CD   ARG A 313       8.207 -37.986 -19.273  1.00 35.05           C
ATOM  2217  NE   ARG A 313       9.107 -37.796 -18.129  1.00 41.48           N
ATOM  2218  CZ   ARG A 313       8.876 -37.052 -17.034  1.00 41.71           C
ATOM  2219  NH1  ARG A 313       7.760 -36.304 -16.857  1.00 39.07           N
ATOM  2220  NH2  ARG A 313       9.823 -37.024 -16.107  1.00 42.97           N
ATOM  2221  C    ARG A 313       9.269 -36.993 -23.680  1.00 25.69           C
ATOM  2222  O    ARG A 313       9.724 -38.048 -24.142  1.00 25.64           O
ATOM  2223  N    LYS A 314       8.262 -36.325 -24.242  1.00 25.45           N
ATOM  2224  CA   LYS A 314       7.545 -36.785 -25.428  1.00 25.54           C
ATOM  2225  CB   LYS A 314       6.085 -36.342 -25.363  1.00 25.29           C
ATOM  2226  CG   LYS A 314       5.340 -36.620 -24.069  1.00 27.25           C
ATOM  2227  CD   LYS A 314       5.173 -38.100 -23.775  1.00 29.61           C
ATOM  2228  CE   LYS A 314       4.623 -38.845 -24.985  1.00 30.84           C
ATOM  2229  NZ   LYS A 314       4.254 -40.260 -24.695  1.00 32.80           N
ATOM  2230  C    LYS A 314       8.152 -36.244 -26.721  1.00 25.08           C
ATOM  2231  O    LYS A 314       7.544 -36.346 -27.776  1.00 26.58           O
ATOM  2232  N    GLY A 315       9.340 -35.663 -26.633  1.00 24.55           N
ATOM  2233  CA   GLY A 315      10.007 -35.054 -27.796  1.00 24.39           C
ATOM  2234  C    GLY A 315       9.502 -33.686 -28.241  1.00 22.85           C
ATOM  2235  O    GLY A 315       9.880 -33.206 -29.296  1.00 23.54           O
ATOM  2236  N    VAL A 316       8.665 -33.034 -27.434  1.00 21.71           N
ATOM  2237  CA   VAL A 316       8.251 -31.688 -27.771  1.00 20.17           C
ATOM  2238  CB   VAL A 316       7.139 -31.169 -26.833  1.00 20.00           C
ATOM  2239  CG1  VAL A 316       6.884 -29.636 -27.053  1.00 17.52           C
```

FIGURE 2-32 (COORDINATES)

```
ATOM  2240  CG2 VAL A 316      5.871 -32.028 -27.002  1.00 20.11           C
ATOM  2241  C   VAL A 316      9.487 -30.814 -27.659  1.00 19.81           C
ATOM  2242  O   VAL A 316     10.226 -30.924 -26.683  1.00 20.64           O
ATOM  2243  N   PRO A 317      9.727 -29.937 -28.659  1.00 19.84           N
ATOM  2244  CA  PRO A 317     10.848 -29.072 -28.516  1.00 18.44           C
ATOM  2245  CB  PRO A 317     10.974 -28.433 -29.898  1.00 19.27           C
ATOM  2246  CG  PRO A 317     10.244 -29.356 -30.813  1.00 18.84           C
ATOM  2247  CD  PRO A 317      9.108 -29.789 -29.988  1.00 18.94           C
ATOM  2248  C   PRO A 317     10.565 -28.010 -27.485  1.00 18.59           C
ATOM  2249  O   PRO A 317      9.449 -27.439 -27.432  1.00 18.22           O
ATOM  2250  N   VAL A 318     11.568 -27.768 -26.645  1.00 18.03           N
ATOM  2251  CA  VAL A 318     11.367 -26.850 -25.532  1.00 16.94           C
ATOM  2252  CB  VAL A 318     11.382 -27.570 -24.177  1.00 16.85           C
ATOM  2253  CG1 VAL A 318     11.414 -26.555 -23.037  1.00 15.71           C
ATOM  2254  CG2 VAL A 318     10.181 -28.485 -24.032  1.00 17.16           C
ATOM  2255  C   VAL A 318     12.393 -25.750 -25.549  1.00 17.13           C
ATOM  2256  O   VAL A 318     13.577 -25.982 -25.783  1.00 16.41           O
ATOM  2257  N   LEU A 319     11.928 -24.536 -25.272  1.00 15.63           N
ATOM  2258  CA  LEU A 319     12.801 -23.464 -24.934  1.00 15.99           C
ATOM  2259  CB  LEU A 319     12.576 -22.327 -25.912  1.00 16.38           C
ATOM  2260  CG  LEU A 319     13.592 -21.236 -25.978  1.00 19.00           C
ATOM  2261  CD1 LEU A 319     15.033 -21.780 -26.268  1.00 16.35           C
ATOM  2262  CD2 LEU A 319     13.114 -20.233 -27.058  1.00 18.16           C
ATOM  2263  C   LEU A 319     12.443 -23.059 -23.508  1.00 15.53           C
ATOM  2264  O   LEU A 319     11.363 -22.550 -23.254  1.00 14.15           O
ATOM  2265  N   HIS A 320     13.340 -23.349 -22.567  1.00 14.98           N
ATOM  2266  CA  HIS A 320     13.027 -23.187 -21.164  1.00 14.86           C
ATOM  2267  CB  HIS A 320     13.561 -24.376 -20.357  1.00 15.70           C
ATOM  2268  CG  HIS A 320     13.064 -24.420 -18.949  1.00 14.43           C
ATOM  2269  ND1 HIS A 320     13.674 -25.182 -17.983  1.00 14.35           N
ATOM  2270  CE1 HIS A 320     13.052 -25.019 -16.830  1.00 14.01           C
ATOM  2271  NE2 HIS A 320     12.048 -24.179 -17.015  1.00 14.06           N
ATOM  2272  CD2 HIS A 320     12.056 -23.759 -18.328  1.00 13.44           C
ATOM  2273  C   HIS A 320     13.634 -21.863 -20.672  1.00 15.02           C
ATOM  2274  O   HIS A 320     14.875 -21.736 -20.454  1.00 14.77           O
ATOM  2275  N   LEU A 321     12.765 -20.875 -20.519  1.00 12.17           N
ATOM  2276  CA  LEU A 321     13.219 -19.554 -20.164  1.00 13.28           C
ATOM  2277  CB  LEU A 321     12.542 -18.421 -20.940  1.00 13.42           C
ATOM  2278  CG  LEU A 321     12.601 -18.512 -22.463  1.00 15.59           C
ATOM  2279  CD1 LEU A 321     12.098 -17.241 -23.079  1.00 19.87           C
ATOM  2280  CD2 LEU A 321     14.044 -18.775 -22.881  1.00 19.76           C
ATOM  2281  C   LEU A 321     12.996 -19.399 -18.684  1.00 12.39           C
ATOM  2282  O   LEU A 321     12.088 -18.717 -18.251  1.00 13.27           O
ATOM  2283  N   ILE A 322     13.897 -20.023 -17.934  1.00 12.86           N
ATOM  2284  CA  ILE A 322     13.949 -19.922 -16.485  1.00 12.95           C
ATOM  2285  CB  ILE A 322     13.792 -21.292 -15.834  1.00 13.09           C
ATOM  2286  CG1 ILE A 322     13.720 -21.181 -14.297  1.00 11.46           C
ATOM  2287  CD1 ILE A 322     13.190 -22.511 -13.661  1.00  9.48           C
ATOM  2288  CG2 ILE A 322     14.950 -22.265 -16.292  1.00 12.84           C
ATOM  2289  C   ILE A 322     15.270 -19.249 -16.112  1.00 13.91           C
ATOM  2290  O   ILE A 322     16.308 -19.523 -16.734  1.00 14.79           O
ATOM  2291  N   ALA A 323     15.221 -18.360 -15.124  1.00 13.87           N
ATOM  2292  CA  ALA A 323     16.418 -17.614 -14.726  1.00 13.90           C
ATOM  2293  CB  ALA A 323     16.061 -16.424 -13.865  1.00 13.86           C
ATOM  2294  C   ALA A 323     17.220 -18.578 -13.931  1.00 15.00           C
ATOM  2295  O   ALA A 323     16.688 -19.267 -13.065  1.00 14.28           O
ATOM  2296  N   SER A 324     18.502 -18.625 -14.229  1.00 16.11           N
ATOM  2297  CA  SER A 324     19.408 -19.467 -13.508  1.00 16.89           C
ATOM  2298  CB  SER A 324     19.538 -20.858 -14.117  1.00 17.55           C
ATOM  2299  OG  SER A 324     20.562 -21.554 -13.427  1.00 17.79           O
ATOM  2300  C   SER A 324     20.722 -18.692 -13.504  1.00 16.44           C
ATOM  2301  O   SER A 324     21.264 -18.357 -14.578  1.00 17.42           O
ATOM  2302  N   PRO A 325     21.201 -18.355 -12.296  1.00 16.22           N
ATOM  2303  CA  PRO A 325     20.679 -18.850 -10.997  1.00 15.46           C
ATOM  2304  CB  PRO A 325     21.757 -18.402  -9.977  1.00 14.90           C
ATOM  2305  CG  PRO A 325     22.711 -17.556 -10.720  1.00 18.75           C
ATOM  2306  CD  PRO A 325     22.202 -17.289 -12.110  1.00 15.63           C
ATOM  2307  C   PRO A 325     19.296 -18.298 -10.616  1.00 14.71           C
ATOM  2308  O   PRO A 325     18.846 -17.240 -11.097  1.00 12.26           O
ATOM  2309  N   PHE A 326     18.601 -19.048  -9.781  1.00 13.91           N
```

FIGURE 2-33 (COORDINATES)

```
ATOM   2310  CA   PHE A 326      17.319 -18.600  -9.287  1.00 13.58           C
ATOM   2311  CB   PHE A 326      16.668 -19.636  -8.385  1.00 13.06           C
ATOM   2312  CG   PHE A 326      16.323 -20.937  -9.064  1.00 14.04           C
ATOM   2313  CD1  PHE A 326      16.410 -21.104 -10.440  1.00 12.45           C
ATOM   2314  CE1  PHE A 326      16.063 -22.316 -11.026  1.00 11.95           C
ATOM   2315  CZ   PHE A 326      15.615 -23.370 -10.242  1.00 14.32           C
ATOM   2316  CE2  PHE A 326      15.525 -23.226  -8.883  1.00 13.90           C
ATOM   2317  CD2  PHE A 326      15.868 -22.004  -8.296  1.00 15.32           C
ATOM   2318  C    PHE A 326      17.524 -17.293  -8.516  1.00 14.42           C
ATOM   2319  O    PHE A 326      18.582 -17.081  -7.966  1.00 14.51           O
ATOM   2320  N    PRO A 327      16.524 -16.408  -8.542  1.00 14.60           N
ATOM   2321  CA   PRO A 327      16.481 -15.225  -7.719  1.00 15.07           C
ATOM   2322  CB   PRO A 327      15.037 -14.734  -7.902  1.00 15.24           C
ATOM   2323  CG   PRO A 327      14.588 -15.293  -9.205  1.00 14.73           C
ATOM   2324  CD   PRO A 327      15.273 -16.620  -9.299  1.00 15.06           C
ATOM   2325  C    PRO A 327      16.719 -15.584  -6.246  1.00 14.53           C
ATOM   2326  O    PRO A 327      16.295 -16.649  -5.770  1.00 14.83           O
ATOM   2327  N    GLU A 328      17.391 -14.681  -5.536  1.00 15.25           N
ATOM   2328  CA   GLU A 328      17.615 -14.823  -4.109  1.00 14.78           C
ATOM   2329  CB   GLU A 328      18.225 -13.518  -3.531  1.00 15.92           C
ATOM   2330  CG   GLU A 328      18.779 -13.682  -2.120  1.00 15.82           C
ATOM   2331  CD   GLU A 328      17.742 -13.553  -1.028  1.00 19.25           C
ATOM   2332  OE1  GLU A 328      16.730 -12.877  -1.248  1.00 19.38           O
ATOM   2333  OE2  GLU A 328      17.953 -14.149   0.055  1.00 19.46           O
ATOM   2334  C    GLU A 328      16.276 -15.076  -3.431  1.00 14.62           C
ATOM   2335  O    GLU A 328      16.184 -15.877  -2.506  1.00 15.61           O
ATOM   2336  N    VAL A 329      15.223 -14.436  -3.936  1.00 14.08           N
ATOM   2337  CA   VAL A 329      13.890 -14.495  -3.312  1.00 14.92           C
ATOM   2338  CB   VAL A 329      13.016 -13.314  -3.718  1.00 15.40           C
ATOM   2339  CG1  VAL A 329      13.664 -11.983  -3.299  1.00 16.24           C
ATOM   2340  CG2  VAL A 329      12.661 -13.375  -5.239  1.00 14.49           C
ATOM   2341  C    VAL A 329      13.109 -15.772  -3.579  1.00 13.87           C
ATOM   2342  O    VAL A 329      12.005 -15.969  -3.044  1.00 13.90           O
ATOM   2343  N    TRP A 330      13.693 -16.633  -4.393  1.00 14.16           N
ATOM   2344  CA   TRP A 330      13.064 -17.912  -4.789  1.00 14.22           C
ATOM   2345  CB   TRP A 330      14.059 -18.779  -5.520  1.00 13.85           C
ATOM   2346  CG   TRP A 330      13.464 -20.007  -6.061  1.00 15.13           C
ATOM   2347  CD1  TRP A 330      12.682 -20.107  -7.184  1.00 11.50           C
ATOM   2348  NE1  TRP A 330      12.340 -21.409  -7.388  1.00 12.68           N
ATOM   2349  CE2  TRP A 330      12.917 -22.188  -6.421  1.00 13.75           C
ATOM   2350  CD2  TRP A 330      13.635 -21.333  -5.565  1.00 12.36           C
ATOM   2351  CE3  TRP A 330      14.325 -21.889  -4.469  1.00 14.98           C
ATOM   2352  CZ3  TRP A 330      14.271 -23.228  -4.274  1.00 13.25           C
ATOM   2353  CH2  TRP A 330      13.553 -24.070  -5.173  1.00 15.21           C
ATOM   2354  CZ2  TRP A 330      12.871 -23.557  -6.231  1.00 13.39           C
ATOM   2355  C    TRP A 330      12.497 -18.680  -3.619  1.00 13.75           C
ATOM   2356  O    TRP A 330      13.201 -18.999  -2.659  1.00 12.74           O
ATOM   2357  N    HIS A 331      11.187 -18.918  -3.697  1.00 13.71           N
ATOM   2358  CA   HIS A 331      10.416 -19.667  -2.678  1.00 14.36           C
ATOM   2359  CB   HIS A 331      10.842 -21.112  -2.628  1.00 13.92           C
ATOM   2360  CG   HIS A 331      10.391 -21.895  -3.818  1.00 16.10           C
ATOM   2361  ND1  HIS A 331      10.576 -23.252  -3.931  1.00 13.14           N
ATOM   2362  CE1  HIS A 331      10.095 -23.664  -5.088  1.00 14.97           C
ATOM   2363  NE2  HIS A 331       9.584 -22.629  -5.716  1.00 11.19           N
ATOM   2364  CD2  HIS A 331       9.760 -21.504  -4.950  1.00 13.36           C
ATOM   2365  C    HIS A 331      10.519 -19.056  -1.304  1.00 15.94           C
ATOM   2366  O    HIS A 331      10.471 -19.759  -0.297  1.00 15.62           O
ATOM   2367  N    THR A 332      10.666 -17.744  -1.269  1.00 14.69           N
ATOM   2368  CA   THR A 332      10.614 -17.022  -0.001  1.00 14.11           C
ATOM   2369  CB   THR A 332      11.883 -16.189   0.238  1.00 13.06           C
ATOM   2370  OG1  THR A 332      11.844 -15.031  -0.616  1.00 12.72           O
ATOM   2371  CG2  THR A 332      13.161 -16.993   0.025  1.00 13.49           C
ATOM   2372  C    THR A 332       9.462 -16.052  -0.133  1.00 14.75           C
ATOM   2373  O    THR A 332       9.004 -15.744  -1.260  1.00 14.39           O
ATOM   2374  N    MET A 333       9.041 -15.487   0.989  1.00 14.92           N
ATOM   2375  CA   MET A 333       7.983 -14.468   0.991  1.00 16.50           C
ATOM   2376  CB   MET A 333       7.586 -14.070   2.416  1.00 17.28           C
ATOM   2377  CG   MET A 333       7.010 -15.185   3.206  1.00 21.90           C
ATOM   2378  SD   MET A 333       5.479 -15.638   2.456  1.00 29.04           S
ATOM   2379  CE   MET A 333       4.949 -16.723   3.734  1.00 19.68           C
```

FIGURE 2-34 (COORDINATES)

```
ATOM   2380  C   MET A 333       8.343 -13.189   0.270  1.00 15.73           C
ATOM   2381  O   MET A 333       7.479 -12.390  -0.016  1.00 16.78           O
ATOM   2382  N   ASP A 334       9.624 -12.979   0.029  1.00 14.32           N
ATOM   2383  CA  ASP A 334      10.090 -11.797  -0.608  1.00 14.74           C
ATOM   2384  CB  ASP A 334      11.501 -11.475  -0.123  1.00 14.26           C
ATOM   2385  CG  ASP A 334      11.504 -11.213   1.343  1.00 18.99           C
ATOM   2386  OD1 ASP A 334      10.768 -10.291   1.774  1.00 22.02           O
ATOM   2387  OD2 ASP A 334      12.125 -12.014   2.048  1.00 16.46           O
ATOM   2388  C   ASP A 334      10.058 -11.959  -2.080  1.00 13.36           C
ATOM   2389  O   ASP A 334      10.467 -11.063  -2.787  1.00 14.36           O
ATOM   2390  N   ASP A 335       9.589 -13.119  -2.553  1.00 12.97           N
ATOM   2391  CA  ASP A 335       9.306 -13.183  -3.987  1.00 12.60           C
ATOM   2392  CB  ASP A 335       9.332 -14.589  -4.538  1.00 12.03           C
ATOM   2393  CG  ASP A 335       9.121 -14.602  -6.032  1.00 12.62           C
ATOM   2394  OD1 ASP A 335       9.135 -13.514  -6.667  1.00 12.31           O
ATOM   2395  OD2 ASP A 335       8.966 -15.683  -6.566  1.00 13.81           O
ATOM   2396  C   ASP A 335       7.981 -12.486  -4.212  1.00 12.32           C
ATOM   2397  O   ASP A 335       6.922 -13.106  -4.370  1.00 11.12           O
ATOM   2398  N   ASN A 336       8.068 -11.160  -4.180  1.00 12.74           N
ATOM   2399  CA  ASN A 336       6.885 -10.358  -4.111  1.00 13.75           C
ATOM   2400  CB  ASN A 336       6.681  -9.833  -2.671  1.00 14.50           C
ATOM   2401  CG  ASN A 336       7.882  -9.050  -2.129  1.00 14.78           C
ATOM   2402  OD1 ASN A 336       8.091  -8.969  -0.892  1.00 20.34           O
ATOM   2403  ND2 ASN A 336       8.686  -8.508  -3.010  1.00 10.78           N
ATOM   2404  C   ASN A 336       6.996  -9.227  -5.099  1.00 13.37           C
ATOM   2405  O   ASN A 336       7.988  -9.088  -5.797  1.00 13.47           O
ATOM   2406  N   GLU A 337       5.962  -8.424  -5.164  1.00 14.40           N
ATOM   2407  CA  GLU A 337       5.961  -7.278  -6.058  1.00 15.85           C
ATOM   2408  CB  GLU A 337       4.685  -6.474  -5.843  1.00 17.20           C
ATOM   2409  CG  GLU A 337       4.562  -5.383  -6.878  1.00 18.84           C
ATOM   2410  CD  GLU A 337       3.215  -4.758  -6.837  1.00 19.10           C
ATOM   2411  OE1 GLU A 337       2.403  -5.178  -5.991  1.00 17.04           O
ATOM   2412  OE2 GLU A 337       2.925  -3.900  -7.686  1.00 19.10           O
ATOM   2413  C   GLU A 337       7.136  -6.341  -5.892  1.00 16.68           C
ATOM   2414  O   GLU A 337       7.777  -5.957  -6.880  1.00 14.47           O
ATOM   2415  N   GLU A 338       7.428  -6.003  -4.636  1.00 17.87           N
ATOM   2416  CA  GLU A 338       8.514  -5.081  -4.317  1.00 19.29           C
ATOM   2417  CB  GLU A 338       8.657  -4.932  -2.807  1.00 20.00           C
ATOM   2418  CG  GLU A 338       9.756  -3.965  -2.445  1.00 27.00           C
ATOM   2419  CD  GLU A 338       9.836  -3.699  -0.946  1.00 32.73           C
ATOM   2420  OE1 GLU A 338       9.207  -4.459  -0.167  1.00 33.93           O
ATOM   2421  OE2 GLU A 338      10.522  -2.718  -0.566  1.00 36.37           O
ATOM   2422  C   GLU A 338       9.844  -5.465  -4.927  1.00 19.45           C
ATOM   2423  O   GLU A 338      10.610  -4.596  -5.335  1.00 18.95           O
ATOM   2424  N   ASN A 339      10.123  -6.763  -4.986  1.00 19.52           N
ATOM   2425  CA  ASN A 339      11.424  -7.239  -5.451  1.00 19.02           C
ATOM   2426  CB  ASN A 339      11.815  -8.496  -4.700  1.00 19.27           C
ATOM   2427  CG  ASN A 339      12.180  -8.199  -3.261  1.00 20.35           C
ATOM   2428  OD1 ASN A 339      11.339  -8.276  -2.382  1.00 19.99           O
ATOM   2429  ND2 ASN A 339      13.422  -7.785  -3.037  1.00 24.60           N
ATOM   2430  C   ASN A 339      11.479  -7.487  -6.942  1.00 18.41           C
ATOM   2431  O   ASN A 339      12.495  -7.941  -7.465  1.00 18.65           O
ATOM   2432  N   LEU A 340      10.381  -7.185  -7.615  1.00 18.37           N
ATOM   2433  CA  LEU A 340      10.358  -7.254  -9.070  1.00 17.52           C
ATOM   2434  CB  LEU A 340       8.927  -7.287  -9.567  1.00 16.85           C
ATOM   2435  CG  LEU A 340       8.130  -8.544  -9.265  1.00 15.20           C
ATOM   2436  CD1 LEU A 340       6.783  -8.426  -9.950  1.00 13.61           C
ATOM   2437  CD2 LEU A 340       8.882  -9.818  -9.675  1.00 11.28           C
ATOM   2438  C   LEU A 340      11.085  -6.060  -9.698  1.00 18.20           C
ATOM   2439  O   LEU A 340      11.073  -4.944  -9.161  1.00 19.25           O
ATOM   2440  N   HIS A 341      11.724  -6.305 -10.826  1.00 18.86           N
ATOM   2441  CA  HIS A 341      12.477  -5.257 -11.506  1.00 18.57           C
ATOM   2442  CB  HIS A 341      13.932  -5.673 -11.657  1.00 19.43           C
ATOM   2443  CG  HIS A 341      14.840  -4.537 -12.033  1.00 25.59           C
ATOM   2444  ND1 HIS A 341      15.748  -4.613 -13.072  1.00 28.17           N
ATOM   2445  CE1 HIS A 341      16.402  -3.468 -13.166  1.00 26.96           C
ATOM   2446  NE2 HIS A 341      15.937  -2.642 -12.243  1.00 27.25           N
ATOM   2447  CD2 HIS A 341      14.966  -3.289 -11.514  1.00 28.97           C
ATOM   2448  C   HIS A 341      11.772  -4.992 -12.830  1.00 17.52           C
ATOM   2449  O   HIS A 341      11.821  -5.792 -13.738  1.00 17.18           O
```

FIGURE 2-35 (COORDINATES)

```
ATOM   2450  N    ALA A 342      11.085  -3.867 -12.911  1.00 16.99           N
ATOM   2451  CA   ALA A 342      10.160  -3.626 -14.002  1.00 16.75           C
ATOM   2452  CB   ALA A 342       9.350  -2.368 -13.781  1.00 17.55           C
ATOM   2453  C    ALA A 342      10.864  -3.555 -15.334  1.00 16.43           C
ATOM   2454  O    ALA A 342      10.352  -4.086 -16.310  1.00 16.83           O
ATOM   2455  N    SER A 343      12.025  -2.899 -15.397  1.00 15.29           N
ATOM   2456  CA   SER A 343      12.686  -2.734 -16.686  1.00 15.90           C
ATOM   2457  CB   SER A 343      13.961  -1.883 -16.604  1.00 15.91           C
ATOM   2458  OG   SER A 343      14.917  -2.515 -15.778  1.00 21.20           O
ATOM   2459  C    SER A 343      13.055  -4.090 -17.216  1.00 14.63           C
ATOM   2460  O    SER A 343      12.985  -4.312 -18.405  1.00 14.87           O
ATOM   2461  N    THR A 344      13.451  -5.004 -16.334  1.00 13.47           N
ATOM   2462  CA   THR A 344      13.890  -6.285 -16.791  1.00 13.60           C
ATOM   2463  CB   THR A 344      14.436  -7.138 -15.619  1.00 13.23           C
ATOM   2464  OG1  THR A 344      15.534  -6.450 -14.995  1.00 15.54           O
ATOM   2465  CG2  THR A 344      14.913  -8.438 -16.139  1.00 14.94           C
ATOM   2466  C    THR A 344      12.708  -7.005 -17.434  1.00 12.43           C
ATOM   2467  O    THR A 344      12.844  -7.646 -18.466  1.00 12.08           O
ATOM   2468  N    ILE A 345      11.549  -6.927 -16.782  1.00 12.03           N
ATOM   2469  CA   ILE A 345      10.350  -7.620 -17.289  1.00 12.44           C
ATOM   2470  CB   ILE A 345       9.206  -7.499 -16.256  1.00 12.00           C
ATOM   2471  CG1  ILE A 345       9.619  -8.194 -14.955  1.00 13.99           C
ATOM   2472  CD1  ILE A 345       8.704  -7.861 -13.812  1.00 12.97           C
ATOM   2473  CG2  ILE A 345       7.882  -8.081 -16.834  1.00 14.11           C
ATOM   2474  C    ILE A 345       9.933  -6.983 -18.624  1.00 12.40           C
ATOM   2475  O    ILE A 345       9.604  -7.671 -19.616  1.00 12.47           O
ATOM   2476  N    ASP A 346       9.997  -5.652 -18.649  1.00 13.39           N
ATOM   2477  CA   ASP A 346       9.655  -4.894 -19.826  1.00 13.05           C
ATOM   2478  CB   ASP A 346       9.808  -3.390 -19.513  1.00 13.94           C
ATOM   2479  CG   ASP A 346       9.274  -2.510 -20.630  1.00 15.71           C
ATOM   2480  OD1  ASP A 346       8.259  -2.874 -21.295  1.00 15.36           O
ATOM   2481  OD2  ASP A 346       9.902  -1.436 -20.852  1.00 18.36           O
ATOM   2482  C    ASP A 346      10.598  -5.290 -20.974  1.00 12.40           C
ATOM   2483  O    ASP A 346      10.143  -5.603 -22.060  1.00 11.01           O
ATOM   2484  N    ASN A 347      11.905  -5.329 -20.728  1.00 13.20           N
ATOM   2485  CA   ASN A 347      12.822  -5.788 -21.778  1.00 12.55           C
ATOM   2486  CB   ASN A 347      14.265  -5.790 -21.289  1.00 13.21           C
ATOM   2487  CG   ASN A 347      14.736  -4.413 -20.946  1.00 12.40           C
ATOM   2488  OD1  ASN A 347      14.233  -3.438 -21.479  1.00 16.79           O
ATOM   2489  ND2  ASN A 347      15.665  -4.315 -20.025  1.00 12.47           N
ATOM   2490  C    ASN A 347      12.446  -7.168 -22.282  1.00 12.66           C
ATOM   2491  O    ASN A 347      12.403  -7.422 -23.483  1.00 12.17           O
ATOM   2492  N    LEU A 348      12.177  -8.067 -21.354  1.00 11.63           N
ATOM   2493  CA   LEU A 348      11.938  -9.433 -21.731  1.00 11.96           C
ATOM   2494  CB   LEU A 348      11.967 -10.319 -20.502  1.00 10.70           C
ATOM   2495  CG   LEU A 348      13.399 -10.606 -19.984  1.00 13.17           C
ATOM   2496  CD1  LEU A 348      13.274 -11.270 -18.586  1.00 13.55           C
ATOM   2497  CD2  LEU A 348      14.204 -11.474 -20.932  1.00 11.82           C
ATOM   2498  C    LEU A 348      10.604  -9.531 -22.452  1.00 11.47           C
ATOM   2499  O    LEU A 348      10.466 -10.317 -23.388  1.00 12.54           O
ATOM   2500  N    ASN A 349       9.643  -8.721 -22.023  1.00 11.75           N
ATOM   2501  CA   ASN A 349       8.396  -8.574 -22.804  1.00 10.69           C
ATOM   2502  CB   ASN A 349       7.456  -7.532 -22.237  1.00 10.95           C
ATOM   2503  CG   ASN A 349       6.716  -8.035 -21.038  1.00 11.56           C
ATOM   2504  OD1  ASN A 349       6.632  -9.228 -20.851  1.00 12.18           O
ATOM   2505  ND2  ASN A 349       6.199  -7.140 -20.223  1.00 15.45           N
ATOM   2506  C    ASN A 349       8.680  -8.214 -24.234  1.00 12.45           C
ATOM   2507  O    ASN A 349       8.175  -8.870 -25.125  1.00 12.91           O
ATOM   2508  N    LYS A 350       9.512  -7.192 -24.447  1.00 13.19           N
ATOM   2509  CA   LYS A 350       9.854  -6.797 -25.844  1.00 14.03           C
ATOM   2510  CB   LYS A 350      10.757  -5.585 -25.836  1.00 13.95           C
ATOM   2511  CG   LYS A 350       9.995  -4.318 -25.388  1.00 16.48           C
ATOM   2512  CD   LYS A 350      10.916  -3.197 -24.941  1.00 16.89           C
ATOM   2513  CE   LYS A 350      10.122  -1.951 -24.594  1.00 13.79           C
ATOM   2514  NZ   LYS A 350      11.086  -0.841 -24.210  1.00 15.25           N
ATOM   2515  C    LYS A 350      10.490  -7.959 -26.597  1.00 13.33           C
ATOM   2516  O    LYS A 350      10.084  -8.298 -27.723  1.00 14.08           O
ATOM   2517  N    ILE A 351      11.489  -8.579 -25.963  1.00 13.33           N
ATOM   2518  CA   ILE A 351      12.248  -9.664 -26.566  1.00 13.18           C
ATOM   2519  CB   ILE A 351      13.381 -10.126 -25.604  1.00 14.51           C
```

FIGURE 2-36 (COORDINATES)

```
ATOM   2520  CG1 ILE A 351      14.429  -9.023 -25.458  1.00 13.99           C
ATOM   2521  CD1 ILE A 351      15.396  -9.176 -24.327  1.00 12.40           C
ATOM   2522  CG2 ILE A 351      14.039 -11.375 -26.144  1.00 14.92           C
ATOM   2523  C   ILE A 351      11.350 -10.817 -26.969  1.00 12.46           C
ATOM   2524  O   ILE A 351      11.409 -11.323 -28.105  1.00 11.47           O
ATOM   2525  N   ILE A 352      10.528 -11.264 -26.015  1.00 12.29           N
ATOM   2526  CA  ILE A 352       9.643 -12.383 -26.246  1.00 11.55           C
ATOM   2527  CB  ILE A 352       9.111 -12.945 -24.916  1.00 11.04           C
ATOM   2528  CG1 ILE A 352      10.306 -13.496 -24.141  1.00 11.46           C
ATOM   2529  CD1 ILE A 352       9.988 -13.732 -22.632  1.00 12.57           C
ATOM   2530  CG2 ILE A 352       8.078 -14.047 -25.139  1.00 10.77           C
ATOM   2531  C   ILE A 352       8.571 -12.091 -27.273  1.00 12.26           C
ATOM   2532  O   ILE A 352       8.315 -12.908 -28.153  1.00 12.02           O
ATOM   2533  N   GLN A 353       8.021 -10.892 -27.209  1.00 11.91           N
ATOM   2534  CA  GLN A 353       7.013 -10.479 -28.146  1.00 12.09           C
ATOM   2535  CB  GLN A 353       6.572  -9.119 -27.740  1.00 12.34           C
ATOM   2536  CG  GLN A 353       5.549  -9.195 -26.572  1.00 12.14           C
ATOM   2537  CD  GLN A 353       5.149  -7.838 -26.107  1.00 13.93           C
ATOM   2538  OE1 GLN A 353       5.126  -6.882 -26.893  1.00 14.23           O
ATOM   2539  NE2 GLN A 353       4.815  -7.722 -24.828  1.00 13.89           N
ATOM   2540  C   GLN A 353       7.574 -10.484 -29.564  1.00 12.26           C
ATOM   2541  O   GLN A 353       6.951 -10.990 -30.469  1.00 11.84           O
ATOM   2542  N   VAL A 354       8.787  -9.960 -29.719  1.00 12.88           N
ATOM   2543  CA  VAL A 354       9.502 -10.015 -31.002  1.00 13.42           C
ATOM   2544  CB  VAL A 354      10.887  -9.308 -30.918  1.00 13.06           C
ATOM   2545  CG1 VAL A 354      11.712  -9.648 -32.186  1.00 13.23           C
ATOM   2546  CG2 VAL A 354      10.727  -7.799 -30.757  1.00 12.00           C
ATOM   2547  C   VAL A 354       9.661 -11.482 -31.429  1.00 14.29           C
ATOM   2548  O   VAL A 354       9.341 -11.862 -32.552  1.00 15.21           O
ATOM   2549  N   PHE A 355      10.143 -12.315 -30.511  1.00 14.38           N
ATOM   2550  CA  PHE A 355      10.368 -13.719 -30.786  1.00 14.56           C
ATOM   2551  CB  PHE A 355      10.806 -14.456 -29.501  1.00 14.68           C
ATOM   2552  CG  PHE A 355      11.095 -15.910 -29.726  1.00 14.50           C
ATOM   2553  CD1 PHE A 355      12.370 -16.321 -30.051  1.00 13.46           C
ATOM   2554  CE1 PHE A 355      12.630 -17.664 -30.290  1.00 14.33           C
ATOM   2555  CZ  PHE A 355      11.617 -18.611 -30.221  1.00 14.16           C
ATOM   2556  CE2 PHE A 355      10.331 -18.218 -29.902  1.00 17.56           C
ATOM   2557  CD2 PHE A 355      10.066 -16.861 -29.685  1.00 15.50           C
ATOM   2558  C   PHE A 355       9.087 -14.327 -31.348  1.00 14.66           C
ATOM   2559  O   PHE A 355       9.086 -14.991 -32.369  1.00 13.53           O
ATOM   2560  N   VAL A 356       7.982 -14.054 -30.669  1.00 14.64           N
ATOM   2561  CA  VAL A 356       6.704 -14.651 -31.029  1.00 14.33           C
ATOM   2562  CB  VAL A 356       5.666 -14.454 -29.923  1.00 14.51           C
ATOM   2563  CG1 VAL A 356       4.217 -14.783 -30.420  1.00 15.27           C
ATOM   2564  CG2 VAL A 356       6.065 -15.384 -28.763  1.00 13.73           C
ATOM   2565  C   VAL A 356       6.246 -14.148 -32.401  1.00 14.66           C
ATOM   2566  O   VAL A 356       5.874 -14.940 -33.267  1.00 14.84           O
ATOM   2567  N   LEU A 357       6.277 -12.844 -32.595  1.00 14.88           N
ATOM   2568  CA  LEU A 357       5.919 -12.295 -33.920  1.00 14.82           C
ATOM   2569  CB  LEU A 357       6.062 -10.790 -33.909  1.00 14.36           C
ATOM   2570  CG  LEU A 357       4.965 -10.088 -33.136  1.00 15.10           C
ATOM   2571  CD1 LEU A 357       5.168  -8.589 -33.303  1.00 19.82           C
ATOM   2572  CD2 LEU A 357       3.560 -10.481 -33.614  1.00 15.54           C
ATOM   2573  C   LEU A 357       6.761 -12.884 -35.018  1.00 16.04           C
ATOM   2574  O   LEU A 357       6.253 -13.256 -36.077  1.00 15.91           O
ATOM   2575  N   GLU A 358       8.056 -12.980 -34.767  1.00 16.61           N
ATOM   2576  CA  GLU A 358       8.950 -13.521 -35.757  1.00 18.72           C
ATOM   2577  CB  GLU A 358      10.405 -13.272 -35.385  1.00 18.31           C
ATOM   2578  CG  GLU A 358      10.773 -11.798 -35.428  1.00 19.37           C
ATOM   2579  CD  GLU A 358      12.257 -11.596 -35.251  1.00 21.84           C
ATOM   2580  OE1 GLU A 358      12.888 -12.498 -34.666  1.00 22.09           O
ATOM   2581  OE2 GLU A 358      12.772 -10.542 -35.679  1.00 24.08           O
ATOM   2582  C   GLU A 358       8.693 -14.978 -36.008  1.00 19.71           C
ATOM   2583  O   GLU A 358       8.670 -15.395 -37.160  1.00 20.11           O
ATOM   2584  N   TYR A 359       8.457 -15.759 -34.943  1.00 18.55           N
ATOM   2585  CA  TYR A 359       8.096 -17.140 -35.110  1.00 19.34           C
ATOM   2586  CB  TYR A 359       7.892 -17.838 -33.744  1.00 17.42           C
ATOM   2587  CG  TYR A 359       7.921 -19.323 -33.874  1.00 19.24           C
ATOM   2588  CD1 TYR A 359       9.076 -20.047 -33.520  1.00 18.40           C
ATOM   2589  CE1 TYR A 359       9.116 -21.398 -33.638  1.00 16.91           C
```

FIGURE 2-37 (COORDINATES)

```
ATOM   2590  CZ  TYR A 359       8.018 -22.074 -34.109  1.00 16.01           C
ATOM   2591  OH  TYR A 359       8.092 -23.430 -34.223  1.00 21.32           O
ATOM   2592  CE2 TYR A 359       6.858 -21.410 -34.444  1.00 17.86           C
ATOM   2593  CD2 TYR A 359       6.820 -20.026 -34.346  1.00 14.83           C
ATOM   2594  C   TYR A 359       6.845 -17.315 -35.956  1.00 19.08           C
ATOM   2595  O   TYR A 359       6.790 -18.198 -36.804  1.00 20.07           O
ATOM   2596  N   LEU A 360       5.861 -16.461 -35.719  1.00 20.31           N
ATOM   2597  CA  LEU A 360       4.563 -16.560 -36.354  1.00 20.51           C
ATOM   2598  CB  LEU A 360       3.483 -15.972 -35.452  1.00 19.42           C
ATOM   2599  CG  LEU A 360       3.198 -16.868 -34.239  1.00 18.50           C
ATOM   2600  CD1 LEU A 360       2.234 -16.211 -33.325  1.00 13.67           C
ATOM   2601  CD2 LEU A 360       2.623 -18.139 -34.756  1.00 17.43           C
ATOM   2602  C   LEU A 360       4.534 -15.861 -37.711  1.00 21.53           C
ATOM   2603  O   LEU A 360       3.528 -15.930 -38.413  1.00 22.49           O
ATOM   2604  N   HIS A 361       5.617 -15.181 -38.063  1.00 22.59           N
ATOM   2605  CA  HIS A 361       5.669 -14.419 -39.318  1.00 24.21           C
ATOM   2606  CB  HIS A 361       5.520 -15.348 -40.542  1.00 24.54           C
ATOM   2607  CG  HIS A 361       6.685 -16.269 -40.755  1.00 27.41           C
ATOM   2608  ND1 HIS A 361       7.094 -16.674 -42.010  1.00 29.84           N
ATOM   2609  CE1 HIS A 361       8.119 -17.500 -41.892  1.00 31.59           C
ATOM   2610  NE2 HIS A 361       8.386 -17.651 -40.607  1.00 29.65           N
ATOM   2611  CD2 HIS A 361       7.511 -16.883 -39.877  1.00 27.54           C
ATOM   2612  C   HIS A 361       4.609 -13.320 -39.324  1.00 24.67           C
ATOM   2613  O   HIS A 361       3.863 -13.136 -40.304  1.00 25.51           O
ATOM   2614  N   LEU A 362       4.560 -12.580 -38.220  1.00 23.05           N
ATOM   2615  CA  LEU A 362       3.601 -11.531 -38.057  1.00 23.44           C
ATOM   2616  CB  LEU A 362       2.757 -11.771 -36.818  1.00 22.43           C
ATOM   2617  CG  LEU A 362       1.685 -12.831 -36.963  1.00 22.07           C
ATOM   2618  CD1 LEU A 362       0.984 -13.054 -35.591  1.00 21.59           C
ATOM   2619  CD2 LEU A 362       0.659 -12.369 -38.035  1.00 21.18           C
ATOM   2620  C   LEU A 362       4.322 -10.234 -37.889  1.00 23.25           C
ATOM   2621  O   LEU A 362       3.663  -9.206 -37.918  1.00 25.40           O
ATOM   2622  OXT LEU A 362       5.529 -10.192 -37.674  1.00 23.32           O
ATOM   2623 ZN   ZN  A 601       8.671 -22.225  -7.510  1.00 12.72          ZN
ATOM   2624  O   HOH B   1       6.976 -23.703 -41.254  1.00 25.50           O
ATOM   2625  O   HOH B   3       2.787  -4.556 -30.438  1.00 17.88           O
ATOM   2626  O   HOH B   4     -12.596 -10.483 -32.278  1.00 31.02           O
ATOM   2627  O   HOH B   5      20.234 -15.031  -8.588  1.00 27.67           O
ATOM   2628  O   HOH B   6       3.896 -28.642   2.758  1.00 28.75           O
ATOM   2629  O   HOH B   7      18.387 -12.358  -9.686  1.00 25.84           O
ATOM   2630  O   HOH B  10      10.900  -9.425   3.959  1.00 24.22           O
ATOM   2631  O   HOH B  14       8.351 -39.058  -6.424  1.00 26.21           O
ATOM   2632  O   HOH B  15       3.290 -10.186  -1.531  1.00 16.36           O
ATOM   2633  O   HOH B  16      21.901  -7.536 -17.017  1.00 39.57           O
ATOM   2634  O   HOH B  17      -8.932 -26.808  -9.875  1.00 22.51           O
ATOM   2635  O   HOH B  18      -2.008 -12.767 -40.642  1.00 36.36           O
ATOM   2636  O   HOH B  19       1.275  -9.478   6.202  1.00 27.78           O
ATOM   2637  O   HOH B  20      11.420 -24.882  -2.033  1.00 19.36           O
ATOM   2638  O   HOH B  21      16.181  -8.515  -8.179  1.00 21.70           O
ATOM   2639  O   HOH B  22       1.859 -11.484   2.216  1.00 25.69           O
ATOM   2640  O   HOH B  23      -5.743 -17.616  -1.915  1.00 15.31           O
ATOM   2641  O   HOH B  24      19.921   3.405 -32.445  1.00 36.10           O
ATOM   2642  O   HOH B  25       2.211 -18.852   1.807  1.00 23.84           O
ATOM   2643  O   HOH B  27      -6.422 -25.813  -8.529  1.00 15.47           O
ATOM   2644  O   HOH B  28      16.469 -21.274 -22.494  1.00 21.41           O
ATOM   2645  O   HOH B  29       3.602  -9.082  -3.911  1.00 17.04           O
ATOM   2646  O   HOH B  33      -1.229 -27.748 -32.502  1.00 22.18           O
ATOM   2647  O   HOH B  35      15.987 -23.803 -23.333  1.00 12.64           O
ATOM   2648  O   HOH B  36      10.973 -38.823  -4.443  1.00 39.89           O
ATOM   2649  O   HOH B  37       2.278 -26.138  -3.879  1.00 17.36           O
ATOM   2650  O   HOH B  39      -1.061 -34.748 -12.411  1.00 22.53           O
ATOM   2651  O   HOH B  41       6.798  -5.502  -0.101  1.00 32.06           O
ATOM   2652  O   HOH B  42       6.535 -39.848 -20.778  1.00 37.08           O
ATOM   2653  O   HOH B  43      -2.207  -5.220 -30.906  1.00 22.67           O
ATOM   2654  O   HOH B  44      -4.987 -37.152 -12.478  1.00 30.50           O
ATOM   2655  O   HOH B  45       6.158 -31.339 -30.735  1.00 24.16           O
ATOM   2656  O   HOH B  50      11.736  -1.830 -10.758  1.00 38.22           O
ATOM   2657  O   HOH B  51      -6.743 -42.247 -26.249  1.00 17.05           O
ATOM   2658  O   HOH B  53      20.915  -0.989 -34.426  1.00 54.10           O
ATOM   2659  O   HOH B  54      19.742 -15.725 -34.963  1.00 36.24           O
```

FIGURE 2-38 (COORDINATES)

```
ATOM   2660  O   HOH B  55       2.230 -28.209 -13.641  1.00 12.65           O
ATOM   2661  O   HOH B  56       5.099 -26.553  -0.978  1.00 14.71           O
ATOM   2662  O   HOH B  57      14.445 -13.629 -12.584  1.00 11.45           O
ATOM   2663  O   HOH B  58       4.319  -4.876 -28.330  1.00 12.29           O
ATOM   2664  O   HOH B  60       6.439 -20.718 -15.010  1.00  8.43           O
ATOM   2665  O   HOH B  63      -3.639 -22.911  -8.552  1.00 15.93           O
ATOM   2666  O   HOH B  67      17.979 -12.381  -7.118  1.00 23.07           O
ATOM   2667  O   HOH B  68       5.865  -6.348  -2.308  1.00 18.55           O
ATOM   2668  O   HOH B  70       1.195 -26.635  -6.756  1.00 19.65           O
ATOM   2669  O   HOH B  71       7.866  -1.090 -39.540  1.00 30.55           O
ATOM   2670  O   HOH B  72      20.877 -31.927 -18.109  1.00 29.30           O
ATOM   2671  O   HOH B  73       2.161 -12.141  11.139  1.00 24.49           O
ATOM   2672  O   HOH B  74       6.060  -4.404 -21.143  1.00 16.96           O
ATOM   2673  O   HOH B  76      -4.818 -27.625  -1.780  1.00 17.42           O
ATOM   2674  O   HOH B  78      -3.552  -8.839 -21.042  1.00 18.79           O
ATOM   2675  O   HOH B  79      13.014  -1.205 -13.076  1.00 22.32           O
ATOM   2676  O   HOH B  81      12.546 -10.572  -7.611  1.00 17.29           O
ATOM   2677  O   HOH B  87      17.722 -31.308 -27.351  1.00 24.38           O
ATOM   2678  O   HOH B  88      -3.535 -22.130 -39.976  1.00 26.50           O
ATOM   2679  S   MBI C   1      14.285 -27.531  -7.187  1.00 33.53           S
ATOM   2680  CD  MBI C   1      15.285 -27.365  -8.390  1.00 25.98           C
ATOM   2681  NB  MBI C   1      16.579 -27.081  -8.154  1.00 24.58           N
ATOM   2682  CA  MBI C   1      17.479 -26.966  -9.131  1.00 23.43           C
ATOM   2683  CE  MBI C   1      17.688 -28.163  -9.765  1.00 23.84           C
ATOM   2684  CH  MBI C   1      18.558 -28.281 -10.812  1.00 24.95           C
ATOM   2685  CL  MBI C   1      19.256 -27.183 -11.224  1.00 24.63           C
ATOM   2686  OB  MBI C   1      20.095 -27.501 -12.270  1.00 27.49           O
ATOM   2687  CM  MBI C   1      20.537 -26.629 -13.337  1.00 32.82           C
ATOM   2688  CG  MBI C   1      19.064 -25.924 -10.604  1.00 21.64           C
ATOM   2689  OA  MBI C   1      19.829 -24.894 -11.084  1.00 19.21           O
ATOM   2690  CK  MBI C   1      19.743 -23.527 -10.762  1.00 16.57           C
ATOM   2691  CB  MBI C   1      18.162 -25.790  -9.517  1.00 23.08           C
ATOM   2692  NA  MBI C   1      14.795 -27.499  -9.615  1.00 20.26           N
ATOM   2693  CJ  MBI C   1      13.361 -27.484  -9.828  1.00 15.87           C
ATOM   2694  CO  MBI C   1      12.819 -26.051  -9.792  1.00 13.84           C
ATOM   2695  CN  MBI C   1      11.317 -26.120 -10.067  1.00 12.18           C
ATOM   2696  ND  MBI C   1      10.706 -24.781  -9.936  1.00 14.19           N
ATOM   2697  CF  MBI C   1      10.112 -24.418  -8.815  1.00 14.14           C
ATOM   2698  NC  MBI C   1       9.604 -23.191  -8.951  1.00 14.58           N
ATOM   2699  CC  MBI C   1       9.900 -22.785 -10.215  1.00 15.15           C
ATOM   2700  CI  MBI C   1      10.571 -23.810 -10.846  1.00 14.25           C
ATOM   2701  O   HOH D   1      18.168  -6.161 -16.305  1.00 22.49           O
ATOM   2702  O   HOH D   3       1.821  -7.092  -4.139  1.00 18.63           O
ATOM   2703  O   HOH D   4       6.602 -13.064  10.455  1.00 20.12           O
ATOM   2704  O   HOH D   8       2.541 -17.428   6.226  1.00 15.45           O
ATOM   2705  O   HOH D  10      -5.247 -14.769   3.223  1.00 34.55           O
ATOM   2706  O   HOH D  12       6.705 -34.319 -11.674  1.00 16.37           O
ATOM   2707  O   HOH D  14       9.842 -18.156  -6.067  1.00 13.98           O
ATOM   2708  O   HOH D  16       5.867 -14.307  -2.174  1.00 16.48           O
ATOM   2709  O   HOH D  17      19.291 -15.496 -13.156  1.00 15.12           O
ATOM   2710  O   HOH D  18      10.213 -33.038 -11.128  1.00 25.59           O
ATOM   2711  O   HOH D  19      -9.674  -5.859 -26.605  1.00 23.38           O
ATOM   2712  O   HOH D  20     -10.046 -13.364 -26.804  1.00 16.25           O
ATOM   2713  O   HOH D  21      -1.537  -5.671 -19.902  1.00 16.03           O
ATOM   2714  O   HOH D  24       7.823 -26.681  -5.479  1.00 14.65           O
ATOM   2715  O   HOH D  26      -7.489 -23.977 -25.997  1.00 16.58           O
ATOM   2716  O   HOH D  27      -0.406  -6.371 -32.627  1.00 19.39           O
ATOM   2717  O   HOH D  31      10.938 -26.253 -32.333  1.00 21.58           O
ATOM   2718  O   HOH D  33      11.098 -16.588 -33.199  1.00 17.70           O
ATOM   2719  O   HOH D  34       0.818 -20.767   0.402  1.00 22.60           O
ATOM   2720  O   HOH D  37      -7.277  -5.686 -27.567  1.00 24.34           O
ATOM   2721  O   HOH D  38      -5.446 -18.821   0.429  1.00 18.93           O
ATOM   2722  O   HOH D  39       1.288 -19.713  -2.314  1.00 15.59           O
ATOM   2723  O   HOH D  41      -4.235 -36.642 -18.658  1.00 23.93           O
ATOM   2724  O   HOH D  42      -3.456  -3.764 -19.898  1.00 18.56           O
ATOM   2725  O   HOH D  43      -9.030 -19.013 -33.050  1.00 19.14           O
ATOM   2726  O   HOH D  44      14.084 -28.806 -26.525  1.00 20.41           O
ATOM   2727  O   HOH D  45      -0.771 -20.885   3.125  1.00 19.27           O
ATOM   2728  O   HOH D  46      18.453  -0.392 -25.442  1.00 18.78           O
ATOM   2729  O   HOH D  47     -13.065 -26.502 -14.684  1.00 20.56           O
```

FIGURE 2-39 (COORDINATES)

```
ATOM   2730  O   HOH D  48       9.982 -16.319   3.400  1.00 17.17           O
ATOM   2731  O   HOH D  50      16.784  -3.813 -16.865  1.00 21.19           O
ATOM   2732  O   HOH D  51      26.342  -3.402 -23.911  1.00 24.57           O
ATOM   2733  O   HOH D  55      -6.926 -26.625 -29.066  1.00 29.24           O
ATOM   2734  O   HOH D  56      10.918 -34.260 -34.539  1.00 37.83           O
ATOM   2735  O   HOH D  57       2.665 -36.777 -18.398  1.00 24.54           O
ATOM   2736  O   HOH D  58      23.573  -6.470 -18.847  1.00 25.70           O
ATOM   2737  O   HOH D  59      10.614 -14.325   5.248  1.00 21.11           O
ATOM   2738  O   HOH D  61      17.065 -16.673 -38.392  1.00 22.12           O
ATOM   2739  O   HOH D  64       4.550 -12.413  -0.447  1.00 21.30           O
ATOM   2740  O   HOH D  65      15.633 -29.740 -11.358  1.00 20.62           O
ATOM   2741  O   HOH D  66      17.240 -31.428 -12.937  1.00 33.89           O
ATOM   2742  O   HOH D  67      -7.196  -6.551 -14.506  1.00 15.37           O
ATOM   2743  O   HOH D  68      10.686 -24.611 -34.636  1.00 17.67           O
ATOM   2744  O   HOH D  70     -14.153  -9.760 -26.773  1.00 39.33           O
ATOM   2745  O   HOH D  73       6.443 -19.743   4.245  1.00 26.04           O
ATOM   2746  O   HOH D  74      18.507 -25.875 -32.612  1.00 28.34           O
ATOM   2747  O   HOH D  75      -6.910  -3.454 -19.697  1.00 27.34           O
ATOM   2748  O   HOH D  76       8.138 -19.101   1.608  1.00 29.97           O
ATOM   2749  O   HOH D  77       4.491 -35.742 -46.454  1.00 36.89           O
ATOM   2750  O   HOH D  78      -0.441  -0.141 -24.246  1.00 30.28           O
ATOM   2751  O   HOH D  79      18.089   3.070 -19.815  1.00 38.08           O
ATOM   2752  O   HOH D  81       7.932 -11.067   3.190  1.00 31.79           O
ATOM   2753  O   HOH D  82      28.747 -10.977 -20.486  1.00 22.68           O
ATOM   2754  O   HOH D  85      17.170 -24.607 -39.448  1.00 43.29           O
ATOM   2755  O   HOH D  87      21.054  -9.220 -33.318  1.00 26.05           O
ATOM   2756  O   HOH D  88      -6.226  -7.706 -36.680  1.00 29.50           O
ATOM   2757  O   HOH D  90      14.482 -30.898  -9.260  1.00 26.21           O
ATOM   2758  O   HOH D  91       5.037 -37.024 -20.615  1.00 29.24           O
ATOM   2759  O   HOH D  92      24.442 -23.930 -28.728  1.00 43.89           O
ATOM   2760  O   HOH D  93       4.595 -28.812 -34.893  1.00 25.44           O
ATOM   2761  O   HOH D  94      23.225 -19.075 -16.117  1.00 34.25           O
ATOM   2762  O   HOH D  95     -12.372 -30.194  -9.476  1.00 28.27           O
ATOM   2763  O   HOH D  97      -2.429  -7.650  -5.673  1.00 29.14           O
ATOM   2764  O   HOH D  99       0.264  -2.945 -28.569  1.00 28.23           O
ATOM   2765  O   HOH D 100      20.203 -31.113 -14.351  1.00 21.67           O
ATOM   2766  O   HOH D 102      -0.605 -28.540 -30.294  1.00 23.63           O
ATOM   2767  O   HOH D 103       7.870 -35.588 -13.804  1.00 26.11           O
ATOM   2768  O   HOH D 104      -8.485 -14.510  -4.396  1.00 27.90           O
ATOM   2769  O   HOH D 105      23.621 -22.139 -21.472  1.00 20.66           O
ATOM   2770  O   HOH D 108       0.276 -27.608   6.311  1.00 35.19           O
ATOM   2771  O   HOH D 109      -9.057  -9.647 -14.479  1.00 26.97           O
ATOM   2772  O   HOH D 110      -7.014 -41.105 -23.229  1.00 28.77           O
ATOM   2773  O   HOH D 111       9.837 -21.211 -42.226  1.00 30.12           O
ATOM   2774  O   HOH D 112      -8.577 -24.915 -28.266  1.00 21.12           O
ATOM   2775  O   HOH D 113      17.994   2.599 -23.479  1.00 43.91           O
ATOM   2776  O   HOH D 114     -12.529 -14.442  -7.530  1.00 33.40           O
ATOM   2777  O   HOH D 115     -10.270 -13.119 -10.581  1.00 24.17           O
ATOM   2778  O   HOH D 116      13.153 -15.003 -34.233  1.00 25.39           O
ATOM   2779  O   HOH D 119      23.031 -21.243 -13.004  1.00 24.91           O
ATOM   2780  O   HOH D 120      24.972 -21.217 -30.884  1.00 36.38           O
ATOM   2781  O   HOH D 121      22.091   1.543 -27.693  1.00 44.76           O
ATOM   2782  O   HOH D 122      -3.465 -19.025   3.609  1.00 17.57           O
ATOM   2783  O   HOH D 123      14.980  -9.572 -35.688  1.00 26.86           O
ATOM   2784  O   HOH D 124      12.237 -12.294   4.566  1.00 25.07           O
ATOM   2785  O   HOH D 126      19.118  -0.664 -22.547  1.00 35.57           O
ATOM   2786  O   HOH D 127      13.140 -27.475 -32.783  1.00 37.64           O
ATOM   2787  O   HOH D 128      -7.492 -40.236 -27.478  1.00 28.87           O
ATOM   2788  O   HOH D 129     -11.411 -20.333 -33.394  1.00 26.33           O
ATOM   2789  O   HOH D 130      19.061 -18.850 -34.770  1.00 27.16           O
ATOM   2790  O   HOH D 131      -8.922  -6.493 -17.031  1.00 24.71           O
ATOM   2791  O   HOH D 136      28.144 -22.653 -25.382  1.00 32.37           O
ATOM   2792  O   HOH D 138       7.681 -35.410 -31.588  1.00 59.74           O
ATOM   2793  O   HOH D 140       3.004  -0.371 -31.256  1.00 37.86           O
ATOM   2794  O   HOH D 142      10.369 -15.429   7.537  1.00 21.21           O
ATOM   2795  O   HOH D 143      23.001  -3.502 -17.827  1.00 35.43           O
ATOM   2796  O   HOH D 146      16.362 -26.938 -41.555  1.00 40.84           O
ATOM   2797  O   HOH D 147      12.163 -16.769  -7.725  1.00 20.63           O
ATOM   2798  O   HOH D 148     -13.404 -31.509  -7.577  1.00 27.26           O
ATOM   2799  O   HOH D 149      17.700 -10.483 -36.186  1.00 33.12           O
```

FIGURE 2-40 (COORDINATES)

```
ATOM   2800  O   HOH D 153      11.963 -34.211  -9.452  1.00 33.38           O
ATOM   2801  O   HOH D 154      -6.876  -6.015 -31.319  1.00 26.00           O
ATOM   2802  O   HOH D 155      15.279   4.463 -20.172  1.00 37.54           O
ATOM   2803  O   HOH D 157      24.197 -22.146 -18.869  1.00 33.08           O
ATOM   2804  O   HOH D 158       9.107 -25.597 -41.705  1.00 29.67           O
ATOM   2805  O   HOH D 160      19.866 -15.374 -37.484  1.00 35.94           O
ATOM   2806  O   HOH D 163      22.777 -11.182 -33.700  1.00 28.70           O
ATOM   2807  O   HOH D 167      21.533 -13.990 -13.134  1.00 33.42           O
ATOM   2808  O   HOH D 171      20.939 -23.769 -15.210  1.00 24.33           O
ATOM   2809  O   HOH D 173       5.201 -37.035 -17.380  1.00 25.89           O
ATOM   2810  O   HOH D 175      15.333   0.164 -14.125  1.00 31.06           O
ATOM   2811  O   HOH D 176       3.575 -19.481   4.338  1.00 25.58           O
ATOM   2812  O   HOH D 177      11.667 -36.643 -17.841  1.00 37.26           O
ATOM   2813  O   HOH D 178     -14.388  -9.726 -30.120  1.00 38.22           O
ATOM   2814  O   HOH D 182      -0.294  -4.221 -34.483  1.00 40.13           O
ATOM   2815  O   HOH D 183      21.137 -20.197 -35.026  1.00 36.18           O
ATOM   2816  O   HOH D 184       4.285 -11.054   9.630  1.00 39.07           O
ATOM   2817  O   HOH D 186      -6.974 -16.715   1.097  1.00 28.57           O
ATOM   2818  O   HOH D 187       1.680 -37.847   2.204  1.00 38.20           O
ATOM   2819  O   HOH D 188      24.150 -17.765 -33.214  1.00 53.31           O
ATOM   2820  O   HOH D 189     -13.238  -7.062 -25.150  1.00 26.58           O
ATOM   2821  O   HOH D 192      -9.493 -17.755 -35.274  1.00 33.57           O
ATOM   2822  O   HOH D 193      23.101 -23.411 -16.950  1.00 27.74           O
ATOM   2823  O   HOH D 195       6.090 -35.183 -34.060  1.00 35.62           O
ATOM   2824  O   HOH D 197      -6.280 -22.561 -38.978  1.00 37.39           O
ATOM   2825  O   HOH D 198       5.802 -29.443 -37.417  1.00 30.82           O
ATOM   2826  O   HOH D 199     -13.531 -27.424 -16.921  1.00 43.87           O
ATOM   2827  O   HOH D 200      21.036 -12.784 -10.590  1.00 40.12           O
ATOM   2828  O   HOH D 201      -7.585  -9.327 -38.407  1.00 38.69           O
ATOM   2829  O   HOH D 202      11.767 -32.499 -32.453  1.00 53.91           O
ATOM   2830  O   HOH D 203      13.903 -35.194 -16.330  1.00 32.90           O
ATOM   2831  O   HOH D 204      17.595  -0.606 -12.310  1.00 40.87           O
ATOM   2832  O   HOH D 205      26.775 -23.566 -28.253  1.00 41.49           O
ATOM   2833  O   HOH D 206       3.587   1.536 -32.787  1.00 42.27           O
ATOM   2834  O   HOH D 210      -9.337  -2.734 -18.901  1.00 44.76           O
ATOM   2835  O   HOH D 211      10.437 -23.508 -43.204  1.00 39.61           O
ATOM   2836  O   HOH D 212      14.895 -34.968 -18.805  1.00 52.52           O
ATOM   2837  O   HOH D 213      25.168 -25.165 -31.073  1.00 46.68           O
ATOM   2838  O   HOH D 214       2.001 -40.127 -23.001  1.00 51.42           O
ATOM   2839  O   HOH D 215       4.329 -37.819 -31.064  1.00 43.91           O
ATOM   2840  O   HOH D 216       7.984 -40.927  -8.124  1.00 57.61           O
ATOM   2841  O   HOH D 218      13.507 -35.807 -11.282  1.00 41.27           O
ATOM   2842  O   HOH D 219      -4.514  -6.790 -39.508  1.00 40.36           O
ATOM   2843  O   HOH D 222       1.849 -29.484   6.359  1.00 44.69           O
ATOM   2844  O   HOH D 225      -0.393  -1.471 -26.522  1.00 34.58           O
ATOM   2845  O   HOH D 226      28.932 -25.433 -26.482  1.00 48.72           O
ATOM   2846  O   HOH D 229      22.274 -13.002 -35.225  1.00 33.43           O
ATOM   2847  O   HOH D 231      10.181  -7.007   3.834  1.00 46.98           O
ATOM   2848  O   HOH D 232      -1.161  -8.746 -38.977  1.00 31.02           O
ATOM   2849  O   HOH D 235      26.102  -2.199 -18.073  1.00 42.08           O
ATOM   2850  O   HOH D 236      10.528 -37.195 -30.723  1.00 39.32           O
ATOM   2851  O   HOH D 237       7.523  -7.083   2.067  1.00 35.46           O
ATOM   2852  O   HOH D 242       2.079 -39.569 -18.860  1.00 37.54           O
ATOM   2853  O   HOH D 243      28.844  -4.766 -23.597  1.00 36.15           O
ATOM   2854  O   HOH D 244      20.408   0.884 -20.598  1.00 36.76           O
ATOM   2855  O   HOH D 245     -12.730 -17.273 -29.602  1.00 34.85           O
ATOM   2856  O   HOH D 248      22.226 -10.320  -9.778  1.00 45.50           O
ATOM   2857  O   HOH D 249      -5.094  -8.541  -4.652  1.00 39.28           O
ATOM   2858  O   HOH D 251      13.327 -34.954  -7.200  1.00 50.83           O
ATOM   2859  O   HOH D 254      -8.267  -1.312 -17.168  1.00 51.42           O
ATOM   2860  O   HOH D 255       1.977 -37.459  -8.705  1.00 34.30           O
ATOM   2861  O   HOH D 256       4.184  -8.041  -0.373  1.00 29.01           O
ATOM   2862  O   HOH D 257      20.159 -10.433  -7.628  1.00 46.37           O
ATOM   2863  O   HOH D 258      -3.293 -28.666 -30.530  1.00 35.62           O
ATOM   2864  O   HOH D 259       1.480  -8.323 -39.066  1.00 36.64           O
ATOM   2865  O   HOH D 260      21.075   2.151 -25.383  1.00 48.22           O
ATOM   2866  O   HOH D 263      16.939   1.944 -37.664  1.00 48.00           O
ATOM   2867  O   HOH D 264       7.219 -41.222 -10.681  1.00 48.84           O
ATOM   2868  O   HOH D 265      24.275 -25.741 -15.848  1.00 34.94           O
ATOM   2869  O   HOH D 268     -10.925  -4.676 -17.477  1.00 40.13           O
```

FIGURE 2-41 (COORDINATES)

```
ATOM   2870  O   HOH D 269      19.991 -25.933 -34.998  1.00 37.47           O
ATOM   2871  O   HOH D 277       2.850  -5.560 -32.621  1.00 40.68           O
ATOM   2872  O   HOH D 278      17.013 -14.020 -11.878  1.00 20.23           O
ATOM   2873  O   HOH D 279      15.319 -31.313 -26.443  1.00 20.25           O
ATOM   2874  O   HOH D 280       6.158 -37.282 -35.845  1.00 48.55           O
ATOM   2875  O   HOH D 281      -8.166 -12.257  -5.474  1.00 34.24           O
ATOM   2876  O   HOH D 282      -7.721  -6.548 -33.890  1.00 37.41           O
ATOM   2877  O   HOH D 283      23.146 -12.401 -31.387  1.00 25.79           O
ATOM   2878  O   HOH D 284      25.380 -19.377 -12.704  1.00 25.84           O
ATOM   2879  O   HOH D 285      -9.374 -40.958 -24.972  1.00 21.41           O
ATOM   2880  O   HOH D 286     -11.097 -11.520 -12.792  1.00 27.23           O
ATOM   2881  O   HOH D 287     -12.002 -32.536 -11.328  1.00 31.51           O
ATOM   2882  O   HOH D 288       6.994 -38.402 -13.360  1.00 30.96           O
ATOM   2883  O   HOH D 289      -6.872 -15.048  -2.023  1.00 34.95           O
ATOM   2884  O   HOH D 290       8.519  -7.588 -40.857  1.00 40.66           O
ATOM   2885  O   HOH D 291      20.036 -13.499 -39.358  1.00 45.62           O
ATOM   2886  O   HOH D 292      26.879 -19.617 -15.347  1.00 32.57           O
ATOM   2887  O   HOH D 293      22.549 -18.295 -35.294  1.00 41.90           O
ATOM   2888  O   HOH D 295      14.703 -37.398  -8.810  1.00 45.06           O
ATOM   2889  O   HOH D 296       3.018 -39.738 -10.112  1.00 29.34           O
ATOM   2890  O   HOH D 297      24.341 -11.664 -28.882  1.00 45.85           O
ATOM   2891  O   HOH D 300       1.577 -40.495 -11.953  1.00 50.70           O
ATOM   2892  O   HOH D 301      18.976 -13.837 -41.706  1.00 38.63           O
ATOM   2893  O   HOH D 302      17.186 -36.745 -10.659  1.00 42.98           O
ATOM   2894  O   HOH E   1       5.033  -9.968 -22.988  1.00 13.99           O
ATOM   2895  O   HOH E   2      -7.755 -14.537 -34.028  1.00 29.22           O
ATOM   2896  O   HOH E   3      17.483 -24.416 -25.520  1.00 18.82           O
ATOM   2897  O   HOH E   4      10.071 -10.994  -6.586  1.00 15.39           O
ATOM   2898  O   HOH E   5       2.436 -18.679 -10.601  1.00 11.24           O
ATOM   2899  O   HOH E   6      12.251  -1.642 -21.844  1.00 17.38           O
ATOM   2900  O   HOH E   7      -4.272 -11.555 -28.517  1.00 13.83           O
ATOM   2901  O   HOH E   8       6.490 -23.505 -15.040  1.00 13.11           O
ATOM   2902  O   HOH E   9       5.191 -20.595  -6.923  1.00 14.36           O
ATOM   2903  O   HOH E  10      21.526 -10.371 -16.690  1.00 29.76           O
ATOM   2904  O   HOH E  11      19.237 -18.070  -5.610  1.00 14.24           O
ATOM   2905  O   HOH E  12      10.725   1.657 -26.235  1.00 31.15           O
ATOM   2906  O   HOH E  13      13.952 -11.557 -14.352  1.00 17.28           O
ATOM   2907  O   HOH E  14      14.685 -20.197  -0.800  1.00 20.77           O
ATOM   2908  O   HOH E  15      -9.290 -23.763  -7.886  1.00 31.94           O
ATOM   2909  O   HOH E  16      -6.075  -8.349 -21.876  1.00 12.84           O
ATOM   2910  O   HOH E  17      26.848 -24.891 -18.698  1.00 33.41           O
ATOM   2911  O   HOH E  18      15.590 -27.119 -18.164  1.00 18.87           O
ATOM   2912  O   HOH E  19      22.374 -15.365 -31.583  1.00 37.77           O
ATOM   2913  O   HOH E  20      13.681 -13.113 -42.112  1.00 33.83           O
ATOM   2914  O   HOH E  21      -3.311 -13.813  -1.266  1.00 19.82           O
ATOM   2915  O   HOH E  23      -3.265 -39.102  -8.985  1.00 32.37           O
ATOM   2916  O   HOH E  24     -12.214 -12.737 -29.371  1.00 26.95           O
ATOM   2917  O   HOH E  26      26.963 -10.265 -22.004  1.00 27.55           O
ATOM   2918  O   HOH E  28      -3.240   3.244 -19.140  1.00 31.94           O
ATOM   2919  O   HOH E  29       2.162 -36.609  -4.826  1.00 26.51           O
ATOM   2920  O   HOH E  30      13.750 -13.800   0.972  1.00 20.99           O
ATOM   2921  O   HOH E  31      14.546   2.330 -24.388  1.00 27.17           O
ATOM   2922  O   HOH E  32       4.563   1.435 -18.836  1.00 30.59           O
ATOM   2923  O   HOH E  33      -6.853 -31.633 -31.434  1.00 29.64           O
ATOM   2924  O   HOH E  34      -0.532  -8.039  -4.136  1.00 27.15           O
ATOM   2925  O   HOH E  35       0.440 -27.870 -43.337  1.00 40.78           O
ATOM   2926  O   HOH E  36     -10.953 -34.349 -15.297  1.00 27.53           O
ATOM   2927  O   HOH E  37      23.347 -10.737 -14.134  1.00 51.63           O
ATOM   2928  O   HOH E  38      -4.156 -15.523   1.255  1.00 32.76           O
ATOM   2929  O   HOH E  39      -2.059 -40.703 -22.691  1.00 41.14           O
ATOM   2930  O   HOH E  40       7.322 -11.645 -39.132  1.00 28.43           O
ATOM   2931  O   HOH E  41      -5.915 -31.554 -24.830  1.00 36.19           O
ATOM   2932  O   HOH E  42     -11.468 -30.460 -17.813  1.00 38.20           O
ATOM   2933  O   HOH E  43       6.834 -34.739  -1.285  1.00 38.69           O
ATOM   2934  O   HOH E  44      16.891 -21.133 -37.718  1.00 35.32           O
ATOM   2935  O   HOH E  45      15.103   3.456 -31.753  1.00 33.44           O
ATOM   2936  O   HOH E  46      27.735 -27.241 -23.678  1.00 38.49           O
ATOM   2937  O   HOH E  47      10.178   2.437 -41.357  1.00 36.00           O
ATOM   2938  O   HOH E  48      -8.865 -34.659 -30.795  1.00 37.40           O
ATOM   2939  O   HOH E  49      23.922 -28.010 -12.868  1.00 41.77           O
```

FIGURE 2-42 (COORDINATES)

```
ATOM  2940  O   HOH E  50    -0.425   1.681 -15.935  1.00 28.60           O
ATOM  2941  O   HOH E  51    13.768 -31.922  -4.189  1.00 38.10           O
ATOM  2942  O   HOH E  53    26.370 -16.147 -24.258  1.00 32.71           O
ATOM  2943  O   HOH E  55     7.112 -11.233 -41.469  1.00 35.05           O
ATOM  2944  O   HOH E  56    -1.702 -35.727 -38.968  1.00 24.87           O
ATOM  2945  O   HOH E  57    25.128  -9.856 -34.061  1.00 36.44           O
ATOM  2946  O   HOH E  58    10.058  -5.796 -40.117  1.00 36.70           O
ATOM  2947  O   HOH E  59     2.665 -38.505 -14.259  1.00 28.00           O
ATOM  2948  O   HOH E  60   -12.912 -19.464 -25.448  1.00 33.67           O
ATOM  2949  O   HOH E  61    -5.190 -26.750 -30.987  1.00 37.87           O
ATOM  2950  O   HOH E  62   -14.134  -6.300 -27.871  1.00 36.47           O
ATOM  2951  O   HOH E  63    -0.580 -14.615 -40.730  1.00 36.73           O
ATOM  2952  O   HOH E  65     7.611 -31.465   7.046  1.00 46.24           O
ATOM  2953  O   HOH E  66     9.434   0.874 -18.771  1.00 49.07           O
ATOM  2954  O   HOH E  67    23.841  -6.867  -9.202  1.00 42.40           O
ATOM  2955  O   HOH E  68   -13.827 -18.615 -27.957  1.00 37.78           O
ATOM  2956  O   HOH E  69    -5.241 -27.267 -40.179  1.00 32.65           O
ATOM  2957  O   HOH E  70    -0.644 -37.417  -8.559  1.00 39.31           O
ATOM  2958  O   HOH E  71     9.640 -30.180   2.374  1.00 46.05           O
ATOM  2959  O   HOH E  72    -7.973 -37.202  -0.736  1.00 40.83           O
ATOM  2960  O   HOH E  74    -3.380 -33.924   4.445  1.00 40.23           O
ATOM  2961  O   HOH E  78    -4.102  -4.657 -27.796  1.00 35.89           O
ATOM  2962  O   HOH E  79     5.366  -6.963 -37.038  1.00 39.02           O
ATOM  2963  O   HOH E  82    21.569 -28.232 -31.869  1.00 37.40           O
ATOM  2964  O   HOH E  83     9.836 -34.130 -31.798  1.00 48.70           O
ATOM  2965  O   HOH E  84    19.347 -29.481 -20.412  1.00 35.02           O
ATOM  2966  O   HOH E  85   -11.574 -21.312 -35.543  1.00 39.97           O
ATOM  2967  O   HOH E  86    -5.355 -32.233   3.973  1.00 33.16           O
ATOM  2968  O   HOH E  87   -10.520  -1.891 -24.213  1.00 45.01           O
ATOM  2969  O   HOH E  89     1.472 -35.256 -43.115  1.00 41.67           O
ATOM  2970  O   HOH E  91    -3.455 -11.327   6.735  1.00 45.87           O
ATOM  2971  O   HOH E  92     5.033 -30.560 -44.792  1.00 42.98           O
ATOM  2972  O   HOH E  93    10.174 -34.607 -13.121  1.00 44.96           O
ATOM  2973  O   HOH E  94    -1.428 -11.211  -1.806  1.00 37.32           O
ATOM  2974  O   HOH E  95     5.000 -31.507   7.152  1.00 46.21           O
ATOM  2975  O   HOH E  96   -11.951 -17.443  -4.931  1.00 38.29           O
ATOM  2976  O   HOH E  97    17.856 -19.550  -3.969  1.00 20.26           O
ATOM  2977  O   HOH E  98     1.177 -32.989 -44.285  1.00 37.41           O
ATOM  2978  O   HOH E  99     0.957 -10.437  -0.423  1.00 25.10           O
ATOM  2979  O   HOH E 100   -14.036 -19.239  -5.485  1.00 32.14           O
ATOM  2980  O   HOH E 101    10.789 -28.563  -1.850  1.00 46.25           O
ATOM  2981  O   HOH E 102     9.824 -30.187   6.396  1.00 36.32           O
ATOM  2982  O   HOH E 103    23.597 -25.735 -13.424  1.00 26.57           O
ATOM  2983  O   HOH E 104    20.407  -5.972  -8.814  1.00 37.72           O
ATOM  2984  O   HOH E 105     3.397 -33.451   6.163  1.00 44.63           O
ATOM  2985  O   HOH E 106   -11.413  -3.642 -25.904  1.00 35.74           O
ATOM  2986  O   HOH E 107   -11.203 -14.488  -3.559  1.00 46.40           O
ATOM  2987  O   HOH E 109     2.628 -33.292   3.864  1.00 38.57           O
ATOM  2988  S   SO4 F   1    -5.909  -2.963 -24.930  1.00 50.59           S
ATOM  2989  O1  SO4 F   1    -4.578  -2.401 -25.171  1.00 48.25           O
ATOM  2990  O2  SO4 F   1    -6.860  -2.254 -25.793  1.00 48.08           O
ATOM  2991  O3  SO4 F   1    -5.998  -4.416 -25.193  1.00 47.38           O
ATOM  2992  O4  SO4 F   1    -6.233  -2.728 -23.515  1.00 48.88           O
```

FIGURE 2-43 (COORDINATES)

```
HEADER    ----                                    XX-XXX-XX   xxxx
COMPND    ---
REMARK   3
REMARK   3 REFINEMENT.
REMARK   3   PROGRAM     : REFMAC 5.4.0062
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :    1.80
REMARK   3   RESOLUTION RANGE LOW  (ANGSTROMS) :   19.81
REMARK   3   DATA CUTOFF            (SIGMA(F)) :  NONE
REMARK   3   COMPLETENESS FOR RANGE        (%) :  100.00
REMARK   3   NUMBER OF REFLECTIONS             :   29995
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.19307
REMARK   3   R VALUE            (WORKING SET) : 0.18988
REMARK   3   FREE R VALUE                     : 0.25449
REMARK   3   FREE R VALUE TEST SET SIZE   (%) : 5.0
REMARK   3   FREE R VALUE TEST SET COUNT      : 1580
REMARK   3
REMARK   3  FIT IN THE HIGHEST RESOLUTION BIN.
REMARK   3   TOTAL NUMBER OF BINS USED            :       20
REMARK   3   BIN RESOLUTION RANGE HIGH            :    1.800
REMARK   3   BIN RESOLUTION RANGE LOW             :    1.846
REMARK   3   REFLECTION IN BIN     (WORKING SET) :     2147
REMARK   3   BIN COMPLETENESS (WORKING+TEST) (%) :   100.00
REMARK   3   BIN R VALUE           (WORKING SET) :    0.271
REMARK   3   BIN FREE R VALUE SET COUNT           :      114
REMARK   3   BIN FREE R VALUE                     :    0.394
REMARK   3
REMARK   3  NUMBER OF NON-HYDROGEN ATOMS USED IN REFINEMENT.
REMARK   3   ALL ATOMS                : 2992
REMARK   3
REMARK   3  B VALUES.
REMARK   3   FROM WILSON PLOT           (A**2) : NULL
REMARK   3   MEAN B VALUE      (OVERALL, A**2) :  21.004
REMARK   3   OVERALL ANISOTROPIC B VALUE.
REMARK   3    B11 (A**2) :    -0.39
REMARK   3    B22 (A**2) :    -0.30
REMARK   3    B33 (A**2) :     0.69
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                        (A):   0.142
REMARK   3   ESU BASED ON FREE R VALUE                   (A):   0.147
REMARK   3   ESU BASED ON MAXIMUM LIKELIHOOD             (A):   0.104
REMARK   3   ESU FOR B VALUES BASED ON MAXIMUM LIKELIHOOD (A**2):  3.337
REMARK   3
REMARK   3 CORRELATION COEFFICIENTS.
REMARK   3   CORRELATION COEFFICIENT FO-FC       :  0.952
REMARK   3   CORRELATION COEFFICIENT FO-FC FREE  :  0.917
REMARK   3
REMARK   3  RMS DEVIATIONS FROM IDEAL VALUES        COUNT    RMS    WEIGHT
REMARK   3   BOND LENGTHS REFINED ATOMS        (A):  2726 ; 0.015 ; 0.021
REMARK   3   BOND ANGLES REFINED ATOMS   (DEGREES):  3702 ; 1.637 ; 1.952
REMARK   3   TORSION ANGLES, PERIOD 1    (DEGREES):   320 ; 5.786 ; 5.000
REMARK   3   TORSION ANGLES, PERIOD 2    (DEGREES):   137 ;34.195 ;23.796
REMARK   3   TORSION ANGLES, PERIOD 3    (DEGREES):   445 ;12.352 ;15.000
REMARK   3   TORSION ANGLES, PERIOD 4    (DEGREES):    17 ;16.487 ;15.000
REMARK   3   CHIRAL-CENTER RESTRAINTS       (A**3):   389 ; 0.095 ; 0.200
REMARK   3   GENERAL PLANES REFINED ATOMS     (A):  2112 ; 0.008 ; 0.021
REMARK   3
REMARK   3  ISOTROPIC THERMAL FACTOR RESTRAINTS.    COUNT    RMS    WEIGHT
```

FIGURE 2-44 (REMARKS)

```
REMARK   3    MAIN-CHAIN BOND REFINED ATOMS   (A**2):   1617 ; 0.871 ; 1.500
REMARK   3    MAIN-CHAIN ANGLE REFINED ATOMS  (A**2):   2611 ; 1.543 ; 2.000
REMARK   3    SIDE-CHAIN BOND REFINED ATOMS   (A**2):   1109 ; 2.598 ; 3.000
REMARK   3    SIDE-CHAIN ANGLE REFINED ATOMS  (A**2):   1091 ; 3.956 ; 4.500
REMARK   3
REMARK   3  NCS RESTRAINTS STATISTICS
REMARK   3    NUMBER OF NCS GROUPS : NULL
REMARK   3
REMARK   3
REMARK   3  TLS DETAILS
REMARK   3    NUMBER OF TLS GROUPS  : NULL
REMARK   3
REMARK   3
REMARK   3  BULK SOLVENT MODELLING.
REMARK   3    METHOD USED :  MASK
REMARK   3    PARAMETERS FOR MASK CALCULATION
REMARK   3    VDW PROBE RADIUS    :    1.20
REMARK   3    ION PROBE RADIUS    :    0.80
REMARK   3    SHRINKAGE RADIUS    :    0.80
REMARK   3
REMARK   3  OTHER REFINEMENT REMARKS:
REMARK   3   HYDROGENS HAVE BEEN ADDED IN THE RIDING POSITIONS
REMARK   3
SSBOND   1 CYS A  140    CYS A  165
CISPEP   1 ASP A  160    SER A  161                         0.00
LINK            ASP A 184              PRO A 190                        gap
CISPEP   2 HIS A  229    PRO A  230                         0.00
CISPEP   3 SER A  324    PRO A  325                         0.00
CRYST1   41.760   83.060   95.710  90.00  90.00  90.00 P 21 21 21
SCALE1      0.023946  0.000000  0.000000        0.00000
SCALE2      0.000000  0.012039  0.000000        0.00000
SCALE3      0.000000  0.000000  0.010448        0.00000
```

FIGURE 2-45 (REMARKS)

```
       ATOM TYPE RES        x       y       z    Occ   B
ATOM    1  N    ALA A  36   6.320   6.282   4.039  1.00 39.59       N
ATOM    2  CA   ALA A  36   4.978   6.648   4.583  1.00 39.27       C
ATOM    3  CB   ALA A  36   4.442   5.527   5.492  1.00 39.28       C
ATOM    4  C    ALA A  36   5.007   8.002   5.328  1.00 39.02       C
ATOM    5  O    ALA A  36   6.092   8.556   5.607  1.00 38.73       O
ATOM    6  N    TRP A  37   3.811   8.513   5.628  1.00 38.57       N
ATOM    7  CA   TRP A  37   3.603   9.823   6.270  1.00 38.01       C
ATOM    8  CB   TRP A  37   2.118  10.153   6.350  1.00 37.27       C
ATOM    9  CG   TRP A  37   1.295   9.440   7.448  1.00 37.74       C
ATOM   10  CD1  TRP A  37   0.446   8.375   7.266  1.00 36.35       C
ATOM   11  NE1  TRP A  37  -0.155   8.029   8.460  1.00 36.20       N
ATOM   12  CE2  TRP A  37   0.293   8.875   9.449  1.00 37.91       C
ATOM   13  CD2  TRP A  37   1.199   9.790   8.852  1.00 36.30       C
ATOM   14  CE3  TRP A  37   1.802  10.775   9.665  1.00 35.92       C
ATOM   15  CZ3  TRP A  37   1.487  10.816  11.023  1.00 35.20       C
ATOM   16  CH2  TRP A  37   0.567   9.899  11.589  1.00 36.80       C
ATOM   17  CZ2  TRP A  37  -0.034   8.922  10.823  1.00 36.89       C
ATOM   18  C    TRP A  37   4.228   9.933   7.656  1.00 37.98       C
ATOM   19  O    TRP A  37   4.531  11.034   8.130  1.00 37.51       O
ATOM   20  N    THR A  38   4.423   8.785   8.294  1.00 37.92       N
ATOM   21  CA   THR A  38   5.044   8.721   9.610  1.00 38.28       C
ATOM   22  CB   THR A  38   4.841   7.359  10.262  1.00 38.38       C
ATOM   23  OG1  THR A  38   5.309   6.330   9.377  1.00 40.26       O
ATOM   24  CG2  THR A  38   3.375   7.126  10.602  1.00 37.74       C
ATOM   25  C    THR A  38   6.541   9.027   9.544  1.00 38.59       C
ATOM   26  O    THR A  38   7.191   9.125  10.579  1.00 38.99       O
ATOM   27  N    GLN A  39   7.085   9.203   8.339  1.00 38.32       N
ATOM   28  CA   GLN A  39   8.508   9.541   8.191  1.00 38.34       C
ATOM   29  CB   GLN A  39   9.159   8.760   7.047  1.00 38.93       C
ATOM   30  CG   GLN A  39   9.450   7.307   7.366  1.00 41.86       C
ATOM   31  CD   GLN A  39  10.382   7.146   8.552  1.00 47.20       C
ATOM   32  OE1  GLN A  39  10.021   6.514   9.553  1.00 49.89       O
ATOM   33  NE2  GLN A  39  11.579   7.724   8.458  1.00 47.68       N
ATOM   34  C    GLN A  39   8.705  11.005   7.915  1.00 37.54       C
ATOM   35  O    GLN A  39   9.828  11.491   7.924  1.00 37.73       O
ATOM   36  N    GLU A  40   7.623  11.716   7.639  1.00 36.57       N
ATOM   37  CA   GLU A  40   7.749  13.123   7.303  1.00 36.37       C
ATOM   38  CB   GLU A  40   6.399  13.709   6.904  1.00 36.49       C
ATOM   39  CG   GLU A  40   5.930  13.209   5.533  1.00 37.13       C
ATOM   40  CD   GLU A  40   4.452  13.437   5.301  1.00 39.80       C
ATOM   41  OE1  GLU A  40   3.852  14.299   5.999  1.00 38.44       O
ATOM   42  OE2  GLU A  40   3.892  12.764   4.402  1.00 40.66       O
ATOM   43  C    GLU A  40   8.456  13.933   8.410  1.00 35.69       C
ATOM   44  O    GLU A  40   9.267  14.800   8.105  1.00 34.85       O
ATOM   45  N    LYS A  41   8.201  13.604   9.681  1.00 35.74       N
ATOM   46  CA   LYS A  41   8.848  14.318  10.788  1.00 35.42       C
ATOM   47  CB   LYS A  41   8.375  13.807  12.154  1.00 35.86       C
ATOM   48  CG   LYS A  41   8.516  12.300  12.422  1.00 36.31       C
ATOM   49  CD   LYS A  41   8.113  11.991  13.830  1.00 35.06       C
ATOM   50  CE   LYS A  41   7.924  10.528  14.107  1.00 37.96       C
ATOM   51  NZ   LYS A  41   9.194   9.784  14.037  1.00 39.37       N
ATOM   52  C    LYS A  41  10.378  14.311  10.681  1.00 36.33       C
ATOM   53  O    LYS A  41  11.031  15.256  11.125  1.00 34.97       O
ATOM   54  N    ASN A  42  10.933  13.261  10.063  1.00 36.90       N
ATOM   55  CA   ASN A  42  12.398  13.092   9.912  1.00 37.73       C
ATOM   56  CB   ASN A  42  12.742  11.606   9.659  1.00 38.45       C
ATOM   57  CG   ASN A  42  12.197  10.687  10.738  1.00 39.90       C
ATOM   58  OD1  ASN A  42  11.577   9.675  10.442  1.00 43.08       O
ATOM   59  ND2  ASN A  42  12.400  11.060  12.004  1.00 43.80       N
ATOM   60  C    ASN A  42  13.045  13.950   8.836  1.00 37.41       C
ATOM   61  O    ASN A  42  14.270  14.114   8.802  1.00 37.95       O
ATOM   62  N    HIS A  43  12.236  14.497   7.941  1.00 37.62       N
ATOM   63  CA   HIS A  43  12.775  15.348   6.866  1.00 37.08       C
ATOM   64  CB   HIS A  43  12.498  14.713   5.502  1.00 38.53       C
ATOM   65  CG   HIS A  43  12.725  13.227   5.496  1.00 42.91       C
ATOM   66  ND1  HIS A  43  13.981  12.665   5.385  1.00 46.11       N
ATOM   67  CE1  HIS A  43  13.882  11.349   5.466  1.00 46.95       C
ATOM   68  NE2  HIS A  43  12.612  11.039   5.650  1.00 47.04       N
ATOM   69  CD2  HIS A  43  11.869  12.196   5.690  1.00 44.84       C
```

FIGURE 3-1 (COORDINATES)

```
ATOM   70  C   HIS A  43      12.222  16.753   6.957  1.00 35.46           C
ATOM   71  O   HIS A  43      12.499  17.602   6.104  1.00 35.22           O
ATOM   72  N   HIS A  44      11.437  16.998   8.013  1.00 33.33           N
ATOM   73  CA  HIS A  44      10.762  18.278   8.163  1.00 30.89           C
ATOM   74  CB  HIS A  44       9.731  18.276   9.288  1.00 29.97           C
ATOM   75  CG  HIS A  44       8.945  19.540   9.345  1.00 26.52           C
ATOM   76  ND1 HIS A  44       7.956  19.838   8.429  1.00 22.85           N
ATOM   77  CE1 HIS A  44       7.461  21.032   8.694  1.00 24.17           C
ATOM   78  NE2 HIS A  44       8.079  21.514   9.759  1.00 24.04           N
ATOM   79  CD2 HIS A  44       9.034  20.613  10.168  1.00 27.15           C
ATOM   80  C   HIS A  44      11.768  19.363   8.417  1.00 29.86           C
ATOM   81  O   HIS A  44      12.600  19.261   9.312  1.00 29.50           O
ATOM   82  N   GLN A  45      11.659  20.409   7.624  1.00 30.15           N
ATOM   83  CA  GLN A  45      12.553  21.544   7.710  1.00 30.82           C
ATOM   84  CB  GLN A  45      13.189  21.763   6.331  1.00 31.85           C
ATOM   85  CG  GLN A  45      14.001  20.573   5.875  1.00 34.86           C
ATOM   86  CD  GLN A  45      15.139  20.301   6.825  1.00 37.02           C
ATOM   87  OE1 GLN A  45      15.811  21.223   7.267  1.00 39.89           O
ATOM   88  NE2 GLN A  45      15.361  19.035   7.151  1.00 39.84           N
ATOM   89  C   GLN A  45      11.744  22.769   8.122  1.00 30.24           C
ATOM   90  O   GLN A  45      10.598  22.899   7.711  1.00 30.31           O
ATOM   91  N   PRO A  46      12.330  23.663   8.947  1.00 29.84           N
ATOM   92  CA  PRO A  46      11.653  24.916   9.321  1.00 29.62           C
ATOM   93  CB  PRO A  46      12.497  25.424  10.488  1.00 29.63           C
ATOM   94  CG  PRO A  46      13.884  24.846  10.207  1.00 29.83           C
ATOM   95  CD  PRO A  46      13.672  23.544   9.555  1.00 29.26           C
ATOM   96  C   PRO A  46      11.671  25.944   8.173  1.00 30.14           C
ATOM   97  O   PRO A  46      12.582  25.908   7.296  1.00 28.20           O
ATOM   98  N   ALA A  47      10.691  26.847   8.169  1.00 30.56           N
ATOM   99  CA  ALA A  47      10.737  27.989   7.255  1.00 31.82           C
ATOM  100  CB  ALA A  47       9.387  28.187   6.553  1.00 32.54           C
ATOM  101  C   ALA A  47      11.111  29.210   8.054  1.00 32.79           C
ATOM  102  O   ALA A  47      10.287  29.690   8.853  1.00 33.65           O
ATOM  103  N   HIS A  48      12.344  29.691   7.859  1.00 33.27           N
ATOM  104  CA  HIS A  48      12.957  30.762   8.677  1.00 33.45           C
ATOM  105  CB  HIS A  48      14.419  31.003   8.295  1.00 33.37           C
ATOM  106  CG  HIS A  48      15.324  29.814   8.464  1.00 34.07           C
ATOM  107  ND1 HIS A  48      16.698  29.925   8.431  1.00 34.74           N
ATOM  108  CE1 HIS A  48      17.239  28.728   8.584  1.00 36.22           C
ATOM  109  NE2 HIS A  48      16.267  27.844   8.721  1.00 33.37           N
ATOM  110  CD2 HIS A  48      15.061  28.500   8.665  1.00 34.24           C
ATOM  111  C   HIS A  48      12.249  32.097   8.524  1.00 34.15           C
ATOM  112  O   HIS A  48      11.796  32.433   7.417  1.00 34.43           O
ATOM  113  N   LEU A  49      12.197  32.879   9.609  1.00 33.60           N
ATOM  114  CA  LEU A  49      11.615  34.214   9.539  1.00 33.61           C
ATOM  115  CB  LEU A  49      10.917  34.614  10.846  1.00 32.78           C
ATOM  116  CG  LEU A  49       9.858  33.725  11.499  1.00 30.71           C
ATOM  117  CD1 LEU A  49       9.363  34.402  12.778  1.00 26.66           C
ATOM  118  CD2 LEU A  49       8.708  33.395  10.566  1.00 31.65           C
ATOM  119  C   LEU A  49      12.692  35.228   9.220  1.00 34.80           C
ATOM  120  O   LEU A  49      13.802  35.156   9.753  1.00 35.46           O
ATOM  121  N   ASN A  50      12.366  36.188   8.362  1.00 35.92           N
ATOM  122  CA  ASN A  50      13.274  37.308   8.095  1.00 36.95           C
ATOM  123  CB  ASN A  50      12.878  37.992   6.782  1.00 37.92           C
ATOM  124  CG  ASN A  50      11.401  38.429   6.762  1.00 41.62           C
ATOM  125  OD1 ASN A  50      10.792  38.689   7.821  1.00 40.00           O
ATOM  126  ND2 ASN A  50      10.814  38.509   5.549  1.00 46.18           N
ATOM  127  C   ASN A  50      13.189  38.286   9.266  1.00 37.14           C
ATOM  128  O   ASN A  50      12.319  38.120  10.131  1.00 36.03           O
ATOM  129  N   SER A  51      14.051  39.313   9.270  1.00 36.87           N
ATOM  130  CA  SER A  51      14.149  40.280  10.373  1.00 37.12           C
ATOM  131  CB  SER A  51      15.180  41.358  10.052  1.00 37.45           C
ATOM  132  OG  SER A  51      16.463  40.765   9.896  1.00 42.03           O
ATOM  133  C   SER A  51      12.837  40.953  10.757  1.00 36.70           C
ATOM  134  O   SER A  51      12.649  41.333  11.921  1.00 36.10           O
ATOM  135  N   SER A  52      11.963  41.120   9.764  1.00 35.94           N
ATOM  136  CA  SER A  52      10.695  41.825   9.913  1.00 35.67           C
ATOM  137  CB  SER A  52      10.198  42.286   8.525  1.00 36.31           C
ATOM  138  OG  SER A  52       9.629  43.590   8.583  1.00 38.07           O
ATOM  139  C   SER A  52       9.630  40.986  10.647  1.00 34.36           C
```

FIGURE 3-2 (COORDINATES)

```
ATOM    140  O    SER A  52       8.882  41.488  11.494  1.00 34.53           O
ATOM    141  N    SER A  53       9.555  39.701  10.316  1.00 33.29           N
ATOM    142  CA   SER A  53       8.658  38.808  11.006  1.00 31.32           C
ATOM    143  CB   SER A  53       8.495  37.518  10.207  1.00 32.28           C
ATOM    144  OG   SER A  53       8.434  37.830   8.834  1.00 33.74           O
ATOM    145  C    SER A  53       9.201  38.558  12.420  1.00 29.61           C
ATOM    146  O    SER A  53       8.420  38.474  13.368  1.00 28.44           O
ATOM    147  N    LEU A  54      10.535  38.501  12.558  1.00 27.61           N
ATOM    148  CA   LEU A  54      11.194  38.386  13.877  1.00 25.93           C
ATOM    149  CB   LEU A  54      12.724  38.300  13.767  1.00 25.87           C
ATOM    150  CG   LEU A  54      13.334  37.053  13.113  1.00 23.93           C
ATOM    151  CD1  LEU A  54      14.862  37.240  13.065  1.00 23.50           C
ATOM    152  CD2  LEU A  54      12.971  35.770  13.841  1.00 19.37           C
ATOM    153  C    LEU A  54      10.843  39.559  14.761  1.00 25.43           C
ATOM    154  O    LEU A  54      10.493  39.368  15.943  1.00 23.70           O
ATOM    155  N    GLN A  55      10.922  40.776  14.215  1.00 24.81           N
ATOM    156  CA   GLN A  55      10.555  41.935  15.025  1.00 24.09           C
ATOM    157  CB   GLN A  55      11.020  43.246  14.379  1.00 26.15           C
ATOM    158  CG   GLN A  55      10.256  44.503  14.746  0.00 29.31           C
ATOM    159  CD   GLN A  55      11.299  45.603  14.729  0.00 33.26           C
ATOM    160  OE1  GLN A  55      12.500  45.337  14.778  0.00 41.23           O
ATOM    161  NE2  GLN A  55      10.844  46.849  14.660  0.00 40.50           N
ATOM    162  C    GLN A  55       9.041  41.920  15.373  1.00 24.24           C
ATOM    163  O    GLN A  55       8.661  42.276  16.489  1.00 22.93           O
ATOM    164  N    GLN A  56       8.205  41.440  14.454  1.00 23.98           N
ATOM    165  CA   GLN A  56       6.780  41.246  14.727  1.00 26.14           C
ATOM    166  CB   GLN A  56       6.050  40.693  13.487  1.00 25.40           C
ATOM    167  CG   GLN A  56       4.520  40.611  13.672  1.00 28.70           C
ATOM    168  CD   GLN A  56       3.758  39.898  12.554  1.00 31.12           C
ATOM    169  OE1  GLN A  56       4.330  39.429  11.535  1.00 38.36           O
ATOM    170  NE2  GLN A  56       2.441  39.789  12.750  1.00 36.54           N
ATOM    171  C    GLN A  56       6.522  40.291  15.913  1.00 24.87           C
ATOM    172  O    GLN A  56       5.705  40.579  16.787  1.00 25.07           O
ATOM    173  N    VAL A  57       7.149  39.116  15.891  1.00 23.83           N
ATOM    174  CA   VAL A  57       7.055  38.190  17.057  1.00 22.00           C
ATOM    175  CB   VAL A  57       7.883  36.891  16.831  1.00 22.55           C
ATOM    176  CG1  VAL A  57       7.801  35.958  18.059  1.00 21.69           C
ATOM    177  CG2  VAL A  57       7.391  36.178  15.596  1.00 22.46           C
ATOM    178  C    VAL A  57       7.474  38.868  18.358  1.00 20.31           C
ATOM    179  O    VAL A  57       6.757  38.796  19.340  1.00 19.19           O
ATOM    180  N    ALA A  58       8.630  39.531  18.368  1.00 19.50           N
ATOM    181  CA   ALA A  58       9.096  40.186  19.563  1.00 19.88           C
ATOM    182  CB   ALA A  58      10.483  40.796  19.307  1.00 20.36           C
ATOM    183  C    ALA A  58       8.090  41.230  20.093  1.00 20.46           C
ATOM    184  O    ALA A  58       7.867  41.341  21.310  1.00 20.54           O
ATOM    185  N    GLU A  59       7.444  41.961  19.178  1.00 19.88           N
ATOM    186  CA   GLU A  59       6.470  42.991  19.566  1.00 21.12           C
ATOM    187  CB   GLU A  59       6.215  43.982  18.416  1.00 20.32           C
ATOM    188  CG   GLU A  59       7.468  44.702  17.958  1.00 24.65           C
ATOM    189  CD   GLU A  59       7.217  45.642  16.764  1.00 24.38           C
ATOM    190  OE1  GLU A  59       6.181  45.489  16.010  1.00 25.45           O
ATOM    191  OE2  GLU A  59       8.077  46.524  16.617  1.00 30.48           O
ATOM    192  C    GLU A  59       5.133  42.416  20.003  1.00 19.56           C
ATOM    193  O    GLU A  59       4.450  43.044  20.785  1.00 18.41           O
ATOM    194  N    GLY A  60       4.783  41.222  19.517  1.00 19.46           N
ATOM    195  CA   GLY A  60       3.435  40.679  19.686  1.00 18.02           C
ATOM    196  C    GLY A  60       3.217  39.944  20.997  1.00 18.58           C
ATOM    197  O    GLY A  60       2.086  39.476  21.287  1.00 16.67           O
ATOM    198  N    THR A  61       4.291  39.818  21.780  1.00 18.70           N
ATOM    199  CA   THR A  61       4.221  39.135  23.082  1.00 18.39           C
ATOM    200  CB   THR A  61       5.243  37.923  23.157  1.00 18.08           C
ATOM    201  OG1  THR A  61       5.030  37.162  24.356  1.00 16.34           O
ATOM    202  CG2  THR A  61       6.670  38.385  23.103  1.00 18.25           C
ATOM    203  C    THR A  61       4.392  40.132  24.236  1.00 18.69           C
ATOM    204  O    THR A  61       5.213  41.043  24.152  1.00 17.57           O
ATOM    205  N    SER A  62       3.587  39.983  25.295  1.00 18.35           N
ATOM    206  CA   SER A  62       3.601  40.922  26.419  1.00 19.15           C
ATOM    207  CB   SER A  62       2.236  41.651  26.559  1.00 19.03           C
ATOM    208  OG   SER A  62       2.245  42.410  27.780  1.00 22.19           O
ATOM    209  C    SER A  62       3.846  40.106  27.694  1.00 19.43           C
```

FIGURE 3-3 (COORDINATES)

```
ATOM  210  O    SER A  62      2.978  39.333  28.098  1.00 19.24           O
ATOM  211  N    ILE A  63      5.000  40.312  28.337  1.00 19.37           N
ATOM  212  CA   ILE A  63      5.319  39.625  29.569  1.00 18.24           C
ATOM  213  CB   ILE A  63      6.837  39.748  29.933  1.00 17.84           C
ATOM  214  CG1  ILE A  63      7.238  38.782  31.055  1.00 16.37           C
ATOM  215  CD1  ILE A  63      6.984  37.309  30.681  1.00 13.05           C
ATOM  216  CG2  ILE A  63      7.213  41.186  30.324  1.00 21.60           C
ATOM  217  C    ILE A  63      4.391  40.029  30.741  1.00 18.67           C
ATOM  218  O    ILE A  63      4.008  39.188  31.532  1.00 17.37           O
ATOM  219  N    SER A  64      4.039  41.311  30.838  1.00 19.05           N
ATOM  220  CA   SER A  64      3.085  41.770  31.856  1.00 19.93           C
ATOM  221  CB   SER A  64      3.135  43.302  32.051  1.00 20.46           C
ATOM  222  OG   SER A  64      2.522  43.979  30.977  1.00 23.78           O
ATOM  223  C    SER A  64      1.631  41.267  31.684  1.00 19.59           C
ATOM  224  O    SER A  64      0.990  40.921  32.664  1.00 19.50           O
ATOM  225  N    GLU A  65      1.115  41.218  30.468  1.00 19.62           N
ATOM  226  CA   GLU A  65     -0.198  40.600  30.233  1.00 20.96           C
ATOM  227  CB   GLU A  65     -0.686  40.900  28.805  1.00 20.89           C
ATOM  228  CG   GLU A  65     -0.977  42.408  28.535  1.00 24.53           C
ATOM  229  CD   GLU A  65     -1.576  42.657  27.134  1.00 26.70           C
ATOM  230  OE1  GLU A  65     -1.065  42.095  26.113  1.00 33.15           O
ATOM  231  OE2  GLU A  65     -2.603  43.371  27.077  1.00 33.50           O
ATOM  232  C    GLU A  65     -0.195  39.080  30.549  1.00 19.95           C
ATOM  233  O    GLU A  65     -1.105  38.585  31.210  1.00 18.21           O
ATOM  234  N    MET A  66      0.844  38.348  30.120  1.00 19.55           N
ATOM  235  CA   MET A  66      1.015  36.943  30.559  1.00 19.70           C
ATOM  236  CB   MET A  66      2.325  36.348  30.033  1.00 19.93           C
ATOM  237  CG   MET A  66      2.465  34.821  30.309  1.00 19.80           C
ATOM  238  SD   MET A  66      4.162  34.173  30.396  1.00 18.38           S
ATOM  239  CE   MET A  66      4.642  34.748  32.017  1.00 16.51           C
ATOM  240  C    MET A  66      1.031  36.848  32.080  1.00 19.91           C
ATOM  241  O    MET A  66      0.325  36.028  32.654  1.00 19.91           O
ATOM  242  N    TRP A  67      1.837  37.706  32.724  1.00 18.88           N
ATOM  243  CA   TRP A  67      1.964  37.683  34.175  1.00 19.45           C
ATOM  244  CB   TRP A  67      2.821  38.835  34.657  1.00 18.74           C
ATOM  245  CG   TRP A  67      3.663  38.505  35.905  1.00 18.32           C
ATOM  246  CD1  TRP A  67      3.291  38.565  37.214  1.00 16.80           C
ATOM  247  NE1  TRP A  67      4.361  38.187  38.043  1.00 17.48           N
ATOM  248  CE2  TRP A  67      5.429  37.883  37.232  1.00 18.18           C
ATOM  249  CD2  TRP A  67      5.011  38.057  35.882  1.00 18.24           C
ATOM  250  CE3  TRP A  67      5.922  37.810  34.848  1.00 15.22           C
ATOM  251  CZ3  TRP A  67      7.184  37.362  35.172  1.00 17.53           C
ATOM  252  CH2  TRP A  67      7.560  37.187  36.525  1.00 19.16           C
ATOM  253  CZ2  TRP A  67      6.696  37.448  37.556  1.00 18.70           C
ATOM  254  C    TRP A  67      0.567  37.821  34.830  1.00 20.13           C
ATOM  255  O    TRP A  67      0.193  37.054  35.694  1.00 19.16           O
ATOM  256  N    GLN A  68     -0.184  38.812  34.403  1.00 20.00           N
ATOM  257  CA   GLN A  68     -1.419  39.152  35.079  1.00 20.80           C
ATOM  258  CB   GLN A  68     -1.797  40.611  34.763  1.00 22.20           C
ATOM  259  CG   GLN A  68     -2.879  41.279  35.637  1.00 25.55           C
ATOM  260  CD   GLN A  68     -2.631  41.136  37.138  1.00 29.23           C
ATOM  261  OE1  GLN A  68     -3.565  40.854  37.897  1.00 36.90           O
ATOM  262  NE2  GLN A  68     -1.384  41.298  37.575  1.00 30.72           N
ATOM  263  C    GLN A  68     -2.502  38.196  34.684  1.00 19.77           C
ATOM  264  O    GLN A  68     -3.235  37.721  35.559  1.00 19.83           O
ATOM  265  N    ASN A  69     -2.583  37.857  33.396  1.00 18.22           N
ATOM  266  CA   ASN A  69     -3.720  37.085  32.872  1.00 19.13           C
ATOM  267  CB   ASN A  69     -4.216  37.626  31.525  1.00 18.37           C
ATOM  268  CG   ASN A  69     -4.552  39.092  31.600  1.00 20.75           C
ATOM  269  OD1  ASN A  69     -5.118  39.525  32.599  1.00 18.51           O
ATOM  270  ND2  ASN A  69     -4.137  39.885  30.584  1.00 20.19           N
ATOM  271  C    ASN A  69     -3.543  35.565  32.788  1.00 18.98           C
ATOM  272  O    ASN A  69     -4.536  34.829  32.863  1.00 17.67           O
ATOM  273  N    ASP A  70     -2.299  35.109  32.604  1.00 18.59           N
ATOM  274  CA   ASP A  70     -2.057  33.654  32.467  1.00 18.65           C
ATOM  275  CB   ASP A  70     -1.280  33.292  31.185  1.00 18.91           C
ATOM  276  CG   ASP A  70     -2.063  33.585  29.911  1.00 23.43           C
ATOM  277  OD1  ASP A  70     -3.179  33.049  29.774  1.00 26.01           O
ATOM  278  OD2  ASP A  70     -1.543  34.317  29.037  1.00 25.42           O
ATOM  279  C    ASP A  70     -1.351  33.051  33.672  1.00 17.14           C
```

FIGURE 3-4 (COORDINATES)

```
ATOM  280  O    ASP A  70   -1.733  31.993  34.097  1.00  16.84           O
ATOM  281  N    LEU A  71   -0.305  33.713  34.176  1.00  16.35           N
ATOM  282  CA   LEU A  71    0.507  33.178  35.277  1.00  16.60           C
ATOM  283  CB   LEU A  71    1.898  33.854  35.292  1.00  15.84           C
ATOM  284  CG   LEU A  71    2.819  33.412  36.447  1.00  16.68           C
ATOM  285  CD1  LEU A  71    3.179  31.893  36.352  1.00  13.72           C
ATOM  286  CD2  LEU A  71    4.056  34.306  36.407  1.00  17.87           C
ATOM  287  C    LEU A  71   -0.116  33.284  36.661  1.00  17.17           C
ATOM  288  O    LEU A  71   -0.255  32.287  37.400  1.00  15.94           O
ATOM  289  N    ARG A  72   -0.477  34.510  37.042  1.00  16.10           N
ATOM  290  CA   ARG A  72   -0.989  34.741  38.390  1.00  17.57           C
ATOM  291  CB   ARG A  72   -1.256  36.245  38.583  1.00  17.81           C
ATOM  292  CG   ARG A  72   -0.001  36.913  39.024  1.00  18.32           C
ATOM  293  CD   ARG A  72   -0.202  38.396  39.337  1.00  22.71           C
ATOM  294  NE   ARG A  72    1.017  38.986  39.901  1.00  25.14           N
ATOM  295  CZ   ARG A  72    1.182  40.296  40.115  1.00  25.59           C
ATOM  296  NH1  ARG A  72    0.211  41.142  39.809  1.00  24.90           N
ATOM  297  NH2  ARG A  72    2.311  40.755  40.653  1.00  26.88           N
ATOM  298  C    ARG A  72   -2.156  33.838  38.830  1.00  17.92           C
ATOM  299  O    ARG A  72   -2.146  33.282  39.962  1.00  17.54           O
ATOM  300  N    PRO A  73   -3.143  33.629  37.941  1.00  17.66           N
ATOM  301  CA   PRO A  73   -4.183  32.700  38.345  1.00  18.39           C
ATOM  302  CB   PRO A  73   -5.201  32.802  37.191  1.00  18.62           C
ATOM  303  CG   PRO A  73   -4.959  34.134  36.615  1.00  16.74           C
ATOM  304  CD   PRO A  73   -3.468  34.271  36.646  1.00  17.93           C
ATOM  305  C    PRO A  73   -3.702  31.240  38.594  1.00  19.41           C
ATOM  306  O    PRO A  73   -4.381  30.476  39.279  1.00  17.91           O
ATOM  307  N    LEU A  74   -2.538  30.872  38.055  1.00  18.98           N
ATOM  308  CA   LEU A  74   -1.963  29.528  38.310  1.00  19.44           C
ATOM  309  CB   LEU A  74   -1.082  29.059  37.147  1.00  19.20           C
ATOM  310  CG   LEU A  74   -1.767  28.811  35.826  1.00  20.34           C
ATOM  311  CD1  LEU A  74   -0.717  28.572  34.702  1.00  23.27           C
ATOM  312  CD2  LEU A  74   -2.738  27.642  35.934  1.00  23.00           C
ATOM  313  C    LEU A  74   -1.113  29.507  39.583  1.00  19.35           C
ATOM  314  O    LEU A  74   -0.726  28.436  40.035  1.00  20.21           O
ATOM  315  N    LEU A  75   -0.800  30.662  40.165  1.00  18.51           N
ATOM  316  CA   LEU A  75    0.098  30.635  41.296  1.00  19.11           C
ATOM  317  CB   LEU A  75    0.925  31.914  41.386  1.00  18.88           C
ATOM  318  CG   LEU A  75    1.911  32.068  40.227  1.00  16.84           C
ATOM  319  CD1  LEU A  75    2.498  33.444  40.247  1.00  13.74           C
ATOM  320  CD2  LEU A  75    3.010  31.030  40.356  1.00  18.92           C
ATOM  321  C    LEU A  75   -0.618  30.286  42.609  1.00  19.66           C
ATOM  322  O    LEU A  75   -0.655  31.068  43.553  1.00  19.74           O
ATOM  323  N    ILE A  76   -1.156  29.075  42.640  1.00  20.09           N
ATOM  324  CA   ILE A  76   -1.977  28.594  43.771  1.00  19.89           C
ATOM  325  CB   ILE A  76   -3.479  28.706  43.439  1.00  19.38           C
ATOM  326  CG1  ILE A  76   -3.786  27.991  42.118  1.00  19.30           C
ATOM  327  CD1  ILE A  76   -5.273  28.058  41.599  1.00  21.58           C
ATOM  328  CG2  ILE A  76   -3.901  30.185  43.335  1.00  20.75           C
ATOM  329  C    ILE A  76   -1.577  27.129  44.016  1.00  19.51           C
ATOM  330  O    ILE A  76   -1.060  26.447  43.109  1.00  19.02           O
ATOM  331  N    GLU A  77   -1.838  26.638  45.219  1.00  19.30           N
ATOM  332  CA   GLU A  77   -1.678  25.226  45.526  1.00  20.39           C
ATOM  333  CB   GLU A  77   -1.954  25.008  47.030  1.00  20.09           C
ATOM  334  CG   GLU A  77   -2.197  23.595  47.425  1.00  23.45           C
ATOM  335  CD   GLU A  77   -2.276  23.439  48.947  1.00  23.36           C
ATOM  336  OE1  GLU A  77   -3.172  24.072  49.544  1.00  26.68           O
ATOM  337  OE2  GLU A  77   -1.446  22.693  49.510  1.00  26.63           O
ATOM  338  C    GLU A  77   -2.617  24.422  44.619  1.00  19.93           C
ATOM  339  O    GLU A  77   -3.819  24.646  44.627  1.00  20.26           O
ATOM  340  N    ARG A  78   -2.070  23.514  43.808  1.00  19.10           N
ATOM  341  CA   ARG A  78   -2.859  22.836  42.774  1.00  18.23           C
ATOM  342  CB   ARG A  78   -2.837  23.637  41.433  1.00  19.32           C
ATOM  343  CG   ARG A  78   -1.414  23.847  40.859  1.00  16.53           C
ATOM  344  CD   ARG A  78   -1.299  24.907  39.676  1.00  16.59           C
ATOM  345  NE   ARG A  78    0.092  24.905  39.208  1.00  13.05           N
ATOM  346  CZ   ARG A  78    1.122  25.462  39.869  1.00  12.85           C
ATOM  347  NH1  ARG A  78    0.951  26.131  41.016  1.00  13.56           N
ATOM  348  NH2  ARG A  78    2.360  25.309  39.426  1.00  14.05           N
ATOM  349  C    ARG A  78   -2.373  21.374  42.607  1.00  19.01           C
```

FIGURE 3-5 (COORDINATES)

```
ATOM    350  O   ARG A  78      -2.209  20.850  41.496  1.00 18.21           O
ATOM    351  N   TYR A  79      -2.107  20.706  43.734  1.00 19.35           N
ATOM    352  CA  TYR A  79      -1.763  19.278  43.664  1.00 20.12           C
ATOM    353  CB  TYR A  79      -1.071  18.816  44.987  1.00 21.00           C
ATOM    354  CG  TYR A  79      -1.950  18.836  46.223  1.00 19.69           C
ATOM    355  CD1 TYR A  79      -1.904  19.898  47.127  1.00 17.37           C
ATOM    356  CE1 TYR A  79      -2.704  19.907  48.305  1.00 18.31           C
ATOM    357  CZ  TYR A  79      -3.544  18.853  48.580  1.00 19.36           C
ATOM    358  OH  TYR A  79      -4.303  18.831  49.759  1.00 23.58           O
ATOM    359  CE2 TYR A  79      -3.614  17.781  47.692  1.00 21.11           C
ATOM    360  CD2 TYR A  79      -2.795  17.763  46.522  1.00 22.89           C
ATOM    361  C   TYR A  79      -3.062  18.504  43.316  1.00 20.35           C
ATOM    362  O   TYR A  79      -4.193  19.049  43.479  1.00 18.98           O
ATOM    363  N   PRO A  80      -2.926  17.294  42.718  1.00 20.90           N
ATOM    364  CA  PRO A  80      -4.095  16.587  42.215  1.00 21.57           C
ATOM    365  CB  PRO A  80      -3.514  15.253  41.768  1.00 21.84           C
ATOM    366  CG  PRO A  80      -2.143  15.604  41.349  1.00 20.68           C
ATOM    367  CD  PRO A  80      -1.691  16.569  42.393  1.00 21.27           C
ATOM    368  C   PRO A  80      -5.155  16.397  43.298  1.00 21.86           C
ATOM    369  O   PRO A  80      -4.808  15.995  44.407  1.00 23.17           O
ATOM    370  N   GLY A  81      -6.392  16.806  43.002  1.00 21.10           N
ATOM    371  CA  GLY A  81      -7.499  16.719  43.941  1.00 21.40           C
ATOM    372  C   GLY A  81      -7.827  18.015  44.663  1.00 21.72           C
ATOM    373  O   GLY A  81      -8.939  18.184  45.109  1.00 20.79           O
ATOM    374  N   SER A  82      -6.862  18.925  44.776  1.00 21.22           N
ATOM    375  CA  SER A  82      -7.070  20.169  45.509  1.00 21.83           C
ATOM    376  CB  SER A  82      -5.714  20.833  45.776  1.00 22.00           C
ATOM    377  OG  SER A  82      -5.131  21.318  44.565  1.00 19.66           O
ATOM    378  C   SER A  82      -8.067  21.124  44.806  1.00 22.77           C
ATOM    379  O   SER A  82      -8.292  21.001  43.587  1.00 22.41           O
ATOM    380  N   PRO A  83      -8.704  22.065  45.566  1.00 22.59           N
ATOM    381  CA  PRO A  83      -9.510  23.079  44.851  1.00 22.39           C
ATOM    382  CB  PRO A  83      -9.958  24.033  45.968  1.00 22.79           C
ATOM    383  CG  PRO A  83      -9.916  23.188  47.219  1.00 23.25           C
ATOM    384  CD  PRO A  83      -8.747  22.254  47.028  1.00 23.08           C
ATOM    385  C   PRO A  83      -8.708  23.833  43.752  1.00 22.19           C
ATOM    386  O   PRO A  83      -9.236  24.065  42.669  1.00 22.31           O
ATOM    387  N   GLY A  84      -7.455  24.189  44.035  1.00 20.87           N
ATOM    388  CA  GLY A  84      -6.587  24.825  43.056  1.00 20.15           C
ATOM    389  C   GLY A  84      -6.366  23.998  41.770  1.00 20.43           C
ATOM    390  O   GLY A  84      -6.182  24.575  40.711  1.00 19.91           O
ATOM    391  N   SER A  85      -6.338  22.657  41.853  1.00 20.06           N
ATOM    392  CA  SER A  85      -6.253  21.796  40.651  1.00 20.42           C
ATOM    393  CB  SER A  85      -6.238  20.318  41.061  1.00 20.28           C
ATOM    394  OG  SER A  85      -6.373  19.442  39.937  1.00 20.19           O
ATOM    395  C   SER A  85      -7.429  22.083  39.714  1.00 21.48           C
ATOM    396  O   SER A  85      -7.276  22.221  38.502  1.00 20.27           O
ATOM    397  N   TYR A  86      -8.626  22.147  40.285  1.00 23.02           N
ATOM    398  CA  TYR A  86      -9.798  22.462  39.482  1.00 24.55           C
ATOM    399  CB  TYR A  86     -11.088  22.196  40.282  1.00 27.90           C
ATOM    400  CG  TYR A  86     -12.323  22.528  39.490  1.00 31.54           C
ATOM    401  CD1 TYR A  86     -12.811  21.635  38.535  1.00 35.55           C
ATOM    402  CE1 TYR A  86     -13.951  21.941  37.770  1.00 37.97           C
ATOM    403  CZ  TYR A  86     -14.595  23.168  37.958  1.00 36.82           C
ATOM    404  OH  TYR A  86     -15.732  23.470  37.204  1.00 38.44           O
ATOM    405  CE2 TYR A  86     -14.113  24.080  38.896  1.00 36.69           C
ATOM    406  CD2 TYR A  86     -12.967  23.754  39.652  1.00 34.88           C
ATOM    407  C   TYR A  86      -9.761  23.910  38.927  1.00 22.95           C
ATOM    408  O   TYR A  86     -10.087  24.143  37.757  1.00 22.35           O
ATOM    409  N   SER A  87      -9.391  24.875  39.761  1.00 21.82           N
ATOM    410  CA  SER A  87      -9.302  26.270  39.301  1.00 22.09           C
ATOM    411  CB  SER A  87      -8.899  27.186  40.416  1.00 21.72           C
ATOM    412  OG  SER A  87     -10.004  27.340  41.262  1.00 31.09           O
ATOM    413  C   SER A  87      -8.274  26.440  38.196  1.00 21.07           C
ATOM    414  O   SER A  87      -8.537  27.124  37.206  1.00 20.49           O
ATOM    415  N   ALA A  88      -7.096  25.848  38.393  1.00 19.23           N
ATOM    416  CA  ALA A  88      -6.035  25.848  37.347  1.00 18.95           C
ATOM    417  CB  ALA A  88      -4.756  25.127  37.852  1.00 18.24           C
ATOM    418  C   ALA A  88      -6.518  25.241  36.036  1.00 18.38           C
ATOM    419  O   ALA A  88      -6.314  25.819  34.968  1.00 16.43           O
```

FIGURE 3-6 (COORDINATES)

```
ATOM    420  N   ARG A  89      -7.132  24.060  36.114  1.00 18.75           N
ATOM    421  CA  ARG A  89      -7.662  23.384  34.951  1.00 19.70           C
ATOM    422  CB  ARG A  89      -8.289  22.055  35.364  1.00 20.06           C
ATOM    423  CG  ARG A  89      -8.922  21.266  34.232  1.00 20.41           C
ATOM    424  CD  ARG A  89      -9.002  19.760  34.580  1.00 24.79           C
ATOM    425  NE  ARG A  89      -9.818  19.531  35.778  1.00 25.05           N
ATOM    426  CZ  ARG A  89      -9.370  19.340  37.021  1.00 26.42           C
ATOM    427  NH1 ARG A  89      -8.058  19.311  37.318  1.00 24.30           N
ATOM    428  NH2 ARG A  89     -10.256  19.138  37.995  1.00 26.12           N
ATOM    429  C   ARG A  89      -8.702  24.250  34.181  1.00 20.13           C
ATOM    430  O   ARG A  89      -8.647  24.340  32.927  1.00 19.74           O
ATOM    431  N   GLN A  90      -9.644  24.836  34.925  1.00 19.21           N
ATOM    432  CA  GLN A  90     -10.676  25.705  34.346  1.00 20.19           C
ATOM    433  CB  GLN A  90     -11.740  26.107  35.394  1.00 20.57           C
ATOM    434  CG  GLN A  90     -12.709  24.942  35.797  1.00 27.63           C
ATOM    435  CD  GLN A  90     -13.559  24.412  34.617  1.00 34.11           C
ATOM    436  OE1 GLN A  90     -14.046  25.186  33.770  1.00 39.08           O
ATOM    437  NE2 GLN A  90     -13.741  23.091  34.565  1.00 36.46           N
ATOM    438  C   GLN A  90     -10.070  26.993  33.767  1.00 17.96           C
ATOM    439  O   GLN A  90     -10.534  27.491  32.757  1.00 16.86           O
ATOM    440  N   HIS A  91      -9.043  27.517  34.417  1.00 16.17           N
ATOM    441  CA  HIS A  91      -8.371  28.714  33.911  1.00 16.63           C
ATOM    442  CB  HIS A  91      -7.365  29.204  34.983  1.00 15.88           C
ATOM    443  CG  HIS A  91      -6.316  30.142  34.476  1.00 17.46           C
ATOM    444  ND1 HIS A  91      -6.596  31.423  34.049  1.00 14.95           N
ATOM    445  CE1 HIS A  91      -5.472  32.010  33.671  1.00 17.89           C
ATOM    446  NE2 HIS A  91      -4.473  31.170  33.870  1.00 17.50           N
ATOM    447  CD2 HIS A  91      -4.968  30.002  34.390  1.00 17.86           C
ATOM    448  C   HIS A  91      -7.682  28.416  32.542  1.00 16.88           C
ATOM    449  O   HIS A  91      -7.788  29.203  31.575  1.00 16.34           O
ATOM    450  N   ILE A  92      -6.980  27.283  32.478  1.00 16.99           N
ATOM    451  CA  ILE A  92      -6.213  26.883  31.291  1.00 16.41           C
ATOM    452  CB  ILE A  92      -5.415  25.582  31.543  1.00 14.72           C
ATOM    453  CG1 ILE A  92      -4.162  25.853  32.393  1.00 14.91           C
ATOM    454  CD1 ILE A  92      -3.574  24.590  33.116  1.00 15.76           C
ATOM    455  CG2 ILE A  92      -5.004  24.901  30.169  1.00 11.36           C
ATOM    456  C   ILE A  92      -7.226  26.728  30.140  1.00 17.25           C
ATOM    457  O   ILE A  92      -7.042  27.255  29.065  1.00 15.30           O
ATOM    458  N   MET A  93      -8.345  26.070  30.420  1.00 19.26           N
ATOM    459  CA  MET A  93      -9.354  25.870  29.399  1.00 21.27           C
ATOM    460  CB  MET A  93     -10.393  24.835  29.856  1.00 21.21           C
ATOM    461  CG  MET A  93      -9.796  23.469  30.023  1.00 23.60           C
ATOM    462  SD  MET A  93     -10.896  22.158  30.596  1.00 29.25           S
ATOM    463  CE  MET A  93     -11.692  22.867  32.010  1.00 18.56           C
ATOM    464  C   MET A  93     -10.009  27.188  28.958  1.00 20.73           C
ATOM    465  O   MET A  93     -10.260  27.371  27.775  1.00 21.58           O
ATOM    466  N   GLN A  94     -10.273  28.100  29.894  1.00 20.43           N
ATOM    467  CA  GLN A  94     -10.899  29.384  29.560  1.00 20.71           C
ATOM    468  CB  GLN A  94     -11.204  30.159  30.858  1.00 20.64           C
ATOM    469  CG  GLN A  94     -12.034  31.491  30.735  1.00 22.15           C
ATOM    470  CD  GLN A  94     -11.227  32.777  30.418  1.00 25.88           C
ATOM    471  OE1 GLN A  94     -10.096  32.956  30.879  1.00 29.15           O
ATOM    472  NE2 GLN A  94     -11.838  33.692  29.635  1.00 23.86           N
ATOM    473  C   GLN A  94      -9.972  30.217  28.629  1.00 19.65           C
ATOM    474  O   GLN A  94     -10.419  30.819  27.620  1.00 19.10           O
ATOM    475  N   ARG A  95      -8.689  30.252  28.987  1.00 17.74           N
ATOM    476  CA  ARG A  95      -7.717  31.057  28.237  1.00 17.52           C
ATOM    477  CB  ARG A  95      -6.380  31.136  28.964  1.00 17.32           C
ATOM    478  CG  ARG A  95      -6.458  31.898  30.299  1.00 15.26           C
ATOM    479  CD  ARG A  95      -6.857  33.412  30.104  1.00 15.57           C
ATOM    480  NE  ARG A  95      -5.753  34.125  29.454  1.00 19.91           N
ATOM    481  CZ  ARG A  95      -5.773  35.403  29.074  1.00 22.64           C
ATOM    482  NH1 ARG A  95      -6.863  36.140  29.247  1.00 18.81           N
ATOM    483  NH2 ARG A  95      -4.702  35.948  28.489  1.00 23.68           N
ATOM    484  C   ARG A  95      -7.530  30.539  26.826  1.00 18.15           C
ATOM    485  O   ARG A  95      -7.174  31.300  25.926  1.00 18.13           O
ATOM    486  N   ILE A  96      -7.743  29.248  26.624  1.00 16.95           N
ATOM    487  CA  ILE A  96      -7.646  28.686  25.294  1.00 17.31           C
ATOM    488  CB  ILE A  96      -7.309  27.188  25.337  1.00 17.26           C
ATOM    489  CG1 ILE A  96      -5.845  27.021  25.821  1.00 18.08           C
```

FIGURE 3-7 (COORDINATES)

```
ATOM    490  CD1 ILE A  96      -5.504  25.636  26.355  1.00 20.02           C
ATOM    491  CG2 ILE A  96      -7.485  26.502  23.926  1.00 17.68           C
ATOM    492  C   ILE A  96      -8.943  28.962  24.543  1.00 19.11           C
ATOM    493  O   ILE A  96      -8.887  29.374  23.399  1.00 19.54           O
ATOM    494  N   GLN A  97     -10.089  28.725  25.187  1.00 19.21           N
ATOM    495  CA  GLN A  97     -11.411  28.876  24.543  1.00 21.13           C
ATOM    496  CB  GLN A  97     -12.536  28.258  25.437  1.00 20.97           C
ATOM    497  CG  GLN A  97     -12.629  26.692  25.210  1.00 28.88           C
ATOM    498  CD  GLN A  97     -13.053  25.904  26.452  1.00 36.44           C
ATOM    499  OE1 GLN A  97     -13.062  26.439  27.558  1.00 41.57           O
ATOM    500  NE2 GLN A  97     -13.426  24.630  26.269  1.00 40.16           N
ATOM    501  C   GLN A  97     -11.747  30.305  24.097  1.00 20.38           C
ATOM    502  O   GLN A  97     -12.467  30.473  23.138  1.00 21.34           O
ATOM    503  N   ARG A  98     -11.244  31.320  24.800  1.00 20.35           N
ATOM    504  CA  ARG A  98     -11.436  32.734  24.417  1.00 19.89           C
ATOM    505  CB  ARG A  98     -10.967  33.662  25.534  1.00 20.40           C
ATOM    506  CG  ARG A  98      -9.445  33.595  25.784  1.00 19.12           C
ATOM    507  CD  ARG A  98      -9.029  34.523  26.854  1.00 15.31           C
ATOM    508  NE  ARG A  98      -9.332  35.881  26.438  1.00 24.02           N
ATOM    509  CZ  ARG A  98      -8.504  36.647  25.747  1.00 25.76           C
ATOM    510  NH1 ARG A  98      -7.265  36.202  25.466  1.00 18.67           N
ATOM    511  NH2 ARG A  98      -8.909  37.868  25.365  1.00 24.62           N
ATOM    512  C   ARG A  98     -10.736  33.146  23.103  1.00 21.76           C
ATOM    513  O   ARG A  98     -11.036  34.233  22.558  1.00 21.51           O
ATOM    514  N   LEU A  99      -9.833  32.298  22.595  1.00 20.73           N
ATOM    515  CA  LEU A  99      -9.026  32.635  21.426  1.00 21.15           C
ATOM    516  CB  LEU A  99      -7.723  31.815  21.423  1.00 20.65           C
ATOM    517  CG  LEU A  99      -6.784  32.172  22.594  1.00 20.20           C
ATOM    518  CD1 LEU A  99      -5.576  31.210  22.685  1.00 20.62           C
ATOM    519  CD2 LEU A  99      -6.319  33.649  22.558  1.00 22.29           C
ATOM    520  C   LEU A  99      -9.782  32.402  20.116  1.00 21.27           C
ATOM    521  O   LEU A  99     -10.770  31.679  20.105  1.00 21.08           O
ATOM    522  N   GLN A 100      -9.307  32.997  19.013  1.00 20.32           N
ATOM    523  CA  GLN A 100      -9.981  32.829  17.726  1.00 19.42           C
ATOM    524  CB  GLN A 100      -9.721  34.000  16.743  1.00 19.55           C
ATOM    525  CG  GLN A 100      -9.993  35.372  17.338  1.00 19.08           C
ATOM    526  CD  GLN A 100     -11.465  35.552  17.618  1.00 26.03           C
ATOM    527  OE1 GLN A 100     -12.303  35.194  16.795  1.00 29.21           O
ATOM    528  NE2 GLN A 100     -11.790  36.072  18.783  1.00 22.70           N
ATOM    529  C   GLN A 100      -9.624  31.532  17.065  1.00 19.61           C
ATOM    530  O   GLN A 100     -10.508  30.914  16.454  1.00 17.82           O
ATOM    531  N   ALA A 101      -8.354  31.098  17.151  1.00 18.43           N
ATOM    532  CA  ALA A 101      -7.993  29.776  16.571  1.00 19.03           C
ATOM    533  CB  ALA A 101      -6.532  29.416  16.829  1.00 18.38           C
ATOM    534  C   ALA A 101      -8.910  28.677  17.100  1.00 19.95           C
ATOM    535  O   ALA A 101      -9.378  28.743  18.240  1.00 19.70           O
ATOM    536  N   GLU A 102      -9.163  27.679  16.270  1.00 21.35           N
ATOM    537  CA  GLU A 102     -10.223  26.706  16.541  1.00 24.06           C
ATOM    538  CB  GLU A 102     -10.909  26.274  15.217  1.00 24.23           C
ATOM    539  CG  GLU A 102     -11.592  27.486  14.499  1.00 28.09           C
ATOM    540  CD  GLU A 102     -12.176  27.207  13.096  1.00 29.38           C
ATOM    541  OE1 GLU A 102     -12.110  26.045  12.597  1.00 34.11           O
ATOM    542  OE2 GLU A 102     -12.687  28.187  12.474  1.00 35.33           O
ATOM    543  C   GLU A 102      -9.677  25.532  17.382  1.00 22.08           C
ATOM    544  O   GLU A 102      -9.550  24.374  16.927  1.00 21.15           O
ATOM    545  N   TRP A 103      -9.302  25.868  18.611  1.00 20.64           N
ATOM    546  CA  TRP A 103      -8.725  24.869  19.517  1.00 19.80           C
ATOM    547  CB  TRP A 103      -8.140  25.537  20.754  1.00 18.62           C
ATOM    548  CG  TRP A 103      -6.859  26.271  20.502  1.00 17.84           C
ATOM    549  CD1 TRP A 103      -6.710  27.606  20.300  1.00 16.53           C
ATOM    550  NE1 TRP A 103      -5.348  27.912  20.096  1.00 18.44           N
ATOM    551  CE2 TRP A 103      -4.623  26.748  20.152  1.00 17.82           C
ATOM    552  CD2 TRP A 103      -5.538  25.691  20.433  1.00 17.49           C
ATOM    553  CE3 TRP A 103      -5.048  24.376  20.539  1.00 14.65           C
ATOM    554  CZ3 TRP A 103      -3.671  24.164  20.436  1.00 15.12           C
ATOM    555  CH2 TRP A 103      -2.784  25.238  20.174  1.00 14.40           C
ATOM    556  CZ2 TRP A 103      -3.234  26.535  20.052  1.00 16.66           C
ATOM    557  C   TRP A 103      -9.854  23.959  19.979  1.00 20.77           C
ATOM    558  O   TRP A 103     -10.916  24.435  20.392  1.00 22.05           O
ATOM    559  N   VAL A 104      -9.598  22.665  19.931  1.00 21.72           N
```

FIGURE 3-8 (COORDINATES)

```
ATOM    560  CA  VAL A 104     -10.483  21.648  20.461  1.00 22.76           C
ATOM    561  CB  VAL A 104     -10.570  20.477  19.467  1.00 23.27           C
ATOM    562  CG1 VAL A 104     -11.430  19.321  20.031  1.00 27.19           C
ATOM    563  CG2 VAL A 104     -11.132  20.961  18.110  1.00 25.37           C
ATOM    564  C   VAL A 104      -9.846  21.184  21.778  1.00 22.28           C
ATOM    565  O   VAL A 104      -8.753  20.618  21.773  1.00 20.59           O
ATOM    566  N   VAL A 105     -10.524  21.465  22.885  1.00 21.19           N
ATOM    567  CA  VAL A 105     -10.040  21.128  24.212  1.00 22.42           C
ATOM    568  CB  VAL A 105     -10.345  22.272  25.210  1.00 22.63           C
ATOM    569  CG1 VAL A 105      -9.975  21.877  26.666  1.00 23.28           C
ATOM    570  CG2 VAL A 105      -9.680  23.591  24.766  1.00 20.93           C
ATOM    571  C   VAL A 105     -10.662  19.827  24.699  1.00 23.61           C
ATOM    572  O   VAL A 105     -11.903  19.637  24.606  1.00 24.46           O
ATOM    573  N   GLU A 106      -9.817  18.928  25.199  1.00 23.83           N
ATOM    574  CA  GLU A 106     -10.206  17.617  25.720  1.00 26.16           C
ATOM    575  CB  GLU A 106      -9.594  16.496  24.902  1.00 26.52           C
ATOM    576  CG  GLU A 106     -10.232  16.202  23.565  1.00 30.32           C
ATOM    577  CD  GLU A 106      -9.455  15.127  22.783  1.00 32.64           C
ATOM    578  OE1 GLU A 106     -10.130  14.358  22.048  1.00 41.81           O
ATOM    579  OE2 GLU A 106      -8.179  15.054  22.878  1.00 39.66           O
ATOM    580  C   GLU A 106      -9.618  17.453  27.098  1.00 25.59           C
ATOM    581  O   GLU A 106      -8.508  17.940  27.375  1.00 22.86           O
ATOM    582  N   VAL A 107     -10.336  16.736  27.954  1.00 25.61           N
ATOM    583  CA  VAL A 107      -9.819  16.395  29.281  1.00 26.91           C
ATOM    584  CB  VAL A 107     -10.632  17.061  30.398  1.00 27.09           C
ATOM    585  CG1 VAL A 107     -10.027  16.763  31.714  1.00 27.16           C
ATOM    586  CG2 VAL A 107     -10.607  18.568  30.257  1.00 29.45           C
ATOM    587  C   VAL A 107      -9.778  14.870  29.432  1.00 27.37           C
ATOM    588  O   VAL A 107     -10.800  14.200  29.214  1.00 28.61           O
ATOM    589  N   ASP A 108      -8.583  14.342  29.717  1.00 26.68           N
ATOM    590  CA  ASP A 108      -8.313  12.926  29.932  1.00 25.88           C
ATOM    591  CB  ASP A 108      -6.952  12.552  29.324  1.00 26.64           C
ATOM    592  CG  ASP A 108      -6.467  11.149  29.722  1.00 27.49           C
ATOM    593  OD1 ASP A 108      -7.316  10.253  29.902  1.00 26.85           O
ATOM    594  OD2 ASP A 108      -5.228  10.926  29.829  1.00 27.44           O
ATOM    595  C   ASP A 108      -8.302  12.683  31.442  1.00 25.40           C
ATOM    596  O   ASP A 108      -7.256  12.823  32.079  1.00 24.67           O
ATOM    597  N   THR A 109      -9.482  12.392  32.001  1.00 23.23           N
ATOM    598  CA  THR A 109      -9.655  12.160  33.430  1.00 23.22           C
ATOM    599  CB  THR A 109     -10.971  12.805  33.894  1.00 23.66           C
ATOM    600  OG1 THR A 109     -10.951  14.206  33.565  1.00 25.75           O
ATOM    601  CG2 THR A 109     -11.241  12.598  35.429  1.00 22.33           C
ATOM    602  C   THR A 109      -9.666  10.633  33.718  1.00 23.03           C
ATOM    603  O   THR A 109     -10.338   9.898  33.013  1.00 21.99           O
ATOM    604  N   PHE A 110      -8.959  10.192  34.767  1.00 23.27           N
ATOM    605  CA  PHE A 110      -8.762   8.784  35.112  1.00 24.15           C
ATOM    606  CB  PHE A 110      -7.642   8.147  34.274  1.00 24.18           C
ATOM    607  CG  PHE A 110      -6.298   8.815  34.460  1.00 25.62           C
ATOM    608  CD1 PHE A 110      -5.363   8.315  35.376  1.00 23.65           C
ATOM    609  CE1 PHE A 110      -4.128   8.945  35.565  1.00 25.76           C
ATOM    610  CZ  PHE A 110      -3.819  10.114  34.838  1.00 23.31           C
ATOM    611  CE2 PHE A 110      -4.748  10.610  33.948  1.00 24.89           C
ATOM    612  CD2 PHE A 110      -5.986   9.967  33.761  1.00 24.97           C
ATOM    613  C   PHE A 110      -8.366   8.703  36.590  1.00 25.01           C
ATOM    614  O   PHE A 110      -7.983   9.727  37.206  1.00 23.99           O
ATOM    615  N   LEU A 111      -8.469   7.488  37.147  1.00 24.76           N
ATOM    616  CA  LEU A 111      -8.031   7.202  38.522  1.00 26.07           C
ATOM    617  CB  LEU A 111      -9.081   6.408  39.317  1.00 26.19           C
ATOM    618  CG  LEU A 111     -10.460   7.036  39.442  1.00 27.35           C
ATOM    619  CD1 LEU A 111     -11.420   6.108  40.225  1.00 31.04           C
ATOM    620  CD2 LEU A 111     -10.362   8.411  40.095  1.00 25.51           C
ATOM    621  C   LEU A 111      -6.779   6.385  38.473  1.00 26.47           C
ATOM    622  O   LEU A 111      -6.630   5.491  37.627  1.00 26.58           O
ATOM    623  N   SER A 112      -5.879   6.675  39.402  1.00 26.65           N
ATOM    624  CA  SER A 112      -4.653   5.933  39.471  1.00 27.41           C
ATOM    625  CB  SER A 112      -3.564   6.720  38.767  1.00 27.95           C
ATOM    626  OG  SER A 112      -2.450   5.921  38.561  1.00 29.72           O
ATOM    627  C   SER A 112      -4.290   5.741  40.917  1.00 27.85           C
ATOM    628  O   SER A 112      -4.586   6.601  41.751  1.00 27.60           O
ATOM    629  N   ARG A 113      -3.656   4.612  41.239  1.00 28.25           N
```

FIGURE 3-9 (COORDINATES)

```
ATOM   630  CA   ARG A 113      -3.268   4.374  42.634  1.00 29.71           C
ATOM   631  CB   ARG A 113      -3.102   2.869  42.931  1.00 30.10           C
ATOM   632  CG   ARG A 113      -2.202   2.590  44.121  1.00 31.17           C
ATOM   633  CD   ARG A 113      -2.075   1.124  44.435  1.00 32.88           C
ATOM   634  NE   ARG A 113      -3.194   0.722  45.265  1.00 40.73           N
ATOM   635  CZ   ARG A 113      -3.094   0.466  46.565  1.00 46.47           C
ATOM   636  NH1  ARG A 113      -4.182   0.119  47.246  1.00 49.27           N
ATOM   637  NH2  ARG A 113      -1.907   0.536  47.181  1.00 48.09           N
ATOM   638  C    ARG A 113      -1.994   5.118  42.974  1.00 28.60           C
ATOM   639  O    ARG A 113      -1.002   5.036  42.233  1.00 28.61           O
ATOM   640  N    THR A 114      -2.029   5.837  44.095  1.00 27.37           N
ATOM   641  CA   THR A 114      -0.881   6.568  44.612  1.00 27.14           C
ATOM   642  CB   THR A 114      -1.205   8.078  44.749  1.00 27.04           C
ATOM   643  OG1  THR A 114      -2.010   8.273  45.921  1.00 25.58           O
ATOM   644  CG2  THR A 114      -1.961   8.620  43.522  1.00 25.80           C
ATOM   645  C    THR A 114      -0.571   6.020  46.041  1.00 27.55           C
ATOM   646  O    THR A 114      -1.350   5.232  46.568  1.00 28.62           O
ATOM   647  N    PRO A 115       0.510   6.494  46.687  1.00 27.60           N
ATOM   648  CA   PRO A 115       0.825   6.148  48.091  1.00 27.57           C
ATOM   649  CB   PRO A 115       2.126   6.911  48.353  1.00 27.68           C
ATOM   650  CG   PRO A 115       2.741   7.107  46.989  1.00 26.96           C
ATOM   651  CD   PRO A 115       1.558   7.359  46.100  1.00 27.13           C
ATOM   652  C    PRO A 115      -0.227   6.565  49.125  1.00 28.62           C
ATOM   653  O    PRO A 115      -0.196   6.089  50.262  1.00 28.50           O
ATOM   654  N    TYR A 116      -1.126   7.475  48.745  1.00 28.63           N
ATOM   655  CA   TYR A 116      -2.227   7.895  49.604  1.00 28.06           C
ATOM   656  CB   TYR A 116      -2.392   9.419  49.551  1.00 28.30           C
ATOM   657  CG   TYR A 116      -1.264  10.187  50.209  1.00 29.88           C
ATOM   658  CD1  TYR A 116      -1.264  10.434  51.585  1.00 32.04           C
ATOM   659  CE1  TYR A 116      -0.209  11.140  52.184  1.00 32.56           C
ATOM   660  CZ   TYR A 116       0.844  11.596  51.388  1.00 30.72           C
ATOM   661  OH   TYR A 116       1.904  12.287  51.931  1.00 33.26           O
ATOM   662  CE2  TYR A 116       0.852  11.355  50.039  1.00 27.97           C
ATOM   663  CD2  TYR A 116      -0.190  10.655  49.463  1.00 27.68           C
ATOM   664  C    TYR A 116      -3.538   7.178  49.211  1.00 27.73           C
ATOM   665  O    TYR A 116      -4.610   7.468  49.758  1.00 27.54           O
ATOM   666  N    GLY A 117      -3.443   6.229  48.286  1.00 26.96           N
ATOM   667  CA   GLY A 117      -4.626   5.531  47.779  1.00 26.65           C
ATOM   668  C    GLY A 117      -5.029   6.058  46.399  1.00 26.77           C
ATOM   669  O    GLY A 117      -4.261   6.782  45.764  1.00 26.30           O
ATOM   670  N    TYR A 118      -6.229   5.703  45.927  1.00 26.79           N
ATOM   671  CA   TYR A 118      -6.639   6.044  44.567  1.00 26.42           C
ATOM   672  CB   TYR A 118      -7.793   5.162  44.080  1.00 28.99           C
ATOM   673  CG   TYR A 118      -7.309   3.884  43.402  1.00 31.30           C
ATOM   674  CD1  TYR A 118      -7.130   3.826  42.019  1.00 34.02           C
ATOM   675  CE1  TYR A 118      -6.670   2.651  41.384  1.00 34.36           C
ATOM   676  CZ   TYR A 118      -6.395   1.498  42.146  1.00 35.43           C
ATOM   677  OH   TYR A 118      -5.932   0.335  41.510  1.00 35.25           O
ATOM   678  CE2  TYR A 118      -6.581   1.525  43.524  1.00 34.95           C
ATOM   679  CD2  TYR A 118      -7.027   2.729  44.151  1.00 34.07           C
ATOM   680  C    TYR A 118      -6.952   7.528  44.473  1.00 24.98           C
ATOM   681  O    TYR A 118      -7.568   8.091  45.387  1.00 23.46           O
ATOM   682  N    ARG A 119      -6.465   8.164  43.396  1.00 23.51           N
ATOM   683  CA   ARG A 119      -6.681   9.608  43.166  1.00 22.10           C
ATOM   684  CB   ARG A 119      -5.446  10.458  43.552  1.00 20.83           C
ATOM   685  CG   ARG A 119      -5.021  10.446  45.023  1.00 22.92           C
ATOM   686  CD   ARG A 119      -6.090  11.068  45.916  1.00 21.49           C
ATOM   687  NE   ARG A 119      -5.720  11.164  47.337  1.00 24.12           N
ATOM   688  CZ   ARG A 119      -6.028  10.234  48.243  1.00 26.01           C
ATOM   689  NH1  ARG A 119      -6.680   9.144  47.865  1.00 26.56           N
ATOM   690  NH2  ARG A 119      -5.704  10.394  49.522  1.00 26.93           N
ATOM   691  C    ARG A 119      -7.092   9.877  41.696  1.00 21.83           C
ATOM   692  O    ARG A 119      -6.727   9.115  40.775  1.00 19.77           O
ATOM   693  N    SER A 120      -7.839  10.967  41.499  1.00 21.45           N
ATOM   694  CA   SER A 120      -8.263  11.390  40.170  1.00 22.03           C
ATOM   695  CB   SER A 120      -9.623  12.090  40.207  1.00 22.65           C
ATOM   696  OG   SER A 120     -10.108  12.212  38.887  1.00 26.59           O
ATOM   697  C    SER A 120      -7.236  12.367  39.570  1.00 21.80           C
ATOM   698  O    SER A 120      -6.662  13.225  40.282  1.00 21.32           O
ATOM   699  N    PHE A 121      -7.017  12.205  38.272  1.00 20.25           N
```

FIGURE 3-10 (COORDINATES)

```
ATOM  700  CA   PHE A 121     -6.135  13.048  37.520  1.00 19.83           C
ATOM  701  CB   PHE A 121     -4.870  12.312  37.144  1.00 19.20           C
ATOM  702  CG   PHE A 121     -4.071  11.834  38.323  1.00 17.45           C
ATOM  703  CD1  PHE A 121     -3.060  12.621  38.850  1.00 17.04           C
ATOM  704  CE1  PHE A 121     -2.309  12.181  39.957  1.00 17.50           C
ATOM  705  CZ   PHE A 121     -2.589  10.917  40.525  1.00 18.71           C
ATOM  706  CE2  PHE A 121     -3.606  10.152  40.020  1.00 16.48           C
ATOM  707  CD2  PHE A 121     -4.346  10.587  38.912  1.00 18.92           C
ATOM  708  C    PHE A 121     -6.838  13.465  36.239  1.00 19.16           C
ATOM  709  O    PHE A 121     -7.620  12.678  35.669  1.00 18.61           O
ATOM  710  N    SER A 122     -6.542  14.682  35.781  1.00 17.66           N
ATOM  711  CA   SER A 122     -7.072  15.142  34.475  1.00 17.36           C
ATOM  712  CB   SER A 122     -8.194  16.148  34.696  1.00 17.17           C
ATOM  713  OG   SER A 122     -9.257  15.629  35.499  1.00 21.02           O
ATOM  714  C    SER A 122     -5.987  15.821  33.597  1.00 17.29           C
ATOM  715  O    SER A 122     -5.665  16.986  33.842  1.00 16.75           O
ATOM  716  N    ASN A 123     -5.453  15.138  32.591  1.00 16.86           N
ATOM  717  CA   ASN A 123     -4.641  15.844  31.575  1.00 18.00           C
ATOM  718  CB   ASN A 123     -3.954  14.856  30.608  1.00 17.99           C
ATOM  719  CG   ASN A 123     -3.107  13.827  31.342  1.00 18.32           C
ATOM  720  OD1  ASN A 123     -3.200  12.595  31.111  1.00 21.01           O
ATOM  721  ND2  ASN A 123     -2.287  14.311  32.218  1.00 11.45           N
ATOM  722  C    ASN A 123     -5.525  16.796  30.761  1.00 17.99           C
ATOM  723  O    ASN A 123     -6.686  16.471  30.505  1.00 18.43           O
ATOM  724  N    ILE A 124     -4.988  17.972  30.392  1.00 17.52           N
ATOM  725  CA   ILE A 124     -5.677  18.891  29.448  1.00 16.34           C
ATOM  726  CB   ILE A 124     -5.723  20.371  29.969  1.00 16.07           C
ATOM  727  CG1  ILE A 124     -6.325  20.420  31.376  1.00 14.93           C
ATOM  728  CD1  ILE A 124     -5.897  21.634  32.188  1.00 17.13           C
ATOM  729  CG2  ILE A 124     -6.574  21.253  28.976  1.00 16.82           C
ATOM  730  C    ILE A 124     -4.999  18.832  28.071  1.00 15.98           C
ATOM  731  O    ILE A 124     -3.782  19.006  27.961  1.00 14.86           O
ATOM  732  N    ILE A 125     -5.771  18.503  27.032  1.00 15.14           N
ATOM  733  CA   ILE A 125     -5.225  18.458  25.671  1.00 16.46           C
ATOM  734  CB   ILE A 125     -5.272  17.027  25.021  1.00 16.89           C
ATOM  735  CG1  ILE A 125     -4.622  16.008  25.963  1.00 15.87           C
ATOM  736  CD1  ILE A 125     -5.570  15.345  26.941  1.00 19.26           C
ATOM  737  CG2  ILE A 125     -4.547  16.981  23.622  1.00 14.61           C
ATOM  738  C    ILE A 125     -5.960  19.469  24.815  1.00 17.47           C
ATOM  739  O    ILE A 125     -7.205  19.408  24.670  1.00 17.24           O
ATOM  740  N    SER A 126     -5.193  20.370  24.220  1.00 17.73           N
ATOM  741  CA   SER A 126     -5.727  21.407  23.336  1.00 18.30           C
ATOM  742  CB   SER A 126     -5.251  22.770  23.848  1.00 19.16           C
ATOM  743  OG   SER A 126     -6.092  23.714  23.248  1.00 25.32           O
ATOM  744  C    SER A 126     -5.173  21.170  21.941  1.00 18.24           C
ATOM  745  O    SER A 126     -3.941  21.117  21.763  1.00 16.93           O
ATOM  746  N    THR A 127     -6.048  20.994  20.943  1.00 18.45           N
ATOM  747  CA   THR A 127     -5.580  20.568  19.638  1.00 18.88           C
ATOM  748  CB   THR A 127     -5.949  19.076  19.350  1.00 18.23           C
ATOM  749  OG1  THR A 127     -5.485  18.217  20.391  1.00 18.49           O
ATOM  750  CG2  THR A 127     -5.342  18.620  18.056  1.00 19.97           C
ATOM  751  C    THR A 127     -6.114  21.463  18.529  1.00 19.95           C
ATOM  752  O    THR A 127     -7.348  21.655  18.439  1.00 21.24           O
ATOM  753  N    LEU A 128     -5.218  22.039  17.704  1.00 20.04           N
ATOM  754  CA   LEU A 128     -5.623  22.686  16.444  1.00 20.88           C
ATOM  755  CB   LEU A 128     -4.665  23.815  16.033  1.00 20.75           C
ATOM  756  CG   LEU A 128     -4.813  25.157  16.774  1.00 23.08           C
ATOM  757  CD1  LEU A 128     -3.799  26.188  16.263  1.00 22.08           C
ATOM  758  CD2  LEU A 128     -6.247  25.667  16.602  1.00 23.94           C
ATOM  759  C    LEU A 128     -5.671  21.628  15.332  1.00 21.32           C
ATOM  760  O    LEU A 128     -4.810  20.756  15.279  1.00 21.28           O
ATOM  761  N    ASN A 129     -6.689  21.680  14.465  1.00 22.49           N
ATOM  762  CA   ASN A 129     -6.842  20.679  13.397  1.00 23.32           C
ATOM  763  CB   ASN A 129     -5.841  20.952  12.257  1.00 24.17           C
ATOM  764  CG   ASN A 129     -5.847  22.417  11.807  1.00 26.00           C
ATOM  765  OD1  ASN A 129     -6.567  22.792  10.857  1.00 31.47           O
ATOM  766  ND2  ASN A 129     -5.070  23.251  12.476  1.00 23.13           N
ATOM  767  C    ASN A 129     -6.705  19.233  13.878  1.00 24.08           C
ATOM  768  O    ASN A 129     -5.750  18.513  13.506  1.00 23.30           O
ATOM  769  N    PRO A 130     -7.652  18.782  14.695  1.00 25.03           N
```

FIGURE 3-11 (COORDINATES)

```
ATOM    770  CA  PRO A 130      -7.502  17.418  15.182  1.00 26.84           C
ATOM    771  CB  PRO A 130      -8.702  17.224  16.121  1.00 26.69           C
ATOM    772  CG  PRO A 130      -9.620  18.304  15.849  1.00 26.62           C
ATOM    773  CD  PRO A 130      -8.869  19.434  15.211  1.00 25.81           C
ATOM    774  C   PRO A 130      -7.444  16.348  14.077  1.00 28.00           C
ATOM    775  O   PRO A 130      -6.908  15.278  14.317  1.00 28.07           O
ATOM    776  N   GLU A 131      -7.911  16.679  12.865  1.00 29.09           N
ATOM    777  CA  GLU A 131      -7.883  15.752  11.720  1.00 29.99           C
ATOM    778  CB  GLU A 131      -8.904  16.199  10.635  1.00 30.90           C
ATOM    779  CG  GLU A 131      -8.593  17.516   9.788  1.00 34.08           C
ATOM    780  CD  GLU A 131      -8.656  18.876  10.578  1.00 37.91           C
ATOM    781  OE1 GLU A 131      -8.961  18.845  11.794  1.00 37.10           O
ATOM    782  OE2 GLU A 131      -8.406  19.971   9.966  1.00 37.15           O
ATOM    783  C   GLU A 131      -6.475  15.536  11.132  1.00 29.90           C
ATOM    784  O   GLU A 131      -6.149  14.439  10.644  1.00 30.75           O
ATOM    785  N   ALA A 132      -5.635  16.571  11.180  1.00 28.77           N
ATOM    786  CA  ALA A 132      -4.255  16.477  10.652  1.00 27.58           C
ATOM    787  CB  ALA A 132      -3.494  17.783  10.929  1.00 27.36           C
ATOM    788  C   ALA A 132      -3.466  15.263  11.179  1.00 26.89           C
ATOM    789  O   ALA A 132      -3.483  14.938  12.385  1.00 26.52           O
ATOM    790  N   LYS A 133      -2.775  14.595  10.264  1.00 26.10           N
ATOM    791  CA  LYS A 133      -1.969  13.452  10.590  1.00 26.14           C
ATOM    792  CB  LYS A 133      -1.389  12.813   9.314  1.00 26.29           C
ATOM    793  CG  LYS A 133      -2.451  12.024   8.459  1.00 27.70           C
ATOM    794  CD  LYS A 133      -1.812  11.133   7.383  1.00 28.42           C
ATOM    795  CE  LYS A 133      -0.973  11.944   6.364  1.00 33.05           C
ATOM    796  NZ  LYS A 133      -1.718  13.074   5.676  1.00 37.05           N
ATOM    797  C   LYS A 133      -0.857  13.797  11.606  1.00 25.61           C
ATOM    798  O   LYS A 133      -0.516  12.956  12.446  1.00 25.51           O
ATOM    799  N   ARG A 134      -0.343  15.031  11.537  1.00 24.03           N
ATOM    800  CA  ARG A 134       0.874  15.460  12.274  1.00 23.21           C
ATOM    801  CB  ARG A 134       2.009  15.732  11.298  1.00 22.26           C
ATOM    802  CG  ARG A 134       2.414  14.500  10.489  1.00 23.24           C
ATOM    803  CD  ARG A 134       3.362  14.853   9.314  1.00 24.53           C
ATOM    804  NE  ARG A 134       4.508  15.652   9.739  1.00 26.16           N
ATOM    805  CZ  ARG A 134       5.105  16.574   8.977  1.00 27.29           C
ATOM    806  NH1 ARG A 134       4.657  16.805   7.746  1.00 26.86           N
ATOM    807  NH2 ARG A 134       6.125  17.297   9.443  1.00 22.54           N
ATOM    808  C   ARG A 134       0.643  16.699  13.132  1.00 21.63           C
ATOM    809  O   ARG A 134      -0.045  17.625  12.730  1.00 21.84           O
ATOM    810  N   HIS A 135       1.156  16.663  14.349  1.00 20.53           N
ATOM    811  CA  HIS A 135       1.171  17.841  15.208  1.00 19.34           C
ATOM    812  CB  HIS A 135       0.103  17.756  16.299  1.00 19.45           C
ATOM    813  CG  HIS A 135      -1.300  17.823  15.784  1.00 17.43           C
ATOM    814  ND1 HIS A 135      -1.907  16.778  15.116  1.00 18.39           N
ATOM    815  CE1 HIS A 135      -3.145  17.121  14.799  1.00 19.41           C
ATOM    816  NE2 HIS A 135      -3.350  18.359  15.219  1.00 21.27           N
ATOM    817  CD2 HIS A 135      -2.202  18.822  15.821  1.00 15.51           C
ATOM    818  C   HIS A 135       2.537  18.043  15.870  1.00 18.48           C
ATOM    819  O   HIS A 135       3.184  17.096  16.329  1.00 17.68           O
ATOM    820  N   LEU A 136       2.937  19.304  15.942  1.00 18.30           N
ATOM    821  CA  LEU A 136       4.018  19.705  16.842  1.00 17.33           C
ATOM    822  CB  LEU A 136       4.541  21.083  16.426  1.00 17.08           C
ATOM    823  CG  LEU A 136       5.482  21.786  17.400  1.00 16.40           C
ATOM    824  CD1 LEU A 136       6.785  20.900  17.647  1.00 10.91           C
ATOM    825  CD2 LEU A 136       5.795  23.194  16.832  1.00 17.31           C
ATOM    826  C   LEU A 136       3.312  19.792  18.181  1.00 16.13           C
ATOM    827  O   LEU A 136       2.218  20.318  18.250  1.00 15.83           O
ATOM    828  N   VAL A 137       3.924  19.273  19.234  1.00 15.63           N
ATOM    829  CA  VAL A 137       3.293  19.299  20.559  1.00 15.03           C
ATOM    830  CB  VAL A 137       3.044  17.880  21.092  1.00 15.02           C
ATOM    831  CG1 VAL A 137       2.185  17.926  22.368  1.00 13.71           C
ATOM    832  CG2 VAL A 137       2.419  16.976  20.000  1.00 17.11           C
ATOM    833  C   VAL A 137       4.174  20.078  21.522  1.00 15.20           C
ATOM    834  O   VAL A 137       5.380  19.771  21.653  1.00 16.04           O
ATOM    835  N   LEU A 138       3.591  21.085  22.175  1.00 16.06           N
ATOM    836  CA  LEU A 138       4.227  21.708  23.352  1.00 17.01           C
ATOM    837  CB  LEU A 138       4.187  23.230  23.259  1.00 17.75           C
ATOM    838  CG  LEU A 138       5.269  24.012  22.478  1.00 22.60           C
ATOM    839  CD1 LEU A 138       5.671  23.373  21.129  1.00 21.22           C
```

FIGURE 3-12 (COORDINATES)

```
ATOM    840  CD2 LEU A 138       4.747  25.478  22.275  1.00 21.02           C
ATOM    841  C   LEU A 138       3.548  21.266  24.613  1.00 15.10           C
ATOM    842  O   LEU A 138       2.310  21.066  24.647  1.00 15.43           O
ATOM    843  N   ALA A 139       4.330  21.107  25.682  1.00 14.38           N
ATOM    844  CA  ALA A 139       3.781  20.578  26.922  1.00 12.40           C
ATOM    845  CB  ALA A 139       3.903  19.039  26.922  1.00 11.34           C
ATOM    846  C   ALA A 139       4.406  21.091  28.208  1.00 12.91           C
ATOM    847  O   ALA A 139       5.569  21.484  28.222  1.00 11.88           O
ATOM    848  N   CYS A 140       3.639  20.981  29.303  1.00 12.52           N
ATOM    849  CA  CYS A 140       4.086  21.341  30.668  1.00 14.12           C
ATOM    850  CB  CYS A 140       3.761  22.851  31.024  1.00 13.15           C
ATOM    851  SG  CYS A 140       1.999  23.201  31.219  1.00 17.52           S
ATOM    852  C   CYS A 140       3.303  20.410  31.587  1.00 13.48           C
ATOM    853  O   CYS A 140       2.353  19.723  31.139  1.00 14.34           O
ATOM    854  N   HIS A 141       3.617  20.440  32.883  1.00 14.98           N
ATOM    855  CA  HIS A 141       2.726  19.838  33.882  1.00 13.56           C
ATOM    856  CB  HIS A 141       3.459  18.816  34.818  1.00 14.16           C
ATOM    857  CG  HIS A 141       4.229  19.429  35.967  1.00 13.65           C
ATOM    858  ND1 HIS A 141       5.573  19.745  35.900  1.00 16.48           N
ATOM    859  CE1 HIS A 141       5.973  20.225  37.065  1.00 10.46           C
ATOM    860  NE2 HIS A 141       4.956  20.162  37.901  1.00 14.31           N
ATOM    861  CD2 HIS A 141       3.864  19.663  37.247  1.00 11.84           C
ATOM    862  C   HIS A 141       2.091  20.972  34.669  1.00 14.89           C
ATOM    863  O   HIS A 141       2.792  21.932  35.078  1.00 13.95           O
ATOM    864  N   TYR A 142       0.785  20.869  34.866  1.00 14.03           N
ATOM    865  CA  TYR A 142       0.062  21.920  35.575  1.00 15.49           C
ATOM    866  CB  TYR A 142      -1.230  22.337  34.847  1.00 15.04           C
ATOM    867  CG  TYR A 142      -2.430  21.473  35.065  1.00 15.68           C
ATOM    868  CD1 TYR A 142      -3.354  21.761  36.088  1.00 17.45           C
ATOM    869  CE1 TYR A 142      -4.497  20.973  36.268  1.00 13.53           C
ATOM    870  CZ  TYR A 142      -4.695  19.885  35.456  1.00 14.30           C
ATOM    871  OH  TYR A 142      -5.826  19.113  35.648  1.00 14.98           O
ATOM    872  CE2 TYR A 142      -3.811  19.578  34.423  1.00 13.55           C
ATOM    873  CD2 TYR A 142      -2.680  20.359  34.239  1.00 14.80           C
ATOM    874  C   TYR A 142      -0.183  21.651  37.052  1.00 15.15           C
ATOM    875  O   TYR A 142      -0.628  22.534  37.742  1.00 17.23           O
ATOM    876  N   ASP A 143       0.135  20.450  37.532  1.00 15.46           N
ATOM    877  CA  ASP A 143      -0.032  20.134  38.962  1.00 16.18           C
ATOM    878  CB  ASP A 143      -0.073  18.601  39.178  1.00 15.13           C
ATOM    879  CG  ASP A 143       1.227  17.911  38.778  1.00 18.31           C
ATOM    880  OD1 ASP A 143       1.669  18.071  37.598  1.00 13.56           O
ATOM    881  OD2 ASP A 143       1.788  17.192  39.646  1.00 15.31           O
ATOM    882  C   ASP A 143       1.112  20.765  39.748  1.00 15.98           C
ATOM    883  O   ASP A 143       2.171  21.017  39.190  1.00 16.06           O
ATOM    884  N   SER A 144       0.908  21.072  41.031  1.00 15.23           N
ATOM    885  CA  SER A 144       2.031  21.468  41.858  1.00 15.53           C
ATOM    886  CB  SER A 144       1.794  22.805  42.552  1.00 16.19           C
ATOM    887  OG  SER A 144       0.669  22.703  43.418  1.00 18.15           O
ATOM    888  C   SER A 144       2.227  20.321  42.892  1.00 15.99           C
ATOM    889  O   SER A 144       1.308  19.630  43.221  1.00 15.16           O
ATOM    890  N   LYS A 145       3.449  20.107  43.327  1.00 16.12           N
ATOM    891  CA  LYS A 145       3.785  18.994  44.177  1.00 16.67           C
ATOM    892  CB  LYS A 145       5.321  18.969  44.299  1.00 16.03           C
ATOM    893  CG  LYS A 145       5.894  17.899  45.229  1.00 18.41           C
ATOM    894  CD  LYS A 145       7.424  17.704  45.063  1.00 17.59           C
ATOM    895  CE  LYS A 145       7.973  16.658  46.075  1.00 17.86           C
ATOM    896  NZ  LYS A 145       7.348  15.336  45.831  1.00 17.51           N
ATOM    897  C   LYS A 145       3.093  19.133  45.549  1.00 16.85           C
ATOM    898  O   LYS A 145       3.021  20.230  46.115  1.00 16.66           O
ATOM    899  N   TYR A 146       2.585  18.024  46.077  1.00 18.05           N
ATOM    900  CA  TYR A 146       2.014  18.029  47.413  1.00 19.15           C
ATOM    901  CB  TYR A 146       1.084  16.826  47.640  1.00 20.02           C
ATOM    902  CG  TYR A 146       0.685  16.687  49.111  1.00 21.23           C
ATOM    903  CD1 TYR A 146      -0.308  17.505  49.663  1.00 19.78           C
ATOM    904  CE1 TYR A 146      -0.677  17.387  50.990  1.00 19.68           C
ATOM    905  CZ  TYR A 146      -0.008  16.492  51.793  1.00 21.27           C
ATOM    906  OH  TYR A 146      -0.353  16.387  53.126  1.00 22.11           O
ATOM    907  CE2 TYR A 146       0.999  15.681  51.281  1.00 19.16           C
ATOM    908  CD2 TYR A 146       1.344  15.791  49.955  1.00 22.41           C
ATOM    909  C   TYR A 146       3.102  18.126  48.502  1.00 18.93           C
```

FIGURE 3-13 (COORDINATES)

```
ATOM   910  O    TYR A 146       4.083  17.397  48.495  1.00 19.66           O
ATOM   911  N    PHE A 147       2.941  19.088  49.397  1.00 19.89           N
ATOM   912  CA   PHE A 147       3.654  19.141  50.657  1.00 20.91           C
ATOM   913  CB   PHE A 147       4.630  20.317  50.650  1.00 21.45           C
ATOM   914  CG   PHE A 147       5.796  20.109  49.726  1.00 22.62           C
ATOM   915  CD1  PHE A 147       6.898  19.367  50.145  1.00 23.07           C
ATOM   916  CE1  PHE A 147       7.976  19.161  49.294  1.00 26.30           C
ATOM   917  CZ   PHE A 147       7.952  19.683  47.999  1.00 23.67           C
ATOM   918  CE2  PHE A 147       6.824  20.396  47.542  1.00 22.15           C
ATOM   919  CD2  PHE A 147       5.754  20.591  48.416  1.00 23.06           C
ATOM   920  C    PHE A 147       2.667  19.281  51.818  1.00 21.97           C
ATOM   921  O    PHE A 147       1.659  19.983  51.705  1.00 22.33           O
ATOM   922  N    PRO A 148       2.925  18.585  52.926  1.00 23.88           N
ATOM   923  CA   PRO A 148       2.005  18.729  54.066  1.00 24.98           C
ATOM   924  CB   PRO A 148       2.690  17.916  55.188  1.00 25.58           C
ATOM   925  CG   PRO A 148       3.513  16.925  54.500  1.00 26.18           C
ATOM   926  CD   PRO A 148       3.976  17.582  53.188  1.00 24.31           C
ATOM   927  C    PRO A 148       1.784  20.167  54.491  1.00 25.43           C
ATOM   928  O    PRO A 148       2.744  20.943  54.529  1.00 25.74           O
ATOM   929  N    ARG A 149       0.532  20.523  54.806  1.00 26.16           N
ATOM   930  CA   ARG A 149       0.187  21.875  55.302  1.00 26.53           C
ATOM   931  CB   ARG A 149      -1.319  22.174  55.123  1.00 26.28           C
ATOM   932  CG   ARG A 149      -1.704  23.677  55.161  1.00 25.91           C
ATOM   933  CD   ARG A 149      -0.956  24.529  54.100  1.00 26.18           C
ATOM   934  NE   ARG A 149      -1.234  25.972  54.227  1.00 27.46           N
ATOM   935  CZ   ARG A 149      -2.284  26.575  53.660  1.00 29.40           C
ATOM   936  NH1  ARG A 149      -2.491  27.891  53.817  1.00 26.74           N
ATOM   937  NH2  ARG A 149      -3.128  25.861  52.924  1.00 29.59           N
ATOM   938  C    ARG A 149       0.551  22.026  56.794  1.00 27.66           C
ATOM   939  O    ARG A 149      -0.304  21.751  57.675  1.00 26.06           O
ATOM   940  N    TRP A 150       1.800  22.435  57.061  1.00 27.59           N
ATOM   941  CA   TRP A 150       2.284  22.680  58.431  1.00 29.38           C
ATOM   942  CB   TRP A 150       3.776  22.296  58.574  1.00 29.14           C
ATOM   943  CG   TRP A 150       4.721  22.714  58.204  0.00 39.35           C
ATOM   944  CD1  TRP A 150       5.207  22.524  56.924  0.00 43.35           C
ATOM   945  NE1  TRP A 150       6.340  23.309  56.717  0.00 44.28           N
ATOM   946  CE2  TRP A 150       6.608  24.012  57.869  0.00 42.94           C
ATOM   947  CD2  TRP A 150       5.613  23.660  58.834  0.00 41.96           C
ATOM   948  CE3  TRP A 150       5.653  24.265  60.112  0.00 41.94           C
ATOM   949  CZ3  TRP A 150       6.673  25.189  60.390  0.00 42.49           C
ATOM   950  CH2  TRP A 150       7.659  25.525  59.405  0.00 42.06           C
ATOM   951  CZ2  TRP A 150       7.639  24.949  58.146  0.00 42.62           C
ATOM   952  C    TRP A 150       2.102  24.133  58.884  1.00 30.35           C
ATOM   953  O    TRP A 150       1.950  24.391  60.085  1.00 30.66           O
ATOM   954  N    ASP A 151       2.154  25.083  57.945  1.00 30.63           N
ATOM   955  CA   ASP A 151       2.088  26.527  58.304  1.00 31.36           C
ATOM   956  CB   ASP A 151       3.501  27.121  58.571  1.00 32.18           C
ATOM   957  CG   ASP A 151       4.410  27.140  57.313  1.00 36.58           C
ATOM   958  OD1  ASP A 151       3.920  27.130  56.165  1.00 36.64           O
ATOM   959  OD2  ASP A 151       5.645  27.181  57.485  1.00 41.65           O
ATOM   960  C    ASP A 151       1.291  27.313  57.258  1.00 30.05           C
ATOM   961  O    ASP A 151       0.600  26.694  56.442  1.00 30.10           O
ATOM   962  N    SER A 152       1.346  28.642  57.291  1.00 29.13           N
ATOM   963  CA   SER A 152       0.559  29.452  56.374  1.00 29.70           C
ATOM   964  CB   SER A 152       0.644  30.942  56.690  1.00 30.04           C
ATOM   965  OG   SER A 152       1.989  31.387  56.667  1.00 34.15           O
ATOM   966  C    SER A 152       0.933  29.276  54.913  1.00 28.90           C
ATOM   967  O    SER A 152       0.078  29.407  54.033  1.00 27.62           O
ATOM   968  N    ARG A 153       2.210  29.001  54.676  1.00 28.40           N
ATOM   969  CA   ARG A 153       2.756  28.960  53.313  1.00 28.85           C
ATOM   970  CB   ARG A 153       4.273  29.075  53.362  1.00 29.15           C
ATOM   971  CG   ARG A 153       4.759  30.443  53.779  1.00 32.77           C
ATOM   972  CD   ARG A 153       6.280  30.481  53.728  1.00 39.79           C
ATOM   973  NE   ARG A 153       6.844  29.455  54.618  1.00 46.78           N
ATOM   974  CZ   ARG A 153       8.093  28.981  54.538  1.00 49.22           C
ATOM   975  NH1  ARG A 153       8.936  29.420  53.588  1.00 49.99           N
ATOM   976  NH2  ARG A 153       8.498  28.058  55.410  1.00 49.16           N
ATOM   977  C    ARG A 153       2.372  27.703  52.569  1.00 26.90           C
ATOM   978  O    ARG A 153       2.172  26.656  53.178  1.00 27.30           O
ATOM   979  N    VAL A 154       2.264  27.831  51.248  1.00 26.17           N
```

FIGURE 3-14 (COORDINATES)

```
ATOM    980  CA  VAL A 154      2.004  26.724  50.352  1.00 24.09           C
ATOM    981  CB  VAL A 154      0.537  26.718  49.774  1.00 24.20           C
ATOM    982  CG1 VAL A 154     -0.431  26.196  50.831  1.00 25.05           C
ATOM    983  CG2 VAL A 154      0.132  28.075  49.248  1.00 25.74           C
ATOM    984  C   VAL A 154      2.982  26.698  49.199  1.00 23.34           C
ATOM    985  O   VAL A 154      3.510  27.733  48.790  1.00 22.43           O
ATOM    986  N   PHE A 155      3.244  25.499  48.691  1.00 21.69           N
ATOM    987  CA  PHE A 155      4.098  25.366  47.530  1.00 20.36           C
ATOM    988  CB  PHE A 155      4.707  23.980  47.474  1.00 20.08           C
ATOM    989  CG  PHE A 155      5.568  23.762  46.287  1.00 19.80           C
ATOM    990  CD1 PHE A 155      6.830  24.317  46.220  1.00 16.08           C
ATOM    991  CE1 PHE A 155      7.630  24.117  45.106  1.00 16.85           C
ATOM    992  CZ  PHE A 155      7.186  23.337  44.078  1.00 16.79           C
ATOM    993  CE2 PHE A 155      5.919  22.780  44.141  1.00 20.35           C
ATOM    994  CD2 PHE A 155      5.117  22.999  45.223  1.00 18.00           C
ATOM    995  C   PHE A 155      3.264  25.628  46.287  1.00 19.72           C
ATOM    996  O   PHE A 155      2.230  24.991  46.075  1.00 19.64           O
ATOM    997  N   VAL A 156      3.704  26.584  45.479  1.00 19.14           N
ATOM    998  CA  VAL A 156      2.984  26.918  44.249  1.00 17.31           C
ATOM    999  CB  VAL A 156      2.482  28.410  44.218  1.00 16.11           C
ATOM   1000  CG1 VAL A 156      1.582  28.710  45.450  1.00 14.88           C
ATOM   1001  CG2 VAL A 156      3.643  29.396  44.181  1.00 13.75           C
ATOM   1002  C   VAL A 156      3.774  26.601  42.983  1.00 17.44           C
ATOM   1003  O   VAL A 156      3.262  26.814  41.902  1.00 18.13           O
ATOM   1004  N   GLY A 157      5.000  26.091  43.116  1.00 17.51           N
ATOM   1005  CA  GLY A 157      5.806  25.724  41.952  1.00 15.23           C
ATOM   1006  C   GLY A 157      5.752  26.752  40.835  1.00 14.91           C
ATOM   1007  O   GLY A 157      5.296  26.453  39.717  1.00 15.15           O
ATOM   1008  N   ALA A 158      6.214  27.968  41.086  1.00 14.66           N
ATOM   1009  CA  ALA A 158      6.197  28.947  40.006  1.00 14.11           C
ATOM   1010  CB  ALA A 158      6.629  30.309  40.521  1.00 14.06           C
ATOM   1011  C   ALA A 158      7.022  28.525  38.770  1.00 14.19           C
ATOM   1012  O   ALA A 158      6.560  28.685  37.628  1.00 13.29           O
ATOM   1013  N   THR A 159      8.264  28.075  38.958  1.00 13.67           N
ATOM   1014  CA  THR A 159      9.075  27.572  37.788  1.00 14.23           C
ATOM   1015  CB  THR A 159     10.620  27.527  38.096  1.00 15.14           C
ATOM   1016  OG1 THR A 159     10.850  26.555  39.110  1.00 15.06           O
ATOM   1017  CG2 THR A 159     11.153  28.848  38.560  1.00 13.68           C
ATOM   1018  C   THR A 159      8.667  26.147  37.397  1.00 14.28           C
ATOM   1019  O   THR A 159      8.989  25.651  36.305  1.00 14.68           O
ATOM   1020  N   ASP A 160      7.905  25.513  38.285  1.00 14.56           N
ATOM   1021  CA  ASP A 160      7.671  24.056  38.282  1.00 14.76           C
ATOM   1022  CB  ASP A 160      8.545  23.483  39.408  1.00 13.61           C
ATOM   1023  CG  ASP A 160      8.598  21.941  39.460  1.00 13.98           C
ATOM   1024  OD1 ASP A 160      8.189  21.233  38.541  1.00 13.21           O
ATOM   1025  OD2 ASP A 160      9.072  21.414  40.494  1.00 14.15           O
ATOM   1026  C   ASP A 160      6.183  23.708  38.512  1.00 14.55           C
ATOM   1027  O   ASP A 160      5.842  23.160  39.552  1.00 15.48           O
ATOM   1028  N   SER A 161      5.290  23.968  37.552  1.00 14.44           N
ATOM   1029  CA  SER A 161      5.597  24.549  36.259  1.00 14.14           C
ATOM   1030  CB  SER A 161      5.607  23.470  35.161  1.00 13.55           C
ATOM   1031  OG  SER A 161      6.861  22.832  35.152  1.00 17.19           O
ATOM   1032  C   SER A 161      4.567  25.588  35.879  1.00 13.45           C
ATOM   1033  O   SER A 161      4.098  25.575  34.748  1.00 13.01           O
ATOM   1034  N   ALA A 162      4.201  26.497  36.799  1.00 14.03           N
ATOM   1035  CA  ALA A 162      3.192  27.518  36.462  1.00 14.09           C
ATOM   1036  CB  ALA A 162      2.886  28.429  37.714  1.00 14.81           C
ATOM   1037  C   ALA A 162      3.691  28.386  35.294  1.00 13.82           C
ATOM   1038  O   ALA A 162      2.932  28.760  34.372  1.00 13.49           O
ATOM   1039  N   VAL A 163      4.976  28.731  35.323  1.00 12.55           N
ATOM   1040  CA  VAL A 163      5.561  29.546  34.246  1.00 11.99           C
ATOM   1041  CB  VAL A 163      6.956  30.072  34.649  1.00 12.44           C
ATOM   1042  CG1 VAL A 163      7.731  30.597  33.417  1.00 10.58           C
ATOM   1043  CG2 VAL A 163      6.812  31.190  35.691  1.00 10.79           C
ATOM   1044  C   VAL A 163      5.547  28.847  32.852  1.00 12.13           C
ATOM   1045  O   VAL A 163      4.964  29.428  31.886  1.00 13.00           O
ATOM   1046  N   PRO A 164      6.150  27.611  32.735  1.00 12.38           N
ATOM   1047  CA  PRO A 164      5.967  26.790  31.528  1.00 11.80           C
ATOM   1048  CB  PRO A 164      6.389  25.417  31.995  1.00 11.50           C
ATOM   1049  CG  PRO A 164      7.652  25.766  32.839  1.00 11.66           C
```

FIGURE 3-15 (COORDINATES)

```
ATOM   1050  CD   PRO A 164       7.107  26.928  33.654  1.00 12.29           C
ATOM   1051  C    PRO A 164       4.537  26.808  30.969  1.00 13.02           C
ATOM   1052  O    PRO A 164       4.370  26.975  29.767  1.00 12.54           O
ATOM   1053  N    CYS A 165       3.541  26.615  31.824  1.00 12.63           N
ATOM   1054  CA   CYS A 165       2.150  26.550  31.385  1.00 13.18           C
ATOM   1055  CB   CYS A 165       1.251  26.056  32.537  1.00 14.82           C
ATOM   1056  SG   CYS A 165       1.575  24.282  32.979  1.00 20.97           S
ATOM   1057  C    CYS A 165       1.704  27.931  30.913  1.00 12.88           C
ATOM   1058  O    CYS A 165       1.049  28.040  29.901  1.00 13.00           O
ATOM   1059  N    ALA A 166       2.029  28.987  31.669  1.00 12.77           N
ATOM   1060  CA   ALA A 166       1.619  30.326  31.275  1.00 13.61           C
ATOM   1061  CB   ALA A 166       1.907  31.299  32.409  1.00 12.78           C
ATOM   1062  C    ALA A 166       2.268  30.763  29.942  1.00 12.84           C
ATOM   1063  O    ALA A 166       1.674  31.484  29.132  1.00 13.06           O
ATOM   1064  N    MET A 167       3.491  30.302  29.713  1.00 13.54           N
ATOM   1065  CA   MET A 167       4.212  30.558  28.482  1.00 13.63           C
ATOM   1066  CB   MET A 167       5.650  29.995  28.558  1.00 13.48           C
ATOM   1067  CG   MET A 167       6.534  30.722  29.554  1.00 14.51           C
ATOM   1068  SD   MET A 167       8.205  29.955  29.747  1.00 14.81           S
ATOM   1069  CE   MET A 167       8.864  30.157  28.117  1.00 13.17           C
ATOM   1070  C    MET A 167       3.487  29.929  27.313  1.00 14.97           C
ATOM   1071  O    MET A 167       3.366  30.571  26.259  1.00 14.66           O
ATOM   1072  N    MET A 168       3.022  28.659  27.472  1.00 14.45           N
ATOM   1073  CA   MET A 168       2.173  28.027  26.441  1.00 14.92           C
ATOM   1074  CB   MET A 168       1.809  26.580  26.812  1.00 15.62           C
ATOM   1075  CG   MET A 168       3.050  25.652  26.725  1.00 16.14           C
ATOM   1076  SD   MET A 168       2.906  24.138  27.734  1.00 16.78           S
ATOM   1077  CE   MET A 168       1.392  23.402  27.037  1.00 12.61           C
ATOM   1078  C    MET A 168       0.887  28.784  26.149  1.00 14.37           C
ATOM   1079  O    MET A 168       0.521  28.911  24.983  1.00 14.35           O
ATOM   1080  N    LEU A 169       0.204  29.274  27.197  1.00 13.43           N
ATOM   1081  CA   LEU A 169      -1.026  30.039  27.018  1.00 13.57           C
ATOM   1082  CB   LEU A 169      -1.685  30.315  28.389  1.00 11.66           C
ATOM   1083  CG   LEU A 169      -2.189  29.049  29.141  1.00 12.52           C
ATOM   1084  CD1  LEU A 169      -2.586  29.346  30.566  1.00 11.57           C
ATOM   1085  CD2  LEU A 169      -3.398  28.407  28.358  1.00 12.64           C
ATOM   1086  C    LEU A 169      -0.722  31.370  26.301  1.00 14.11           C
ATOM   1087  O    LEU A 169      -1.480  31.811  25.407  1.00 14.71           O
ATOM   1088  N    GLU A 170       0.376  32.008  26.709  1.00 13.68           N
ATOM   1089  CA   GLU A 170       0.846  33.247  26.064  1.00 14.95           C
ATOM   1090  CB   GLU A 170       2.034  33.843  26.871  1.00 13.83           C
ATOM   1091  CG   GLU A 170       2.768  35.105  26.280  1.00 15.16           C
ATOM   1092  CD   GLU A 170       1.870  36.256  25.755  1.00 17.71           C
ATOM   1093  OE1  GLU A 170       0.711  36.484  26.211  1.00 13.82           O
ATOM   1094  OE2  GLU A 170       2.393  37.010  24.902  1.00 18.08           O
ATOM   1095  C    GLU A 170       1.194  33.034  24.589  1.00 13.91           C
ATOM   1096  O    GLU A 170       0.920  33.882  23.724  1.00 15.75           O
ATOM   1097  N    LEU A 171       1.830  31.913  24.287  1.00 15.30           N
ATOM   1098  CA   LEU A 171       2.150  31.580  22.909  1.00 14.78           C
ATOM   1099  CB   LEU A 171       2.939  30.271  22.855  1.00 15.14           C
ATOM   1100  CG   LEU A 171       3.327  29.781  21.438  1.00 16.30           C
ATOM   1101  CD1  LEU A 171       4.724  29.161  21.463  1.00 16.48           C
ATOM   1102  CD2  LEU A 171       2.270  28.850  20.829  1.00 14.86           C
ATOM   1103  C    LEU A 171       0.871  31.445  22.056  1.00 16.07           C
ATOM   1104  O    LEU A 171       0.799  31.957  20.918  1.00 15.96           O
ATOM   1105  N    ALA A 172      -0.083  30.677  22.558  1.00 14.81           N
ATOM   1106  CA   ALA A 172      -1.367  30.516  21.871  1.00 15.32           C
ATOM   1107  CB   ALA A 172      -2.296  29.553  22.669  1.00 15.10           C
ATOM   1108  C    ALA A 172      -2.044  31.861  21.627  1.00 14.63           C
ATOM   1109  O    ALA A 172      -2.535  32.084  20.534  1.00 15.98           O
ATOM   1110  N    ARG A 173      -1.991  32.775  22.602  1.00 15.13           N
ATOM   1111  CA   ARG A 173      -2.546  34.124  22.467  1.00 15.51           C
ATOM   1112  CB   ARG A 173      -2.644  34.819  23.841  1.00 15.45           C
ATOM   1113  CG   ARG A 173      -3.323  36.231  23.782  1.00 14.52           C
ATOM   1114  CD   ARG A 173      -2.794  37.194  24.862  1.00 16.88           C
ATOM   1115  NE   ARG A 173      -1.387  37.543  24.629  1.00 17.20           N
ATOM   1116  CZ   ARG A 173      -0.960  38.431  23.733  1.00 23.51           C
ATOM   1117  NH1  ARG A 173      -1.839  39.098  22.971  1.00 21.96           N
ATOM   1118  NH2  ARG A 173       0.347  38.656  23.598  1.00 22.24           N
ATOM   1119  C    ARG A 173      -1.742  35.030  21.502  1.00 17.14           C
```

FIGURE 3-16 (COORDINATES)

```
ATOM   1120  O    ARG A 173      -2.307  35.685  20.610  1.00 17.02           O
ATOM   1121  N    ALA A 174      -0.430  35.110  21.713  1.00 16.13           N
ATOM   1122  CA   ALA A 174       0.436  35.892  20.841  1.00 16.04           C
ATOM   1123  CB   ALA A 174       1.894  35.833  21.353  1.00 14.71           C
ATOM   1124  C    ALA A 174       0.352  35.454  19.384  1.00 16.31           C
ATOM   1125  O    ALA A 174       0.339  36.311  18.463  1.00 18.70           O
ATOM   1126  N    LEU A 175       0.288  34.149  19.141  1.00 15.28           N
ATOM   1127  CA   LEU A 175       0.293  33.640  17.765  1.00 15.65           C
ATOM   1128  CB   LEU A 175       1.153  32.378  17.662  1.00 15.54           C
ATOM   1129  CG   LEU A 175       2.562  32.457  18.231  1.00 16.42           C
ATOM   1130  CD1  LEU A 175       3.287  31.173  17.886  1.00 14.82           C
ATOM   1131  CD2  LEU A 175       3.277  33.727  17.698  1.00 17.84           C
ATOM   1132  C    LEU A 175      -1.085  33.349  17.174  1.00 16.04           C
ATOM   1133  O    LEU A 175      -1.176  32.686  16.130  1.00 15.87           O
ATOM   1134  N    ASP A 176      -2.126  33.814  17.852  1.00 15.44           N
ATOM   1135  CA   ASP A 176      -3.510  33.362  17.610  1.00 17.34           C
ATOM   1136  CB   ASP A 176      -4.463  34.091  18.569  1.00 16.32           C
ATOM   1137  CG   ASP A 176      -5.936  33.604  18.452  1.00 17.25           C
ATOM   1138  OD1  ASP A 176      -6.181  32.409  18.258  1.00 15.27           O
ATOM   1139  OD2  ASP A 176      -6.847  34.435  18.607  1.00 16.98           O
ATOM   1140  C    ASP A 176      -3.916  33.632  16.163  1.00 18.45           C
ATOM   1141  O    ASP A 176      -4.512  32.765  15.516  1.00 18.68           O
ATOM   1142  N    LYS A 177      -3.584  34.825  15.673  1.00 19.11           N
ATOM   1143  CA   LYS A 177      -3.982  35.193  14.303  1.00 20.35           C
ATOM   1144  CB   LYS A 177      -3.712  36.681  14.022  1.00 21.99           C
ATOM   1145  CG   LYS A 177      -3.962  37.044  12.559  1.00 25.80           C
ATOM   1146  CD   LYS A 177      -3.594  38.471  12.223  1.00 30.02           C
ATOM   1147  CE   LYS A 177      -3.773  38.691  10.691  1.00 34.30           C
ATOM   1148  NZ   LYS A 177      -2.840  39.761  10.136  1.00 36.35           N
ATOM   1149  C    LYS A 177      -3.330  34.274  13.272  1.00 19.79           C
ATOM   1150  O    LYS A 177      -4.008  33.740  12.394  1.00 19.69           O
ATOM   1151  N    LYS A 178      -2.026  34.032  13.397  1.00 19.63           N
ATOM   1152  CA   LYS A 178      -1.361  33.109  12.494  1.00 20.44           C
ATOM   1153  CB   LYS A 178       0.171  33.220  12.627  1.00 21.07           C
ATOM   1154  CG   LYS A 178       0.680  34.514  12.009  1.00 23.70           C
ATOM   1155  CD   LYS A 178       2.162  34.669  12.209  1.00 28.44           C
ATOM   1156  CE   LYS A 178       2.685  36.008  11.644  1.00 31.48           C
ATOM   1157  NZ   LYS A 178       3.916  36.418  12.419  1.00 35.89           N
ATOM   1158  C    LYS A 178      -1.792  31.672  12.697  1.00 20.07           C
ATOM   1159  O    LYS A 178      -1.946  30.935  11.726  1.00 21.47           O
ATOM   1160  N    LEU A 179      -1.991  31.248  13.938  1.00 20.21           N
ATOM   1161  CA   LEU A 179      -2.464  29.861  14.162  1.00 20.43           C
ATOM   1162  CB   LEU A 179      -2.428  29.493  15.655  1.00 20.07           C
ATOM   1163  CG   LEU A 179      -1.018  29.427  16.285  1.00 20.31           C
ATOM   1164  CD1  LEU A 179      -1.106  29.255  17.816  1.00 16.67           C
ATOM   1165  CD2  LEU A 179      -0.269  28.318  15.601  1.00 22.17           C
ATOM   1166  C    LEU A 179      -3.880  29.673  13.618  1.00 21.84           C
ATOM   1167  O    LEU A 179      -4.226  28.594  13.113  1.00 20.97           O
ATOM   1168  N    HIS A 180      -4.702  30.718  13.747  1.00 23.16           N
ATOM   1169  CA   HIS A 180      -6.090  30.658  13.249  1.00 25.49           C
ATOM   1170  CB   HIS A 180      -6.826  31.960  13.628  1.00 25.48           C
ATOM   1171  CG   HIS A 180      -8.297  31.977  13.310  1.00 29.40           C
ATOM   1172  ND1  HIS A 180      -9.028  30.843  13.001  1.00 32.72           N
ATOM   1173  CE1  HIS A 180     -10.292  31.174  12.796  1.00 28.91           C
ATOM   1174  NE2  HIS A 180     -10.411  32.477  12.973  1.00 32.98           N
ATOM   1175  CD2  HIS A 180      -9.179  33.004  13.294  1.00 28.76           C
ATOM   1176  C    HIS A 180      -6.079  30.337  11.738  1.00 26.57           C
ATOM   1177  O    HIS A 180      -6.941  29.578  11.222  1.00 27.18           O
ATOM   1178  N    SER A 181      -5.063  30.837  11.039  1.00 27.00           N
ATOM   1179  CA   SER A 181      -4.985  30.647   9.591  1.00 28.82           C
ATOM   1180  CB   SER A 181      -3.918  31.568   8.988  1.00 28.15           C
ATOM   1181  OG   SER A 181      -2.627  31.084   9.258  1.00 26.71           O
ATOM   1182  C    SER A 181      -4.783  29.172   9.170  1.00 30.59           C
ATOM   1183  O    SER A 181      -5.101  28.801   8.036  1.00 31.08           O
ATOM   1184  N    LEU A 182      -4.284  28.338  10.083  1.00 31.63           N
ATOM   1185  CA   LEU A 182      -4.206  26.892   9.868  1.00 34.42           C
ATOM   1186  CB   LEU A 182      -3.474  26.213  11.036  1.00 33.71           C
ATOM   1187  CG   LEU A 182      -1.973  26.448  11.240  1.00 31.95           C
ATOM   1188  CD1  LEU A 182      -1.540  26.031  12.659  1.00 28.99           C
ATOM   1189  CD2  LEU A 182      -1.145  25.723  10.196  1.00 32.50           C
```

FIGURE 3-17 (COORDINATES)

```
ATOM   1190  C   LEU A 182      -5.573  26.199   9.681  1.00 36.87           C
ATOM   1191  O   LEU A 182      -5.620  24.998   9.419  1.00 37.85           O
ATOM   1192  N   LYS A 183      -6.678  26.924   9.837  1.00 39.31           N
ATOM   1193  CA  LYS A 183      -7.997  26.345   9.569  1.00 42.71           C
ATOM   1194  CB  LYS A 183      -9.130  27.252  10.087  1.00 42.15           C
ATOM   1195  CG  LYS A 183      -9.452  28.419   9.174  1.00 42.85           C
ATOM   1196  CD  LYS A 183     -10.304  29.489   9.875  1.00 43.17           C
ATOM   1197  CE  LYS A 183     -10.531  30.660   9.544  0.00 47.29           C
ATOM   1198  NZ  LYS A 183     -10.976  30.626   8.125  0.00 46.20           N
ATOM   1199  C   LYS A 183      -8.178  26.029   8.078  1.00 44.41           C
ATOM   1200  O   LYS A 183      -9.119  25.327   7.704  1.00 45.39           O
ATOM   1201  N   ASP A 184      -7.264  26.537   7.244  1.00 46.86           N
ATOM   1202  CA  ASP A 184      -7.322  26.376   5.781  1.00 48.37           C
ATOM   1203  CB  ASP A 184      -6.940  27.686   5.068  1.00 49.15           C
ATOM   1204  CG  ASP A 184      -7.733  28.914   5.586  1.00 51.52           C
ATOM   1205  OD1 ASP A 184      -8.979  28.829   5.763  1.00 53.31           O
ATOM   1206  OD2 ASP A 184      -7.098  29.976   5.807  1.00 53.68           O
ATOM   1207  C   ASP A 184      -6.447  25.223   5.283  1.00 49.00           C
ATOM   1208  O   ASP A 184      -6.761  24.566   4.267  1.00 49.83           O
ATOM   1209  N   PRO A 190       2.650  20.730   4.623  1.00 37.83           N
ATOM   1210  CA  PRO A 190       2.384  19.432   5.263  1.00 36.63           C
ATOM   1211  CB  PRO A 190       3.524  19.304   6.299  1.00 36.64           C
ATOM   1212  CG  PRO A 190       4.081  20.690   6.457  1.00 36.98           C
ATOM   1213  CD  PRO A 190       3.920  21.311   5.097  1.00 37.98           C
ATOM   1214  C   PRO A 190       1.017  19.417   5.957  1.00 35.97           C
ATOM   1215  O   PRO A 190       0.453  20.491   6.231  1.00 36.08           O
ATOM   1216  N   ASP A 191       0.496  18.205   6.208  1.00 33.39           N
ATOM   1217  CA  ASP A 191      -0.743  17.978   6.942  1.00 31.24           C
ATOM   1218  CB  ASP A 191      -1.218  16.558   6.629  1.00 32.30           C
ATOM   1219  CG  ASP A 191      -2.594  16.262   7.164  1.00 34.55           C
ATOM   1220  OD1 ASP A 191      -3.332  17.224   7.483  1.00 40.28           O
ATOM   1221  OD2 ASP A 191      -2.939  15.070   7.270  1.00 33.32           O
ATOM   1222  C   ASP A 191      -0.397  18.125   8.452  1.00 28.13           C
ATOM   1223  O   ASP A 191      -0.268  17.140   9.161  1.00 26.79           O
ATOM   1224  N   LEU A 192      -0.198  19.357   8.902  1.00 25.04           N
ATOM   1225  CA  LEU A 192       0.571  19.577  10.146  1.00 23.34           C
ATOM   1226  CB  LEU A 192       2.079  19.765   9.850  1.00 23.04           C
ATOM   1227  CG  LEU A 192       3.014  20.311  10.958  1.00 23.35           C
ATOM   1228  CD1 LEU A 192       3.311  19.226  12.014  1.00 17.39           C
ATOM   1229  CD2 LEU A 192       4.296  20.836  10.370  1.00 22.13           C
ATOM   1230  C   LEU A 192       0.038  20.759  10.895  1.00 22.09           C
ATOM   1231  O   LEU A 192      -0.155  21.855  10.331  1.00 21.97           O
ATOM   1232  N   SER A 193      -0.166  20.554  12.196  1.00 19.87           N
ATOM   1233  CA  SER A 193      -0.665  21.632  13.047  1.00 17.77           C
ATOM   1234  CB  SER A 193      -2.193  21.640  13.053  1.00 16.46           C
ATOM   1235  OG  SER A 193      -2.704  22.893  13.511  1.00 15.61           O
ATOM   1236  C   SER A 193      -0.061  21.517  14.462  1.00 17.01           C
ATOM   1237  O   SER A 193       0.967  20.863  14.651  1.00 15.69           O
ATOM   1238  N   LEU A 194      -0.683  22.207  15.412  1.00 16.21           N
ATOM   1239  CA  LEU A 194      -0.135  22.368  16.762  1.00 14.62           C
ATOM   1240  CB  LEU A 194      -0.027  23.875  17.076  1.00 13.05           C
ATOM   1241  CG  LEU A 194       0.669  24.392  18.350  1.00 15.58           C
ATOM   1242  CD1 LEU A 194       2.139  23.839  18.520  1.00 11.80           C
ATOM   1243  CD2 LEU A 194       0.658  25.927  18.421  1.00 12.44           C
ATOM   1244  C   LEU A 194      -1.040  21.703  17.802  1.00 14.44           C
ATOM   1245  O   LEU A 194      -2.265  21.779  17.707  1.00 15.66           O
ATOM   1246  N   GLN A 195      -0.435  21.124  18.833  1.00 14.28           N
ATOM   1247  CA  GLN A 195      -1.190  20.625  19.976  1.00 13.91           C
ATOM   1248  CB  GLN A 195      -1.191  19.118  19.920  1.00 13.40           C
ATOM   1249  CG  GLN A 195      -1.921  18.443  21.086  1.00 16.55           C
ATOM   1250  CD  GLN A 195      -2.068  16.955  20.812  1.00 18.76           C
ATOM   1251  OE1 GLN A 195      -3.137  16.465  20.388  1.00 22.26           O
ATOM   1252  NE2 GLN A 195      -1.005  16.243  21.006  1.00 16.21           N
ATOM   1253  C   GLN A 195      -0.496  21.136  21.247  1.00 14.34           C
ATOM   1254  O   GLN A 195       0.752  21.287  21.256  1.00 14.11           O
ATOM   1255  N   LEU A 196      -1.283  21.435  22.278  1.00 14.29           N
ATOM   1256  CA  LEU A 196      -0.726  21.710  23.620  1.00 14.29           C
ATOM   1257  CB  LEU A 196      -1.124  23.120  24.132  1.00 14.32           C
ATOM   1258  CG  LEU A 196      -0.918  24.307  23.180  1.00 15.13           C
ATOM   1259  CD1 LEU A 196      -1.533  25.578  23.777  1.00 13.76           C
```

FIGURE 3-18 (COORDINATES)

```
ATOM   1260  CD2 LEU A 196      0.548  24.544  22.886  1.00 12.74           C
ATOM   1261  C   LEU A 196     -1.220  20.663  24.599  1.00 14.41           C
ATOM   1262  O   LEU A 196     -2.405  20.283  24.555  1.00 14.24           O
ATOM   1263  N   ILE A 197     -0.316  20.204  25.481  1.00 14.34           N
ATOM   1264  CA  ILE A 197     -0.679  19.239  26.558  1.00 14.54           C
ATOM   1265  CB  ILE A 197     -0.063  17.799  26.382  1.00 12.79           C
ATOM   1266  CG1 ILE A 197     -0.466  17.182  25.012  1.00 17.86           C
ATOM   1267  CD1 ILE A 197      0.183  15.797  24.696  1.00 15.82           C
ATOM   1268  CG2 ILE A 197     -0.529  16.837  27.494  1.00 13.04           C
ATOM   1269  C   ILE A 197     -0.261  19.810  27.901  1.00 13.79           C
ATOM   1270  O   ILE A 197      0.885  20.185  28.091  1.00 15.12           O
ATOM   1271  N   PHE A 198     -1.198  19.841  28.832  1.00 13.70           N
ATOM   1272  CA  PHE A 198     -0.940  20.299  30.201  1.00 13.89           C
ATOM   1273  CB  PHE A 198     -1.934  21.375  30.597  1.00 13.09           C
ATOM   1274  CG  PHE A 198     -1.911  22.606  29.731  1.00 13.06           C
ATOM   1275  CD1 PHE A 198     -1.310  23.769  30.193  1.00 10.46           C
ATOM   1276  CE1 PHE A 198     -1.294  24.942  29.414  1.00 13.12           C
ATOM   1277  CZ  PHE A 198     -1.903  24.962  28.169  1.00 11.45           C
ATOM   1278  CE2 PHE A 198     -2.532  23.824  27.675  1.00 13.16           C
ATOM   1279  CD2 PHE A 198     -2.541  22.627  28.478  1.00 14.24           C
ATOM   1280  C   PHE A 198     -1.148  19.031  31.059  1.00 14.63           C
ATOM   1281  O   PHE A 198     -2.289  18.592  31.297  1.00 14.77           O
ATOM   1282  N   PHE A 199     -0.054  18.378  31.432  1.00 15.10           N
ATOM   1283  CA  PHE A 199     -0.156  17.098  32.129  1.00 15.79           C
ATOM   1284  CB  PHE A 199      1.194  16.357  32.138  1.00 15.17           C
ATOM   1285  CG  PHE A 199      1.631  15.844  30.796  1.00 15.43           C
ATOM   1286  CD1 PHE A 199      1.004  14.725  30.202  1.00 15.67           C
ATOM   1287  CE1 PHE A 199      1.466  14.219  28.968  1.00 15.50           C
ATOM   1288  CZ  PHE A 199      2.536  14.828  28.328  1.00 14.19           C
ATOM   1289  CE2 PHE A 199      3.158  15.973  28.912  1.00 12.91           C
ATOM   1290  CD2 PHE A 199      2.701  16.445  30.141  1.00 15.54           C
ATOM   1291  C   PHE A 199     -0.547  17.344  33.567  1.00 16.21           C
ATOM   1292  O   PHE A 199     -0.057  18.310  34.209  1.00 16.95           O
ATOM   1293  N   ASP A 200     -1.345  16.422  34.098  1.00 16.05           N
ATOM   1294  CA  ASP A 200     -1.637  16.412  35.557  1.00 15.54           C
ATOM   1295  CB  ASP A 200     -3.095  16.027  35.801  1.00 14.59           C
ATOM   1296  CG  ASP A 200     -3.576  16.384  37.207  1.00 13.95           C
ATOM   1297  OD1 ASP A 200     -2.804  16.942  37.988  1.00 17.61           O
ATOM   1298  OD2 ASP A 200     -4.751  16.132  37.526  1.00 15.56           O
ATOM   1299  C   ASP A 200     -0.693  15.391  36.204  1.00 14.75           C
ATOM   1300  O   ASP A 200     -0.127  14.534  35.521  1.00 15.51           O
ATOM   1301  N   GLY A 201     -0.532  15.456  37.522  1.00 15.86           N
ATOM   1302  CA  GLY A 201      0.214  14.400  38.239  1.00 14.96           C
ATOM   1303  C   GLY A 201      1.644  14.086  37.792  1.00 14.86           C
ATOM   1304  O   GLY A 201      2.080  12.936  37.878  1.00 15.90           O
ATOM   1305  N   GLU A 202      2.394  15.084  37.331  1.00 15.20           N
ATOM   1306  CA  GLU A 202      3.850  14.889  37.090  1.00 13.93           C
ATOM   1307  CB  GLU A 202      4.458  16.155  36.461  1.00 14.18           C
ATOM   1308  CG  GLU A 202      5.920  16.004  35.873  1.00 13.86           C
ATOM   1309  CD  GLU A 202      7.019  16.300  36.904  1.00 19.75           C
ATOM   1310  OE1 GLU A 202      6.655  16.610  38.046  1.00 16.57           O
ATOM   1311  OE2 GLU A 202      8.246  16.254  36.577  1.00 19.65           O
ATOM   1312  C   GLU A 202      4.575  14.489  38.382  1.00 14.10           C
ATOM   1313  O   GLU A 202      5.412  13.551  38.415  1.00 14.05           O
ATOM   1314  N   GLU A 203      4.236  15.193  39.460  1.00 14.89           N
ATOM   1315  CA  GLU A 203      4.938  15.106  40.728  1.00 15.73           C
ATOM   1316  CB  GLU A 203      4.664  16.369  41.566  1.00 15.56           C
ATOM   1317  CG  GLU A 203      5.162  17.683  40.895  1.00 14.55           C
ATOM   1318  CD  GLU A 203      6.658  17.905  40.998  1.00 16.43           C
ATOM   1319  OE1 GLU A 203      7.433  16.990  41.355  1.00 19.13           O
ATOM   1320  OE2 GLU A 203      7.088  19.020  40.704  1.00 14.51           O
ATOM   1321  C   GLU A 203      4.594  13.861  41.544  1.00 16.38           C
ATOM   1322  O   GLU A 203      3.443  13.391  41.547  1.00 15.98           O
ATOM   1323  N   ALA A 204      5.585  13.352  42.273  1.00 17.74           N
ATOM   1324  CA  ALA A 204      5.346  12.282  43.240  1.00 18.94           C
ATOM   1325  CB  ALA A 204      6.689  11.726  43.780  1.00 19.48           C
ATOM   1326  C   ALA A 204      4.515  12.842  44.397  1.00 20.47           C
ATOM   1327  O   ALA A 204      4.648  14.014  44.766  1.00 20.91           O
ATOM   1328  N   PHE A 205      3.657  12.002  44.949  1.00 22.05           N
ATOM   1329  CA  PHE A 205      2.935  12.290  46.188  1.00 23.59           C
```

FIGURE 3-19 (COORDINATES)

```
ATOM   1330  CB   PHE A 205       1.710  11.382  46.313  1.00 23.05           C
ATOM   1331  CG   PHE A 205       0.536  11.856  45.521  1.00 23.10           C
ATOM   1332  CD1  PHE A 205       0.441  11.596  44.164  1.00 21.77           C
ATOM   1333  CE1  PHE A 205      -0.661  12.079  43.409  1.00 20.97           C
ATOM   1334  CZ   PHE A 205      -1.678  12.806  44.006  1.00 21.61           C
ATOM   1335  CE2  PHE A 205      -1.590  13.117  45.375  1.00 25.17           C
ATOM   1336  CD2  PHE A 205      -0.477  12.627  46.130  1.00 25.03           C
ATOM   1337  C    PHE A 205       3.847  12.142  47.399  1.00 25.59           C
ATOM   1338  O    PHE A 205       3.723  12.903  48.370  1.00 24.82           O
ATOM   1339  N    HIS A 206       4.767  11.182  47.343  1.00 28.26           N
ATOM   1340  CA   HIS A 206       5.597  10.868  48.506  1.00 32.25           C
ATOM   1341  CB   HIS A 206       5.145   9.564  49.174  1.00 33.34           C
ATOM   1342  CG   HIS A 206       5.778   9.323  50.510  1.00 38.84           C
ATOM   1343  ND1  HIS A 206       7.107   8.972  50.659  1.00 42.62           N
ATOM   1344  CE1  HIS A 206       7.386   8.827  51.943  1.00 44.05           C
ATOM   1345  NE2  HIS A 206       6.286   9.069  52.637  1.00 45.36           N
ATOM   1346  CD2  HIS A 206       5.265   9.382  51.764  1.00 43.92           C
ATOM   1347  C    HIS A 206       7.101  10.845  48.189  1.00 33.07           C
ATOM   1348  O    HIS A 206       7.812  11.744  48.591  1.00 34.81           O
ATOM   1349  N    HIS A 207       7.575   9.845  47.449  1.00 33.40           N
ATOM   1350  CA   HIS A 207       8.999   9.746  47.099  1.00 33.28           C
ATOM   1351  CB   HIS A 207       9.638   8.670  47.902  0.00 36.18           C
ATOM   1352  CG   HIS A 207      11.092   8.478  47.585  0.00 41.34           C
ATOM   1353  ND1  HIS A 207      11.598   7.282  47.105  0.00 44.70           N
ATOM   1354  CE1  HIS A 207      12.901   7.404  46.909  0.00 45.75           C
ATOM   1355  NE2  HIS A 207      13.260   8.632  47.247  0.00 46.43           N
ATOM   1356  CD2  HIS A 207      12.149   9.325  47.674  0.00 44.55           C
ATOM   1357  C    HIS A 207       9.088   9.490  45.598  1.00 32.62           C
ATOM   1358  O    HIS A 207       8.489   8.534  45.091  1.00 32.48           O
ATOM   1359  N    TRP A 208       9.823  10.345  44.895  1.00 32.47           N
ATOM   1360  CA   TRP A 208       9.936  10.212  43.444  1.00 32.47           C
ATOM   1361  CB   TRP A 208      10.933  11.229  42.858  1.00 32.09           C
ATOM   1362  CG   TRP A 208      10.971  11.189  41.330  1.00 31.53           C
ATOM   1363  CD1  TRP A 208      11.736  10.355  40.546  1.00 30.76           C
ATOM   1364  NE1  TRP A 208      11.475  10.590  39.215  1.00 30.99           N
ATOM   1365  CE2  TRP A 208      10.524  11.579  39.108  1.00 29.82           C
ATOM   1366  CD2  TRP A 208      10.177  11.979  40.421  1.00 28.59           C
ATOM   1367  CE3  TRP A 208       9.226  12.998  40.587  1.00 30.87           C
ATOM   1368  CZ3  TRP A 208       8.643  13.591  39.424  1.00 29.36           C
ATOM   1369  CH2  TRP A 208       8.999  13.153  38.148  1.00 29.52           C
ATOM   1370  CZ2  TRP A 208       9.940  12.157  37.965  1.00 30.30           C
ATOM   1371  C    TRP A 208      10.353   8.778  43.122  1.00 32.76           C
ATOM   1372  O    TRP A 208      11.349   8.284  43.656  1.00 32.86           O
ATOM   1373  N    SER A 209       9.566   8.110  42.277  1.00 32.33           N
ATOM   1374  CA   SER A 209       9.880   6.764  41.811  1.00 32.09           C
ATOM   1375  CB   SER A 209       9.551   5.752  42.915  1.00 32.15           C
ATOM   1376  OG   SER A 209       8.148   5.562  43.012  1.00 30.86           O
ATOM   1377  C    SER A 209       9.040   6.467  40.561  1.00 32.20           C
ATOM   1378  O    SER A 209       8.052   7.141  40.338  1.00 32.31           O
ATOM   1379  N    PRO A 210       9.443   5.483  39.715  1.00 32.37           N
ATOM   1380  CA   PRO A 210       8.575   4.988  38.621  1.00 31.43           C
ATOM   1381  CB   PRO A 210       9.222   3.649  38.242  1.00 32.25           C
ATOM   1382  CG   PRO A 210      10.687   3.882  38.493  1.00 33.12           C
ATOM   1383  CD   PRO A 210      10.784   4.860  39.670  1.00 32.56           C
ATOM   1384  C    PRO A 210       7.095   4.800  38.973  1.00 30.40           C
ATOM   1385  O    PRO A 210       6.208   5.147  38.179  1.00 30.31           O
ATOM   1386  N    GLN A 211       6.818   4.255  40.143  1.00 28.22           N
ATOM   1387  CA   GLN A 211       5.443   4.069  40.585  1.00 26.61           C
ATOM   1388  CB   GLN A 211       5.401   2.985  41.728  0.00 30.03           C
ATOM   1389  CG   GLN A 211       5.759   1.557  41.253  0.00 33.85           C
ATOM   1390  CD   GLN A 211       7.282   1.256  41.206  0.00 39.64           C
ATOM   1391  OE1  GLN A 211       8.119   1.932  41.853  0.00 40.58           O
ATOM   1392  NE2  GLN A 211       7.640   0.221  40.439  0.00 42.98           N
ATOM   1393  C    GLN A 211       4.766   5.341  41.121  1.00 24.44           C
ATOM   1394  O    GLN A 211       3.550   5.444  41.076  1.00 25.08           O
ATOM   1395  N    ASP A 212       5.552   6.274  41.632  1.00 22.76           N
ATOM   1396  CA   ASP A 212       5.037   7.525  42.195  1.00 22.41           C
ATOM   1397  CB   ASP A 212       5.352   7.604  43.697  1.00 21.94           C
ATOM   1398  CG   ASP A 212       4.619   8.759  44.403  1.00 21.01           C
ATOM   1399  OD1  ASP A 212       3.577   9.259  43.897  1.00 20.87           O
```

FIGURE 3-20 (COORDINATES)

```
ATOM   1400  OD2 ASP A 212      5.086   9.152  45.484  1.00 20.31           O
ATOM   1401  C   ASP A 212      5.615   8.733  41.464  1.00 22.07           C
ATOM   1402  O   ASP A 212      6.449   9.461  42.008  1.00 22.16           O
ATOM   1403  N   SER A 213      5.162   8.936  40.221  1.00 21.00           N
ATOM   1404  CA  SER A 213      5.495  10.118  39.406  1.00 19.56           C
ATOM   1405  CB  SER A 213      7.001  10.262  39.230  1.00 19.96           C
ATOM   1406  OG  SER A 213      7.505   9.182  38.452  1.00 19.22           O
ATOM   1407  C   SER A 213      4.845   9.909  38.039  1.00 18.58           C
ATOM   1408  O   SER A 213      4.456   8.779  37.704  1.00 18.45           O
ATOM   1409  N   LEU A 214      4.698  10.985  37.258  1.00 17.53           N
ATOM   1410  CA  LEU A 214      4.264  10.892  35.848  1.00 15.72           C
ATOM   1411  CB  LEU A 214      5.344  10.219  34.970  1.00 16.54           C
ATOM   1412  CG  LEU A 214      6.780  10.663  35.177  1.00 17.04           C
ATOM   1413  CD1 LEU A 214      7.735  10.028  34.161  1.00 17.32           C
ATOM   1414  CD2 LEU A 214      6.891  12.241  35.224  1.00 13.78           C
ATOM   1415  C   LEU A 214      2.937  10.188  35.666  1.00 17.17           C
ATOM   1416  O   LEU A 214      2.766   9.444  34.719  1.00 17.09           O
ATOM   1417  N   TYR A 215      2.006  10.392  36.601  1.00 17.24           N
ATOM   1418  CA  TYR A 215      0.684   9.747  36.525  1.00 18.08           C
ATOM   1419  CB  TYR A 215     -0.169  10.141  37.740  1.00 17.51           C
ATOM   1420  CG  TYR A 215      0.339   9.584  39.057  1.00 18.84           C
ATOM   1421  CD1 TYR A 215     -0.023   8.300  39.481  1.00 22.83           C
ATOM   1422  CE1 TYR A 215      0.443   7.762  40.705  1.00 21.13           C
ATOM   1423  CZ  TYR A 215      1.240   8.532  41.512  1.00 19.28           C
ATOM   1424  OH  TYR A 215      1.703   8.046  42.722  1.00 20.55           O
ATOM   1425  CE2 TYR A 215      1.615   9.821  41.112  1.00 19.29           C
ATOM   1426  CD2 TYR A 215      1.140  10.338  39.888  1.00 17.00           C
ATOM   1427  C   TYR A 215     -0.028  10.114  35.225  1.00 18.27           C
ATOM   1428  O   TYR A 215     -0.441   9.228  34.459  1.00 18.85           O
ATOM   1429  N   GLY A 216     -0.148  11.426  34.978  1.00 16.28           N
ATOM   1430  CA  GLY A 216     -0.793  11.939  33.787  1.00 15.56           C
ATOM   1431  C   GLY A 216     -0.120  11.560  32.501  1.00 14.74           C
ATOM   1432  O   GLY A 216     -0.785  11.102  31.595  1.00 14.99           O
ATOM   1433  N   SER A 217      1.207  11.718  32.411  1.00 16.57           N
ATOM   1434  CA  SER A 217      1.938  11.380  31.163  1.00 15.81           C
ATOM   1435  CB  SER A 217      3.348  11.988  31.118  1.00 16.32           C
ATOM   1436  OG  SER A 217      4.118  11.661  32.288  1.00 16.26           O
ATOM   1437  C   SER A 217      2.013   9.901  30.883  1.00 16.77           C
ATOM   1438  O   SER A 217      1.891   9.485  29.724  1.00 16.94           O
ATOM   1439  N   ARG A 218      2.205   9.077  31.914  1.00 17.95           N
ATOM   1440  CA  ARG A 218      2.149   7.612  31.681  1.00 18.88           C
ATOM   1441  CB  ARG A 218      2.527   6.850  32.947  1.00 19.14           C
ATOM   1442  CG  ARG A 218      4.048   6.753  33.191  1.00 19.06           C
ATOM   1443  CD  ARG A 218      4.401   5.905  34.414  1.00 21.00           C
ATOM   1444  NE  ARG A 218      3.934   6.492  35.676  1.00 20.29           N
ATOM   1445  CZ  ARG A 218      2.864   6.071  36.344  1.00 23.10           C
ATOM   1446  NH1 ARG A 218      2.152   5.049  35.889  1.00 23.12           N
ATOM   1447  NH2 ARG A 218      2.512   6.651  37.477  1.00 20.10           N
ATOM   1448  C   ARG A 218      0.771   7.184  31.131  1.00 19.10           C
ATOM   1449  O   ARG A 218      0.678   6.379  30.185  1.00 19.94           O
ATOM   1450  N   HIS A 219     -0.303   7.742  31.682  1.00 19.05           N
ATOM   1451  CA  HIS A 219     -1.662   7.429  31.225  1.00 18.56           C
ATOM   1452  CB  HIS A 219     -2.697   8.053  32.171  1.00 17.80           C
ATOM   1453  CG  HIS A 219     -4.107   7.647  31.871  1.00 21.51           C
ATOM   1454  ND1 HIS A 219     -4.942   8.401  31.085  1.00 22.74           N
ATOM   1455  CE1 HIS A 219     -6.115   7.802  30.990  1.00 26.45           C
ATOM   1456  NE2 HIS A 219     -6.069   6.681  31.686  1.00 27.24           N
ATOM   1457  CD2 HIS A 219     -4.822   6.554  32.246  1.00 21.85           C
ATOM   1458  C   HIS A 219     -1.957   7.876  29.801  1.00 18.58           C
ATOM   1459  O   HIS A 219     -2.588   7.172  29.015  1.00 18.33           O
ATOM   1460  N   LEU A 220     -1.537   9.088  29.461  1.00 18.43           N
ATOM   1461  CA  LEU A 220     -1.850   9.633  28.161  1.00 17.00           C
ATOM   1462  CB  LEU A 220     -1.721  11.199  28.172  1.00 17.18           C
ATOM   1463  CG  LEU A 220     -2.202  11.936  26.887  1.00 18.97           C
ATOM   1464  CD1 LEU A 220     -3.699  11.640  26.557  1.00 18.57           C
ATOM   1465  CD2 LEU A 220     -1.933  13.475  26.957  1.00 16.61           C
ATOM   1466  C   LEU A 220     -1.023   9.002  27.041  1.00 16.65           C
ATOM   1467  O   LEU A 220     -1.544   8.765  25.930  1.00 17.01           O
ATOM   1468  N   ALA A 221      0.264   8.760  27.295  1.00 15.43           N
ATOM   1469  CA  ALA A 221      1.094   8.070  26.330  1.00 17.68           C
```

FIGURE 3-21 (COORDINATES)

```
ATOM   1470  CB   ALA A 221       2.522   7.856  26.890  1.00 15.64           C
ATOM   1471  C    ALA A 221       0.433   6.705  25.994  1.00 19.73           C
ATOM   1472  O    ALA A 221       0.416   6.244  24.830  1.00 20.76           O
ATOM   1473  N    GLN A 222      -0.107   6.070  27.026  1.00 21.93           N
ATOM   1474  CA   GLN A 222      -0.788   4.778  26.884  1.00 24.38           C
ATOM   1475  CB   GLN A 222      -1.015   4.195  28.290  1.00 24.69           C
ATOM   1476  CG   GLN A 222      -1.995   3.014  28.339  1.00 29.70           C
ATOM   1477  CD   GLN A 222      -1.290   1.716  28.374  1.00 37.05           C
ATOM   1478  OE1  GLN A 222      -0.689   1.292  27.362  1.00 40.32           O
ATOM   1479  NE2  GLN A 222      -1.329   1.051  29.546  1.00 35.76           N
ATOM   1480  C    GLN A 222      -2.119   4.907  26.087  1.00 24.15           C
ATOM   1481  O    GLN A 222      -2.404   4.140  25.164  1.00 24.53           O
ATOM   1482  N    LYS A 223      -2.915   5.894  26.458  1.00 24.16           N
ATOM   1483  CA   LYS A 223      -4.142   6.232  25.766  1.00 25.27           C
ATOM   1484  CB   LYS A 223      -4.839   7.385  26.498  1.00 25.23           C
ATOM   1485  CG   LYS A 223      -6.255   7.604  26.068  1.00 28.36           C
ATOM   1486  CD   LYS A 223      -6.891   8.707  26.884  1.00 34.51           C
ATOM   1487  CE   LYS A 223      -8.316   8.983  26.394  1.00 36.73           C
ATOM   1488  NZ   LYS A 223      -9.021   9.855  27.373  1.00 38.30           N
ATOM   1489  C    LYS A 223      -3.883   6.560  24.270  1.00 24.89           C
ATOM   1490  O    LYS A 223      -4.578   6.055  23.389  1.00 22.71           O
ATOM   1491  N    MET A 224      -2.847   7.357  24.002  1.00 25.04           N
ATOM   1492  CA   MET A 224      -2.494   7.720  22.630  1.00 25.58           C
ATOM   1493  CB   MET A 224      -1.480   8.864  22.608  1.00 25.07           C
ATOM   1494  CG   MET A 224      -2.100  10.244  22.949  1.00 23.73           C
ATOM   1495  SD   MET A 224      -0.841  11.556  22.899  1.00 23.50           S
ATOM   1496  CE   MET A 224      -1.923  13.009  23.263  1.00 27.56           C
ATOM   1497  C    MET A 224      -1.996   6.543  21.803  1.00 27.02           C
ATOM   1498  O    MET A 224      -2.223   6.493  20.595  1.00 28.22           O
ATOM   1499  N    ALA A 225      -1.310   5.619  22.465  1.00 27.86           N
ATOM   1500  CA   ALA A 225      -0.899   4.349  21.863  1.00 30.13           C
ATOM   1501  CB   ALA A 225       0.037   3.599  22.809  1.00 29.85           C
ATOM   1502  C    ALA A 225      -2.080   3.467  21.462  1.00 30.72           C
ATOM   1503  O    ALA A 225      -1.911   2.627  20.626  1.00 31.73           O
ATOM   1504  N    SER A 226      -3.265   3.685  22.043  1.00 32.50           N
ATOM   1505  CA   SER A 226      -4.506   2.938  21.741  1.00 34.22           C
ATOM   1506  CB   SER A 226      -5.140   2.368  23.029  1.00 33.96           C
ATOM   1507  OG   SER A 226      -4.197   1.643  23.814  1.00 37.14           O
ATOM   1508  C    SER A 226      -5.569   3.798  21.025  1.00 35.34           C
ATOM   1509  O    SER A 226      -6.796   3.553  21.149  1.00 36.17           O
ATOM   1510  N    SER A 227      -5.118   4.825  20.310  1.00 35.69           N
ATOM   1511  CA   SER A 227      -6.032   5.666  19.560  1.00 35.99           C
ATOM   1512  CB   SER A 227      -6.103   7.078  20.138  1.00 35.90           C
ATOM   1513  OG   SER A 227      -6.399   7.068  21.518  1.00 35.66           O
ATOM   1514  C    SER A 227      -5.475   5.707  18.151  1.00 36.38           C
ATOM   1515  O    SER A 227      -4.554   6.463  17.899  1.00 36.32           O
ATOM   1516  N    PRO A 228      -5.999   4.852  17.237  1.00 36.84           N
ATOM   1517  CA   PRO A 228      -5.526   4.925  15.862  1.00 36.15           C
ATOM   1518  CB   PRO A 228      -6.423   3.925  15.120  1.00 36.29           C
ATOM   1519  CG   PRO A 228      -7.605   3.695  16.011  1.00 37.13           C
ATOM   1520  CD   PRO A 228      -7.038   3.808  17.396  1.00 37.77           C
ATOM   1521  C    PRO A 228      -5.706   6.346  15.295  1.00 35.33           C
ATOM   1522  O    PRO A 228      -6.703   7.031  15.545  1.00 34.84           O
ATOM   1523  N    HIS A 229      -4.717   6.767  14.529  1.00 34.69           N
ATOM   1524  CA   HIS A 229      -4.721   8.088  13.980  1.00 33.68           C
ATOM   1525  CB   HIS A 229      -3.962   9.042  14.907  1.00 33.07           C
ATOM   1526  CG   HIS A 229      -4.034  10.464  14.464  1.00 32.63           C
ATOM   1527  ND1  HIS A 229      -5.170  11.231  14.615  1.00 32.33           N
ATOM   1528  CE1  HIS A 229      -4.963  12.423  14.082  1.00 31.76           C
ATOM   1529  NE2  HIS A 229      -3.732  12.456  13.607  1.00 31.56           N
ATOM   1530  CD2  HIS A 229      -3.130  11.244  13.831  1.00 30.72           C
ATOM   1531  C    HIS A 229      -4.017   8.025  12.650  1.00 33.29           C
ATOM   1532  O    HIS A 229      -2.925   7.492  12.589  1.00 33.76           O
ATOM   1533  N    PRO A 230      -4.608   8.598  11.594  1.00 33.82           N
ATOM   1534  CA   PRO A 230      -5.965   9.174  11.484  1.00 34.65           C
ATOM   1535  CB   PRO A 230      -6.071   9.603  10.011  1.00 34.67           C
ATOM   1536  CG   PRO A 230      -4.813   9.151   9.331  1.00 33.22           C
ATOM   1537  CD   PRO A 230      -3.801   8.808  10.376  1.00 33.78           C
ATOM   1538  C    PRO A 230      -7.058   8.171  11.847  1.00 36.29           C
ATOM   1539  O    PRO A 230      -6.822   6.976  11.787  1.00 36.16           O
```

FIGURE 3-22 (COORDINATES)

```
ATOM   1540  N   PRO A 231      -8.244   8.644  12.278  1.00 38.04           N
ATOM   1541  CA  PRO A 231      -9.260   7.629  12.604  1.00 38.96           C
ATOM   1542  CB  PRO A 231     -10.508   8.466  12.901  1.00 39.33           C
ATOM   1543  CG  PRO A 231      -9.984   9.831  13.297  1.00 38.54           C
ATOM   1544  CD  PRO A 231      -8.740  10.022  12.471  1.00 38.20           C
ATOM   1545  C   PRO A 231      -9.507   6.614  11.441  1.00 39.90           C
ATOM   1546  O   PRO A 231      -9.543   7.002  10.263  1.00 39.99           O
ATOM   1547  N   GLY A 232      -9.649   5.326  11.777  1.00 40.64           N
ATOM   1548  CA  GLY A 232      -9.862   4.269  10.758  1.00 40.15           C
ATOM   1549  C   GLY A 232      -8.538   3.785  10.197  1.00 40.24           C
ATOM   1550  O   GLY A 232      -8.476   2.969   9.247  1.00 40.54           O
ATOM   1551  N   SER A 233      -7.462   4.297  10.783  1.00 39.06           N
ATOM   1552  CA  SER A 233      -6.130   3.832  10.451  1.00 38.70           C
ATOM   1553  CB  SER A 233      -5.071   4.801  10.969  1.00 38.91           C
ATOM   1554  OG  SER A 233      -4.290   5.247   9.884  1.00 41.43           O
ATOM   1555  C   SER A 233      -6.002   2.484  11.133  1.00 37.70           C
ATOM   1556  O   SER A 233      -6.617   2.255  12.186  1.00 37.90           O
ATOM   1557  N   ARG A 234      -5.225   1.603  10.518  1.00 35.92           N
ATOM   1558  CA  ARG A 234      -5.096   0.217  10.960  1.00 35.04           C
ATOM   1559  CB  ARG A 234      -4.823  -0.699   9.757  1.00 34.63           C
ATOM   1560  CG  ARG A 234      -4.802   0.016   8.328  1.00 37.84           C
ATOM   1561  CD  ARG A 234      -4.567   1.603   8.348  1.00 32.45           C
ATOM   1562  NE  ARG A 234      -3.464   2.047   7.515  1.00 29.36           N
ATOM   1563  CZ  ARG A 234      -2.208   2.152   7.912  1.00 28.77           C
ATOM   1564  NH1 ARG A 234      -1.313   2.580   7.068  1.00 36.66           N
ATOM   1565  NH2 ARG A 234      -1.826   1.854   9.149  1.00 31.38           N
ATOM   1566  C   ARG A 234      -3.967   0.112  11.984  1.00 33.69           C
ATOM   1567  O   ARG A 234      -4.157  -0.428  13.080  1.00 33.08           O
ATOM   1568  N   GLY A 235      -2.804   0.642  11.611  1.00 32.31           N
ATOM   1569  CA  GLY A 235      -1.569   0.454  12.359  1.00 32.78           C
ATOM   1570  C   GLY A 235      -0.847   1.696  12.853  1.00 32.53           C
ATOM   1571  O   GLY A 235       0.211   1.587  13.474  1.00 33.86           O
ATOM   1572  N   THR A 236      -1.376   2.877  12.548  1.00 32.46           N
ATOM   1573  CA  THR A 236      -0.779   4.151  13.024  1.00 30.74           C
ATOM   1574  CB  THR A 236      -0.620   5.229  11.917  1.00 31.02           C
ATOM   1575  OG1 THR A 236      -1.887   5.533  11.343  1.00 28.24           O
ATOM   1576  CG2 THR A 236       0.341   4.795  10.810  1.00 31.61           C
ATOM   1577  C   THR A 236      -1.666   4.681  14.135  1.00 30.06           C
ATOM   1578  O   THR A 236      -2.897   4.637  14.024  1.00 29.32           O
ATOM   1579  N   ASN A 237      -1.042   5.155  15.223  1.00 29.21           N
ATOM   1580  CA  ASN A 237      -1.785   5.734  16.348  1.00 28.12           C
ATOM   1581  CB  ASN A 237      -1.492   4.945  17.639  1.00 28.60           C
ATOM   1582  CG  ASN A 237       0.000   4.730  17.874  1.00 29.36           C
ATOM   1583  OD1 ASN A 237       0.808   5.593  17.556  1.00 32.13           O
ATOM   1584  ND2 ASN A 237       0.374   3.576  18.449  1.00 31.23           N
ATOM   1585  C   ASN A 237      -1.472   7.240  16.534  1.00 26.94           C
ATOM   1586  O   ASN A 237      -0.735   7.830  15.760  1.00 24.58           O
ATOM   1587  N   GLN A 238      -2.031   7.841  17.569  1.00 25.98           N
ATOM   1588  CA  GLN A 238      -1.740   9.253  17.888  1.00 26.40           C
ATOM   1589  CB  GLN A 238      -2.682   9.757  18.967  1.00 25.54           C
ATOM   1590  CG  GLN A 238      -4.135   9.934  18.489  1.00 26.43           C
ATOM   1591  CD  GLN A 238      -5.089  10.257  19.654  1.00 28.56           C
ATOM   1592  OE1 GLN A 238      -4.692  10.217  20.834  1.00 33.22           O
ATOM   1593  NE2 GLN A 238      -6.341  10.572  19.337  1.00 28.62           N
ATOM   1594  C   GLN A 238      -0.259   9.545  18.241  1.00 25.14           C
ATOM   1595  O   GLN A 238       0.210  10.651  18.046  1.00 25.17           O
ATOM   1596  N   LEU A 239       0.487   8.559  18.730  1.00 24.46           N
ATOM   1597  CA  LEU A 239       1.915   8.772  18.981  1.00 25.06           C
ATOM   1598  CB  LEU A 239       2.493   7.666  19.860  1.00 25.25           C
ATOM   1599  CG  LEU A 239       1.811   7.408  21.223  1.00 24.88           C
ATOM   1600  CD1 LEU A 239       2.445   6.213  21.854  1.00 27.20           C
ATOM   1601  CD2 LEU A 239       1.944   8.622  22.171  1.00 26.58           C
ATOM   1602  C   LEU A 239       2.734   8.947  17.694  1.00 25.49           C
ATOM   1603  O   LEU A 239       3.695   9.713  17.659  1.00 25.00           O
ATOM   1604  N   ASP A 240       2.328   8.236  16.637  1.00 25.72           N
ATOM   1605  CA  ASP A 240       2.899   8.387  15.305  1.00 25.86           C
ATOM   1606  CB  ASP A 240       2.225   7.387  14.363  1.00 27.26           C
ATOM   1607  CG  ASP A 240       2.630   5.936  14.653  1.00 28.72           C
ATOM   1608  OD1 ASP A 240       3.844   5.653  14.807  1.00 29.98           O
ATOM   1609  OD2 ASP A 240       1.728   5.098  14.729  1.00 29.91           O
```

FIGURE 3-23 (COORDINATES)

```
ATOM   1610  C    ASP A 240       2.690   9.810  14.788  1.00 24.81           C
ATOM   1611  O    ASP A 240       3.518  10.352  14.086  1.00 25.27           O
ATOM   1612  N    GLY A 241       1.585  10.415  15.183  1.00 25.36           N
ATOM   1613  CA   GLY A 241       1.252  11.787  14.805  1.00 25.73           C
ATOM   1614  C    GLY A 241       2.074  12.871  15.469  1.00 24.73           C
ATOM   1615  O    GLY A 241       2.131  13.997  14.967  1.00 25.30           O
ATOM   1616  N    MET A 242       2.713  12.545  16.595  1.00 23.39           N
ATOM   1617  CA   MET A 242       3.550  13.525  17.288  1.00 23.39           C
ATOM   1618  CB   MET A 242       3.791  13.128  18.759  1.00 23.12           C
ATOM   1619  CG   MET A 242       2.526  12.924  19.561  1.00 23.54           C
ATOM   1620  SD   MET A 242       2.848  12.392  21.297  1.00 26.36           S
ATOM   1621  CE   MET A 242       3.630  13.879  21.948  1.00 21.20           C
ATOM   1622  C    MET A 242       4.878  13.714  16.550  1.00 22.71           C
ATOM   1623  O    MET A 242       5.791  12.879  16.653  1.00 22.80           O
ATOM   1624  N    ASP A 243       4.974  14.806  15.792  1.00 22.35           N
ATOM   1625  CA   ASP A 243       6.210  15.145  15.098  1.00 21.38           C
ATOM   1626  CB   ASP A 243       6.040  16.460  14.376  1.00 21.70           C
ATOM   1627  CG   ASP A 243       5.848  16.272  12.909  1.00 21.93           C
ATOM   1628  OD1  ASP A 243       5.114  15.325  12.543  1.00 25.19           O
ATOM   1629  OD2  ASP A 243       6.436  17.081  12.147  1.00 19.35           O
ATOM   1630  C    ASP A 243       7.365  15.316  16.073  1.00 20.81           C
ATOM   1631  O    ASP A 243       8.493  14.900  15.795  1.00 20.53           O
ATOM   1632  N    LEU A 244       7.052  15.972  17.193  1.00 19.30           N
ATOM   1633  CA   LEU A 244       8.024  16.482  18.118  1.00 17.83           C
ATOM   1634  CB   LEU A 244       8.734  17.708  17.567  1.00 17.76           C
ATOM   1635  CG   LEU A 244       9.874  18.300  18.421  1.00 17.06           C
ATOM   1636  CD1  LEU A 244      10.951  17.250  18.765  1.00 16.59           C
ATOM   1637  CD2  LEU A 244      10.502  19.496  17.746  1.00 18.18           C
ATOM   1638  C    LEU A 244       7.260  16.891  19.370  1.00 17.79           C
ATOM   1639  O    LEU A 244       6.234  17.545  19.269  1.00 17.28           O
ATOM   1640  N    LEU A 245       7.785  16.472  20.524  1.00 16.71           N
ATOM   1641  CA   LEU A 245       7.268  16.850  21.819  1.00 16.66           C
ATOM   1642  CB   LEU A 245       7.053  15.600  22.687  1.00 16.06           C
ATOM   1643  CG   LEU A 245       6.623  15.872  24.137  1.00 19.11           C
ATOM   1644  CD1  LEU A 245       5.286  16.652  24.163  1.00 19.27           C
ATOM   1645  CD2  LEU A 245       6.571  14.532  24.947  1.00 19.06           C
ATOM   1646  C    LEU A 245       8.299  17.799  22.432  1.00 15.61           C
ATOM   1647  O    LEU A 245       9.425  17.412  22.679  1.00 15.42           O
ATOM   1648  N    VAL A 246       7.913  19.057  22.593  1.00 15.39           N
ATOM   1649  CA   VAL A 246       8.741  20.084  23.223  1.00 14.66           C
ATOM   1650  CB   VAL A 246       8.655  21.434  22.472  1.00 13.79           C
ATOM   1651  CG1  VAL A 246       9.581  22.527  23.122  1.00 15.08           C
ATOM   1652  CG2  VAL A 246       9.008  21.235  20.940  1.00 13.95           C
ATOM   1653  C    VAL A 246       8.179  20.231  24.635  1.00 14.74           C
ATOM   1654  O    VAL A 246       7.058  20.745  24.846  1.00 15.69           O
ATOM   1655  N    LEU A 247       8.925  19.713  25.587  1.00 13.40           N
ATOM   1656  CA   LEU A 247       8.482  19.697  26.987  1.00 12.83           C
ATOM   1657  CB   LEU A 247       8.815  18.331  27.619  1.00 12.64           C
ATOM   1658  CG   LEU A 247       8.401  18.199  29.107  1.00 14.52           C
ATOM   1659  CD1  LEU A 247       6.897  18.554  29.323  1.00 12.50           C
ATOM   1660  CD2  LEU A 247       8.822  16.823  29.749  1.00 10.26           C
ATOM   1661  C    LEU A 247       9.144  20.817  27.767  1.00 13.35           C
ATOM   1662  O    LEU A 247      10.378  20.809  27.891  1.00 13.48           O
ATOM   1663  N    LEU A 248       8.360  21.773  28.278  1.00 13.39           N
ATOM   1664  CA   LEU A 248       8.935  22.902  29.056  1.00 14.52           C
ATOM   1665  CB   LEU A 248       8.187  24.214  28.755  1.00 13.30           C
ATOM   1666  CG   LEU A 248       8.321  24.952  27.429  1.00 16.23           C
ATOM   1667  CD1  LEU A 248       7.466  26.243  27.499  1.00 16.57           C
ATOM   1668  CD2  LEU A 248       7.878  24.126  26.231  1.00 19.90           C
ATOM   1669  C    LEU A 248       8.867  22.647  30.552  1.00 14.73           C
ATOM   1670  O    LEU A 248       7.802  22.296  31.062  1.00 13.93           O
ATOM   1671  N    ASP A 249       9.984  22.823  31.270  1.00 14.90           N
ATOM   1672  CA   ASP A 249       9.961  22.529  32.720  1.00 14.97           C
ATOM   1673  CB   ASP A 249      10.180  21.022  32.998  1.00 14.84           C
ATOM   1674  CG   ASP A 249       9.532  20.567  34.333  1.00 14.32           C
ATOM   1675  OD1  ASP A 249       9.230  21.420  35.179  1.00 14.51           O
ATOM   1676  OD2  ASP A 249       9.346  19.345  34.557  1.00 15.34           O
ATOM   1677  C    ASP A 249      11.026  23.337  33.444  1.00 15.30           C
ATOM   1678  O    ASP A 249      12.087  23.599  32.887  1.00 14.95           O
ATOM   1679  N    LEU A 250      10.716  23.779  34.659  1.00 16.05           N
```

FIGURE 3-24 (COORDINATES)

```
ATOM   1680  CA  LEU A 250      11.684  24.502  35.484  1.00 16.09           C
ATOM   1681  CB  LEU A 250      12.862  23.568  35.861  1.00 16.02           C
ATOM   1682  CG  LEU A 250      12.495  22.238  36.508  1.00 14.23           C
ATOM   1683  CD1 LEU A 250      13.763  21.520  37.003  1.00 15.65           C
ATOM   1684  CD2 LEU A 250      11.475  22.475  37.660  1.00 17.76           C
ATOM   1685  C   LEU A 250      12.210  25.781  34.802  1.00 17.42           C
ATOM   1686  O   LEU A 250      13.450  26.022  34.701  1.00 18.42           O
ATOM   1687  N   ILE A 251      11.286  26.568  34.279  1.00 16.11           N
ATOM   1688  CA  ILE A 251      11.625  27.844  33.619  1.00 15.37           C
ATOM   1689  CB  ILE A 251      10.983  27.968  32.218  1.00 15.83           C
ATOM   1690  CG1 ILE A 251      11.432  26.788  31.299  1.00 13.84           C
ATOM   1691  CD1 ILE A 251      10.895  26.801  29.924  1.00 12.77           C
ATOM   1692  CG2 ILE A 251      11.308  29.335  31.650  1.00 13.26           C
ATOM   1693  C   ILE A 251      11.099  28.999  34.510  1.00 16.85           C
ATOM   1694  O   ILE A 251       9.945  28.975  34.967  1.00 14.98           O
ATOM   1695  N   GLY A 252      11.950  29.998  34.729  1.00 16.68           N
ATOM   1696  CA  GLY A 252      11.543  31.218  35.386  1.00 18.00           C
ATOM   1697  C   GLY A 252      12.645  31.816  36.243  1.00 19.08           C
ATOM   1698  O   GLY A 252      12.594  32.995  36.558  1.00 20.24           O
ATOM   1699  N   ALA A 253      13.604  31.008  36.664  1.00 19.26           N
ATOM   1700  CA  ALA A 253      14.811  31.527  37.350  1.00 21.16           C
ATOM   1701  CB  ALA A 253      15.568  30.414  38.042  1.00 20.07           C
ATOM   1702  C   ALA A 253      15.761  32.289  36.418  1.00 22.60           C
ATOM   1703  O   ALA A 253      15.738  32.111  35.185  1.00 22.82           O
ATOM   1704  N   ALA A 254      16.596  33.139  37.008  1.00 23.08           N
ATOM   1705  CA  ALA A 254      17.998  32.806  37.229  1.00 23.64           C
ATOM   1706  CB  ALA A 254      18.156  32.002  38.511  1.00 23.88           C
ATOM   1707  C   ALA A 254      18.577  32.041  36.044  1.00 23.37           C
ATOM   1708  O   ALA A 254      18.086  30.971  35.683  1.00 24.99           O
ATOM   1709  N   ASN A 255      19.624  32.596  35.443  1.00 22.39           N
ATOM   1710  CA  ASN A 255      20.044  32.191  34.106  1.00 22.58           C
ATOM   1711  CB  ASN A 255      19.346  33.043  33.044  0.00 32.11           C
ATOM   1712  CG  ASN A 255      20.008  32.936  31.685  0.00 38.14           C
ATOM   1713  OD1 ASN A 255      21.138  32.464  31.567  0.00 44.11           O
ATOM   1714  ND2 ASN A 255      19.304  33.376  30.648  0.00 40.98           N
ATOM   1715  C   ASN A 255      19.784  30.711  33.845  1.00 22.24           C
ATOM   1716  O   ASN A 255      20.357  29.844  34.504  1.00 22.28           O
ATOM   1717  N   PRO A 256      18.916  30.430  32.879  1.00 21.43           N
ATOM   1718  CA  PRO A 256      18.851  29.100  32.264  1.00 20.00           C
ATOM   1719  CB  PRO A 256      17.795  29.276  31.171  1.00 19.80           C
ATOM   1720  CG  PRO A 256      16.916  30.363  31.678  1.00 19.18           C
ATOM   1721  CD  PRO A 256      17.815  31.302  32.431  1.00 20.77           C
ATOM   1722  C   PRO A 256      20.185  28.697  31.644  1.00 20.59           C
ATOM   1723  O   PRO A 256      20.890  29.544  31.094  1.00 20.04           O
ATOM   1724  N   THR A 257      20.522  27.415  31.734  1.00 20.59           N
ATOM   1725  CA  THR A 257      21.164  26.712  30.630  1.00 22.16           C
ATOM   1726  CB  THR A 257      22.624  26.351  30.964  1.00 22.56           C
ATOM   1727  OG1 THR A 257      22.677  25.689  32.233  1.00 30.74           O
ATOM   1728  CG2 THR A 257      23.484  27.605  31.014  1.00 22.36           C
ATOM   1729  C   THR A 257      20.405  25.439  30.271  1.00 20.78           C
ATOM   1730  O   THR A 257      20.252  24.541  31.099  1.00 20.53           O
ATOM   1731  N   PHE A 258      19.932  25.368  29.031  1.00 20.42           N
ATOM   1732  CA  PHE A 258      19.153  24.223  28.572  1.00 20.78           C
ATOM   1733  CB  PHE A 258      17.958  24.645  27.659  1.00 19.95           C
ATOM   1734  CG  PHE A 258      16.961  25.491  28.375  1.00 19.32           C
ATOM   1735  CD1 PHE A 258      15.936  24.911  29.104  1.00 16.31           C
ATOM   1736  CE1 PHE A 258      15.030  25.714  29.802  1.00 16.63           C
ATOM   1737  CZ  PHE A 258      15.192  27.074  29.789  1.00 16.53           C
ATOM   1738  CE2 PHE A 258      16.217  27.643  29.064  1.00 17.40           C
ATOM   1739  CD2 PHE A 258      17.097  26.858  28.382  1.00 16.78           C
ATOM   1740  C   PHE A 258      20.051  23.306  27.811  1.00 21.57           C
ATOM   1741  O   PHE A 258      20.473  23.674  26.706  1.00 21.23           O
ATOM   1742  N   PRO A 259      20.278  22.089  28.362  1.00 22.54           N
ATOM   1743  CA  PRO A 259      21.129  21.079  27.695  1.00 22.73           C
ATOM   1744  CB  PRO A 259      21.342  19.995  28.782  1.00 23.01           C
ATOM   1745  CG  PRO A 259      20.837  20.632  30.108  1.00 23.35           C
ATOM   1746  CD  PRO A 259      19.781  21.626  29.681  1.00 21.73           C
ATOM   1747  C   PRO A 259      20.478  20.459  26.451  1.00 23.26           C
ATOM   1748  O   PRO A 259      19.238  20.480  26.279  1.00 21.55           O
ATOM   1749  N   ASN A 260      21.338  19.942  25.566  1.00 23.04           N
```

FIGURE 3-25 (COORDINATES)

```
ATOM   1750  CA  ASN A 260      20.878  19.227  24.375  1.00 23.51           C
ATOM   1751  CB  ASN A 260      21.832  19.520  23.234  1.00 23.99           C
ATOM   1752  CG  ASN A 260      21.350  19.017  21.888  1.00 23.92           C
ATOM   1753  OD1 ASN A 260      20.254  18.476  21.737  1.00 25.02           O
ATOM   1754  ND2 ASN A 260      22.186  19.228  20.877  1.00 26.67           N
ATOM   1755  C   ASN A 260      20.876  17.754  24.722  1.00 24.81           C
ATOM   1756  O   ASN A 260      21.926  17.146  24.882  1.00 26.35           O
ATOM   1757  N   PHE A 261      19.705  17.160  24.847  1.00 24.38           N
ATOM   1758  CA  PHE A 261      19.642  15.832  25.434  1.00 25.12           C
ATOM   1759  CB  PHE A 261      18.367  15.662  26.275  1.00 23.77           C
ATOM   1760  CG  PHE A 261      18.379  16.415  27.586  1.00 23.88           C
ATOM   1761  CD1 PHE A 261      17.662  17.587  27.724  1.00 20.45           C
ATOM   1762  CE1 PHE A 261      17.639  18.297  28.950  1.00 20.77           C
ATOM   1763  CZ  PHE A 261      18.381  17.821  30.045  1.00 20.34           C
ATOM   1764  CE2 PHE A 261      19.090  16.624  29.926  1.00 22.23           C
ATOM   1765  CD2 PHE A 261      19.087  15.922  28.691  1.00 23.82           C
ATOM   1766  C   PHE A 261      19.744  14.691  24.434  1.00 25.77           C
ATOM   1767  O   PHE A 261      20.306  13.629  24.766  1.00 25.80           O
ATOM   1768  N   PHE A 262      19.186  14.889  23.241  1.00 25.74           N
ATOM   1769  CA  PHE A 262      18.957  13.786  22.314  1.00 27.06           C
ATOM   1770  CB  PHE A 262      17.451  13.510  22.163  1.00 26.97           C
ATOM   1771  CG  PHE A 262      16.739  13.297  23.469  1.00 27.42           C
ATOM   1772  CD1 PHE A 262      16.893  12.105  24.165  1.00 27.62           C
ATOM   1773  CE1 PHE A 262      16.273  11.915  25.396  1.00 28.26           C
ATOM   1774  CZ  PHE A 262      15.455  12.916  25.921  1.00 25.58           C
ATOM   1775  CE2 PHE A 262      15.283  14.110  25.233  1.00 26.71           C
ATOM   1776  CD2 PHE A 262      15.942  14.304  24.022  1.00 28.89           C
ATOM   1777  C   PHE A 262      19.546  14.026  20.926  1.00 28.19           C
ATOM   1778  O   PHE A 262      19.180  15.022  20.255  1.00 28.18           O
ATOM   1779  N   PRO A 263      20.450  13.115  20.483  1.00 28.32           N
ATOM   1780  CA  PRO A 263      20.933  13.156  19.102  1.00 28.06           C
ATOM   1781  CB  PRO A 263      21.636  11.790  18.912  1.00 27.77           C
ATOM   1782  CG  PRO A 263      21.996  11.300  20.217  1.00 27.38           C
ATOM   1783  CD  PRO A 263      21.086  12.024  21.260  1.00 28.41           C
ATOM   1784  C   PRO A 263      19.791  13.305  18.107  1.00 27.83           C
ATOM   1785  O   PRO A 263      19.910  14.093  17.173  1.00 28.48           O
ATOM   1786  N   LYS A 264      18.700  12.572  18.322  1.00 27.55           N
ATOM   1787  CA  LYS A 264      17.548  12.598  17.427  1.00 27.50           C
ATOM   1788  CB  LYS A 264      16.423  11.736  17.957  1.00 27.81           C
ATOM   1789  CG  LYS A 264      15.294  11.567  16.919  1.00 29.90           C
ATOM   1790  CD  LYS A 264      14.059  10.901  17.495  1.00 32.12           C
ATOM   1791  CE  LYS A 264      14.260   9.381  17.695  1.00 33.98           C
ATOM   1792  NZ  LYS A 264      12.949   8.663  17.842  1.00 34.46           N
ATOM   1793  C   LYS A 264      16.987  14.012  17.181  1.00 26.49           C
ATOM   1794  O   LYS A 264      16.522  14.309  16.098  1.00 27.26           O
ATOM   1795  N   THR A 265      17.040  14.889  18.173  1.00 25.14           N
ATOM   1796  CA  THR A 265      16.453  16.212  18.001  1.00 22.86           C
ATOM   1797  CB  THR A 265      15.350  16.462  19.060  1.00 22.37           C
ATOM   1798  OG1 THR A 265      15.902  16.214  20.361  1.00 20.91           O
ATOM   1799  CG2 THR A 265      14.109  15.546  18.794  1.00 19.67           C
ATOM   1800  C   THR A 265      17.484  17.342  18.003  1.00 23.27           C
ATOM   1801  O   THR A 265      17.101  18.519  18.000  1.00 22.64           O
ATOM   1802  N   THR A 266      18.788  17.009  17.942  1.00 23.24           N
ATOM   1803  CA  THR A 266      19.839  18.022  17.890  1.00 23.86           C
ATOM   1804  CB  THR A 266      21.265  17.408  17.610  1.00 23.91           C
ATOM   1805  OG1 THR A 266      21.535  16.436  18.610  1.00 28.24           O
ATOM   1806  CG2 THR A 266      22.310  18.441  17.760  1.00 22.12           C
ATOM   1807  C   THR A 266      19.582  19.150  16.884  1.00 23.79           C
ATOM   1808  O   THR A 266      19.841  20.315  17.162  1.00 23.59           O
ATOM   1809  N   ARG A 267      19.050  18.814  15.723  1.00 23.38           N
ATOM   1810  CA  ARG A 267      18.857  19.832  14.698  1.00 22.92           C
ATOM   1811  CB  ARG A 267      18.451  19.200  13.363  1.00 23.27           C
ATOM   1812  CG  ARG A 267      17.035  18.623  13.294  1.00 26.05           C
ATOM   1813  CD  ARG A 267      16.993  17.537  12.223  1.00 28.61           C
ATOM   1814  NE  ARG A 267      15.668  16.986  11.939  1.00 30.82           N
ATOM   1815  CZ  ARG A 267      14.774  17.591  11.157  1.00 31.99           C
ATOM   1816  NH1 ARG A 267      15.045  18.795  10.634  1.00 31.23           N
ATOM   1817  NH2 ARG A 267      13.611  16.995  10.901  1.00 32.53           N
ATOM   1818  C   ARG A 267      17.847  20.874  15.167  1.00 23.01           C
ATOM   1819  O   ARG A 267      18.012  22.072  14.897  1.00 22.74           O
```

FIGURE 3-26 (COORDINATES)

```
ATOM   1820  N   TRP A 268      16.833  20.419  15.913  1.00 21.73           N
ATOM   1821  CA  TRP A 268      15.874  21.341  16.515  1.00 21.56           C
ATOM   1822  CB  TRP A 268      14.581  20.617  16.919  1.00 20.69           C
ATOM   1823  CG  TRP A 268      13.929  20.001  15.705  1.00 20.57           C
ATOM   1824  CD1 TRP A 268      13.737  18.675  15.461  1.00 20.72           C
ATOM   1825  NE1 TRP A 268      13.118  18.504  14.232  1.00 21.41           N
ATOM   1826  CE2 TRP A 268      12.919  19.736  13.668  1.00 20.01           C
ATOM   1827  CD2 TRP A 268      13.417  20.700  14.563  1.00 19.16           C
ATOM   1828  CE3 TRP A 268      13.301  22.054  14.226  1.00 18.65           C
ATOM   1829  CZ3 TRP A 268      12.743  22.402  13.014  1.00 20.39           C
ATOM   1830  CH2 TRP A 268      12.276  21.424  12.121  1.00 19.46           C
ATOM   1831  CZ2 TRP A 268      12.349  20.088  12.425  1.00 21.01           C
ATOM   1832  C   TRP A 268      16.467  22.127  17.675  1.00 20.87           C
ATOM   1833  O   TRP A 268      16.180  23.308  17.796  1.00 21.54           O
ATOM   1834  N   PHE A 269      17.274  21.494  18.521  1.00 20.41           N
ATOM   1835  CA  PHE A 269      18.092  22.252  19.496  1.00 20.51           C
ATOM   1836  CB  PHE A 269      19.009  21.338  20.283  1.00 20.66           C
ATOM   1837  CG  PHE A 269      19.716  22.036  21.428  1.00 19.02           C
ATOM   1838  CD1 PHE A 269      19.079  22.170  22.663  1.00 19.42           C
ATOM   1839  CE1 PHE A 269      19.704  22.827  23.735  1.00 18.05           C
ATOM   1840  CZ  PHE A 269      21.009  23.340  23.557  1.00 19.93           C
ATOM   1841  CE2 PHE A 269      21.648  23.212  22.292  1.00 19.97           C
ATOM   1842  CD2 PHE A 269      20.987  22.572  21.250  1.00 18.17           C
ATOM   1843  C   PHE A 269      18.938  23.353  18.832  1.00 21.60           C
ATOM   1844  O   PHE A 269      19.016  24.475  19.363  1.00 22.31           O
ATOM   1845  N   ASN A 270      19.578  23.030  17.692  1.00 21.46           N
ATOM   1846  CA  ASN A 270      20.404  23.986  16.941  1.00 21.26           C
ATOM   1847  CB  ASN A 270      21.167  23.305  15.769  1.00 21.52           C
ATOM   1848  CG  ASN A 270      22.279  22.317  16.254  1.00 25.78           C
ATOM   1849  OD1 ASN A 270      22.774  21.467  15.484  1.00 29.72           O
ATOM   1850  ND2 ASN A 270      22.633  22.407  17.525  1.00 23.52           N
ATOM   1851  C   ASN A 270      19.529  25.155  16.449  1.00 20.47           C
ATOM   1852  O   ASN A 270      19.999  26.264  16.375  1.00 20.27           O
ATOM   1853  N   ARG A 271      18.253  24.894  16.118  1.00 19.26           N
ATOM   1854  CA  ARG A 271      17.369  25.974  15.744  1.00 17.47           C
ATOM   1855  CB  ARG A 271      16.017  25.459  15.212  1.00 17.66           C
ATOM   1856  CG  ARG A 271      16.120  24.770  13.875  1.00 19.11           C
ATOM   1857  CD  ARG A 271      16.738  25.659  12.857  1.00 21.65           C
ATOM   1858  NE  ARG A 271      16.033  26.945  12.726  1.00 20.04           N
ATOM   1859  CZ  ARG A 271      16.624  28.069  12.323  1.00 21.69           C
ATOM   1860  NH1 ARG A 271      17.921  28.045  12.025  1.00 24.07           N
ATOM   1861  NH2 ARG A 271      15.948  29.214  12.218  1.00 21.64           N
ATOM   1862  C   ARG A 271      17.171  26.946  16.886  1.00 17.86           C
ATOM   1863  O   ARG A 271      17.205  28.169  16.688  1.00 16.41           O
ATOM   1864  N   LEU A 272      16.951  26.407  18.088  1.00 17.62           N
ATOM   1865  CA  LEU A 272      16.791  27.267  19.269  1.00 19.10           C
ATOM   1866  CB  LEU A 272      16.486  26.413  20.516  1.00 18.98           C
ATOM   1867  CG  LEU A 272      15.062  25.807  20.555  1.00 19.68           C
ATOM   1868  CD1 LEU A 272      14.928  24.701  21.645  1.00 20.54           C
ATOM   1869  CD2 LEU A 272      13.964  26.900  20.781  1.00 20.81           C
ATOM   1870  C   LEU A 272      18.003  28.159  19.462  1.00 19.79           C
ATOM   1871  O   LEU A 272      17.848  29.369  19.673  1.00 19.92           O
ATOM   1872  N   GLN A 273      19.210  27.587  19.368  1.00 21.39           N
ATOM   1873  CA  GLN A 273      20.452  28.379  19.460  1.00 23.38           C
ATOM   1874  CB  GLN A 273      21.706  27.508  19.266  1.00 23.33           C
ATOM   1875  CG  GLN A 273      21.910  26.440  20.296  1.00 26.18           C
ATOM   1876  CD  GLN A 273      23.303  25.829  20.222  1.00 27.68           C
ATOM   1877  OE1 GLN A 273      23.610  25.069  19.287  1.00 34.98           O
ATOM   1878  NE2 GLN A 273      24.153  26.158  21.202  1.00 29.64           N
ATOM   1879  C   GLN A 273      20.508  29.497  18.422  1.00 21.66           C
ATOM   1880  O   GLN A 273      20.835  30.623  18.771  1.00 22.64           O
ATOM   1881  N   ALA A 274      20.193  29.171  17.165  1.00 21.37           N
ATOM   1882  CA  ALA A 274      20.221  30.139  16.058  1.00 20.38           C
ATOM   1883  CB  ALA A 274      19.988  29.425  14.715  1.00 20.39           C
ATOM   1884  C   ALA A 274      19.214  31.277  16.266  1.00 20.39           C
ATOM   1885  O   ALA A 274      19.516  32.435  16.006  1.00 19.65           O
ATOM   1886  N   ILE A 275      18.010  30.936  16.759  1.00 19.50           N
ATOM   1887  CA  ILE A 275      16.998  31.949  17.096  1.00 17.71           C
ATOM   1888  CB  ILE A 275      15.622  31.279  17.406  1.00 16.45           C
ATOM   1889  CG1 ILE A 275      15.078  30.583  16.125  1.00 17.03           C
```

FIGURE 3-27 (COORDINATES)

```
ATOM  1890  CD1 ILE A 275     14.131  29.352  16.400  1.00 14.90      C
ATOM  1891  CG2 ILE A 275     14.631  32.300  17.905  1.00 15.45      C
ATOM  1892  C   ILE A 275     17.442  32.871  18.236  1.00 18.62      C
ATOM  1893  O   ILE A 275     17.292  34.100  18.159  1.00 18.97      O
ATOM  1894  N   GLU A 276     17.934  32.290  19.321  1.00 18.17      N
ATOM  1895  CA  GLU A 276     18.520  33.098  20.401  1.00 19.00      C
ATOM  1896  CB  GLU A 276     19.224  32.195  21.406  1.00 17.55      C
ATOM  1897  CG  GLU A 276     19.770  33.003  22.612  1.00 18.97      C
ATOM  1898  CD  GLU A 276     20.454  32.157  23.630  1.00 19.03      C
ATOM  1899  OE1 GLU A 276     20.598  30.943  23.395  1.00 23.15      O
ATOM  1900  OE2 GLU A 276     20.801  32.702  24.691  1.00 18.56      O
ATOM  1901  C   GLU A 276     19.542  34.107  19.835  1.00 19.96      C
ATOM  1902  O   GLU A 276     19.513  35.302  20.147  1.00 18.51      O
ATOM  1903  N   LYS A 277     20.441  33.613  18.979  1.00 22.67      N
ATOM  1904  CA  LYS A 277     21.552  34.463  18.451  1.00 23.25      C
ATOM  1905  CB  LYS A 277     22.524  33.584  17.639  1.00 23.64      C
ATOM  1906  CG  LYS A 277     23.761  34.344  17.171  1.00 25.45      C
ATOM  1907  CD  LYS A 277     24.757  33.412  16.492  1.00 25.82      C
ATOM  1908  CE  LYS A 277     25.791  34.214  15.705  1.00 30.71      C
ATOM  1909  NZ  LYS A 277     26.138  33.455  14.458  1.00 32.78      N
ATOM  1910  C   LYS A 277     20.990  35.620  17.608  1.00 22.43      C
ATOM  1911  O   LYS A 277     21.306  36.796  17.848  1.00 23.45      O
ATOM  1912  N   GLU A 278     20.071  35.297  16.704  1.00 21.83      N
ATOM  1913  CA  GLU A 278     19.540  36.275  15.776  1.00 23.34      C
ATOM  1914  CB  GLU A 278     18.918  35.600  14.555  1.00 23.69      C
ATOM  1915  CG  GLU A 278     17.484  35.151  14.734  1.00 27.68      C
ATOM  1916  CD  GLU A 278     17.054  34.116  13.718  1.00 32.23      C
ATOM  1917  OE1 GLU A 278     17.806  33.851  12.754  1.00 35.95      O
ATOM  1918  OE2 GLU A 278     15.955  33.559  13.883  1.00 33.29      O
ATOM  1919  C   GLU A 278     18.631  37.296  16.479  1.00 22.68      C
ATOM  1920  O   GLU A 278     18.781  38.485  16.282  1.00 21.57      O
ATOM  1921  N   LEU A 279     17.764  36.857  17.390  1.00 23.29      N
ATOM  1922  CA  LEU A 279     17.026  37.853  18.191  1.00 22.51      C
ATOM  1923  CB  LEU A 279     16.003  37.186  19.087  1.00 22.40      C
ATOM  1924  CG  LEU A 279     14.810  36.480  18.427  1.00 21.66      C
ATOM  1925  CD1 LEU A 279     14.031  35.744  19.512  1.00 22.07      C
ATOM  1926  CD2 LEU A 279     13.890  37.480  17.667  1.00 20.78      C
ATOM  1927  C   LEU A 279     17.968  38.759  19.024  1.00 22.88      C
ATOM  1928  O   LEU A 279     17.739  39.961  19.136  1.00 21.91      O
ATOM  1929  N   TYR A 280     19.006  38.194  19.621  1.00 23.49      N
ATOM  1930  CA  TYR A 280     19.991  39.024  20.325  1.00 25.50      C
ATOM  1931  CB  TYR A 280     21.120  38.186  20.945  1.00 25.91      C
ATOM  1932  CG  TYR A 280     22.212  39.074  21.484  1.00 25.59      C
ATOM  1933  CD1 TYR A 280     22.042  39.726  22.690  1.00 26.20      C
ATOM  1934  CE1 TYR A 280     22.992  40.576  23.182  1.00 25.61      C
ATOM  1935  CZ  TYR A 280     24.166  40.811  22.450  1.00 25.56      C
ATOM  1936  OH  TYR A 280     25.079  41.677  22.994  1.00 28.02      O
ATOM  1937  CE2 TYR A 280     24.385  40.209  21.237  1.00 25.65      C
ATOM  1938  CD2 TYR A 280     23.396  39.320  20.741  1.00 26.19      C
ATOM  1939  C   TYR A 280     20.628  40.065  19.385  1.00 26.76      C
ATOM  1940  O   TYR A 280     20.748  41.242  19.746  1.00 26.05      O
ATOM  1941  N   GLU A 281     21.058  39.608  18.201  1.00 28.67      N
ATOM  1942  CA  GLU A 281     21.730  40.486  17.229  1.00 30.76      C
ATOM  1943  CB  GLU A 281     22.225  39.702  16.009  1.00 30.64      C
ATOM  1944  CG  GLU A 281     23.461  38.822  16.306  1.00 33.13      C
ATOM  1945  CD  GLU A 281     23.737  37.766  15.221  1.00 34.76      C
ATOM  1946  OE1 GLU A 281     22.801  37.369  14.457  1.00 40.74      O
ATOM  1947  OE2 GLU A 281     24.902  37.311  15.139  1.00 40.84      O
ATOM  1948  C   GLU A 281     20.833  41.651  16.823  1.00 30.49      C
ATOM  1949  O   GLU A 281     21.298  42.786  16.735  1.00 31.21      O
ATOM  1950  N   LEU A 282     19.539  41.377  16.643  1.00 29.83      N
ATOM  1951  CA  LEU A 282     18.558  42.379  16.190  1.00 29.25      C
ATOM  1952  CB  LEU A 282     17.347  41.681  15.545  1.00 29.38      C
ATOM  1953  CG  LEU A 282     17.507  40.995  14.182  1.00 32.84      C
ATOM  1954  CD1 LEU A 282     16.276  40.171  13.917  1.00 32.82      C
ATOM  1955  CD2 LEU A 282     18.779  40.123  13.988  1.00 38.46      C
ATOM  1956  C   LEU A 282     18.089  43.353  17.279  1.00 28.06      C
ATOM  1957  O   LEU A 282     17.286  44.241  16.999  1.00 29.53      O
ATOM  1958  N   GLY A 283     18.581  43.174  18.498  1.00 25.95      N
ATOM  1959  CA  GLY A 283     18.225  43.982  19.648  1.00 25.67      C
```

FIGURE 3-28 (COORDINATES)

```
ATOM   1960  C   GLY A 283      16.832  43.682  20.203  1.00 25.02           C
ATOM   1961  O   GLY A 283      16.223  44.546  20.818  1.00 24.75           O
ATOM   1962  N   LEU A 284      16.342  42.459  19.986  1.00 24.80           N
ATOM   1963  CA  LEU A 284      14.968  42.060  20.347  1.00 24.57           C
ATOM   1964  CB  LEU A 284      14.326  41.285  19.192  1.00 24.92           C
ATOM   1965  CG  LEU A 284      14.284  42.029  17.854  1.00 25.36           C
ATOM   1966  CD1 LEU A 284      13.889  41.047  16.729  1.00 26.36           C
ATOM   1967  CD2 LEU A 284      13.343  43.256  17.923  1.00 26.42           C
ATOM   1968  C   LEU A 284      14.912  41.229  21.640  1.00 24.41           C
ATOM   1969  O   LEU A 284      13.850  40.737  22.015  1.00 24.18           O
ATOM   1970  N   LEU A 285      16.048  41.076  22.313  1.00 23.37           N
ATOM   1971  CA  LEU A 285      16.064  40.445  23.632  1.00 23.60           C
ATOM   1972  CB  LEU A 285      17.071  39.312  23.669  1.00 23.17           C
ATOM   1973  CG  LEU A 285      16.821  38.117  22.752  1.00 21.85           C
ATOM   1974  CD1 LEU A 285      17.824  37.007  23.097  1.00 17.79           C
ATOM   1975  CD2 LEU A 285      15.360  37.565  22.782  1.00 18.14           C
ATOM   1976  C   LEU A 285      16.333  41.470  24.700  1.00 24.74           C
ATOM   1977  O   LEU A 285      16.746  42.580  24.390  1.00 25.73           O
ATOM   1978  N   LYS A 286      16.015  41.157  25.950  1.00 25.54           N
ATOM   1979  CA  LYS A 286      16.198  42.111  27.013  1.00 26.54           C
ATOM   1980  CB  LYS A 286      14.862  42.631  27.597  1.00 26.99           C
ATOM   1981  CG  LYS A 286      14.058  43.534  26.635  1.00 27.20           C
ATOM   1982  CD  LYS A 286      12.647  43.917  27.201  1.00 29.54           C
ATOM   1983  CE  LYS A 286      12.084  45.245  26.612  1.00 31.79           C
ATOM   1984  NZ  LYS A 286      11.080  45.123  25.529  1.00 33.84           N
ATOM   1985  C   LYS A 286      17.069  41.521  28.069  1.00 26.75           C
ATOM   1986  O   LYS A 286      16.894  40.369  28.471  1.00 26.08           O
ATOM   1987  N   ASP A 287      18.044  42.322  28.475  1.00 27.07           N
ATOM   1988  CA  ASP A 287      18.991  42.021  29.564  1.00 27.94           C
ATOM   1989  CB  ASP A 287      18.344  42.262  30.925  1.00 28.61           C
ATOM   1990  CG  ASP A 287      19.336  42.137  32.078  1.00 34.59           C
ATOM   1991  OD1 ASP A 287      20.507  42.579  31.923  1.00 41.06           O
ATOM   1992  OD2 ASP A 287      18.959  41.587  33.148  1.00 42.05           O
ATOM   1993  C   ASP A 287      19.640  40.646  29.464  1.00 27.45           C
ATOM   1994  O   ASP A 287      19.825  39.930  30.440  1.00 27.47           O
ATOM   1995  N   HIS A 288      19.994  40.265  28.257  1.00 27.21           N
ATOM   1996  CA  HIS A 288      20.608  38.963  28.079  1.00 26.56           C
ATOM   1997  CB  HIS A 288      19.562  37.911  27.681  1.00 25.42           C
ATOM   1998  CG  HIS A 288      20.143  36.548  27.440  1.00 22.35           C
ATOM   1999  ND1 HIS A 288      20.237  35.986  26.173  1.00 25.20           N
ATOM   2000  CE1 HIS A 288      20.795  34.786  26.259  1.00 19.31           C
ATOM   2001  NE2 HIS A 288      21.070  34.553  27.538  1.00 22.80           N
ATOM   2002  CD2 HIS A 288      20.683  35.648  28.293  1.00 17.36           C
ATOM   2003  C   HIS A 288      21.622  39.114  26.952  1.00 26.37           C
ATOM   2004  O   HIS A 288      21.248  39.454  25.831  1.00 26.25           O
ATOM   2005  N   SER A 289      22.890  38.878  27.260  1.00 26.21           N
ATOM   2006  CA  SER A 289      23.914  38.814  26.226  1.00 26.44           C
ATOM   2007  CB  SER A 289      25.217  39.427  26.739  1.00 25.94           C
ATOM   2008  OG  SER A 289      25.888  38.524  27.610  1.00 27.09           O
ATOM   2009  C   SER A 289      24.123  37.346  25.830  1.00 25.90           C
ATOM   2010  O   SER A 289      23.497  36.444  26.388  1.00 26.29           O
ATOM   2011  N   LEU A 290      25.032  37.093  24.904  1.00 25.06           N
ATOM   2012  CA  LEU A 290      25.389  35.717  24.565  1.00 23.77           C
ATOM   2013  CB  LEU A 290      25.579  35.574  23.044  1.00 23.68           C
ATOM   2014  CG  LEU A 290      24.344  35.994  22.202  1.00 25.38           C
ATOM   2015  CD1 LEU A 290      24.599  35.897  20.663  1.00 26.15           C
ATOM   2016  CD2 LEU A 290      23.099  35.197  22.581  1.00 22.50           C
ATOM   2017  C   LEU A 290      26.616  35.206  25.367  1.00 23.81           C
ATOM   2018  O   LEU A 290      27.215  34.169  25.030  1.00 22.27           O
ATOM   2019  N   GLU A 291      26.973  35.936  26.422  1.00 22.68           N
ATOM   2020  CA  GLU A 291      28.055  35.551  27.299  1.00 23.95           C
ATOM   2021  CB  GLU A 291      28.349  36.641  28.331  1.00 23.89           C
ATOM   2022  CG  GLU A 291      29.076  37.833  27.762  1.00 26.10           C
ATOM   2023  CD  GLU A 291      30.484  37.442  27.337  1.00 31.81           C
ATOM   2024  OE1 GLU A 291      31.207  36.884  28.183  1.00 31.24           O
ATOM   2025  OE2 GLU A 291      30.826  37.645  26.152  1.00 34.14           O
ATOM   2026  C   GLU A 291      27.734  34.261  28.017  1.00 24.27           C
ATOM   2027  O   GLU A 291      28.622  33.472  28.270  1.00 23.96           O
ATOM   2028  N   ARG A 292      26.454  34.061  28.341  1.00 24.72           N
ATOM   2029  CA  ARG A 292      25.961  32.805  28.877  1.00 25.14           C
```

FIGURE 3-29 (COORDINATES)

```
ATOM   2030  CB   ARG A 292      25.705  32.942  30.380  1.00 27.14           C
ATOM   2031  CG   ARG A 292      26.992  32.827  31.228  1.00 30.80           C
ATOM   2032  CD   ARG A 292      26.953  33.646  32.519  1.00 39.13           C
ATOM   2033  NE   ARG A 292      26.939  35.076  32.197  1.00 47.01           N
ATOM   2034  CZ   ARG A 292      25.876  35.871  32.350  1.00 49.85           C
ATOM   2035  NH1  ARG A 292      24.760  35.382  32.879  1.00 49.42           N
ATOM   2036  NH2  ARG A 292      25.935  37.160  31.995  1.00 50.78           N
ATOM   2037  C    ARG A 292      24.671  32.430  28.146  1.00 24.95           C
ATOM   2038  O    ARG A 292      23.587  32.582  28.683  1.00 23.53           O
ATOM   2039  N    LYS A 293      24.807  31.945  26.917  1.00 23.29           N
ATOM   2040  CA   LYS A 293      23.660  31.646  26.077  1.00 23.36           C
ATOM   2041  CB   LYS A 293      24.136  30.964  24.800  1.00 24.03           C
ATOM   2042  CG   LYS A 293      24.833  31.845  23.787  1.00 25.34           C
ATOM   2043  CD   LYS A 293      25.397  30.919  22.681  1.00 26.51           C
ATOM   2044  CE   LYS A 293      26.879  30.613  22.930  1.00 29.66           C
ATOM   2045  NZ   LYS A 293      27.239  29.413  22.140  1.00 36.21           N
ATOM   2046  C    LYS A 293      22.714  30.673  26.815  1.00 22.56           C
ATOM   2047  O    LYS A 293      23.166  29.834  27.604  1.00 22.84           O
ATOM   2048  N    TYR A 294      21.413  30.772  26.548  1.00 21.08           N
ATOM   2049  CA   TYR A 294      20.454  29.840  27.136  1.00 20.77           C
ATOM   2050  CB   TYR A 294      19.006  30.256  26.809  1.00 19.53           C
ATOM   2051  CG   TYR A 294      18.586  31.592  27.376  1.00 20.10           C
ATOM   2052  CD1  TYR A 294      18.863  31.922  28.688  1.00 17.01           C
ATOM   2053  CE1  TYR A 294      18.446  33.153  29.221  1.00 21.83           C
ATOM   2054  CZ   TYR A 294      17.731  34.061  28.393  1.00 20.92           C
ATOM   2055  OH   TYR A 294      17.332  35.280  28.898  1.00 20.17           O
ATOM   2056  CE2  TYR A 294      17.449  33.740  27.086  1.00 19.93           C
ATOM   2057  CD2  TYR A 294      17.895  32.525  26.570  1.00 18.59           C
ATOM   2058  C    TYR A 294      20.664  28.443  26.626  1.00 20.95           C
ATOM   2059  O    TYR A 294      20.553  27.472  27.385  1.00 21.00           O
ATOM   2060  N    PHE A 295      20.969  28.343  25.338  1.00 22.06           N
ATOM   2061  CA   PHE A 295      21.100  27.073  24.674  1.00 24.31           C
ATOM   2062  CB   PHE A 295      20.192  26.995  23.441  1.00 23.39           C
ATOM   2063  CG   PHE A 295      18.752  27.268  23.771  1.00 22.56           C
ATOM   2064  CD1  PHE A 295      17.953  26.260  24.311  1.00 22.30           C
ATOM   2065  CE1  PHE A 295      16.627  26.522  24.680  1.00 20.83           C
ATOM   2066  CZ   PHE A 295      16.102  27.797  24.505  1.00 18.26           C
ATOM   2067  CE2  PHE A 295      16.880  28.815  23.954  1.00 17.60           C
ATOM   2068  CD2  PHE A 295      18.214  28.555  23.615  1.00 21.63           C
ATOM   2069  C    PHE A 295      22.574  26.854  24.383  1.00 27.53           C
ATOM   2070  O    PHE A 295      23.138  27.408  23.412  1.00 26.28           O
ATOM   2071  N    GLN A 296      23.181  26.132  25.339  1.00 31.74           N
ATOM   2072  CA   GLN A 296      24.553  25.656  25.277  1.00 36.10           C
ATOM   2073  CB   GLN A 296      25.366  26.003  26.538  1.00 36.30           C
ATOM   2074  CG   GLN A 296      25.376  27.447  27.007  1.00 37.82           C
ATOM   2075  CD   GLN A 296      26.534  28.253  26.413  1.00 42.70           C
ATOM   2076  OE1  GLN A 296      26.939  28.032  25.259  1.00 43.50           O
ATOM   2077  NE2  GLN A 296      27.068  29.202  27.199  1.00 42.39           N
ATOM   2078  C    GLN A 296      24.499  24.136  25.172  1.00 38.89           C
ATOM   2079  O    GLN A 296      23.754  23.432  25.930  1.00 38.72           O
ATOM   2080  N    ASN A 297      25.299  23.668  24.219  1.00 41.18           N
ATOM   2081  CA   ASN A 297      25.653  22.281  24.006  1.00 44.03           C
ATOM   2082  CB   ASN A 297      25.101  21.945  22.599  1.00 43.86           C
ATOM   2083  CG   ASN A 297      25.335  20.507  22.167  1.00 43.93           C
ATOM   2084  OD1  ASN A 297      26.058  19.736  22.809  1.00 44.53           O
ATOM   2085  ND2  ASN A 297      24.728  20.142  21.048  1.00 43.76           N
ATOM   2086  C    ASN A 297      27.208  22.309  23.990  1.00 45.31           C
ATOM   2087  O    ASN A 297      27.740  22.709  22.970  1.00 46.31           O
ATOM   2088  N    PHE A 298      27.995  21.936  25.010  1.00 47.70           N
ATOM   2089  CA   PHE A 298      27.778  21.001  26.126  1.00 49.43           C
ATOM   2090  CB   PHE A 298      26.948  21.614  27.266  1.00 51.26           C
ATOM   2091  CG   PHE A 298      27.212  20.993  28.635  1.00 54.14           C
ATOM   2092  CD1  PHE A 298      27.363  21.808  29.768  1.00 57.96           C
ATOM   2093  CE1  PHE A 298      27.608  21.253  31.052  1.00 57.93           C
ATOM   2094  CZ   PHE A 298      27.704  19.871  31.196  1.00 56.93           C
ATOM   2095  CE2  PHE A 298      27.549  19.045  30.073  1.00 57.48           C
ATOM   2096  CD2  PHE A 298      27.303  19.608  28.801  1.00 56.54           C
ATOM   2097  C    PHE A 298      27.186  19.712  25.607  1.00 49.46           C
ATOM   2098  O    PHE A 298      25.980  19.653  25.401  1.00 51.39           O
ATOM   2099  N    GLY A 299      28.011  18.687  25.386  1.00 48.24           N
```

FIGURE 3-30 (COORDINATES)

```
ATOM   2100  CA  GLY A 299      27.560  17.415  24.777  1.00 47.02           C
ATOM   2101  C   GLY A 299      26.230  16.851  25.260  1.00 46.28           C
ATOM   2102  O   GLY A 299      25.574  17.439  26.125  1.00 46.69           O
ATOM   2103  N   TYR A 300      25.816  15.699  24.731  1.00 44.90           N
ATOM   2104  CA  TYR A 300      24.500  15.172  25.088  1.00 43.19           C
ATOM   2105  CB  TYR A 300      24.141  13.904  24.311  1.00 42.99           C
ATOM   2106  CG  TYR A 300      24.026  14.214  22.842  1.00 42.37           C
ATOM   2107  CD1 TYR A 300      23.028  15.054  22.377  1.00 41.99           C
ATOM   2108  CE1 TYR A 300      22.931  15.380  21.055  1.00 43.60           C
ATOM   2109  CZ  TYR A 300      23.853  14.867  20.148  1.00 44.35           C
ATOM   2110  OH  TYR A 300      23.770  15.203  18.813  1.00 43.77           O
ATOM   2111  CE2 TYR A 300      24.866  14.035  20.583  1.00 43.45           C
ATOM   2112  CD2 TYR A 300      24.951  13.722  21.931  1.00 41.63           C
ATOM   2113  C   TYR A 300      24.345  15.013  26.593  1.00 42.57           C
ATOM   2114  O   TYR A 300      25.027  14.172  27.213  1.00 42.01           O
ATOM   2115  N   GLY A 301      23.462  15.868  27.154  1.00 41.17           N
ATOM   2116  CA  GLY A 301      23.046  15.828  28.554  1.00 38.98           C
ATOM   2117  C   GLY A 301      22.526  14.455  28.971  1.00 37.50           C
ATOM   2118  O   GLY A 301      22.052  13.677  28.159  1.00 37.72           O
ATOM   2119  N   ASN A 302      22.660  14.148  30.249  1.00 37.28           N
ATOM   2120  CA  ASN A 302      22.131  12.919  30.821  1.00 35.38           C
ATOM   2121  CB  ASN A 302      22.898  12.536  32.062  1.00 36.30           C
ATOM   2122  CG  ASN A 302      24.311  12.049  31.750  1.00 39.40           C
ATOM   2123  OD1 ASN A 302      24.510  11.073  31.008  1.00 43.70           O
ATOM   2124  ND2 ASN A 302      25.291  12.725  32.312  1.00 38.38           N
ATOM   2125  C   ASN A 302      20.680  13.178  31.173  1.00 33.60           C
ATOM   2126  O   ASN A 302      20.351  14.203  31.774  1.00 32.12           O
ATOM   2127  N   ILE A 303      19.827  12.246  30.754  1.00 31.56           N
ATOM   2128  CA  ILE A 303      18.376  12.395  30.761  1.00 29.41           C
ATOM   2129  CB  ILE A 303      17.742  11.137  30.154  1.00 29.91           C
ATOM   2130  CG1 ILE A 303      16.259  11.332  29.856  1.00 29.86           C
ATOM   2131  CD1 ILE A 303      15.689  10.200  29.021  1.00 32.93           C
ATOM   2132  CG2 ILE A 303      18.007   9.869  31.069  1.00 32.53           C
ATOM   2133  C   ILE A 303      17.872  12.647  32.178  1.00 28.25           C
ATOM   2134  O   ILE A 303      18.412  12.066  33.126  1.00 26.68           O
ATOM   2135  N   ILE A 304      16.892  13.556  32.325  1.00 26.18           N
ATOM   2136  CA  ILE A 304      16.266  13.822  33.634  1.00 24.38           C
ATOM   2137  CB  ILE A 304      16.283  15.325  34.005  1.00 24.67           C
ATOM   2138  CG1 ILE A 304      17.734  15.840  34.105  1.00 23.78           C
ATOM   2139  CD1 ILE A 304      17.877  17.331  33.863  1.00 20.91           C
ATOM   2140  CG2 ILE A 304      15.402  15.617  35.279  1.00 23.90           C
ATOM   2141  C   ILE A 304      14.832  13.287  33.523  1.00 23.20           C
ATOM   2142  O   ILE A 304      14.157  13.533  32.516  1.00 23.96           O
ATOM   2143  N   GLN A 305      14.382  12.506  34.496  1.00 20.87           N
ATOM   2144  CA  GLN A 305      13.016  11.950  34.421  1.00 19.71           C
ATOM   2145  CB  GLN A 305      12.710  10.979  35.574  1.00 19.10           C
ATOM   2146  CG  GLN A 305      13.699   9.803  35.672  1.00 18.76           C
ATOM   2147  CD  GLN A 305      13.717   8.970  34.402  1.00 21.84           C
ATOM   2148  OE1 GLN A 305      12.707   8.333  34.049  1.00 20.70           O
ATOM   2149  NE2 GLN A 305      14.856   8.968  33.705  1.00 21.81           N
ATOM   2150  C   GLN A 305      11.988  13.063  34.414  1.00 18.78           C
ATOM   2151  O   GLN A 305      12.099  14.031  35.187  1.00 19.79           O
ATOM   2152  N   ASP A 306      10.993  12.944  33.540  1.00 17.97           N
ATOM   2153  CA  ASP A 306       9.923  13.974  33.436  1.00 17.33           C
ATOM   2154  CB  ASP A 306      10.520  15.295  32.846  1.00 16.27           C
ATOM   2155  CG  ASP A 306       9.743  16.544  33.218  1.00 15.42           C
ATOM   2156  OD1 ASP A 306       8.629  16.445  33.758  1.00 18.34           O
ATOM   2157  OD2 ASP A 306      10.225  17.648  32.922  1.00 15.86           O
ATOM   2158  C   ASP A 306       8.856  13.414  32.510  1.00 17.10           C
ATOM   2159  O   ASP A 306       8.950  12.265  32.049  1.00 16.68           O
ATOM   2160  N   ASP A 307       7.873  14.252  32.181  1.00 17.46           N
ATOM   2161  CA  ASP A 307       6.704  13.816  31.426  1.00 15.83           C
ATOM   2162  CB  ASP A 307       5.692  14.953  31.340  1.00 15.45           C
ATOM   2163  CG  ASP A 307       4.861  15.098  32.599  1.00 16.86           C
ATOM   2164  OD1 ASP A 307       4.391  14.069  33.190  1.00 17.35           O
ATOM   2165  OD2 ASP A 307       4.630  16.270  32.972  1.00 16.31           O
ATOM   2166  C   ASP A 307       7.014  13.344  30.033  1.00 15.07           C
ATOM   2167  O   ASP A 307       6.156  12.754  29.391  1.00 15.36           O
ATOM   2168  N   HIS A 308       8.213  13.615  29.520  1.00 15.21           N
ATOM   2169  CA  HIS A 308       8.559  13.079  28.176  1.00 16.18           C
```

FIGURE 3-31 (COORDINATES)

```
ATOM   2170  CB  HIS A 308       9.718  13.846  27.584  1.00 15.53           C
ATOM   2171  CG  HIS A 308      10.989  13.735  28.385  1.00 16.80           C
ATOM   2172  ND1 HIS A 308      11.047  13.980  29.738  1.00 15.96           N
ATOM   2173  CE1 HIS A 308      12.290  13.807  30.166  1.00 15.52           C
ATOM   2174  NE2 HIS A 308      13.034  13.453  29.135  1.00 15.44           N
ATOM   2175  CD2 HIS A 308      12.243  13.391  28.013  1.00 17.00           C
ATOM   2176  C   HIS A 308       8.904  11.572  28.172  1.00 17.78           C
ATOM   2177  O   HIS A 308       8.902  10.914  27.103  1.00 18.91           O
ATOM   2178  N   ILE A 309       9.236  11.043  29.344  1.00 18.65           N
ATOM   2179  CA  ILE A 309       9.720   9.660  29.462  1.00 18.90           C
ATOM   2180  CB  ILE A 309      10.111   9.320  30.938  1.00 19.68           C
ATOM   2181  CG1 ILE A 309      11.427  10.043  31.328  1.00 20.14           C
ATOM   2182  CD1 ILE A 309      12.625   9.889  30.382  1.00 20.25           C
ATOM   2183  CG2 ILE A 309      10.131   7.793  31.213  1.00 21.12           C
ATOM   2184  C   ILE A 309       8.789   8.600  28.849  1.00 18.27           C
ATOM   2185  O   ILE A 309       9.256   7.764  28.068  1.00 17.22           O
ATOM   2186  N   PRO A 310       7.477   8.601  29.217  1.00 17.95           N
ATOM   2187  CA  PRO A 310       6.557   7.648  28.586  1.00 17.53           C
ATOM   2188  CB  PRO A 310       5.186   8.019  29.197  1.00 16.92           C
ATOM   2189  CG  PRO A 310       5.503   8.729  30.470  1.00 17.54           C
ATOM   2190  CD  PRO A 310       6.787   9.442  30.220  1.00 16.67           C
ATOM   2191  C   PRO A 310       6.452   7.776  27.074  1.00 19.00           C
ATOM   2192  O   PRO A 310       6.259   6.779  26.394  1.00 18.73           O
ATOM   2193  N   PHE A 311       6.555   9.002  26.550  1.00 19.87           N
ATOM   2194  CA  PHE A 311       6.613   9.228  25.095  1.00 20.16           C
ATOM   2195  CB  PHE A 311       6.254  10.695  24.772  1.00 17.92           C
ATOM   2196  CG  PHE A 311       4.887  11.067  25.248  1.00 18.55           C
ATOM   2197  CD1 PHE A 311       4.692  11.545  26.569  1.00 15.56           C
ATOM   2198  CE1 PHE A 311       3.421  11.847  27.037  1.00 12.98           C
ATOM   2199  CZ  PHE A 311       2.340  11.697  26.220  1.00 16.27           C
ATOM   2200  CE2 PHE A 311       2.496  11.212  24.879  1.00 18.04           C
ATOM   2201  CD2 PHE A 311       3.778  10.882  24.414  1.00 17.11           C
ATOM   2202  C   PHE A 311       7.933   8.825  24.478  1.00 21.11           C
ATOM   2203  O   PHE A 311       7.952   8.198  23.410  1.00 22.13           O
ATOM   2204  N   LEU A 312       9.041   9.198  25.109  1.00 22.95           N
ATOM   2205  CA  LEU A 312      10.359   8.800  24.603  1.00 25.50           C
ATOM   2206  CB  LEU A 312      11.454   9.354  25.515  1.00 24.33           C
ATOM   2207  CG  LEU A 312      12.890   9.309  25.012  1.00 23.62           C
ATOM   2208  CD1 LEU A 312      13.198  10.379  23.960  1.00 25.54           C
ATOM   2209  CD2 LEU A 312      13.787   9.516  26.180  1.00 28.03           C
ATOM   2210  C   LEU A 312      10.491   7.248  24.457  1.00 26.95           C
ATOM   2211  O   LEU A 312      11.048   6.770  23.459  1.00 27.48           O
ATOM   2212  N   ARG A 313      10.070   6.505  25.482  1.00 28.22           N
ATOM   2213  CA  ARG A 313       9.923   5.062  25.343  1.00 29.52           C
ATOM   2214  CB  ARG A 313       8.792   4.522  26.237  1.00 29.96           C
ATOM   2215  CG  ARG A 313       9.053   4.473  27.724  1.00 34.13           C
ATOM   2216  CD  ARG A 313       8.175   3.414  28.390  1.00 38.58           C
ATOM   2217  NE  ARG A 313       8.193   2.179  27.623  1.00 45.70           N
ATOM   2218  CZ  ARG A 313       7.121   1.584  27.117  1.00 46.99           C
ATOM   2219  NH1 ARG A 313       7.255   0.471  26.426  1.00 46.85           N
ATOM   2220  NH2 ARG A 313       5.918   2.080  27.316  1.00 45.52           N
ATOM   2221  C   ARG A 313       9.483   4.903  23.896  1.00 30.71           C
ATOM   2222  O   ARG A 313      10.286   4.633  23.000  1.00 31.34           O
ATOM   2223  N   LYS A 314       8.186   5.106  23.692  1.00 30.43           N
ATOM   2224  CA  LYS A 314       7.517   4.742  22.465  1.00 30.45           C
ATOM   2225  CB  LYS A 314       6.056   5.194  22.518  1.00 31.01           C
ATOM   2226  CG  LYS A 314       5.310   4.826  23.789  1.00 34.41           C
ATOM   2227  CD  LYS A 314       5.099   3.333  23.967  1.00 39.98           C
ATOM   2228  CE  LYS A 314       4.356   2.693  22.813  1.00 41.77           C
ATOM   2229  NZ  LYS A 314       4.039   1.298  23.187  1.00 45.56           N
ATOM   2230  C   LYS A 314       8.173   5.312  21.195  1.00 29.30           C
ATOM   2231  O   LYS A 314       7.609   5.189  20.113  1.00 29.33           O
ATOM   2232  N   GLY A 315       9.337   5.943  21.307  1.00 27.41           N
ATOM   2233  CA  GLY A 315      10.025   6.456  20.100  1.00 26.63           C
ATOM   2234  C   GLY A 315       9.658   7.858  19.596  1.00 25.73           C
ATOM   2235  O   GLY A 315      10.084   8.261  18.485  1.00 27.04           O
ATOM   2236  N   VAL A 316       8.853   8.594  20.368  1.00 23.89           N
ATOM   2237  CA  VAL A 316       8.462   9.989  19.991  1.00 22.35           C
ATOM   2238  CB  VAL A 316       7.273  10.517  20.865  1.00 21.85           C
ATOM   2239  CG1 VAL A 316       6.987  12.031  20.644  1.00 20.98           C
```

FIGURE 3-32 (COORDINATES)

```
ATOM   2240  CG2 VAL A 316       6.012   9.685  20.668  1.00 21.49           C
ATOM   2241  C   VAL A 316       9.690  10.893  20.154  1.00 21.11           C
ATOM   2242  O   VAL A 316      10.359  10.826  21.190  1.00 21.32           O
ATOM   2243  N   PRO A 317      10.025  11.693  19.117  1.00 21.28           N
ATOM   2244  CA  PRO A 317      11.108  12.653  19.210  1.00 20.83           C
ATOM   2245  CB  PRO A 317      11.131  13.285  17.825  1.00 21.79           C
ATOM   2246  CG  PRO A 317      10.514  12.231  16.927  1.00 21.20           C
ATOM   2247  CD  PRO A 317       9.414  11.700  17.766  1.00 20.94           C
ATOM   2248  C   PRO A 317      10.798  13.692  20.269  1.00 20.20           C
ATOM   2249  O   PRO A 317       9.672  14.224  20.332  1.00 19.23           O
ATOM   2250  N   VAL A 318      11.791  13.952  21.115  1.00 20.82           N
ATOM   2251  CA  VAL A 318      11.637  14.872  22.259  1.00 20.43           C
ATOM   2252  CB  VAL A 318      11.703  14.136  23.632  1.00 20.67           C
ATOM   2253  CG1 VAL A 318      11.612  15.160  24.823  1.00 20.11           C
ATOM   2254  CG2 VAL A 318      10.564  13.108  23.758  1.00 21.34           C
ATOM   2255  C   VAL A 318      12.664  15.970  22.251  1.00 20.37           C
ATOM   2256  O   VAL A 318      13.869  15.730  22.030  1.00 20.44           O
ATOM   2257  N   LEU A 319      12.179  17.191  22.494  1.00 19.16           N
ATOM   2258  CA  LEU A 319      13.031  18.300  22.884  1.00 17.98           C
ATOM   2259  CB  LEU A 319      12.794  19.468  21.931  1.00 18.90           C
ATOM   2260  CG  LEU A 319      13.798  20.577  21.751  1.00 20.84           C
ATOM   2261  CD1 LEU A 319      15.225  20.047  21.435  1.00 18.62           C
ATOM   2262  CD2 LEU A 319      13.255  21.438  20.607  1.00 17.60           C
ATOM   2263  C   LEU A 319      12.676  18.689  24.330  1.00 17.95           C
ATOM   2264  O   LEU A 319      11.577  19.207  24.592  1.00 16.61           O
ATOM   2265  N   HIS A 320      13.589  18.412  25.267  1.00 16.03           N
ATOM   2266  CA  HIS A 320      13.274  18.573  26.671  1.00 15.62           C
ATOM   2267  CB  HIS A 320      13.729  17.361  27.495  1.00 15.96           C
ATOM   2268  CG  HIS A 320      13.231  17.373  28.900  1.00 15.04           C
ATOM   2269  ND1 HIS A 320      13.836  16.651  29.905  1.00 17.64           N
ATOM   2270  CE1 HIS A 320      13.169  16.823  31.033  1.00 18.97           C
ATOM   2271  NE2 HIS A 320      12.176  17.671  30.807  1.00 14.34           N
ATOM   2272  CD2 HIS A 320      12.205  18.040  29.481  1.00 13.72           C
ATOM   2273  C   HIS A 320      13.885  19.871  27.140  1.00 16.22           C
ATOM   2274  O   HIS A 320      15.144  20.000  27.351  1.00 16.38           O
ATOM   2275  N   LEU A 321      13.032  20.880  27.198  1.00 14.72           N
ATOM   2276  CA  LEU A 321      13.485  22.209  27.555  1.00 15.88           C
ATOM   2277  CB  LEU A 321      12.737  23.269  26.750  1.00 14.54           C
ATOM   2278  CG  LEU A 321      12.787  23.243  25.205  1.00 15.90           C
ATOM   2279  CD1 LEU A 321      12.250  24.566  24.713  1.00 13.85           C
ATOM   2280  CD2 LEU A 321      14.225  23.105  24.759  1.00 19.17           C
ATOM   2281  C   LEU A 321      13.328  22.424  29.058  1.00 16.38           C
ATOM   2282  O   LEU A 321      12.406  23.106  29.523  1.00 15.94           O
ATOM   2283  N   ILE A 322      14.261  21.836  29.805  1.00 17.73           N
ATOM   2284  CA  ILE A 322      14.322  21.924  31.276  1.00 17.28           C
ATOM   2285  CB  ILE A 322      14.212  20.506  31.928  1.00 18.39           C
ATOM   2286  CG1 ILE A 322      14.158  20.604  33.473  1.00 17.29           C
ATOM   2287  CD1 ILE A 322      13.788  19.266  34.175  1.00 17.43           C
ATOM   2288  CG2 ILE A 322      15.369  19.531  31.445  1.00 16.72           C
ATOM   2289  C   ILE A 322      15.657  22.597  31.674  1.00 19.07           C
ATOM   2290  O   ILE A 322      16.710  22.241  31.135  1.00 17.31           O
ATOM   2291  N   ALA A 323      15.581  23.622  32.531  1.00 18.91           N
ATOM   2292  CA  ALA A 323      16.771  24.303  33.032  1.00 21.86           C
ATOM   2293  CB  ALA A 323      16.370  25.618  33.797  1.00 21.41           C
ATOM   2294  C   ALA A 323      17.559  23.392  33.931  1.00 23.10           C
ATOM   2295  O   ALA A 323      17.017  22.789  34.870  1.00 21.88           O
ATOM   2296  N   SER A 324      18.856  23.293  33.654  1.00 26.89           N
ATOM   2297  CA  SER A 324      19.738  22.377  34.404  1.00 28.70           C
ATOM   2298  CB  SER A 324      19.769  20.955  33.805  1.00 29.80           C
ATOM   2299  OG  SER A 324      20.643  20.100  34.578  1.00 32.77           O
ATOM   2300  C   SER A 324      21.109  22.996  34.445  1.00 29.26           C
ATOM   2301  O   SER A 324      21.716  23.175  33.383  1.00 29.13           O
ATOM   2302  N   PRO A 325      21.571  23.388  35.672  1.00 29.46           N
ATOM   2303  CA  PRO A 325      21.012  22.976  37.004  1.00 28.32           C
ATOM   2304  CB  PRO A 325      22.097  23.482  37.995  1.00 28.69           C
ATOM   2305  CG  PRO A 325      22.592  24.746  37.330  1.00 30.78           C
ATOM   2306  CD  PRO A 325      22.696  24.338  35.845  1.00 29.99           C
ATOM   2307  C   PRO A 325      19.615  23.501  37.413  1.00 25.37           C
ATOM   2308  O   PRO A 325      19.208  24.573  36.987  1.00 26.56           O
ATOM   2309  N   PHE A 326      18.923  22.763  38.271  1.00 23.35           N
```

FIGURE 3-33 (COORDINATES)

```
ATOM   2310  CA   PHE A 326      17.612  23.180  38.834  1.00 21.58           C
ATOM   2311  CB   PHE A 326      17.051  22.139  39.852  1.00 20.63           C
ATOM   2312  CG   PHE A 326      16.748  20.764  39.287  1.00 20.22           C
ATOM   2313  CD1  PHE A 326      16.769  20.497  37.920  1.00 20.05           C
ATOM   2314  CE1  PHE A 326      16.485  19.210  37.450  1.00 20.43           C
ATOM   2315  CZ   PHE A 326      16.171  18.180  38.361  1.00 20.53           C
ATOM   2316  CE2  PHE A 326      16.135  18.443  39.716  1.00 23.83           C
ATOM   2317  CD2  PHE A 326      16.437  19.726  40.167  1.00 21.70           C
ATOM   2318  C    PHE A 326      17.771  24.524  39.583  1.00 21.14           C
ATOM   2319  O    PHE A 326      18.832  24.760  40.145  1.00 20.93           O
ATOM   2320  N    PRO A 327      16.721  25.385  39.584  1.00 19.87           N
ATOM   2321  CA   PRO A 327      16.646  26.624  40.381  1.00 20.07           C
ATOM   2322  CB   PRO A 327      15.163  27.028  40.253  1.00 19.15           C
ATOM   2323  CG   PRO A 327      14.755  26.520  38.836  1.00 19.80           C
ATOM   2324  CD   PRO A 327      15.505  25.180  38.748  1.00 19.84           C
ATOM   2325  C    PRO A 327      16.993  26.316  41.853  1.00 19.69           C
ATOM   2326  O    PRO A 327      16.619  25.252  42.359  1.00 19.42           O
ATOM   2327  N    GLU A 328      17.693  27.227  42.524  1.00 20.41           N
ATOM   2328  CA   GLU A 328      17.912  27.152  43.980  1.00 20.73           C
ATOM   2329  CB   GLU A 328      18.538  28.473  44.510  1.00 22.13           C
ATOM   2330  CG   GLU A 328      19.086  28.359  45.954  1.00 23.64           C
ATOM   2331  CD   GLU A 328      18.059  28.487  47.061  1.00 27.54           C
ATOM   2332  OE1  GLU A 328      17.038  29.197  46.890  1.00 28.74           O
ATOM   2333  OE2  GLU A 328      18.295  27.863  48.128  1.00 27.87           O
ATOM   2334  C    GLU A 328      16.614  26.900  44.716  1.00 20.21           C
ATOM   2335  O    GLU A 328      16.577  26.145  45.705  1.00 19.93           O
ATOM   2336  N    VAL A 329      15.532  27.520  44.226  1.00 19.28           N
ATOM   2337  CA   VAL A 329      14.228  27.437  44.876  1.00 18.59           C
ATOM   2338  CB   VAL A 329      13.324  28.624  44.485  1.00 20.12           C
ATOM   2339  CG1  VAL A 329      13.998  29.902  44.851  1.00 18.65           C
ATOM   2340  CG2  VAL A 329      12.944  28.565  42.991  1.00 18.38           C
ATOM   2341  C    VAL A 329      13.459  26.142  44.610  1.00 18.12           C
ATOM   2342  O    VAL A 329      12.377  25.940  45.178  1.00 17.90           O
ATOM   2343  N    TRP A 330      14.024  25.258  43.781  1.00 18.28           N
ATOM   2344  CA   TRP A 330      13.370  23.973  43.415  1.00 18.35           C
ATOM   2345  CB   TRP A 330      14.339  23.097  42.612  1.00 18.06           C
ATOM   2346  CG   TRP A 330      13.745  21.800  42.066  1.00 18.69           C
ATOM   2347  CD1  TRP A 330      13.016  21.651  40.912  1.00 19.24           C
ATOM   2348  NE1  TRP A 330      12.714  20.306  40.706  1.00 17.21           N
ATOM   2349  CE2  TRP A 330      13.218  19.581  41.757  1.00 17.98           C
ATOM   2350  CD2  TRP A 330      13.894  20.478  42.617  1.00 19.43           C
ATOM   2351  CE3  TRP A 330      14.548  19.962  43.756  1.00 22.25           C
ATOM   2352  CZ3  TRP A 330      14.489  18.601  43.997  1.00 18.41           C
ATOM   2353  CH2  TRP A 330      13.790  17.742  43.130  1.00 20.86           C
ATOM   2354  CZ2  TRP A 330      13.154  18.218  42.010  1.00 17.16           C
ATOM   2355  C    TRP A 330      12.813  23.175  44.612  1.00 19.20           C
ATOM   2356  O    TRP A 330      13.551  22.835  45.561  1.00 19.19           O
ATOM   2357  N    HIS A 331      11.510  22.893  44.549  1.00 17.83           N
ATOM   2358  CA   HIS A 331      10.747  22.161  45.590  1.00 17.95           C
ATOM   2359  CB   HIS A 331      11.162  20.664  45.664  1.00 16.85           C
ATOM   2360  CG   HIS A 331      10.675  19.852  44.494  1.00 18.00           C
ATOM   2361  ND1  HIS A 331      10.748  18.470  44.443  1.00 16.15           N
ATOM   2362  CE1  HIS A 331      10.287  18.047  43.276  1.00 17.22           C
ATOM   2363  NE2  HIS A 331       9.844  19.095  42.596  1.00 16.46           N
ATOM   2364  CD2  HIS A 331      10.087  20.240  43.328  1.00 15.86           C
ATOM   2365  C    HIS A 331      10.793  22.841  46.973  1.00 19.07           C
ATOM   2366  O    HIS A 331      10.644  22.178  47.984  1.00 18.71           O
ATOM   2367  N    THR A 332      10.966  24.163  46.994  1.00 18.07           N
ATOM   2368  CA   THR A 332      10.848  24.936  48.232  1.00 18.12           C
ATOM   2369  CB   THR A 332      12.134  25.773  48.533  1.00 17.50           C
ATOM   2370  OG1  THR A 332      12.190  26.940  47.684  1.00 16.90           O
ATOM   2371  CG2  THR A 332      13.348  24.933  48.324  1.00 14.55           C
ATOM   2372  C    THR A 332       9.682  25.872  48.121  1.00 18.89           C
ATOM   2373  O    THR A 332       9.244  26.208  46.993  1.00 18.88           O
ATOM   2374  N    MET A 333       9.210  26.344  49.263  1.00 19.82           N
ATOM   2375  CA   MET A 333       8.141  27.365  49.316  1.00 22.28           C
ATOM   2376  CB   MET A 333       7.786  27.740  50.759  1.00 23.07           C
ATOM   2377  CG   MET A 333       7.287  26.606  51.620  1.00 29.02           C
ATOM   2378  SD   MET A 333       5.720  25.970  51.077  1.00 38.79           S
ATOM   2379  CE   MET A 333       5.434  24.610  52.190  1.00 27.71           C
```

FIGURE 3-34 (COORDINATES)

```
ATOM   2380  C    MET A 333       8.524  28.651  48.599  1.00 21.65           C
ATOM   2381  O    MET A 333       7.656  29.466  48.328  1.00 23.07           O
ATOM   2382  N    ASP A 334       9.811  28.835  48.314  1.00 21.09           N
ATOM   2383  CA   ASP A 334      10.309  30.055  47.648  1.00 20.69           C
ATOM   2384  CB   ASP A 334      11.696  30.413  48.157  1.00 20.60           C
ATOM   2385  CG   ASP A 334      11.672  30.773  49.653  1.00 23.32           C
ATOM   2386  OD1  ASP A 334      11.022  31.785  50.019  1.00 24.62           O
ATOM   2387  OD2  ASP A 334      12.269  30.015  50.437  1.00 22.45           O
ATOM   2388  C    ASP A 334      10.336  29.945  46.147  1.00 19.29           C
ATOM   2389  O    ASP A 334      10.842  30.839  45.465  1.00 18.50           O
ATOM   2390  N    ASP A 335       9.826  28.830  45.639  1.00 18.18           N
ATOM   2391  CA   ASP A 335       9.588  28.729  44.196  1.00 17.79           C
ATOM   2392  CB   ASP A 335       9.580  27.292  43.703  1.00 16.70           C
ATOM   2393  CG   ASP A 335       9.465  27.216  42.191  1.00 16.83           C
ATOM   2394  OD1  ASP A 335       9.500  28.249  41.521  1.00 15.35           O
ATOM   2395  OD2  ASP A 335       9.399  26.115  41.678  1.00 18.57           O
ATOM   2396  C    ASP A 335       8.269  29.427  43.934  1.00 17.07           C
ATOM   2397  O    ASP A 335       7.222  28.814  43.795  1.00 16.21           O
ATOM   2398  N    ASN A 336       8.360  30.746  43.932  1.00 17.57           N
ATOM   2399  CA   ASN A 336       7.196  31.616  43.919  1.00 18.15           C
ATOM   2400  CB   ASN A 336       6.890  32.156  45.322  1.00 17.60           C
ATOM   2401  CG   ASN A 336       8.054  32.970  45.958  1.00 20.15           C
ATOM   2402  OD1  ASN A 336       8.093  33.115  47.185  1.00 23.48           O
ATOM   2403  ND2  ASN A 336       8.973  33.488  45.153  1.00 12.61           N
ATOM   2404  C    ASN A 336       7.386  32.769  42.935  1.00 17.57           C
ATOM   2405  O    ASN A 336       8.420  32.859  42.273  1.00 16.61           O
ATOM   2406  N    GLU A 337       6.387  33.640  42.865  1.00 18.29           N
ATOM   2407  CA   GLU A 337       6.417  34.831  41.967  1.00 20.87           C
ATOM   2408  CB   GLU A 337       5.077  35.604  42.105  1.00 20.99           C
ATOM   2409  CG   GLU A 337       5.012  36.835  41.304  1.00 23.14           C
ATOM   2410  CD   GLU A 337       3.658  37.451  41.268  1.00 23.53           C
ATOM   2411  OE1  GLU A 337       2.756  37.072  42.040  1.00 25.02           O
ATOM   2412  OE2  GLU A 337       3.488  38.328  40.407  1.00 31.74           O
ATOM   2413  C    GLU A 337       7.639  35.766  42.163  1.00 21.04           C
ATOM   2414  O    GLU A 337       8.287  36.188  41.199  1.00 19.93           O
ATOM   2415  N    GLU A 338       7.963  36.045  43.427  1.00 21.83           N
ATOM   2416  CA   GLU A 338       9.072  36.904  43.801  1.00 22.29           C
ATOM   2417  CB   GLU A 338       9.110  37.054  45.337  1.00 23.14           C
ATOM   2418  CG   GLU A 338      10.284  37.641  45.990  0.00 32.82           C
ATOM   2419  CD   GLU A 338      10.107  37.821  47.503  0.00 33.96           C
ATOM   2420  OE1  GLU A 338      10.150  36.793  48.248  0.00 40.52           O
ATOM   2421  OE2  GLU A 338       9.905  38.995  47.941  0.00 43.76           O
ATOM   2422  C    GLU A 338      10.434  36.448  43.286  1.00 23.23           C
ATOM   2423  O    GLU A 338      11.288  37.282  42.976  1.00 22.91           O
ATOM   2424  N    ASN A 339      10.658  35.136  43.189  1.00 22.31           N
ATOM   2425  CA   ASN A 339      11.964  34.636  42.747  1.00 22.14           C
ATOM   2426  CB   ASN A 339      12.319  33.350  43.508  1.00 23.35           C
ATOM   2427  CG   ASN A 339      12.666  33.633  44.948  1.00 25.81           C
ATOM   2428  OD1  ASN A 339      11.807  33.595  45.825  1.00 28.61           O
ATOM   2429  ND2  ASN A 339      13.926  33.960  45.191  1.00 29.79           N
ATOM   2430  C    ASN A 339      12.114  34.423  41.246  1.00 21.54           C
ATOM   2431  O    ASN A 339      13.165  33.938  40.774  1.00 21.70           O
ATOM   2432  N    LEU A 340      11.082  34.796  40.501  1.00 20.16           N
ATOM   2433  CA   LEU A 340      11.113  34.672  39.043  1.00 21.18           C
ATOM   2434  CB   LEU A 340       9.692  34.613  38.453  1.00 18.83           C
ATOM   2435  CG   LEU A 340       8.740  33.475  38.832  1.00 17.44           C
ATOM   2436  CD1  LEU A 340       7.311  33.712  38.237  1.00 12.96           C
ATOM   2437  CD2  LEU A 340       9.293  32.121  38.403  1.00 15.52           C
ATOM   2438  C    LEU A 340      11.835  35.893  38.454  1.00 21.59           C
ATOM   2439  O    LEU A 340      11.830  36.969  39.053  1.00 21.25           O
ATOM   2440  N    HIS A 341      12.414  35.699  37.270  1.00 21.65           N
ATOM   2441  CA   HIS A 341      13.156  36.731  36.563  1.00 22.00           C
ATOM   2442  CB   HIS A 341      14.623  36.296  36.400  1.00 21.67           C
ATOM   2443  CG   HIS A 341      15.540  37.427  36.045  1.00 28.19           C
ATOM   2444  ND1  HIS A 341      16.229  37.486  34.852  1.00 32.67           N
ATOM   2445  CE1  HIS A 341      16.949  38.597  34.814  1.00 33.46           C
ATOM   2446  NE2  HIS A 341      16.728  39.273  35.930  1.00 32.79           N
ATOM   2447  CD2  HIS A 341      15.856  38.562  36.716  1.00 31.36           C
ATOM   2448  C    HIS A 341      12.433  36.988  35.236  1.00 20.49           C
ATOM   2449  O    HIS A 341      12.494  36.175  34.320  1.00 20.33           O
```

FIGURE 3-35 (COORDINATES)

```
ATOM   2450  N    ALA A 342      11.724  38.111  35.179  1.00 19.50           N
ATOM   2451  CA   ALA A 342      10.763  38.419  34.130  1.00 20.16           C
ATOM   2452  CB   ALA A 342      10.028  39.726  34.452  1.00 19.51           C
ATOM   2453  C    ALA A 342      11.407  38.500  32.745  1.00 20.30           C
ATOM   2454  O    ALA A 342      10.863  37.941  31.782  1.00 19.90           O
ATOM   2455  N    SER A 343      12.570  39.162  32.644  1.00 19.93           N
ATOM   2456  CA   SER A 343      13.223  39.347  31.329  1.00 18.82           C
ATOM   2457  CB   SER A 343      14.462  40.255  31.415  1.00 20.13           C
ATOM   2458  OG   SER A 343      15.475  39.687  32.249  1.00 20.91           O
ATOM   2459  C    SER A 343      13.578  37.992  30.743  1.00 18.04           C
ATOM   2460  O    SER A 343      13.436  37.791  29.547  1.00 18.84           O
ATOM   2461  N    THR A 344      13.984  37.038  31.583  1.00 17.90           N
ATOM   2462  CA   THR A 344      14.369  35.708  31.107  1.00 16.79           C
ATOM   2463  CB   THR A 344      14.896  34.802  32.246  1.00 17.92           C
ATOM   2464  OG1  THR A 344      16.017  35.416  32.910  1.00 18.97           O
ATOM   2465  CG2  THR A 344      15.350  33.479  31.680  1.00 17.99           C
ATOM   2466  C    THR A 344      13.160  35.016  30.477  1.00 15.96           C
ATOM   2467  O    THR A 344      13.255  34.415  29.410  1.00 14.74           O
ATOM   2468  N    ILE A 345      12.026  35.065  31.172  1.00 14.74           N
ATOM   2469  CA   ILE A 345      10.793  34.472  30.643  1.00 13.88           C
ATOM   2470  CB   ILE A 345       9.633  34.520  31.685  1.00 14.10           C
ATOM   2471  CG1  ILE A 345      10.140  33.951  33.020  1.00 13.01           C
ATOM   2472  CD1  ILE A 345       9.198  34.197  34.284  1.00 13.21           C
ATOM   2473  CG2  ILE A 345       8.369  33.767  31.105  1.00 13.15           C
ATOM   2474  C    ILE A 345      10.393  35.115  29.328  1.00 14.63           C
ATOM   2475  O    ILE A 345      10.050  34.422  28.352  1.00 13.69           O
ATOM   2476  N    ASP A 346      10.412  36.445  29.299  1.00 15.04           N
ATOM   2477  CA   ASP A 346      10.058  37.181  28.066  1.00 14.65           C
ATOM   2478  CB   ASP A 346      10.200  38.683  28.376  1.00 16.02           C
ATOM   2479  CG   ASP A 346       9.658  39.592  27.272  1.00 18.95           C
ATOM   2480  OD1  ASP A 346       8.619  39.279  26.639  1.00 18.49           O
ATOM   2481  OD2  ASP A 346      10.270  40.679  27.090  1.00 20.87           O
ATOM   2482  C    ASP A 346      10.960  36.797  26.895  1.00 14.09           C
ATOM   2483  O    ASP A 346      10.480  36.630  25.735  1.00 14.31           O
ATOM   2484  N    ASN A 347      12.274  36.677  27.149  1.00 13.61           N
ATOM   2485  CA   ASN A 347      13.213  36.253  26.080  1.00 13.46           C
ATOM   2486  CB   ASN A 347      14.677  36.281  26.595  1.00 12.24           C
ATOM   2487  CG   ASN A 347      15.181  37.696  26.814  1.00 13.53           C
ATOM   2488  OD1  ASN A 347      14.744  38.627  26.130  1.00 17.93           O
ATOM   2489  ND2  ASN A 347      16.091  37.866  27.732  1.00 15.67           N
ATOM   2490  C    ASN A 347      12.861  34.863  25.538  1.00 13.01           C
ATOM   2491  O    ASN A 347      12.835  34.638  24.347  1.00 14.52           O
ATOM   2492  N    LEU A 348      12.560  33.936  26.447  1.00 12.53           N
ATOM   2493  CA   LEU A 348      12.308  32.542  26.078  1.00 13.09           C
ATOM   2494  CB   LEU A 348      12.348  31.652  27.342  1.00 13.61           C
ATOM   2495  CG   LEU A 348      13.794  31.457  27.884  1.00 14.31           C
ATOM   2496  CD1  LEU A 348      13.767  30.812  29.307  1.00 15.59           C
ATOM   2497  CD2  LEU A 348      14.508  30.567  26.917  1.00 10.87           C
ATOM   2498  C    LEU A 348      10.957  32.465  25.382  1.00 13.40           C
ATOM   2499  O    LEU A 348      10.778  31.685  24.437  1.00 13.03           O
ATOM   2500  N    ASN A 349      10.039  33.336  25.778  1.00 13.80           N
ATOM   2501  CA   ASN A 349       8.745  33.457  25.024  1.00 14.63           C
ATOM   2502  CB   ASN A 349       7.832  34.543  25.639  1.00 13.35           C
ATOM   2503  CG   ASN A 349       7.036  34.050  26.844  1.00 15.78           C
ATOM   2504  OD1  ASN A 349       6.836  32.840  27.031  1.00 14.49           O
ATOM   2505  ND2  ASN A 349       6.532  34.995  27.650  1.00 10.44           N
ATOM   2506  C    ASN A 349       8.975  33.813  23.566  1.00 15.12           C
ATOM   2507  O    ASN A 349       8.405  33.199  22.680  1.00 16.40           O
ATOM   2508  N    LYS A 350       9.814  34.823  23.311  1.00 15.17           N
ATOM   2509  CA   LYS A 350      10.132  35.210  21.931  1.00 16.33           C
ATOM   2510  CB   LYS A 350      11.018  36.462  21.906  1.00 16.72           C
ATOM   2511  CG   LYS A 350      10.312  37.705  22.414  1.00 17.57           C
ATOM   2512  CD   LYS A 350      11.275  38.833  22.748  1.00 16.20           C
ATOM   2513  CE   LYS A 350      10.500  40.077  23.233  1.00 11.89           C
ATOM   2514  NZ   LYS A 350      11.412  41.276  23.653  1.00 18.04           N
ATOM   2515  C    LYS A 350      10.797  34.084  21.167  1.00 15.06           C
ATOM   2516  O    LYS A 350      10.418  33.812  20.028  1.00 16.14           O
ATOM   2517  N    ILE A 351      11.788  33.432  21.788  1.00 15.45           N
ATOM   2518  CA   ILE A 351      12.512  32.327  21.154  1.00 14.48           C
ATOM   2519  CB   ILE A 351      13.723  31.866  22.016  1.00 15.58           C
```

FIGURE 3-36 (COORDINATES)

```
ATOM   2520  CG1 ILE A 351      14.764  33.005  22.162  1.00 15.82           C
ATOM   2521  CD1 ILE A 351      15.693  32.788  23.406  1.00 15.01           C
ATOM   2522  CG2 ILE A 351      14.360  30.520  21.488  1.00 15.02           C
ATOM   2523  C   ILE A 351      11.591  31.156  20.812  1.00 14.51           C
ATOM   2524  O   ILE A 351      11.629  30.629  19.680  1.00 13.78           O
ATOM   2525  N   ILE A 352      10.770  30.728  21.780  1.00 13.38           N
ATOM   2526  CA  ILE A 352       9.881  29.595  21.547  1.00 13.77           C
ATOM   2527  CB  ILE A 352       9.325  29.057  22.909  1.00 13.23           C
ATOM   2528  CG1 ILE A 352      10.526  28.504  23.734  1.00 11.93           C
ATOM   2529  CD1 ILE A 352      10.206  28.255  25.245  1.00 16.74           C
ATOM   2530  CG2 ILE A 352       8.358  27.935  22.667  1.00 14.29           C
ATOM   2531  C   ILE A 352       8.773  29.929  20.511  1.00 13.37           C
ATOM   2532  O   ILE A 352       8.421  29.102  19.671  1.00 13.62           O
ATOM   2533  N   GLN A 353       8.211  31.133  20.594  1.00 14.32           N
ATOM   2534  CA  GLN A 353       7.215  31.541  19.591  1.00 14.89           C
ATOM   2535  CB  GLN A 353       6.634  32.903  19.937  1.00 15.36           C
ATOM   2536  CG  GLN A 353       5.606  32.857  21.122  1.00 13.51           C
ATOM   2537  CD  GLN A 353       5.276  34.229  21.639  1.00 18.21           C
ATOM   2538  OE1 GLN A 353       5.208  35.198  20.870  1.00 18.88           O
ATOM   2539  NE2 GLN A 353       5.047  34.331  22.940  1.00 16.12           N
ATOM   2540  C   GLN A 353       7.802  31.522  18.158  1.00 15.10           C
ATOM   2541  O   GLN A 353       7.134  31.070  17.253  1.00 16.05           O
ATOM   2542  N   VAL A 354       9.017  32.051  17.956  1.00 15.62           N
ATOM   2543  CA  VAL A 354       9.723  31.981  16.631  1.00 15.87           C
ATOM   2544  CB  VAL A 354      11.111  32.725  16.677  1.00 16.17           C
ATOM   2545  CG1 VAL A 354      11.944  32.500  15.409  1.00 14.61           C
ATOM   2546  CG2 VAL A 354      10.924  34.201  16.870  1.00 14.00           C
ATOM   2547  C   VAL A 354       9.871  30.528  16.191  1.00 16.87           C
ATOM   2548  O   VAL A 354       9.542  30.128  15.049  1.00 17.04           O
ATOM   2549  N   PHE A 355      10.320  29.701  17.116  1.00 17.72           N
ATOM   2550  CA  PHE A 355      10.520  28.283  16.825  1.00 17.46           C
ATOM   2551  CB  PHE A 355      11.098  27.565  18.072  1.00 17.03           C
ATOM   2552  CG  PHE A 355      11.255  26.071  17.881  1.00 18.27           C
ATOM   2553  CD1 PHE A 355      12.497  25.519  17.566  1.00 17.56           C
ATOM   2554  CE1 PHE A 355      12.643  24.141  17.331  1.00 19.69           C
ATOM   2555  CZ  PHE A 355      11.561  23.308  17.431  1.00 18.33           C
ATOM   2556  CE2 PHE A 355      10.293  23.848  17.761  1.00 20.85           C
ATOM   2557  CD2 PHE A 355      10.155  25.233  17.975  1.00 18.33           C
ATOM   2558  C   PHE A 355       9.233  27.621  16.304  1.00 17.05           C
ATOM   2559  O   PHE A 355       9.210  26.967  15.259  1.00 16.20           O
ATOM   2560  N   VAL A 356       8.139  27.832  17.026  1.00 16.69           N
ATOM   2561  CA  VAL A 356       6.855  27.273  16.649  1.00 16.31           C
ATOM   2562  CB  VAL A 356       5.781  27.573  17.739  1.00 16.75           C
ATOM   2563  CG1 VAL A 356       4.350  27.293  17.224  1.00 17.49           C
ATOM   2564  CG2 VAL A 356       6.093  26.748  18.999  1.00 14.47           C
ATOM   2565  C   VAL A 356       6.419  27.804  15.275  1.00 17.05           C
ATOM   2566  O   VAL A 356       5.992  27.022  14.429  1.00 18.76           O
ATOM   2567  N   LEU A 357       6.549  29.103  15.034  1.00 16.71           N
ATOM   2568  CA  LEU A 357       6.115  29.670  13.738  1.00 17.96           C
ATOM   2569  CB  LEU A 357       6.227  31.205  13.738  1.00 18.04           C
ATOM   2570  CG  LEU A 357       5.156  32.007  14.500  1.00 16.38           C
ATOM   2571  CD1 LEU A 357       5.392  33.445  14.284  1.00 18.38           C
ATOM   2572  CD2 LEU A 357       3.661  31.659  14.076  1.00 19.31           C
ATOM   2573  C   LEU A 357       6.914  29.097  12.595  1.00 19.03           C
ATOM   2574  O   LEU A 357       6.359  28.786  11.518  1.00 18.43           O
ATOM   2575  N   GLU A 358       8.218  28.986  12.827  1.00 18.54           N
ATOM   2576  CA  GLU A 358       9.137  28.425  11.852  1.00 20.78           C
ATOM   2577  CB  GLU A 358      10.615  28.684  12.257  1.00 20.06           C
ATOM   2578  CG  GLU A 358      10.998  30.139  12.131  1.00 19.47           C
ATOM   2579  CD  GLU A 358      12.485  30.410  12.354  1.00 21.48           C
ATOM   2580  OE1 GLU A 358      13.206  29.526  12.887  1.00 23.80           O
ATOM   2581  OE2 GLU A 358      12.924  31.529  12.025  1.00 21.11           O
ATOM   2582  C   GLU A 358       8.859  26.950  11.561  1.00 20.90           C
ATOM   2583  O   GLU A 358       8.943  26.546  10.404  1.00 21.54           O
ATOM   2584  N   TYR A 359       8.518  26.170  12.597  1.00 21.02           N
ATOM   2585  CA  TYR A 359       8.182  24.741  12.447  1.00 20.65           C
ATOM   2586  CB  TYR A 359       7.895  24.061  13.818  1.00 20.77           C
ATOM   2587  CG  TYR A 359       7.999  22.546  13.730  1.00 20.85           C
ATOM   2588  CD1 TYR A 359       9.183  21.904  14.045  1.00 18.99           C
ATOM   2589  CE1 TYR A 359       9.295  20.524  13.934  1.00 20.72           C
```

FIGURE 3-37 (COORDINATES)

```
ATOM   2590  CZ   TYR A 359       8.221  19.793  13.486  1.00 19.87           C
ATOM   2591  OH   TYR A 359       8.356  18.444  13.361  1.00 22.26           O
ATOM   2592  CE2  TYR A 359       7.020  20.402  13.195  1.00 17.18           C
ATOM   2593  CD2  TYR A 359       6.917  21.763  13.277  1.00 18.60           C
ATOM   2594  C    TYR A 359       6.933  24.618  11.576  1.00 20.71           C
ATOM   2595  O    TYR A 359       6.847  23.772  10.662  1.00 20.79           O
ATOM   2596  N    LEU A 360       5.965  25.467  11.878  1.00 20.14           N
ATOM   2597  CA   LEU A 360       4.684  25.421  11.204  1.00 22.04           C
ATOM   2598  CB   LEU A 360       3.594  25.945  12.125  1.00 20.85           C
ATOM   2599  CG   LEU A 360       3.336  25.054  13.376  1.00 20.45           C
ATOM   2600  CD1  LEU A 360       2.429  25.762  14.353  1.00 17.60           C
ATOM   2601  CD2  LEU A 360       2.724  23.749  13.000  1.00 19.51           C
ATOM   2602  C    LEU A 360       4.630  26.129   9.854  1.00 22.86           C
ATOM   2603  O    LEU A 360       3.599  26.076   9.208  1.00 23.30           O
ATOM   2604  N    HIS A 361       5.721  26.779   9.437  1.00 24.52           N
ATOM   2605  CA   HIS A 361       5.744  27.566   8.164  1.00 26.12           C
ATOM   2606  CB   HIS A 361       5.610  26.648   6.928  1.00 26.07           C
ATOM   2607  CG   HIS A 361       6.774  25.718   6.741  1.00 30.21           C
ATOM   2608  ND1  HIS A 361       7.243  25.347   5.501  1.00 33.74           N
ATOM   2609  CE1  HIS A 361       8.281  24.542   5.647  1.00 34.09           C
ATOM   2610  NE2  HIS A 361       8.512  24.384   6.936  1.00 30.64           N
ATOM   2611  CD2  HIS A 361       7.595  25.122   7.643  1.00 30.44           C
ATOM   2612  C    HIS A 361       4.665  28.635   8.184  1.00 26.70           C
ATOM   2613  O    HIS A 361       3.940  28.854   7.197  1.00 28.28           O
ATOM   2614  N    LEU A 362       4.547  29.285   9.334  1.00 26.03           N
ATOM   2615  CA   LEU A 362       3.637  30.380   9.534  1.00 26.02           C
ATOM   2616  CB   LEU A 362       2.809  30.160  10.809  1.00 25.96           C
ATOM   2617  CG   LEU A 362       1.724  29.112  10.684  1.00 25.94           C
ATOM   2618  CD1  LEU A 362       1.038  28.923  12.051  1.00 26.14           C
ATOM   2619  CD2  LEU A 362       0.719  29.534   9.567  1.00 27.84           C
ATOM   2620  C    LEU A 362       4.453  31.638   9.683  1.00 26.12           C
ATOM   2621  O    LEU A 362       3.904  32.726   9.631  1.00 25.59           O
ATOM   2622  OXT  LEU A 362       5.670  31.563   9.877  1.00 26.02           O
ATOM   2623  N4   PQ4 B   1      15.533  14.340  43.100  1.00 36.27           N
ATOM   2624  C18  PQ4 B   1      15.218  14.365  41.986  1.00 38.71           C
ATOM   2625  N1   PQ4 B   1      14.888  14.391  40.822  1.00 36.46           N
ATOM   2626  C1   PQ4 B   1      15.764  14.329  39.918  1.00 36.49           C
ATOM   2627  N3   PQ4 B   1      17.050  14.234  40.243  1.00 33.66           N
ATOM   2628  C2   PQ4 B   1      17.970  13.969  39.291  1.00 36.50           C
ATOM   2629  C3   PQ4 B   1      18.398  15.000  38.455  1.00 38.16           C
ATOM   2630  C4   PQ4 B   1      19.343  14.777  37.461  1.00 36.67           C
ATOM   2631  O1   PQ4 B   1      19.753  15.801  36.648  1.00 32.53           O
ATOM   2632  C8   PQ4 B   1      19.883  17.120  37.173  1.00 31.06           C
ATOM   2633  C5   PQ4 B   1      19.900  13.413  37.294  1.00 35.22           C
ATOM   2634  O2   PQ4 B   1      20.834  13.145  36.328  1.00 35.29           O
ATOM   2635  C9   PQ4 B   1      20.777  13.821  35.074  1.00 35.52           C
ATOM   2636  C6   PQ4 B   1      19.415  12.350  38.205  1.00 36.33           C
ATOM   2637  O3   PQ4 B   1      19.893  11.070  38.099  1.00 33.15           O
ATOM   2638  C10  PQ4 B   1      19.046   9.965  38.406  1.00 35.19           C
ATOM   2639  C7   PQ4 B   1      18.467  12.672  39.170  1.00 38.28           C
ATOM   2640  N2   PQ4 B   1      15.402  14.357  38.638  1.00 35.14           N
ATOM   2641  C15  PQ4 B   1      14.007  14.303  38.244  1.00 34.13           C
ATOM   2642  C16  PQ4 B   1      13.237  15.537  38.699  1.00 24.47           C
ATOM   2643  C17  PQ4 B   1      11.737  15.345  38.509  1.00 19.51           C
ATOM   2644  N5   PQ4 B   1      11.065  16.642  38.585  1.00 17.66           N
ATOM   2645  C11  PQ4 B   1      11.007  17.566  37.628  1.00 16.93           C
ATOM   2646  C14  PQ4 B   1      11.550  17.646  36.226  1.00 12.68           C
ATOM   2647  C12  PQ4 B   1      10.288  18.665  38.053  1.00 18.95           C
ATOM   2648  N6   PQ4 B   1       9.911  18.365  39.316  1.00 19.64           N
ATOM   2649  C13  PQ4 B   1      10.388  17.134  39.631  1.00 20.96           C
ATOM   2650  ZN   ZN  C 121       8.897  19.481  40.707  1.00 17.14          ZN
ATOM   2651  O    HOH E   1      14.934  28.238  35.442  1.00 16.86           O
ATOM   2652  O    HOH E   2      -1.745  18.677  54.031  1.00 25.16           O
ATOM   2653  O    HOH E   3      17.795  17.467  22.305  1.00 23.69           O
ATOM   2654  O    HOH E   4       5.278  32.005  24.826  1.00 14.27           O
ATOM   2655  O    HOH E   5      26.658  39.823  30.438  1.00 32.07           O
ATOM   2656  O    HOH E   6      -0.909  13.156  17.394  1.00 24.57           O
ATOM   2657  O    HOH E   7      18.153  10.153  20.262  1.00 25.44           O
ATOM   2658  O    HOH E   8       2.279  13.333  34.409  1.00 15.83           O
ATOM   2659  O    HOH E   9       1.754   8.134   3.278  1.00 40.48           O
```

FIGURE 3-38 (COORDINATES)

```
ATOM   2660  O   HOH E   10     -0.435  35.765  15.129  1.00 27.01           O
ATOM   2661  O   HOH E   11      6.633  18.416  32.927  1.00 14.06           O
ATOM   2662  O   HOH E   12     10.071  23.525  42.090  1.00 15.47           O
ATOM   2663  O   HOH E   13     -5.661  23.355  48.829  1.00 22.32           O
ATOM   2664  O   HOH E   14    -11.954  11.765  30.306  1.00 46.80           O
ATOM   2665  O   HOH E   15     21.713  29.464  37.524  1.00 38.41           O
ATOM   2666  O   HOH E   16      6.601  20.967  32.977  1.00 12.87           O
ATOM   2667  O   HOH E   17     12.719  40.448  26.041  1.00 18.81           O
ATOM   2668  O   HOH E   18     15.947  12.069  36.764  1.00 20.55           O
ATOM   2669  O   HOH E   19     13.952  28.593   5.395  1.00 35.19           O
ATOM   2670  O   HOH E   20     10.492  30.883  41.551  1.00 19.81           O
ATOM   2671  O   HOH E   21      7.040  41.449  26.314  1.00 21.62           O
ATOM   2672  O   HOH E   23      9.224  35.528   7.018  1.00 33.82           O
ATOM   2673  O   HOH E   24      2.584  23.096  37.431  1.00 13.65           O
ATOM   2674  O   HOH E   25      6.486  37.670  26.853  1.00 19.09           O
ATOM   2675  O   HOH E   26     16.305  28.159  49.981  1.00 21.35           O
ATOM   2676  O   HOH E   27     -7.974  27.527  13.674  1.00 28.28           O
ATOM   2677  O   HOH E   28     -3.706  26.695  49.418  1.00 24.63           O
ATOM   2678  O   HOH E   29     14.319  12.824  21.145  1.00 26.19           O
ATOM   2679  O   HOH E   30      2.598   4.636  29.679  1.00 26.17           O
ATOM   2680  O   HOH E   31     16.645  16.721   8.271  1.00 43.93           O
ATOM   2681  O   HOH E   32     -7.470  17.823  22.042  1.00 21.42           O
ATOM   2682  O   HOH E   33     13.383  27.020  13.506  1.00 26.22           O
ATOM   2683  O   HOH E   34     15.919  14.818  29.785  1.00 19.43           O
ATOM   2684  O   HOH E   35      5.314  21.272  41.273  1.00 15.68           O
ATOM   2685  O   HOH E   36     -3.706  18.796  39.690  1.00 23.64           O
ATOM   2686  O   HOH E   37     -1.267  36.455  28.010  1.00 19.16           O
ATOM   2687  O   HOH E   38      6.845  18.253   6.178  1.00 27.18           O
ATOM   2688  O   HOH E   39      6.185  27.688  46.113  1.00 23.92           O
ATOM   2689  O   HOH E   40      3.051   3.485  19.068  1.00 39.71           O
ATOM   2690  O   HOH E   41      2.843  37.445  17.246  1.00 24.68           O
ATOM   2691  O   HOH E   42     18.587  45.146  27.589  1.00 34.76           O
ATOM   2692  O   HOH E   43     -3.474  19.935   7.431  1.00 38.10           O
ATOM   2693  O   HOH E   44     26.962  38.702  23.706  1.00 25.87           O
ATOM   2694  O   HOH E   45     -4.211  30.439  19.244  1.00 19.00           O
ATOM   2695  O   HOH E   46     24.049  35.785  28.916  1.00 23.74           O
ATOM   2696  O   HOH E   47      4.567  37.284  19.368  1.00 16.50           O
ATOM   2697  O   HOH E   48      6.115  35.634  45.876  1.00 18.04           O
ATOM   2698  O   HOH E   49     -5.833  24.286  46.269  1.00 18.30           O
ATOM   2699  O   HOH E   50     17.578  27.557  36.484  1.00 25.41           O
ATOM   2700  O   HOH E   51     15.367  10.175  21.306  1.00 30.35           O
ATOM   2701  O   HOH E   52     -6.438  34.313  10.803  1.00 33.64           O
ATOM   2702  O   HOH E   53      2.401  15.704  44.476  1.00 20.39           O
ATOM   2703  O   HOH E   54     11.401  25.379  14.410  1.00 20.77           O
ATOM   2704  O   HOH E   55     11.538  16.800  46.467  1.00 28.04           O
ATOM   2705  O   HOH E   56     20.403  45.784  16.679  1.00 42.22           O
ATOM   2706  O   HOH E   57      9.721  20.511   5.233  1.00 28.22           O
ATOM   2707  O   HOH E   58     18.219  31.600  11.409  1.00 33.82           O
ATOM   2708  O   HOH E   60    -12.720  15.481  26.859  1.00 31.63           O
ATOM   2709  O   HOH E   61      6.273  10.311  17.149  1.00 24.80           O
ATOM   2710  O   HOH E   62     10.710  17.023  13.022  1.00 25.17           O
ATOM   2711  O   HOH E   63     -6.005  33.675  25.974  1.00 16.60           O
ATOM   2712  O   HOH E   64      8.023  15.054  43.025  1.00 20.73           O
ATOM   2713  O   HOH E   65     -3.471  38.464  28.084  1.00 23.24           O
ATOM   2714  O   HOH E   66     -4.184  37.638  20.190  1.00 30.63           O
ATOM   2715  O   HOH E   67     10.574   7.064  35.105  1.00 31.54           O
ATOM   2716  O   HOH E   68      2.719  24.459  54.953  1.00 26.43           O
ATOM   2717  O   HOH E   69     19.997  26.229  34.697  1.00 25.80           O
ATOM   2718  O   HOH E   70     -9.308  14.849  38.013  1.00 25.35           O
ATOM   2719  O   HOH E   71     -9.870  36.231  21.008  1.00 28.96           O
ATOM   2720  O   HOH E   72      6.974   7.316  36.509  1.00 25.01           O
ATOM   2721  O   HOH E   73      5.572   4.437  27.482  1.00 33.80           O
ATOM   2722  O   HOH E   74     -2.283  29.273   6.622  1.00 48.52           O
ATOM   2723  O   HOH E   75     -6.326  20.818  49.256  1.00 21.83           O
ATOM   2724  O   HOH E   76     -6.614  36.055  16.410  1.00 29.52           O
ATOM   2725  O   HOH E   77     13.231  41.460   6.959  1.00 35.62           O
ATOM   2726  O   HOH E   78     -3.519  33.081  27.093  1.00 23.52           O
ATOM   2727  O   HOH E   79     11.267   7.208  13.250  1.00 44.52           O
ATOM   2728  O   HOH E   80     17.375  10.587  34.988  1.00 25.99           O
ATOM   2729  O   HOH E   81     16.904  20.529  25.069  1.00 24.60           O
```

FIGURE 3-39 (COORDINATES)

```
ATOM   2730  O   HOH E   82       7.517  30.532   8.522  1.00 27.16           O
ATOM   2731  O   HOH E   84      10.288  25.752  51.786  1.00 23.40           O
ATOM   2732  O   HOH E   85      -8.636  12.514  26.013  1.00 42.91           O
ATOM   2733  O   HOH E   86      -9.519  24.326  12.382  1.00 26.28           O
ATOM   2734  O   HOH E   87      -9.089  35.653  30.816  1.00 22.97           O
ATOM   2735  O   HOH E   88      -7.387  36.497  20.165  1.00 32.70           O
ATOM   2736  O   HOH E   89      -6.563  16.261  39.707  1.00 27.54           O
ATOM   2737  O   HOH E   90      18.220  29.678  41.046  1.00 24.80           O
ATOM   2738  O   HOH E   91      -3.417  40.546  26.064  1.00 26.37           O
ATOM   2739  O   HOH E   92      -3.209  28.264  47.215  1.00 25.16           O
ATOM   2740  O   HOH E   93       4.570  12.695  12.868  1.00 27.79           O
ATOM   2741  O   HOH E   94      -9.194  22.904  14.840  1.00 28.44           O
ATOM   2742  O   HOH E   95      16.940  21.095   9.804  1.00 52.33           O
ATOM   2743  O   HOH E   96       8.227  31.296  51.267  1.00 41.01           O
ATOM   2744  O   HOH E   97      26.789  39.413  13.747  1.00 58.04           O
ATOM   2745  O   HOH E   98      -6.946  38.907  28.303  1.00 33.12           O
ATOM   2746  O   HOH E   99       0.222  14.451  54.942  1.00 28.44           O
ATOM   2747  O   HOH E  100      26.488  37.397  16.957  1.00 38.17           O
ATOM   2748  O   HOH E  101      20.078  25.941  12.569  1.00 44.81           O
ATOM   2749  O   HOH E  102       5.065  20.750  54.751  1.00 44.03           O
ATOM   2750  O   HOH E  103       3.775  32.956  44.069  1.00 19.43           O
ATOM   2751  O   HOH E  104      15.295   7.104  31.090  1.00 39.71           O
ATOM   2752  O   HOH E  105      11.390  43.870  21.693  1.00 39.51           O
ATOM   2753  O   HOH E  106      -5.750  13.892  21.448  1.00 42.19           O
ATOM   2754  O   HOH E  107      11.098  15.509  15.345  1.00 22.71           O
ATOM   2755  O   HOH E  108      13.462  35.258  47.920  1.00 40.44           O
ATOM   2756  O   HOH E  109      17.270  25.315   8.968  1.00 35.71           O
ATOM   2757  O   HOH E  110       1.256  22.313  46.012  1.00 22.63           O
ATOM   2758  O   HOH E  111      -9.166  32.355  33.557  1.00 21.89           O
ATOM   2759  O   HOH E  112       0.326  39.415  19.699  1.00 29.37           O
ATOM   2760  O   HOH E  113       0.910  21.602  48.713  1.00 33.11           O
ATOM   2761  O   HOH E  114      -8.662  27.785  43.891  1.00 28.81           O
ATOM   2762  O   HOH E  115       9.752  42.750  25.039  1.00 23.85           O
ATOM   2763  O   HOH E  116      22.695  27.008  15.689  1.00 32.94           O
ATOM   2764  O   HOH E  117      23.272  31.875  38.127  1.00 51.41           O
ATOM   2765  O   HOH E  118      23.979  19.611  26.239  1.00 24.11           O
ATOM   2766  O   HOH E  119     -13.109  22.346  22.110  1.00 35.23           O
ATOM   2767  O   HOH E  120      -7.419  26.732  46.154  1.00 37.19           O
ATOM   2768  O   HOH E  121       3.439  42.379  16.566  1.00 30.60           O
ATOM   2769  O   HOH E  122      -3.221  29.180  51.064  1.00 34.64           O
ATOM   2770  O   HOH E  123       2.500  30.550  50.554  1.00 33.95           O
ATOM   2771  O   HOH E  124      22.299  29.984  21.865  1.00 37.21           O
ATOM   2772  O   HOH E  125      13.169  31.089  40.678  1.00 27.69           O
ATOM   2773  O   HOH E  126      -6.393  15.051  18.160  1.00 40.28           O
ATOM   2774  O   HOH E  127      -0.879  44.024  39.493  1.00 31.17           O
ATOM   2775  O   HOH E  128     -13.388  15.112  33.070  1.00 36.35           O
ATOM   2776  O   HOH E  129      -0.224  34.229  44.015  1.00 29.81           O
ATOM   2777  O   HOH E  130      -0.882   6.768  35.676  1.00 29.28           O
ATOM   2778  O   HOH E  131      19.310  23.025  12.503  1.00 28.39           O
ATOM   2779  O   HOH E  132      27.295  25.862  23.520  1.00 39.78           O
ATOM   2780  O   HOH E  133      -8.731  16.726  19.481  1.00 28.18           O
ATOM   2781  O   HOH E  134      -3.299   2.308  39.440  1.00 37.95           O
ATOM   2782  O   HOH E  135       5.257  15.122  47.353  1.00 23.18           O
ATOM   2783  O   HOH E  136      18.858  41.861  22.298  1.00 20.50           O
ATOM   2784  O   HOH E  137     -10.283  29.232  37.289  1.00 27.67           O
ATOM   2785  O   HOH E  138      21.158   9.369  30.064  1.00 42.41           O
ATOM   2786  O   HOH E  139       7.501  42.705  23.538  1.00 27.05           O
ATOM   2787  O   HOH E  140     -11.087  38.890  22.096  1.00 36.02           O
ATOM   2788  O   HOH E  141       8.834  16.168   5.901  1.00 34.60           O
ATOM   2789  O   HOH E  142     -13.149  30.996  27.336  1.00 30.59           O
ATOM   2790  O   HOH E  143       6.114  15.407  50.390  1.00 46.02           O
ATOM   2791  O   HOH E  144      -0.104  37.783  13.091  1.00 52.33           O
ATOM   2792  O   HOH E  145      15.159  32.684  11.825  1.00 35.87           O
ATOM   2793  O   HOH E  146       2.414  23.087  50.069  1.00 24.77           O
ATOM   2794  O   HOH E  147       5.436   3.108  36.749  1.00 40.39           O
ATOM   2795  O   HOH E  148      23.606  15.920  34.346  1.00 34.48           O
ATOM   2796  O   HOH E  149      10.364  18.273   3.797  1.00 42.61           O
ATOM   2797  O   HOH E  150      19.729  41.655  25.312  1.00 40.13           O
ATOM   2798  O   HOH E  151      -0.011  14.291   3.641  1.00 47.27           O
ATOM   2799  O   HOH E  152      20.570  10.371  33.433  1.00 32.11           O
```

FIGURE 3-40 (COORDINATES)

```
ATOM   2800  O   HOH E 153      21.468  32.753  14.132  1.00 30.62           O
ATOM   2801  O   HOH E 154       1.941  34.981  43.868  1.00 21.34           O
ATOM   2802  O   HOH E 155       4.289  19.938  57.802  1.00 49.61           O
ATOM   2803  O   HOH E 156       7.866  41.224   8.084  1.00 41.25           O
ATOM   2804  O   HOH E 157       2.518  30.059  59.781  1.00 43.24           O
ATOM   2805  O   HOH E 158      22.517  27.707  34.135  1.00 33.27           O
ATOM   2806  O   HOH E 159      -9.895   9.568  29.531  1.00 37.61           O
ATOM   2807  O   HOH E 160       1.226  31.679  47.791  1.00 39.28           O
ATOM   2808  O   HOH E 161      15.968  24.615   6.941  1.00 46.36           O
ATOM   2809  O   HOH E 162     -13.005  26.883  31.973  1.00 26.81           O
ATOM   2810  O   HOH E 163      -3.431  21.960   8.496  1.00 43.75           O
ATOM   2811  O   HOH E 164      -7.141  35.634  33.471  1.00 22.16           O
ATOM   2812  O   HOH E 165      -6.861  12.538  24.191  1.00 52.74           O
ATOM   2813  O   HOH E 166      12.232  24.687  40.329  1.00 32.97           O
ATOM   2814  O   HOH E 167       8.248  22.588  50.169  1.00 35.54           O
ATOM   2815  O   HOH E 168      16.372  33.696  39.719  1.00 37.46           O
ATOM   2816  O   HOH E 169      -9.092  39.224  17.832  1.00 45.78           O
ATOM   2817  O   HOH E 170      -7.182  10.099  16.460  1.00 39.07           O
ATOM   2818  O   HOH E 171      -7.855  30.423  42.699  1.00 35.60           O
ATOM   2819  O   HOH E 172      28.228  14.141  23.852  1.00 40.47           O
ATOM   2820  O   HOH E 173      21.162  43.259  27.225  1.00 33.70           O
ATOM   2821  O   HOH E 174      17.436  45.845  34.616  1.00 37.61           O
ATOM   2822  O   HOH E 175      16.244  46.614  37.406  1.00 52.22           O
ATOM   2823  O   HOH E 176       2.230  23.487  52.671  1.00 30.65           O
ATOM   2824  O   HOH E 177      15.897  36.675  39.612  1.00 30.35           O
ATOM   2825  O   HOH E 178       5.696  32.437  49.262  1.00 44.58           O
ATOM   2826  O   HOH E 179       3.157   1.680  37.833  1.00 35.75           O
ATOM   2827  O   HOH E 180      -1.005  32.642   6.436  1.00 59.07           O
ATOM   2828  O   HOH E 181       8.388  33.072   7.168  1.00 51.94           O
ATOM   2829  O   HOH E 183      21.845  10.088  35.970  1.00 48.97           O
ATOM   2830  O   HOH E 184      16.031  46.273  17.534  1.00 43.52           O
ATOM   2831  O   HOH E 185      -1.553  30.641  47.283  1.00 39.40           O
ATOM   2832  O   HOH E 186     -12.962  31.893  15.801  1.00 31.73           O
ATOM   2833  O   HOH E 187       8.848  13.639   3.618  1.00 47.77           O
ATOM   2834  O   HOH E 188       0.128  42.080  23.521  1.00 49.00           O
ATOM   2835  O   HOH E 189     -11.592  26.040  43.461  1.00 45.63           O
ATOM   2836  O   HOH E 190      28.934  19.542  22.538  1.00 44.59           O
ATOM   2837  O   HOH E 191       3.122  45.336  17.453  1.00 53.32           O
ATOM   2838  O   HOH E 192      26.454  13.287  29.176  1.00 75.42           O
ATOM   2839  O   HOH E 193      22.443  35.170  13.350  1.00 31.55           O
ATOM   2840  O   HOH E 194      -5.262   9.916  52.625  1.00 30.69           O
ATOM   2841  O   HOH E 195      16.265  42.118  33.942  1.00 31.11           O
ATOM   2842  O   HOH E 196      15.017  10.499  38.834  1.00 37.80           O
ATOM   2843  O   HOH E 197       6.480   6.750  46.677  1.00 47.83           O
ATOM   2844  O   HOH E 198       1.288   3.725  50.690  1.00 46.32           O
ATOM   2845  O   HOH E 199      15.485   7.629  37.834  1.00 44.84           O
ATOM   2846  O   HOH E 200      -0.553  21.385  51.721  1.00 33.59           O
ATOM   2847  O   HOH E 201       5.231   4.491  30.647  1.00 41.50           O
ATOM   2848  O   HOH E 202      10.890  42.112  29.500  1.00 43.55           O
ATOM   2849  O   HOH E 203     -14.983  13.335  34.560  1.00 39.64           O
ATOM   2850  O   HOH E 204      -3.093  26.070   6.364  1.00 43.26           O
ATOM   2851  O   HOH E 205      24.385  41.598  13.026  1.00 57.10           O
ATOM   2852  O   HOH E 206       6.645  29.340  59.285  1.00 42.35           O
ATOM   2853  O   HOH E 207      -6.147  10.482  22.952  1.00 46.07           O
ATOM   2854  O   HOH E 208      -7.938   1.517  20.569  1.00 26.38           O
ATOM   2855  O   HOH E 209       5.728  12.231  10.232  1.00 33.35           O
ATOM   2856  O   HOH E 210      16.740  36.466  10.366  1.00 37.02           O
ATOM   2857  O   HOH E 211      -0.543  27.541   6.413  1.00 47.79           O
ATOM   2858  O   HOH E 212       3.970  13.267  51.027  1.00 35.11           O
ATOM   2859  O   HOH E 213       0.990   7.425  52.944  1.00 46.95           O
ATOM   2860  O   HOH E 214       5.627  35.322  11.041  1.00 44.33           O
ATOM   2861  O   HOH E 215      23.655  29.463  16.283  1.00 34.26           O
ATOM   2862  O   HOH E 216      25.322  14.974  30.987  1.00 51.72           O
ATOM   2863  O   HOH E 217     -10.986  -2.006   5.363  1.00 43.70           O
ATOM   2864  O   HOH E 218       4.115  31.064  57.715  1.00 42.62           O
ATOM   2865  O   HOH E 219      -7.904  32.763   9.713  1.00 35.66           O
ATOM   2866  O   HOH E 220      -9.882   0.246  11.258  1.00 41.00           O
ATOM   2867  O   HOH E 221      12.145   7.574  38.770  1.00 57.55           O
ATOM   2868  O   HOH E 222       5.287  46.754  12.648  1.00 36.73           O
ATOM   2869  O   HOH E 223      -2.450   0.631  25.617  1.00 44.29           O
```

FIGURE 3-41 (COORDINATES)

```
ATOM  2870  O  HOH E 224   12.208  47.920  24.388  1.00 58.60       O
ATOM  2871  O  HOH E 225   -3.364   7.644  53.165  1.00 46.77       O
ATOM  2872  O  HOH E 226   14.333  36.658  45.689  1.00 41.95       O
ATOM  2873  O  HOH E 227   23.426   9.626  29.223  1.00 58.17       O
ATOM  2874  O  HOH E 228  -13.880  13.791  30.606  1.00 52.52       O
ATOM  2875  O  HOH E 229   27.705  38.675  20.651  1.00 32.77       O
ATOM  2876  O  HOH E 230   30.292  15.809  21.724  1.00 59.52       O
ATOM  2877  O  HOH E 231   -6.426  32.470   6.539  1.00 48.68       O
ATOM  2878  O  HOH E 232   -7.988  35.785  13.731  1.00 36.49       O
ATOM  2879  O  HOH E 233   15.365  10.838  41.258  1.00 44.09       O
ATOM  2880  O  HOH E 234    3.497  31.931  46.667  1.00 26.11       O
ATOM  2881  O  HOH E 235   27.321  16.515  29.456  1.00 44.96       O
ATOM  2882  O  HOH E 236   15.686  30.305  41.932  1.00 34.39       O
ATOM  2883  O  HOH E 237   19.813  25.731   9.704  1.00 54.60       O
ATOM  2884  O  HOH E 238  -11.134  30.653  35.013  1.00 29.66       O
ATOM  2885  O  HOH E 239   23.349  30.978  13.948  1.00 33.76       O
ATOM  2886  O  HOH E 240   27.984  12.143  25.936  1.00 53.12       O
ATOM  2887  O  HOH E 241   14.013   5.713  36.597  1.00 54.98       O
ATOM  2888  O  HOH E 242   -5.186   1.488  18.826  1.00 32.58       O
ATOM  2889  O  HOH E 243   17.801  11.638  42.280  1.00 56.32       O
ATOM  2890  O  HOH E 244   20.626  28.165   8.296  1.00 37.66       O
ATOM  2891  O  HOH E 245  -14.266  32.089  20.710  1.00 32.75       O
ATOM  2892  O  HOH E 246   16.359  17.921  24.357  1.00 16.40       O
ATOM  2893  O  HOH E 247   22.245  44.385  20.123  1.00 41.45       O
ATOM  2894  O  HOH E 248   16.604  38.833   6.473  1.00 41.36       O
ATOM  2895  O  HOH E 249    1.076  14.727  41.637  1.00 33.82       O
ATOM  2896  O  HOH E 250    3.943  39.022  -0.155  1.00 41.55       O
ATOM  2897  O  HOH E 251  -15.181  32.467  18.218  1.00 49.25       O
ATOM  2898  O  HOH E 252   -3.094  20.166  52.393  1.00 24.32       O
ATOM  2899  O  HOH E 253   14.447  30.328  33.548  1.00 20.57       O
ATOM  2900  O  HOH E 254   -2.134  37.126  16.954  1.00 25.93       O
ATOM  2901  O  HOH E 255  -12.588  11.384  38.812  1.00 34.44       O
ATOM  2902  O  HOH E 256   23.643  38.647  29.846  1.00 35.49       O
ATOM  2903  O  HOH E 257   14.012  28.085  49.305  1.00 28.33       O
ATOM  2904  O  HOH E 258  -13.431  35.306  22.811  1.00 29.88       O
ATOM  2905  O  HOH E 259   19.014  29.486  38.079  1.00 37.62       O
ATOM  2906  O  HOH E 260    9.973  47.838  12.738  1.00 30.92       O
ATOM  2907  O  HOH E 261   -1.393  14.038  15.147  1.00 21.88       O
ATOM  2908  O  HOH E 262    2.823  38.719   2.203  1.00 53.72       O
ATOM  2909  O  HOH E 263    4.887  29.829  47.793  1.00 31.79       O
ATOM  2910  O  HOH E 264    1.500  33.328   8.416  1.00 36.22       O
ATOM  2911  O  HOH E 265   -6.130  32.441  41.081  1.00 46.06       O
ATOM  2912  O  HOH E 266   -8.651  12.686  43.706  1.00 35.57       O
ATOM  2913  O  HOH E 267   10.509  34.023  48.640  1.00 39.55       O
ATOM  2914  O  HOH E 268    7.176  10.404   3.577  1.00 47.64       O
ATOM  2915  O  HOH E 269   11.589   8.923  15.291  1.00 42.78       O
ATOM  2916  O  HOH E 270    6.292  43.048  11.922  1.00 45.68       O
ATOM  2917  O  HOH E 271   -4.204  38.109  38.107  1.00 28.93       O
ATOM  2918  O  HOH E 272   -6.801  -2.869   6.062  1.00 40.05       O
ATOM  2919  O  HOH E 273    1.444  26.092   7.278  1.00 49.84       O
ATOM  2920  O  HOH E 274   -6.913  25.237  12.871  1.00 43.34       O
ATOM  2921  O  HOH E 275  -13.375  37.539  24.144  1.00 40.14       O
ATOM  2922  O  HOH E 276   -4.654  36.578  39.953  1.00 32.76       O
ATOM  2923  O  HOH E 277    3.005  36.560  15.059  1.00 37.66       O
ATOM  2924  O  HOH E 278  -10.376  14.770  42.516  1.00 45.45       O
ATOM  2925  O  HOH E 279   27.692  31.614  25.606  1.00 30.93       O
ATOM  2926  O  HOH E 280   -9.989  19.656  42.190  1.00 31.89       O
ATOM  2927  O  HOH E 281   -1.407  34.927  42.164  1.00 40.14       O
ATOM  2928  O  HOH E 282   -8.559   4.753  23.570  1.00 43.17       O
ATOM  2929  O  HOH E 283    1.711  32.850  54.362  1.00 47.56       O
ATOM  2930  O  HOH E 284   -9.196   7.241  17.304  1.00 47.58       O
ATOM  2931  O  HOH E 285   -3.657  13.519  20.161  1.00 32.40       O
ATOM  2932  O  HOH E 286   26.578  27.734  19.336  1.00 37.48       O
ATOM  2933  O  HOH E 287   10.661  44.828   6.336  1.00 52.79       O
ATOM  2934  O  HOH E 288  -10.255   9.632  43.912  1.00 37.67       O
ATOM  2935  O  HOH E 289   18.783  15.932  14.718  1.00 30.28       O
ATOM  2936  O  HOH E 290   12.591   9.124  20.690  1.00 44.22       O
ATOM  2937  O  HOH E 291    2.299   3.040  33.877  1.00 31.50       O
ATOM  2938  O  HOH E 292   24.925  12.665  17.248  1.00 44.45       O
ATOM  2939  O  HOH E 293   -4.555  33.946  43.703  1.00 43.28       O
```

FIGURE 3-42 (COORDINATES)

```
ATOM   2940  O    HOH E 294     -12.934  34.544  14.175  1.00 48.53           O
ATOM   2941  O    HOH E 295       2.989  36.445   4.116  1.00 52.96           O
ATOM   2942  O    HOH E 296      -6.463  16.342   6.891  1.00 47.66           O
ATOM   2943  O    HOH E 297       1.574  15.609   5.271  1.00 49.91           O
ATOM   2944  O    HOH E 298      -2.522  37.244  42.297  1.00 43.41           O
ATOM   2945  O    HOH E 299      25.203  30.570  18.660  1.00 47.45           O
ATOM   2946  O    HOH E 300      21.715  32.555  35.288  1.00 32.07           O
ATOM   2947  O    HOH E 301      16.719  44.025  31.980  1.00 45.99           O
ATOM   2948  O    HOH E 303       1.261  40.642   6.610  1.00 46.02           O
ATOM   2949  O    HOH E 304      24.621  42.769  25.439  1.00 39.41           O
ATOM   2950  O    HOH E 305      10.536  10.538  50.434  1.00 53.76           O
ATOM   2951  O    HOH E 307      21.463  16.396  32.762  1.00 31.33           O
ATOM   2952  O    HOH E 308       5.195   4.565  18.978  1.00 43.10           O
ATOM   2953  O    HOH E 309      14.303  44.678  22.864  1.00 42.30           O
ATOM   2954  O    HOH E 310       0.259  22.941   7.991  1.00 38.23           O
ATOM   2955  O    HOH E 311      12.478  43.043  33.361  1.00 32.56           O
ATOM   2956  O    HOH E 313      13.290   5.889  32.367  1.00 39.11           O
ATOM   2957  O    HOH E 314      -1.865  43.572  23.446  1.00 47.85           O
ATOM   2958  O    HOH E 315       2.009   4.950  43.244  1.00 33.70           O
ATOM   2959  O    HOH E 316       1.738   4.162  39.356  1.00 40.89           O
ATOM   2960  O    HOH E 317      13.571   6.235  15.325  1.00 61.76           O
ATOM   2961  O    HOH E 318      -3.990  42.094  22.126  1.00 37.70           O
ATOM   2962  O    HOH E 319      17.191  38.308  31.067  1.00 23.86           O
ATOM   2963  O    HOH E 320     -14.614  24.472  28.802  1.00 51.68           O
ATOM   2964  O    HOH E 321       8.248   6.225  34.037  1.00 32.07           O
ATOM   2965  O    HOH E 322       7.556   5.504  31.513  1.00 34.91           O
ATOM   2966  O    HOH E 323     -14.134  36.388  20.154  1.00 38.20           O
ATOM   2967  O    HOH E 324      13.299  46.995  16.513  1.00 47.10           O
ATOM   2968  O    HOH E 325     -10.712   4.564  14.674  1.00 46.06           O
ATOM   2969  O    HOH E 326       5.613   8.465  13.195  1.00 43.55           O
ATOM   2970  C1   NAG D   1       8.675  38.245   4.353  1.00 59.58           C
ATOM   2971  O1   NAG D   1       9.421  38.709   5.456  1.00 53.80           O
ATOM   2972  C2   NAG D   1       8.255  39.396   3.380  1.00 60.57           C
ATOM   2973  N2   NAG D   1       9.193  40.513   3.177  1.00 62.68           N
ATOM   2974  C7   NAG D   1       9.978  41.204   4.016  1.00 63.26           C
ATOM   2975  O7   NAG D   1      11.181  41.344   3.812  1.00 64.11           O
ATOM   2976  C8   NAG D   1       9.381  41.866   5.218  1.00 64.58           C
ATOM   2977  C3   NAG D   1       6.847  39.954   3.588  1.00 61.38           C
ATOM   2978  O3   NAG D   1       6.428  40.646   2.447  1.00 62.43           O
ATOM   2979  C4   NAG D   1       5.871  38.824   3.843  1.00 62.73           C
ATOM   2980  O4   NAG D   1       4.568  39.369   3.980  1.00 63.82           O
ATOM   2981  C5   NAG D   1       6.441  38.167   5.111  1.00 63.20           C
ATOM   2982  C6   NAG D   1       5.416  37.451   5.981  1.00 65.07           C
ATOM   2983  O6   NAG D   1       4.873  38.385   6.902  1.00 66.70           O
ATOM   2984  O5   NAG D   1       7.591  37.403   4.775  1.00 59.86           O
ATOM   2985  OXT  ACT F1428       7.846  40.253  39.356  1.00 36.10           O
ATOM   2986  C    ACT F1428       8.963  39.666  39.260  1.00 35.22           C
ATOM   2987  O    ACT F1428       9.280  38.800  40.117  1.00 34.60           O
ATOM   2988  CH3  ACT F1428       9.910  39.993  38.159  1.00 33.70           C
ATOM   2989  O3   GOL G   3      13.798  40.303  39.234  1.00 42.88           O
ATOM   2990  C3   GOL G   3      14.116  41.354  38.331  1.00 42.33           C
ATOM   2991  C2   GOL G   3      13.006  41.418  37.278  1.00 40.38           C
ATOM   2992  O2   GOL G   3      12.597  40.111  36.969  1.00 37.46           O
ATOM   2993  C1   GOL G   3      13.479  42.030  35.970  1.00 39.45           C
ATOM   2994  O1   GOL G   3      13.483  40.998  35.004  1.00 32.21           O
ATOM   2995  OXT  ACT H1428      -6.243  39.506  24.314  1.00 33.25           O
ATOM   2996  C    ACT H1428      -5.766  39.203  23.207  1.00 31.68           C
ATOM   2997  O    ACT H1428      -6.205  38.181  22.662  1.00 32.81           O
ATOM   2998  CH3  ACT H1428      -4.685  39.990  22.607  1.00 31.88           C
ATOM   2999  O7   NAG I   1      22.349  30.938  31.199  1.00 20.00           O
ATOM   3000  C7   NAG I   1      21.964  32.088  31.163  1.00 20.00           C
ATOM   3001  C8   NAG I   1      21.528  32.745  29.898  1.00 20.00           C
ATOM   3002  N2   NAG I   1      21.882  32.874  32.233  1.00 20.00           N
ATOM   3003  C2   NAG I   1      21.421  34.274  32.162  1.00 20.00           C
ATOM   3004  C1   NAG I   1      21.887  34.810  30.841  1.00 20.00           C
ATOM   3005  O1   NAG I   1      23.268  34.546  30.695  1.00 20.00           O
ATOM   3006  C3   NAG I   1      19.917  34.335  32.032  1.00 20.00           C
ATOM   3007  O3   NAG I   1      19.625  33.636  30.834  1.00 20.00           O
ATOM   3008  C4   NAG I   1      19.450  35.771  31.851  1.00 20.00           C
ATOM   3009  O4   NAG I   1      18.133  35.732  31.330  1.00 20.00           O
```

FIGURE 3-43 (COORDINATES)

```
ATOM   3010  C5   NAG I   1      20.310  36.565  30.869  1.00 20.00           C
ATOM   3011  O5   NAG I   1      21.672  36.195  30.915  1.00 20.00           O
ATOM   3012  C6   NAG I   1      20.301  38.058  31.189  1.00 20.00           C
ATOM   3013  O6   NAG I   1      21.482  38.429  31.921  1.00 20.00           O
END
```

FIGURE 3-44 (COORDINATES)

```
HEADER    ----                                        XX-XXX-9-  xxxx
COMPND    ---
REMARK   3
REMARK   3 REFINEMENT.
REMARK   3   PROGRAM     : REFMAC 5.2.0019
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   1.98
REMARK   3   RESOLUTION RANGE LOW  (ANGSTROMS) :  32.00
REMARK   3   DATA CUTOFF            (SIGMA(F)) : NONE
REMARK   3   COMPLETENESS FOR RANGE        (%) : 100.00
REMARK   3   NUMBER OF REFLECTIONS             :  23586
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.18063
REMARK   3   R VALUE            (WORKING SET) : 0.17757
REMARK   3   FREE R VALUE                     : 0.23945
REMARK   3   FREE R VALUE TEST SET SIZE   (%) : 5.0
REMARK   3   FREE R VALUE TEST SET COUNT      : 1242
REMARK   3
REMARK   3  FIT IN THE HIGHEST RESOLUTION BIN.
REMARK   3   TOTAL NUMBER OF BINS USED           :     20
REMARK   3   BIN RESOLUTION RANGE HIGH           :  1.980
REMARK   3   BIN RESOLUTION RANGE LOW            :  2.031
REMARK   3   REFLECTION IN BIN     (WORKING SET) :   1553
REMARK   3   BIN COMPLETENESS (WORKING+TEST) (%) : 100.00
REMARK   3   BIN R VALUE           (WORKING SET) :  0.222
REMARK   3   BIN FREE R VALUE SET COUNT          :     82
REMARK   3   BIN FREE R VALUE                    :  0.301
REMARK   3
REMARK   3  NUMBER OF NON-HYDROGEN ATOMS USED IN REFINEMENT.
REMARK   3   ALL ATOMS                :    2960
REMARK   3
REMARK   3  B VALUES.
REMARK   3   FROM WILSON PLOT           (A**2) : NULL
REMARK   3   MEAN B VALUE      (OVERALL, A**2) :  24.785
REMARK   3   OVERALL ANISOTROPIC B VALUE.
REMARK   3    B11 (A**2) :  -0.40
REMARK   3    B22 (A**2) :  -0.54
REMARK   3    B33 (A**2) :   0.94
REMARK   3    B12 (A**2) :   0.00
REMARK   3    B13 (A**2) :   0.00
REMARK   3    B23 (A**2) :   0.00
REMARK   3
REMARK   3  ESTIMATED OVERALL COORDINATE ERROR.
REMARK   3   ESU BASED ON R VALUE                     (A):   0.180
REMARK   3   ESU BASED ON FREE R VALUE                (A):   0.171
REMARK   3   ESU BASED ON MAXIMUM LIKELIHOOD          (A):   0.117
REMARK   3   ESU FOR B VALUES BASED ON MAXIMUM LIKELIHOOD (A**2):   4.096
REMARK   3
REMARK   3 CORRELATION COEFFICIENTS.
REMARK   3   CORRELATION COEFFICIENT FO-FC      :  0.956
REMARK   3   CORRELATION COEFFICIENT FO-FC FREE :  0.921
REMARK   3
REMARK   3  RMS DEVIATIONS FROM IDEAL VALUES        COUNT    RMS    WEIGHT
REMARK   3   BOND LENGTHS REFINED ATOMS        (A):  2713 ; 0.018 ; 0.021
REMARK   3   BOND ANGLES REFINED ATOMS   (DEGREES):  3679 ; 2.166 ; 1.967
REMARK   3   TORSION ANGLES, PERIOD 1    (DEGREES):   320 ; 6.086 ; 5.000
REMARK   3   TORSION ANGLES, PERIOD 2    (DEGREES):   130 ;33.552 ;23.769
REMARK   3   TORSION ANGLES, PERIOD 3    (DEGREES):   433 ;13.778 ;15.000
REMARK   3   TORSION ANGLES, PERIOD 4    (DEGREES):    16 ;14.967 ;15.000
REMARK   3   CHIRAL-CENTER RESTRAINTS       (A**3):   392 ; 0.111 ; 0.200
REMARK   3   GENERAL PLANES REFINED ATOMS     (A):  2092 ; 0.009 ; 0.020
REMARK   3   NON-BONDED CONTACTS REFINED ATOMS (A): 1345 ; 0.219 ; 0.200
REMARK   3   NON-BONDED TORSION REFINED ATOMS  (A): 1820 ; 0.308 ; 0.200
```

FIGURE 3-45 (REMARKS)

```
REMARK   3    H-BOND (X...Y) REFINED ATOMS       (A):    249 ; 0.154 ; 0.200
REMARK   3    POTENTIAL METAL-ION REFINED ATOMS  (A):      3 ; 0.109 ; 0.200
REMARK   3    SYMMETRY VDW REFINED ATOMS         (A):     54 ; 0.299 ; 0.200
REMARK   3    SYMMETRY H-BOND REFINED ATOMS      (A):     19 ; 0.239 ; 0.200
REMARK   3
REMARK   3  ISOTROPIC THERMAL FACTOR RESTRAINTS.    COUNT   RMS    WEIGHT
REMARK   3    MAIN-CHAIN BOND REFINED ATOMS  (A**2):  1672 ; 1.106 ; 1.500
REMARK   3    MAIN-CHAIN ANGLE REFINED ATOMS (A**2):  2600 ; 1.718 ; 2.000
REMARK   3    SIDE-CHAIN BOND REFINED ATOMS  (A**2):  1203 ; 2.687 ; 3.000
REMARK   3    SIDE-CHAIN ANGLE REFINED ATOMS (A**2):  1079 ; 3.861 ; 4.500
REMARK   3
REMARK   3  NCS RESTRAINTS STATISTICS
REMARK   3    NUMBER OF NCS GROUPS : NULL
REMARK   3
REMARK   3
REMARK   3  TLS DETAILS
REMARK   3    NUMBER OF TLS GROUPS  : NULL
REMARK   3
REMARK   3
REMARK   3  BULK SOLVENT MODELLING.
REMARK   3    METHOD USED : MASK
REMARK   3    PARAMETERS FOR MASK CALCULATION
REMARK   3    VDW PROBE RADIUS   :   1.20
REMARK   3    ION PROBE RADIUS   :   0.80
REMARK   3    SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3
SSBOND   1 CYS A   140     CYS A   165
LINK            ND2 ASN A   50            1.400   O1 NAG D   1                   ASN-NAG
CISPEP   1 ASP A   160     SER A   161                   0.00
LINK            ASP A  184                   PRO A  190                          gap
CISPEP   2 HIS A   229     PRO A   230                   0.00
CISPEP   3 ASN A   297     PHE A   298                   0.00
CISPEP   4 SER A   324     PRO A   325                   0.00
MODRES      NAG D    1   NAG-a-D                                                 RENAME
CRYST1   42.739   84.657   96.554  90.00  90.00  90.00 P 21 21 21
SCALE1     0.023398  0.000000  0.000000       0.00000
SCALE2     0.000000  0.011812  0.000000       0.00000
SCALE3     0.000000  0.000000  0.010357       0.00000
```

FIGURE 3-46 (REMARKS)

|      | ATOM | RES |   | #  | x      | y      | z      | Occ  | B     |   |
|------|------|-----|---|----|--------|--------|--------|------|-------|---|
| ATOM | 1    | N   | ALA A | 36 | 4.961  | 5.892  | 5.468  | 1.00 | 46.95 | N |
| ATOM | 2    | CA  | ALA A | 36 | 5.776  | 7.002  | 4.888  | 1.00 | 46.91 | C |
| ATOM | 3    | CB  | ALA A | 36 | 5.497  | 7.153  | 3.390  | 1.00 | 47.37 | C |
| ATOM | 4    | C   | ALA A | 36 | 5.536  | 8.330  | 5.598  | 1.00 | 46.66 | C |
| ATOM | 5    | O   | ALA A | 36 | 6.483  | 9.086  | 5.821  | 1.00 | 46.55 | O |
| ATOM | 6    | N   | TRP A | 37 | 4.273  | 8.613  | 5.931  | 1.00 | 46.05 | N |
| ATOM | 7    | CA  | TRP A | 37 | 3.901  | 9.893  | 6.551  | 1.00 | 45.73 | C |
| ATOM | 8    | CB  | TRP A | 37 | 2.385  | 10.138 | 6.516  | 1.00 | 44.90 | C |
| ATOM | 9    | CG  | TRP A | 37 | 1.547  | 9.425  | 7.544  | 1.00 | 44.52 | C |
| ATOM | 10   | CD1 | TRP A | 37 | 0.715  | 8.352  | 7.325  | 1.00 | 44.30 | C |
| ATOM | 11   | NE1 | TRP A | 37 | 0.078  | 7.999  | 8.494  | 1.00 | 43.82 | N |
| ATOM | 12   | CE2 | TRP A | 37 | 0.488  | 8.839  | 9.503  | 1.00 | 44.59 | C |
| ATOM | 13   | CD2 | TRP A | 37 | 1.402  | 9.764  | 8.941  | 1.00 | 44.44 | C |
| ATOM | 14   | CE3 | TRP A | 37 | 1.968  | 10.751 | 9.774  | 1.00 | 43.83 | C |
| ATOM | 15   | CZ3 | TRP A | 37 | 1.610  | 10.778 | 11.130 | 1.00 | 43.42 | C |
| ATOM | 16   | CH2 | TRP A | 37 | 0.692  | 9.851  | 11.659 | 1.00 | 44.20 | C |
| ATOM | 17   | CZ2 | TRP A | 37 | 0.124  | 8.873  | 10.870 | 1.00 | 44.79 | C |
| ATOM | 18   | C   | TRP A | 37 | 4.462  | 10.031 | 7.966  | 1.00 | 45.81 | C |
| ATOM | 19   | O   | TRP A | 37 | 4.791  | 11.140 | 8.418  | 1.00 | 45.42 | O |
| ATOM | 20   | N   | THR A | 38 | 4.590  | 8.888  | 8.636  | 1.00 | 45.76 | N |
| ATOM | 21   | CA  | THR A | 38 | 5.164  | 8.812  | 9.976  | 1.00 | 45.88 | C |
| ATOM | 22   | CB  | THR A | 38 | 4.875  | 7.450  | 10.618 | 1.00 | 45.85 | C |
| ATOM | 23   | OG1 | THR A | 38 | 5.508  | 6.430  | 9.840  | 1.00 | 46.36 | O |
| ATOM | 24   | CG2 | THR A | 38 | 3.369  | 7.176  | 10.695 | 1.00 | 44.57 | C |
| ATOM | 25   | C   | THR A | 38 | 6.681  | 9.048  | 9.938  | 1.00 | 46.26 | C |
| ATOM | 26   | O   | THR A | 38 | 7.364  | 8.983  | 10.969 | 1.00 | 46.64 | O |
| ATOM | 27   | N   | GLN A | 39 | 7.196  | 9.348  | 8.751  | 1.00 | 46.30 | N |
| ATOM | 28   | CA  | GLN A | 39 | 8.622  | 9.562  | 8.546  | 1.00 | 46.35 | C |
| ATOM | 29   | CB  | GLN A | 39 | 9.105  | 8.667  | 7.401  | 1.00 | 46.78 | C |
| ATOM | 30   | CG  | GLN A | 39 | 10.569 | 8.280  | 7.474  | 1.00 | 49.47 | C |
| ATOM | 31   | CD  | GLN A | 39 | 10.882 | 7.441  | 8.693  | 1.00 | 52.20 | C |
| ATOM | 32   | OE1 | GLN A | 39 | 10.078 | 6.609  | 9.109  | 1.00 | 53.33 | O |
| ATOM | 33   | NE2 | GLN A | 39 | 12.052 | 7.664  | 9.280  | 1.00 | 54.55 | N |
| ATOM | 34   | C   | GLN A | 39 | 8.960  | 11.030 | 8.263  | 1.00 | 45.73 | C |
| ATOM | 35   | O   | GLN A | 39 | 10.120 | 11.432 | 8.297  | 1.00 | 45.68 | O |
| ATOM | 36   | N   | GLU A | 40 | 7.937  | 11.833 | 7.990  | 1.00 | 45.60 | N |
| ATOM | 37   | CA  | GLU A | 40 | 8.122  | 13.245 | 7.634  | 1.00 | 44.97 | C |
| ATOM | 38   | CB  | GLU A | 40 | 6.779  | 13.853 | 7.228  | 1.00 | 45.07 | C |
| ATOM | 39   | CG  | GLU A | 40 | 6.227  | 13.201 | 5.961  | 1.00 | 44.58 | C |
| ATOM | 40   | CD  | GLU A | 40 | 4.774  | 13.533 | 5.669  | 1.00 | 45.13 | C |
| ATOM | 41   | OE1 | GLU A | 40 | 4.192  | 14.458 | 6.279  | 1.00 | 43.95 | O |
| ATOM | 42   | OE2 | GLU A | 40 | 4.210  | 12.852 | 4.795  | 1.00 | 47.69 | O |
| ATOM | 43   | C   | GLU A | 40 | 8.838  | 14.089 | 8.704  | 1.00 | 44.51 | C |
| ATOM | 44   | O   | GLU A | 40 | 9.661  | 14.940 | 8.377  | 1.00 | 44.05 | O |
| ATOM | 45   | N   | LYS A | 41 | 8.561  | 13.815 | 9.976  | 1.00 | 44.08 | N |
| ATOM | 46   | CA  | LYS A | 41 | 9.186  | 14.552 | 11.075 | 1.00 | 43.84 | C |
| ATOM | 47   | CB  | LYS A | 41 | 8.682  | 14.058 | 12.429 | 1.00 | 43.67 | C |
| ATOM | 48   | CG  | LYS A | 41 | 8.903  | 12.584 | 12.716 | 1.00 | 42.66 | C |
| ATOM | 49   | CD  | LYS A | 41 | 8.314  | 12.279 | 14.071 | 1.00 | 41.50 | C |
| ATOM | 50   | CE  | LYS A | 41 | 7.805  | 10.877 | 14.172 | 1.00 | 42.74 | C |
| ATOM | 51   | NZ  | LYS A | 41 | 8.924  | 9.921  | 14.161 | 1.00 | 42.46 | N |
| ATOM | 52   | C   | LYS A | 41 | 10.719 | 14.558 | 11.060 | 1.00 | 43.93 | C |
| ATOM | 53   | O   | LYS A | 41 | 11.337 | 15.508 | 11.547 | 1.00 | 43.44 | O |
| ATOM | 54   | N   | ASN A | 42 | 11.324 | 13.504 | 10.509 | 1.00 | 44.20 | N |
| ATOM | 55   | CA  | ASN A | 42 | 12.785 | 13.415 | 10.421 | 1.00 | 44.25 | C |
| ATOM | 56   | CB  | ASN A | 42 | 13.248 | 12.012 | 10.168 | 0.00 | 44.03 | C |
| ATOM | 57   | CG  | ASN A | 42 | 11.567 | 10.498 | 11.101 | 1.00 | 52.28 | C |
| ATOM | 58   | OD1 | ASN A | 42 | 10.844 | 9.498  | 11.105 | 1.00 | 53.88 | O |
| ATOM | 59   | ND2 | ASN A | 42 | 12.699 | 10.542 | 10.405 | 1.00 | 51.12 | N |
| ATOM | 60   | C   | ASN A | 42 | 13.241 | 14.084 | 9.147  | 1.00 | 44.51 | C |
| ATOM | 61   | O   | ASN A | 42 | 14.403 | 14.455 | 9.011  | 1.00 | 45.36 | O |
| ATOM | 62   | N   | HIS A | 43 | 12.315 | 14.240 | 8.208  | 1.00 | 44.60 | N |
| ATOM | 63   | CA  | HIS A | 43 | 12.183 | 15.194 | 6.977  | 0.00 | 42.02 | C |
| ATOM | 64   | CB  | HIS A | 43 | 13.300 | 14.804 | 6.007  | 0.00 | 42.75 | C |
| ATOM | 65   | CG  | HIS A | 43 | 13.431 | 13.327 | 5.799  | 0.00 | 44.68 | C |
| ATOM | 66   | ND1 | HIS A | 43 | 13.531 | 10.479 | 6.598  | 1.00 | 52.13 | N |
| ATOM | 67   | CE1 | HIS A | 43 | 12.707 | 11.378 | 6.084  | 1.00 | 51.42 | C |
| ATOM | 68   | NE2 | HIS A | 43 | 13.397 | 12.464 | 5.776  | 1.00 | 50.85 | N |
| ATOM | 69   | CD2 | HIS A | 43 | 14.720 | 12.276 | 6.106  | 1.00 | 51.37 | C |

FIGURE 4-1 (COORDINATES)

| | | | | | | | | | |
|---|---|---|---|---|---|---|---|---|---|
| ATOM | 70 | C | HIS | A | 43 | 12.675 | 16.857 | 7.571 | 1.00 35.84 | C |
| ATOM | 71 | O | HIS | A | 43 | 12.852 | 17.670 | 6.644 | 1.00 36.61 | O |
| ATOM | 72 | N | HIS | A | 44 | 11.726 | 17.025 | 8.498 | 1.00 35.08 | N |
| ATOM | 73 | CA | HIS | A | 44 | 10.992 | 18.282 | 8.570 | 1.00 33.53 | C |
| ATOM | 74 | CB | HIS | A | 44 | 9.898 | 18.280 | 9.646 | 1.00 33.52 | C |
| ATOM | 75 | CG | HIS | A | 44 | 9.142 | 19.579 | 9.730 | 1.00 31.37 | C |
| ATOM | 76 | ND1 | HIS | A | 44 | 8.161 | 19.929 | 8.824 | 1.00 32.14 | N |
| ATOM | 77 | CE1 | HIS | A | 44 | 7.684 | 21.123 | 9.132 | 1.00 30.94 | C |
| ATOM | 78 | NE2 | HIS | A | 44 | 8.307 | 21.555 | 10.215 | 1.00 29.51 | N |
| ATOM | 79 | CD2 | HIS | A | 44 | 9.230 | 20.611 | 10.604 | 1.00 30.54 | C |
| ATOM | 80 | C | HIS | A | 44 | 11.980 | 19.381 | 8.842 | 1.00 33.40 | C |
| ATOM | 81 | O | HIS | A | 44 | 12.840 | 19.260 | 9.714 | 1.00 33.05 | O |
| ATOM | 82 | N | GLN | A | 45 | 11.851 | 20.441 | 8.061 | 1.00 33.71 | N |
| ATOM | 83 | CA | GLN | A | 45 | 12.692 | 21.604 | 8.175 | 1.00 34.38 | C |
| ATOM | 84 | CB | GLN | A | 45 | 13.407 | 21.862 | 6.848 | 1.00 34.86 | C |
| ATOM | 85 | CG | GLN | A | 45 | 14.333 | 20.713 | 6.435 | 1.00 35.58 | C |
| ATOM | 86 | CD | GLN | A | 45 | 15.424 | 20.445 | 7.464 | 1.00 36.28 | C |
| ATOM | 87 | OE1 | GLN | A | 45 | 15.955 | 21.365 | 8.082 | 1.00 37.00 | O |
| ATOM | 88 | NE2 | GLN | A | 45 | 15.771 | 19.176 | 7.638 | 1.00 39.53 | N |
| ATOM | 89 | C | GLN | A | 45 | 11.855 | 22.814 | 8.551 | 1.00 34.89 | C |
| ATOM | 90 | O | GLN | A | 45 | 10.696 | 22.925 | 8.124 | 1.00 34.43 | O |
| ATOM | 91 | N | PRO | A | 46 | 12.442 | 23.731 | 9.354 | 1.00 35.25 | N |
| ATOM | 92 | CA | PRO | A | 46 | 11.737 | 24.966 | 9.687 | 1.00 35.35 | C |
| ATOM | 93 | CB | PRO | A | 46 | 12.485 | 25.463 | 10.919 | 1.00 34.92 | C |
| ATOM | 94 | CG | PRO | A | 46 | 13.891 | 24.975 | 10.709 | 1.00 35.87 | C |
| ATOM | 95 | CD | PRO | A | 46 | 13.779 | 23.662 | 9.982 | 1.00 34.37 | C |
| ATOM | 96 | C | PRO | A | 46 | 11.847 | 25.985 | 8.541 | 1.00 36.31 | C |
| ATOM | 97 | O | PRO | A | 46 | 12.839 | 25.977 | 7.779 | 1.00 35.66 | O |
| ATOM | 98 | N | ALA | A | 47 | 10.834 | 26.841 | 8.412 | 1.00 36.48 | N |
| ATOM | 99 | CA | ALA | A | 47 | 10.931 | 27.985 | 7.523 | 1.00 37.43 | C |
| ATOM | 100 | CB | ALA | A | 47 | 9.593 | 28.241 | 6.818 | 1.00 37.56 | C |
| ATOM | 101 | C | ALA | A | 47 | 11.306 | 29.154 | 8.394 | 1.00 37.93 | C |
| ATOM | 102 | O | ALA | A | 47 | 10.474 | 29.617 | 9.180 | 1.00 39.30 | O |
| ATOM | 103 | N | HIS | A | 48 | 12.549 | 29.614 | 8.273 | 1.00 37.80 | N |
| ATOM | 104 | CA | HIS | A | 48 | 13.094 | 30.712 | 9.087 | 1.00 38.23 | C |
| ATOM | 105 | CB | HIS | A | 48 | 14.569 | 30.986 | 8.743 | 1.00 38.09 | C |
| ATOM | 106 | CG | HIS | A | 48 | 15.467 | 29.788 | 8.861 | 1.00 38.38 | C |
| ATOM | 107 | ND1 | HIS | A | 48 | 16.833 | 29.901 | 8.986 | 1.00 39.47 | N |
| ATOM | 108 | CE1 | HIS | A | 48 | 17.370 | 28.695 | 9.057 | 1.00 38.46 | C |
| ATOM | 109 | NE2 | HIS | A | 48 | 16.400 | 27.802 | 8.995 | 1.00 37.09 | N |
| ATOM | 110 | CD2 | HIS | A | 48 | 15.200 | 28.457 | 8.869 | 1.00 38.46 | C |
| ATOM | 111 | C | HIS | A | 48 | 12.305 | 32.005 | 8.910 | 1.00 38.55 | C |
| ATOM | 112 | O | HIS | A | 48 | 11.745 | 32.247 | 7.840 | 1.00 39.28 | O |
| ATOM | 113 | N | LEU | A | 49 | 12.254 | 32.826 | 9.956 | 1.00 38.36 | N |
| ATOM | 114 | CA | LEU | A | 49 | 11.588 | 34.124 | 9.876 | 1.00 38.34 | C |
| ATOM | 115 | CB | LEU | A | 49 | 11.019 | 34.563 | 11.238 | 1.00 37.78 | C |
| ATOM | 116 | CG | LEU | A | 49 | 9.886 | 33.748 | 11.884 | 1.00 37.33 | C |
| ATOM | 117 | CD1 | LEU | A | 49 | 9.326 | 34.457 | 13.122 | 1.00 34.47 | C |
| ATOM | 118 | CD2 | LEU | A | 49 | 8.769 | 33.375 | 10.906 | 1.00 35.59 | C |
| ATOM | 119 | C | LEU | A | 49 | 12.607 | 35.134 | 9.416 | 1.00 38.87 | C |
| ATOM | 120 | O | LEU | A | 49 | 13.771 | 35.035 | 9.787 | 1.00 39.04 | O |
| ATOM | 121 | N | ASN | A | 50 | 12.188 | 36.096 | 8.600 | 1.00 39.73 | N |
| ATOM | 122 | CA | ASN | A | 50 | 13.051 | 37.251 | 8.318 | 1.00 40.57 | C |
| ATOM | 123 | CB | ASN | A | 50 | 12.640 | 37.954 | 7.020 | 1.00 41.04 | C |
| ATOM | 124 | CG | ASN | A | 50 | 11.135 | 38.191 | 6.931 | 1.00 44.27 | C |
| ATOM | 125 | OD1 | ASN | A | 50 | 10.433 | 38.244 | 7.955 | 1.00 45.96 | O |
| ATOM | 126 | ND2 | ASN | A | 50 | 10.628 | 38.328 | 5.703 | 1.00 46.84 | N |
| ATOM | 127 | C | ASN | A | 50 | 13.041 | 38.220 | 9.494 | 1.00 40.27 | C |
| ATOM | 128 | O | ASN | A | 50 | 12.297 | 38.031 | 10.458 | 1.00 39.72 | O |
| ATOM | 129 | N | SER | A | 51 | 13.871 | 39.252 | 9.389 | 1.00 40.11 | N |
| ATOM | 130 | CA | SER | A | 51 | 14.090 | 40.265 | 10.432 | 1.00 40.21 | C |
| ATOM | 131 | CB | SER | A | 51 | 15.121 | 41.265 | 9.918 | 1.00 40.26 | C |
| ATOM | 132 | OG | SER | A | 51 | 15.787 | 41.926 | 10.983 | 1.00 42.69 | O |
| ATOM | 133 | C | SER | A | 51 | 12.824 | 41.026 | 10.871 | 1.00 39.73 | C |
| ATOM | 134 | O | SER | A | 51 | 12.723 | 41.473 | 12.031 | 1.00 39.17 | O |
| ATOM | 135 | N | SER | A | 52 | 11.892 | 41.177 | 9.929 | 1.00 39.05 | N |
| ATOM | 136 | CA | SER | A | 52 | 10.622 | 41.894 | 10.127 | 1.00 38.74 | C |
| ATOM | 137 | CB | SER | A | 52 | 10.018 | 42.381 | 8.777 | 1.00 38.55 | C |
| ATOM | 138 | OG | SER | A | 52 | 8.877 | 41.616 | 8.334 | 1.00 39.04 | O |
| ATOM | 139 | C | SER | A | 52 | 9.621 | 41.044 | 10.919 | 1.00 37.57 | C |

FIGURE 4-2 (COORDINATES)

```
ATOM    140  O    SER A  52       9.025  41.528  11.897  1.00 37.54           O
ATOM    141  N    SER A  53       9.428  39.793  10.492  1.00 36.00           N
ATOM    142  CA   SER A  53       8.666  38.838  11.273  1.00 34.60           C
ATOM    143  CB   SER A  53       8.511  37.534  10.518  1.00 35.08           C
ATOM    144  OG   SER A  53       8.135  37.811   9.187  1.00 35.34           O
ATOM    145  C    SER A  53       9.250  38.614  12.686  1.00 33.32           C
ATOM    146  O    SER A  53       8.492  38.490  13.650  1.00 33.21           O
ATOM    147  N    LEU A  54      10.580  38.611  12.822  1.00 31.52           N
ATOM    148  CA   LEU A  54      11.188  38.478  14.153  1.00 29.60           C
ATOM    149  CB   LEU A  54      12.702  38.273  14.095  1.00 29.26           C
ATOM    150  CG   LEU A  54      13.254  36.999  13.446  1.00 27.56           C
ATOM    151  CD1  LEU A  54      14.765  37.134  13.318  1.00 26.87           C
ATOM    152  CD2  LEU A  54      12.910  35.729  14.231  1.00 26.69           C
ATOM    153  C    LEU A  54      10.807  39.633  15.088  1.00 29.09           C
ATOM    154  O    LEU A  54      10.416  39.392  16.233  1.00 28.00           O
ATOM    155  N    GLN A  55      10.884  40.872  14.592  1.00 28.27           N
ATOM    156  CA   GLN A  55      10.445  42.044  15.373  1.00 27.84           C
ATOM    157  CB   GLN A  55      10.796  43.339  14.651  1.00 28.76           C
ATOM    158  CG   GLN A  55      10.259  44.599  15.315  1.00 34.65           C
ATOM    159  CD   GLN A  55      11.255  45.753  15.315  1.00 41.78           C
ATOM    160  OE1  GLN A  55      12.478  45.538  15.267  1.00 44.11           O
ATOM    161  NE2  GLN A  55      10.733  46.999  15.380  1.00 43.53           N
ATOM    162  C    GLN A  55       8.949  41.999  15.708  1.00 26.23           C
ATOM    163  O    GLN A  55       8.548  42.350  16.802  1.00 24.77           O
ATOM    164  N    GLN A  56       8.151  41.550  14.751  1.00 25.57           N
ATOM    165  CA   GLN A  56       6.715  41.313  14.926  1.00 25.06           C
ATOM    166  CB   GLN A  56       6.086  40.829  13.617  0.00 30.12           C
ATOM    167  CG   GLN A  56       4.601  40.547  13.762  0.00 32.53           C
ATOM    168  CD   GLN A  56       3.951  39.961  12.513  0.00 34.06           C
ATOM    169  OE1  GLN A  56       4.617  39.367  11.644  0.00 38.66           O
ATOM    170  NE2  GLN A  56       2.625  40.098  12.438  0.00 36.67           N
ATOM    171  C    GLN A  56       6.435  40.340  16.074  1.00 23.91           C
ATOM    172  O    GLN A  56       5.610  40.640  16.955  1.00 24.03           O
ATOM    173  N    VAL A  57       7.122  39.192  16.083  1.00 22.22           N
ATOM    174  CA   VAL A  57       6.994  38.265  17.215  1.00 20.72           C
ATOM    175  CB   VAL A  57       7.770  36.905  17.027  1.00 21.38           C
ATOM    176  CG1  VAL A  57       7.600  36.026  18.260  1.00 21.02           C
ATOM    177  CG2  VAL A  57       7.274  36.162  15.835  1.00 21.36           C
ATOM    178  C    VAL A  57       7.409  38.925  18.520  1.00 19.85           C
ATOM    179  O    VAL A  57       6.681  38.836  19.502  1.00 19.13           O
ATOM    180  N    ALA A  58       8.565  39.605  18.546  1.00 19.11           N
ATOM    181  CA   ALA A  58       9.029  40.203  19.781  1.00 18.39           C
ATOM    182  CB   ALA A  58      10.415  40.860  19.615  1.00 18.52           C
ATOM    183  C    ALA A  58       8.020  41.226  20.306  1.00 18.63           C
ATOM    184  O    ALA A  58       7.827  41.331  21.502  1.00 18.82           O
ATOM    185  N    GLU A  59       7.402  41.980  19.399  1.00 19.43           N
ATOM    186  CA   GLU A  59       6.442  43.020  19.768  1.00 21.16           C
ATOM    187  CB   GLU A  59       6.205  44.004  18.601  1.00 21.09           C
ATOM    188  CG   GLU A  59       7.399  44.878  18.181  1.00 24.67           C
ATOM    189  CD   GLU A  59       7.082  45.729  16.937  1.00 25.54           C
ATOM    190  OE1  GLU A  59       6.013  45.485  16.292  1.00 30.17           O
ATOM    191  OE2  GLU A  59       7.880  46.654  16.610  1.00 32.26           O
ATOM    192  C    GLU A  59       5.090  42.461  20.176  1.00 19.66           C
ATOM    193  O    GLU A  59       4.362  43.117  20.909  1.00 19.87           O
ATOM    194  N    GLY A  60       4.737  41.271  19.701  1.00 18.91           N
ATOM    195  CA   GLY A  60       3.382  40.759  19.898  1.00 18.31           C
ATOM    196  C    GLY A  60       3.146  40.002  21.191  1.00 18.29           C
ATOM    197  O    GLY A  60       2.023  39.543  21.448  1.00 17.25           O
ATOM    198  N    THR A  61       4.208  39.812  21.977  1.00 18.76           N
ATOM    199  CA   THR A  61       4.098  39.140  23.273  1.00 18.32           C
ATOM    200  CB   THR A  61       5.103  37.932  23.389  1.00 18.70           C
ATOM    201  OG1  THR A  61       4.857  37.216  24.607  1.00 18.33           O
ATOM    202  CG2  THR A  61       6.570  38.382  23.331  1.00 15.07           C
ATOM    203  C    THR A  61       4.205  40.130  24.444  1.00 19.00           C
ATOM    204  O    THR A  61       4.997  41.076  24.403  1.00 19.05           O
ATOM    205  N    SER A  62       3.395  39.922  25.481  1.00 18.60           N
ATOM    206  CA   SER A  62       3.375  40.829  26.620  1.00 18.73           C
ATOM    207  CB   SER A  62       2.031  41.615  26.685  1.00 18.17           C
ATOM    208  OG   SER A  62       2.031  42.427  27.863  1.00 19.74           O
ATOM    209  C    SER A  62       3.609  40.107  27.931  1.00 18.29           C
```

FIGURE 4-3 (COORDINATES)

```
ATOM    210  O    SER A  62       2.726  39.392  28.413  1.00 17.45           O
ATOM    211  N    ILE A  63       4.773  40.343  28.540  1.00 19.05           N
ATOM    212  CA   ILE A  63       5.100  39.712  29.794  1.00 19.57           C
ATOM    213  CB   ILE A  63       6.610  39.931  30.180  1.00 20.19           C
ATOM    214  CG1  ILE A  63       7.033  39.009  31.333  1.00 20.30           C
ATOM    215  CD1  ILE A  63       6.865  37.515  30.996  1.00 18.85           C
ATOM    216  CG2  ILE A  63       6.898  41.386  30.476  1.00 20.61           C
ATOM    217  C    ILE A  63       4.121  40.064  30.929  1.00 19.89           C
ATOM    218  O    ILE A  63       3.778  39.203  31.749  1.00 19.85           O
ATOM    219  N    SER A  64       3.668  41.329  30.968  1.00 20.75           N
ATOM    220  CA   SER A  64       2.807  41.801  32.049  1.00 20.73           C
ATOM    221  CB   SER A  64       2.883  43.336  32.208  1.00 21.73           C
ATOM    222  OG   SER A  64       2.341  43.991  31.068  1.00 25.13           O
ATOM    223  C    SER A  64       1.359  41.315  31.891  1.00 19.63           C
ATOM    224  O    SER A  64       0.676  41.060  32.882  1.00 19.57           O
ATOM    225  N    GLU A  65       0.902  41.167  30.659  1.00 19.35           N
ATOM    226  CA   GLU A  65      -0.424  40.597  30.433  1.00 20.01           C
ATOM    227  CB   GLU A  65      -0.901  40.841  29.021  1.00 21.08           C
ATOM    228  CG   GLU A  65      -1.253  42.293  28.746  1.00 23.55           C
ATOM    229  CD   GLU A  65      -1.730  42.505  27.310  1.00 29.75           C
ATOM    230  OE1  GLU A  65      -1.360  41.719  26.409  1.00 33.35           O
ATOM    231  OE2  GLU A  65      -2.490  43.457  27.081  1.00 32.77           O
ATOM    232  C    GLU A  65      -0.422  39.111  30.743  1.00 19.80           C
ATOM    233  O    GLU A  65      -1.325  38.614  31.407  1.00 20.19           O
ATOM    234  N    MET A  66       0.606  38.405  30.282  1.00 19.06           N
ATOM    235  CA   MET A  66       0.809  37.017  30.736  1.00 18.35           C
ATOM    236  CB   MET A  66       2.110  36.416  30.191  1.00 16.58           C
ATOM    237  CG   MET A  66       2.258  34.894  30.609  1.00 17.01           C
ATOM    238  SD   MET A  66       3.957  34.254  30.605  1.00 18.95           S
ATOM    239  CE   MET A  66       4.562  34.789  32.182  1.00 13.77           C
ATOM    240  C    MET A  66       0.794  36.966  32.259  1.00 18.44           C
ATOM    241  O    MET A  66       0.046  36.181  32.833  1.00 18.73           O
ATOM    242  N    TRP A  67       1.601  37.809  32.911  1.00 18.40           N
ATOM    243  CA   TRP A  67       1.739  37.764  34.359  1.00 18.57           C
ATOM    244  CB   TRP A  67       2.676  38.882  34.811  1.00 19.20           C
ATOM    245  CG   TRP A  67       3.469  38.548  36.040  1.00 19.12           C
ATOM    246  CD1  TRP A  67       3.050  38.619  37.328  1.00 19.46           C
ATOM    247  NE1  TRP A  67       4.073  38.241  38.169  1.00 22.94           N
ATOM    248  CE2  TRP A  67       5.170  37.892  37.420  1.00 21.01           C
ATOM    249  CD2  TRP A  67       4.823  38.059  36.073  1.00 19.18           C
ATOM    250  CE3  TRP A  67       5.773  37.769  35.088  1.00 19.66           C
ATOM    251  CZ3  TRP A  67       7.031  37.319  35.468  1.00 19.84           C
ATOM    252  CH2  TRP A  67       7.355  37.164  36.825  1.00 19.97           C
ATOM    253  CZ2  TRP A  67       6.439  37.439  37.818  1.00 21.62           C
ATOM    254  C    TRP A  67       0.379  37.897  35.072  1.00 19.11           C
ATOM    255  O    TRP A  67       0.043  37.139  35.978  1.00 19.14           O
ATOM    256  N    GLN A  68      -0.409  38.871  34.651  1.00 19.60           N
ATOM    257  CA   GLN A  68      -1.657  39.185  35.328  1.00 19.16           C
ATOM    258  CB   GLN A  68      -2.038  40.667  35.081  1.00 20.57           C
ATOM    259  CG   GLN A  68      -3.038  41.304  36.062  1.00 24.70           C
ATOM    260  CD   GLN A  68      -2.684  41.162  37.554  1.00 28.71           C
ATOM    261  OE1  GLN A  68      -3.568  40.900  38.384  1.00 35.40           O
ATOM    262  NE2  GLN A  68      -1.417  41.345  37.904  1.00 29.97           N
ATOM    263  C    GLN A  68      -2.742  38.225  34.898  1.00 18.18           C
ATOM    264  O    GLN A  68      -3.476  37.742  35.737  1.00 18.55           O
ATOM    265  N    ASN A  69      -2.824  37.900  33.607  1.00 17.41           N
ATOM    266  CA   ASN A  69      -3.934  37.104  33.092  1.00 17.36           C
ATOM    267  CB   ASN A  69      -4.409  37.617  31.733  1.00 16.31           C
ATOM    268  CG   ASN A  69      -4.824  39.059  31.798  1.00 19.76           C
ATOM    269  OD1  ASN A  69      -5.304  39.508  32.829  1.00 17.18           O
ATOM    270  ND2  ASN A  69      -4.521  39.816  30.756  1.00 19.56           N
ATOM    271  C    ASN A  69      -3.720  35.597  32.996  1.00 16.74           C
ATOM    272  O    ASN A  69      -4.680  34.859  33.043  1.00 15.49           O
ATOM    273  N    ASP A  70      -2.479  35.144  32.818  1.00 17.88           N
ATOM    274  CA   ASP A  70      -2.264  33.697  32.602  1.00 17.81           C
ATOM    275  CB   ASP A  70      -1.489  33.437  31.310  1.00 17.91           C
ATOM    276  CG   ASP A  70      -2.360  33.487  30.067  1.00 20.08           C
ATOM    277  OD1  ASP A  70      -3.448  32.874  30.045  1.00 25.10           O
ATOM    278  OD2  ASP A  70      -1.930  34.090  29.059  1.00 24.80           O
ATOM    279  C    ASP A  70      -1.574  33.060  33.823  1.00 18.08           C
```

FIGURE 4-4 (COORDINATES)

```
ATOM    280  O   ASP A  70      -1.944  31.970  34.240  1.00 18.45           O
ATOM    281  N   LEU A  71      -0.625  33.778  34.425  1.00 17.85           N
ATOM    282  CA  LEU A  71       0.245  33.252  35.489  1.00 17.51           C
ATOM    283  CB  LEU A  71       1.605  33.985  35.468  1.00 17.34           C
ATOM    284  CG  LEU A  71       2.551  33.651  36.645  1.00 17.62           C
ATOM    285  CD1 LEU A  71       2.936  32.143  36.701  1.00 17.01           C
ATOM    286  CD2 LEU A  71       3.778  34.551  36.669  1.00 17.14           C
ATOM    287  C   LEU A  71      -0.348  33.344  36.885  1.00 17.96           C
ATOM    288  O   LEU A  71      -0.472  32.334  37.597  1.00 16.69           O
ATOM    289  N   ARG A  72      -0.717  34.566  37.283  1.00 17.50           N
ATOM    290  CA  ARG A  72      -1.216  34.808  38.642  1.00 17.84           C
ATOM    291  CB  ARG A  72      -1.529  36.299  38.840  1.00 18.11           C
ATOM    292  CG  ARG A  72      -0.285  37.025  39.310  1.00 19.09           C
ATOM    293  CD  ARG A  72      -0.482  38.507  39.474  1.00 20.21           C
ATOM    294  NE  ARG A  72       0.721  39.112  40.037  1.00 25.35           N
ATOM    295  CZ  ARG A  72       0.864  40.412  40.279  1.00 27.38           C
ATOM    296  NH1 ARG A  72      -0.132  41.251  39.998  1.00 27.94           N
ATOM    297  NH2 ARG A  72       1.988  40.860  40.814  1.00 26.20           N
ATOM    298  C   ARG A  72      -2.383  33.898  39.095  1.00 17.57           C
ATOM    299  O   ARG A  72      -2.351  33.359  40.220  1.00 18.42           O
ATOM    300  N   PRO A  73      -3.380  33.669  38.226  1.00 17.17           N
ATOM    301  CA  PRO A  73      -4.432  32.719  38.594  1.00 17.78           C
ATOM    302  CB  PRO A  73      -5.371  32.762  37.377  1.00 18.08           C
ATOM    303  CG  PRO A  73      -5.077  34.082  36.721  1.00 17.09           C
ATOM    304  CD  PRO A  73      -3.621  34.239  36.886  1.00 16.89           C
ATOM    305  C   PRO A  73      -3.920  31.273  38.794  1.00 18.59           C
ATOM    306  O   PRO A  73      -4.622  30.457  39.374  1.00 18.04           O
ATOM    307  N   LEU A  74      -2.726  30.955  38.282  1.00 19.07           N
ATOM    308  CA  LEU A  74      -2.133  29.618  38.523  1.00 19.02           C
ATOM    309  CB  LEU A  74      -1.266  29.147  37.345  1.00 18.24           C
ATOM    310  CG  LEU A  74      -1.942  28.921  36.002  1.00 18.61           C
ATOM    311  CD1 LEU A  74      -0.939  28.598  34.921  1.00 20.23           C
ATOM    312  CD2 LEU A  74      -3.003  27.832  36.087  1.00 24.40           C
ATOM    313  C   LEU A  74      -1.318  29.532  39.805  1.00 19.00           C
ATOM    314  O   LEU A  74      -0.989  28.420  40.254  1.00 18.51           O
ATOM    315  N   LEU A  75      -0.999  30.683  40.401  1.00 18.75           N
ATOM    316  CA  LEU A  75      -0.127  30.709  41.580  1.00 19.26           C
ATOM    317  CB  LEU A  75       0.626  32.030  41.680  1.00 18.59           C
ATOM    318  CG  LEU A  75       1.661  32.207  40.565  1.00 18.28           C
ATOM    319  CD1 LEU A  75       2.166  33.617  40.534  1.00 18.08           C
ATOM    320  CD2 LEU A  75       2.858  31.169  40.712  1.00 17.64           C
ATOM    321  C   LEU A  75      -0.853  30.356  42.886  1.00 19.84           C
ATOM    322  O   LEU A  75      -0.880  31.123  43.862  1.00 19.55           O
ATOM    323  N   ILE A  76      -1.402  29.140  42.885  1.00 20.98           N
ATOM    324  CA  ILE A  76      -2.270  28.633  43.954  1.00 21.01           C
ATOM    325  CB  ILE A  76      -3.775  28.708  43.537  1.00 21.76           C
ATOM    326  CG1 ILE A  76      -4.032  27.923  42.231  1.00 21.02           C
ATOM    327  CD1 ILE A  76      -5.482  27.842  41.792  1.00 21.98           C
ATOM    328  CG2 ILE A  76      -4.228  30.163  43.401  1.00 21.71           C
ATOM    329  C   ILE A  76      -1.864  27.172  44.194  1.00 21.39           C
ATOM    330  O   ILE A  76      -1.276  26.510  43.321  1.00 19.88           O
ATOM    331  N   GLU A  77      -2.158  26.674  45.384  1.00 21.94           N
ATOM    332  CA  GLU A  77      -1.918  25.283  45.670  1.00 22.96           C
ATOM    333  CB  GLU A  77      -2.140  25.035  47.157  1.00 24.12           C
ATOM    334  CG  GLU A  77      -2.080  23.609  47.571  1.00 27.03           C
ATOM    335  CD  GLU A  77      -2.238  23.440  49.073  1.00 34.00           C
ATOM    336  OE1 GLU A  77      -3.132  24.099  49.663  1.00 33.10           O
ATOM    337  OE2 GLU A  77      -1.463  22.627  49.655  1.00 35.52           O
ATOM    338  C   GLU A  77      -2.810  24.453  44.754  1.00 22.21           C
ATOM    339  O   GLU A  77      -4.017  24.681  44.685  1.00 23.84           O
ATOM    340  N   ARG A  78      -2.224  23.532  43.995  1.00 21.10           N
ATOM    341  CA  ARG A  78      -2.982  22.802  42.973  1.00 20.02           C
ATOM    342  CB  ARG A  78      -3.015  23.592  41.642  1.00 19.95           C
ATOM    343  CG  ARG A  78      -1.615  23.879  41.055  1.00 19.81           C
ATOM    344  CD  ARG A  78      -1.528  24.946  39.912  1.00 19.48           C
ATOM    345  NE  ARG A  78      -0.150  24.947  39.387  1.00 14.15           N
ATOM    346  CZ  ARG A  78       0.882  25.485  40.029  1.00 15.48           C
ATOM    347  NH1 ARG A  78       0.666  26.148  41.158  1.00 13.69           N
ATOM    348  NH2 ARG A  78       2.126  25.403  39.534  1.00 14.28           N
ATOM    349  C   ARG A  78      -2.497  21.348  42.798  1.00 20.05           C
```

FIGURE 4-5 (COORDINATES)

```
ATOM    350  O   ARG A  78     -2.384  20.806  41.691  1.00 18.90           O
ATOM    351  N   TYR A  79     -2.223  20.696  43.912  1.00 20.75           N
ATOM    352  CA  TYR A  79     -1.958  19.259  43.873  1.00 21.95           C
ATOM    353  CB  TYR A  79     -1.300  18.808  45.175  1.00 22.86           C
ATOM    354  CG  TYR A  79     -2.150  18.938  46.416  1.00 22.98           C
ATOM    355  CD1 TYR A  79     -2.102  20.075  47.214  1.00 20.22           C
ATOM    356  CE1 TYR A  79     -2.878  20.158  48.372  1.00 24.36           C
ATOM    357  CZ  TYR A  79     -3.688  19.100  48.721  1.00 24.02           C
ATOM    358  OH  TYR A  79     -4.462  19.112  49.866  1.00 28.29           O
ATOM    359  CE2 TYR A  79     -3.750  17.978  47.935  1.00 24.00           C
ATOM    360  CD2 TYR A  79     -2.986  17.892  46.806  1.00 25.17           C
ATOM    361  C   TYR A  79     -3.253  18.488  43.529  1.00 22.21           C
ATOM    362  O   TYR A  79     -4.365  19.034  43.684  1.00 21.93           O
ATOM    363  N   PRO A  80     -3.125  17.252  42.989  1.00 22.21           N
ATOM    364  CA  PRO A  80     -4.306  16.525  42.517  1.00 22.25           C
ATOM    365  CB  PRO A  80     -3.722  15.168  42.075  1.00 22.57           C
ATOM    366  CG  PRO A  80     -2.309  15.501  41.719  1.00 21.96           C
ATOM    367  CD  PRO A  80     -1.901  16.462  42.786  1.00 21.96           C
ATOM    368  C   PRO A  80     -5.393  16.365  43.605  1.00 22.32           C
ATOM    369  O   PRO A  80     -5.085  16.017  44.751  1.00 22.35           O
ATOM    370  N   GLY A  81     -6.632  16.711  43.247  1.00 22.08           N
ATOM    371  CA  GLY A  81     -7.783  16.647  44.155  1.00 21.23           C
ATOM    372  C   GLY A  81     -8.076  17.938  44.904  1.00 21.02           C
ATOM    373  O   GLY A  81     -9.152  18.087  45.475  1.00 20.61           O
ATOM    374  N   SER A  82     -7.123  18.870  44.927  1.00 20.60           N
ATOM    375  CA  SER A  82     -7.292  20.104  45.669  1.00 20.56           C
ATOM    376  CB  SER A  82     -5.908  20.772  45.924  1.00 21.23           C
ATOM    377  OG  SER A  82     -5.356  21.310  44.735  1.00 17.64           O
ATOM    378  C   SER A  82     -8.288  21.058  44.958  1.00 21.06           C
ATOM    379  O   SER A  82     -8.515  20.938  43.764  1.00 21.00           O
ATOM    380  N   PRO A  83     -8.907  21.991  45.696  1.00 21.86           N
ATOM    381  CA  PRO A  83     -9.727  22.973  44.964  1.00 21.95           C
ATOM    382  CB  PRO A  83    -10.190  23.930  46.065  1.00 21.92           C
ATOM    383  CG  PRO A  83    -10.121  23.094  47.316  1.00 22.29           C
ATOM    384  CD  PRO A  83     -8.917  22.246  47.149  1.00 21.53           C
ATOM    385  C   PRO A  83     -8.902  23.728  43.913  1.00 21.91           C
ATOM    386  O   PRO A  83     -9.406  23.984  42.815  1.00 23.50           O
ATOM    387  N   GLY A  84     -7.656  24.073  44.240  1.00 22.12           N
ATOM    388  CA  GLY A  84     -6.768  24.726  43.280  1.00 21.63           C
ATOM    389  C   GLY A  84     -6.617  23.918  42.005  1.00 21.61           C
ATOM    390  O   GLY A  84     -6.480  24.486  40.920  1.00 22.24           O
ATOM    391  N   SER A  85     -6.608  22.588  42.113  1.00 21.50           N
ATOM    392  CA  SER A  85     -6.503  21.731  40.905  1.00 21.67           C
ATOM    393  CB  SER A  85     -6.414  20.242  41.290  1.00 20.85           C
ATOM    394  OG  SER A  85     -6.474  19.430  40.142  1.00 22.08           O
ATOM    395  C   SER A  85     -7.653  21.990  39.889  1.00 21.93           C
ATOM    396  O   SER A  85     -7.428  22.153  38.700  1.00 20.71           O
ATOM    397  N   TYR A  86     -8.887  22.006  40.374  1.00 23.04           N
ATOM    398  CA  TYR A  86    -10.051  22.375  39.550  1.00 23.80           C
ATOM    399  CB  TYR A  86    -11.324  22.024  40.336  1.00 26.22           C
ATOM    400  CG  TYR A  86    -12.631  22.496  39.736  1.00 29.89           C
ATOM    401  CD1 TYR A  86    -13.289  21.731  38.770  1.00 33.55           C
ATOM    402  CE1 TYR A  86    -14.522  22.154  38.204  1.00 34.88           C
ATOM    403  CZ  TYR A  86    -15.102  23.352  38.633  1.00 33.94           C
ATOM    404  OH  TYR A  86    -16.313  23.743  38.080  1.00 35.63           O
ATOM    405  CE2 TYR A  86    -14.464  24.145  39.597  1.00 34.45           C
ATOM    406  CD2 TYR A  86    -13.221  23.710  40.145  1.00 33.43           C
ATOM    407  C   TYR A  86    -10.036  23.861  39.055  1.00 22.43           C
ATOM    408  O   TYR A  86    -10.313  24.118  37.901  1.00 20.96           O
ATOM    409  N   SER A  87     -9.717  24.823  39.926  1.00 22.03           N
ATOM    410  CA  SER A  87     -9.566  26.229  39.504  1.00 21.97           C
ATOM    411  CB  SER A  87     -9.110  27.120  40.652  1.00 22.39           C
ATOM    412  OG  SER A  87     -9.996  27.012  41.744  1.00 28.87           O
ATOM    413  C   SER A  87     -8.534  26.396  38.382  1.00 20.73           C
ATOM    414  O   SER A  87     -8.784  27.088  37.409  1.00 20.41           O
ATOM    415  N   ALA A  88     -7.353  25.792  38.549  1.00 19.27           N
ATOM    416  CA  ALA A  88     -6.286  25.894  37.540  1.00 18.22           C
ATOM    417  CB  ALA A  88     -4.978  25.240  38.051  1.00 17.76           C
ATOM    418  C   ALA A  88     -6.710  25.279  36.236  1.00 17.55           C
ATOM    419  O   ALA A  88     -6.479  25.850  35.177  1.00 17.64           O
```

FIGURE 4-6 (COORDINATES)

```
ATOM    420  N    ARG A  89      -7.341  24.108  36.301  1.00 16.88           N
ATOM    421  CA   ARG A  89      -7.806  23.423  35.106  1.00 16.82           C
ATOM    422  CB   ARG A  89      -8.409  22.081  35.491  1.00 17.60           C
ATOM    423  CG   ARG A  89      -8.873  21.245  34.305  1.00 18.81           C
ATOM    424  CD   ARG A  89      -8.969  19.739  34.698  1.00 23.18           C
ATOM    425  NE   ARG A  89      -9.837  19.516  35.849  1.00 22.96           N
ATOM    426  CZ   ARG A  89      -9.445  19.241  37.103  1.00 27.02           C
ATOM    427  NH1  ARG A  89      -8.158  19.144  37.447  1.00 26.24           N
ATOM    428  NH2  ARG A  89     -10.363  19.049  38.038  1.00 26.80           N
ATOM    429  C    ARG A  89      -8.863  24.232  34.331  1.00 17.17           C
ATOM    430  O    ARG A  89      -8.832  24.295  33.086  1.00 17.25           O
ATOM    431  N    GLN A  90      -9.821  24.795  35.065  1.00 17.23           N
ATOM    432  CA   GLN A  90     -10.826  25.686  34.474  1.00 18.77           C
ATOM    433  CB   GLN A  90     -11.913  26.046  35.502  1.00 19.23           C
ATOM    434  CG   GLN A  90     -12.912  24.920  35.868  1.00 25.10           C
ATOM    435  CD   GLN A  90     -13.654  24.344  34.661  1.00 31.90           C
ATOM    436  OE1  GLN A  90     -14.354  25.063  33.931  1.00 37.56           O
ATOM    437  NE2  GLN A  90     -13.506  23.038  34.451  1.00 34.76           N
ATOM    438  C    GLN A  90     -10.194  27.001  33.915  1.00 17.55           C
ATOM    439  O    GLN A  90     -10.618  27.483  32.871  1.00 17.73           O
ATOM    440  N    HIS A  91      -9.233  27.582  34.638  1.00 17.40           N
ATOM    441  CA   HIS A  91      -8.474  28.735  34.142  1.00 17.65           C
ATOM    442  CB   HIS A  91      -7.434  29.180  35.171  1.00 18.89           C
ATOM    443  CG   HIS A  91      -6.442  30.184  34.652  1.00 20.05           C
ATOM    444  ND1  HIS A  91      -6.808  31.436  34.203  1.00 17.95           N
ATOM    445  CE1  HIS A  91      -5.732  32.091  33.804  1.00 19.39           C
ATOM    446  NE2  HIS A  91      -4.675  31.314  33.991  1.00 20.32           N
ATOM    447  CD2  HIS A  91      -5.094  30.111  34.508  1.00 20.64           C
ATOM    448  C    HIS A  91      -7.817  28.416  32.786  1.00 16.83           C
ATOM    449  O    HIS A  91      -8.021  29.153  31.823  1.00 16.67           O
ATOM    450  N    ILE A  92      -7.058  27.307  32.693  1.00 15.86           N
ATOM    451  CA   ILE A  92      -6.385  26.917  31.428  1.00 14.94           C
ATOM    452  CB   ILE A  92      -5.531  25.568  31.630  1.00 15.01           C
ATOM    453  CG1  ILE A  92      -4.340  25.818  32.543  1.00 14.72           C
ATOM    454  CD1  ILE A  92      -3.780  24.522  33.241  1.00 15.07           C
ATOM    455  CG2  ILE A  92      -5.107  24.920  30.301  1.00 12.23           C
ATOM    456  C    ILE A  92      -7.403  26.797  30.280  1.00 16.16           C
ATOM    457  O    ILE A  92      -7.197  27.278  29.170  1.00 13.89           O
ATOM    458  N    MET A  93      -8.549  26.183  30.565  1.00 17.15           N
ATOM    459  CA   MET A  93      -9.474  25.883  29.520  1.00 19.22           C
ATOM    460  CB   MET A  93     -10.451  24.771  29.956  1.00 18.88           C
ATOM    461  CG   MET A  93      -9.781  23.395  30.032  1.00 21.89           C
ATOM    462  SD   MET A  93     -10.872  22.014  30.535  1.00 25.76           S
ATOM    463  CE   MET A  93     -11.443  22.602  32.088  1.00 18.84           C
ATOM    464  C    MET A  93     -10.178  27.172  29.081  1.00 18.58           C
ATOM    465  O    MET A  93     -10.440  27.334  27.901  1.00 19.05           O
ATOM    466  N    GLN A  94     -10.465  28.066  30.033  1.00 18.67           N
ATOM    467  CA   GLN A  94     -11.091  29.362  29.768  1.00 18.70           C
ATOM    468  CB   GLN A  94     -11.342  30.120  31.099  1.00 18.71           C
ATOM    469  CG   GLN A  94     -12.126  31.477  31.031  1.00 21.67           C
ATOM    470  CD   GLN A  94     -11.261  32.735  30.744  1.00 30.04           C
ATOM    471  OE1  GLN A  94     -10.183  32.914  31.325  1.00 33.01           O
ATOM    472  NE2  GLN A  94     -11.771  33.637  29.876  1.00 31.82           N
ATOM    473  C    GLN A  94     -10.169  30.199  28.880  1.00 18.01           C
ATOM    474  O    GLN A  94     -10.623  30.792  27.919  1.00 18.45           O
ATOM    475  N    ARG A  95      -8.875  30.235  29.213  1.00 16.93           N
ATOM    476  CA   ARG A  95      -7.898  31.050  28.455  1.00 16.58           C
ATOM    477  CB   ARG A  95      -6.556  31.106  29.198  1.00 16.35           C
ATOM    478  CG   ARG A  95      -6.631  31.873  30.515  1.00 15.29           C
ATOM    479  CD   ARG A  95      -7.022  33.357  30.315  1.00 13.18           C
ATOM    480  NE   ARG A  95      -5.909  34.054  29.657  1.00 18.44           N
ATOM    481  CZ   ARG A  95      -5.930  35.299  29.203  1.00 21.69           C
ATOM    482  NH1  ARG A  95      -7.036  36.054  29.325  1.00 19.81           N
ATOM    483  NH2  ARG A  95      -4.825  35.798  28.648  1.00 21.19           N
ATOM    484  C    ARG A  95      -7.689  30.551  27.027  1.00 17.35           C
ATOM    485  O    ARG A  95      -7.422  31.346  26.114  1.00 17.65           O
ATOM    486  N    ILE A  96      -7.832  29.249  26.808  1.00 16.65           N
ATOM    487  CA   ILE A  96      -7.741  28.714  25.456  1.00 17.92           C
ATOM    488  CB   ILE A  96      -7.428  27.187  25.459  1.00 18.76           C
ATOM    489  CG1  ILE A  96      -5.984  26.934  25.921  1.00 19.76           C
```

FIGURE 4-7 (COORDINATES)

```
ATOM    490  CD1 ILE A   96      -5.739  25.581  26.522  1.00 22.79           C
ATOM    491  CG2 ILE A   96      -7.523  26.602  24.048  1.00 18.16           C
ATOM    492  C   ILE A   96      -9.044  28.966  24.672  1.00 19.29           C
ATOM    493  O   ILE A   96      -9.001  29.368  23.515  1.00 19.10           O
ATOM    494  N   GLN A   97     -10.186  28.699  25.294  1.00 20.08           N
ATOM    495  CA  GLN A   97     -11.492  28.806  24.617  1.00 22.90           C
ATOM    496  CB  GLN A   97     -12.575  28.160  25.501  1.00 22.08           C
ATOM    497  CG  GLN A   97     -12.368  26.609  25.513  1.00 26.53           C
ATOM    498  CD  GLN A   97     -13.063  25.847  26.667  1.00 28.35           C
ATOM    499  OE1 GLN A   97     -13.212  26.366  27.782  1.00 36.52           O
ATOM    500  NE2 GLN A   97     -13.448  24.589  26.404  1.00 35.99           N
ATOM    501  C   GLN A   97     -11.841  30.240  24.171  1.00 21.94           C
ATOM    502  O   GLN A   97     -12.558  30.446  23.180  1.00 21.72           O
ATOM    503  N   ARG A   98     -11.299  31.231  24.869  1.00 22.37           N
ATOM    504  CA  ARG A   98     -11.568  32.642  24.526  1.00 22.94           C
ATOM    505  CB  ARG A   98     -11.150  33.553  25.685  1.00 22.48           C
ATOM    506  CG  ARG A   98      -9.628  33.514  25.938  1.00 24.22           C
ATOM    507  CD  ARG A   98      -9.186  34.469  27.012  1.00 20.37           C
ATOM    508  NE  ARG A   98      -9.490  35.856  26.670  1.00 24.32           N
ATOM    509  CZ  ARG A   98      -8.671  36.630  25.962  1.00 25.54           C
ATOM    510  NH1 ARG A   98      -7.514  36.132  25.533  1.00 19.03           N
ATOM    511  NH2 ARG A   98      -8.999  37.898  25.686  1.00 22.85           N
ATOM    512  C   ARG A   98     -10.857  33.074  23.230  1.00 23.26           C
ATOM    513  O   ARG A   98     -11.105  34.164  22.717  1.00 23.71           O
ATOM    514  N   LEU A   99      -9.978  32.226  22.696  1.00 23.01           N
ATOM    515  CA  LEU A   99      -9.124  32.612  21.560  1.00 22.37           C
ATOM    516  CB  LEU A   99      -7.794  31.830  21.593  1.00 21.74           C
ATOM    517  CG  LEU A   99      -6.876  32.219  22.755  1.00 18.10           C
ATOM    518  CD1 LEU A   99      -5.671  31.229  22.830  1.00 17.10           C
ATOM    519  CD2 LEU A   99      -6.408  33.630  22.546  1.00 14.83           C
ATOM    520  C   LEU A   99      -9.837  32.384  20.244  1.00 22.81           C
ATOM    521  O   LEU A   99     -10.826  31.658  20.220  1.00 23.12           O
ATOM    522  N   GLN A  100      -9.336  32.976  19.157  1.00 22.29           N
ATOM    523  CA  GLN A  100      -9.982  32.813  17.848  1.00 22.13           C
ATOM    524  CB  GLN A  100      -9.636  33.943  16.854  1.00 22.78           C
ATOM    525  CG  GLN A  100     -10.041  35.355  17.320  1.00 24.26           C
ATOM    526  CD  GLN A  100     -11.520  35.471  17.655  1.00 27.97           C
ATOM    527  OE1 GLN A  100     -12.387  35.113  16.848  1.00 32.12           O
ATOM    528  NE2 GLN A  100     -11.817  35.952  18.849  1.00 28.44           N
ATOM    529  C   GLN A  100      -9.639  31.496  17.205  1.00 22.56           C
ATOM    530  O   GLN A  100     -10.497  30.908  16.510  1.00 21.78           O
ATOM    531  N   ALA A  101      -8.388  31.038  17.366  1.00 21.12           N
ATOM    532  CA  ALA A  101      -8.007  29.777  16.756  1.00 20.06           C
ATOM    533  CB  ALA A  101      -6.535  29.430  17.024  1.00 19.72           C
ATOM    534  C   ALA A  101      -8.954  28.686  17.273  1.00 20.27           C
ATOM    535  O   ALA A  101      -9.429  28.740  18.403  1.00 20.43           O
ATOM    536  N   GLU A  102      -9.219  27.707  16.422  1.00 20.49           N
ATOM    537  CA  GLU A  102     -10.240  26.700  16.666  1.00 22.23           C
ATOM    538  CB  GLU A  102     -10.799  26.252  15.299  1.00 23.19           C
ATOM    539  CG  GLU A  102     -11.690  27.345  14.725  1.00 27.88           C
ATOM    540  CD  GLU A  102     -12.232  27.049  13.338  1.00 34.88           C
ATOM    541  OE1 GLU A  102     -12.242  25.872  12.898  1.00 36.09           O
ATOM    542  OE2 GLU A  102     -12.677  28.023  12.691  1.00 38.57           O
ATOM    543  C   GLU A  102      -9.696  25.518  17.475  1.00 21.40           C
ATOM    544  O   GLU A  102      -9.592  24.390  16.976  1.00 21.06           O
ATOM    545  N   TRP A  103      -9.321  25.812  18.716  1.00 20.44           N
ATOM    546  CA  TRP A  103      -8.751  24.818  19.645  1.00 20.28           C
ATOM    547  CB  TRP A  103      -8.216  25.539  20.869  1.00 18.18           C
ATOM    548  CG  TRP A  103      -6.924  26.283  20.637  1.00 17.12           C
ATOM    549  CD1 TRP A  103      -6.772  27.621  20.435  1.00 17.80           C
ATOM    550  NE1 TRP A  103      -5.427  27.931  20.257  1.00 18.60           N
ATOM    551  CE2 TRP A  103      -4.689  26.773  20.357  1.00 17.56           C
ATOM    552  CD2 TRP A  103      -5.595  25.712  20.587  1.00 17.96           C
ATOM    553  CE3 TRP A  103      -5.088  24.400  20.718  1.00 15.36           C
ATOM    554  CZ3 TRP A  103      -3.720  24.200  20.639  1.00 14.86           C
ATOM    555  CH2 TRP A  103      -2.839  25.274  20.408  1.00 16.28           C
ATOM    556  CZ2 TRP A  103      -3.296  26.565  20.266  1.00 17.48           C
ATOM    557  C   TRP A  103      -9.851  23.871  20.124  1.00 21.32           C
ATOM    558  O   TRP A  103     -10.917  24.334  20.584  1.00 22.32           O
ATOM    559  N   VAL A  104      -9.596  22.576  19.989  1.00 21.66           N
```

FIGURE 4-8 (COORDINATES)

```
ATOM   560  CA   VAL A 104    -10.451  21.519  20.546  1.00 22.18           C
ATOM   561  CB   VAL A 104    -10.579  20.348  19.547  1.00 22.16           C
ATOM   562  CG1  VAL A 104    -11.352  19.169  20.150  1.00 24.64           C
ATOM   563  CG2  VAL A 104    -11.293  20.835  18.284  1.00 22.84           C
ATOM   564  C    VAL A 104     -9.856  21.069  21.894  1.00 21.89           C
ATOM   565  O    VAL A 104     -8.774  20.506  21.945  1.00 21.18           O
ATOM   566  N    VAL A 105    -10.572  21.370  22.968  1.00 22.46           N
ATOM   567  CA   VAL A 105    -10.140  21.145  24.324  1.00 23.71           C
ATOM   568  CB   VAL A 105    -10.535  22.341  25.177  1.00 24.17           C
ATOM   569  CG1  VAL A 105    -10.204  22.103  26.627  1.00 25.43           C
ATOM   570  CG2  VAL A 105     -9.848  23.612  24.660  1.00 21.97           C
ATOM   571  C    VAL A 105    -10.728  19.841  24.893  1.00 25.65           C
ATOM   572  O    VAL A 105    -11.959  19.654  24.877  1.00 25.21           O
ATOM   573  N    GLU A 106     -9.845  18.931  25.339  1.00 25.95           N
ATOM   574  CA   GLU A 106    -10.204  17.599  25.865  1.00 28.40           C
ATOM   575  CB   GLU A 106     -9.599  16.479  25.006  1.00 28.43           C
ATOM   576  CG   GLU A 106    -10.316  16.188  23.685  1.00 32.56           C
ATOM   577  CD   GLU A 106     -9.565  15.189  22.828  1.00 33.17           C
ATOM   578  OE1  GLU A 106    -10.238  14.362  22.170  1.00 39.64           O
ATOM   579  OE2  GLU A 106     -8.296  15.210  22.816  1.00 40.18           O
ATOM   580  C    GLU A 106     -9.600  17.428  27.254  1.00 27.66           C
ATOM   581  O    GLU A 106     -8.467  17.845  27.496  1.00 26.43           O
ATOM   582  N    VAL A 107    -10.335  16.768  28.142  1.00 27.23           N
ATOM   583  CA   VAL A 107     -9.802  16.399  29.449  1.00 27.45           C
ATOM   584  CB   VAL A 107    -10.635  16.996  30.582  1.00 27.21           C
ATOM   585  CG1  VAL A 107     -9.956  16.798  31.910  1.00 27.85           C
ATOM   586  CG2  VAL A 107    -10.835  18.486  30.359  1.00 28.40           C
ATOM   587  C    VAL A 107     -9.692  14.872  29.552  1.00 27.69           C
ATOM   588  O    VAL A 107    -10.672  14.175  29.285  1.00 28.19           O
ATOM   589  N    ASP A 108     -8.492  14.371  29.888  1.00 26.48           N
ATOM   590  CA   ASP A 108     -8.234  12.947  30.126  1.00 25.81           C
ATOM   591  CB   ASP A 108     -6.854  12.563  29.568  1.00 25.98           C
ATOM   592  CG   ASP A 108     -6.419  11.134  29.935  1.00 27.47           C
ATOM   593  OD1  ASP A 108     -7.316  10.253  30.039  1.00 24.77           O
ATOM   594  OD2  ASP A 108     -5.182  10.883  30.092  1.00 23.14           O
ATOM   595  C    ASP A 108     -8.276  12.734  31.643  1.00 25.52           C
ATOM   596  O    ASP A 108     -7.269  12.942  32.308  1.00 23.52           O
ATOM   597  N    THR A 109     -9.449  12.355  32.177  1.00 24.86           N
ATOM   598  CA   THR A 109     -9.665  12.160  33.623  1.00 24.57           C
ATOM   599  CB   THR A 109    -10.968  12.833  34.107  1.00 25.12           C
ATOM   600  OG1  THR A 109    -10.886  14.255  33.902  1.00 25.10           O
ATOM   601  CG2  THR A 109    -11.230  12.555  35.596  1.00 24.53           C
ATOM   602  C    THR A 109     -9.678  10.647  33.933  1.00 24.95           C
ATOM   603  O    THR A 109    -10.323   9.871  33.226  1.00 24.77           O
ATOM   604  N    PHE A 110     -8.942  10.232  34.963  1.00 24.80           N
ATOM   605  CA   PHE A 110     -8.785   8.799  35.292  1.00 25.43           C
ATOM   606  CB   PHE A 110     -7.651   8.174  34.467  1.00 24.69           C
ATOM   607  CG   PHE A 110     -6.328   8.856  34.681  1.00 24.21           C
ATOM   608  CD1  PHE A 110     -5.393   8.350  35.604  1.00 21.27           C
ATOM   609  CE1  PHE A 110     -4.195   8.982  35.818  1.00 23.30           C
ATOM   610  CZ   PHE A 110     -3.894  10.166  35.132  1.00 22.38           C
ATOM   611  CE2  PHE A 110     -4.810  10.687  34.223  1.00 21.65           C
ATOM   612  CD2  PHE A 110     -6.025  10.031  33.994  1.00 23.76           C
ATOM   613  C    PHE A 110     -8.417   8.712  36.759  1.00 25.73           C
ATOM   614  O    PHE A 110     -8.019   9.734  37.370  1.00 25.32           O
ATOM   615  N    LEU A 111     -8.536   7.501  37.316  1.00 25.53           N
ATOM   616  CA   LEU A 111     -8.058   7.205  38.674  1.00 25.84           C
ATOM   617  CB   LEU A 111     -9.103   6.445  39.497  1.00 26.78           C
ATOM   618  CG   LEU A 111    -10.486   7.019  39.701  1.00 27.39           C
ATOM   619  CD1  LEU A 111    -11.250   6.101  40.689  1.00 29.31           C
ATOM   620  CD2  LEU A 111    -10.421   8.436  40.247  1.00 27.37           C
ATOM   621  C    LEU A 111     -6.818   6.350  38.634  1.00 25.79           C
ATOM   622  O    LEU A 111     -6.656   5.513  37.745  1.00 25.57           O
ATOM   623  N    SER A 112     -5.955   6.537  39.626  1.00 25.69           N
ATOM   624  CA   SER A 112     -4.656   5.882  39.643  1.00 25.67           C
ATOM   625  CB   SER A 112     -3.648   6.753  38.899  1.00 25.78           C
ATOM   626  OG   SER A 112     -2.451   6.066  38.603  1.00 27.74           O
ATOM   627  C    SER A 112     -4.255   5.771  41.092  1.00 25.70           C
ATOM   628  O    SER A 112     -4.502   6.687  41.887  1.00 24.77           O
ATOM   629  N    ARG A 113     -3.642   4.646  41.441  1.00 25.84           N
```

FIGURE 4-9 (COORDINATES)

```
ATOM    630  CA  ARG A 113      -3.235   4.398  42.821  1.00 26.36           C
ATOM    631  CB  ARG A 113      -2.930   2.912  43.031  1.00 26.39           C
ATOM    632  CG  ARG A 113      -2.889   2.492  44.488  1.00 28.39           C
ATOM    633  CD  ARG A 113      -2.237   1.115  44.666  1.00 29.52           C
ATOM    634  NE  ARG A 113      -3.113   1.805  46.327  0.00 45.97           N
ATOM    635  CZ  ARG A 113      -2.376   2.055  47.423  0.00 50.13           C
ATOM    636  NH1 ARG A 113      -2.958   2.553  48.522  0.00 50.88           N
ATOM    637  NH2 ARG A 113      -1.064   1.801  47.449  0.00 50.82           N
ATOM    638  C   ARG A 113      -2.000   5.204  43.186  1.00 26.07           C
ATOM    639  O   ARG A 113      -0.978   5.164  42.478  1.00 26.11           O
ATOM    640  N   THR A 114      -2.086   5.884  44.318  1.00 26.01           N
ATOM    641  CA  THR A 114      -0.989   6.687  44.851  1.00 26.05           C
ATOM    642  CB  THR A 114      -1.407   8.169  44.971  1.00 25.82           C
ATOM    643  OG1 THR A 114      -2.265   8.340  46.110  1.00 24.01           O
ATOM    644  CG2 THR A 114      -2.128   8.635  43.705  1.00 24.32           C
ATOM    645  C   THR A 114      -0.654   6.129  46.254  1.00 27.25           C
ATOM    646  O   THR A 114      -1.416   5.350  46.784  1.00 27.60           O
ATOM    647  N   PRO A 115       0.479   6.526  46.856  1.00 27.84           N
ATOM    648  CA  PRO A 115       0.714   6.162  48.284  1.00 28.41           C
ATOM    649  CB  PRO A 115       1.978   6.957  48.635  1.00 28.38           C
ATOM    650  CG  PRO A 115       2.716   7.034  47.326  1.00 27.26           C
ATOM    651  CD  PRO A 115       1.633   7.246  46.283  1.00 27.33           C
ATOM    652  C   PRO A 115      -0.410   6.505  49.280  1.00 29.05           C
ATOM    653  O   PRO A 115      -0.439   5.943  50.366  1.00 29.36           O
ATOM    654  N   TYR A 116      -1.298   7.436  48.934  1.00 29.07           N
ATOM    655  CA  TYR A 116      -2.406   7.803  49.808  1.00 29.03           C
ATOM    656  CB  TYR A 116      -2.601   9.329  49.805  1.00 29.60           C
ATOM    657  CG  TYR A 116      -1.481  10.105  50.458  1.00 31.09           C
ATOM    658  CD1 TYR A 116      -1.510  10.374  51.831  1.00 33.40           C
ATOM    659  CE1 TYR A 116      -0.493  11.090  52.448  1.00 34.35           C
ATOM    660  CZ  TYR A 116       0.576  11.545  51.685  1.00 32.45           C
ATOM    661  OH  TYR A 116       1.578  12.240  52.299  1.00 33.04           O
ATOM    662  CE2 TYR A 116       0.632  11.303  50.325  1.00 30.69           C
ATOM    663  CD2 TYR A 116      -0.399  10.584  49.714  1.00 30.80           C
ATOM    664  C   TYR A 116      -3.707   7.108  49.393  1.00 29.08           C
ATOM    665  O   TYR A 116      -4.782   7.421  49.915  1.00 30.00           O
ATOM    666  N   GLY A 117      -3.622   6.186  48.439  1.00 28.93           N
ATOM    667  CA  GLY A 117      -4.806   5.517  47.917  1.00 28.39           C
ATOM    668  C   GLY A 117      -5.168   6.033  46.534  1.00 28.42           C
ATOM    669  O   GLY A 117      -4.439   6.826  45.964  1.00 28.10           O
ATOM    670  N   TYR A 118      -6.305   5.599  46.000  1.00 27.58           N
ATOM    671  CA  TYR A 118      -6.729   5.998  44.663  1.00 27.27           C
ATOM    672  CB  TYR A 118      -7.852   5.085  44.124  1.00 28.60           C
ATOM    673  CG  TYR A 118      -7.337   3.827  43.386  1.00 31.60           C
ATOM    674  CD1 TYR A 118      -7.271   3.790  41.993  1.00 31.92           C
ATOM    675  CE1 TYR A 118      -6.809   2.655  41.306  1.00 32.81           C
ATOM    676  CZ  TYR A 118      -6.403   1.533  42.006  1.00 33.34           C
ATOM    677  OH  TYR A 118      -5.940   0.429  41.296  1.00 34.31           O
ATOM    678  CE2 TYR A 118      -6.462   1.518  43.393  1.00 33.61           C
ATOM    679  CD2 TYR A 118      -6.932   2.674  44.082  1.00 33.81           C
ATOM    680  C   TYR A 118      -7.058   7.495  44.593  1.00 25.96           C
ATOM    681  O   TYR A 118      -7.687   8.066  45.516  1.00 25.26           O
ATOM    682  N   ARG A 119      -6.559   8.147  43.530  1.00 24.16           N
ATOM    683  CA  ARG A 119      -6.825   9.582  43.300  1.00 22.39           C
ATOM    684  CB  ARG A 119      -5.611  10.476  43.694  1.00 21.82           C
ATOM    685  CG  ARG A 119      -5.166  10.453  45.159  1.00 20.38           C
ATOM    686  CD  ARG A 119      -6.201  11.076  46.058  1.00 22.30           C
ATOM    687  NE  ARG A 119      -5.815  11.118  47.466  1.00 23.23           N
ATOM    688  CZ  ARG A 119      -6.185  10.216  48.374  1.00 25.22           C
ATOM    689  NH1 ARG A 119      -6.964   9.189  48.020  1.00 29.52           N
ATOM    690  NH2 ARG A 119      -5.810  10.355  49.648  1.00 26.20           N
ATOM    691  C   ARG A 119      -7.214   9.852  41.845  1.00 20.94           C
ATOM    692  O   ARG A 119      -6.852   9.107  40.934  1.00 19.62           O
ATOM    693  N   SER A 120      -7.917  10.960  41.651  1.00 19.74           N
ATOM    694  CA  SER A 120      -8.357  11.403  40.349  1.00 19.13           C
ATOM    695  CB  SER A 120      -9.705  12.088  40.468  1.00 18.61           C
ATOM    696  OG  SER A 120     -10.207  12.256  39.171  1.00 22.31           O
ATOM    697  C   SER A 120      -7.346  12.414  39.770  1.00 18.75           C
ATOM    698  O   SER A 120      -6.857  13.293  40.491  1.00 18.97           O
ATOM    699  N   PHE A 121      -7.028  12.237  38.491  1.00 17.77           N
```

FIGURE 4-10 (COORDINATES)

```
ATOM    700  CA  PHE A 121      -6.153  13.137  37.736  1.00 17.50           C
ATOM    701  CB  PHE A 121      -4.859  12.452  37.367  1.00 17.08           C
ATOM    702  CG  PHE A 121      -4.112  11.878  38.554  1.00 18.11           C
ATOM    703  CD1 PHE A 121      -3.065  12.585  39.128  1.00 14.54           C
ATOM    704  CE1 PHE A 121      -2.365  12.073  40.234  1.00 17.96           C
ATOM    705  CZ  PHE A 121      -2.740  10.837  40.795  1.00 17.75           C
ATOM    706  CE2 PHE A 121      -3.785  10.118  40.240  1.00 16.59           C
ATOM    707  CD2 PHE A 121      -4.490  10.641  39.110  1.00 16.80           C
ATOM    708  C   PHE A 121      -6.863  13.513  36.438  1.00 17.88           C
ATOM    709  O   PHE A 121      -7.675  12.718  35.909  1.00 16.58           O
ATOM    710  N   SER A 122      -6.544  14.709  35.932  1.00 17.63           N
ATOM    711  CA  SER A 122      -7.104  15.204  34.668  1.00 17.43           C
ATOM    712  CB  SER A 122      -8.261  16.159  34.955  1.00 17.01           C
ATOM    713  OG  SER A 122      -9.337  15.458  35.565  1.00 21.59           O
ATOM    714  C   SER A 122      -6.038  15.905  33.850  1.00 17.43           C
ATOM    715  O   SER A 122      -5.628  17.024  34.197  1.00 16.96           O
ATOM    716  N   ASN A 123      -5.565  15.243  32.796  1.00 17.34           N
ATOM    717  CA  ASN A 123      -4.708  15.926  31.835  1.00 17.23           C
ATOM    718  CB  ASN A 123      -3.992  14.961  30.875  1.00 17.18           C
ATOM    719  CG  ASN A 123      -3.115  13.924  31.585  1.00 17.20           C
ATOM    720  OD1 ASN A 123      -3.198  12.709  31.287  1.00 21.48           O
ATOM    721  ND2 ASN A 123      -2.296  14.372  32.515  1.00  9.17           N
ATOM    722  C   ASN A 123      -5.625  16.831  30.995  1.00 17.35           C
ATOM    723  O   ASN A 123      -6.772  16.485  30.738  1.00 17.31           O
ATOM    724  N   ILE A 124      -5.094  17.961  30.550  1.00 16.80           N
ATOM    725  CA  ILE A 124      -5.769  18.834  29.582  1.00 16.16           C
ATOM    726  CB  ILE A 124      -5.892  20.294  30.118  1.00 16.30           C
ATOM    727  CG1 ILE A 124      -6.447  20.299  31.543  1.00 14.16           C
ATOM    728  CD1 ILE A 124      -6.001  21.538  32.384  1.00 16.11           C
ATOM    729  CG2 ILE A 124      -6.711  21.162  29.095  1.00 14.60           C
ATOM    730  C   ILE A 124      -5.005  18.788  28.252  1.00 16.33           C
ATOM    731  O   ILE A 124      -3.787  18.984  28.175  1.00 15.84           O
ATOM    732  N   ILE A 125      -5.726  18.463  27.199  1.00 16.61           N
ATOM    733  CA  ILE A 125      -5.164  18.445  25.871  1.00 17.34           C
ATOM    734  CB  ILE A 125      -5.239  17.037  25.210  1.00 18.05           C
ATOM    735  CG1 ILE A 125      -4.630  15.965  26.131  1.00 17.51           C
ATOM    736  CD1 ILE A 125      -5.686  15.267  27.017  1.00 18.96           C
ATOM    737  CG2 ILE A 125      -4.515  17.051  23.821  1.00 17.27           C
ATOM    738  C   ILE A 125      -5.911  19.470  25.001  1.00 17.49           C
ATOM    739  O   ILE A 125      -7.124  19.437  24.922  1.00 16.00           O
ATOM    740  N   SER A 126      -5.171  20.373  24.361  1.00 17.95           N
ATOM    741  CA  SER A 126      -5.765  21.387  23.485  1.00 18.88           C
ATOM    742  CB  SER A 126      -5.333  22.786  23.949  1.00 20.01           C
ATOM    743  OG  SER A 126      -6.413  23.683  23.783  1.00 26.95           O
ATOM    744  C   SER A 126      -5.219  21.143  22.092  1.00 18.05           C
ATOM    745  O   SER A 126      -4.010  21.141  21.925  1.00 17.36           O
ATOM    746  N   THR A 127      -6.071  20.976  21.085  1.00 17.96           N
ATOM    747  CA  THR A 127      -5.568  20.576  19.767  1.00 18.54           C
ATOM    748  CB  THR A 127      -5.893  19.072  19.477  1.00 19.16           C
ATOM    749  OG1 THR A 127      -5.451  18.242  20.566  1.00 18.32           O
ATOM    750  CG2 THR A 127      -5.235  18.614  18.185  1.00 19.33           C
ATOM    751  C   THR A 127      -6.102  21.443  18.646  1.00 19.49           C
ATOM    752  O   THR A 127      -7.320  21.670  18.565  1.00 20.97           O
ATOM    753  N   LEU A 128      -5.206  21.947  17.792  1.00 19.59           N
ATOM    754  CA  LEU A 128      -5.625  22.594  16.559  1.00 20.90           C
ATOM    755  CB  LEU A 128      -4.702  23.769  16.167  1.00 20.05           C
ATOM    756  CG  LEU A 128      -4.910  25.110  16.898  1.00 19.61           C
ATOM    757  CD1 LEU A 128      -3.862  26.165  16.553  1.00 15.42           C
ATOM    758  CD2 LEU A 128      -6.306  25.656  16.619  1.00 18.72           C
ATOM    759  C   LEU A 128      -5.620  21.538  15.464  1.00 21.70           C
ATOM    760  O   LEU A 128      -4.678  20.734  15.371  1.00 22.05           O
ATOM    761  N   ASN A 129      -6.657  21.542  14.626  1.00 23.38           N
ATOM    762  CA  ASN A 129      -6.759  20.569  13.520  1.00 24.45           C
ATOM    763  CB  ASN A 129      -5.738  20.880  12.398  1.00 24.76           C
ATOM    764  CG  ASN A 129      -5.776  22.335  11.931  1.00 27.04           C
ATOM    765  OD1 ASN A 129      -6.436  22.648  10.939  1.00 30.45           O
ATOM    766  ND2 ASN A 129      -5.047  23.220  12.611  1.00 25.50           N
ATOM    767  C   ASN A 129      -6.577  19.110  13.984  1.00 24.87           C
ATOM    768  O   ASN A 129      -5.614  18.470  13.612  1.00 25.05           O
ATOM    769  N   PRO A 130      -7.520  18.573  14.774  1.00 26.14           N
```

FIGURE 4-11 (COORDINATES)

| | | | | | | | | | |
|---|---|---|---|---|---|---|---|---|---|
| ATOM | 770 | CA | PRO | A | 130 | -7.346 | 17.185 | 15.270 | 1.00 27.19 | C |
| ATOM | 771 | CB | PRO | A | 130 | -8.626 | 16.919 | 16.066 | 1.00 27.35 | C |
| ATOM | 772 | CG | PRO | A | 130 | -9.232 | 18.238 | 16.324 | 1.00 26.75 | C |
| ATOM | 773 | CD | PRO | A | 130 | -8.782 | 19.173 | 15.242 | 1.00 25.62 | C |
| ATOM | 774 | C | PRO | A | 130 | -7.194 | 16.110 | 14.184 | 1.00 27.85 | C |
| ATOM | 775 | O | PRO | A | 130 | -6.578 | 15.099 | 14.458 | 1.00 28.55 | O |
| ATOM | 776 | N | GLU | A | 131 | -7.708 | 16.342 | 12.969 | 1.00 29.03 | N |
| ATOM | 777 | CA | GLU | A | 131 | -7.645 | 15.348 | 11.870 | 1.00 28.90 | C |
| ATOM | 778 | CB | GLU | A | 131 | -8.761 | 15.830 | 10.856 | 0.00 31.31 | C |
| ATOM | 779 | CG | GLU | A | 131 | -8.493 | 17.183 | 10.074 | 0.00 35.16 | C |
| ATOM | 780 | CD | GLU | A | 131 | -8.524 | 19.053 | 10.754 | 1.00 42.85 | C |
| ATOM | 781 | OE1 | GLU | A | 131 | -9.131 | 18.600 | 11.758 | 1.00 42.16 | O |
| ATOM | 782 | OE2 | GLU | A | 131 | -8.615 | 20.243 | 10.364 | 1.00 42.96 | O |
| ATOM | 783 | C | GLU | A | 131 | -6.264 | 15.316 | 11.221 | 1.00 29.65 | C |
| ATOM | 784 | O | GLU | A | 131 | -5.859 | 14.303 | 10.623 | 1.00 30.03 | O |
| ATOM | 785 | N | ALA | A | 132 | -5.518 | 16.412 | 11.355 | 1.00 29.63 | N |
| ATOM | 786 | CA | ALA | A | 132 | -4.152 | 16.476 | 10.798 | 1.00 28.55 | C |
| ATOM | 787 | CB | ALA | A | 132 | -3.483 | 17.820 | 11.126 | 1.00 28.36 | C |
| ATOM | 788 | C | ALA | A | 132 | -3.323 | 15.307 | 11.309 | 1.00 27.89 | C |
| ATOM | 789 | O | ALA | A | 132 | -3.385 | 14.965 | 12.493 | 1.00 27.89 | O |
| ATOM | 790 | N | LYS | A | 133 | -2.564 | 14.678 | 10.417 | 1.00 27.62 | N |
| ATOM | 791 | CA | LYS | A | 133 | -1.786 | 13.506 | 10.798 | 1.00 27.51 | C |
| ATOM | 792 | CB | LYS | A | 133 | -1.167 | 12.802 | 9.587 | 1.00 27.21 | C |
| ATOM | 793 | CG | LYS | A | 133 | -2.204 | 12.072 | 8.701 | 1.00 28.81 | C |
| ATOM | 794 | CD | LYS | A | 133 | -1.552 | 11.278 | 7.548 | 1.00 28.00 | C |
| ATOM | 795 | CE | LYS | A | 133 | -0.693 | 12.080 | 6.601 | 0.00 35.95 | C |
| ATOM | 796 | NZ | LYS | A | 133 | -1.265 | 13.280 | 5.840 | 0.00 38.90 | N |
| ATOM | 797 | C | LYS | A | 133 | -0.727 | 13.875 | 11.841 | 1.00 26.84 | C |
| ATOM | 798 | O | LYS | A | 133 | -0.515 | 13.119 | 12.789 | 1.00 26.77 | O |
| ATOM | 799 | N | ARG | A | 134 | -0.116 | 15.058 | 11.670 | 1.00 25.69 | N |
| ATOM | 800 | CA | ARG | A | 134 | 1.021 | 15.523 | 12.486 | 1.00 25.09 | C |
| ATOM | 801 | CB | ARG | A | 134 | 2.211 | 15.822 | 11.587 | 1.00 24.60 | C |
| ATOM | 802 | CG | ARG | A | 134 | 2.688 | 14.615 | 10.822 | 1.00 28.65 | C |
| ATOM | 803 | CD | ARG | A | 134 | 3.435 | 15.012 | 9.589 | 1.00 29.95 | C |
| ATOM | 804 | NE | ARG | A | 134 | 4.638 | 15.740 | 9.945 | 1.00 31.75 | N |
| ATOM | 805 | CZ | ARG | A | 134 | 5.272 | 16.591 | 9.154 | 1.00 32.66 | C |
| ATOM | 806 | NH1 | ARG | A | 134 | 4.821 | 16.806 | 7.930 | 1.00 33.89 | N |
| ATOM | 807 | NH2 | ARG | A | 134 | 6.368 | 17.215 | 9.587 | 1.00 32.49 | N |
| ATOM | 808 | C | ARG | A | 134 | 0.740 | 16.738 | 13.375 | 1.00 24.04 | C |
| ATOM | 809 | O | ARG | A | 134 | 0.051 | 17.673 | 12.988 | 1.00 23.62 | O |
| ATOM | 810 | N | HIS | A | 135 | 1.302 | 16.710 | 14.573 | 1.00 23.65 | N |
| ATOM | 811 | CA | HIS | A | 135 | 1.249 | 17.840 | 15.495 | 1.00 22.68 | C |
| ATOM | 812 | CB | HIS | A | 135 | 0.141 | 17.667 | 16.565 | 1.00 23.33 | C |
| ATOM | 813 | CG | HIS | A | 135 | -1.248 | 17.758 | 16.011 | 1.00 23.84 | C |
| ATOM | 814 | ND1 | HIS | A | 135 | -1.833 | 16.738 | 15.288 | 1.00 25.87 | N |
| ATOM | 815 | CE1 | HIS | A | 135 | -3.050 | 17.103 | 14.922 | 1.00 25.31 | C |
| ATOM | 816 | NE2 | HIS | A | 135 | -3.271 | 18.327 | 15.369 | 1.00 25.23 | N |
| ATOM | 817 | CD2 | HIS | A | 135 | -2.158 | 18.758 | 16.053 | 1.00 24.87 | C |
| ATOM | 818 | C | HIS | A | 135 | 2.609 | 18.025 | 16.140 | 1.00 22.06 | C |
| ATOM | 819 | O | HIS | A | 135 | 3.316 | 17.062 | 16.480 | 1.00 22.30 | O |
| ATOM | 820 | N | LEU | A | 136 | 3.002 | 19.288 | 16.215 | 1.00 20.70 | N |
| ATOM | 821 | CA | LEU | A | 136 | 4.060 | 19.716 | 17.098 | 1.00 19.06 | C |
| ATOM | 822 | CB | LEU | A | 136 | 4.595 | 21.067 | 16.636 | 1.00 18.20 | C |
| ATOM | 823 | CG | LEU | A | 136 | 5.516 | 21.759 | 17.636 | 1.00 16.81 | C |
| ATOM | 824 | CD1 | LEU | A | 136 | 6.823 | 20.955 | 17.810 | 1.00 12.53 | C |
| ATOM | 825 | CD2 | LEU | A | 136 | 5.765 | 23.155 | 17.111 | 1.00 14.02 | C |
| ATOM | 826 | C | LEU | A | 136 | 3.362 | 19.845 | 18.440 | 1.00 18.66 | C |
| ATOM | 827 | O | LEU | A | 136 | 2.268 | 20.399 | 18.511 | 1.00 17.84 | O |
| ATOM | 828 | N | VAL | A | 137 | 3.981 | 19.332 | 19.500 | 1.00 17.13 | N |
| ATOM | 829 | CA | VAL | A | 137 | 3.336 | 19.360 | 20.791 | 1.00 16.48 | C |
| ATOM | 830 | CB | VAL | A | 137 | 3.076 | 17.913 | 21.332 | 1.00 16.65 | C |
| ATOM | 831 | CG1 | VAL | A | 137 | 2.279 | 17.965 | 22.570 | 1.00 16.33 | C |
| ATOM | 832 | CG2 | VAL | A | 137 | 2.392 | 17.036 | 20.286 | 1.00 18.55 | C |
| ATOM | 833 | C | VAL | A | 137 | 4.168 | 20.164 | 21.794 | 1.00 15.79 | C |
| ATOM | 834 | O | VAL | A | 137 | 5.382 | 19.942 | 21.930 | 1.00 15.46 | O |
| ATOM | 835 | N | LEU | A | 138 | 3.517 | 21.103 | 22.490 | 1.00 14.74 | N |
| ATOM | 836 | CA | LEU | A | 138 | 4.127 | 21.762 | 23.638 | 1.00 15.60 | C |
| ATOM | 837 | CB | LEU | A | 138 | 4.043 | 23.279 | 23.532 | 1.00 15.93 | C |
| ATOM | 838 | CG | LEU | A | 138 | 5.133 | 24.102 | 22.800 | 1.00 20.39 | C |
| ATOM | 839 | CD1 | LEU | A | 138 | 5.593 | 23.463 | 21.444 | 1.00 20.55 | C |

FIGURE 4-12 (COORDINATES)

```
ATOM    840  CD2 LEU A 138       4.585  25.527  22.586  1.00 19.71           C
ATOM    841  C   LEU A 138       3.456  21.295  24.906  1.00 14.01           C
ATOM    842  O   LEU A 138       2.231  21.095  24.952  1.00 13.91           O
ATOM    843  N   ALA A 139       4.250  21.146  25.958  1.00 12.20           N
ATOM    844  CA  ALA A 139       3.724  20.617  27.196  1.00 13.07           C
ATOM    845  CB  ALA A 139       3.825  19.069  27.197  1.00 12.07           C
ATOM    846  C   ALA A 139       4.340  21.187  28.473  1.00 11.82           C
ATOM    847  O   ALA A 139       5.453  21.705  28.464  1.00 11.94           O
ATOM    848  N   CYS A 140       3.550  21.134  29.543  1.00 11.89           N
ATOM    849  CA  CYS A 140       3.958  21.428  30.930  1.00 12.58           C
ATOM    850  CB  CYS A 140       3.687  22.904  31.334  1.00 11.98           C
ATOM    851  SG  CYS A 140       1.927  23.275  31.485  1.00 16.29           S
ATOM    852  C   CYS A 140       3.155  20.480  31.851  1.00 12.19           C
ATOM    853  O   CYS A 140       2.250  19.778  31.390  1.00 12.30           O
ATOM    854  N   HIS A 141       3.486  20.459  33.142  1.00 12.23           N
ATOM    855  CA  HIS A 141       2.593  19.901  34.154  1.00 12.81           C
ATOM    856  CB  HIS A 141       3.309  18.877  35.096  1.00 11.89           C
ATOM    857  CG  HIS A 141       4.113  19.500  36.212  1.00 13.30           C
ATOM    858  ND1 HIS A 141       5.447  19.852  36.079  1.00 16.62           N
ATOM    859  CE1 HIS A 141       5.899  20.329  37.226  1.00 10.84           C
ATOM    860  NE2 HIS A 141       4.911  20.285  38.100  1.00 14.35           N
ATOM    861  CD2 HIS A 141       3.779  19.802  37.489  1.00  8.38           C
ATOM    862  C   HIS A 141       1.941  21.037  34.912  1.00 13.17           C
ATOM    863  O   HIS A 141       2.625  22.006  35.309  1.00 14.77           O
ATOM    864  N   TYR A 142       0.635  20.932  35.124  1.00 13.55           N
ATOM    865  CA  TYR A 142      -0.116  21.989  35.800  1.00 13.80           C
ATOM    866  CB  TYR A 142      -1.387  22.347  35.007  1.00 14.64           C
ATOM    867  CG  TYR A 142      -2.586  21.448  35.240  1.00 15.36           C
ATOM    868  CD1 TYR A 142      -3.519  21.749  36.251  1.00 17.58           C
ATOM    869  CE1 TYR A 142      -4.621  20.950  36.477  1.00 14.42           C
ATOM    870  CZ  TYR A 142      -4.827  19.846  35.667  1.00 16.15           C
ATOM    871  OH  TYR A 142      -5.939  19.077  35.866  1.00 15.85           O
ATOM    872  CE2 TYR A 142      -3.955  19.539  34.634  1.00 11.10           C
ATOM    873  CD2 TYR A 142      -2.829  20.337  34.432  1.00 15.85           C
ATOM    874  C   TYR A 142      -0.378  21.730  37.294  1.00 14.35           C
ATOM    875  O   TYR A 142      -0.792  22.642  38.025  1.00 14.86           O
ATOM    876  N   ASP A 143      -0.061  20.524  37.765  1.00 13.90           N
ATOM    877  CA  ASP A 143      -0.205  20.180  39.182  1.00 15.91           C
ATOM    878  CB  ASP A 143      -0.227  18.632  39.364  1.00 15.57           C
ATOM    879  CG  ASP A 143       1.082  17.972  38.947  1.00 17.44           C
ATOM    880  OD1 ASP A 143       1.505  18.137  37.763  1.00 16.13           O
ATOM    881  OD2 ASP A 143       1.689  17.264  39.810  1.00 14.57           O
ATOM    882  C   ASP A 143       0.960  20.803  39.968  1.00 15.93           C
ATOM    883  O   ASP A 143       2.028  21.068  39.396  1.00 16.19           O
ATOM    884  N   SER A 144       0.764  21.066  41.254  1.00 15.78           N
ATOM    885  CA  SER A 144       1.852  21.505  42.119  1.00 16.23           C
ATOM    886  CB  SER A 144       1.533  22.837  42.829  1.00 16.45           C
ATOM    887  OG  SER A 144       0.421  22.661  43.719  1.00 18.60           O
ATOM    888  C   SER A 144       2.075  20.380  43.135  1.00 16.53           C
ATOM    889  O   SER A 144       1.148  19.649  43.448  1.00 16.74           O
ATOM    890  N   LYS A 145       3.312  20.213  43.595  1.00 16.45           N
ATOM    891  CA  LYS A 145       3.664  19.132  44.527  1.00 16.75           C
ATOM    892  CB  LYS A 145       5.180  19.126  44.784  1.00 14.85           C
ATOM    893  CG  LYS A 145       5.699  17.885  45.519  1.00 15.58           C
ATOM    894  CD  LYS A 145       7.220  17.819  45.494  1.00 16.39           C
ATOM    895  CE  LYS A 145       7.822  16.776  46.492  1.00 14.69           C
ATOM    896  NZ  LYS A 145       7.186  15.469  46.223  1.00 16.31           N
ATOM    897  C   LYS A 145       2.907  19.270  45.848  1.00 17.64           C
ATOM    898  O   LYS A 145       2.791  20.360  46.381  1.00 16.87           O
ATOM    899  N   TYR A 146       2.382  18.154  46.358  1.00 19.34           N
ATOM    900  CA  TYR A 146       1.775  18.146  47.679  1.00 20.72           C
ATOM    901  CB  TYR A 146       0.862  16.916  47.872  1.00 20.88           C
ATOM    902  CG  TYR A 146       0.449  16.768  49.314  1.00 21.23           C
ATOM    903  CD1 TYR A 146      -0.549  17.591  49.850  1.00 20.86           C
ATOM    904  CE1 TYR A 146      -0.928  17.494  51.161  1.00 20.32           C
ATOM    905  CZ  TYR A 146      -0.296  16.559  51.987  1.00 21.65           C
ATOM    906  OH  TYR A 146      -0.688  16.487  53.297  1.00 22.41           O
ATOM    907  CE2 TYR A 146       0.701  15.723  51.504  1.00 17.94           C
ATOM    908  CD2 TYR A 146       1.079  15.839  50.160  1.00 22.45           C
ATOM    909  C   TYR A 146       2.830  18.177  48.779  1.00 21.36           C
```

FIGURE 4-13 (COORDINATES)

```
ATOM    910  O   TYR A 146       3.759  17.383  48.792  1.00 21.18           O
ATOM    911  N   PHE A 147       2.672  19.099  49.710  1.00 22.81           N
ATOM    912  CA  PHE A 147       3.454  19.095  50.929  1.00 24.74           C
ATOM    913  CB  PHE A 147       4.432  20.259  50.951  1.00 25.00           C
ATOM    914  CG  PHE A 147       5.593  20.082  50.030  1.00 25.94           C
ATOM    915  CD1 PHE A 147       6.679  19.285  50.397  1.00 26.41           C
ATOM    916  CE1 PHE A 147       7.761  19.112  49.520  1.00 26.91           C
ATOM    917  CZ  PHE A 147       7.764  19.768  48.305  1.00 24.84           C
ATOM    918  CE2 PHE A 147       6.689  20.539  47.918  1.00 24.63           C
ATOM    919  CD2 PHE A 147       5.606  20.710  48.791  1.00 27.99           C
ATOM    920  C   PHE A 147       2.501  19.205  52.123  1.00 26.27           C
ATOM    921  O   PHE A 147       1.529  19.950  52.065  1.00 25.17           O
ATOM    922  N   PRO A 148       2.763  18.444  53.196  1.00 28.50           N
ATOM    923  CA  PRO A 148       1.894  18.570  54.389  1.00 30.09           C
ATOM    924  CB  PRO A 148       2.633  17.731  55.449  1.00 29.42           C
ATOM    925  CG  PRO A 148       3.217  16.625  54.618  1.00 29.83           C
ATOM    926  CD  PRO A 148       3.765  17.376  53.381  1.00 28.33           C
ATOM    927  C   PRO A 148       1.640  20.006  54.851  1.00 31.23           C
ATOM    928  O   PRO A 148       2.559  20.807  54.880  1.00 31.43           O
ATOM    929  N   ARG A 149       0.381  20.320  55.169  1.00 32.47           N
ATOM    930  CA  ARG A 149       0.015  21.680  55.569  1.00 34.19           C
ATOM    931  CB  ARG A 149      -1.432  21.975  55.214  1.00 34.05           C
ATOM    932  CG  ARG A 149      -1.821  23.448  55.373  1.00 35.30           C
ATOM    933  CD  ARG A 149      -3.287  23.613  55.070  1.00 36.50           C
ATOM    934  NE  ARG A 149      -3.649  22.866  53.861  1.00 37.02           N
ATOM    935  CZ  ARG A 149      -3.586  23.361  52.631  1.00 37.30           C
ATOM    936  NH1 ARG A 149      -3.912  22.603  51.608  1.00 38.28           N
ATOM    937  NH2 ARG A 149      -3.193  24.616  52.424  1.00 38.81           N
ATOM    938  C   ARG A 149       0.226  21.916  57.061  1.00 35.12           C
ATOM    939  O   ARG A 149      -0.694  21.665  57.856  1.00 34.09           O
ATOM    940  N   TRP A 150       1.431  22.398  57.415  1.00 35.94           N
ATOM    941  CA  TRP A 150       1.791  22.729  58.810  1.00 37.12           C
ATOM    942  CB  TRP A 150       3.177  22.157  59.199  1.00 37.24           C
ATOM    943  CG  TRP A 150       4.331  22.617  58.344  1.00 37.99           C
ATOM    944  CD1 TRP A 150       4.592  22.174  57.519  0.00 44.87           C
ATOM    945  NE1 TRP A 150       5.790  22.804  57.238  0.00 45.99           N
ATOM    946  CE2 TRP A 150       6.089  23.677  58.253  0.00 44.94           C
ATOM    947  CD2 TRP A 150       5.031  23.597  59.202  0.00 44.29           C
ATOM    948  CE3 TRP A 150       5.083  24.410  60.352  0.00 45.16           C
ATOM    949  CZ3 TRP A 150       6.187  25.273  60.523  0.00 44.27           C
ATOM    950  CH2 TRP A 150       7.228  25.332  59.554  0.00 44.77           C
ATOM    951  CZ2 TRP A 150       7.195  24.544  58.414  0.00 44.36           C
ATOM    952  C   TRP A 150       1.698  24.232  59.150  1.00 37.61           C
ATOM    953  O   TRP A 150       1.612  24.599  60.318  1.00 38.04           O
ATOM    954  N   ASP A 151       1.677  25.102  58.141  1.00 37.56           N
ATOM    955  CA  ASP A 151       1.747  26.548  58.403  1.00 37.80           C
ATOM    956  CB  ASP A 151       3.222  27.013  58.481  1.00 38.49           C
ATOM    957  CG  ASP A 151       3.955  26.879  57.143  1.00 40.74           C
ATOM    958  OD1 ASP A 151       4.301  25.742  56.721  1.00 42.74           O
ATOM    959  OD2 ASP A 151       4.191  27.923  56.511  1.00 43.38           O
ATOM    960  C   ASP A 151       0.949  27.352  57.370  1.00 36.54           C
ATOM    961  O   ASP A 151       0.303  26.761  56.519  1.00 36.92           O
ATOM    962  N   SER A 152       0.973  28.681  57.455  1.00 35.39           N
ATOM    963  CA  SER A 152       0.239  29.539  56.516  1.00 34.86           C
ATOM    964  CB  SER A 152       0.288  31.002  56.965  1.00 35.40           C
ATOM    965  OG  SER A 152       1.614  31.507  56.888  1.00 36.34           O
ATOM    966  C   SER A 152       0.760  29.438  55.087  1.00 34.18           C
ATOM    967  O   SER A 152       0.013  29.624  54.136  1.00 34.52           O
ATOM    968  N   ARG A 153       2.049  29.150  54.935  1.00 33.07           N
ATOM    969  CA  ARG A 153       2.669  29.119  53.609  1.00 31.73           C
ATOM    970  CB  ARG A 153       4.192  29.173  53.713  1.00 31.53           C
ATOM    971  CG  ARG A 153       4.718  30.504  54.190  1.00 33.03           C
ATOM    972  CD  ARG A 153       6.237  30.563  54.053  1.00 33.97           C
ATOM    973  NE  ARG A 153       6.359  29.014  55.207  0.00 45.64           N
ATOM    974  CZ  ARG A 153       7.559  28.569  55.586  0.00 47.44           C
ATOM    975  NH1 ARG A 153       8.664  29.241  55.268  0.00 47.57           N
ATOM    976  NH2 ARG A 153       7.655  27.439  56.283  0.00 49.34           N
ATOM    977  C   ARG A 153       2.243  27.887  52.823  1.00 30.00           C
ATOM    978  O   ARG A 153       2.047  26.814  53.382  1.00 30.31           O
ATOM    979  N   VAL A 154       2.046  28.052  51.527  1.00 27.82           N
```

FIGURE 4-14 (COORDINATES)

```
ATOM    980  CA  VAL A 154       1.793  26.898  50.696  1.00 26.30           C
ATOM    981  CB  VAL A 154       0.321  26.790  50.198  1.00 26.65           C
ATOM    982  CG1 VAL A 154      -0.658  26.471  51.386  1.00 28.38           C
ATOM    983  CG2 VAL A 154      -0.090  28.017  49.410  1.00 28.21           C
ATOM    984  C   VAL A 154       2.753  26.871  49.516  1.00 24.82           C
ATOM    985  O   VAL A 154       3.359  27.890  49.155  1.00 22.73           O
ATOM    986  N   PHE A 155       2.891  25.687  48.940  1.00 22.59           N
ATOM    987  CA  PHE A 155       3.745  25.515  47.790  1.00 21.76           C
ATOM    988  CB  PHE A 155       4.350  24.122  47.764  1.00 20.98           C
ATOM    989  CG  PHE A 155       5.304  23.913  46.628  1.00 20.70           C
ATOM    990  CD1 PHE A 155       6.569  24.494  46.651  1.00 20.14           C
ATOM    991  CE1 PHE A 155       7.463  24.302  45.588  1.00 19.98           C
ATOM    992  CZ  PHE A 155       7.073  23.536  44.513  1.00 17.21           C
ATOM    993  CE2 PHE A 155       5.805  22.975  44.487  1.00 20.20           C
ATOM    994  CD2 PHE A 155       4.931  23.169  45.535  1.00 18.27           C
ATOM    995  C   PHE A 155       2.913  25.750  46.557  1.00 21.04           C
ATOM    996  O   PHE A 155       1.908  25.066  46.346  1.00 20.94           O
ATOM    997  N   VAL A 156       3.329  26.726  45.753  1.00 19.76           N
ATOM    998  CA  VAL A 156       2.625  27.056  44.498  1.00 18.83           C
ATOM    999  CB  VAL A 156       2.102  28.517  44.475  1.00 18.66           C
ATOM   1000  CG1 VAL A 156       1.157  28.746  45.678  1.00 18.20           C
ATOM   1001  CG2 VAL A 156       3.265  29.548  44.466  1.00 16.84           C
ATOM   1002  C   VAL A 156       3.431  26.752  43.250  1.00 17.87           C
ATOM   1003  O   VAL A 156       2.946  26.970  42.138  1.00 18.95           O
ATOM   1004  N   GLY A 157       4.661  26.275  43.426  1.00 17.13           N
ATOM   1005  CA  GLY A 157       5.468  25.837  42.289  1.00 15.81           C
ATOM   1006  C   GLY A 157       5.463  26.806  41.126  1.00 14.97           C
ATOM   1007  O   GLY A 157       5.037  26.441  40.002  1.00 14.82           O
ATOM   1008  N   ALA A 158       5.947  28.032  41.368  1.00 14.14           N
ATOM   1009  CA  ALA A 158       6.007  29.067  40.297  1.00 13.93           C
ATOM   1010  CB  ALA A 158       6.459  30.390  40.816  1.00 12.85           C
ATOM   1011  C   ALA A 158       6.833  28.654  39.090  1.00 14.07           C
ATOM   1012  O   ALA A 158       6.372  28.767  37.969  1.00 13.91           O
ATOM   1013  N   THR A 159       8.057  28.169  39.308  1.00 14.56           N
ATOM   1014  CA  THR A 159       8.858  27.665  38.185  1.00 14.13           C
ATOM   1015  CB  THR A 159      10.372  27.655  38.488  1.00 13.48           C
ATOM   1016  OG1 THR A 159      10.658  26.754  39.578  1.00 16.59           O
ATOM   1017  CG2 THR A 159      10.856  29.064  38.804  1.00 13.87           C
ATOM   1018  C   THR A 159       8.437  26.252  37.758  1.00 12.89           C
ATOM   1019  O   THR A 159       8.771  25.779  36.664  1.00 11.03           O
ATOM   1020  N   ASP A 160       7.663  25.625  38.631  1.00 13.20           N
ATOM   1021  CA  ASP A 160       7.496  24.176  38.651  1.00 13.52           C
ATOM   1022  CB  ASP A 160       8.329  23.630  39.827  1.00 12.80           C
ATOM   1023  CG  ASP A 160       8.385  22.077  39.888  1.00 13.08           C
ATOM   1024  OD1 ASP A 160       8.007  21.384  38.932  1.00 14.02           O
ATOM   1025  OD2 ASP A 160       8.853  21.543  40.901  1.00 15.11           O
ATOM   1026  C   ASP A 160       6.002  23.805  38.807  1.00 12.49           C
ATOM   1027  O   ASP A 160       5.631  23.254  39.834  1.00 12.77           O
ATOM   1028  N   SER A 161       5.140  24.059  37.811  1.00 13.38           N
ATOM   1029  CA  SER A 161       5.445  24.660  36.496  1.00 12.99           C
ATOM   1030  CB  SER A 161       5.540  23.615  35.386  1.00 12.25           C
ATOM   1031  OG  SER A 161       6.773  22.919  35.457  1.00 15.53           O
ATOM   1032  C   SER A 161       4.380  25.670  36.097  1.00 13.07           C
ATOM   1033  O   SER A 161       3.921  25.683  34.975  1.00 12.97           O
ATOM   1034  N   ALA A 162       4.001  26.544  37.017  1.00 12.97           N
ATOM   1035  CA  ALA A 162       3.024  27.587  36.701  1.00 12.78           C
ATOM   1036  CB  ALA A 162       2.791  28.465  37.946  1.00 11.58           C
ATOM   1037  C   ALA A 162       3.524  28.440  35.540  1.00 12.20           C
ATOM   1038  O   ALA A 162       2.765  28.803  34.626  1.00 13.21           O
ATOM   1039  N   VAL A 163       4.816  28.770  35.556  1.00 13.47           N
ATOM   1040  CA  VAL A 163       5.369  29.635  34.497  1.00 12.32           C
ATOM   1041  CB  VAL A 163       6.761  30.230  34.881  1.00 13.33           C
ATOM   1042  CG1 VAL A 163       7.469  30.829  33.599  1.00 12.07           C
ATOM   1043  CG2 VAL A 163       6.620  31.293  36.001  1.00 12.01           C
ATOM   1044  C   VAL A 163       5.370  28.935  33.128  1.00 12.79           C
ATOM   1045  O   VAL A 163       4.870  29.509  32.161  1.00 13.16           O
ATOM   1046  N   PRO A 164       5.970  27.714  33.018  1.00 12.55           N
ATOM   1047  CA  PRO A 164       5.777  26.955  31.782  1.00 13.00           C
ATOM   1048  CB  PRO A 164       6.346  25.562  32.139  1.00 11.98           C
ATOM   1049  CG  PRO A 164       7.487  25.926  32.987  1.00 12.72           C
```

FIGURE 4-15 (COORDINATES)

```
ATOM   1050  CD  PRO A 164       6.909  26.987  33.915  1.00 12.38           C
ATOM   1051  C   PRO A 164       4.337  26.887  31.242  1.00 13.45           C
ATOM   1052  O   PRO A 164       4.143  26.997  30.042  1.00 13.46           O
ATOM   1053  N   CYS A 165       3.349  26.652  32.096  1.00 15.12           N
ATOM   1054  CA  CYS A 165       1.956  26.614  31.648  1.00 15.33           C
ATOM   1055  CB  CYS A 165       1.044  26.053  32.755  1.00 16.36           C
ATOM   1056  SG  CYS A 165       1.530  24.324  33.246  1.00 19.73           S
ATOM   1057  C   CYS A 165       1.480  28.013  31.161  1.00 15.22           C
ATOM   1058  O   CYS A 165       0.920  28.122  30.079  1.00 15.81           O
ATOM   1059  N   ALA A 166       1.726  29.062  31.941  1.00 15.72           N
ATOM   1060  CA  ALA A 166       1.448  30.464  31.523  1.00 15.36           C
ATOM   1061  CB  ALA A 166       1.885  31.458  32.644  1.00 15.89           C
ATOM   1062  C   ALA A 166       2.141  30.824  30.196  1.00 14.63           C
ATOM   1063  O   ALA A 166       1.580  31.512  29.360  1.00 12.54           O
ATOM   1064  N   MET A 167       3.350  30.299  29.981  1.00 13.80           N
ATOM   1065  CA  MET A 167       4.069  30.575  28.747  1.00 13.69           C
ATOM   1066  CB  MET A 167       5.524  30.039  28.810  1.00 13.98           C
ATOM   1067  CG  MET A 167       6.445  30.803  29.758  1.00 15.02           C
ATOM   1068  SD  MET A 167       8.081  30.029  29.985  1.00 15.57           S
ATOM   1069  CE  MET A 167       8.777  30.270  28.377  1.00 11.93           C
ATOM   1070  C   MET A 167       3.359  29.952  27.584  1.00 14.10           C
ATOM   1071  O   MET A 167       3.285  30.534  26.508  1.00 14.01           O
ATOM   1072  N   MET A 168       2.837  28.737  27.781  1.00 13.61           N
ATOM   1073  CA  MET A 168       2.079  28.073  26.713  1.00 13.39           C
ATOM   1074  CB  MET A 168       1.750  26.624  27.092  1.00 11.89           C
ATOM   1075  CG  MET A 168       3.024  25.710  27.019  1.00 11.75           C
ATOM   1076  SD  MET A 168       2.742  24.238  27.974  1.00 16.46           S
ATOM   1077  CE  MET A 168       1.319  23.473  27.202  1.00 12.04           C
ATOM   1078  C   MET A 168       0.775  28.818  26.381  1.00 12.73           C
ATOM   1079  O   MET A 168       0.445  28.964  25.236  1.00 11.99           O
ATOM   1080  N   LEU A 169       0.056  29.256  27.407  1.00 12.95           N
ATOM   1081  CA  LEU A 169      -1.140  30.076  27.267  1.00 13.09           C
ATOM   1082  CB  LEU A 169      -1.688  30.371  28.672  1.00 13.16           C
ATOM   1083  CG  LEU A 169      -2.270  29.150  29.434  1.00 13.47           C
ATOM   1084  CD1 LEU A 169      -2.783  29.517  30.804  1.00 15.53           C
ATOM   1085  CD2 LEU A 169      -3.394  28.513  28.608  1.00 12.81           C
ATOM   1086  C   LEU A 169      -0.821  31.400  26.531  1.00 14.85           C
ATOM   1087  O   LEU A 169      -1.531  31.802  25.575  1.00 15.16           O
ATOM   1088  N   GLU A 170       0.241  32.077  26.985  1.00 14.38           N
ATOM   1089  CA  GLU A 170       0.748  33.298  26.287  1.00 15.10           C
ATOM   1090  CB  GLU A 170       1.918  33.949  27.078  1.00 15.48           C
ATOM   1091  CG  GLU A 170       2.639  35.154  26.357  1.00 14.24           C
ATOM   1092  CD  GLU A 170       1.721  36.326  25.910  1.00 18.32           C
ATOM   1093  OE1 GLU A 170       0.585  36.491  26.418  1.00 18.28           O
ATOM   1094  OE2 GLU A 170       2.164  37.131  25.040  1.00 22.51           O
ATOM   1095  C   GLU A 170       1.104  33.038  24.825  1.00 15.02           C
ATOM   1096  O   GLU A 170       0.826  33.860  23.948  1.00 15.32           O
ATOM   1097  N   LEU A 171       1.699  31.880  24.539  1.00 14.48           N
ATOM   1098  CA  LEU A 171       2.017  31.552  23.164  1.00 13.67           C
ATOM   1099  CB  LEU A 171       2.874  30.259  23.086  1.00 14.52           C
ATOM   1100  CG  LEU A 171       3.346  29.809  21.704  1.00 14.19           C
ATOM   1101  CD1 LEU A 171       4.780  29.164  21.737  1.00 14.07           C
ATOM   1102  CD2 LEU A 171       2.325  28.860  21.130  1.00 11.88           C
ATOM   1103  C   LEU A 171       0.750  31.407  22.318  1.00 14.03           C
ATOM   1104  O   LEU A 171       0.709  31.889  21.185  1.00 13.88           O
ATOM   1105  N   ALA A 172      -0.272  30.730  22.846  1.00 12.22           N
ATOM   1106  CA  ALA A 172      -1.503  30.555  22.099  1.00 12.48           C
ATOM   1107  CB  ALA A 172      -2.503  29.655  22.864  1.00 12.45           C
ATOM   1108  C   ALA A 172      -2.130  31.907  21.834  1.00 13.20           C
ATOM   1109  O   ALA A 172      -2.637  32.140  20.735  1.00 14.41           O
ATOM   1110  N   ARG A 173      -2.082  32.790  22.833  1.00 12.68           N
ATOM   1111  CA  ARG A 173      -2.644  34.127  22.709  1.00 14.05           C
ATOM   1112  CB  ARG A 173      -2.675  34.835  24.076  1.00 13.22           C
ATOM   1113  CG  ARG A 173      -3.422  36.212  24.044  1.00 13.60           C
ATOM   1114  CD  ARG A 173      -2.889  37.163  25.104  1.00 15.04           C
ATOM   1115  NE  ARG A 173      -1.512  37.555  24.823  1.00 16.15           N
ATOM   1116  CZ  ARG A 173      -1.135  38.445  23.906  1.00 20.91           C
ATOM   1117  NH1 ARG A 173      -2.049  39.100  23.143  1.00 16.03           N
ATOM   1118  NH2 ARG A 173       0.173  38.700  23.754  1.00 17.40           N
ATOM   1119  C   ARG A 173      -1.830  34.995  21.726  1.00 15.42           C
```

FIGURE 4-16 (COORDINATES)

```
ATOM   1120  O    ARG A 173      -2.396  35.605  20.847  1.00 16.28           O
ATOM   1121  N    ALA A 174      -0.517  35.091  21.939  1.00 16.15           N
ATOM   1122  CA   ALA A 174       0.359  35.919  21.085  1.00 16.96           C
ATOM   1123  CB   ALA A 174       1.779  35.825  21.568  1.00 16.34           C
ATOM   1124  C    ALA A 174       0.265  35.499  19.619  1.00 17.80           C
ATOM   1125  O    ALA A 174       0.184  36.368  18.717  1.00 19.22           O
ATOM   1126  N    LEU A 175       0.259  34.184  19.367  1.00 17.12           N
ATOM   1127  CA   LEU A 175       0.226  33.663  17.990  1.00 16.90           C
ATOM   1128  CB   LEU A 175       1.143  32.441  17.842  1.00 17.49           C
ATOM   1129  CG   LEU A 175       2.582  32.550  18.381  1.00 17.30           C
ATOM   1130  CD1  LEU A 175       3.268  31.241  18.137  1.00 18.50           C
ATOM   1131  CD2  LEU A 175       3.358  33.753  17.696  1.00 17.25           C
ATOM   1132  C    LEU A 175      -1.183  33.354  17.464  1.00 17.89           C
ATOM   1133  O    LEU A 175      -1.338  32.730  16.418  1.00 18.18           O
ATOM   1134  N    ASP A 176      -2.207  33.814  18.170  1.00 19.04           N
ATOM   1135  CA   ASP A 176      -3.602  33.419  17.862  1.00 20.46           C
ATOM   1136  CB   ASP A 176      -4.582  34.156  18.764  1.00 19.80           C
ATOM   1137  CG   ASP A 176      -5.986  33.573  18.713  1.00 20.48           C
ATOM   1138  OD1  ASP A 176      -6.129  32.346  18.464  1.00 20.17           O
ATOM   1139  OD2  ASP A 176      -6.941  34.365  18.925  1.00 16.91           O
ATOM   1140  C    ASP A 176      -3.960  33.650  16.402  1.00 21.34           C
ATOM   1141  O    ASP A 176      -4.508  32.753  15.743  1.00 21.20           O
ATOM   1142  N    LYS A 177      -3.643  34.836  15.879  1.00 21.92           N
ATOM   1143  CA   LYS A 177      -4.026  35.131  14.475  1.00 23.93           C
ATOM   1144  CB   LYS A 177      -3.883  36.618  14.141  1.00 23.72           C
ATOM   1145  CG   LYS A 177      -3.978  36.887  12.624  1.00 26.28           C
ATOM   1146  CD   LYS A 177      -3.845  38.370  12.288  1.00 26.80           C
ATOM   1147  CE   LYS A 177      -4.038  38.607  10.799  1.00 32.55           C
ATOM   1148  NZ   LYS A 177      -2.873  39.416  10.297  1.00 36.71           N
ATOM   1149  C    LYS A 177      -3.338  34.246  13.402  1.00 23.11           C
ATOM   1150  O    LYS A 177      -3.989  33.767  12.483  1.00 23.73           O
ATOM   1151  N    LYS A 178      -2.031  34.043  13.521  1.00 23.22           N
ATOM   1152  CA   LYS A 178      -1.310  33.093  12.678  1.00 22.72           C
ATOM   1153  CB   LYS A 178       0.199  33.184  12.931  1.00 22.40           C
ATOM   1154  CG   LYS A 178       0.899  34.414  12.287  1.00 23.30           C
ATOM   1155  CD   LYS A 178       2.002  34.799  12.717  0.00 31.67           C
ATOM   1156  CE   LYS A 178       2.631  36.051  12.061  0.00 35.82           C
ATOM   1157  NZ   LYS A 178       4.039  36.288  12.567  0.00 39.29           N
ATOM   1158  C    LYS A 178      -1.788  31.644  12.915  1.00 23.15           C
ATOM   1159  O    LYS A 178      -1.983  30.889  11.958  1.00 23.04           O
ATOM   1160  N    LEU A 179      -1.975  31.248  14.171  1.00 23.01           N
ATOM   1161  CA   LEU A 179      -2.459  29.860  14.434  1.00 24.15           C
ATOM   1162  CB   LEU A 179      -2.404  29.507  15.931  1.00 23.07           C
ATOM   1163  CG   LEU A 179      -0.999  29.434  16.577  1.00 21.30           C
ATOM   1164  CD1  LEU A 179      -1.036  29.384  18.125  1.00 16.26           C
ATOM   1165  CD2  LEU A 179      -0.175  28.297  16.004  1.00 18.12           C
ATOM   1166  C    LEU A 179      -3.865  29.641  13.848  1.00 25.61           C
ATOM   1167  O    LEU A 179      -4.165  28.568  13.300  1.00 25.74           O
ATOM   1168  N    HIS A 180      -4.725  30.659  13.951  1.00 27.81           N
ATOM   1169  CA   HIS A 180      -6.073  30.586  13.349  1.00 29.61           C
ATOM   1170  CB   HIS A 180      -6.902  31.839  13.679  1.00 29.78           C
ATOM   1171  CG   HIS A 180      -8.364  31.703  13.373  1.00 33.32           C
ATOM   1172  ND1  HIS A 180      -8.951  30.503  13.018  1.00 36.07           N
ATOM   1173  CE1  HIS A 180     -10.246  30.686  12.831  1.00 35.31           C
ATOM   1174  NE2  HIS A 180     -10.526  31.954  13.070  1.00 35.35           N
ATOM   1175  CD2  HIS A 180      -9.365  32.613  13.405  1.00 34.67           C
ATOM   1176  C    HIS A 180      -6.043  30.260  11.835  1.00 30.06           C
ATOM   1177  O    HIS A 180      -6.847  29.456  11.348  1.00 30.37           O
ATOM   1178  N    SER A 181      -5.089  30.847  11.116  1.00 31.00           N
ATOM   1179  CA   SER A 181      -4.931  30.660   9.673  1.00 31.62           C
ATOM   1180  CB   SER A 181      -3.789  31.545   9.158  1.00 31.67           C
ATOM   1181  OG   SER A 181      -2.526  30.978   9.496  1.00 29.81           O
ATOM   1182  C    SER A 181      -4.674  29.195   9.288  1.00 33.29           C
ATOM   1183  O    SER A 181      -4.864  28.808   8.130  1.00 33.99           O
ATOM   1184  N    LEU A 182      -4.235  28.388  10.257  1.00 34.34           N
ATOM   1185  CA   LEU A 182      -4.076  26.949  10.078  1.00 35.41           C
ATOM   1186  CB   LEU A 182      -3.477  26.317  11.339  1.00 35.26           C
ATOM   1187  CG   LEU A 182      -1.970  26.455  11.591  1.00 34.52           C
ATOM   1188  CD1  LEU A 182      -1.660  26.121  13.062  1.00 32.69           C
ATOM   1189  CD2  LEU A 182      -1.191  25.556  10.667  1.00 33.87           C
```

FIGURE 4-17 (COORDINATES)

```
ATOM   1190  C   LEU A 182      -5.376  26.216   9.718  1.00 36.41           C
ATOM   1191  O   LEU A 182      -5.314  25.117   9.185  1.00 37.45           O
ATOM   1192  N   LYS A 183      -6.536  26.802  10.020  1.00 37.11           N
ATOM   1193  CA  LYS A 183      -7.826  26.204   9.645  1.00 38.28           C
ATOM   1194  CB  LYS A 183      -8.986  26.854  10.396  1.00 38.10           C
ATOM   1195  CG  LYS A 183      -9.493  28.147   9.764  1.00 38.17           C
ATOM   1196  CD  LYS A 183     -10.727  28.526  10.255  0.00 46.53           C
ATOM   1197  CE  LYS A 183     -11.031  30.018  10.017  0.00 49.49           C
ATOM   1198  NZ  LYS A 183     -10.801  30.500   8.611  0.00 49.28           N
ATOM   1199  C   LYS A 183      -8.056  26.338   8.151  1.00 38.85           C
ATOM   1200  O   LYS A 183      -8.050  25.340   7.438  1.00 40.41           O
ATOM   1201  N   ASP A 184      -7.548  27.059   7.355  0.00 48.24           N
ATOM   1202  CA  ASP A 184      -7.448  27.092   5.885  0.00 49.58           C
ATOM   1203  CB  ASP A 184      -6.930  28.462   5.372  0.00 50.08           C
ATOM   1204  CG  ASP A 184      -7.433  29.660   6.208  0.00 51.66           C
ATOM   1205  OD1 ASP A 184      -8.633  29.689   6.568  0.00 53.49           O
ATOM   1206  OD2 ASP A 184      -6.622  30.579   6.494  0.00 52.49           O
ATOM   1207  C   ASP A 184      -6.511  25.984   5.396  0.00 49.42           C
ATOM   1208  O   ASP A 184      -6.963  24.936   4.936  0.00 49.67           O
ATOM   1209  N   PRO A 190       2.774  20.708   4.759  1.00 38.16           N
ATOM   1210  CA  PRO A 190       2.509  19.429   5.422  1.00 37.54           C
ATOM   1211  CB  PRO A 190       3.634  19.334   6.465  1.00 37.24           C
ATOM   1212  CG  PRO A 190       4.173  20.715   6.597  1.00 38.28           C
ATOM   1213  CD  PRO A 190       4.042  21.296   5.219  1.00 38.96           C
ATOM   1214  C   PRO A 190       1.140  19.407   6.111  1.00 36.69           C
ATOM   1215  O   PRO A 190       0.556  20.468   6.369  1.00 37.55           O
ATOM   1216  N   ASP A 191       0.633  18.207   6.389  1.00 34.84           N
ATOM   1217  CA  ASP A 191      -0.569  18.039   7.202  1.00 32.43           C
ATOM   1218  CB  ASP A 191      -1.196  16.680   6.886  1.00 33.05           C
ATOM   1219  CG  ASP A 191      -2.546  16.489   7.539  1.00 35.52           C
ATOM   1220  OD1 ASP A 191      -3.225  17.507   7.856  1.00 39.49           O
ATOM   1221  OD2 ASP A 191      -2.928  15.314   7.733  1.00 34.93           O
ATOM   1222  C   ASP A 191      -0.130  18.129   8.676  1.00 30.03           C
ATOM   1223  O   ASP A 191       0.054  17.112   9.344  1.00 28.41           O
ATOM   1224  N   LEU A 192       0.070  19.366   9.151  1.00 27.44           N
ATOM   1225  CA  LEU A 192       0.810  19.616  10.395  1.00 25.04           C
ATOM   1226  CB  LEU A 192       2.308  19.848  10.100  1.00 24.97           C
ATOM   1227  CG  LEU A 192       3.244  20.340  11.224  1.00 25.69           C
ATOM   1228  CD1 LEU A 192       3.442  19.276  12.316  1.00 22.18           C
ATOM   1229  CD2 LEU A 192       4.551  20.757  10.662  1.00 22.70           C
ATOM   1230  C   LEU A 192       0.218  20.791  11.149  1.00 24.40           C
ATOM   1231  O   LEU A 192       0.058  21.899  10.588  1.00 24.74           O
ATOM   1232  N   SER A 193      -0.138  20.553  12.414  1.00 22.65           N
ATOM   1233  CA  SER A 193      -0.643  21.629  13.267  1.00 20.42           C
ATOM   1234  CB  SER A 193      -2.159  21.592  13.318  1.00 20.18           C
ATOM   1235  OG  SER A 193      -2.648  22.841  13.761  1.00 19.09           O
ATOM   1236  C   SER A 193      -0.016  21.583  14.684  1.00 19.62           C
ATOM   1237  O   SER A 193       1.070  21.038  14.860  1.00 20.34           O
ATOM   1238  N   LEU A 194      -0.707  22.161  15.667  1.00 17.91           N
ATOM   1239  CA  LEU A 194      -0.189  22.369  17.018  1.00 16.50           C
ATOM   1240  CB  LEU A 194      -0.054  23.873  17.324  1.00 15.96           C
ATOM   1241  CG  LEU A 194       0.633  24.330  18.626  1.00 16.92           C
ATOM   1242  CD1 LEU A 194       2.095  23.796  18.706  1.00 13.44           C
ATOM   1243  CD2 LEU A 194       0.558  25.854  18.893  1.00 14.97           C
ATOM   1244  C   LEU A 194      -1.073  21.727  18.089  1.00 16.82           C
ATOM   1245  O   LEU A 194      -2.303  21.849  18.066  1.00 15.90           O
ATOM   1246  N   GLN A 195      -0.423  21.119  19.086  1.00 15.91           N
ATOM   1247  CA  GLN A 195      -1.136  20.594  20.243  1.00 15.30           C
ATOM   1248  CB  GLN A 195      -1.121  19.071  20.203  1.00 14.61           C
ATOM   1249  CG  GLN A 195      -2.004  18.441  21.236  1.00 16.81           C
ATOM   1250  CD  GLN A 195      -2.156  16.959  21.024  1.00 17.97           C
ATOM   1251  OE1 GLN A 195      -3.244  16.470  20.691  1.00 23.01           O
ATOM   1252  NE2 GLN A 195      -1.089  16.241  21.219  1.00 14.72           N
ATOM   1253  C   GLN A 195      -0.466  21.114  21.516  1.00 15.23           C
ATOM   1254  O   GLN A 195       0.763  21.265  21.558  1.00 14.56           O
ATOM   1255  N   LEU A 196      -1.271  21.402  22.534  1.00 15.08           N
ATOM   1256  CA  LEU A 196      -0.734  21.704  23.880  1.00 14.90           C
ATOM   1257  CB  LEU A 196      -1.214  23.078  24.355  1.00 15.53           C
ATOM   1258  CG  LEU A 196      -0.963  24.250  23.389  1.00 14.76           C
ATOM   1259  CD1 LEU A 196      -1.668  25.449  23.982  1.00 13.08           C
```

FIGURE 4-18 (COORDINATES)

```
ATOM   1260  CD2 LEU A 196       0.533  24.581  23.136  1.00 13.70           C
ATOM   1261  C   LEU A 196      -1.192  20.657  24.870  1.00 14.60           C
ATOM   1262  O   LEU A 196      -2.356  20.236  24.832  1.00 14.17           O
ATOM   1263  N   ILE A 197      -0.289  20.257  25.780  1.00 14.91           N
ATOM   1264  CA  ILE A 197      -0.663  19.309  26.841  1.00 14.60           C
ATOM   1265  CB  ILE A 197      -0.060  17.891  26.607  1.00 15.21           C
ATOM   1266  CG1 ILE A 197      -0.537  17.329  25.261  1.00 15.30           C
ATOM   1267  CD1 ILE A 197       0.194  15.998  24.811  1.00 15.89           C
ATOM   1268  CG2 ILE A 197      -0.456  16.917  27.778  1.00 13.24           C
ATOM   1269  C   ILE A 197      -0.296  19.841  28.217  1.00 13.71           C
ATOM   1270  O   ILE A 197       0.828  20.246  28.438  1.00 14.19           O
ATOM   1271  N   PHE A 198      -1.275  19.895  29.119  1.00 13.56           N
ATOM   1272  CA  PHE A 198      -1.037  20.301  30.498  1.00 13.95           C
ATOM   1273  CB  PHE A 198      -2.014  21.419  30.935  1.00 12.49           C
ATOM   1274  CG  PHE A 198      -1.997  22.626  30.013  1.00 14.60           C
ATOM   1275  CD1 PHE A 198      -1.326  23.799  30.394  1.00 11.41           C
ATOM   1276  CE1 PHE A 198      -1.296  24.941  29.562  1.00 13.55           C
ATOM   1277  CZ  PHE A 198      -1.921  24.901  28.306  1.00 12.39           C
ATOM   1278  CE2 PHE A 198      -2.584  23.734  27.888  1.00 15.33           C
ATOM   1279  CD2 PHE A 198      -2.637  22.587  28.761  1.00 10.77           C
ATOM   1280  C   PHE A 198      -1.222  19.032  31.297  1.00 13.96           C
ATOM   1281  O   PHE A 198      -2.356  18.612  31.568  1.00 14.69           O
ATOM   1282  N   PHE A 199      -0.101  18.396  31.644  1.00 14.16           N
ATOM   1283  CA  PHE A 199      -0.151  17.166  32.419  1.00 14.16           C
ATOM   1284  CB  PHE A 199       1.216  16.467  32.411  1.00 13.28           C
ATOM   1285  CG  PHE A 199       1.623  15.934  31.075  1.00 13.43           C
ATOM   1286  CD1 PHE A 199       1.002  14.803  30.552  1.00 14.07           C
ATOM   1287  CE1 PHE A 199       1.383  14.282  29.318  1.00 14.94           C
ATOM   1288  CZ  PHE A 199       2.414  14.861  28.607  1.00 12.67           C
ATOM   1289  CE2 PHE A 199       3.067  16.010  29.117  1.00 12.79           C
ATOM   1290  CD2 PHE A 199       2.664  16.532  30.362  1.00 11.67           C
ATOM   1291  C   PHE A 199      -0.564  17.447  33.857  1.00 14.47           C
ATOM   1292  O   PHE A 199      -0.120  18.448  34.481  1.00 13.59           O
ATOM   1293  N   ASP A 200      -1.364  16.519  34.391  1.00 15.76           N
ATOM   1294  CA  ASP A 200      -1.676  16.453  35.822  1.00 15.90           C
ATOM   1295  CB  ASP A 200      -3.145  16.106  36.052  1.00 15.61           C
ATOM   1296  CG  ASP A 200      -3.634  16.449  37.460  1.00 16.89           C
ATOM   1297  OD1 ASP A 200      -2.882  17.024  38.274  1.00 13.71           O
ATOM   1298  OD2 ASP A 200      -4.835  16.184  37.743  1.00 18.50           O
ATOM   1299  C   ASP A 200      -0.796  15.375  36.423  1.00 16.48           C
ATOM   1300  O   ASP A 200      -0.222  14.581  35.680  1.00 16.91           O
ATOM   1301  N   GLY A 201      -0.679  15.372  37.753  1.00 17.02           N
ATOM   1302  CA  GLY A 201       0.134  14.379  38.488  1.00 17.27           C
ATOM   1303  C   GLY A 201       1.545  14.067  38.024  1.00 17.86           C
ATOM   1304  O   GLY A 201       1.958  12.898  38.016  1.00 18.58           O
ATOM   1305  N   GLU A 202       2.314  15.090  37.643  1.00 17.85           N
ATOM   1306  CA  GLU A 202       3.732  14.899  37.368  1.00 16.90           C
ATOM   1307  CB  GLU A 202       4.337  16.159  36.721  1.00 16.91           C
ATOM   1308  CG  GLU A 202       5.792  16.071  36.233  1.00 15.58           C
ATOM   1309  CD  GLU A 202       6.857  16.457  37.263  1.00 19.38           C
ATOM   1310  OE1 GLU A 202       6.499  16.709  38.419  1.00 16.93           O
ATOM   1311  OE2 GLU A 202       8.088  16.521  36.905  1.00 18.52           O
ATOM   1312  C   GLU A 202       4.471  14.544  38.666  1.00 16.87           C
ATOM   1313  O   GLU A 202       5.347  13.672  38.684  1.00 15.59           O
ATOM   1314  N   GLU A 203       4.089  15.237  39.740  1.00 16.75           N
ATOM   1315  CA  GLU A 203       4.776  15.158  41.015  1.00 16.29           C
ATOM   1316  CB  GLU A 203       4.498  16.423  41.848  1.00 15.68           C
ATOM   1317  CG  GLU A 203       4.921  17.779  41.155  1.00 14.71           C
ATOM   1318  CD  GLU A 203       6.410  18.096  41.258  1.00 12.03           C
ATOM   1319  OE1 GLU A 203       7.236  17.252  41.692  1.00 14.02           O
ATOM   1320  OE2 GLU A 203       6.794  19.214  40.914  1.00 12.25           O
ATOM   1321  C   GLU A 203       4.435  13.900  41.815  1.00 17.52           C
ATOM   1322  O   GLU A 203       3.291  13.400  41.819  1.00 16.81           O
ATOM   1323  N   ALA A 204       5.459  13.390  42.498  1.00 19.24           N
ATOM   1324  CA  ALA A 204       5.285  12.386  43.549  1.00 19.52           C
ATOM   1325  CB  ALA A 204       6.648  12.001  44.096  1.00 19.28           C
ATOM   1326  C   ALA A 204       4.400  12.895  44.684  1.00 20.67           C
ATOM   1327  O   ALA A 204       4.485  14.062  45.095  1.00 21.10           O
ATOM   1328  N   PHE A 205       3.553  12.013  45.199  1.00 21.42           N
ATOM   1329  CA  PHE A 205       2.797  12.305  46.418  1.00 23.25           C
```

FIGURE 4-19 (COORDINATES)

```
ATOM   1330  CB   PHE A 205       1.562  11.409  46.513  1.00 22.83           C
ATOM   1331  CG   PHE A 205       0.392  11.944  45.773  1.00 23.21           C
ATOM   1332  CD1  PHE A 205       0.254  11.723  44.413  1.00 21.74           C
ATOM   1333  CE1  PHE A 205      -0.830  12.238  43.722  1.00 23.17           C
ATOM   1334  CZ   PHE A 205      -1.800  13.004  44.384  1.00 22.64           C
ATOM   1335  CE2  PHE A 205      -1.665  13.257  45.727  1.00 24.39           C
ATOM   1336  CD2  PHE A 205      -0.560  12.728  46.428  1.00 24.32           C
ATOM   1337  C    PHE A 205       3.638  12.166  47.673  1.00 25.12           C
ATOM   1338  O    PHE A 205       3.501  12.963  48.602  1.00 24.47           O
ATOM   1339  N    HIS A 206       4.495  11.146  47.707  1.00 27.43           N
ATOM   1340  CA   HIS A 206       5.376  10.954  48.851  1.00 31.20           C
ATOM   1341  CB   HIS A 206       5.035   9.689  49.649  1.00 32.65           C
ATOM   1342  CG   HIS A 206       5.804   9.586  50.932  1.00 37.53           C
ATOM   1343  ND1  HIS A 206       6.838   8.687  51.117  1.00 42.40           N
ATOM   1344  CE1  HIS A 206       7.346   8.848  52.329  1.00 42.98           C
ATOM   1345  NE2  HIS A 206       6.685   9.824  52.932  1.00 43.46           N
ATOM   1346  CD2  HIS A 206       5.725  10.309  52.076  1.00 41.44           C
ATOM   1347  C    HIS A 206       6.872  11.010  48.516  1.00 31.65           C
ATOM   1348  O    HIS A 206       7.545  11.945  48.930  1.00 33.22           O
ATOM   1349  N    HIS A 207       7.383  10.048  47.756  1.00 31.74           N
ATOM   1350  CA   HIS A 207       8.817  10.024  47.395  1.00 31.56           C
ATOM   1351  CB   HIS A 207       9.588   9.004  48.261  1.00 31.25           C
ATOM   1352  CG   HIS A 207      10.068  10.346  49.481  0.00 42.40           C
ATOM   1353  ND1  HIS A 207      10.645  11.594  49.330  0.00 45.96           N
ATOM   1354  CE1  HIS A 207      10.791  12.159  50.516  0.00 46.94           C
ATOM   1355  NE2  HIS A 207      10.317  11.331  51.431  0.00 47.77           N
ATOM   1356  CD2  HIS A 207       9.850  10.194  50.811  0.00 45.77           C
ATOM   1357  C    HIS A 207       8.942   9.672  45.920  1.00 30.55           C
ATOM   1358  O    HIS A 207       8.344   8.693  45.474  1.00 29.90           O
ATOM   1359  N    TRP A 208       9.689  10.482  45.169  1.00 30.50           N
ATOM   1360  CA   TRP A 208       9.781  10.302  43.715  1.00 30.32           C
ATOM   1361  CB   TRP A 208      10.707  11.340  43.067  1.00 29.83           C
ATOM   1362  CG   TRP A 208      10.747  11.274  41.536  1.00 29.90           C
ATOM   1363  CD1  TRP A 208      11.509  10.427  40.752  1.00 29.83           C
ATOM   1364  NE1  TRP A 208      11.246  10.658  39.411  1.00 30.27           N
ATOM   1365  CE2  TRP A 208      10.315  11.668  39.311  1.00 29.29           C
ATOM   1366  CD2  TRP A 208       9.985  12.084  40.624  1.00 29.26           C
ATOM   1367  CE3  TRP A 208       9.059  13.127  40.792  1.00 29.18           C
ATOM   1368  CZ3  TRP A 208       8.491  13.716  39.645  1.00 28.98           C
ATOM   1369  CH2  TRP A 208       8.846  13.279  38.358  1.00 29.09           C
ATOM   1370  CZ2  TRP A 208       9.753  12.268  38.169  1.00 28.17           C
ATOM   1371  C    TRP A 208      10.256   8.882  43.437  1.00 30.75           C
ATOM   1372  O    TRP A 208      11.259   8.427  43.999  1.00 30.50           O
ATOM   1373  N    SER A 209       9.503   8.178  42.599  1.00 30.78           N
ATOM   1374  CA   SER A 209       9.811   6.805  42.206  1.00 31.09           C
ATOM   1375  CB   SER A 209       9.396   5.824  43.315  1.00 30.83           C
ATOM   1376  OG   SER A 209       8.050   5.437  43.166  1.00 28.26           O
ATOM   1377  C    SER A 209       9.026   6.525  40.928  1.00 31.52           C
ATOM   1378  O    SER A 209       8.165   7.325  40.572  1.00 31.31           O
ATOM   1379  N    PRO A 210       9.308   5.394  40.227  1.00 31.76           N
ATOM   1380  CA   PRO A 210       8.529   5.091  39.005  1.00 30.72           C
ATOM   1381  CB   PRO A 210       9.149   3.774  38.501  1.00 31.38           C
ATOM   1382  CG   PRO A 210      10.475   3.683  39.143  1.00 31.18           C
ATOM   1383  CD   PRO A 210      10.362   4.379  40.467  1.00 32.20           C
ATOM   1384  C    PRO A 210       7.026   4.876  39.251  1.00 29.88           C
ATOM   1385  O    PRO A 210       6.217   5.129  38.376  1.00 29.31           O
ATOM   1386  N    GLN A 211       6.680   4.388  40.434  1.00 28.21           N
ATOM   1387  CA   GLN A 211       5.296   4.163  40.808  1.00 27.38           C
ATOM   1388  CB   GLN A 211       4.909   3.053  41.769  0.00 30.97           C
ATOM   1389  CG   GLN A 211       5.331   1.659  41.291  0.00 34.90           C
ATOM   1390  CD   GLN A 211       6.731   1.320  41.770  0.00 42.72           C
ATOM   1391  OE1  GLN A 211       7.027   1.449  42.972  0.00 45.24           O
ATOM   1392  NE2  GLN A 211       7.612   0.914  40.841  0.00 45.31           N
ATOM   1393  C    GLN A 211       4.649   5.434  41.346  1.00 25.76           C
ATOM   1394  O    GLN A 211       3.420   5.567  41.293  1.00 25.83           O
ATOM   1395  N    ASP A 212       5.463   6.350  41.872  1.00 23.70           N
ATOM   1396  CA   ASP A 212       4.935   7.568  42.477  1.00 23.44           C
ATOM   1397  CB   ASP A 212       5.242   7.610  43.989  1.00 22.97           C
ATOM   1398  CG   ASP A 212       4.546   8.789  44.718  1.00 21.78           C
ATOM   1399  OD1  ASP A 212       3.546   9.370  44.221  1.00 18.49           O
```

FIGURE 4-20 (COORDINATES)

```
ATOM   1400  OD2 ASP A 212       4.997   9.126  45.816  1.00 22.42           O
ATOM   1401  C   ASP A 212       5.526   8.772  41.753  1.00 22.97           C
ATOM   1402  O   ASP A 212       6.412   9.455  42.281  1.00 24.40           O
ATOM   1403  N   SER A 213       5.055   8.998  40.523  1.00 21.68           N
ATOM   1404  CA  SER A 213       5.411  10.174  39.713  1.00 19.51           C
ATOM   1405  CB  SER A 213       6.929  10.329  39.575  1.00 18.96           C
ATOM   1406  OG  SER A 213       7.477   9.226  38.876  1.00 18.88           O
ATOM   1407  C   SER A 213       4.767  10.014  38.351  1.00 18.59           C
ATOM   1408  O   SER A 213       4.340   8.911  38.008  1.00 19.11           O
ATOM   1409  N   LEU A 214       4.603  11.113  37.609  1.00 16.40           N
ATOM   1410  CA  LEU A 214       4.244  11.033  36.192  1.00 15.80           C
ATOM   1411  CB  LEU A 214       5.358  10.418  35.307  1.00 15.44           C
ATOM   1412  CG  LEU A 214       6.810  10.804  35.528  1.00 16.78           C
ATOM   1413  CD1 LEU A 214       7.674  10.061  34.565  1.00 17.04           C
ATOM   1414  CD2 LEU A 214       6.920  12.367  35.370  1.00 14.82           C
ATOM   1415  C   LEU A 214       2.938  10.295  35.931  1.00 15.71           C
ATOM   1416  O   LEU A 214       2.802   9.595  34.930  1.00 15.43           O
ATOM   1417  N   TYR A 215       1.995  10.432  36.855  1.00 16.13           N
ATOM   1418  CA  TYR A 215       0.697   9.769  36.735  1.00 16.61           C
ATOM   1419  CB  TYR A 215      -0.165  10.156  37.932  1.00 17.26           C
ATOM   1420  CG  TYR A 215       0.318   9.620  39.274  1.00 17.79           C
ATOM   1421  CD1 TYR A 215      -0.095   8.346  39.732  1.00 20.44           C
ATOM   1422  CE1 TYR A 215       0.321   7.846  40.969  1.00 20.90           C
ATOM   1423  CZ  TYR A 215       1.156   8.614  41.773  1.00 20.54           C
ATOM   1424  OH  TYR A 215       1.563   8.134  42.998  1.00 19.14           O
ATOM   1425  CE2 TYR A 215       1.577   9.892  41.345  1.00 20.34           C
ATOM   1426  CD2 TYR A 215       1.142  10.377  40.090  1.00 20.00           C
ATOM   1427  C   TYR A 215      -0.005  10.160  35.427  1.00 16.34           C
ATOM   1428  O   TYR A 215      -0.502   9.293  34.692  1.00 16.36           O
ATOM   1429  N   GLY A 216      -0.030  11.471  35.144  1.00 16.48           N
ATOM   1430  CA  GLY A 216      -0.722  12.039  33.981  1.00 15.04           C
ATOM   1431  C   GLY A 216      -0.099  11.611  32.684  1.00 15.01           C
ATOM   1432  O   GLY A 216      -0.788  11.089  31.832  1.00 15.56           O
ATOM   1433  N   SER A 217       1.223  11.776  32.556  1.00 15.00           N
ATOM   1434  CA  SER A 217       1.945  11.442  31.331  1.00 15.29           C
ATOM   1435  CB  SER A 217       3.356  12.028  31.315  1.00 14.81           C
ATOM   1436  OG  SER A 217       4.000  11.785  32.545  1.00 15.63           O
ATOM   1437  C   SER A 217       2.037   9.962  31.082  1.00 15.42           C
ATOM   1438  O   SER A 217       2.051   9.556  29.913  1.00 14.88           O
ATOM   1439  N   ARG A 218       2.119   9.146  32.145  1.00 16.17           N
ATOM   1440  CA  ARG A 218       2.101   7.672  31.928  1.00 16.79           C
ATOM   1441  CB  ARG A 218       2.425   6.894  33.208  1.00 17.07           C
ATOM   1442  CG  ARG A 218       3.950   6.768  33.495  1.00 17.45           C
ATOM   1443  CD  ARG A 218       4.290   5.976  34.771  1.00 19.07           C
ATOM   1444  NE  ARG A 218       3.824   6.597  36.032  1.00 21.40           N
ATOM   1445  CZ  ARG A 218       2.837   6.106  36.777  1.00 20.21           C
ATOM   1446  NH1 ARG A 218       2.193   5.003  36.382  1.00 23.09           N
ATOM   1447  NH2 ARG A 218       2.481   6.696  37.909  1.00 17.11           N
ATOM   1448  C   ARG A 218       0.741   7.249  31.343  1.00 17.15           C
ATOM   1449  O   ARG A 218       0.664   6.445  30.411  1.00 16.78           O
ATOM   1450  N   HIS A 219      -0.322   7.835  31.873  1.00 17.53           N
ATOM   1451  CA  HIS A 219      -1.658   7.510  31.438  1.00 18.81           C
ATOM   1452  CB  HIS A 219      -2.684   8.152  32.355  1.00 18.70           C
ATOM   1453  CG  HIS A 219      -4.082   7.720  32.046  1.00 21.75           C
ATOM   1454  ND1 HIS A 219      -4.940   8.468  31.270  1.00 23.53           N
ATOM   1455  CE1 HIS A 219      -6.089   7.825  31.149  1.00 23.51           C
ATOM   1456  NE2 HIS A 219      -6.000   6.682  31.806  1.00 24.88           N
ATOM   1457  CD2 HIS A 219      -4.750   6.581  32.360  1.00 22.03           C
ATOM   1458  C   HIS A 219      -1.961   7.920  30.005  1.00 19.57           C
ATOM   1459  O   HIS A 219      -2.585   7.160  29.235  1.00 18.90           O
ATOM   1460  N   LEU A 220      -1.577   9.155  29.665  1.00 19.39           N
ATOM   1461  CA  LEU A 220      -1.787   9.704  28.342  1.00 18.42           C
ATOM   1462  CB  LEU A 220      -1.634  11.246  28.355  1.00 19.08           C
ATOM   1463  CG  LEU A 220      -2.111  11.999  27.072  1.00 18.76           C
ATOM   1464  CD1 LEU A 220      -3.607  11.751  26.754  1.00 17.92           C
ATOM   1465  CD2 LEU A 220      -1.819  13.522  27.124  1.00 17.96           C
ATOM   1466  C   LEU A 220      -0.938   9.063  27.240  1.00 19.09           C
ATOM   1467  O   LEU A 220      -1.446   8.814  26.116  1.00 18.60           O
ATOM   1468  N   ALA A 221       0.347   8.827  27.506  1.00 19.50           N
ATOM   1469  CA  ALA A 221       1.177   8.090  26.567  1.00 20.53           C
```

FIGURE 4-21 (COORDINATES)

```
ATOM   1470  CB  ALA A 221       2.597   7.865  27.142  1.00 21.27           C
ATOM   1471  C   ALA A 221       0.513   6.741  26.251  1.00 22.41           C
ATOM   1472  O   ALA A 221       0.518   6.263  25.099  1.00 22.73           O
ATOM   1473  N   GLN A 222      -0.059   6.136  27.282  1.00 24.07           N
ATOM   1474  CA  GLN A 222      -0.694   4.826  27.167  1.00 26.24           C
ATOM   1475  CB  GLN A 222      -1.002   4.298  28.563  1.00 25.89           C
ATOM   1476  CG  GLN A 222      -1.944   3.124  28.599  1.00 30.17           C
ATOM   1477  CD  GLN A 222      -1.205   1.841  28.519  1.00 35.20           C
ATOM   1478  OE1 GLN A 222      -0.711   1.459  27.437  1.00 38.18           O
ATOM   1479  NE2 GLN A 222      -1.083   1.156  29.664  1.00 32.04           N
ATOM   1480  C   GLN A 222      -1.972   4.925  26.310  1.00 26.56           C
ATOM   1481  O   GLN A 222      -2.167   4.138  25.377  1.00 27.34           O
ATOM   1482  N   LYS A 223      -2.809   5.907  26.633  1.00 27.14           N
ATOM   1483  CA  LYS A 223      -4.044   6.208  25.929  1.00 28.20           C
ATOM   1484  CB  LYS A 223      -4.810   7.328  26.653  1.00 28.49           C
ATOM   1485  CG  LYS A 223      -6.256   7.571  26.176  1.00 28.26           C
ATOM   1486  CD  LYS A 223      -6.928   8.661  27.000  1.00 29.03           C
ATOM   1487  CE  LYS A 223      -8.209   8.917  26.489  0.00 37.06           C
ATOM   1488  NZ  LYS A 223      -8.954   9.770  27.461  0.00 38.88           N
ATOM   1489  C   LYS A 223      -3.795   6.560  24.465  1.00 28.75           C
ATOM   1490  O   LYS A 223      -4.500   6.065  23.594  1.00 29.01           O
ATOM   1491  N   MET A 224      -2.792   7.398  24.191  1.00 29.07           N
ATOM   1492  CA  MET A 224      -2.410   7.735  22.817  1.00 28.91           C
ATOM   1493  CB  MET A 224      -1.430   8.913  22.794  1.00 28.44           C
ATOM   1494  CG  MET A 224      -2.043  10.227  23.303  1.00 26.60           C
ATOM   1495  SD  MET A 224      -0.887  11.610  23.069  1.00 24.68           S
ATOM   1496  CE  MET A 224      -1.966  12.993  23.483  1.00 28.20           C
ATOM   1497  C   MET A 224      -1.845   6.545  22.014  1.00 31.16           C
ATOM   1498  O   MET A 224      -2.068   6.451  20.800  1.00 31.11           O
ATOM   1499  N   ALA A 225      -1.121   5.651  22.686  1.00 32.81           N
ATOM   1500  CA  ALA A 225      -0.576   4.449  22.041  1.00 35.05           C
ATOM   1501  CB  ALA A 225       0.370   3.716  22.991  1.00 34.80           C
ATOM   1502  C   ALA A 225      -1.666   3.497  21.548  1.00 35.98           C
ATOM   1503  O   ALA A 225      -1.414   2.669  20.696  1.00 37.08           O
ATOM   1504  N   SER A 226      -2.865   3.641  22.103  1.00 37.50           N
ATOM   1505  CA  SER A 226      -4.005   2.763  21.872  1.00 38.65           C
ATOM   1506  CB  SER A 226      -4.415   2.105  23.201  1.00 38.71           C
ATOM   1507  OG  SER A 226      -3.259   1.625  23.915  1.00 39.74           O
ATOM   1508  C   SER A 226      -5.168   3.581  21.274  1.00 39.76           C
ATOM   1509  O   SER A 226      -6.367   3.288  21.488  1.00 41.02           O
ATOM   1510  N   SER A 227      -4.813   4.638  20.548  1.00 39.84           N
ATOM   1511  CA  SER A 227      -5.797   5.448  19.849  1.00 39.69           C
ATOM   1512  CB  SER A 227      -5.911   6.833  20.478  1.00 39.98           C
ATOM   1513  OG  SER A 227      -6.298   6.753  21.830  1.00 39.24           O
ATOM   1514  C   SER A 227      -5.295   5.578  18.424  1.00 39.72           C
ATOM   1515  O   SER A 227      -4.375   6.341  18.188  1.00 39.89           O
ATOM   1516  N   PRO A 228      -5.868   4.801  17.470  1.00 39.36           N
ATOM   1517  CA  PRO A 228      -5.415   4.928  16.071  1.00 38.34           C
ATOM   1518  CB  PRO A 228      -6.300   3.918  15.313  1.00 38.97           C
ATOM   1519  CG  PRO A 228      -7.494   3.661  16.224  1.00 39.25           C
ATOM   1520  CD  PRO A 228      -6.941   3.791  17.618  1.00 40.07           C
ATOM   1521  C   PRO A 228      -5.561   6.366  15.502  1.00 37.08           C
ATOM   1522  O   PRO A 228      -6.505   7.108  15.812  1.00 35.64           O
ATOM   1523  N   HIS A 229      -4.597   6.747  14.687  1.00 36.43           N
ATOM   1524  CA  HIS A 229      -4.557   8.073  14.130  1.00 35.79           C
ATOM   1525  CB  HIS A 229      -3.878   9.048  15.103  1.00 35.82           C
ATOM   1526  CG  HIS A 229      -3.913  10.464  14.637  1.00 33.56           C
ATOM   1527  ND1 HIS A 229      -5.023  11.265  14.780  1.00 31.09           N
ATOM   1528  CE1 HIS A 229      -4.779  12.448  14.247  1.00 31.45           C
ATOM   1529  NE2 HIS A 229      -3.550  12.440  13.763  1.00 30.49           N
ATOM   1530  CD2 HIS A 229      -2.984  11.213  14.002  1.00 32.95           C
ATOM   1531  C   HIS A 229      -3.764   7.994  12.859  1.00 36.10           C
ATOM   1532  O   HIS A 229      -2.683   7.420  12.865  1.00 36.54           O
ATOM   1533  N   PRO A 230      -4.289   8.545  11.754  1.00 36.66           N
ATOM   1534  CA  PRO A 230      -5.622   9.153  11.602  1.00 37.64           C
ATOM   1535  CB  PRO A 230      -5.698   9.476  10.108  1.00 37.86           C
ATOM   1536  CG  PRO A 230      -4.262   9.576   9.659  1.00 37.39           C
ATOM   1537  CD  PRO A 230      -3.488   8.627  10.517  1.00 36.44           C
ATOM   1538  C   PRO A 230      -6.750   8.203  12.003  1.00 38.60           C
ATOM   1539  O   PRO A 230      -6.591   6.994  11.855  1.00 38.48           O
```

FIGURE 4-22 (COORDINATES)

```
ATOM   1540  N    PRO A 231      -7.877   8.747  12.515  1.00 39.50           N
ATOM   1541  CA   PRO A 231      -8.964   7.943  13.107  1.00 39.91           C
ATOM   1542  CB   PRO A 231      -9.886   9.000  13.726  1.00 40.02           C
ATOM   1543  CG   PRO A 231      -9.659  10.226  12.888  1.00 39.66           C
ATOM   1544  CD   PRO A 231      -8.193  10.192  12.538  1.00 39.67           C
ATOM   1545  C    PRO A 231      -9.753   7.123  12.082  1.00 40.71           C
ATOM   1546  O    PRO A 231      -9.198   6.218  11.451  1.00 41.29           O
ATOM   1547  N    GLY A 232      -9.356   5.439  12.238  0.00 43.14           N
ATOM   1548  CA   GLY A 232      -9.666   4.347  11.295  0.00 43.33           C
ATOM   1549  C    GLY A 232      -8.461   3.891  10.489  0.00 43.48           C
ATOM   1550  O    GLY A 232      -8.562   2.996   9.633  0.00 43.36           O
ATOM   1551  N    SER A 233      -7.553   4.347  10.517  1.00 41.98           N
ATOM   1552  CA   SER A 233      -6.166   3.934  10.324  1.00 41.65           C
ATOM   1553  CB   SER A 233      -5.204   4.990  10.882  1.00 41.90           C
ATOM   1554  OG   SER A 233      -4.067   5.135  10.048  1.00 42.50           O
ATOM   1555  C    SER A 233      -5.985   2.620  11.070  1.00 41.34           C
ATOM   1556  O    SER A 233      -6.624   2.413  12.115  1.00 41.43           O
ATOM   1557  N    ARG A 234      -5.123   1.739  10.554  1.00 40.02           N
ATOM   1558  CA   ARG A 234      -4.972   0.394  11.149  1.00 38.65           C
ATOM   1559  CB   ARG A 234      -4.874  -0.681  10.065  1.00 38.93           C
ATOM   1560  CG   ARG A 234      -6.056  -1.633  10.051  1.00 39.92           C
ATOM   1561  CD   ARG A 234      -7.275  -1.092   9.383  1.00 38.40           C
ATOM   1562  NE   ARG A 234      -7.865  -2.151   8.577  1.00 39.94           N
ATOM   1563  CZ   ARG A 234      -9.001  -2.777   8.865  1.00 40.22           C
ATOM   1564  NH1  ARG A 234      -9.710  -2.426   9.943  1.00 40.24           N
ATOM   1565  NH2  ARG A 234      -9.438  -3.737   8.057  1.00 35.46           N
ATOM   1566  C    ARG A 234      -3.827   0.216  12.135  1.00 37.48           C
ATOM   1567  O    ARG A 234      -4.031  -0.325  13.234  1.00 36.84           O
ATOM   1568  N    GLY A 235      -2.640   0.656  11.721  1.00 35.92           N
ATOM   1569  CA   GLY A 235      -1.403   0.417  12.459  1.00 35.30           C
ATOM   1570  C    GLY A 235      -0.697   1.640  13.027  1.00 34.76           C
ATOM   1571  O    GLY A 235       0.434   1.526  13.507  1.00 35.12           O
ATOM   1572  N    THR A 236      -1.350   2.804  12.966  1.00 34.00           N
ATOM   1573  CA   THR A 236      -0.749   4.064  13.439  1.00 32.87           C
ATOM   1574  CB   THR A 236      -0.489   5.111  12.312  1.00 32.90           C
ATOM   1575  OG1  THR A 236      -1.714   5.429  11.639  1.00 31.98           O
ATOM   1576  CG2  THR A 236       0.541   4.610  11.320  1.00 32.91           C
ATOM   1577  C    THR A 236      -1.604   4.678  14.528  1.00 32.14           C
ATOM   1578  O    THR A 236      -2.836   4.580  14.488  1.00 32.06           O
ATOM   1579  N    ASN A 237      -0.941   5.287  15.517  1.00 30.76           N
ATOM   1580  CA   ASN A 237      -1.651   5.851  16.657  1.00 29.59           C
ATOM   1581  CB   ASN A 237      -1.287   5.084  17.943  1.00 29.36           C
ATOM   1582  CG   ASN A 237       0.212   4.915  18.106  1.00 31.38           C
ATOM   1583  OD1  ASN A 237       0.980   5.831  17.821  1.00 30.91           O
ATOM   1584  ND2  ASN A 237       0.639   3.733  18.566  1.00 32.92           N
ATOM   1585  C    ASN A 237      -1.343   7.348  16.796  1.00 28.29           C
ATOM   1586  O    ASN A 237      -0.610   7.919  15.999  1.00 27.87           O
ATOM   1587  N    GLN A 238      -1.899   7.955  17.826  1.00 27.53           N
ATOM   1588  CA   GLN A 238      -1.618   9.358  18.163  1.00 27.01           C
ATOM   1589  CB   GLN A 238      -2.549   9.822  19.262  1.00 26.51           C
ATOM   1590  CG   GLN A 238      -3.997   9.863  18.783  1.00 28.00           C
ATOM   1591  CD   GLN A 238      -4.960  10.276  19.867  1.00 30.16           C
ATOM   1592  OE1  GLN A 238      -4.611  10.308  21.056  1.00 32.71           O
ATOM   1593  NE2  GLN A 238      -6.185  10.597  19.476  1.00 28.91           N
ATOM   1594  C    GLN A 238      -0.160   9.638  18.492  1.00 27.01           C
ATOM   1595  O    GLN A 238       0.315  10.730  18.234  1.00 26.62           O
ATOM   1596  N    LEU A 239       0.568   8.638  18.993  1.00 26.74           N
ATOM   1597  CA   LEU A 239       2.005   8.775  19.243  1.00 26.70           C
ATOM   1598  CB   LEU A 239       2.531   7.609  20.089  1.00 26.52           C
ATOM   1599  CG   LEU A 239       1.988   7.485  21.519  1.00 26.53           C
ATOM   1600  CD1  LEU A 239       2.663   6.317  22.213  1.00 27.19           C
ATOM   1601  CD2  LEU A 239       2.270   8.789  22.295  1.00 26.92           C
ATOM   1602  C    LEU A 239       2.831   8.954  17.971  1.00 26.85           C
ATOM   1603  O    LEU A 239       3.797   9.725  17.953  1.00 26.72           O
ATOM   1604  N    ASP A 240       2.447   8.229  16.912  1.00 27.05           N
ATOM   1605  CA   ASP A 240       3.029   8.380  15.594  1.00 26.25           C
ATOM   1606  CB   ASP A 240       2.392   7.386  14.615  1.00 27.48           C
ATOM   1607  CG   ASP A 240       2.833   5.948  14.864  1.00 28.60           C
ATOM   1608  OD1  ASP A 240       4.061   5.679  14.844  1.00 27.78           O
ATOM   1609  OD2  ASP A 240       1.927   5.126  15.095  1.00 28.42           O
```

FIGURE 4-23 (COORDINATES)

```
ATOM   1610  C   ASP A 240      2.761   9.765  15.062  1.00 25.68           C
ATOM   1611  O   ASP A 240      3.527  10.276  14.268  1.00 25.70           O
ATOM   1612  N   GLY A 241      1.642  10.345  15.471  1.00 25.59           N
ATOM   1613  CA  GLY A 241      1.292  11.710  15.090  1.00 25.71           C
ATOM   1614  C   GLY A 241      2.140  12.816  15.724  1.00 24.89           C
ATOM   1615  O   GLY A 241      2.199  13.943  15.211  1.00 24.53           O
ATOM   1616  N   MET A 242      2.808  12.504  16.831  1.00 24.86           N
ATOM   1617  CA  MET A 242      3.590  13.521  17.526  1.00 24.93           C
ATOM   1618  CB  MET A 242      3.814  13.167  19.004  1.00 24.72           C
ATOM   1619  CG  MET A 242      2.555  12.911  19.797  1.00 25.44           C
ATOM   1620  SD  MET A 242      2.915  12.450  21.512  1.00 27.43           S
ATOM   1621  CE  MET A 242      3.658  13.943  22.142  1.00 21.66           C
ATOM   1622  C   MET A 242      4.920  13.722  16.833  1.00 24.68           C
ATOM   1623  O   MET A 242      5.821  12.899  16.957  1.00 24.66           O
ATOM   1624  N   ASP A 243      5.043  14.838  16.119  1.00 23.98           N
ATOM   1625  CA  ASP A 243      6.277  15.180  15.445  1.00 23.21           C
ATOM   1626  CB  ASP A 243      6.101  16.496  14.722  1.00 24.01           C
ATOM   1627  CG  ASP A 243      5.925  16.308  13.267  1.00 24.10           C
ATOM   1628  OD1 ASP A 243      5.240  15.332  12.894  1.00 27.48           O
ATOM   1629  OD2 ASP A 243      6.462  17.130  12.509  1.00 21.49           O
ATOM   1630  C   ASP A 243      7.447  15.347  16.394  1.00 23.23           C
ATOM   1631  O   ASP A 243      8.560  14.878  16.127  1.00 23.13           O
ATOM   1632  N   LEU A 244      7.166  16.067  17.475  1.00 21.02           N
ATOM   1633  CA  LEU A 244      8.146  16.549  18.404  1.00 20.32           C
ATOM   1634  CB  LEU A 244      8.927  17.737  17.828  1.00 20.39           C
ATOM   1635  CG  LEU A 244     10.031  18.353  18.717  1.00 20.90           C
ATOM   1636  CD1 LEU A 244     11.187  17.375  19.100  1.00 20.47           C
ATOM   1637  CD2 LEU A 244     10.575  19.615  18.108  1.00 19.72           C
ATOM   1638  C   LEU A 244      7.326  16.986  19.611  1.00 19.75           C
ATOM   1639  O   LEU A 244      6.268  17.639  19.469  1.00 18.61           O
ATOM   1640  N   LEU A 245      7.787  16.544  20.774  1.00 17.64           N
ATOM   1641  CA  LEU A 245      7.232  16.955  22.046  1.00 17.51           C
ATOM   1642  CB  LEU A 245      6.910  15.734  22.924  1.00 17.14           C
ATOM   1643  CG  LEU A 245      6.533  15.960  24.404  1.00 19.10           C
ATOM   1644  CD1 LEU A 245      5.237  16.778  24.592  1.00 19.00           C
ATOM   1645  CD2 LEU A 245      6.513  14.639  25.214  1.00 19.61           C
ATOM   1646  C   LEU A 245      8.261  17.879  22.700  1.00 16.80           C
ATOM   1647  O   LEU A 245      9.391  17.466  23.017  1.00 15.89           O
ATOM   1648  N   VAL A 246      7.876  19.145  22.842  1.00 15.18           N
ATOM   1649  CA  VAL A 246      8.677  20.138  23.531  1.00 15.32           C
ATOM   1650  CB  VAL A 246      8.692  21.515  22.773  1.00 16.06           C
ATOM   1651  CG1 VAL A 246      9.730  22.505  23.397  1.00 16.04           C
ATOM   1652  CG2 VAL A 246      8.965  21.312  21.279  1.00 16.05           C
ATOM   1653  C   VAL A 246      8.099  20.302  24.913  1.00 14.90           C
ATOM   1654  O   VAL A 246      7.009  20.833  25.072  1.00 14.11           O
ATOM   1655  N   LEU A 247      8.851  19.847  25.911  1.00 14.70           N
ATOM   1656  CA  LEU A 247      8.401  19.867  27.290  1.00 14.43           C
ATOM   1657  CB  LEU A 247      8.664  18.493  27.951  1.00 14.56           C
ATOM   1658  CG  LEU A 247      8.251  18.397  29.443  1.00 15.20           C
ATOM   1659  CD1 LEU A 247      6.727  18.583  29.559  1.00 13.23           C
ATOM   1660  CD2 LEU A 247      8.699  17.062  30.082  1.00 12.97           C
ATOM   1661  C   LEU A 247      9.109  20.952  28.092  1.00 14.25           C
ATOM   1662  O   LEU A 247     10.316  20.885  28.297  1.00 13.48           O
ATOM   1663  N   LEU A 248      8.346  21.910  28.616  1.00 14.00           N
ATOM   1664  CA  LEU A 248      8.923  23.023  29.358  1.00 13.96           C
ATOM   1665  CB  LEU A 248      8.137  24.316  29.062  1.00 14.81           C
ATOM   1666  CG  LEU A 248      8.140  25.023  27.713  1.00 18.81           C
ATOM   1667  CD1 LEU A 248      7.244  26.290  27.842  1.00 21.49           C
ATOM   1668  CD2 LEU A 248      7.628  24.155  26.589  1.00 23.25           C
ATOM   1669  C   LEU A 248      8.788  22.722  30.833  1.00 14.18           C
ATOM   1670  O   LEU A 248      7.692  22.341  31.287  1.00 12.81           O
ATOM   1671  N   ASP A 249      9.871  22.920  31.597  1.00 12.87           N
ATOM   1672  CA  ASP A 249      9.840  22.634  33.057  1.00 14.28           C
ATOM   1673  CB  ASP A 249     10.069  21.134  33.363  1.00 14.37           C
ATOM   1674  CG  ASP A 249      9.437  20.685  34.696  1.00 13.62           C
ATOM   1675  OD1 ASP A 249      9.103  21.551  35.536  1.00 12.43           O
ATOM   1676  OD2 ASP A 249      9.279  19.452  34.913  1.00 14.78           O
ATOM   1677  C   ASP A 249     10.894  23.485  33.774  1.00 14.46           C
ATOM   1678  O   ASP A 249     11.963  23.708  33.228  1.00 15.56           O
ATOM   1679  N   LEU A 250     10.564  23.961  34.972  1.00 14.63           N
```

FIGURE 4-24 (COORDINATES)

```
ATOM   1680  CA   LEU A 250      11.500  24.697  35.829  1.00 15.56           C
ATOM   1681  CB   LEU A 250      12.675  23.790  36.301  1.00 15.19           C
ATOM   1682  CG   LEU A 250      12.270  22.445  36.951  1.00 13.36           C
ATOM   1683  CD1  LEU A 250      13.535  21.743  37.474  1.00 13.02           C
ATOM   1684  CD2  LEU A 250      11.346  22.721  38.125  1.00 13.89           C
ATOM   1685  C    LEU A 250      12.001  25.988  35.158  1.00 16.17           C
ATOM   1686  O    LEU A 250      13.214  26.276  35.133  1.00 18.04           O
ATOM   1687  N    ILE A 251      11.072  26.769  34.617  1.00 14.99           N
ATOM   1688  CA   ILE A 251      11.430  28.033  33.964  1.00 14.93           C
ATOM   1689  CB   ILE A 251      10.861  28.134  32.504  1.00 15.18           C
ATOM   1690  CG1  ILE A 251      11.485  27.025  31.610  1.00 13.88           C
ATOM   1691  CD1  ILE A 251      10.869  26.821  30.266  1.00 14.88           C
ATOM   1692  CG2  ILE A 251      11.109  29.537  31.954  1.00 14.15           C
ATOM   1693  C    ILE A 251      10.925  29.201  34.822  1.00 15.53           C
ATOM   1694  O    ILE A 251       9.803  29.171  35.315  1.00 14.63           O
ATOM   1695  N    GLY A 252      11.764  30.224  35.010  1.00 15.42           N
ATOM   1696  CA   GLY A 252      11.324  31.435  35.656  1.00 15.69           C
ATOM   1697  C    GLY A 252      12.385  32.051  36.564  1.00 17.59           C
ATOM   1698  O    GLY A 252      12.275  33.226  36.921  1.00 18.18           O
ATOM   1699  N    ALA A 253      13.375  31.261  36.975  1.00 17.90           N
ATOM   1700  CA   ALA A 253      14.542  31.814  37.699  1.00 19.48           C
ATOM   1701  CB   ALA A 253      15.290  30.717  38.479  1.00 19.21           C
ATOM   1702  C    ALA A 253      15.524  32.536  36.752  1.00 20.49           C
ATOM   1703  O    ALA A 253      15.601  32.238  35.559  1.00 19.60           O
ATOM   1704  N    ALA A 254      16.293  33.471  37.319  1.00 22.28           N
ATOM   1705  CA   ALA A 254      17.354  34.165  36.622  1.00 23.43           C
ATOM   1706  CB   ALA A 254      17.959  35.224  37.543  1.00 23.61           C
ATOM   1707  C    ALA A 254      18.431  33.170  36.133  1.00 25.65           C
ATOM   1708  O    ALA A 254      18.603  32.077  36.689  1.00 26.11           O
ATOM   1709  N    ASN A 255      19.197  33.612  35.143  1.00 27.47           N
ATOM   1710  CA   ASN A 255      19.698  32.774  34.071  1.00 29.04           C
ATOM   1711  CB   ASN A 255      20.810  33.439  33.221  1.00 31.27           C
ATOM   1712  CG   ASN A 255      20.335  34.724  32.477  1.00 33.71           C
ATOM   1713  OD1  ASN A 255      19.292  35.338  32.820  1.00 35.14           O
ATOM   1714  ND2  ASN A 255      21.143  35.167  31.496  1.00 35.61           N
ATOM   1715  C    ASN A 255      19.823  31.252  34.222  1.00 28.50           C
ATOM   1716  O    ASN A 255      20.734  30.687  34.879  1.00 28.58           O
ATOM   1717  N    PRO A 256      18.855  30.597  33.583  1.00 26.97           N
ATOM   1718  CA   PRO A 256      18.736  29.182  33.348  1.00 25.80           C
ATOM   1719  CB   PRO A 256      17.312  29.060  32.824  1.00 25.13           C
ATOM   1720  CG   PRO A 256      17.082  30.371  32.110  1.00 25.23           C
ATOM   1721  CD   PRO A 256      17.742  31.361  32.976  1.00 25.95           C
ATOM   1722  C    PRO A 256      19.731  28.776  32.254  1.00 25.26           C
ATOM   1723  O    PRO A 256      20.169  29.607  31.438  1.00 25.14           O
ATOM   1724  N    THR A 257      20.108  27.513  32.257  1.00 24.89           N
ATOM   1725  CA   THR A 257      20.806  26.938  31.130  1.00 25.41           C
ATOM   1726  CB   THR A 257      22.295  26.613  31.451  1.00 25.53           C
ATOM   1727  OG1  THR A 257      22.349  25.752  32.599  1.00 31.74           O
ATOM   1728  CG2  THR A 257      23.021  27.836  31.795  1.00 23.61           C
ATOM   1729  C    THR A 257      20.026  25.689  30.836  1.00 24.13           C
ATOM   1730  O    THR A 257      19.679  24.971  31.767  1.00 24.22           O
ATOM   1731  N    PHE A 258      19.709  25.483  29.554  1.00 23.51           N
ATOM   1732  CA   PHE A 258      18.975  24.329  29.047  1.00 23.70           C
ATOM   1733  CB   PHE A 258      17.838  24.792  28.111  1.00 23.01           C
ATOM   1734  CG   PHE A 258      16.871  25.711  28.777  1.00 21.94           C
ATOM   1735  CD1  PHE A 258      15.782  25.197  29.468  1.00 22.59           C
ATOM   1736  CE1  PHE A 258      14.897  26.049  30.114  1.00 20.98           C
ATOM   1737  CZ   PHE A 258      15.109  27.411  30.109  1.00 20.88           C
ATOM   1738  CE2  PHE A 258      16.198  27.941  29.454  1.00 20.50           C
ATOM   1739  CD2  PHE A 258      17.083  27.084  28.790  1.00 22.43           C
ATOM   1740  C    PHE A 258      19.936  23.436  28.279  1.00 24.96           C
ATOM   1741  O    PHE A 258      20.398  23.818  27.202  1.00 24.90           O
ATOM   1742  N    PRO A 259      20.281  22.262  28.853  1.00 25.97           N
ATOM   1743  CA   PRO A 259      21.156  21.306  28.171  1.00 26.25           C
ATOM   1744  CB   PRO A 259      21.421  20.225  29.237  1.00 26.46           C
ATOM   1745  CG   PRO A 259      21.013  20.817  30.534  1.00 26.33           C
ATOM   1746  CD   PRO A 259      19.921  21.808  30.211  1.00 26.02           C
ATOM   1747  C    PRO A 259      20.491  20.658  26.975  1.00 26.64           C
ATOM   1748  O    PRO A 259      19.248  20.633  26.864  1.00 26.07           O
ATOM   1749  N    ASN A 260      21.326  20.151  26.070  1.00 26.79           N
```

FIGURE 4-25 (COORDINATES)

```
ATOM   1750  CA   ASN A 260      20.849  19.353  24.964  1.00 27.21           C
ATOM   1751  CB   ASN A 260      21.658  19.659  23.715  1.00 27.37           C
ATOM   1752  CG   ASN A 260      21.126  18.952  22.479  1.00 28.52           C
ATOM   1753  OD1  ASN A 260      19.977  18.530  22.433  1.00 29.85           O
ATOM   1754  ND2  ASN A 260      21.983  18.808  21.472  1.00 31.12           N
ATOM   1755  C    ASN A 260      20.934  17.877  25.312  1.00 27.82           C
ATOM   1756  O    ASN A 260      22.026  17.325  25.423  1.00 28.57           O
ATOM   1757  N    PHE A 261      19.788  17.232  25.470  1.00 28.10           N
ATOM   1758  CA   PHE A 261      19.746  15.859  25.977  1.00 28.38           C
ATOM   1759  CB   PHE A 261      18.481  15.625  26.814  1.00 27.88           C
ATOM   1760  CG   PHE A 261      18.390  16.459  28.075  1.00 27.42           C
ATOM   1761  CD1  PHE A 261      17.638  17.625  28.096  1.00 25.66           C
ATOM   1762  CE1  PHE A 261      17.525  18.387  29.265  1.00 25.07           C
ATOM   1763  CZ   PHE A 261      18.157  17.961  30.429  1.00 25.45           C
ATOM   1764  CE2  PHE A 261      18.883  16.758  30.424  1.00 23.75           C
ATOM   1765  CD2  PHE A 261      18.993  16.029  29.259  1.00 26.20           C
ATOM   1766  C    PHE A 261      19.835  14.766  24.891  1.00 29.23           C
ATOM   1767  O    PHE A 261      20.452  13.721  25.123  1.00 29.65           O
ATOM   1768  N    PHE A 262      19.217  14.983  23.724  1.00 29.72           N
ATOM   1769  CA   PHE A 262      18.973  13.869  22.785  1.00 29.86           C
ATOM   1770  CB   PHE A 262      17.473  13.564  22.697  1.00 29.58           C
ATOM   1771  CG   PHE A 262      16.788  13.435  24.033  1.00 28.36           C
ATOM   1772  CD1  PHE A 262      16.966  12.290  24.812  1.00 27.73           C
ATOM   1773  CE1  PHE A 262      16.338  12.160  26.029  1.00 28.74           C
ATOM   1774  CZ   PHE A 262      15.477  13.190  26.504  1.00 26.92           C
ATOM   1775  CE2  PHE A 262      15.267  14.321  25.732  1.00 27.32           C
ATOM   1776  CD2  PHE A 262      15.930  14.438  24.492  1.00 28.55           C
ATOM   1777  C    PHE A 262      19.519  14.090  21.378  1.00 30.81           C
ATOM   1778  O    PHE A 262      19.166  15.085  20.739  1.00 31.50           O
ATOM   1779  N    PRO A 263      20.377  13.158  20.878  1.00 30.99           N
ATOM   1780  CA   PRO A 263      20.848  13.237  19.483  1.00 30.32           C
ATOM   1781  CB   PRO A 263      21.608  11.903  19.270  1.00 30.14           C
ATOM   1782  CG   PRO A 263      22.013  11.453  20.607  1.00 30.78           C
ATOM   1783  CD   PRO A 263      20.957  11.996  21.588  1.00 31.33           C
ATOM   1784  C    PRO A 263      19.703  13.354  18.475  1.00 30.01           C
ATOM   1785  O    PRO A 263      19.832  14.109  17.521  1.00 30.20           O
ATOM   1786  N    LYS A 264      18.608  12.622  18.701  1.00 29.64           N
ATOM   1787  CA   LYS A 264      17.413  12.657  17.860  1.00 29.80           C
ATOM   1788  CB   LYS A 264      16.263  11.948  18.572  1.00 30.56           C
ATOM   1789  CG   LYS A 264      15.101  11.434  17.669  1.00 32.38           C
ATOM   1790  CD   LYS A 264      14.215  10.825  18.135  0.00 34.65           C
ATOM   1791  CE   LYS A 264      14.246   9.309  17.916  0.00 35.80           C
ATOM   1792  NZ   LYS A 264      12.913   8.708  18.241  0.00 35.90           N
ATOM   1793  C    LYS A 264      17.013  14.111  17.528  1.00 29.18           C
ATOM   1794  O    LYS A 264      16.674  14.436  16.383  1.00 29.51           O
ATOM   1795  N    THR A 265      17.106  14.997  18.512  1.00 27.94           N
ATOM   1796  CA   THR A 265      16.519  16.333  18.374  1.00 26.58           C
ATOM   1797  CB   THR A 265      15.373  16.540  19.410  1.00 25.99           C
ATOM   1798  OG1  THR A 265      15.875  16.308  20.739  1.00 23.95           O
ATOM   1799  CG2  THR A 265      14.223  15.583  19.118  1.00 25.57           C
ATOM   1800  C    THR A 265      17.532  17.458  18.490  1.00 26.63           C
ATOM   1801  O    THR A 265      17.143  18.611  18.648  1.00 26.36           O
ATOM   1802  N    THR A 266      18.826  17.132  18.410  1.00 26.44           N
ATOM   1803  CA   THR A 266      19.890  18.143  18.464  1.00 26.52           C
ATOM   1804  CB   THR A 266      21.318  17.476  18.354  1.00 26.72           C
ATOM   1805  OG1  THR A 266      21.666  16.925  19.629  1.00 28.47           O
ATOM   1806  CG2  THR A 266      22.377  18.482  18.000  1.00 26.03           C
ATOM   1807  C    THR A 266      19.700  19.284  17.430  1.00 26.38           C
ATOM   1808  O    THR A 266      20.017  20.448  17.711  1.00 26.71           O
ATOM   1809  N    ARG A 267      19.183  18.962  16.248  1.00 25.15           N
ATOM   1810  CA   ARG A 267      18.985  19.993  15.216  1.00 25.03           C
ATOM   1811  CB   ARG A 267      18.600  19.382  13.874  1.00 24.18           C
ATOM   1812  CG   ARG A 267      17.278  18.632  13.841  1.00 26.48           C
ATOM   1813  CD   ARG A 267      17.272  17.735  12.620  1.00 29.77           C
ATOM   1814  NE   ARG A 267      15.988  17.121  12.332  1.00 30.57           N
ATOM   1815  CZ   ARG A 267      15.050  17.671  11.560  1.00 32.49           C
ATOM   1816  NH1  ARG A 267      15.240  18.880  11.023  1.00 29.46           N
ATOM   1817  NH2  ARG A 267      13.916  17.003  11.336  1.00 30.51           N
ATOM   1818  C    ARG A 267      17.920  21.007  15.615  1.00 24.44           C
ATOM   1819  O    ARG A 267      17.991  22.161  15.212  1.00 24.72           O
```

FIGURE 4-26 (COORDINATES)

```
ATOM   1820  N    TRP A 268      16.927  20.561  16.384  1.00 23.64           N
ATOM   1821  CA   TRP A 268      15.926  21.479  16.917  1.00 22.82           C
ATOM   1822  CB   TRP A 268      14.637  20.736  17.272  1.00 22.70           C
ATOM   1823  CG   TRP A 268      14.007  20.105  16.079  1.00 22.95           C
ATOM   1824  CD1  TRP A 268      13.837  18.767  15.853  1.00 23.21           C
ATOM   1825  NE1  TRP A 268      13.234  18.568  14.626  1.00 24.48           N
ATOM   1826  CE2  TRP A 268      13.020  19.783  14.033  1.00 23.93           C
ATOM   1827  CD2  TRP A 268      13.491  20.776  14.917  1.00 23.70           C
ATOM   1828  CE3  TRP A 268      13.378  22.121  14.539  1.00 23.48           C
ATOM   1829  CZ3  TRP A 268      12.801  22.429  13.315  1.00 23.08           C
ATOM   1830  CH2  TRP A 268      12.340  21.411  12.447  1.00 23.64           C
ATOM   1831  CZ2  TRP A 268      12.437  20.093  12.789  1.00 24.59           C
ATOM   1832  C    TRP A 268      16.476  22.283  18.099  1.00 23.41           C
ATOM   1833  O    TRP A 268      16.138  23.458  18.247  1.00 23.33           O
ATOM   1834  N    PHE A 269      17.306  21.665  18.944  1.00 22.45           N
ATOM   1835  CA   PHE A 269      18.045  22.408  19.964  1.00 22.01           C
ATOM   1836  CB   PHE A 269      18.932  21.464  20.794  1.00 22.08           C
ATOM   1837  CG   PHE A 269      19.619  22.143  21.935  1.00 21.19           C
ATOM   1838  CD1  PHE A 269      19.003  22.237  23.175  1.00 18.58           C
ATOM   1839  CE1  PHE A 269      19.639  22.890  24.239  1.00 21.13           C
ATOM   1840  CZ   PHE A 269      20.922  23.475  24.047  1.00 22.13           C
ATOM   1841  CE2  PHE A 269      21.526  23.392  22.804  1.00 23.06           C
ATOM   1842  CD2  PHE A 269      20.880  22.713  21.757  1.00 21.94           C
ATOM   1843  C    PHE A 269      18.896  23.541  19.367  1.00 22.49           C
ATOM   1844  O    PHE A 269      18.969  24.658  19.924  1.00 21.86           O
ATOM   1845  N    ASN A 270      19.552  23.234  18.251  1.00 22.59           N
ATOM   1846  CA   ASN A 270      20.396  24.190  17.526  1.00 23.32           C
ATOM   1847  CB   ASN A 270      21.189  23.498  16.404  1.00 23.53           C
ATOM   1848  CG   ASN A 270      22.234  22.467  16.936  1.00 26.94           C
ATOM   1849  OD1  ASN A 270      22.500  21.452  16.279  1.00 31.72           O
ATOM   1850  ND2  ASN A 270      22.813  22.731  18.108  1.00 24.91           N
ATOM   1851  C    ASN A 270      19.573  25.333  16.939  1.00 23.02           C
ATOM   1852  O    ASN A 270      20.075  26.434  16.800  1.00 22.54           O
ATOM   1853  N    ARG A 271      18.321  25.048  16.585  1.00 22.85           N
ATOM   1854  CA   ARG A 271      17.409  26.072  16.124  1.00 22.66           C
ATOM   1855  CB   ARG A 271      16.083  25.466  15.605  1.00 23.50           C
ATOM   1856  CG   ARG A 271      16.132  24.825  14.213  1.00 24.09           C
ATOM   1857  CD   ARG A 271      16.760  25.742  13.170  1.00 26.35           C
ATOM   1858  NE   ARG A 271      16.073  27.038  13.102  1.00 28.63           N
ATOM   1859  CZ   ARG A 271      16.656  28.191  12.782  1.00 30.28           C
ATOM   1860  NH1  ARG A 271      17.948  28.210  12.479  1.00 30.03           N
ATOM   1861  NH2  ARG A 271      15.945  29.323  12.754  1.00 29.06           N
ATOM   1862  C    ARG A 271      17.155  27.046  17.271  1.00 22.13           C
ATOM   1863  O    ARG A 271      17.125  28.252  17.068  1.00 21.24           O
ATOM   1864  N    LEU A 272      16.998  26.524  18.487  1.00 21.50           N
ATOM   1865  CA   LEU A 272      16.782  27.418  19.631  1.00 22.29           C
ATOM   1866  CB   LEU A 272      16.357  26.638  20.896  1.00 21.89           C
ATOM   1867  CG   LEU A 272      14.929  26.030  20.843  1.00 23.35           C
ATOM   1868  CD1  LEU A 272      14.761  24.989  21.927  1.00 22.32           C
ATOM   1869  CD2  LEU A 272      13.795  27.102  20.932  1.00 20.92           C
ATOM   1870  C    LEU A 272      17.968  28.342  19.888  1.00 22.32           C
ATOM   1871  O    LEU A 272      17.779  29.548  20.159  1.00 21.87           O
ATOM   1872  N    GLN A 273      19.178  27.778  19.825  1.00 22.57           N
ATOM   1873  CA   GLN A 273      20.444  28.563  19.935  1.00 23.74           C
ATOM   1874  CB   GLN A 273      21.697  27.669  19.735  1.00 23.34           C
ATOM   1875  CG   GLN A 273      21.728  26.410  20.589  1.00 25.92           C
ATOM   1876  CD   GLN A 273      23.106  25.693  20.581  1.00 27.78           C
ATOM   1877  OE1  GLN A 273      23.236  24.567  20.072  1.00 35.23           O
ATOM   1878  NE2  GLN A 273      24.107  26.330  21.159  1.00 26.32           N
ATOM   1879  C    GLN A 273      20.518  29.683  18.900  1.00 22.63           C
ATOM   1880  O    GLN A 273      20.892  30.818  19.211  1.00 22.28           O
ATOM   1881  N    ALA A 274      20.190  29.331  17.660  1.00 22.47           N
ATOM   1882  CA   ALA A 274      20.210  30.266  16.528  1.00 22.75           C
ATOM   1883  CB   ALA A 274      19.987  29.498  15.208  1.00 22.48           C
ATOM   1884  C    ALA A 274      19.173  31.384  16.705  1.00 22.72           C
ATOM   1885  O    ALA A 274      19.483  32.561  16.549  1.00 23.28           O
ATOM   1886  N    ILE A 275      17.958  31.016  17.084  1.00 21.96           N
ATOM   1887  CA   ILE A 275      16.911  32.012  17.421  1.00 20.32           C
ATOM   1888  CB   ILE A 275      15.565  31.303  17.734  1.00 19.95           C
ATOM   1889  CG1  ILE A 275      15.070  30.571  16.483  1.00 19.24           C
```

FIGURE 4-27 (COORDINATES)

```
ATOM   1890  CD1 ILE A 275      13.940  29.528  16.730  1.00 18.75           C
ATOM   1891  CG2 ILE A 275      14.515  32.315  18.263  1.00 18.22           C
ATOM   1892  C   ILE A 275      17.342  32.918  18.568  1.00 20.80           C
ATOM   1893  O   ILE A 275      17.165  34.133  18.495  1.00 21.91           O
ATOM   1894  N   GLU A 276      17.919  32.351  19.632  1.00 21.13           N
ATOM   1895  CA  GLU A 276      18.404  33.163  20.739  1.00 20.59           C
ATOM   1896  CB  GLU A 276      19.076  32.277  21.799  1.00 20.26           C
ATOM   1897  CG  GLU A 276      19.744  33.094  22.922  1.00 18.65           C
ATOM   1898  CD  GLU A 276      20.330  32.272  24.035  1.00 20.27           C
ATOM   1899  OE1 GLU A 276      20.459  31.047  23.875  1.00 22.79           O
ATOM   1900  OE2 GLU A 276      20.659  32.855  25.094  1.00 20.09           O
ATOM   1901  C   GLU A 276      19.418  34.239  20.270  1.00 21.52           C
ATOM   1902  O   GLU A 276      19.364  35.405  20.665  1.00 20.52           O
ATOM   1903  N   LYS A 277      20.382  33.790  19.476  1.00 23.26           N
ATOM   1904  CA  LYS A 277      21.492  34.645  18.983  1.00 23.75           C
ATOM   1905  CB  LYS A 277      22.541  33.768  18.273  1.00 22.86           C
ATOM   1906  CG  LYS A 277      23.748  34.540  17.708  1.00 25.78           C
ATOM   1907  CD  LYS A 277      24.653  33.648  16.847  1.00 25.53           C
ATOM   1908  CE  LYS A 277      25.645  34.256  16.179  0.00 37.87           C
ATOM   1909  NZ  LYS A 277      26.067  33.658  14.859  0.00 41.25           N
ATOM   1910  C   LYS A 277      20.967  35.768  18.061  1.00 23.50           C
ATOM   1911  O   LYS A 277      21.320  36.941  18.238  1.00 24.29           O
ATOM   1912  N   GLU A 278      20.103  35.412  17.123  1.00 24.34           N
ATOM   1913  CA  GLU A 278      19.539  36.368  16.174  1.00 26.28           C
ATOM   1914  CB  GLU A 278      18.892  35.655  14.975  1.00 26.37           C
ATOM   1915  CG  GLU A 278      17.459  35.148  15.173  1.00 28.85           C
ATOM   1916  CD  GLU A 278      17.009  34.195  14.091  1.00 29.76           C
ATOM   1917  OE1 GLU A 278      17.708  34.067  13.060  1.00 34.66           O
ATOM   1918  OE2 GLU A 278      15.947  33.553  14.265  1.00 34.38           O
ATOM   1919  C   GLU A 278      18.616  37.402  16.833  1.00 26.10           C
ATOM   1920  O   GLU A 278      18.731  38.594  16.542  1.00 25.11           O
ATOM   1921  N   LEU A 279      17.739  36.959  17.750  1.00 26.56           N
ATOM   1922  CA  LEU A 279      16.962  37.907  18.573  1.00 26.05           C
ATOM   1923  CB  LEU A 279      15.937  37.184  19.483  1.00 24.89           C
ATOM   1924  CG  LEU A 279      14.794  36.435  18.784  1.00 21.93           C
ATOM   1925  CD1 LEU A 279      13.910  35.741  19.828  1.00 16.46           C
ATOM   1926  CD2 LEU A 279      13.956  37.327  17.869  1.00 22.45           C
ATOM   1927  C   LEU A 279      17.851  38.848  19.392  1.00 26.60           C
ATOM   1928  O   LEU A 279      17.566  40.056  19.491  1.00 26.92           O
ATOM   1929  N   TYR A 280      18.904  38.307  19.998  1.00 27.58           N
ATOM   1930  CA  TYR A 280      19.847  39.151  20.757  1.00 29.05           C
ATOM   1931  CB  TYR A 280      20.983  38.340  21.415  1.00 29.69           C
ATOM   1932  CG  TYR A 280      22.096  39.236  21.928  1.00 29.94           C
ATOM   1933  CD1 TYR A 280      21.950  39.918  23.118  1.00 28.06           C
ATOM   1934  CE1 TYR A 280      22.929  40.753  23.598  1.00 30.72           C
ATOM   1935  CZ  TYR A 280      24.089  40.929  22.885  1.00 32.07           C
ATOM   1936  OH  TYR A 280      25.037  41.775  23.407  1.00 35.00           O
ATOM   1937  CE2 TYR A 280      24.286  40.279  21.676  1.00 32.86           C
ATOM   1938  CD2 TYR A 280      23.276  39.426  21.198  1.00 31.51           C
ATOM   1939  C   TYR A 280      20.466  40.207  19.841  1.00 29.48           C
ATOM   1940  O   TYR A 280      20.528  41.394  20.197  1.00 29.71           O
ATOM   1941  N   GLU A 281      20.912  39.764  18.661  1.00 30.11           N
ATOM   1942  CA  GLU A 281      21.629  40.637  17.716  1.00 31.40           C
ATOM   1943  CB  GLU A 281      22.307  39.813  16.612  1.00 31.35           C
ATOM   1944  CG  GLU A 281      23.430  38.887  17.231  1.00 32.96           C
ATOM   1945  CD  GLU A 281      24.135  37.988  16.227  1.00 35.41           C
ATOM   1946  OE1 GLU A 281      23.549  37.702  15.146  1.00 40.05           O
ATOM   1947  OE2 GLU A 281      25.282  37.543  16.535  1.00 40.51           O
ATOM   1948  C   GLU A 281      20.724  41.749  17.193  1.00 30.73           C
ATOM   1949  O   GLU A 281      21.144  42.902  17.088  1.00 30.93           O
ATOM   1950  N   LEU A 282      19.459  41.416  16.956  1.00 29.97           N
ATOM   1951  CA  LEU A 282      18.429  42.393  16.548  1.00 29.29           C
ATOM   1952  CB  LEU A 282      17.205  41.638  16.047  1.00 29.24           C
ATOM   1953  CG  LEU A 282      17.137  41.384  14.541  1.00 32.01           C
ATOM   1954  CD1 LEU A 282      16.432  40.081  14.263  1.00 30.31           C
ATOM   1955  CD2 LEU A 282      18.503  41.394  13.852  1.00 34.17           C
ATOM   1956  C   LEU A 282      17.993  43.402  17.612  1.00 27.99           C
ATOM   1957  O   LEU A 282      17.145  44.260  17.349  1.00 29.19           O
ATOM   1958  N   GLY A 283      18.530  43.294  18.811  1.00 26.32           N
ATOM   1959  CA  GLY A 283      18.110  44.155  19.914  1.00 25.92           C
```

FIGURE 4-28 (COORDINATES)

```
ATOM   1960  C   GLY A 283      16.730  43.801  20.500  1.00 25.56           C
ATOM   1961  O   GLY A 283      16.106  44.630  21.183  1.00 24.51           O
ATOM   1962  N   LEU A 284      16.274  42.568  20.270  1.00 25.05           N
ATOM   1963  CA  LEU A 284      14.936  42.153  20.695  1.00 25.25           C
ATOM   1964  CB  LEU A 284      14.203  41.408  19.553  1.00 25.50           C
ATOM   1965  CG  LEU A 284      14.077  42.180  18.218  1.00 25.35           C
ATOM   1966  CD1 LEU A 284      13.739  41.253  17.076  1.00 24.06           C
ATOM   1967  CD2 LEU A 284      13.047  43.319  18.302  1.00 27.49           C
ATOM   1968  C   LEU A 284      14.830  41.373  22.022  1.00 25.98           C
ATOM   1969  O   LEU A 284      13.725  40.956  22.394  1.00 26.52           O
ATOM   1970  N   LEU A 285      15.932  41.174  22.743  1.00 25.23           N
ATOM   1971  CA  LEU A 285      15.812  40.599  24.087  1.00 25.27           C
ATOM   1972  CB  LEU A 285      16.700  39.382  24.254  1.00 24.31           C
ATOM   1973  CG  LEU A 285      16.684  38.294  23.186  1.00 24.89           C
ATOM   1974  CD1 LEU A 285      17.677  37.188  23.582  1.00 22.59           C
ATOM   1975  CD2 LEU A 285      15.275  37.719  22.939  1.00 21.99           C
ATOM   1976  C   LEU A 285      16.129  41.654  25.125  1.00 26.07           C
ATOM   1977  O   LEU A 285      16.634  42.724  24.775  1.00 27.14           O
ATOM   1978  N   LYS A 286      15.799  41.400  26.384  1.00 25.52           N
ATOM   1979  CA  LYS A 286      16.100  42.339  27.445  1.00 26.88           C
ATOM   1980  CB  LYS A 286      14.826  42.877  28.127  1.00 27.26           C
ATOM   1981  CG  LYS A 286      13.822  43.543  27.193  1.00 28.87           C
ATOM   1982  CD  LYS A 286      12.648  44.180  27.999  1.00 29.26           C
ATOM   1983  CE  LYS A 286      11.782  45.113  27.111  1.00 31.20           C
ATOM   1984  NZ  LYS A 286      11.744  44.659  25.685  1.00 34.37           N
ATOM   1985  C   LYS A 286      16.979  41.685  28.496  1.00 26.47           C
ATOM   1986  O   LYS A 286      16.869  40.483  28.749  1.00 24.83           O
ATOM   1987  N   ASP A 287      17.815  42.528  29.121  1.00 26.47           N
ATOM   1988  CA  ASP A 287      18.780  42.174  30.179  1.00 26.72           C
ATOM   1989  CB  ASP A 287      18.202  42.373  31.594  1.00 27.04           C
ATOM   1990  CG  ASP A 287      17.557  43.760  31.755  0.00 35.77           C
ATOM   1991  OD1 ASP A 287      18.110  44.748  31.173  0.00 40.70           O
ATOM   1992  OD2 ASP A 287      16.492  43.852  32.421  0.00 38.85           O
ATOM   1993  C   ASP A 287      19.404  40.799  30.013  1.00 26.64           C
ATOM   1994  O   ASP A 287      19.430  40.002  30.940  1.00 27.58           O
ATOM   1995  N   HIS A 288      19.912  40.543  28.824  1.00 26.34           N
ATOM   1996  CA  HIS A 288      20.512  39.276  28.500  1.00 27.33           C
ATOM   1997  CB  HIS A 288      19.429  38.288  28.031  1.00 26.57           C
ATOM   1998  CG  HIS A 288      19.951  36.916  27.776  1.00 25.08           C
ATOM   1999  ND1 HIS A 288      19.996  36.352  26.516  1.00 23.85           N
ATOM   2000  CE1 HIS A 288      20.514  35.138  26.601  1.00 22.72           C
ATOM   2001  NE2 HIS A 288      20.821  34.905  27.864  1.00 23.97           N
ATOM   2002  CD2 HIS A 288      20.475  35.999  28.621  1.00 20.78           C
ATOM   2003  C   HIS A 288      21.542  39.430  27.376  1.00 27.77           C
ATOM   2004  O   HIS A 288      21.189  39.737  26.228  1.00 28.24           O
ATOM   2005  N   SER A 289      22.800  39.182  27.707  1.00 28.36           N
ATOM   2006  CA  SER A 289      23.861  39.046  26.702  1.00 28.64           C
ATOM   2007  CB  SER A 289      25.165  39.614  27.260  1.00 28.32           C
ATOM   2008  OG  SER A 289      25.654  38.764  28.290  1.00 28.33           O
ATOM   2009  C   SER A 289      24.042  37.545  26.398  1.00 28.97           C
ATOM   2010  O   SER A 289      23.456  36.700  27.090  1.00 29.19           O
ATOM   2011  N   LEU A 290      24.864  37.219  25.400  1.00 28.71           N
ATOM   2012  CA  LEU A 290      25.195  35.808  25.074  1.00 28.47           C
ATOM   2013  CB  LEU A 290      25.385  35.626  23.564  1.00 27.84           C
ATOM   2014  CG  LEU A 290      24.207  36.091  22.720  1.00 28.69           C
ATOM   2015  CD1 LEU A 290      24.593  36.059  21.231  1.00 29.81           C
ATOM   2016  CD2 LEU A 290      22.969  35.232  23.026  1.00 26.14           C
ATOM   2017  C   LEU A 290      26.428  35.264  25.808  1.00 28.53           C
ATOM   2018  O   LEU A 290      26.985  34.223  25.412  1.00 29.01           O
ATOM   2019  N   GLU A 291      26.846  35.975  26.851  1.00 28.00           N
ATOM   2020  CA  GLU A 291      27.949  35.587  27.712  1.00 29.35           C
ATOM   2021  CB  GLU A 291      28.218  36.690  28.748  1.00 29.44           C
ATOM   2022  CG  GLU A 291      28.931  37.899  28.184  1.00 30.23           C
ATOM   2023  CD  GLU A 291      30.325  37.555  27.677  1.00 33.67           C
ATOM   2024  OE1 GLU A 291      31.160  37.153  28.508  1.00 36.13           O
ATOM   2025  OE2 GLU A 291      30.584  37.673  26.456  1.00 32.49           O
ATOM   2026  C   GLU A 291      27.629  34.292  28.428  1.00 30.18           C
ATOM   2027  O   GLU A 291      28.521  33.476  28.713  1.00 30.72           O
ATOM   2028  N   ARG A 292      26.341  34.143  28.739  1.00 30.27           N
ATOM   2029  CA  ARG A 292      25.774  32.946  29.360  1.00 30.91           C
```

FIGURE 4-29 (COORDINATES)

```
ATOM   2030  CB  ARG A 292      25.472  33.193  30.851  1.00 30.75           C
ATOM   2031  CG  ARG A 292      26.710  33.338  31.743  1.00 32.64           C
ATOM   2032  CD  ARG A 292      26.364  34.029  33.094  1.00 32.35           C
ATOM   2033  NE  ARG A 292      25.584  35.000  33.334  0.00 43.95           N
ATOM   2034  CZ  ARG A 292      25.100  35.465  34.498  0.00 47.33           C
ATOM   2035  NH1 ARG A 292      25.452  34.922  35.674  0.00 46.26           N
ATOM   2036  NH2 ARG A 292      24.244  36.481  34.493  0.00 47.41           N
ATOM   2037  C   ARG A 292      24.489  32.650  28.586  1.00 29.53           C
ATOM   2038  O   ARG A 292      23.397  32.980  29.022  1.00 30.27           O
ATOM   2039  N   LYS A 293      24.650  32.047  27.422  1.00 28.14           N
ATOM   2040  CA  LYS A 293      23.554  31.744  26.535  1.00 27.20           C
ATOM   2041  CB  LYS A 293      24.094  31.051  25.270  1.00 27.25           C
ATOM   2042  CG  LYS A 293      24.698  31.973  24.214  1.00 28.44           C
ATOM   2043  CD  LYS A 293      25.251  31.160  23.022  1.00 29.04           C
ATOM   2044  CE  LYS A 293      26.651  30.606  23.369  1.00 33.59           C
ATOM   2045  NZ  LYS A 293      27.064  29.554  22.413  1.00 39.10           N
ATOM   2046  C   LYS A 293      22.595  30.777  27.252  1.00 25.79           C
ATOM   2047  O   LYS A 293      23.033  29.881  27.960  1.00 24.73           O
ATOM   2048  N   TYR A 294      21.295  30.971  27.075  1.00 23.92           N
ATOM   2049  CA  TYR A 294      20.319  30.020  27.624  1.00 22.91           C
ATOM   2050  CB  TYR A 294      18.894  30.429  27.254  1.00 21.39           C
ATOM   2051  CG  TYR A 294      18.453  31.758  27.785  1.00 19.44           C
ATOM   2052  CD1 TYR A 294      18.710  32.118  29.097  1.00 17.77           C
ATOM   2053  CE1 TYR A 294      18.299  33.349  29.592  1.00 19.50           C
ATOM   2054  CZ  TYR A 294      17.579  34.227  28.770  1.00 19.88           C
ATOM   2055  OH  TYR A 294      17.194  35.452  29.276  1.00 17.57           O
ATOM   2056  CE2 TYR A 294      17.314  33.896  27.449  1.00 18.64           C
ATOM   2057  CD2 TYR A 294      17.759  32.660  26.958  1.00 19.28           C
ATOM   2058  C   TYR A 294      20.575  28.616  27.078  1.00 23.15           C
ATOM   2059  O   TYR A 294      20.545  27.656  27.818  1.00 24.35           O
ATOM   2060  N   PHE A 295      20.815  28.506  25.783  1.00 23.36           N
ATOM   2061  CA  PHE A 295      20.933  27.204  25.155  1.00 26.03           C
ATOM   2062  CB  PHE A 295      20.059  27.101  23.906  1.00 24.16           C
ATOM   2063  CG  PHE A 295      18.617  27.379  24.199  1.00 24.44           C
ATOM   2064  CD1 PHE A 295      17.777  26.364  24.671  1.00 19.85           C
ATOM   2065  CE1 PHE A 295      16.449  26.641  25.001  1.00 21.96           C
ATOM   2066  CZ  PHE A 295      15.955  27.952  24.845  1.00 20.55           C
ATOM   2067  CE2 PHE A 295      16.786  28.971  24.387  1.00 20.43           C
ATOM   2068  CD2 PHE A 295      18.117  28.690  24.084  1.00 22.24           C
ATOM   2069  C   PHE A 295      22.389  26.888  24.900  1.00 28.38           C
ATOM   2070  O   PHE A 295      22.996  27.322  23.906  1.00 28.60           O
ATOM   2071  N   GLN A 296      22.936  26.178  25.879  1.00 31.67           N
ATOM   2072  CA  GLN A 296      24.337  25.796  25.917  1.00 34.99           C
ATOM   2073  CB  GLN A 296      24.947  26.150  27.278  1.00 35.50           C
ATOM   2074  CG  GLN A 296      25.119  27.654  27.577  1.00 37.35           C
ATOM   2075  CD  GLN A 296      26.396  28.282  26.980  1.00 40.34           C
ATOM   2076  OE1 GLN A 296      26.689  28.145  25.780  1.00 39.54           O
ATOM   2077  NE2 GLN A 296      27.153  28.994  27.830  1.00 40.76           N
ATOM   2078  C   GLN A 296      24.377  24.293  25.694  1.00 36.14           C
ATOM   2079  O   GLN A 296      23.775  23.511  26.464  1.00 36.77           O
ATOM   2080  N   ASN A 297      25.057  23.910  24.619  1.00 37.45           N
ATOM   2081  CA  ASN A 297      25.288  22.518  24.267  1.00 38.87           C
ATOM   2082  CB  ASN A 297      25.160  22.394  22.743  1.00 39.37           C
ATOM   2083  CG  ASN A 297      25.112  20.966  22.254  1.00 40.34           C
ATOM   2084  OD1 ASN A 297      25.608  20.032  22.902  1.00 42.98           O
ATOM   2085  ND2 ASN A 297      24.537  20.788  21.072  1.00 42.19           N
ATOM   2086  C   ASN A 297      26.692  22.095  24.751  1.00 39.41           C
ATOM   2087  O   ASN A 297      27.695  22.456  24.136  1.00 38.79           O
ATOM   2088  N   PHE A 298      26.732  21.364  25.875  1.00 40.42           N
ATOM   2089  CA  PHE A 298      27.956  20.812  26.462  1.00 41.21           C
ATOM   2090  CB  PHE A 298      27.967  21.008  27.968  1.00 42.07           C
ATOM   2091  CG  PHE A 298      28.045  22.421  28.418  1.00 45.09           C
ATOM   2092  CD1 PHE A 298      29.107  22.839  29.203  1.00 46.50           C
ATOM   2093  CE1 PHE A 298      29.169  24.140  29.666  1.00 46.60           C
ATOM   2094  CZ  PHE A 298      28.178  25.026  29.355  1.00 44.86           C
ATOM   2095  CE2 PHE A 298      27.106  24.620  28.586  1.00 47.69           C
ATOM   2096  CD2 PHE A 298      27.032  23.322  28.131  1.00 46.82           C
ATOM   2097  C   PHE A 298      28.008  19.306  26.284  1.00 40.97           C
ATOM   2098  O   PHE A 298      28.488  18.587  27.180  1.00 41.16           O
ATOM   2099  N   GLY A 299      27.521  18.820  25.154  1.00 40.69           N
```

FIGURE 4-30 (COORDINATES)

```
ATOM   2100  CA  GLY A 299      27.392  17.382  24.951  1.00 41.01           C
ATOM   2101  C   GLY A 299      26.089  16.916  25.557  1.00 41.18           C
ATOM   2102  O   GLY A 299      25.353  17.708  26.150  1.00 41.72           O
ATOM   2103  N   TYR A 300      25.775  15.637  25.425  1.00 40.70           N
ATOM   2104  CA  TYR A 300      24.482  15.189  25.904  1.00 40.39           C
ATOM   2105  CB  TYR A 300      24.064  13.889  25.224  1.00 40.95           C
ATOM   2106  CG  TYR A 300      23.966  14.097  23.731  1.00 41.91           C
ATOM   2107  CD1 TYR A 300      23.005  14.944  23.195  1.00 40.89           C
ATOM   2108  CE1 TYR A 300      22.923  15.156  21.838  1.00 42.16           C
ATOM   2109  CZ  TYR A 300      23.819  14.524  20.988  1.00 43.40           C
ATOM   2110  OH  TYR A 300      23.743  14.740  19.626  1.00 44.40           O
ATOM   2111  CE2 TYR A 300      24.798  13.696  21.494  1.00 42.79           C
ATOM   2112  CD2 TYR A 300      24.871  13.493  22.861  1.00 42.40           C
ATOM   2113  C   TYR A 300      24.386  15.124  27.424  1.00 39.91           C
ATOM   2114  O   TYR A 300      25.151  14.398  28.071  1.00 39.96           O
ATOM   2115  N   GLY A 301      23.460  15.923  27.973  1.00 38.65           N
ATOM   2116  CA  GLY A 301      23.051  15.802  29.359  1.00 36.83           C
ATOM   2117  C   GLY A 301      22.544  14.411  29.725  1.00 35.78           C
ATOM   2118  O   GLY A 301      21.911  13.732  28.919  1.00 36.46           O
ATOM   2119  N   ASN A 302      22.869  13.975  30.942  1.00 34.86           N
ATOM   2120  CA  ASN A 302      22.183  12.874  31.604  1.00 33.23           C
ATOM   2121  CB  ASN A 302      22.747  12.659  33.003  1.00 34.04           C
ATOM   2122  CG  ASN A 302      24.251  12.507  33.016  1.00 36.44           C
ATOM   2123  OD1 ASN A 302      24.802  11.657  32.325  1.00 39.54           O
ATOM   2124  ND2 ASN A 302      24.924  13.324  33.821  1.00 37.47           N
ATOM   2125  C   ASN A 302      20.710  13.231  31.751  1.00 31.73           C
ATOM   2126  O   ASN A 302      20.359  14.325  32.208  1.00 30.19           O
ATOM   2127  N   ILE A 303      19.868  12.271  31.391  1.00 30.57           N
ATOM   2128  CA  ILE A 303      18.427  12.440  31.294  1.00 29.00           C
ATOM   2129  CB  ILE A 303      17.792  11.188  30.627  1.00 29.57           C
ATOM   2130  CG1 ILE A 303      16.271  11.265  30.647  1.00 31.96           C
ATOM   2131  CD1 ILE A 303      15.624  10.391  29.583  1.00 38.33           C
ATOM   2132  CG2 ILE A 303      18.262   9.891  31.322  1.00 31.03           C
ATOM   2133  C   ILE A 303      17.834  12.721  32.668  1.00 27.14           C
ATOM   2134  O   ILE A 303      18.238  12.091  33.649  1.00 26.70           O
ATOM   2135  N   ILE A 304      16.917  13.698  32.748  1.00 23.70           N
ATOM   2136  CA  ILE A 304      16.186  13.969  33.999  1.00 21.86           C
ATOM   2137  CB  ILE A 304      16.129  15.491  34.330  1.00 21.98           C
ATOM   2138  CG1 ILE A 304      17.550  16.065  34.411  1.00 20.49           C
ATOM   2139  CD1 ILE A 304      17.651  17.550  34.268  1.00 19.30           C
ATOM   2140  CG2 ILE A 304      15.332  15.748  35.652  1.00 22.75           C
ATOM   2141  C   ILE A 304      14.765  13.387  33.862  1.00 20.46           C
ATOM   2142  O   ILE A 304      14.085  13.702  32.904  1.00 20.23           O
ATOM   2143  N   GLN A 305      14.325  12.555  34.799  1.00 19.14           N
ATOM   2144  CA  GLN A 305      12.958  12.030  34.785  1.00 18.39           C
ATOM   2145  CB  GLN A 305      12.689  11.091  35.960  1.00 19.18           C
ATOM   2146  CG  GLN A 305      13.651   9.856  36.030  1.00 20.23           C
ATOM   2147  CD  GLN A 305      13.649   9.081  34.734  1.00 26.05           C
ATOM   2148  OE1 GLN A 305      12.639   8.479  34.370  1.00 28.55           O
ATOM   2149  NE2 GLN A 305      14.771   9.122  34.004  1.00 28.50           N
ATOM   2150  C   GLN A 305      11.935  13.182  34.825  1.00 17.70           C
ATOM   2151  O   GLN A 305      12.039  14.100  35.671  1.00 17.34           O
ATOM   2152  N   ASP A 306      10.952  13.092  33.925  1.00 16.07           N
ATOM   2153  CA  ASP A 306       9.875  14.106  33.789  1.00 15.71           C
ATOM   2154  CB  ASP A 306      10.492  15.407  33.229  1.00 14.40           C
ATOM   2155  CG  ASP A 306       9.671  16.659  33.538  1.00 16.20           C
ATOM   2156  OD1 ASP A 306       8.555  16.537  34.090  1.00 15.24           O
ATOM   2157  OD2 ASP A 306      10.172  17.773  33.200  1.00 15.04           O
ATOM   2158  C   ASP A 306       8.794  13.536  32.846  1.00 16.00           C
ATOM   2159  O   ASP A 306       8.934  12.397  32.343  1.00 14.32           O
ATOM   2160  N   ASP A 307       7.743  14.333  32.596  1.00 15.61           N
ATOM   2161  CA  ASP A 307       6.597  13.930  31.790  1.00 15.75           C
ATOM   2162  CB  ASP A 307       5.571  15.084  31.669  1.00 15.65           C
ATOM   2163  CG  ASP A 307       4.754  15.292  32.944  1.00 18.36           C
ATOM   2164  OD1 ASP A 307       4.337  14.294  33.611  1.00 18.91           O
ATOM   2165  OD2 ASP A 307       4.524  16.483  33.272  1.00 17.08           O
ATOM   2166  C   ASP A 307       6.928  13.409  30.392  1.00 15.08           C
ATOM   2167  O   ASP A 307       6.099  12.748  29.756  1.00 13.07           O
ATOM   2168  N   HIS A 308       8.112  13.717  29.887  1.00 15.09           N
ATOM   2169  CA  HIS A 308       8.506  13.199  28.553  1.00 16.02           C
```

FIGURE 4-31 (COORDINATES)

```
ATOM   2170  CB  HIS A 308       9.686  14.007  28.033  1.00 14.55           C
ATOM   2171  CG  HIS A 308      10.936  13.875  28.861  1.00 16.18           C
ATOM   2172  ND1 HIS A 308      10.979  14.176  30.206  1.00 14.81           N
ATOM   2173  CE1 HIS A 308      12.208  13.999  30.660  1.00 14.70           C
ATOM   2174  NE2 HIS A 308      12.963  13.567  29.661  1.00 17.99           N
ATOM   2175  CD2 HIS A 308      12.193  13.488  28.522  1.00 14.55           C
ATOM   2176  C   HIS A 308       8.893  11.695  28.514  1.00 17.56           C
ATOM   2177  O   HIS A 308       8.911  11.061  27.438  1.00 18.12           O
ATOM   2178  N   ILE A 309       9.233  11.142  29.673  1.00 19.15           N
ATOM   2179  CA  ILE A 309       9.745   9.757  29.772  1.00 20.17           C
ATOM   2180  CB  ILE A 309      10.154   9.394  31.237  1.00 19.98           C
ATOM   2181  CG1 ILE A 309      11.383  10.200  31.654  1.00 20.95           C
ATOM   2182  CD1 ILE A 309      12.581  10.014  30.776  1.00 21.52           C
ATOM   2183  CG2 ILE A 309      10.402   7.852  31.417  1.00 20.05           C
ATOM   2184  C   ILE A 309       8.787   8.708  29.147  1.00 20.54           C
ATOM   2185  O   ILE A 309       9.220   7.892  28.302  1.00 20.98           O
ATOM   2186  N   PRO A 310       7.494   8.725  29.538  1.00 20.60           N
ATOM   2187  CA  PRO A 310       6.567   7.743  28.946  1.00 20.33           C
ATOM   2188  CB  PRO A 310       5.237   8.067  29.623  1.00 19.87           C
ATOM   2189  CG  PRO A 310       5.618   8.803  30.886  1.00 20.69           C
ATOM   2190  CD  PRO A 310       6.806   9.598  30.510  1.00 20.33           C
ATOM   2191  C   PRO A 310       6.428   7.906  27.438  1.00 20.58           C
ATOM   2192  O   PRO A 310       6.037   6.966  26.768  1.00 21.47           O
ATOM   2193  N   PHE A 311       6.746   9.088  26.905  1.00 20.37           N
ATOM   2194  CA  PHE A 311       6.697   9.308  25.452  1.00 20.36           C
ATOM   2195  CB  PHE A 311       6.277  10.769  25.092  1.00 19.34           C
ATOM   2196  CG  PHE A 311       4.883  11.126  25.551  1.00 16.53           C
ATOM   2197  CD1 PHE A 311       4.668  11.657  26.824  1.00 14.18           C
ATOM   2198  CE1 PHE A 311       3.402  11.975  27.243  1.00 13.99           C
ATOM   2199  CZ  PHE A 311       2.322  11.765  26.418  1.00 17.05           C
ATOM   2200  CE2 PHE A 311       2.509  11.237  25.131  1.00 16.02           C
ATOM   2201  CD2 PHE A 311       3.789  10.922  24.715  1.00 15.41           C
ATOM   2202  C   PHE A 311       8.021   8.919  24.812  1.00 21.33           C
ATOM   2203  O   PHE A 311       8.031   8.258  23.790  1.00 22.05           O
ATOM   2204  N   LEU A 312       9.136   9.351  25.403  1.00 22.73           N
ATOM   2205  CA  LEU A 312      10.452   8.915  24.962  1.00 24.69           C
ATOM   2206  CB  LEU A 312      11.531   9.467  25.885  1.00 23.81           C
ATOM   2207  CG  LEU A 312      12.998   9.410  25.467  1.00 23.43           C
ATOM   2208  CD1 LEU A 312      13.336  10.427  24.388  1.00 21.04           C
ATOM   2209  CD2 LEU A 312      13.844   9.692  26.693  1.00 23.42           C
ATOM   2210  C   LEU A 312      10.546   7.374  24.870  1.00 26.63           C
ATOM   2211  O   LEU A 312      11.117   6.851  23.901  1.00 27.77           O
ATOM   2212  N   ARG A 313       9.980   6.686  25.866  1.00 27.46           N
ATOM   2213  CA  ARG A 313       9.883   5.217  25.958  1.00 28.79           C
ATOM   2214  CB  ARG A 313       8.900   4.875  27.084  1.00 29.12           C
ATOM   2215  CG  ARG A 313       9.269   3.750  28.014  1.00 31.10           C
ATOM   2216  CD  ARG A 313       8.000   3.178  28.691  1.00 32.60           C
ATOM   2217  NE  ARG A 313      10.086   4.217  29.354  0.00 43.79           N
ATOM   2218  CZ  ARG A 313      10.525   4.320  30.605  0.00 44.49           C
ATOM   2219  NH1 ARG A 313       9.776   3.883  31.609  0.00 44.14           N
ATOM   2220  NH2 ARG A 313      11.716   4.860  30.848  0.00 45.50           N
ATOM   2221  C   ARG A 313       9.341   4.614  24.653  1.00 29.73           C
ATOM   2222  O   ARG A 313       9.816   3.565  24.162  1.00 29.26           O
ATOM   2223  N   LYS A 314       8.340   5.295  24.089  1.00 29.70           N
ATOM   2224  CA  LYS A 314       7.657   4.847  22.889  1.00 29.72           C
ATOM   2225  CB  LYS A 314       6.176   5.239  22.944  1.00 29.60           C
ATOM   2226  CG  LYS A 314       5.471   4.975  24.273  1.00 32.35           C
ATOM   2227  CD  LYS A 314       5.141   3.483  24.465  1.00 36.07           C
ATOM   2228  CE  LYS A 314       4.407   2.915  23.251  1.00 38.42           C
ATOM   2229  NZ  LYS A 314       4.291   1.423  23.305  1.00 39.77           N
ATOM   2230  C   LYS A 314       8.274   5.410  21.613  1.00 29.01           C
ATOM   2231  O   LYS A 314       7.672   5.327  20.556  1.00 29.42           O
ATOM   2232  N   GLY A 315       9.455   6.002  21.697  1.00 28.57           N
ATOM   2233  CA  GLY A 315      10.092   6.564  20.489  1.00 28.06           C
ATOM   2234  C   GLY A 315       9.659   7.954  20.005  1.00 27.52           C
ATOM   2235  O   GLY A 315      10.103   8.405  18.951  1.00 27.94           O
ATOM   2236  N   VAL A 316       8.823   8.657  20.769  1.00 25.91           N
ATOM   2237  CA  VAL A 316       8.440  10.035  20.392  1.00 23.72           C
ATOM   2238  CB  VAL A 316       7.265  10.549  21.270  1.00 24.41           C
ATOM   2239  CG1 VAL A 316       6.938  12.033  20.953  1.00 21.66           C
```

FIGURE 4-32 (COORDINATES)

```
ATOM   2240  CG2 VAL A 316       6.038   9.656  21.081  1.00 23.30           C
ATOM   2241  C   VAL A 316       9.666  10.971  20.451  1.00 22.68           C
ATOM   2242  O   VAL A 316      10.404  10.959  21.441  1.00 21.48           O
ATOM   2243  N   PRO A 317       9.925  11.752  19.375  1.00 21.83           N
ATOM   2244  CA  PRO A 317      11.022  12.698  19.518  1.00 22.00           C
ATOM   2245  CB  PRO A 317      11.140  13.338  18.118  1.00 22.01           C
ATOM   2246  CG  PRO A 317      10.411  12.379  17.184  1.00 22.60           C
ATOM   2247  CD  PRO A 317       9.288  11.842  18.044  1.00 21.78           C
ATOM   2248  C   PRO A 317      10.765  13.755  20.597  1.00 21.79           C
ATOM   2249  O   PRO A 317       9.679  14.348  20.643  1.00 21.53           O
ATOM   2250  N   VAL A 318      11.763  13.984  21.457  1.00 21.72           N
ATOM   2251  CA  VAL A 318      11.618  14.940  22.598  1.00 20.70           C
ATOM   2252  CB  VAL A 318      11.612  14.201  23.996  1.00 19.96           C
ATOM   2253  CG1 VAL A 318      11.582  15.222  25.185  1.00 21.38           C
ATOM   2254  CG2 VAL A 318      10.459  13.197  24.104  1.00 20.00           C
ATOM   2255  C   VAL A 318      12.661  16.066  22.613  1.00 20.70           C
ATOM   2256  O   VAL A 318      13.871  15.833  22.416  1.00 19.63           O
ATOM   2257  N   LEU A 319      12.186  17.288  22.870  1.00 19.12           N
ATOM   2258  CA  LEU A 319      13.044  18.396  23.297  1.00 19.03           C
ATOM   2259  CB  LEU A 319      12.813  19.603  22.380  1.00 19.13           C
ATOM   2260  CG  LEU A 319      13.895  20.619  22.103  1.00 20.80           C
ATOM   2261  CD1 LEU A 319      15.187  19.941  21.609  1.00 18.30           C
ATOM   2262  CD2 LEU A 319      13.341  21.636  21.066  1.00 19.03           C
ATOM   2263  C   LEU A 319      12.670  18.768  24.725  1.00 18.19           C
ATOM   2264  O   LEU A 319      11.565  19.250  24.965  1.00 17.25           O
ATOM   2265  N   HIS A 320      13.581  18.541  25.673  1.00 17.67           N
ATOM   2266  CA  HIS A 320      13.289  18.747  27.090  1.00 17.28           C
ATOM   2267  CB  HIS A 320      13.739  17.510  27.920  1.00 17.41           C
ATOM   2268  CG  HIS A 320      13.250  17.501  29.339  1.00 15.00           C
ATOM   2269  ND1 HIS A 320      13.866  16.760  30.326  1.00 14.46           N
ATOM   2270  CE1 HIS A 320      13.218  16.924  31.466  1.00 15.32           C
ATOM   2271  NE2 HIS A 320      12.244  17.802  31.271  1.00 14.42           N
ATOM   2272  CD2 HIS A 320      12.242  18.177  29.950  1.00 12.31           C
ATOM   2273  C   HIS A 320      13.888  20.082  27.570  1.00 17.67           C
ATOM   2274  O   HIS A 320      15.114  20.236  27.794  1.00 17.96           O
ATOM   2275  N   LEU A 321      13.016  21.076  27.696  1.00 17.51           N
ATOM   2276  CA  LEU A 321      13.470  22.421  27.986  1.00 17.39           C
ATOM   2277  CB  LEU A 321      12.745  23.453  27.104  1.00 17.62           C
ATOM   2278  CG  LEU A 321      12.875  23.291  25.573  1.00 18.44           C
ATOM   2279  CD1 LEU A 321      12.375  24.490  24.833  1.00 19.64           C
ATOM   2280  CD2 LEU A 321      14.336  23.091  25.176  1.00 21.10           C
ATOM   2281  C   LEU A 321      13.277  22.627  29.476  1.00 17.27           C
ATOM   2282  O   LEU A 321      12.331  23.274  29.927  1.00 16.80           O
ATOM   2283  N   ILE A 322      14.166  21.988  30.234  1.00 17.40           N
ATOM   2284  CA  ILE A 322      14.218  22.079  31.676  1.00 17.37           C
ATOM   2285  CB  ILE A 322      14.132  20.676  32.313  1.00 18.47           C
ATOM   2286  CG1 ILE A 322      14.012  20.766  33.823  1.00 15.54           C
ATOM   2287  CD1 ILE A 322      13.502  19.439  34.477  1.00 15.78           C
ATOM   2288  CG2 ILE A 322      15.361  19.722  31.879  1.00 16.66           C
ATOM   2289  C   ILE A 322      15.516  22.781  32.098  1.00 18.70           C
ATOM   2290  O   ILE A 322      16.577  22.463  31.573  1.00 18.76           O
ATOM   2291  N   ALA A 323      15.428  23.726  33.034  1.00 18.76           N
ATOM   2292  CA  ALA A 323      16.610  24.456  33.484  1.00 20.55           C
ATOM   2293  CB  ALA A 323      16.199  25.713  34.269  1.00 20.46           C
ATOM   2294  C   ALA A 323      17.454  23.548  34.367  1.00 21.58           C
ATOM   2295  O   ALA A 323      16.927  22.825  35.232  1.00 21.06           O
ATOM   2296  N   SER A 324      18.752  23.576  34.141  1.00 23.47           N
ATOM   2297  CA  SER A 324      19.686  22.719  34.884  1.00 25.69           C
ATOM   2298  CB  SER A 324      19.882  21.337  34.235  1.00 26.47           C
ATOM   2299  OG  SER A 324      20.852  20.612  35.001  1.00 28.42           O
ATOM   2300  C   SER A 324      21.019  23.416  34.947  1.00 26.05           C
ATOM   2301  O   SER A 324      21.652  23.577  33.894  1.00 26.92           O
ATOM   2302  N   PRO A 325      21.466  23.802  36.176  1.00 25.69           N
ATOM   2303  CA  PRO A 325      20.930  23.284  37.460  1.00 24.33           C
ATOM   2304  CB  PRO A 325      21.989  23.717  38.512  1.00 23.81           C
ATOM   2305  CG  PRO A 325      23.017  24.518  37.763  1.00 26.24           C
ATOM   2306  CD  PRO A 325      22.481  24.852  36.394  1.00 25.51           C
ATOM   2307  C   PRO A 325      19.547  23.822  37.843  1.00 22.91           C
ATOM   2308  O   PRO A 325      19.152  24.906  37.391  1.00 22.48           O
ATOM   2309  N   PHE A 326      18.835  23.067  38.684  1.00 21.63           N
```

FIGURE 4-33 (COORDINATES)

```
ATOM   2310  CA   PHE A 326      17.483  23.453  39.156  1.00 20.93           C
ATOM   2311  CB   PHE A 326      16.845  22.368  40.053  1.00 20.49           C
ATOM   2312  CG   PHE A 326      16.449  21.106  39.319  1.00 19.95           C
ATOM   2313  CD1  PHE A 326      16.800  20.895  37.985  1.00 19.08           C
ATOM   2314  CE1  PHE A 326      16.439  19.708  37.332  1.00 20.40           C
ATOM   2315  CZ   PHE A 326      15.716  18.715  38.029  1.00 21.31           C
ATOM   2316  CE2  PHE A 326      15.384  18.900  39.345  1.00 21.85           C
ATOM   2317  CD2  PHE A 326      15.762  20.096  39.995  1.00 21.75           C
ATOM   2318  C    PHE A 326      17.569  24.766  39.916  1.00 20.78           C
ATOM   2319  O    PHE A 326      18.624  25.093  40.464  1.00 20.45           O
ATOM   2320  N    PRO A 327      16.483  25.562  39.893  1.00 20.42           N
ATOM   2321  CA   PRO A 327      16.430  26.765  40.734  1.00 19.94           C
ATOM   2322  CB   PRO A 327      14.972  27.228  40.603  1.00 20.11           C
ATOM   2323  CG   PRO A 327      14.486  26.643  39.309  1.00 19.42           C
ATOM   2324  CD   PRO A 327      15.280  25.390  39.052  1.00 19.68           C
ATOM   2325  C    PRO A 327      16.739  26.436  42.187  1.00 20.14           C
ATOM   2326  O    PRO A 327      16.382  25.349  42.665  1.00 19.80           O
ATOM   2327  N    GLU A 328      17.429  27.352  42.872  1.00 20.77           N
ATOM   2328  CA   GLU A 328      17.675  27.255  44.321  1.00 21.32           C
ATOM   2329  CB   GLU A 328      18.338  28.562  44.840  1.00 22.11           C
ATOM   2330  CG   GLU A 328      18.951  28.480  46.252  1.00 24.64           C
ATOM   2331  CD   GLU A 328      17.949  28.481  47.407  1.00 26.36           C
ATOM   2332  OE1  GLU A 328      16.931  29.174  47.330  1.00 27.88           O
ATOM   2333  OE2  GLU A 328      18.201  27.787  48.419  1.00 29.06           O
ATOM   2334  C    GLU A 328      16.381  27.011  45.077  1.00 20.62           C
ATOM   2335  O    GLU A 328      16.360  26.264  46.063  1.00 21.21           O
ATOM   2336  N    VAL A 329      15.294  27.627  44.616  1.00 19.88           N
ATOM   2337  CA   VAL A 329      13.993  27.519  45.290  1.00 18.83           C
ATOM   2338  CB   VAL A 329      13.040  28.689  44.911  1.00 19.85           C
ATOM   2339  CG1  VAL A 329      13.619  30.028  45.373  1.00 19.57           C
ATOM   2340  CG2  VAL A 329      12.765  28.680  43.416  1.00 18.49           C
ATOM   2341  C    VAL A 329      13.218  26.222  45.026  1.00 17.76           C
ATOM   2342  O    VAL A 329      12.170  26.004  45.622  1.00 17.05           O
ATOM   2343  N    TRP A 330      13.722  25.381  44.132  1.00 17.77           N
ATOM   2344  CA   TRP A 330      13.088  24.092  43.771  1.00 18.06           C
ATOM   2345  CB   TRP A 330      14.049  23.231  42.949  1.00 17.72           C
ATOM   2346  CG   TRP A 330      13.447  21.921  42.407  1.00 17.65           C
ATOM   2347  CD1  TRP A 330      12.617  21.779  41.314  1.00 16.81           C
ATOM   2348  NE1  TRP A 330      12.313  20.436  41.130  1.00 15.94           N
ATOM   2349  CE2  TRP A 330      12.938  19.700  42.109  1.00 16.90           C
ATOM   2350  CD2  TRP A 330      13.658  20.599  42.930  1.00 16.96           C
ATOM   2351  CE3  TRP A 330      14.404  20.080  44.019  1.00 19.39           C
ATOM   2352  CZ3  TRP A 330      14.396  18.701  44.240  1.00 16.83           C
ATOM   2353  CH2  TRP A 330      13.658  17.841  43.404  1.00 17.42           C
ATOM   2354  CZ2  TRP A 330      12.944  18.319  42.330  1.00 13.87           C
ATOM   2355  C    TRP A 330      12.576  23.300  44.960  1.00 18.67           C
ATOM   2356  O    TRP A 330      13.338  22.979  45.892  1.00 18.74           O
ATOM   2357  N    HIS A 331      11.269  23.041  44.927  1.00 18.13           N
ATOM   2358  CA   HIS A 331      10.534  22.314  45.965  1.00 18.41           C
ATOM   2359  CB   HIS A 331      10.978  20.836  46.019  1.00 17.81           C
ATOM   2360  CG   HIS A 331      10.469  20.021  44.872  1.00 17.09           C
ATOM   2361  ND1  HIS A 331      10.566  18.646  44.825  1.00 14.35           N
ATOM   2362  CE1  HIS A 331      10.065  18.213  43.675  1.00 16.56           C
ATOM   2363  NE2  HIS A 331       9.627  19.255  42.987  1.00 17.90           N
ATOM   2364  CD2  HIS A 331       9.861  20.396  43.718  1.00 16.64           C
ATOM   2365  C    HIS A 331      10.641  22.941  47.335  1.00 18.48           C
ATOM   2366  O    HIS A 331      10.698  22.230  48.329  1.00 19.16           O
ATOM   2367  N    THR A 332      10.730  24.272  47.388  1.00 18.90           N
ATOM   2368  CA   THR A 332      10.649  25.022  48.656  1.00 17.97           C
ATOM   2369  CB   THR A 332      11.936  25.858  48.908  1.00 17.60           C
ATOM   2370  OG1  THR A 332      12.001  26.956  47.984  1.00 17.89           O
ATOM   2371  CG2  THR A 332      13.192  25.029  48.760  1.00 13.61           C
ATOM   2372  C    THR A 332       9.480  25.977  48.537  1.00 19.14           C
ATOM   2373  O    THR A 332       9.053  26.275  47.429  1.00 18.78           O
ATOM   2374  N    MET A 333       9.008  26.508  49.667  1.00 20.86           N
ATOM   2375  CA   MET A 333       7.925  27.504  49.680  1.00 22.25           C
ATOM   2376  CB   MET A 333       7.513  27.902  51.116  1.00 23.57           C
ATOM   2377  CG   MET A 333       6.919  26.832  52.019  1.00 27.02           C
ATOM   2378  SD   MET A 333       5.647  25.824  51.282  1.00 36.71           S
ATOM   2379  CE   MET A 333       4.980  24.965  52.708  1.00 31.36           C
```

FIGURE 4-34 (COORDINATES)

```
ATOM   2380  C   MET A 333       8.310  28.782  48.960  1.00 21.88           C
ATOM   2381  O   MET A 333       7.432  29.605  48.663  1.00 22.56           O
ATOM   2382  N   ASP A 334       9.611  28.970  48.714  1.00 21.16           N
ATOM   2383  CA  ASP A 334      10.119  30.162  48.044  1.00 20.41           C
ATOM   2384  CB  ASP A 334      11.534  30.526  48.549  1.00 20.81           C
ATOM   2385  CG  ASP A 334      11.555  30.828  50.029  1.00 21.80           C
ATOM   2386  OD1 ASP A 334      10.879  31.803  50.447  1.00 25.75           O
ATOM   2387  OD2 ASP A 334      12.211  30.086  50.785  1.00 20.20           O
ATOM   2388  C   ASP A 334      10.107  30.030  46.546  1.00 19.49           C
ATOM   2389  O   ASP A 334      10.556  30.931  45.868  1.00 19.28           O
ATOM   2390  N   ASP A 335       9.596  28.907  46.018  1.00 18.96           N
ATOM   2391  CA  ASP A 335       9.338  28.839  44.569  1.00 17.76           C
ATOM   2392  CB  ASP A 335       9.248  27.408  44.051  1.00 17.41           C
ATOM   2393  CG  ASP A 335       9.133  27.326  42.537  1.00 15.88           C
ATOM   2394  OD1 ASP A 335       9.267  28.351  41.833  1.00 15.45           O
ATOM   2395  OD2 ASP A 335       8.956  26.189  42.043  1.00 19.56           O
ATOM   2396  C   ASP A 335       8.041  29.566  44.336  1.00 17.66           C
ATOM   2397  O   ASP A 335       7.000  28.962  44.228  1.00 16.57           O
ATOM   2398  N   ASN A 336       8.137  30.882  44.265  1.00 18.03           N
ATOM   2399  CA  ASN A 336       6.965  31.741  44.287  1.00 18.64           C
ATOM   2400  CB  ASN A 336       6.715  32.290  45.714  1.00 18.65           C
ATOM   2401  CG  ASN A 336       7.899  33.093  46.286  1.00 18.83           C
ATOM   2402  OD1 ASN A 336       8.035  33.181  47.501  1.00 20.53           O
ATOM   2403  ND2 ASN A 336       8.740  33.673  45.426  1.00 15.85           N
ATOM   2404  C   ASN A 336       7.140  32.851  43.262  1.00 19.00           C
ATOM   2405  O   ASN A 336       8.138  32.872  42.543  1.00 19.03           O
ATOM   2406  N   GLU A 337       6.163  33.750  43.176  1.00 19.48           N
ATOM   2407  CA  GLU A 337       6.238  34.896  42.269  1.00 20.70           C
ATOM   2408  CB  GLU A 337       4.913  35.675  42.348  1.00 21.52           C
ATOM   2409  CG  GLU A 337       4.911  36.855  41.440  1.00 23.78           C
ATOM   2410  CD  GLU A 337       3.598  37.584  41.469  1.00 25.32           C
ATOM   2411  OE1 GLU A 337       2.679  37.163  42.199  1.00 23.10           O
ATOM   2412  OE2 GLU A 337       3.494  38.578  40.736  1.00 29.37           O
ATOM   2413  C   GLU A 337       7.402  35.877  42.519  1.00 21.00           C
ATOM   2414  O   GLU A 337       8.055  36.341  41.576  1.00 19.87           O
ATOM   2415  N   GLU A 338       7.657  36.191  43.783  1.00 21.73           N
ATOM   2416  CA  GLU A 338       8.775  37.089  44.147  1.00 22.82           C
ATOM   2417  CB  GLU A 338       8.880  37.256  45.671  1.00 23.41           C
ATOM   2418  CG  GLU A 338      10.027  37.881  46.269  0.00 33.64           C
ATOM   2419  CD  GLU A 338       9.821  38.446  47.673  0.00 42.39           C
ATOM   2420  OE1 GLU A 338      10.648  38.155  48.569  0.00 47.17           O
ATOM   2421  OE2 GLU A 338       8.821  39.171  47.887  0.00 46.79           O
ATOM   2422  C   GLU A 338      10.115  36.644  43.611  1.00 23.40           C
ATOM   2423  O   GLU A 338      10.977  37.489  43.302  1.00 23.68           O
ATOM   2424  N   ASN A 339      10.302  35.327  43.467  1.00 23.11           N
ATOM   2425  CA  ASN A 339      11.594  34.800  43.034  1.00 23.23           C
ATOM   2426  CB  ASN A 339      11.930  33.516  43.796  1.00 23.02           C
ATOM   2427  CG  ASN A 339      12.405  33.799  45.198  1.00 26.46           C
ATOM   2428  OD1 ASN A 339      11.646  33.685  46.163  1.00 32.14           O
ATOM   2429  ND2 ASN A 339      13.649  34.233  45.319  1.00 29.57           N
ATOM   2430  C   ASN A 339      11.714  34.588  41.535  1.00 22.65           C
ATOM   2431  O   ASN A 339      12.715  34.047  41.060  1.00 22.19           O
ATOM   2432  N   LEU A 340      10.673  34.987  40.806  1.00 22.01           N
ATOM   2433  CA  LEU A 340      10.665  34.897  39.363  1.00 21.21           C
ATOM   2434  CB  LEU A 340       9.225  34.828  38.834  1.00 20.42           C
ATOM   2435  CG  LEU A 340       8.421  33.558  39.146  1.00 18.65           C
ATOM   2436  CD1 LEU A 340       7.028  33.703  38.499  1.00 15.59           C
ATOM   2437  CD2 LEU A 340       9.155  32.250  38.678  1.00 14.09           C
ATOM   2438  C   LEU A 340      11.389  36.102  38.745  1.00 22.36           C
ATOM   2439  O   LEU A 340      11.408  37.202  39.308  1.00 22.02           O
ATOM   2440  N   HIS A 341      11.966  35.880  37.574  1.00 22.55           N
ATOM   2441  CA  HIS A 341      12.711  36.919  36.876  1.00 23.34           C
ATOM   2442  CB  HIS A 341      14.182  36.521  36.772  1.00 23.98           C
ATOM   2443  CG  HIS A 341      15.075  37.653  36.396  1.00 28.75           C
ATOM   2444  ND1 HIS A 341      15.720  37.722  35.179  1.00 32.66           N
ATOM   2445  CE1 HIS A 341      16.435  38.834  35.128  1.00 32.56           C
ATOM   2446  NE2 HIS A 341      16.256  39.498  36.254  1.00 31.24           N
ATOM   2447  CD2 HIS A 341      15.426  38.772  37.073  1.00 31.50           C
ATOM   2448  C   HIS A 341      12.058  37.172  35.521  1.00 21.83           C
ATOM   2449  O   HIS A 341      12.211  36.397  34.595  1.00 21.50           O
```

FIGURE 4-35 (COORDINATES)

```
ATOM   2450  N    ALA A 342      11.303  38.259  35.449  1.00 21.61           N
ATOM   2451  CA   ALA A 342      10.423  38.577  34.322  1.00 21.30           C
ATOM   2452  CB   ALA A 342       9.608  39.869  34.611  1.00 20.46           C
ATOM   2453  C    ALA A 342      11.105  38.667  32.959  1.00 21.51           C
ATOM   2454  O    ALA A 342      10.547  38.159  31.960  1.00 21.53           O
ATOM   2455  N    SER A 343      12.280  39.324  32.883  1.00 20.72           N
ATOM   2456  CA   SER A 343      12.932  39.522  31.567  1.00 20.48           C
ATOM   2457  CB   SER A 343      14.158  40.457  31.606  1.00 21.14           C
ATOM   2458  OG   SER A 343      15.252  39.861  32.298  1.00 22.54           O
ATOM   2459  C    SER A 343      13.331  38.186  30.978  1.00 19.60           C
ATOM   2460  O    SER A 343      13.182  37.988  29.771  1.00 19.04           O
ATOM   2461  N    THR A 344      13.790  37.265  31.829  1.00 18.74           N
ATOM   2462  CA   THR A 344      14.166  35.902  31.380  1.00 18.91           C
ATOM   2463  CB   THR A 344      14.670  35.066  32.568  1.00 18.54           C
ATOM   2464  OG1  THR A 344      15.775  35.725  33.202  1.00 23.33           O
ATOM   2465  CG2  THR A 344      15.130  33.701  32.123  1.00 17.73           C
ATOM   2466  C    THR A 344      12.958  35.170  30.751  1.00 17.79           C
ATOM   2467  O    THR A 344      13.058  34.543  29.692  1.00 18.39           O
ATOM   2468  N    ILE A 345      11.806  35.255  31.404  1.00 17.17           N
ATOM   2469  CA   ILE A 345      10.577  34.592  30.890  1.00 16.17           C
ATOM   2470  CB   ILE A 345       9.420  34.647  31.945  1.00 16.52           C
ATOM   2471  CG1  ILE A 345       9.859  33.966  33.252  1.00 14.45           C
ATOM   2472  CD1  ILE A 345       8.949  34.248  34.474  1.00 14.29           C
ATOM   2473  CG2  ILE A 345       8.104  33.999  31.381  1.00 17.10           C
ATOM   2474  C    ILE A 345      10.136  35.236  29.557  1.00 16.67           C
ATOM   2475  O    ILE A 345       9.808  34.548  28.590  1.00 15.53           O
ATOM   2476  N    ASP A 346      10.159  36.571  29.510  1.00 17.74           N
ATOM   2477  CA   ASP A 346       9.803  37.319  28.306  1.00 17.28           C
ATOM   2478  CB   ASP A 346       9.943  38.808  28.642  1.00 17.84           C
ATOM   2479  CG   ASP A 346       9.415  39.735  27.557  1.00 20.85           C
ATOM   2480  OD1  ASP A 346       8.398  39.414  26.897  1.00 18.13           O
ATOM   2481  OD2  ASP A 346      10.051  40.813  27.363  1.00 24.02           O
ATOM   2482  C    ASP A 346      10.741  36.909  27.140  1.00 16.90           C
ATOM   2483  O    ASP A 346      10.284  36.592  26.063  1.00 16.59           O
ATOM   2484  N    ASN A 347      12.055  36.932  27.351  1.00 16.48           N
ATOM   2485  CA   ASN A 347      13.021  36.440  26.333  1.00 16.07           C
ATOM   2486  CB   ASN A 347      14.479  36.448  26.850  1.00 15.67           C
ATOM   2487  CG   ASN A 347      14.991  37.852  27.168  1.00 17.26           C
ATOM   2488  OD1  ASN A 347      14.496  38.850  26.626  1.00 22.52           O
ATOM   2489  ND2  ASN A 347      15.965  37.934  28.057  1.00 18.00           N
ATOM   2490  C    ASN A 347      12.670  35.037  25.861  1.00 15.41           C
ATOM   2491  O    ASN A 347      12.643  34.795  24.674  1.00 15.55           O
ATOM   2492  N    LEU A 348      12.443  34.105  26.795  1.00 15.28           N
ATOM   2493  CA   LEU A 348      12.135  32.723  26.408  1.00 14.44           C
ATOM   2494  CB   LEU A 348      12.186  31.769  27.594  1.00 13.97           C
ATOM   2495  CG   LEU A 348      13.607  31.562  28.190  1.00 15.40           C
ATOM   2496  CD1  LEU A 348      13.522  31.080  29.648  1.00 14.94           C
ATOM   2497  CD2  LEU A 348      14.464  30.592  27.364  1.00 12.38           C
ATOM   2498  C    LEU A 348      10.809  32.619  25.694  1.00 14.58           C
ATOM   2499  O    LEU A 348      10.674  31.828  24.770  1.00 15.09           O
ATOM   2500  N    ASN A 349       9.823  33.424  26.113  1.00 14.31           N
ATOM   2501  CA   ASN A 349       8.582  33.543  25.327  1.00 14.99           C
ATOM   2502  CB   ASN A 349       7.638  34.619  25.917  1.00 14.29           C
ATOM   2503  CG   ASN A 349       6.813  34.099  27.091  1.00 13.62           C
ATOM   2504  OD1  ASN A 349       6.703  32.904  27.292  1.00 14.62           O
ATOM   2505  ND2  ASN A 349       6.273  35.006  27.885  1.00  9.88           N
ATOM   2506  C    ASN A 349       8.836  33.878  23.875  1.00 14.91           C
ATOM   2507  O    ASN A 349       8.289  33.241  22.988  1.00 15.99           O
ATOM   2508  N    LYS A 350       9.634  34.911  23.626  1.00 14.82           N
ATOM   2509  CA   LYS A 350       9.994  35.289  22.239  1.00 14.44           C
ATOM   2510  CB   LYS A 350      10.908  36.529  22.255  1.00 13.55           C
ATOM   2511  CG   LYS A 350      10.201  37.779  22.809  1.00 15.49           C
ATOM   2512  CD   LYS A 350      11.185  38.958  22.980  1.00 15.29           C
ATOM   2513  CE   LYS A 350      10.454  40.139  23.618  1.00 17.39           C
ATOM   2514  NZ   LYS A 350      11.408  41.259  23.971  1.00 17.49           N
ATOM   2515  C    LYS A 350      10.663  34.169  21.476  1.00 14.71           C
ATOM   2516  O    LYS A 350      10.292  33.855  20.331  1.00 15.29           O
ATOM   2517  N    ILE A 351      11.665  33.552  22.113  1.00 15.66           N
ATOM   2518  CA   ILE A 351      12.389  32.465  21.467  1.00 15.33           C
ATOM   2519  CB   ILE A 351      13.638  32.001  22.315  1.00 16.15           C
```

FIGURE 4-36 (COORDINATES)

```
ATOM   2520  CG1 ILE A 351      14.670  33.147  22.456  1.00 14.49           C
ATOM   2521  CD1 ILE A 351      15.568  32.989  23.739  1.00 15.43           C
ATOM   2522  CG2 ILE A 351      14.282  30.706  21.725  1.00 16.32           C
ATOM   2523  C   ILE A 351      11.485  31.302  21.125  1.00 15.07           C
ATOM   2524  O   ILE A 351      11.557  30.777  20.036  1.00 16.10           O
ATOM   2525  N   ILE A 352      10.630  30.890  22.062  1.00 14.61           N
ATOM   2526  CA  ILE A 352       9.805  29.722  21.842  1.00 14.59           C
ATOM   2527  CB  ILE A 352       9.262  29.158  23.185  1.00 13.34           C
ATOM   2528  CG1 ILE A 352      10.439  28.622  24.024  1.00 14.85           C
ATOM   2529  CD1 ILE A 352      10.064  28.272  25.462  1.00 16.20           C
ATOM   2530  CG2 ILE A 352       8.275  28.051  22.945  1.00 15.93           C
ATOM   2531  C   ILE A 352       8.700  30.041  20.818  1.00 14.85           C
ATOM   2532  O   ILE A 352       8.379  29.216  19.972  1.00 14.96           O
ATOM   2533  N   GLN A 353       8.154  31.244  20.861  1.00 14.59           N
ATOM   2534  CA  GLN A 353       7.178  31.626  19.829  1.00 15.16           C
ATOM   2535  CB  GLN A 353       6.557  32.983  20.174  1.00 15.15           C
ATOM   2536  CG  GLN A 353       5.568  32.892  21.348  1.00 15.31           C
ATOM   2537  CD  GLN A 353       5.201  34.259  21.878  1.00 17.62           C
ATOM   2538  OE1 GLN A 353       5.127  35.230  21.103  1.00 18.78           O
ATOM   2539  NE2 GLN A 353       4.953  34.351  23.200  1.00 16.94           N
ATOM   2540  C   GLN A 353       7.774  31.601  18.403  1.00 15.30           C
ATOM   2541  O   GLN A 353       7.148  31.103  17.464  1.00 16.15           O
ATOM   2542  N   VAL A 354       8.992  32.114  18.235  1.00 15.94           N
ATOM   2543  CA  VAL A 354       9.696  32.041  16.933  1.00 15.45           C
ATOM   2544  CB  VAL A 354      11.108  32.747  16.971  1.00 15.73           C
ATOM   2545  CG1 VAL A 354      11.890  32.448  15.679  1.00 14.34           C
ATOM   2546  CG2 VAL A 354      10.971  34.243  17.227  1.00 15.77           C
ATOM   2547  C   VAL A 354       9.872  30.572  16.518  1.00 16.82           C
ATOM   2548  O   VAL A 354       9.567  30.173  15.393  1.00 16.12           O
ATOM   2549  N   PHE A 355      10.371  29.760  17.442  1.00 17.61           N
ATOM   2550  CA  PHE A 355      10.561  28.342  17.169  1.00 17.41           C
ATOM   2551  CB  PHE A 355      11.031  27.608  18.447  1.00 17.01           C
ATOM   2552  CG  PHE A 355      11.252  26.118  18.233  1.00 18.71           C
ATOM   2553  CD1 PHE A 355      12.511  25.638  17.863  1.00 18.77           C
ATOM   2554  CE1 PHE A 355      12.729  24.262  17.625  1.00 18.68           C
ATOM   2555  CZ  PHE A 355      11.681  23.374  17.747  1.00 16.82           C
ATOM   2556  CE2 PHE A 355      10.401  23.848  18.114  1.00 18.16           C
ATOM   2557  CD2 PHE A 355      10.198  25.213  18.345  1.00 19.79           C
ATOM   2558  C   PHE A 355       9.279  27.725  16.613  1.00 18.16           C
ATOM   2559  O   PHE A 355       9.276  27.063  15.576  1.00 18.53           O
ATOM   2560  N   VAL A 356       8.175  27.962  17.308  1.00 18.33           N
ATOM   2561  CA  VAL A 356       6.894  27.392  16.941  1.00 18.78           C
ATOM   2562  CB  VAL A 356       5.847  27.655  18.064  1.00 18.61           C
ATOM   2563  CG1 VAL A 356       4.413  27.354  17.573  1.00 18.89           C
ATOM   2564  CG2 VAL A 356       6.201  26.814  19.282  1.00 18.10           C
ATOM   2565  C   VAL A 356       6.409  27.870  15.562  1.00 19.57           C
ATOM   2566  O   VAL A 356       5.988  27.061  14.734  1.00 19.29           O
ATOM   2567  N   LEU A 357       6.469  29.179  15.317  1.00 19.87           N
ATOM   2568  CA  LEU A 357       6.118  29.728  13.983  1.00 20.52           C
ATOM   2569  CB  LEU A 357       6.245  31.264  13.962  1.00 19.26           C
ATOM   2570  CG  LEU A 357       5.181  32.020  14.781  1.00 19.26           C
ATOM   2571  CD1 LEU A 357       5.289  33.520  14.490  1.00 20.62           C
ATOM   2572  CD2 LEU A 357       3.793  31.499  14.372  1.00 19.74           C
ATOM   2573  C   LEU A 357       6.992  29.125  12.883  1.00 21.15           C
ATOM   2574  O   LEU A 357       6.518  28.755  11.807  1.00 21.90           O
ATOM   2575  N   GLU A 358       8.273  29.035  13.162  1.00 22.10           N
ATOM   2576  CA  GLU A 358       9.207  28.483  12.183  1.00 23.43           C
ATOM   2577  CB  GLU A 358      10.642  28.740  12.624  1.00 22.74           C
ATOM   2578  CG  GLU A 358      11.010  30.184  12.467  1.00 24.28           C
ATOM   2579  CD  GLU A 358      12.467  30.470  12.715  1.00 27.29           C
ATOM   2580  OE1 GLU A 358      13.149  29.624  13.343  1.00 26.16           O
ATOM   2581  OE2 GLU A 358      12.920  31.563  12.313  1.00 29.38           O
ATOM   2582  C   GLU A 358       8.944  26.989  11.891  1.00 24.12           C
ATOM   2583  O   GLU A 358       9.061  26.561  10.737  1.00 24.93           O
ATOM   2584  N   TYR A 359       8.563  26.221  12.917  1.00 23.58           N
ATOM   2585  CA  TYR A 359       8.282  24.799  12.769  1.00 24.10           C
ATOM   2586  CB  TYR A 359       8.034  24.128  14.146  1.00 23.75           C
ATOM   2587  CG  TYR A 359       8.112  22.614  14.062  1.00 23.68           C
ATOM   2588  CD1 TYR A 359       9.284  21.944  14.392  1.00 21.69           C
ATOM   2589  CE1 TYR A 359       9.369  20.558  14.282  1.00 23.95           C
```

FIGURE 4-37 (COORDINATES)

```
ATOM   2590  CZ  TYR A 359       8.270  19.836  13.834  1.00 22.82           C
ATOM   2591  OH  TYR A 359       8.341  18.486  13.703  1.00 25.66           O
ATOM   2592  CE2 TYR A 359       7.106  20.461  13.517  1.00 22.86           C
ATOM   2593  CD2 TYR A 359       7.023  21.859  13.623  1.00 22.65           C
ATOM   2594  C   TYR A 359       7.051  24.605  11.888  1.00 24.66           C
ATOM   2595  O   TYR A 359       7.020  23.716  11.009  1.00 23.78           O
ATOM   2596  N   LEU A 360       6.051  25.458  12.133  1.00 25.15           N
ATOM   2597  CA  LEU A 360       4.744  25.394  11.485  1.00 26.51           C
ATOM   2598  CB  LEU A 360       3.652  25.929  12.444  1.00 25.92           C
ATOM   2599  CG  LEU A 360       3.359  25.091  13.702  1.00 24.52           C
ATOM   2600  CD1 LEU A 360       2.392  25.776  14.666  1.00 20.55           C
ATOM   2601  CD2 LEU A 360       2.845  23.721  13.320  1.00 22.75           C
ATOM   2602  C   LEU A 360       4.690  26.139  10.140  1.00 28.16           C
ATOM   2603  O   LEU A 360       3.650  26.147   9.482  1.00 29.11           O
ATOM   2604  N   HIS A 361       5.798  26.762   9.746  1.00 29.87           N
ATOM   2605  CA  HIS A 361       5.871  27.592   8.528  1.00 31.63           C
ATOM   2606  CB  HIS A 361       5.801  26.710   7.259  1.00 32.31           C
ATOM   2607  CG  HIS A 361       6.911  25.708   7.162  1.00 34.77           C
ATOM   2608  ND1 HIS A 361       7.319  25.162   5.963  1.00 36.79           N
ATOM   2609  CE1 HIS A 361       8.317  24.321   6.180  1.00 36.62           C
ATOM   2610  NE2 HIS A 361       8.573  24.303   7.474  1.00 36.64           N
ATOM   2611  CD2 HIS A 361       7.713  25.167   8.110  1.00 35.94           C
ATOM   2612  C   HIS A 361       4.783  28.664   8.513  1.00 31.93           C
ATOM   2613  O   HIS A 361       4.029  28.791   7.547  1.00 32.80           O
ATOM   2614  N   LEU A 362       4.687  29.404   9.616  1.00 31.48           N
ATOM   2615  CA  LEU A 362       3.747  30.501   9.762  1.00 30.70           C
ATOM   2616  CB  LEU A 362       2.831  30.263  10.964  1.00 30.22           C
ATOM   2617  CG  LEU A 362       1.837  29.120  10.852  1.00 29.32           C
ATOM   2618  CD1 LEU A 362       1.093  28.914  12.178  1.00 27.52           C
ATOM   2619  CD2 LEU A 362       0.851  29.403   9.695  1.00 28.52           C
ATOM   2620  C   LEU A 362       4.513  31.793   9.969  1.00 30.52           C
ATOM   2621  O   LEU A 362       3.933  32.870   9.934  1.00 30.75           O
ATOM   2622  OXT LEU A 362       5.716  31.782  10.191  1.00 29.63           O
ATOM   2623  ZN   ZN B 121       8.717  19.557  41.054  1.00 16.05          ZN
ATOM   2624  N4  PQ5 C   1      16.252  15.673  43.611  1.00 43.58           N
ATOM   2625  C18 PQ5 C   1      15.812  15.582  42.428  1.00 44.34           C
ATOM   2626  N1  PQ5 C   1      15.575  15.033  41.419  1.00 44.43           N
ATOM   2627  C1  PQ5 C   1      15.781  14.560  40.203  1.00 44.14           C
ATOM   2628  N3  PQ5 C   1      17.068  14.671  39.976  1.00 43.48           N
ATOM   2629  C2  PQ5 C   1      17.795  14.324  38.899  1.00 44.62           C
ATOM   2630  C7  PQ5 C   1      19.225  14.640  38.991  1.00 44.69           C
ATOM   2631  C10 PQ5 C   1      19.577  15.300  40.295  1.00 45.47           C
ATOM   2632  C6  PQ5 C   1      20.164  14.349  37.968  1.00 44.76           C
ATOM   2633  C5  PQ5 C   1      19.742  13.714  36.815  1.00 44.17           C
ATOM   2634  C9  PQ5 C   1      20.613  13.349  35.649  1.00 43.73           C
ATOM   2635  C4  PQ5 C   1      18.502  13.559  36.969  1.00 45.25           C
ATOM   2636  C3  PQ5 C   1      17.410  13.675  37.625  1.00 46.00           C
ATOM   2637  C8  PQ5 C   1      16.037  13.234  37.222  1.00 44.44           C
ATOM   2638  N2  PQ5 C   1      14.903  14.002  39.358  1.00 43.35           N
ATOM   2639  C15 PQ5 C   1      13.465  13.830  39.427  1.00 42.25           C
ATOM   2640  C16 PQ5 C   1      13.003  15.250  38.985  1.00 30.60           C
ATOM   2641  C17 PQ5 C   1      11.484  15.350  38.981  1.00 21.64           C
ATOM   2642  N5  PQ5 C   1      10.913  16.710  39.044  1.00 18.32           N
ATOM   2643  C13 PQ5 C   1      10.227  17.235  40.067  1.00 15.56           C
ATOM   2644  N6  PQ5 C   1       9.826  18.509  39.749  1.00 17.83           N
ATOM   2645  C12 PQ5 C   1      10.223  18.781  38.478  1.00 16.84           C
ATOM   2646  C11 PQ5 C   1      10.873  17.630  38.064  1.00 16.85           C
ATOM   2647  C14 PQ5 C   1      11.430  17.674  36.666  1.00 13.88           C
ATOM   2648  O   HOH E   1       6.488  21.052  33.385  1.00 15.88           O
ATOM   2649  O   HOH E   2      18.166  36.064  31.856  1.00 30.18           O
ATOM   2650  O   HOH E   3      14.707  28.460  35.776  1.00 19.71           O
ATOM   2651  O   HOH E   4      -0.423  35.873  15.178  1.00 29.34           O
ATOM   2652  O   HOH E   5       5.183  32.060  25.229  1.00 15.19           O
ATOM   2653  O   HOH E   6       6.019   6.035  18.041  1.00 44.10           O
ATOM   2654  O   HOH E   7      -6.049  24.337  46.568  1.00 18.79           O
ATOM   2655  O   HOH E   8      16.305  17.989  24.812  1.00 18.74           O
ATOM   2656  O   HOH E   9      16.218  28.022  50.262  1.00 21.88           O
ATOM   2657  O   HOH E  10      11.404  25.445  14.667  1.00 19.29           O
ATOM   2658  O   HOH E  11     -12.538  29.568  18.539  1.00 30.55           O
ATOM   2659  O   HOH E  12       4.387  37.337  19.586  1.00 13.30           O
```

FIGURE 4-38 (COORDINATES)

```
ATOM   2660  O   HOH E   13    -11.832   11.472   30.582  1.00 32.94           O
ATOM   2661  O   HOH E   14      2.201   13.547   34.717  1.00 12.32           O
ATOM   2662  O   HOH E   15      1.709   35.049   44.127  1.00 33.89           O
ATOM   2663  O   HOH E   16     12.215   35.267   48.878  1.00 38.16           O
ATOM   2664  O   HOH E   17     -0.239   41.995   23.890  1.00 35.45           O
ATOM   2665  O   HOH E   18     26.787   38.785   24.096  1.00 24.96           O
ATOM   2666  O   HOH E   19     11.225   15.689   15.766  1.00 29.73           O
ATOM   2667  O   HOH E   20     13.923   29.034    5.710  1.00 32.52           O
ATOM   2668  O   HOH E   21     10.219   31.019   41.932  1.00 16.31           O
ATOM   2669  O   HOH E   22      5.986   35.806   46.318  1.00 16.68           O
ATOM   2670  O   HOH E   23      2.488   23.214   37.683  1.00 10.52           O
ATOM   2671  O   HOH E   24    -13.565   35.291   23.038  1.00 31.50           O
ATOM   2672  O   HOH E   25      6.339   37.786   27.071  1.00 14.60           O
ATOM   2673  O   HOH E   26     -3.516   38.435   28.251  1.00 22.91           O
ATOM   2674  O   HOH E   27     -7.628   17.939   22.041  1.00 22.95           O
ATOM   2675  O   HOH E   28     17.309   27.986   36.816  1.00 19.72           O
ATOM   2676  O   HOH E   29     -1.530   36.512   28.223  1.00 17.03           O
ATOM   2677  O   HOH E   30     18.321   10.430   20.981  1.00 33.46           O
ATOM   2678  O   HOH E   31     27.767   18.557   29.924  1.00 44.14           O
ATOM   2679  O   HOH E   32      9.921   23.721   42.514  1.00 15.98           O
ATOM   2680  O   HOH E   33     15.847   14.722   30.198  1.00 20.84           O
ATOM   2681  O   HOH E   34     -4.283   30.400   19.568  1.00 18.04           O
ATOM   2682  O   HOH E   35     21.901   26.098   13.904  1.00 45.14           O
ATOM   2683  O   HOH E   36     23.377   32.289   34.138  1.00 46.01           O
ATOM   2684  O   HOH E   37     14.266   12.823   21.646  1.00 24.71           O
ATOM   2685  O   HOH E   38      7.901   15.117   43.093  1.00 18.18           O
ATOM   2686  O   HOH E   39     18.753   41.911   22.576  1.00 18.10           O
ATOM   2687  O   HOH E   40     -3.686   33.157   27.135  1.00 19.48           O
ATOM   2688  O   HOH E   41     -3.678   19.667   53.146  1.00 27.23           O
ATOM   2689  O   HOH E   42     27.083   26.151   23.639  1.00 42.11           O
ATOM   2690  O   HOH E   43      5.170   21.317   41.574  1.00 17.17           O
ATOM   2691  O   HOH E   44     -7.976   12.365   25.836  1.00 45.76           O
ATOM   2692  O   HOH E   45     -7.259   26.762   46.697  1.00 46.01           O
ATOM   2693  O   HOH E   46      9.895   20.708    5.544  1.00 39.17           O
ATOM   2694  O   HOH E   47     15.651   10.579   21.658  1.00 26.41           O
ATOM   2695  O   HOH E   48     22.336   30.588   21.710  1.00 49.05           O
ATOM   2696  O   HOH E   49     12.598   40.660   26.447  1.00 19.52           O
ATOM   2697  O   HOH E   50     12.961    5.763   32.994  1.00 43.36           O
ATOM   2698  O   HOH E   51     21.933   31.771   31.367  1.00 28.84           O
ATOM   2699  O   HOH E   52     -8.008   27.518   13.752  1.00 27.56           O
ATOM   2700  O   HOH E   53      7.941   31.379   51.606  1.00 40.89           O
ATOM   2701  O   HOH E   54     16.756   16.883    8.653  1.00 43.18           O
ATOM   2702  O   HOH E   55      0.142   39.261   19.675  1.00 29.23           O
ATOM   2703  O   HOH E   56     13.309   41.109   35.336  1.00 25.96           O
ATOM   2704  O   HOH E   57      5.691   27.946   46.424  1.00 20.43           O
ATOM   2705  O   HOH E   58      6.699    7.319   36.841  1.00 22.59           O
ATOM   2706  O   HOH E   59     11.513   17.017   46.728  1.00 18.29           O
ATOM   2707  O   HOH E   60    -12.816   15.571   27.116  1.00 33.15           O
ATOM   2708  O   HOH E   61    -12.868   31.551   15.811  1.00 35.92           O
ATOM   2709  O   HOH E   62     -3.802   18.886   39.891  1.00 21.70           O
ATOM   2710  O   HOH E   63      2.239   15.840   44.736  1.00 19.78           O
ATOM   2711  O   HOH E   64     14.936   17.880    4.660  1.00 70.16           O
ATOM   2712  O   HOH E   65     10.889   17.128   13.470  1.00 27.34           O
ATOM   2713  O   HOH E   66     18.338   31.468   11.784  1.00 36.49           O
ATOM   2714  O   HOH E   67     10.293    8.650   37.459  1.00 30.66           O
ATOM   2715  O   HOH E   68     -7.239   38.715   28.429  1.00 35.36           O
ATOM   2716  O   HOH E   69     17.301   21.394   10.534  1.00 41.52           O
ATOM   2717  O   HOH E   70      4.621   12.787   13.031  1.00 33.97           O
ATOM   2718  O   HOH E   71     23.601   38.644   30.413  1.00 56.51           O
ATOM   2719  O   HOH E   72     15.182   32.687   12.126  1.00 35.03           O
ATOM   2720  O   HOH E   73     -2.223   25.311    6.377  1.00 44.51           O
ATOM   2721  O   HOH E   74     24.743   23.836   14.126  1.00 40.04           O
ATOM   2722  O   HOH E   75     -3.134    2.547   39.330  1.00 35.45           O
ATOM   2723  O   HOH E   76      6.764   41.550   26.649  1.00 24.23           O
ATOM   2724  O   HOH E   77      6.265    7.185   47.658  1.00 56.47           O
ATOM   2725  O   HOH E   78      2.444   24.441   55.183  1.00 37.25           O
ATOM   2726  O   HOH E   79     17.360   10.499   35.563  1.00 26.10           O
ATOM   2727  O   HOH E   80     -0.310   27.413    7.098  1.00 43.18           O
ATOM   2728  O   HOH E   81      1.046   22.267   46.305  1.00 21.90           O
ATOM   2729  O   HOH E   82     16.926   20.622   25.577  1.00 27.20           O
```

FIGURE 4-39 (COORDINATES)

```
ATOM   2730  O   HOH E   83      17.005  38.492  31.410  1.00 27.23           O
ATOM   2731  O   HOH E   84       0.681  21.385  49.193  1.00 22.37           O
ATOM   2732  O   HOH E   85     -10.413  29.214  37.578  1.00 29.69           O
ATOM   2733  O   HOH E   86      24.831  17.566  22.656  1.00 55.17           O
ATOM   2734  O   HOH E   87      10.118  25.741  52.115  1.00 20.70           O
ATOM   2735  O   HOH E   88      18.298  45.402  28.425  1.00 36.37           O
ATOM   2736  O   HOH E   89     -13.373  14.916  33.248  1.00 34.18           O
ATOM   2737  O   HOH E   90      -6.201  33.771  26.292  1.00 21.09           O
ATOM   2738  O   HOH E   91      -0.987   6.956  35.865  1.00 22.11           O
ATOM   2739  O   HOH E   92     -10.309  28.457  21.137  1.00 24.97           O
ATOM   2740  O   HOH E   93       1.765  33.377   8.557  1.00 45.38           O
ATOM   2741  O   HOH E   94      -9.046  22.758  14.822  1.00 21.99           O
ATOM   2742  O   HOH E   95      11.405  49.637  15.704  1.00 40.89           O
ATOM   2743  O   HOH E   96      -3.962  37.571  20.040  1.00 40.21           O
ATOM   2744  O   HOH E   97       9.580  42.799  25.309  1.00 25.97           O
ATOM   2745  O   HOH E   98      12.797  31.349  40.964  1.00 27.98           O
ATOM   2746  O   HOH E   99      -6.332  34.445  11.204  1.00 30.53           O
ATOM   2747  O   HOH E  100      22.335  36.283  13.692  1.00 37.69           O
ATOM   2748  O   HOH E  101      27.096  39.918  31.189  1.00 46.19           O
ATOM   2749  O   HOH E  102       5.026  15.154  47.855  1.00 22.44           O
ATOM   2750  O   HOH E  103       9.095  16.151   6.055  1.00 44.45           O
ATOM   2751  O   HOH E  104       7.111  42.773  23.493  1.00 30.73           O
ATOM   2752  O   HOH E  105      -4.659   1.552  18.739  1.00 38.69           O
ATOM   2753  O   HOH E  106      18.916  15.805  15.166  1.00 30.30           O
ATOM   2754  O   HOH E  107      -6.030  13.734  21.996  1.00 52.44           O
ATOM   2755  O   HOH E  108      -6.621  16.173  39.913  1.00 25.19           O
ATOM   2756  O   HOH E  109      -1.730  18.617  54.667  1.00 26.75           O
ATOM   2757  O   HOH E  110       6.261  10.358  17.313  1.00 26.83           O
ATOM   2758  O   HOH E  111      24.080  19.730  26.876  1.00 25.33           O
ATOM   2759  O   HOH E  112     -11.269  30.889  35.278  1.00 35.62           O
ATOM   2760  O   HOH E  113       1.669  33.172  54.578  1.00 47.01           O
ATOM   2761  O   HOH E  114     -11.639  21.576  14.490  1.00 44.78           O
ATOM   2762  O   HOH E  115      19.470  41.806  25.122  1.00 36.92           O
ATOM   2763  O   HOH E  116       5.803  15.378  50.614  1.00 55.42           O
ATOM   2764  O   HOH E  117     -13.241  31.181  27.470  1.00 30.99           O
ATOM   2765  O   HOH E  118       9.085  35.287   7.346  1.00 41.75           O
ATOM   2766  O   HOH E  119      -3.484  41.004  19.403  1.00 48.79           O
ATOM   2767  O   HOH E  120      -9.379  35.601  30.812  1.00 33.42           O
ATOM   2768  O   HOH E  121      10.361  42.316  29.563  1.00 48.97           O
ATOM   2769  O   HOH E  122       0.261  14.615  55.090  1.00 38.36           O
ATOM   2770  O   HOH E  123      12.253   9.328  21.188  1.00 32.01           O
ATOM   2771  O   HOH E  124      -4.473  24.139   3.003  1.00 54.94           O
ATOM   2772  O   HOH E  125      12.773  38.534  41.426  1.00 44.39           O
ATOM   2773  O   HOH E  126      -7.282  35.876  33.644  1.00 26.39           O
ATOM   2774  O   HOH E  127      20.458  10.324  33.789  1.00 42.81           O
ATOM   2775  O   HOH E  128       5.699  32.297  49.457  1.00 36.57           O
ATOM   2776  O   HOH E  129      19.887  26.912  35.316  1.00 30.85           O
ATOM   2777  O   HOH E  130      21.129   9.577  30.709  1.00 39.42           O
ATOM   2778  O   HOH E  131      15.883  42.346  33.967  1.00 35.21           O
ATOM   2779  O   HOH E  132      -9.670   9.133  30.119  1.00 36.19           O
ATOM   2780  O   HOH E  133       7.230  18.230   6.297  1.00 37.31           O
ATOM   2781  O   HOH E  134     -13.227  22.336  22.397  1.00 31.69           O
ATOM   2782  O   HOH E  135      -7.094   6.498   8.031  1.00 44.77           O
ATOM   2783  O   HOH E  136       1.893  23.456  50.294  1.00 32.70           O
ATOM   2784  O   HOH E  137       5.839  35.665   9.958  1.00 53.37           O
ATOM   2785  O   HOH E  138      15.204  25.308   6.756  1.00 64.77           O
ATOM   2786  O   HOH E  139       0.853  14.553  41.680  1.00 33.94           O
ATOM   2787  O   HOH E  140     -10.061  19.411  42.311  1.00 39.46           O
ATOM   2788  O   HOH E  141       2.343  30.561  50.808  1.00 47.33           O
ATOM   2789  O   HOH E  142       8.029   6.117  34.268  1.00 31.44           O
ATOM   2790  O   HOH E  143      -8.763   7.740   9.463  1.00 41.70           O
ATOM   2791  O   HOH E  144      -3.281  28.389  47.178  1.00 29.94           O
ATOM   2792  O   HOH E  145      -5.446   9.960  52.914  1.00 32.09           O
ATOM   2793  O   HOH E  146       2.315   3.185  34.195  1.00 40.15           O
ATOM   2794  O   HOH E  147      21.736  16.497  32.797  1.00 39.53           O
ATOM   2795  O   HOH E  148      19.986  19.231   9.980  1.00 45.29           O
ATOM   2796  O   HOH E  149       1.447   3.612  51.081  1.00 47.45           O
ATOM   2797  O   HOH E  150       3.324  42.308  16.817  1.00 36.56           O
ATOM   2798  O   HOH E  151      17.501  25.418   9.370  1.00 45.08           O
ATOM   2799  O   HOH E  152      18.536  29.576  38.819  1.00 42.69           O
```

FIGURE 4-40 (COORDINATES)

```
ATOM   2800  O   HOH E 153       1.942  23.501   8.952  1.00 43.22           O
ATOM   2801  O   HOH E 154     -12.610  11.116  39.127  1.00 40.95           O
ATOM   2802  O   HOH E 155       0.984   1.676  16.088  1.00 41.29           O
ATOM   2803  O   HOH E 156       4.168  33.316  51.430  1.00 61.89           O
ATOM   2804  O   HOH E 157      -3.804  40.507  26.128  1.00 40.99           O
ATOM   2805  O   HOH E 158     -15.018  32.953  18.474  1.00 59.70           O
ATOM   2806  O   HOH E 159      22.128  42.359  31.530  1.00 46.91           O
ATOM   2807  O   HOH E 160       5.617   9.084  13.446  1.00 39.76           O
ATOM   2808  O   HOH E 161      19.775  12.311  27.766  1.00 46.90           O
ATOM   2809  O   HOH E 162      22.253  18.643  14.647  1.00 58.37           O
ATOM   2810  O   HOH E 163       5.826  12.190  10.525  1.00 32.63           O
ATOM   2811  O   HOH E 164      -9.795  24.251  12.633  1.00 36.20           O
ATOM   2812  O   HOH E 165      20.283  27.160  39.797  1.00 35.11           O
ATOM   2813  O   HOH E 166      -7.583  32.920   9.611  1.00 38.44           O
ATOM   2814  O   HOH E 167      -6.217  42.651  28.096  1.00 46.57           O
ATOM   2815  O   HOH E 168      16.374  14.975   5.967  1.00 53.06           O
ATOM   2816  O   HOH E 169      25.415  10.251  28.199  1.00 60.89           O
ATOM   2817  O   HOH E 170      23.725  15.536  34.284  1.00 45.49           O
ATOM   2818  O   HOH E 171     -12.747  28.062  38.672  1.00 42.55           O
ATOM   2819  O   HOH E 172      -6.670  20.885  49.475  1.00 26.96           O
ATOM   2820  O   HOH E 173      11.997  24.935  40.781  1.00 26.91           O
ATOM   2821  O   HOH E 175      22.086  27.953  34.948  1.00 45.61           O
ATOM   2822  O   HOH E 176      16.249   8.181  23.911  1.00 45.96           O
ATOM   2823  O   HOH E 177      24.661  19.484  29.585  1.00 44.33           O
ATOM   2824  O   HOH E 178      13.462   7.003  21.910  1.00 42.81           O
ATOM   2825  O   HOH E 179      27.674  16.424  29.208  1.00 45.30           O
ATOM   2826  O   HOH E 180      20.694  43.118  27.450  1.00 45.13           O
ATOM   2827  O   HOH E 181      13.716  17.002  47.547  1.00 38.93           O
ATOM   2828  O   HOH E 182       3.626  13.340  51.294  1.00 39.84           O
ATOM   2829  O   HOH E 183      12.901  49.363  18.645  1.00 43.36           O
ATOM   2830  O   HOH E 184      -6.734  31.122  40.689  1.00 51.21           O
ATOM   2831  O   HOH E 185      15.507  37.137  40.030  1.00 36.52           O
ATOM   2832  O   HOH E 186       3.498  32.228  47.032  1.00 33.10           O
ATOM   2833  O   HOH E 187      10.588  15.061  43.374  1.00 21.65           O
ATOM   2834  O   HOH E 188      15.392  30.557  42.406  1.00 27.85           O
ATOM   2835  O   HOH E 190      -3.957  27.096  49.696  1.00 46.05           O
ATOM   2836  O   HOH E 191      -8.792  27.619  44.086  1.00 32.10           O
ATOM   2837  O   HOH E 192       3.272  45.238  17.411  1.00 63.47           O
ATOM   2838  O   HOH E 193      23.000  29.536  37.806  1.00 49.27           O
ATOM   2839  O   HOH E 194     -12.264   9.360  36.765  1.00 46.79           O
ATOM   2840  O   HOH E 195       1.243  31.824  48.164  1.00 35.29           O
ATOM   2841  O   HOH E 196      -8.701  31.292  38.494  1.00 42.14           O
ATOM   2842  O   HOH E 197      -9.114  33.927  37.130  1.00 41.74           O
ATOM   2843  O   HOH E 199      21.516  32.999  14.484  1.00 27.31           O
ATOM   2844  O   HOH E 200       6.645  18.321  33.245  1.00 12.80           O
ATOM   2845  O   HOH E 201      13.054  41.627   7.347  1.00 38.93           O
ATOM   2846  O   HOH E 202      12.108  40.572  37.389  1.00 37.36           O
ATOM   2847  O   HOH E 203     -14.559  31.615  20.646  1.00 31.24           O
ATOM   2848  O   HOH E 204      14.317  30.486  33.908  1.00 18.31           O
ATOM   2849  O   HOH E 205       3.527  33.110  44.417  1.00 17.12           O
ATOM   2850  O   HOH E 206      17.686  17.291  22.495  1.00 29.06           O
ATOM   2851  O   HOH E 207       2.814  37.709  17.341  1.00 23.73           O
ATOM   2852  O   HOH E 208      24.096  35.772  29.344  1.00 27.91           O
ATOM   2853  O   HOH E 209      -5.706  23.342  48.919  1.00 30.17           O
ATOM   2854  O   HOH E 210      22.837  26.755  16.523  1.00 36.17           O
ATOM   2855  O   HOH E 211      -9.503  14.990  38.153  1.00 23.99           O
ATOM   2856  O   HOH E 212     -11.967  26.686  21.480  1.00 35.27           O
ATOM   2857  O   HOH E 213      23.357  30.523  32.480  1.00 54.52           O
ATOM   2858  O   HOH E 214      13.340  26.887  13.740  1.00 32.33           O
ATOM   2859  O   HOH E 215      17.927  29.983  41.146  1.00 30.74           O
ATOM   2860  O   HOH E 216      22.781  31.915  39.173  1.00 49.35           O
ATOM   2861  O   HOH E 217      13.687  28.257  49.772  1.00 25.46           O
ATOM   2862  O   HOH E 218       6.481  42.840  11.954  1.00 46.39           O
ATOM   2863  O   HOH E 219      -2.302  37.046  17.078  1.00 25.17           O
ATOM   2864  O   HOH E 220      14.396  11.706  41.886  1.00 39.81           O
ATOM   2865  O   HOH E 221       5.551  39.559   3.485  1.00 55.33           O
ATOM   2866  O   HOH E 222       4.650  29.956  48.108  1.00 34.93           O
ATOM   2867  O   HOH E 223     -12.549  30.134  20.869  1.00 25.08           O
ATOM   2868  O   HOH E 224       3.766  40.451   5.303  1.00 56.63           O
ATOM   2869  O   HOH E 225      24.468  21.898  28.568  1.00 86.22           O
```

FIGURE 4-41 (COORDINATES)

```
ATOM  2870  O   HOH E 226    -8.432  12.639  43.662  1.00 46.53           O
ATOM  2871  O   HOH E 227    14.718  44.493  23.375  1.00 35.24           O
ATOM  2872  O   HOH E 228     0.078  14.357   4.779  1.00 46.40           O
ATOM  2873  O   HOH E 229    -0.901  13.029  17.568  1.00 31.53           O
ATOM  2874  O   HOH E 230    13.983  44.057   7.300  1.00 50.90           O
ATOM  2875  O   HOH E 231   -13.309  27.180  18.800  1.00 52.66           O
ATOM  2876  O   HOH E 232    15.969  46.593  27.632  1.00 44.05           O
ATOM  2877  O   HOH E 233    15.747  11.660  37.240  1.00 29.96           O
ATOM  2878  O   HOH E 234    12.886  37.706  49.169  1.00 45.63           O
ATOM  2879  O   HOH E 235    -1.520   5.732   8.895  1.00 38.71           O
ATOM  2880  O   HOH E 236   -13.525  26.742  31.656  1.00 43.92           O
ATOM  2881  O   HOH E 237    20.402  32.457  40.290  1.00 58.96           O
ATOM  2882  O   HOH E 238    11.014  40.206  42.990  1.00 42.08           O
ATOM  2883  O   HOH E 239    11.876  40.140   2.756  1.00 51.56           O
ATOM  2884  O   HOH E 240    11.027  33.136  52.969  1.00 32.01           O
ATOM  2885  O   HOH E 241   -11.768  25.283  43.330  1.00 44.13           O
ATOM  2886  O   HOH E 242    -3.677  13.537  20.170  1.00 37.10           O
ATOM  2887  O   HOH E 243    -8.132   4.306  23.124  1.00 43.01           O
ATOM  2888  O   HOH E 244    14.417  34.056   6.439  1.00 47.65           O
ATOM  2889  O   HOH E 245    -1.303  14.127  15.335  1.00 29.71           O
ATOM  2890  O   HOH E 246    -2.126  34.824  42.553  1.00 40.81           O
ATOM  2891  O   HOH E 247     1.988   4.116  39.881  1.00 42.21           O
ATOM  2892  O   HOH E 248    26.548  36.806  13.398  1.00 52.67           O
ATOM  2893  O   HOH E 249     2.640   1.685  38.189  1.00 43.18           O
ATOM  2894  O   HOH E 250     2.003  44.513  40.654  1.00 29.03           O
ATOM  2895  O   HOH E 251    -9.862  36.243  21.414  1.00 31.33           O
ATOM  2896  O   HOH E 252    24.228  32.395  36.265  1.00 43.32           O
ATOM  2897  O   HOH E 253    11.688  31.360   5.527  1.00 41.73           O
ATOM  2898  O   HOH E 254   -12.928  34.236  14.101  1.00 41.01           O
ATOM  2899  O   HOH E 255    -1.733  39.176  15.467  1.00 47.82           O
ATOM  2900  O   HOH E 256    10.061  37.977   0.486  1.00 52.33           O
ATOM  2901  O   HOH E 257    17.391  47.913  22.520  1.00 53.74           O
ATOM  2902  O   HOH E 258    17.081  43.856   9.837  1.00 43.73           O
ATOM  2903  O   HOH E 259    29.341  37.203  24.477  1.00 35.13           O
ATOM  2904  O   HOH E 260    -3.227  13.173  17.792  1.00 41.53           O
ATOM  2905  O   HOH E 261    -4.525  34.088  43.543  1.00 42.61           O
ATOM  2906  O   HOH E 262     4.911  39.027   0.446  1.00 35.99           O
ATOM  2907  O   HOH E 263     3.136  38.723   2.465  1.00 71.29           O
ATOM  2908  O   HOH E 264    -0.177  43.074  43.224  1.00 41.23           O
ATOM  2909  O   HOH E 265     8.791  24.903  54.645  1.00 56.09           O
ATOM  2910  O   HOH E 266    -3.916   1.816   8.133  1.00 32.13           O
ATOM  2911  O   HOH E 267    13.434  14.532  15.322  1.00 37.20           O
ATOM  2912  O   HOH E 268    10.641  45.042   6.273  1.00 41.65           O
ATOM  2913  O   HOH E 269    21.804  33.273  35.775  1.00 50.96           O
ATOM  2914  O   HOH E 270    19.304  15.544  42.868  1.00 33.26           O
ATOM  2915  O   HOH E 271    -4.067  41.672  22.380  1.00 42.71           O
ATOM  2916  O   HOH E 272    10.428  33.978  49.033  1.00 30.54           O
ATOM  2917  O   HOH E 273   -14.591  33.233  22.445  1.00 36.40           O
ATOM  2918  O   HOH E 274    -7.744   1.393  20.825  1.00 30.78           O
ATOM  2919  O   HOH E 275   -11.811   2.052   9.032  1.00 50.74           O
ATOM  2920  O   HOH E 276   -12.880  32.187  10.901  1.00 60.81           O
ATOM  2921  O   HOH E 277    28.665  19.541  22.749  1.00 51.28           O
ATOM  2922  O   HOH E 278    12.910  13.998  42.564  1.00 40.94           O
ATOM  2923  O   HOH E 279    24.561  29.781  30.221  1.00 48.08           O
ATOM  2924  O   HOH E 280    -7.531  36.454  20.343  1.00 39.62           O
ATOM  2925  O   HOH E 281    -6.659   9.621  16.850  1.00 43.62           O
ATOM  2926  O   HOH E 282   -14.623  37.065  20.006  1.00 52.04           O
ATOM  2927  O   HOH E 283    15.069  14.997  46.155  1.00 55.72           O
ATOM  2928  O   HOH E 284     9.655  47.565  12.977  1.00 40.25           O
ATOM  2929  O   HOH E 285    16.357  46.963  19.114  1.00 61.24           O
ATOM  2930  O   HOH E 286    -1.867  29.511   6.946  1.00 58.34           O
ATOM  2931  O   HOH E 287    -1.474  43.899  22.728  1.00 40.86           O
ATOM  2932  C1  NAG D   1     8.201  40.796   2.193  1.00 56.77           C
ATOM  2933  O1  NAG D   1     9.171  40.638   1.175  1.00 59.17           O
ATOM  2934  C2  NAG D   1     8.792  40.389   3.537  1.00 54.25           C
ATOM  2935  N2  NAG D   1     7.824  39.643   4.328  1.00 51.31           N
ATOM  2936  C7  NAG D   1     8.191  38.577   5.054  1.00 50.34           C
ATOM  2937  O7  NAG D   1     9.239  38.547   5.701  1.00 48.84           O
ATOM  2938  C8  NAG D   1     7.286  37.375   5.065  1.00 48.35           C
ATOM  2939  C3  NAG D   1     9.289  41.621   4.282  1.00 54.21           C
```

FIGURE 4-42 (COORDINATES)

```
ATOM   2940  O3  NAG D   1      10.610  41.404   4.724  1.00 54.70           O
ATOM   2941  C4  NAG D   1       9.784  42.646   3.542  0.00 63.62           C
ATOM   2942  O4  NAG D   1       9.773  43.671   4.540  0.00 64.33           O
ATOM   2943  C5  NAG D   1       8.817  42.910   2.362  0.00 64.28           C
ATOM   2944  C6  NAG D   1       7.365  43.254   2.741  0.00 65.31           C
ATOM   2945  O6  NAG D   1       6.436  43.168   1.668  0.00 65.23           O
ATOM   2946  O5  NAG D   1       8.851  41.744   1.542  0.00 64.66           O
ATOM   2947  OXT ACT F1428      11.059  12.379  46.917  1.00 48.66           O
ATOM   2948  C   ACT F1428      10.579  13.508  46.650  1.00 48.01           C
ATOM   2949  O   ACT F1428       9.413  13.734  47.045  1.00 47.67           O
ATOM   2950  CH3 ACT F1428      11.371  14.513  45.878  1.00 47.78           C
ATOM   2951  OXT ACT G1428      -5.980  39.593  24.153  1.00 36.63           O
ATOM   2952  C   ACT G1428      -6.351  39.177  23.043  1.00 37.41           C
ATOM   2953  O   ACT G1428      -6.094  37.980  22.795  1.00 37.94           O
ATOM   2954  CH3 ACT G1428      -7.111  40.039  22.071  1.00 38.07           C
```

FIGURE 4-43 (COORDINATES)

```
HEADER      ----                                        XX-XXX-XX    xxxx
COMPND      ---
REMARK   3
REMARK   3 REFINEMENT.
REMARK   3   PROGRAM     : REFMAC 5.2.0019
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   1.90
REMARK   3   RESOLUTION RANGE LOW  (ANGSTROMS) :  30.07
REMARK   3   DATA CUTOFF            (SIGMA(F)) : NONE
REMARK   3   COMPLETENESS FOR RANGE        (%) : 100.00
REMARK   3   NUMBER OF REFLECTIONS             :  20392
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.17892
REMARK   3   R VALUE            (WORKING SET) : 0.17623
REMARK   3   FREE R VALUE                     : 0.22865
REMARK   3   FREE R VALUE TEST SET SIZE   (%) : 5.0
REMARK   3   FREE R VALUE TEST SET COUNT      : 1074
REMARK   3
REMARK   3  FIT IN THE HIGHEST RESOLUTION BIN.
REMARK   3   TOTAL NUMBER OF BINS USED            :    20
REMARK   3   BIN RESOLUTION RANGE HIGH            :  1.900
REMARK   3   BIN RESOLUTION RANGE LOW             :  1.949
REMARK   3   REFLECTION IN BIN     (WORKING SET)  :    498
REMARK   3   BIN COMPLETENESS (WORKING+TEST) (%)  : 100.00
REMARK   3   BIN R VALUE           (WORKING SET)  :  0.206
REMARK   3   BIN FREE R VALUE SET COUNT           :     26
REMARK   3   BIN FREE R VALUE                     :  0.329
REMARK   3
REMARK   3  NUMBER OF NON-HYDROGEN ATOMS USED IN REFINEMENT.
REMARK   3   ALL ATOMS              :   2869
REMARK   3
REMARK   3  B VALUES.
REMARK   3   FROM WILSON PLOT           (A**2) : NULL
REMARK   3   MEAN B VALUE      (OVERALL, A**2) :  24.991
REMARK   3   OVERALL ANISOTROPIC B VALUE.
REMARK   3    B11 (A**2) :   0.32
REMARK   3    B22 (A**2) :  -0.67
REMARK   3    B33 (A**2) :   0.35
REMARK   3    B12 (A**2) :   0.00
REMARK   3    B13 (A**2) :   0.00
REMARK   3    B23 (A**2) :   0.00
REMARK   3
REMARK   3  ESTIMATED OVERALL COORDINATE ERROR.
REMARK   3   ESU BASED ON R VALUE                            (A):  0.193
REMARK   3   ESU BASED ON FREE R VALUE                       (A):  0.166
REMARK   3   ESU BASED ON MAXIMUM LIKELIHOOD                 (A):  0.104
REMARK   3   ESU FOR B VALUES BASED ON MAXIMUM LIKELIHOOD (A**2):  3.492
REMARK   3
REMARK   3 CORRELATION COEFFICIENTS.
REMARK   3   CORRELATION COEFFICIENT FO-FC      :  0.955
REMARK   3   CORRELATION COEFFICIENT FO-FC FREE :  0.927
REMARK   3
REMARK   3  RMS DEVIATIONS FROM IDEAL VALUES        COUNT    RMS    WEIGHT
REMARK   3   BOND LENGTHS REFINED ATOMS       (A):  2651 ; 0.015 ; 0.021
REMARK   3   BOND ANGLES REFINED ATOMS  (DEGREES):  3592 ; 1.747 ; 1.960
REMARK   3   TORSION ANGLES, PERIOD 1   (DEGREES):   315 ; 6.302 ; 5.000
REMARK   3   TORSION ANGLES, PERIOD 2   (DEGREES):   123 ;34.271 ;23.984
REMARK   3   TORSION ANGLES, PERIOD 3   (DEGREES):   413 ;13.497 ;15.000
REMARK   3   TORSION ANGLES, PERIOD 4   (DEGREES):    13 ;15.135 ;15.000
REMARK   3   CHIRAL-CENTER RESTRAINTS      (A**3):   384 ; 0.110 ; 0.200
REMARK   3   GENERAL PLANES REFINED ATOMS     (A):  2045 ; 0.006 ; 0.020
REMARK   3   NON-BONDED CONTACTS REFINED ATOMS(A):  1340 ; 0.219 ; 0.200
REMARK   3   NON-BONDED TORSION REFINED ATOMS (A):  1773 ; 0.307 ; 0.200
```

FIGURE 4-44 (REMARKS)

```
REMARK   3   H-BOND (X...Y) REFINED ATOMS       (A):   256 ; 0.171 ; 0.200
REMARK   3   POTENTIAL METAL-ION REFINED ATOMS  (A):     3 ; 0.049 ; 0.200
REMARK   3   SYMMETRY VDW REFINED ATOMS         (A):    66 ; 0.354 ; 0.200
REMARK   3   SYMMETRY H-BOND REFINED ATOMS      (A):    15 ; 0.252 ; 0.200
REMARK   3
REMARK   3  ISOTROPIC THERMAL FACTOR RESTRAINTS.    COUNT   RMS    WEIGHT
REMARK   3   MAIN-CHAIN BOND REFINED ATOMS   (A**2): 1653 ; 0.931 ; 1.500
REMARK   3   MAIN-CHAIN ANGLE REFINED ATOMS  (A**2): 2574 ; 1.514 ; 2.000
REMARK   3   SIDE-CHAIN BOND REFINED ATOMS   (A**2): 1188 ; 2.346 ; 3.000
REMARK   3   SIDE-CHAIN ANGLE REFINED ATOMS  (A**2): 1018 ; 3.437 ; 4.500
REMARK   3
REMARK   3  NCS RESTRAINTS STATISTICS
REMARK   3   NUMBER OF NCS GROUPS : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS    :   1.20
REMARK   3   ION PROBE RADIUS    :   0.80
REMARK   3   SHRINKAGE RADIUS    :   0.80
REMARK   3
REMARK   3  OTHER REFINEMENT REMARKS:
REMARK   3  HYDROGENS HAVE BEEN ADDED IN THE RIDING POSITIONS
REMARK   3
SSBOND   1 CYS A  140    CYS A  165
LINK         ND2 ASN A   50         1.400    O7  NAG D   1                ASN-NAG
CISPEP   1 ASP A  160    SER A  161                       0.00
LINK            ASP A 184                     PRO A 190                   gap
CISPEP   2 HIS A  229    PRO A  230                       0.00
CISPEP   3 SER A  324    PRO A  325                       0.00
MODRES       NAG D    1  NAG-b-L                                          RENAME
CRYST1   42.713   84.675   97.223  90.00  90.00  90.00 P 21 21 21
SCALE1      0.023412  0.000000  0.000000        0.00000
SCALE2      0.000000  0.011810  0.000000        0.00000
SCALE3      0.000000  0.000000  0.010286        0.00000
```

FIGURE 4-45 (REMARKS)

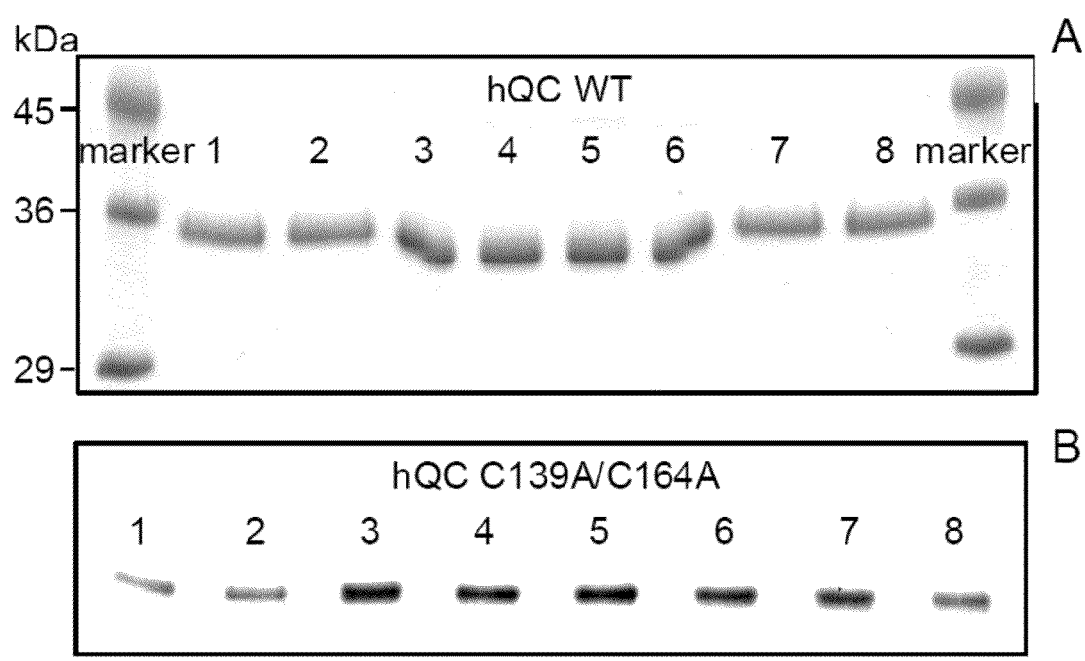
FIGURE 5A-B

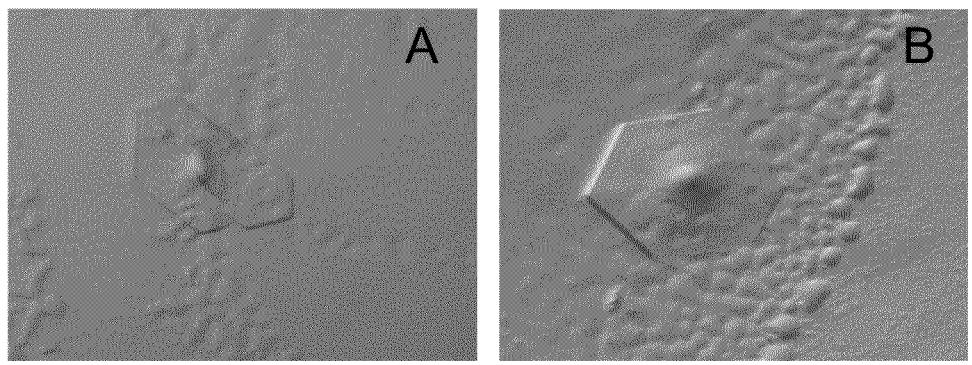
FIGURE 11A-B
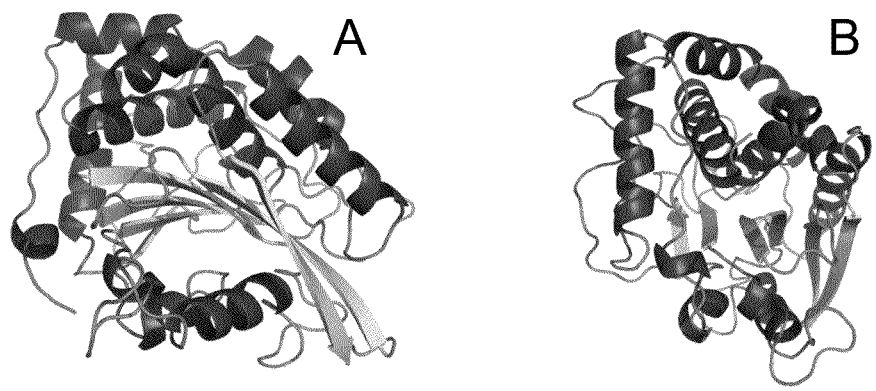
FIGURE 12A-B

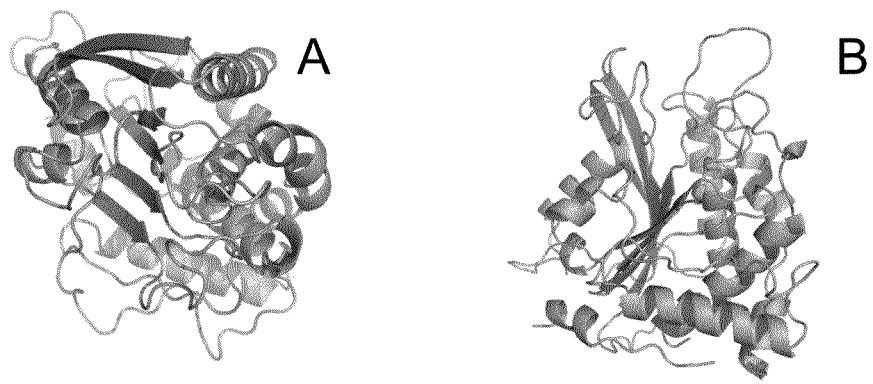
FIGURE 15A-B
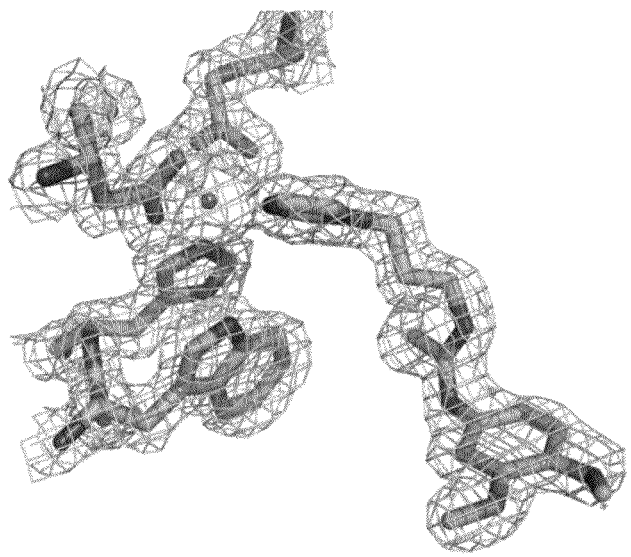
FIGURE 16

SEQUENCE LISTING

<160> NUMBER OF SEQ ID NOS: 13

<210> SEQ ID NO 1
<211> LENGTH: 361
<212> TYPE: PRT
<213> ORGANISM: Human

<400> SEQUENCE: 1

Met Ala Gly Gly Arg His Arg Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly

```
                65                  70                  75                  80
        Ser Pro Gly Ser Tyr Ala Ala Arg Gln His Ile Met Gln Arg Ile Gln
                        85                  90                  95

Arg Leu Gln Ala Asp Trp Val Leu Glu Ile Asp Thr Phe Leu Ser Gln
                        100                 105                 110

Thr Pro Tyr Gly Tyr Arg Ser Phe Ser Asn Ile Ile Ser Thr Leu Asn
                        115                 120                 125

Pro Thr Ala Lys Arg His Leu Val Leu Ala Cys His Tyr Asp Ser Lys
                130                 135                 140

Tyr Phe Ser His Trp Asn Asn Arg Val Phe Val Gly Ala Thr Asp Ser
        145                 150                 155                 160

Ala Val Pro Cys Ala Met Met Leu Glu Leu Ala Arg Ala Leu Asp Lys
                        165                 170                 175

Lys Leu Leu Ser Leu Lys Thr Val Ser Asp Ser Lys Pro Asp Leu Ser
                        180                 185                 190

Leu Gln Leu Ile Phe Phe Asp Gly Glu Glu Ala Phe Leu His Trp Ser
                        195                 200                 205

Pro Gln Asp Ser Leu Tyr Gly Ser Arg His Leu Ala Ala Lys Met Ala
                210                 215                 220

Ser Thr Pro His Pro Pro Gly Ala Arg Gly Thr Ser Gln Leu His Gly
        225                 230                 235                 240

Met Asp Leu Leu Val Leu Leu Asp Leu Ile Gly Ala Pro Asn Pro Thr
                        245                 250                 255

Phe Pro Asn Phe Phe Pro Asn Ser Ala Arg Trp Phe Glu Arg Leu Gln
                        260                 265                 270

Ala Ile Glu His Glu Leu His Glu Leu Gly Leu Leu Lys Asp His Ser
                        275                 280                 285

Leu Glu Gly Arg Tyr Phe Gln Asn Tyr Ser Tyr Gly Gly Val Ile Gln
                        290                 295                 300

Asp Asp His Ile Pro Phe Leu Arg Arg Gly Val Pro Val Leu His Leu
        305                 310                 315                 320

Ile Pro Ser Pro Phe Pro Glu Val Trp His Thr Met Asp Asp Asn Glu
                        325                 330                 335

Glu Asn Leu Asp Glu Ser Thr Ile Asp Asn Leu Asn Lys Ile Leu Gln
                        340                 345                 350

Val Phe Val Leu Glu Tyr Leu His Leu
                        355                 360

<210> SEQ ID NO 2
<211> LENGTH: 51
<212> TYPE: DNA
<213> ORGANISM: Human

<400> SEQUENCE: 2
atatatctgc agcgcatcac catcaccatc acgaggagaa gaattaccac c           51

<210> SEQ ID NO 3
<211> LENGTH: 33
<212> TYPE: DNA
<213> ORGANISM: Human

<400> SEQUENCE: 3
atatatgcgg ccgcttacaa atgaagatat tcc                               33

<210> SEQ ID NO 4
<211> LENGTH: 33
```

```
<212> TYPE: DNA
<213> ORGANISM: Human

<400> SEQUENCE: 4
catttggtcc tcgccgccca ctatgactcc aag                                33

<210> SEQ ID NO 5
<211> LENGTH: 33
<212> TYPE: DNA
<213> ORGANISM: Human

<400> SEQUENCE: 5
cttggagtca tagtgggcgg cgaggaccaa atg                                33

<210> SEQ ID NO 6
<211> LENGTH: 34
<212> TYPE: DNA
<213> ORGANISM: Human

<400> SEQUENCE: 6
gattcagccg tgccagctgc aatgatgttg gaac                               34

<210> SEQ ID NO 7
<211> LENGTH: 34
<212> TYPE: DNA
<213> ORGANISM: Human

<400> SEQUENCE: 7
gttccaacat cattgcagct ggcacggctg aatc                               34

<210> SEQ ID NO 8
<211> LENGTH: 19
<212> TYPE: DNA
<213> ORGANISM: Human

<400> SEQUENCE: 8
ctggagtgac aaatctggc                                                19

<210> SEQ ID NO 9
<211> LENGTH: 32
<212> TYPE: DNA
<213> ORGANISM: Murine

<400> SEQUENCE: 9
atatgcatgc atggcaggca gcgaagacaa gc                                 32

<210> SEQ ID NO 10
<211> LENGTH: 40
<212> TYPE: DNA
<213> ORGANISM: Murine

<400> SEQUENCE: 10
atataagctt ttacaagtga agatattcca acacaaagac                         40

<210> SEQ ID NO 11
<211> LENGTH: 33
<212> TYPE: DNA
<213> ORGANISM: Murine

<400> SEQUENCE: 11
atactcgaga aaagagcctg gacgcaggag aag                                33

<210> SEQ ID NO 12
```

```
<211> LENGTH: 31
<212> TYPE: DNA
<213> ORGANISM: Murine

<400> SEQUENCE: 12
atatctagat tacaagtgaa gatattccaa c                              31

<210> SEQ ID NO 13
<211> LENGTH: 362
<212> TYPE: PRT
<213> ORGANISM: Murine

<400> SEQUENCE: 13
```

Met Ala Gly Ser Glu Asp Lys Leu Val Val Gly Thr Leu His Leu Leu
1               5                   10                  15

Leu Leu Gln Ala Thr Val Leu Ser Leu Thr Ala Gly Asn Leu Ser Leu
            20                  25                  30

Val Ser Ala Ala Trp Thr Gln Glu Lys Asn His His Gln Pro Ala His
        35                  40                  45

Leu Asn Ser Ser Ser Leu Gln Gln Val Ala Glu Gly Thr Ser Ile Ser
    50                  55                  60

Glu Met Trp Gln Asn Asp Leu Arg Pro Leu Leu Ile Glu Arg Tyr Pro
65                  70                  75                  80

Gly Ser Pro Gly Ser Tyr Ser Ala Arg Gln His Ile Met Gln Arg Ile
                85                  90                  95

Gln Arg Leu Gln Ala Glu Trp Val Val Glu Val Asp Thr Phe Leu Ser
            100                 105                 110

Arg Thr Pro Tyr Gly Tyr Arg Ser Phe Ser Asn Ile Ile Ser Thr Leu
        115                 120                 125

Asn Pro Glu Ala Lys Arg His Leu Val Leu Ala Cys His Tyr Asp Ser
    130                 135                 140

Lys Tyr Phe Pro Arg Trp Asp Ser Arg Val Phe Val Gly Ala Thr Asp
145                 150                 155                 160

Ser Ala Val Pro Cys Ala Met Met Leu Glu Leu Ala Arg Ala Leu Asp
                165                 170                 175

Lys Lys Leu His Ser Leu Lys Asp Val Ser Gly Ser Lys Pro Asp Leu
            180                 185                 190

Ser Leu Arg Leu Ile Phe Phe Asp Gly Glu Glu Ala Phe His His Trp
        195                 200                 205

Ser Pro Gln Asp Ser Leu Tyr Gly Ser Arg His Leu Ala Gln Lys Met
    210                 215                 220

Ala Ser Ser Pro His Pro Pro Gly Ser Arg Gly Thr Asn Gln Leu Asp
225                 230                 235                 240

Gly Met Asp Leu Leu Val Leu Leu Asp Leu Ile Gly Ala Ala Asn Pro
                245                 250                 255

Thr Phe Pro Asn Phe Phe Pro Lys Thr Thr Arg Trp Phe Asn Arg Leu
            260                 265                 270

Gln Ala Ile Glu Lys Glu Leu Tyr Glu Leu Gly Leu Leu Lys Asp His
        275                 280                 285

Ser Leu Glu Arg Lys Tyr Phe Gln Asn Phe Gly Tyr Gly Asn Ile Ile
    290                 295                 300

Gln Asp Asp His Ile Pro Phe Leu Arg Lys Gly Val Pro Val Leu His
305                 310                 315                 320

Leu Ile Ala Ser Pro Phe Pro Glu Val Trp His Thr Met Asp Asp Asn
                325                 330                 335

```
Glu Glu Asn Leu His Ala Ser Thr Ile Asp Asn Leu Asn Lys Ile Ile
            340                 345                 350

Gln Val Phe Val Leu Glu Tyr Leu His Leu
            355                 360
```

CRYSTAL STRUCTURE OF GLUTAMINYL CYCLASE

CROSS-REFERENCE TO RELATED APPLICATIONS

This application is a Division of U.S. application Ser. No. 13/213,507, filed Aug. 19, 2011. This application claims priority to U.S. Provisional Application Ser. No. 61/375,103, filed on Aug. 19, 2010. U.S. application Ser. No. 13/213,507 and 61/375,103 are incorporated herein by reference in their entireties to the extent permitted by law.

MATERIAL INCORPORATED-BY-REFERENCE

The Sequence Listing, which is a part of the present disclosure, includes a computer readable form comprising nucleotide and/or amino acid sequences of the present disclosure. The subject matter of the Sequence Listing is incorporated herein by reference in its entirety.

FIELD OF THE INVENTION

The present disclosure relates to the novel crystal structure of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

U.S. Pat. No. 7,572,614 (Wang et al) and Huang et al (2005) PNAS 102(37), 13117-13122 both describe one example of the crystal structure of soluble glutaminyl cyclase. The crystal structure disclosed in Wang et al and Huang et al was generated using a protein expressed in *E. coli*, which results in a lack of glycosylation. It is well known that all mammalian QC contain at least one glycosylation site (Pohl, T. et al. (1991) Proc Natl Acad Sci USA 88, 10059-10063; Song, I. et al. (1994) J Mol Endocrinol 13, 77-86), which is glycosylated in the QC crystallized according to the present disclosure by virtue of being expressed in eukaryotic hosts, which can be observed in the crystal structures presented herein. In addition, all mammalian QCs contain two conserved cysteine residues close to the active site, which form a disulfide bond. In the crystal structure of Wang et al and Huang et al, the disulfide bond is lacking. The expression of mammalian secretory proteins in bacteria frequently results in the absence of disulfide formation (Hannig, G. and Makrides, S. C. (1998) Trends Biotechnol 16, 54-60). The disulfide bond is clearly present in both the human and murine QC crystal structures presented herein. Notably, the mutational analyses provided in the examples described herein suggest an important stabilizing function of the disulfide bond upon the overall structure. Furthermore, in the structure of Wang et al and Huang et al, a segment of residues (L205-H206-W207) close to the active site appears in two different conformations. Due to the orientations, the binding mode of substrates is affected and reliable mechanistic conclusions could not be drawn (Huang et al., 2005). The residue W207 is conserved in mammalian QCs (W208 in murine QC). In the human and murine QC crystal structures presented herein, the orientation is identical, although the adjacent residues L205 and H206 are not conserved. Therefore, the structural orientation of residues appears non-native in the crystal structure of Wang et al and Huang et al.

The expression of the murine and human QC in an eukaryotic host, as described in the present disclosure, allows the crystallization and structural refinement of a native mammalian QC and, importantly, unambiguous determination of the binding modes of inhibitors, as exemplified by the structural resolution of murine QC with three different inhibitory compounds (listed in Table 1 as Inhibitor A, Inhibitor B and Inhibitor C), which have similar inhibitory potency between human and murine QC.

In contrast to the structures described in previous publications by Wang et al and Huang et al., the present disclosure shows that the post-translational modifications disulfide formation and glycosylation lead to a single structural arrangement of the residues L205-H206-W207 in human and murine QC. The residues have a direct effect on the binding mode of active-site directed compounds. The multiple orientations of W207 in previous studies, led to variances in the binding modes of active-site-directed compounds.

TABLE 1

$K_i$-values [μM] of selected inhibitors for murine (mQC) and human QC (hQC)

| Inhibitor | mQC | hQC |
|---|---|---|
| Inhibitor A | 0.173 | 0.0542 |
| Inhibitor B | n.d. | 0.0613 |
| Inhibitor C | 0.0513 | 0.106 |

In contrast, unambigous binding modes of compounds and orientations of W207 were observed with three different inhibitors and even in a structure without inhibitor bound. Thus, the methods as described in the present disclosures provide substantial advances for structure-driven drug design of QC inhibitors.

The conclusion is particularly strengthened by the structural assessment of QCs from two different mammals.

SUMMARY OF THE INVENTION

According to a first embodiment there is provided a crystal comprising human glutaminyl cyclase having a characterised space group of C121 and unit cell dimensions of +/−5% of a=82.6 Å, b=63.9 Å, c=77.5 Å, α=90.0°, β=105.7° and γ=90.0°.

According to a second embodiment there is provided a crystal comprising murine glutaminyl cyclase having a characterised space group of P212121 and having unit cell dimensions of +/−5% of a=42.7 Å, b=84.0 Å and c=96.5 Å.

According to a third embodiment there is provided a method of preparing the crystal of human glutaminyl cyclase as described herein, which comprises the steps of:
  (a) providing a solution of human glutaminyl cyclase, optionally in the presence of a known glutaminyl cyclase inhibitor, in a suitable buffer such as 25 mM Bis-Tris pH6.8/100 mM NaCl buffer;
  (b) mixing the solution with a crystallization solution comprising 30% (v/v) 2-methyl 2,4-pentanediol and 11% (w/v) 4000PEG; and
  (c) incubating the mixture under conditions to promote hanging drop vapor diffusion for a time sufficient to produce the crystal of human glutaminyl cyclase.

According to a further embodiment there is provided a crystal comprising human glutaminyl cyclase obtainable by the crystallisation method as defined herein.

According to a fourth embodiment there is provided a method of preparing the crystal of murine glutaminyl cyclase as described herein, which comprises the steps of:
  (a) providing a solution of murine glutaminyl cyclase, optionally in the presence of a known glutaminyl cyclase inhibitor, in a suitable buffer such as 15 mM Bis-Tris pH6.8/100 mM NaCl buffer;
  (b) mixing the solution with a crystallization solution comprising 0.1M sodium acetate pH 5.3, 0.2M ammonium sulphate and 12% (w/v) 2000 MME-PEG; and
  (c) incubating the mixture under conditions to promote hanging drop vapor diffusion for a time sufficient to produce the crystal of murine glutaminyl cyclase.

According to a further embodiment there is provided a crystal comprising murine glutaminyl cyclase obtainable by the crystallisation method as defined herein.

According to a fifth embodiment there is provided a method of identifying an inhibitor of human glutaminyl cyclase which comprises the following steps:
  (a) generating a 3-dimensional model of human glutaminyl cyclase using the structural coordinates described in FIG. 1;
  (b) analysing the binding pocket provided by residues E202, D159 and H330 of SEQ ID NO: 1 according to the coordinates of FIG. 1;
  (c) performing computer modeling analysis to identify an inhibitor compound which may associate with the binding pocket of human glutaminyl cyclase.

According to a sixth embodiment there is provided a method of identifying an inhibitor of murine glutaminyl cyclase which comprises the following steps:
  (a) generating a 3-dimensional model of murine glutaminyl cyclase using the structural coordinates described in any of FIGS. 2 to 4;
  (b) analysing the binding pocket provided by residues D160, E203 and H331 of SEQ ID NO: 13 according to the coordinates of FIGS. 2 to 4;
  (c) performing computer modeling analysis to identify an inhibitor compound which may associate with the binding pocket of murine glutaminyl cyclase.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIGS. 1-1 to 1-41 describes the X-ray coordinates of human QC crystallized with 0.1M imidazol pH 8, wherein "RES" and "#" correspond to the amino acid residue and number of the amino acid in SEQ ID NO: 1.

FIGS. 2-1 to 2-45 describes the X-ray coordinates of murine QC crystallized with QC inhibitor Inhibitor A, wherein "RES" and "#" correspond to the amino acid residue and number of the amino acid in SEQ ID NO: 13.

FIGS. 3-1 to 3-46 describes the X-ray coordinates of murine QC crystallized with QC inhibitor Inhibitor B, wherein "RES" and "#" correspond to the amino acid residue and number of the amino acid in SEQ ID NO: 13.

FIGS. 4-1 to 4-45 describes the X-ray coordinates of murine QC crystallized with QC inhibitor Inhibitor C, wherein "RES" and "#" correspond to the amino acid residue and number of the amino acid in SEQ ID NO: 13.

FIG. 5A describes the results of SDS-PAGE analysis of hQC WT.

FIG. 5B describes the results of SDS-PAGE analysis of the C139A/C164A mutant.

FIG. 6 describes the CD spectra of the far UV region of hQC WT and the C139A/C164A mutant at 20° C.

FIG. 7 describes temperature dependence of the mean residue ellipticity ($\theta_{MRW}$) of hQC WT and the C139A/C164A mutant at a wavelength of 227 nm.

FIG. 8A describes CD spectra of the far UV region of hQC WT at increasing temperature.

FIG. 8B describes CD spectra of the far UV region of the C139A/C164A mutant at increasing temperature.

FIG. 9A describes fluorescence emission spectra in a wavelength range between 320 and 400 nm of hCQ WT at different GdmCl concentrations.

FIG. 9B describes fluorescence emission spectra wavelength range between 320 and 400 nm of C139A/C164A mutant at different GdmCl concentrations.

FIG. 10 describes dependence of the relative fluorescence from the GdmCl concentration of hQC WT and the C139A/C164A mutant at a wavelength of 337 nm.

FIG. 11A-B demonstrates photographic representations of the crystals of human glutaminyl cyclase grown in buffer consisting of 0.1M imidazol pH 8, 30% (v/v) 2-methyl 2,4-pentanediol and 11% (w/v) 4000PEG.

FIG. 12A describes a cartoon representation of the obtained three dimensional structure of the human glutaminyl cyclase described by the X-ray coordinates shown in FIG. 1. They are shown in light gray β-sheet structures, in dark gray α helices and in green the random coiled loops.

FIG. 12B shows an orthogonal orientation of FIG. 12A.

FIG. 13 demonstrates an overlay of the electron density at 1.5 sigma level with the modeled residues building the active site. With a stick representation are displayed in the lightest gray the active site related residues $D^{159}$, $E^{202}$ and $H^{330}$ and in medium gray an imidazole molecule (see ring structure middle left of figure) coordinating the catalytic zinc cation which is shown with a ball representation in the center of the figure.

FIG. 14 demonstrates a photographic representation of examples of the crystals of the mouse glutaminyl cyclase grown in buffer consisting of 0.1M sodium acetate pH 5.3 0.2M ammonium sulphate 12% (w/v) 2000 MME-PEG and 1 mM Inhibitor A.

FIG. 15A describes a cartoon representation of the obtained three dimensional structure of the mouse glutaminyl cyclase described by the X-ray coordinates shown in FIGS. 2-4. In dark gray β-sheet in Light gray α-helices and in gray strands the random coiled structures are shown.

FIG. 15B shows an orthogonal orientation of FIG. 15A.

FIG. 16 demonstrates an overlay of the electron density at 1.5 sigma level with the modeled residues building the active centre. With a stick representation are displayed in medium gray the active site related residues $D^{160}$, $E^{203}$ and $H^{331}$ (see left upper, left middle, and left lower structures inside of tips) and in light gray the inhibitor molecule Inhibitor A (see right structure) coordinating the catalytic zinc cation shown with a ball representation in grey (see middle of figure).

FIG. 17 demonstrates an overlay of the electron density at 1.5 sigma level with the modeled residues building the disulfide bridge. With a stick representation are displayed the residues involved in the disulfide bridge, $C^{140}$ and $C^{165}$, formation and in cartoon representation are displayed the secondary structures surrounding that disulfide bridge.

FIG. 18 demonstrates an overlay of the electron density at 1.5 sigma level with the modeled residues building the active centre. With a stick representation are displayed in medium gray the active site related residues $D^{160}$, $E^{203}$ and $H^{331}$ (see left middle, left upper, and left lower structures) and in light gray the inhibitor molecule Inhibitor C (see right middle structure) coordinating the catalytic zinc cation shown with a sphere representation in grey (see just left of center of figure) and in ball representation in dark gray are shown water molecules (see small ball structures upper middle and upper right of figure).

FIG. 19 demonstrates an overlay of the electron density at 1.5 sigma level with the modeled residues building the active centre. With a stick representation are displayed in medium gray the active site related residues $D^{160}$, $E^{203}$ and $H^{331}$ (see left upper, left middle, and left lower structures) and in light to medium gray the inhibitor molecule Inhibitor B (see right middle structure) coordinating the catalytic zinc cation shown with a sphere representation in grey (see left of center of figure) and in ball representation in dark gray are shown water molecules (see upper right and middle right of figure).

DETAILED DESCRIPTION OF THE INVENTION

Figure 6:
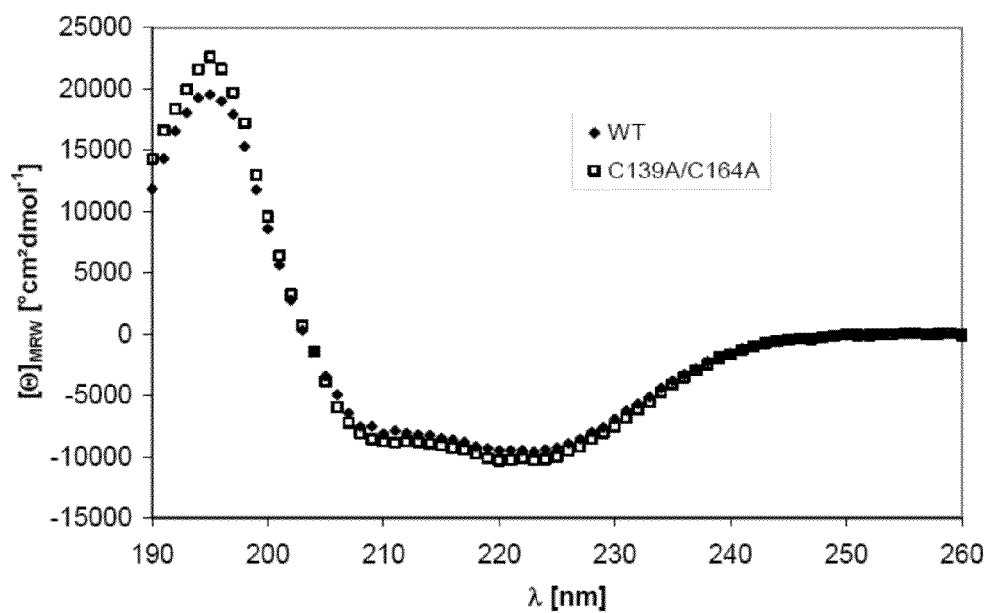

The present disclosure relates to crystals of human and murine glutaminyl cyclase, where the crystals are of sufficient quality and size to allow for the determination of the three-dimensional X-ray diffraction structure of glutaminyl cyclase to a resolution of about 1.8 angstrom and to about 2.1 angstroms in C121 and P212121 space groups, respectively. The present disclosure also relates to methods for preparing and crystallizing human and murine glutaminyl cyclase. The crystals of human and murine glutaminyl cyclase, as well as information derived from their crystal structures, can be used to analyze and modify glutaminyl cyclase as well as to identify compounds that interact with glutaminyl cyclase.

Thus, according to a first embodiment, there is provided a crystal comprising human glutaminyl cyclase having a characterised space group of C121 and unit cell dimensions of +/−5% of a=82.6 Å, b=63.9 Å, c=77.5 Å, α=90.0°, β=105.7° and γ=90.0°.

In an embodiment, the crystal can have unit cell dimensions of a=82.6 Å, b=63.9 Å and c=77.5 Å.

In an embodiment, the crystal can have unit cell dimensions of α=90.0°, β=105.7° and γ=90.0°.

In an embodiment, the crystal can diffract x-rays for determination of atomic co-ordinates of the crystal to a resolution of between 2.08 Å and 11.98 Å.

According to a second embodiment there is provided a crystal comprising murine glutaminyl cyclase having a characterised space group of P212121 and having unit cell dimensions of +1−5% of a=42.7 Å, b=84.0 Å, c=96.5 Å, α=90.0°, β=90.0° and γ=90.0°.

In an embodiment, the crystal can have unit cell dimensions of a=42.7 Å, b=83.0 Å, c=95.7 Å, α=90.0°, β=90.0° and γ=90.0°. This embodiment relates to the crystal structure of murine glutaminyl cyclase complexed with a glutaminyl cyclase inhibitor, referred to herein as Inhibitor A, which has the structure as follows:

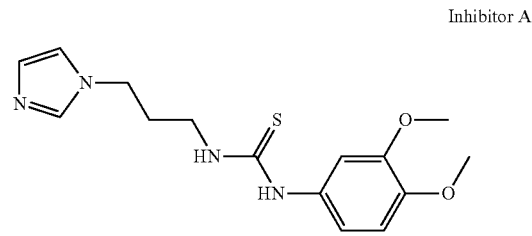 [SMILES: COc1ccc(NC(=S)NCCCn2ccnc2)cc1OC]

Inhibitor A

Inhibitor A can inhibit both human and mouse QC in vitro and moreover, Inhibitor A is soluble in water and therefore useful for crystallization.

In an embodiment, the crystal can have unit cell dimensions of a=42.7 Å, b=84.6 Å, c=96.5 Å, α=90.0°, β=90.0° and γ=90.0°. This embodiment relates to the crystal structure of murine glutaminyl cyclase complexed with a glutaminyl cyclase inhibitor, referred to herein as Inhibitor B, which has the structure as follows:

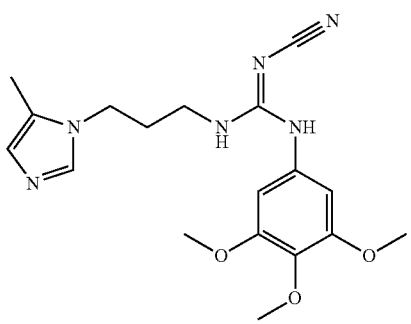

Inhibitor B

In an embodiment, the crystal can have unit cell dimensions of a=42.7 Å, b=84.6 Å, c=97.2 Å, α=90.0°, β=90.0° and γ=90.0°. This embodiment relates to the crystal structure of murine glutaminyl cyclase complexed with a glutaminyl cyclase inhibitor, referred to herein as Inhibitor C, which has the structure as follows:

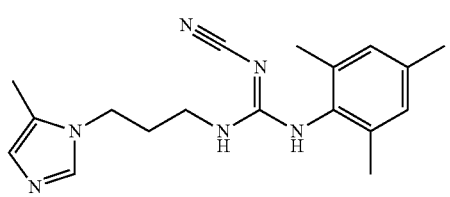

Inhibitor C

In an embodiment, the crystal can have unit cell dimensions of α=90.0°, β=90.0° and γ=90.0°.

In an embodiment, the crystal can diffract x-rays for determination of atomic co-ordinates of the crystal to a resolution of between 1.9 Å and 32.0 Å.

In an embodiment, the crystal can diffract x-rays for determination of atomic co-ordinates of the crystal to a resolution of between 1.8 Å and 19.81 Å. This embodiment relates to the resolution of the crystal structure of murine glutaminyl cyclase complexed with a glutaminyl cyclase inhibitor, referred to herein as Inhibitor A.

In an embodiment, the crystal can diffract x-rays for determination of atomic co-ordinates of the crystal to a resolution of between 1.98 Å and 32.0 Å. This embodiment relates to the resolution of the crystal structure of murine glutaminyl cyclase complexed with a glutaminyl cyclase inhibitor, referred to herein as Inhibitor B.

In an embodiment, the crystal can diffract x-rays for determination of atomic co-ordinates of the crystal to a resolution of between 1.9 Å and 30.7 Å. This embodiment relates to the resolution of the crystal structure of murine glutaminyl cyclase complexed with a glutaminyl cyclase inhibitor, referred to herein as Inhibitor C.

It will be appreciated that the crystals within the scope of the present disclosure can include both apo crystals and co-crystals. The apo crystals generally comprise substantially pure glutaminyl cyclase. The co-crystals generally comprise substantially pure glutaminyl cyclase with a binding ligand, such as a glutaminyl cyclase inhibitor, bound to glutaminyl cyclase. Thus, in some embodiments, there is provided a co-crystal comprising the crystal as defined herein bound to a binding ligand, such as a glutaminyl cyclase inhibitor.

In an embodiment, the human glutaminyl cyclase can comprise or consist of amino acid residues A35 to L361 of SEQ ID NO:1.

In an embodiment, the murine glutaminyl cyclase can comprise or consist of amino acid residues A36 to L362 of SEQ ID NO:13.

It will be appreciated that the crystals comprising glutaminyl cyclase are not limited to those obtainable from naturally occurring or native glutaminyl cyclase. The crystals can include mutants that have one or more amino acid insertions, deletions, or substitutions in native glutaminyl cyclase. Therefore, mutants of native glutaminyl cyclase can be obtained by replacing at least one (such as up to 10, e.g. up to 25) amino acid residue in a native glutaminyl cyclase with a different amino acid residue, or by adding or deleting amino acid residues within the native protein or at the N- or C-terminus of the native protein, and can have substantially the same three-dimensional structure as native glutaminyl cyclase from which the mutant is derived.

By having substantially the same three-dimensional structure is meant as having a set of atomic structure coordinates from an apo- or co-crystal that have a root mean square deviation of less than or equal to about 2 Å when superimposed with the atomic structure coordinates of native glutaminyl cyclase from which the mutant is derived when at least about 50% to about 100% of the alpha carbon atoms of native glutaminyl cyclase are included in the superposition.

In some instances, it may be particularly advantageous or convenient to substitute, delete, or add amino acid residues to native glutaminyl cyclase in order to provide convenient cloning sites in the cDNA encoding the protein, to aid in protein purification, and the like. Such substitutions, deletions, or additions, which do not substantially alter the three dimensional structure of native glutaminyl cyclase, will be apparent to those skilled in the art.

It should be noted that the mutant polypeptides contemplated herein need not exhibit glutaminyl cyclase activity. Indeed, amino acid substitutions, additions, or deletions that interfere with the activity of glutaminyl cyclase but which do not significantly alter the three-dimensional structure of glutaminyl cyclase can also be included. Such polypeptide crystals, or the atomic structure coordinates obtained therefrom, can be used to identify compounds that bind to native glutaminyl cyclase and which may affect the activity of the native glutaminyl cyclase.

The derivative crystals of the present disclosure generally comprise glutaminyl cyclase crystals in non-covalent/covalent association with one or more metal atoms. The polypeptide may correspond to native or mutated glutaminyl cyclase. One such example of a suitable metal atom is zinc.

The co-crystals of glutaminyl cyclase generally comprise crystals comprising glutaminyl cyclase in association with one or more compounds bound to glutaminyl cyclase. The association may be covalent or non-covalent. In one embodiment, the compounds bound to glutaminyl cyclase comprise glutaminyl cyclase inhibitors. Examples of such glutaminyl cyclase inhibitors include those described in WO 2004/098625, WO 2004/098591, WO 2005/039548, WO 2005/075436, WO 2008/055945, WO 2008/055947, WO 2008/055950 and WO 2008/065141.

The native and mutated glutaminyl cyclase described herein may be isolated from natural sources or produced by methods well known to those skilled in the art of molecular biology. Detailed experimental for the preparation of human and murine glutaminyl cyclase is described in Examples 1 and 2 herein, respectively.

The apo, derivative and co-crystals of glutaminyl cyclase can be obtained by techniques well-known in the art of protein crystallography, including batch, liquid bridge, dialysis, vapor diffusion, such as hanging drop vapor diffusion, and the like (See for example, McPherson, 1982, Preparation and Analysis of Protein Crystals, John Wiley, NY; McPherson, 1990, Eur. J. Biochem. 189:1-23; Webber, 1991, Adv. Protein Chem. 41:1-36; Crystallization of Nucleic Acids and Proteins, Edited by Ducruix and Giege, Oxford University Press; Protein Crystallization Techniques, Strategies, and Tips, Edited by Bergfors, International University Line, 1999).

In an embodiment, glutaminyl cyclase crystals, apo or co-crystals can be grown by vapor diffusion, such as hanging drop vapor diffusion.

In an embodiment, there is provided a method of preparing the crystal of human glutaminyl cyclase as described herein, which comprises the steps of:
(a) providing a solution of human glutaminyl cyclase, optionally in the presence of a known glutaminyl cyclase inhibitor, in a suitable buffer such as 25 mM Bis-Tris pH6.8/100 mM NaCl buffer;
(b) mixing the solution with a crystallization solution comprising 30% (v/v) 2-methyl 2,4-pentanediol and 11% (w/v) 4000PEG; and
(c) incubating the mixture under conditions to promote hanging drop vapor diffusion for a time sufficient to produce the crystal of human glutaminyl cyclase.

In an embodiment, there is provided a method of preparing the co-crystal of human glutaminyl cyclase bound to a binding ligand, such as a glutaminyl cyclase inhibitor, which comprises the steps of:
(a) providing a solution of human glutaminyl cyclase in the presence of a binding ligand, such as a glutaminyl cyclase inhibitor, in a suitable buffer such as 25 mM Bis-Tris pH6.8/100 mM NaCl buffer;
(b) mixing the solution with a crystallization solution comprising 30% (v/v) 2-methyl 2,4-pentanediol and 11% (w/v) 4000PEG; and
(c) incubating the mixture under conditions to promote hanging drop vapor diffusion for a time sufficient to produce the co-crystal of human glutaminyl cyclase bound to a binding ligand, such as a glutaminyl cyclase inhibitor.

In an embodiment, there is provided a crystal or co-crystal comprising human glutaminyl cyclase obtainable by the crystallisation method as defined herein.

Crystallization of human glutaminyl cyclase to produce co-crystals can be carried out as described below and in Example 1. As described, purified human glutaminyl cyclase is concentrated to 10 mg/mL in the presence of a suitable buffer, such as 25 mM Bis-Tris pH6.8/100 mM NaCl buffer and the ligand imidazol is added to a final concentration of 0.1 M. Macroscopic plate crystal forms are grown by hanging drop vapor diffusion at 21° C. by mixing an equal volume of protein solution with a crystallization solution comprising 30% (v/v) 2-methyl 2,4-pentanediol and 11% (w/v) 4000PEG. Crystals typically appeared 10-15 days after the experiment was initiated and examples of such crystals obtained following this protocol are shown in FIG. 11. It will be appreciated that to produce apo-crystals, the ligand is omitted in the above protocol.

The human glutaminyl cyclase crystals may be frozen prior to data collection. The crystals can be cryo-protected with for example, either (a) 20-30% saturated glucose present in the crystallization setup, (b) ethanol added to 15-20%, (c) ethylene glycol added to 10-20% and PEG10,000 brought up to 25%, or (d) glycerol added to 15%. In an embodiment, the crystals are cryo-protected with the addition of glycerol added to 15% (v/v). The crystals can be either briefly immersed in the cryo-protectant or soaked in the cryo-protectant for periods as long as a day. Freezing can be accomplished by immersing the crystal in a bath of liquid nitrogen or by placing the crystal in a stream of nitrogen gas at −180° C.

As described in Example 1, the crystal structure of human glutaminyl cyclase in complex with imidazole was obtained. A summary of the crystal's attributes for human glutaminyl cyclase bound to imidazole are listed in Table 3 and the three dimensional structure coordinates for space groups C121 for human glutaminyl cyclase bound to imidazole are shown in FIG. 1.

References herein to "coordinates" include references to Cartesian coordinates derived from the mathematical equations related to the patterns obtained on diffraction of a monochromatic beam of X-ray by the atoms of a protein or protein complex in crystal form. The diffraction data are used to calculate an electron density map of the repeating units of the crystal, The electron density maps are then used to establish the positions of the individual atoms of the molecule or molecular complex.

Figure 13:
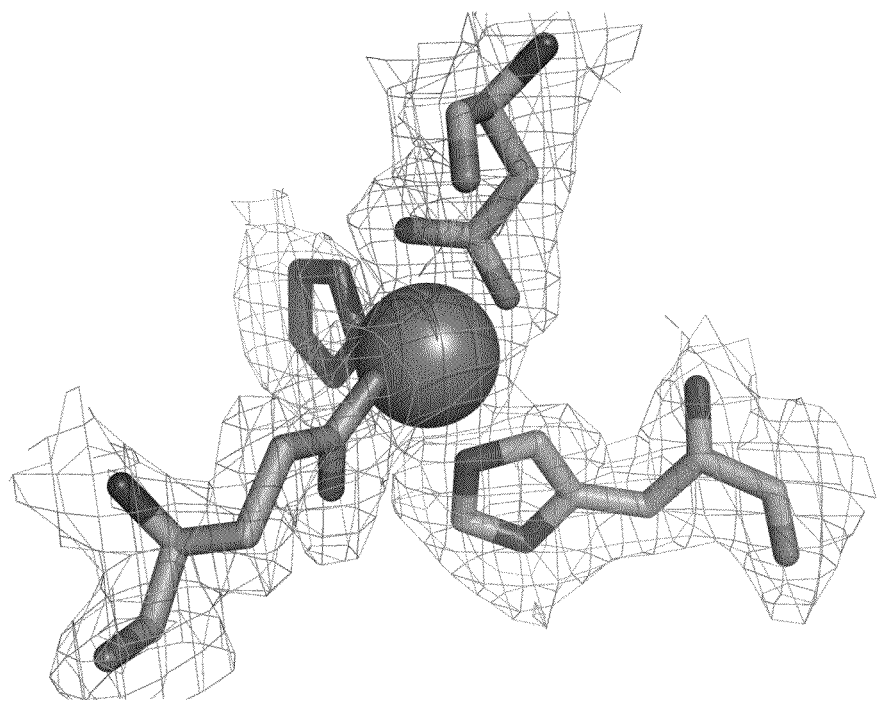

Ribbon and overlay diagrams of human glutaminyl cyclase bound to imidazole based upon the coordinates for space groups C121 are shown in FIGS. 12 and 13, respectively. In particular, it was found that the protein comprised a globular α/β hydrolase fold. A central β-sheet was formed with six β-strands all in parallel fashion but not the second. This β-sheet was observed to be surrounded by α-helices in a sandwich manner with two helices in one side and six more α-helices in the opposite face. The protein's structure was completed with a rather large amount of random coiled loops which are believed to build the active site of the enzyme.

References herein to "active site" include references to a specific region (or atom) in a molecular entity that is capable of entering into a stabilising interaction with another molecular entity. In certain embodiments, the term also refers to the reactive parts of a macromolecule that directly participate in its specific combination with another molecule. In an alternative embodiment, a binding site may be comprised or defined by the three dimensional arrangement of one or more amino acid residues within a folded polypeptide. References to "binding pocket" shall be interpreted in an analogous manner to "active site" and it will be appreciated that these terms may be used interchangeably.

This active site of human glutaminyl cyclase was found to accommodate a zinc ion which is coordinated by three protein residues, $E^{202}$, $D^{159}$ and $H^{330}$. Thus, in an embodiment, the crystal can comprise a binding pocket provided by residues E202, D159 and H330 of SEQ ID NO: 1 according to the coordinates of FIG. 1.

Moreover, the protein shows the presence of a disulfide bridge between residues $C^{139}$ and $C^{164}$. Thus, in an embodiment, the crystal can comprise a disulfide bridge between residues C139 and C164 of SEQ ID NO: 1. As discussed hereinbefore, the presence of such a disulfide bridge has not previously been reported during crystallisation studies with QC (Wang et al, Huang et al).

Additionally four cis-peptide bonds are present between the pair of residues: $D^{159}$-$S^{160}$, $H^{228}$—$P^{229}$, $G^{301}$-$V^{302}$ and $S^{323}$—$P^{324}$. Thus, in an embodiment, the crystal can comprise one or more cis-peptide bonds between any of the following pairs of residues: $D^{159}$-$S^{160}$, $H^{228}$—$P^{229}$, $G^{301}$-$V^{302}$ and $S^{323}$—$P^{324}$.

Finally, in an embodiment, two segments of the polypeptide chain are not visible in the electron density. The gaps include residues between $K^{182}$ and $D^{190}$ and between $F^{146}$ and $N^{150}$.

In an embodiment, there is provided a method of preparing the crystal of murine glutaminyl cyclase as described herein, which comprises the steps of:
(a) providing a solution of murine glutaminyl cyclase, optionally in the presence of a known glutaminyl cyclase inhibitor, in a suitable buffer such as 15 mM Bis-Tris pH6.8/100 mM NaCl buffer;
(b) mixing the solution with a crystallization solution comprising 0.1M sodium acetate pH 5.3, 0.2M ammonium sulphate and 12% (w/v) 2000 MME-PEG; and
(c) incubating the mixture under conditions to promote hanging drop vapor diffusion for a time sufficient to produce the crystal of murine glutaminyl cyclase.

In an embodiment, there is provided a method of preparing the co-crystal of human glutaminyl cyclase bound to a binding ligand, such as a glutaminyl cyclase inhibitor, which comprises the steps of:
(a) providing a solution of murine glutaminyl cyclase in the presence of a known glutaminyl cyclase inhibitor, in a suitable buffer such as 15 mM Bis-Tris pH6.8/100 mM NaCl buffer;
(b) mixing the solution with a crystallization solution comprising 0.1M sodium acetate pH 5.3, 0.2M ammonium sulphate and 12% (w/v) 2000 MME-PEG; and
(c) incubating the mixture under conditions to promote hanging drop vapor diffusion for a time sufficient to produce the co-crystal of murine glutaminyl cyclase bound to a binding ligand, such as a glutaminyl cyclase inhibitor.

In an embodiment, there is provided a crystal or co-crystal comprising murine glutaminyl cyclase obtainable by the crystallisation method as defined herein.

Figure 14:

Crystallization of murine glutaminyl cyclase to produce co-crystals can be carried out as described below and in Example 2. As described, purified murine glutaminyl cyclase is concentrated to 10 mg/mL in the presence of a suitable buffer, such as 15 mM Bis-Tris pH 6.8/100 mM NaCl buffer and the ligand, Inhibitor A, Inhibitor B or Inhibitor C, is added to a final concentration of 1 mM. Macroscopic rod/needle crystal forms are grown by hanging drop vapor diffusion at 21° C. by mixing an equal volume of protein solution with a crystallization solution comprising 0.1M sodium acetate pH 5.3, 0.2M ammonium sulphate and 12% (w/v) 2000 MME-PEG. Crystals typically appeared within 1 week after the experiment was initiated and examples of such crystals obtained following this protocol are shown in FIG. 14. It will be appreciated that to produce apo-crystals, the ligand is omitted in the above protocol.

The murine glutaminyl cyclase crystals may be frozen prior to data collection. The crystals can be cryo-protected with for example, either (a) 20-30% saturated glucose present in the crystallization setup, (b) ethanol added to 15-20%, (c) ethylene glycol added to 10-20% and PEG10,000 brought up to 25%, or (d) glycerol added to 20%. In an embodiment, the crystals can be cryo-protected with the addition of glycerol added to 20% (v/v). The crystals can be either briefly immersed in the cryo-protectant or soaked in the cryo-protectant for periods as long as a day. Freezing can be accomplished by immersing the crystal in a bath of liquid nitrogen or by placing the crystal in a stream of nitrogen gas at −180° C.

As described in Example 2, the crystal structure of murine glutaminyl cyclase in complex with glutaminyl cyclase inhibitors Inhibitor A, Inhibitor B and Inhibitor C was obtained. A summary of the crystal's attributes for murine glutaminyl cyclase bound to glutaminyl cyclase inhibitors Inhibitor A, Inhibitor B and Inhibitor C are listed in Table 4. The three dimensional structure coordinates for space groups P212121 for murine glutaminyl cyclase bound to glutaminyl cyclase inhibitor Inhibitor A is shown in FIG. 2. The three dimensional structure coordinates for space groups P212121 for murine glutaminyl cyclase bound to glutaminyl cyclase inhibitor Inhibitor B is shown in FIG. 3. The three dimensional structure coordinates for space groups P212121 for murine glutaminyl cyclase bound to glutaminyl cyclase inhibitor Inhibitor C is shown in FIG. 4. Ribbon and overlay diagrams of murine glutaminyl cyclase bound to glutaminyl cyclase inhibitors Inhibitor A, Inhibitor B and Inhibitor C based upon the coordinates for space groups P212121 are shown in FIGS. 15 to 19. In particular, it was found that the protein comprised a globular α/β hydrolase fold. A central β-sheet was formed with six β-strands all in parallel fashion but not the second. This β-sheet was observed to be surrounded by α-helices in a sandwich manner with two helices in one side and six more α-helices in the opposite face. The protein's structure was completed with a rather large amount of random coiled loops which appeared to build the active site of the enzyme. This active site accommodates a zinc ion which is coordinated by three protein residues $D^{160}$, $E^{203}$ and $H^{331}$ and an inhibitor molecule. Thus, in an embodiment, the crystal can comprise a binding pocket provided by residues D160, E203 and H331 of SEQ ID NO: 13 according to the coordinates of FIGS. 2 to 4.

Furthermore, the protein demonstrated the presence of a disulfide bridge between residues $C^{140}$ and $C^{165}$. Thus, in an embodiment, the crystal can comprise a disulfide bridge between residues C140 and C165 of SEQ ID NO: 13. As discussed hereinbefore, the presence of such a disulfide bridge has not previously been reported during crystallisation studies with QC (Wang et al, Huang et al).

The present disclosure also provides a machine-readable data storage media having data storage material encoded with machine-readable data that comprises structure coordinates for glutaminyl cyclase. The present invendisclosure also provides a machine readable data storage media having data storage material encoded with machine readable data, which, when read by an appropriate machine, can display a three dimensional representation of a structure of glutaminyl cyclase.

All or a portion of glutaminyl cyclase coordinate data shown in FIGS. 1 to 4, when used in conjunction with a computer programmed with software to translate those coordinates into the three-dimensional structure of glutaminyl cyclase may be used for a variety of purposes, especially for purposes relating to drug discovery. Software for generating three-dimensional graphical representations are known and commercially available. The ready use of the coordinate data requires that it be stored in a computer-readable format. Thus, in accordance with the present disclosure, data capable of being displayed as the three-dimensional structure of glutaminyl cyclase or portions thereof or their structurally similar variants may be stored in a machine-readable storage medium, which is capable of displaying a graphical three-dimensional representation of the structure.

In an embodiment, there is provided a machine-readable data storage medium, comprising a data storage material encoded with machine readable data which, when used by a machine programmed with instructions for using said data, displays a graphical three-dimensional representation comprising glutaminyl cyclase or variant thereof.

Optionally, a computer system can be provided in combination with the machine-readable data storage medium provided herein. In an embodiment, the computer system can comprise a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

The three-dimensional crystal structure of the present disclosure may be used to identify glutaminyl cyclase binding sites, be used as a molecular replacement model to solve the structure of unknown crystallized proteins, to design mutants having desirable binding properties, and ultimately, to design, characterize, identify entities capable of binding and inhibiting glutaminyl cyclase and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The glutaminyl cyclase structural coordinates provided herein are useful for screening and identifying drugs that inhibit glutaminyl cyclase and other structurally similar proteins. For example, the structure encoded by the data may be computationally evaluated for its ability to associate with putative substrates or ligands. Such compounds that associate with glutaminyl cyclase may inhibit glutaminyl cyclase activity, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, in an embodiment, there is provided a method of identifying an inhibitor of human glutaminyl cyclase which comprises the following steps:
(a) generating a 3-dimensional model of human glutaminyl cyclase using the structural coordinates described in FIG. 1;
(b) analysing the binding pocket provided by residues E202, D159 and H330 of SEQ ID NO: 1 according to the coordinates of FIG. 1;
(c) performing computer modeling analysis to identify an inhibitor compound which may associate with the binding pocket of human glutaminyl cyclase.

Furthermore, in an embodiment, there is provided a method of identifying an inhibitor of murine glutaminyl cyclase which comprises the following steps:
(a) generating a 3-dimensional model of murine glutaminyl cyclase using the structural coordinates described in any of FIGS. 2 to 4;
(b) analysing the binding pocket provided by residues D160, E203 and H331 of SEQ ID NO: 13 according to the coordinates of FIGS. 2 to 4;
(c) performing computer modeling analysis to identify an inhibitor compound which may associate with the binding pocket of murine glutaminyl cyclase.

In an embodiment, a method is also provided for evaluating the potential of an entity to associate with glutaminyl cyclase or variant thereof by using all or a portion of the structure coordinates provided in FIGS. 1 to 4 or functional equivalents thereof. In an embodiment, a method is also provided for evaluating the potential of an entity to associate with glutaminyl cyclase or variant thereof by using structure coordinates similar to all or a portion of the structure coordinates provided in FIGS. 1 to 4 or functional equivalents thereof.

In an embodiment, the method can additionally comprise the step of synthesizing the inhibitor compound and contacting the compound with the binding pocket of glutaminyl cyclase to determine the ability of the compound to inhibit glutaminyl cyclase.

In an embodiment, the step of performing computer modeling analysis to identify said inhibitor compound can comprise identifying said compound from a library of compounds.

In an embodiment, the step of performing computer modeling analysis to identify said inhibitor compound can comprise identifying said compound in a database.

In an embodiment, the step of performing computer modeling analysis to identify said inhibitor compound can comprise designing the compound from a known glutaminyl cyclase inhibitor.

With the structures provided herein, the present disclosure permits the use of molecular design techniques to identify, select or design potential inhibitors of glutaminyl cyclase based on the structure of glutaminyl cyclase. Such a predictive model can be valuable in light of the high costs associated with the preparation and testing of the many diverse compounds that may possibly bind to glutaminyl cyclase.

According to the present disclosure, a potential glutaminyl cyclase inhibitor may be evaluated for its ability to bind glutaminyl cyclase prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of glutaminyl cyclase may be computationally evaluated using a series of steps in which chemical entities or fragments are screened and selected for their ability to associate with glutaminyl cyclase.

One skilled in the art may use one of several methods to screen entities (whether chemical or protein) for their ability to associate with glutaminyl cyclase. This process may begin by visual inspection of, for example, glutaminyl cyclase on a computer screen based on the glutaminyl cyclase structure coordinates in FIGS. 1 to 4 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (Miranker et al., "Functionality. Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of glutaminyl cyclase. This may then be followed by manual model building using software such as MOE, QUANTA or Sybyl (Tripos Associates, St. Louis, Mo.).

Useful programs to aid one of skill in the art in connecting the individual chemical entities or fragments include: CAVEAT (Bartlett et al., "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); Lauri and Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Martin, "3D. Database Searching in Drug Design", J. Med. Chem., 35, pp. 2.145-2154 (1992); HOOK (Eisen et al., "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of glutaminyl cyclase in a step-wise fashion one fragment or entity at a time as described above, inhibitory or other glutaminyl cyclase binding compounds may be designed as a whole or "de novo" using either an empty binding site or optionally including some portion(s) of a known inhibitor(s). There are many de novo ligand design methods including: LUDI (Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (Gillet et al., "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with the present disclosure (See, for example, Cohen et al., "Molecular Modeling Software and Methods for Medicinal Chemistry, J. Med. Chem., 33, pp. 883-894 (1990); See also, Navia and Murcko, "The Use of Structural Information in Drug Design", Current Opinions in Structural Biology, 2, pp. 202-210 (1992); Balbes et al., "A Perspective of Modern Methods in Computer-Aided Drug Design", in Reviews in Computational Chemistry, Vol. 5, Lipkowitz and Boyd, Eds., VCH, New York, pp. 337-380 (1994); See also, Guida, "Software For Structure-Based Drug Design", Curr. Opin. Struct. Biology, 4, pp. 777-781 (1994)).

Once an entity has been designed or selected, for example, by the above methods, the efficiency with which that entity may bind to glutaminyl cyclase may be tested and optimized by computational evaluation. For example, an effective glutaminyl cyclase inhibitor preferably demonstrates a relatively small difference in energy between its bound and free states (i.e., a small deformation energy of binding). Thus, the most efficient glutaminyl cyclase inhibitors should preferably be designed with deformation energy of binding of not greater than about 10 kcal/mole, more preferably, not greater than 7 kcal/mole. Glutaminyl cyclase inhibitors may interact with the protein in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to glutaminyl cyclase may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (Frisch, Gaussian, Inc., Pittsburgh, Pa. 1995); AMBER, version 4.1 (Kollman, University of California at San Francisco, 1995); QUANTA/CHARMM (Molecular Simulations, Inc., San Diego, Calif. 1995); Insight II/Discover (Molecular Simulations, Inc., San Diego, Calif. 1995); DelPhi (Molecular Simulations, Inc., San Diego, Calif. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by an embodiment of the present disclosure, is the computational screening of small molecule databases for chemical entities or compounds that can bind in whole, or in part, to glutaminyl cyclase. In this screening, the quality of fit of such entities to the binding site may be judged either by shape complementarities or by estimated interaction energy (Meng et al., J. Comp. Chem., 13, 505-524 (1992)).

In an embodiment, there is provided a compound that associates with glutaminyl cyclase produced or identified by various methods as described hereinbefore.

The structure coordinates set forth in FIGS. 1 to 4 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIGS. 1 to 4 as a molecular replacement model.

By using molecular replacement, all or part of the structure coordinates of glutaminyl cyclase provided by the present disclosure (and set forth in FIGS. 1 to 4) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of glutaminyl cyclase according to FIGS. 1 to 4 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in Meth. Enzymol., 115, pp. 55-77 (1985); Rossmann, ed., "The Molecular Replacement Method", Int. Sci. Rev. Ser., No. 13, Gordon & Breach, New York (1972)).

The structure of any portion of any crystallized molecule or molecular complex that is sufficiently homologous to any portion of glutaminyl cyclase can be resolved by this method.

In one embodiment, the method of molecular replacement is utilized to obtain structural information about the present disclosure and any other glutaminyl cyclase-like molecule.

The structure coordinates of glutaminyl cyclase as provided by the present disclosure are useful in solving the structure of glutaminyl cyclase variants that have amino acid substitutions, additions and/or deletions (referred to collectively as "glutaminyl cyclase mutants", as compared to naturally occurring glutaminyl cyclase). These glutaminyl cyclase mutants may optionally be crystallized in co-complex with a ligand, such as an inhibitor or substrate analogue. The crystal structures of a series of such complexes may then be solved by molecular replacement and compared with that of glutaminyl cyclase. Potential sites for modification within the various binding sites of the enzyme may thus be identified. This information provides an additional tool for determining the most efficient binding interactions such as, for example, increased hydrophobic interactions, between glutaminyl cyclase and a ligand. It is noted that the ligand may be the protein's natural ligand or may be a potential agonist or antagonist of a protein.

In an embodiment, there is provided a method of designing, selecting and/or optimising a chemical entity that binds to all or part of the binding pocket or human or murine glutaminyl cyclase according to any one of FIGS. 1 to 4 comprising the steps of:
 (a) providing the structural coordinates of said binding pocket or human or murine glutaminyl cyclase on a computer comprising the means for generating 3-dimensional structural information from said structural coordinates; and
 (b) designing selecting and/or optimising said chemical entity by performing a fitting operation between said chemical entity and said 3-dimensional structural information of all or part of said binding pocket or human or murine glutaminyl cyclase.

In an embodiment, there is provided a method for evaluating the ability of a chemical entity to associate with all or part of the binding pocket or human or murine glutaminyl cyclase according to any one of FIGS. 1 to 4 comprising the steps of:
 (a) providing the structural coordinates of said binding pocket or human or murine glutaminyl cyclase on a computer comprising the means for generating 3-dimensional structural information from said structural coordinates;
 (b) employing computational means to perform a fitting operation between the chemical entity and all or part of the binding pocket or human or murine glutaminyl cyclase; and
 (c) analyzing the results of said fitting operation to quantitate the association between the chemical entity and all or part of the binding pocket or human or murine glutaminyl cyclase.

In an embodiment, the method can further comprise generating a 3-dimensional graphical representation of all or part of the binding pocket or human or murine glutaminyl cyclase prior to step (b).

In an embodiment, there is provided a method of using a computer for evaluating the ability of a chemical entity to associate with all or part of the binding pocket or human or murine glutaminyl cyclase according to any one of FIGS. 1 to 4, wherein said computer comprises a machine-readable data storage medium comprising a data storage material encoded with said structural coordinates defining said binding pocket or human or murine glutaminyl cyclase and means for generating a three-dimensional graphical representation of the binding pocket or human or murine glutaminyl cyclase, and wherein said method comprises the steps of:
 (a) positioning a first chemical entity within all or part of said binding pocket or human or murine glutaminyl cyclase using a graphical 3-dimensional representation of the structure of the chemical entity and the binding pocket or human or murine glutaminyl cyclase;
 (b) performing a fitting operation between said chemical entity and said binding pocket or human or murine glutaminyl cyclase by employing computational means; and
 (c) analyzing the results of said fitting operation to quantitate the association between said chemical entity and all or part of the binding pocket or human or murine glutaminyl cyclase.

In an embodiment, the method can further comprise the steps of:
 (d) repeating steps (a) through (c) with a second chemical entity; and
 (e) selecting at least one of said first or second chemical entity that associates with said all or part of said binding pocket or human or murine glutaminyl cyclase based on said quantitated association of said first or second chemical entity.

In an embodiment, there is provided a method for identifying an agonist or antagonist of the human or murine glutaminyl cyclase according to any one of FIGS. 1 to 4, comprising the steps of:
 (a) using a 3-dimensional structure of the binding pocket or human or murine glutaminyl cyclase to design or select a chemical entity;
 (b) contacting the chemical entity with the human or murine glutaminyl cyclase;
 (c) monitoring the catalytic activity of the human or murine glutaminyl cyclase; and
 (d) classifying the chemical entity as an agonist or antagonist based on the effect of the chemical entity on the catalytic activity of human or murine glutaminyl cyclase.

In an embodiment, there is provided a method of designing a compound or complex that associates with all or part of the binding pocket or human or murine glutaminyl cyclase according to any one of FIGS. 1 to 4, comprising the steps of:

(a) providing the structural coordinates of said binding pocket or human or murine glutaminyl cyclase on a computer comprising the means for generating 3-dimensional structural information from said structural coordinates; and
(b) using the computer to perform a fitting operation to associate a first chemical entity with all or part of the binding pocket;
(c) performing a fitting operation to associate at least a second chemical entity with all or part of the binding pocket;
(d) quantifying the association between the first and second chemical entity and all or part of the binding pocket;
(e) optionally repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket on a computer screen using the 3-dimensional graphical representation of the binding pocket and said first and second chemical entity; and
(g) assembling the first and second chemical entity into a compound or complex that associates with all or part of said binding pocket by model building.

Any, all or a portion of the complexes referred to above may be studied using well-known X-ray diffraction techniques and may be refined versus 1.5-3.5 Å resolution X-ray data to an R value of about 0.22 or less using computer software, such as X-PLOR (Brunger et al., X-PLOR, Version 3.1, A system for X-ray crystallography and NMR, Yale University, (1992)), CNS (Brunger et al., Crystallography & NMR System (CNS), A new software suite for macromolecular structure determination, Acta Cryst. D54: 905-921 (1998)), TNT (Tronrud et al., An efficient general-Purpose least-squares refinement program for macromolecular structures, Acta Cryst. A43, 489-501 (1987)), Buster (Bricogne, The Bayesian Statistical Viewpoint on Structure Determination: Basic Concepts and Examples", in Methods in Enzymology, 276A, 361-423. Carter & Sweet, eds. (1997)) and Refmac (Murshudov et al., Refinement of macromolecular structures by the maximum-likelihood method, Acta Cryst D53:240-255 (1997)) (See, e.g., Blundell & Johnson, supra; Meth. Enzymol., Vol. 114 & 115, Wyckoff et al., eds., Academic Press (1985)). This information may thus be used to optimize known glutaminyl cyclase inhibitors, and more importantly, to design new glutaminyl cyclase inhibitors.

The structure coordinates described herein may also be used to derive the dihedral angles, phi and psi, that define the conformation of the amino acids in the protein backbone. As will be understood by those skilled in the art, the phi angle refers to the rotation around the bond between the alpha-carbon and the nitrogen, and the psi angle refers to the rotation around the bond between the carbonyl carbon and the alpha-carbon. The subscript "n" identifies the amino acid whose conformation is being described (for a general reference, See Blundell and Johnson, Protein Crystallography, Academic Press, London, 1976).

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Preparation of 1-(3-(1H-Imidazol-1-yl)propyl)-3-(3,4-dimethoxyphenyl)thiourea (Inhibitor A)

4.0 mmol of 3,4-dimethoxyphenyl isothiocyanate and 4.0 mmol of 3-(1H-imidazol-1-yl)alkyl-1-amine were dissolved in 10 mL of absolute ethanol. After stirring for 2 h under reflux, the solvent was evaporated and the resulting solid was recrystallized from ethanol. Yield: 0.66 g (51.3%); mp: 160.0-161.0° C.

$^1$H NMR δ 1.8-2.0 (m, 2H), 3.4-3.5 (m, 2H), 3.75 (s, 6H), 3.9-4.0 (m, 2H), 6.7-6.8 (m, 1H), 6.9 (br m, 2H), 6.95 (s, 1H), 7.15 (s, 1H), 7.55 (br s, 1H), 7.6 (s, 1H), 9.3 (s, 1H); MS m/z 321.2 (M+H), 253.3 (M-C$_3$H$_3$N$_2$.)

Preparation of 2-Cyano(3,4,5-trimethoxyphenyl)-3-(3-(4-methyl-1H-imidazol-1-yl)propyl)-guanidine (Inhibitor B)

Intermediate 1: 4-Methyl-1-trityl-1H-imidazole (D1)

4-Methyl-1H-imidazole (36.53 mmol, 1 eq) of was dissolved in 120 mL of dimethylformamide, triethylamine (73.06 mmol, 2 eq.) and chlorotriphenylmethane (40.1 mmol, 1.1 eq) where added. The mixture was stirred for 3.5 h. The precipitate filtered off and was washed by means of ice-cooled dimethylformamide (2×50 mL) and water (2×50 mL). After removal of the solvent the remaining product was dried over P$_4$O$_{10}$.

Yield: 10.65 g (98.2%). The product was used without further purification.

Intermediate 2: 1-Trityl-3-[3-(1,3-dioxo-1,3-dihydro-2H-isoindol-2-yl)propyl]-1,4-dimethyl-1H-imidazol-3-ium bromide (D2)

4-Methyl-1-trityl-1H-imidazole (i.e 32.85 mmol, 1 eq., which may be prepared as described in D1) was suspended in acetonitrile (10 mL) and 2-(3-bromopropyl)isoindoline-1,3-dione (32.85 mmol, 1 eq.) was added. The mixture was kept under reflux over night. The organic solvent was removed.

Purification was done by flash-chromatography using silica gel and a CHCl$_3$/MeOH-gradient.

Yield: 10.65 g (63.44%).

Intermediate 3: 2-(3-(5-Methyl-1H-imidazol-1-yl)propyl)isoindoline-1,3-dione (D3)

1-Trityl-3-[3-(1,3-dioxo-1,3-dihydro-2H-isoindol-2-yl)propyl]-1,4-dimethyl-1H-imidazol-3-ium bromide (i.e. 7.86 mmol, which may be prepared as described in D2) was dissolved in a stirred solution containing methanol (20 mL) and trifluoracetic acid (4 mL). The mixture was kept under reflux over night. The solvent was then removed by means of reduced pressure and the remaining oil was purified by flash-chromatography using silica gel and a CHCl$_3$/MeOH-gradient.

Yield: 2.05 g (97.0%).

Intermediate 4: 3-(5-Methyl-1H-imidazol-1-yl)propan-1-amine (D4)

2-(3-(5-Methyl-1H-imidazol-1-yl)propyl)isoindoline-1,3-dione (i.e. 8.92 mmol, 1 eq., which may be prepared as described in D3) and hydrazine monohydrate (17.84 mmol, 2 eq.) were dissolved in dry EtOH (50 mL). The mixture was kept under reflux over night, then mixture was concentrated down to a volume of 25 mL. Hydrochloric acid (conc., 55 mL) was then added and the mixture was heated to 50° C. and kept at this temperature for 30 min. The formed precipitate was then filtered. The filtrate was cooled to 0° C. and solid NaOH was added until a final pH-value of 10-12 was reached. The aqueous solution was extracted by means of CHCl$_3$ (3×50 mL). The combined organic layers were dried over Na$_2$SO$_4$, filtered and the solvent was removed. The product was purified by means of flash-chromatography using silica gel and a CHCl$_3$/MeOH-gradient.

Yield: 0.74 g (60%), viscous oil

Yield over all steps: 36.3%

$^1$H-NMR (CDCl$_3$, 499.78 MHz): δ 1.79-1.847 (m, 2H); 2.179 (s, 3H); 2.694-2.721 (m, 2H); 3.891-3.920 (m, 2H); 6.731 (s, H); 7.240 (s, solv.); 7.380 (s; H); ESI-MS m/z: 140.3 (M+H)$^+$, 279.4 (2M+H)$^+$; HPLC (λ=214 nm) rt: dead time (100%)

Intermediate 5: 2-(3-(4/5-methyl-1H-imidazol-1-yl)propyl)isoindoline-1,3-dione (D5)

4-Methyl-1H-imidazole (36.53 mmol, 1 eq) and sodium hydride (60% in mineral oil, 36.53 mmol, 1.0 eq.) were dissolved in 80 mL of dimethylformamide. The mixture was stirred at room temperature for 2 h until the formation of hydrogen gas deceased. 2-(3-Bromopropyl)isoindoline-1,3-dione (34.70 mmol, 0.95 eq.) was added and the mixture was stirred at 90° C. overnight. The solvent was removed and the remaining residue was purified by means of flash-chromatography using silica gel and a CHCl₃/MeOH-gradient.

Yield: 6.1 g (62.0%) of a mixture of 2-(3-(4-methyl-1H-imidazol-1-yl)propyl)isoindoline-1,3-dione and 2-(3-(5-methyl-1H-imidazol-1-yl)propyl)isoindoline-1,3-dione

Intermediate 6: 2-(3-(4-Methyl-1H-imidazol-1-yl)propyl)isoindoline-1,3-dione (D6)

A mixture consisting of 2-(3-(4-methyl-1H-imidazol-1-yl)propyl)isoindoline-1,3-dione and 2-(3-(5-methyl-1H-imidazol-1-yl)propyl)isoindoline-1,3-dione (22.65 mmol, 1 eq., which may be prepared as described in D5) and trityl chloride (13.6 mmol, 0.6 eq.) were dissolved in 40 mL of dichloromethane and kept at a temperature of 0° C. for 10 min and 1.5 h at room temperature. The solvent was removed and the remaining solid was purified by means of flash-chromatography using silica gel and a CHCl₃/MeOH-gradient.

Yield: 0.92 g (15.1%)

Intermediate 7: 3-(4-Methyl-1H-imidazol-1-yl)propan-1-amine (D7)

2-(3-(4-Methyl-1H-imidazol-1-yl)propyl)isoindoline-1,3-dione (3.42 mmol, 1 eq., which may be prepared as described in D6) and hydrazine monohydrate (6.84 mmol, 2 eq.) were dissolved in 20 mL of ethanol and the mixture was stirred for 12 h under reflux. The mixture was kept under reflux over night, then the mixture was concentrated down to a volume of 25 mL. Hydrochloric acid (conc., 55 mL) was then added and the mixture was heated to 50° C. and kept at this temperature for 30 min. The formed precipitate was then filtered. The filtrate was cooled to 0° C. and solid NaOH was added until a final pH-value of 10-12 was reached. The aqueous solution was extracted by means of CHCl₃ (3×50 mL). The combined organic layers were dried over Na₂SO₄, filtered and the solvent was removed. The product was purified by means of flash-chromatography using silica gel and a CHCl₃/MeOH-gradient containing aqueous ammonia (2% v/v).

Yield: 0.31 g (65.1%).

$^1$H-NMR (CDCl₃, 499.78 MHz): δ 1.819-1.874 (m, 2H); 2.188 (s, 3H); 2.699-2.712 (m, 2H); 3.910-3.948 (m, 2H); 6.594 (s, H); 7.240 (s, solv.); 7.328 (s; H); ESI-MS m/z: 140.3 (M+H)⁺, 279.4 (2M+H)⁺; HPLC (λ=214 nm) rt: dead time (100%)

Inhibitor B: 2-Cyano(3,4,5-trimethoxyphenyl)-3-(3-(4-methyl-1H-imidazol-1-yl)propyl)-guanidine Inhibitor B was synthesized from 5-isothiocyanato-1,2,3-trimethoxybenzene (0.162 g, 0.72 mmol) and 3-(4-methyl-1H-imidazol-1-yl)propan-1-amine (0.10 g, 0.72 mmol, which may be prepared as described in D7).

Yield: 0.110 g (41.0%). $^1$H NMR (CDCl₃): δ 1.95-2.01 (m, 2H); 2.14 (s, 3H); 3.22-3.27 (m, 2H); 3.82 (s, 9H); 3.86-3.88 (m, 2H); 5.03 (br s, H); 6.41 (s, 2H); 6.56 (s, H); 7.28 (s, H); 7.46 (s, H). MS m/z 373.3 (M+H)⁺; HPLC (λ=214 nm, [C]): rt 8.64 min (100%)

Preparation of 2-Cyano(mesityl)-3-(3-(4-methyl-1H-imidazol-1-yl)propyl)guanidine (Inhibitor C)

Inhibitor C was synthesized from 2-isothiocyanato-1,3,5-trimethylbenzene (0.106 g, 0.60 mmol) and 3-(4-methyl-1H-imidazol-1-yl)propan-1-amine (0.084 g, 0.60 mmol, which may be prepared as described in D7).

Yield: 0.088 g (45.2%). $^1$H NMR (DMSO-d₆): δ 1.80-1.84 (m, 2H); 2.04 (s, 3H); 2.09 (s, 6H); 2.23 (s, 3H); 3.04-3.06 (m, 2H); 3.80-3.84 (m, 2H); 6.59 (br s, H); 6.80 (s, H); 6.91 (s, 2H); 7.42 (s, H); 8.42 (s, H). MS m/z 325.2 (M+H)⁺; HPLC (λ=214 nm, [C]): rt 10.05 min (98.6%)

Example 1

Isolation, Characterisation and Crystallisation of Human Glutaminyl Cyclase (A) Isolation of Human Glutaminyl Cyclase
Cloning Procedures The hQC cDNA was inserted into the yeast expression vector ρPICZαB (Invitrogen, Germany) via the PstI and NotI restriction sites using the primers:

```
(sense) (P1)
                                        (SEQ ID NO: 2)
5'-ATATATCTGCAGCG CAT CAC CAT CAC CAT CAC GAG GAG AAG AAT TAC CAC C-3';
and (antisense) (P2)
                                        (SEQ ID NO: 3)
5'-ATATATGCGGCCGC TTA CAA ATG AAG ATA TTC C-3'.
```

The disulfide bond-lacking mutant C139A/C164A was obtained via a two-step PCR-mediated site-directed mutagenesis according to standard PCR techniques using the primer pairs:

```
C139A (sense)
                                        (SEQ ID NO: 4)
5'-CAT TTG GTC CTC GCC GCC CAC TAT GAC TCC AAG-

3';

C139A (antisense)
                                        (SEQ ID NO: 5)
5'-CTT GGA GTC ATA GTG GGC GGC GAG GAC CAA ATG-

3';

C164A (sense)
                                        (SEQ ID NO: 6)
5'-GAT TCA GCC GTG CCA GCT GCA ATG ATG TTG GAA C-3';
and C164A (antisense)
                                        (SEQ ID NO: 7)
5'-G TTC CAA CAT CAT TGC AGC TGG CAC GGC TGA ATC- 3'
followed by digestion of the parent DNA using
Dpnl (quik-change II site-directed mutagenesis
kit, Stratagene, USA).
```

Transformation of *Pichia pastoris* and Mini-Scale Expression

Plasmid DNA was amplified in the *Escherichia coli* strain DH5a and purified according to the recommendations of the manufacturer (Qiagen, Germany). 20-30 µg DNA were linearised with PmeI, precipitated, and dissolved in deionised water. 1-5 µg DNA was used for transformation of competent yeast cells (*P. pastoris* strain X33 [AOX1, AOX2]) by electroporation according to the manufacturer's instructions (Bio-Rad, Germany). Yeast was grown, transformed, and analysed according to the manufacturer's instructions (Invitrogen, Germany). Briefly, selection was carried out on YPDS plates containing 150 µg/ml zeocin. To test yeast clones upon expression, recombinants were grown for 24 h in 10 ml conical tubes containing 2 ml of BMGY. Afterwards, the cells were centrifuged and resuspended in 2 ml of BMMY containing 0.5% methanol. This concentration was maintained by addition of methanol every 24 h. QC activity was determined in the supernatant after 72 h. The expression of the C139A/C164A mutant was confirmed by sequence analysis of the hQC gene inserted into the yeast genome applying the primer 5'-CTG GAG TGA CAA ATC TGG C-3' (SEQ ID NO: 8). Therefore genomic DNA was prepared according to standard molecular biological techniques followed by the amplification of the target gene via PCR using primers (P1; SEQ ID NO: 2) and (P2; SEQ ID NO: 3). Clones displaying highest QC activity were chosen for fermentation and further experiments.

Large Scale Expression and Purification

Fermentation of hQC and the C139A/C164A mutant was carried out in a 5 L reactor (Biostad B; Braun Biotech, Germany), essentially as described elsewhere (Schilling, S., Hoffmann, T., Rosche, F., Manhart, S., Wasternack, C., and Demuth, H. U. [2002] Biochemistry 41, 10849-10857). Briefly, fermentation was initiated in basal salt medium supplemented with trace salts at pH 5.5. Biomass was accumulated in a batch and a fed batch phase with glycerol as the sole carbon source for about 28 h. Expression of target protein was induced by methanol feeding according to a three-step profile recommended by Invitrogen ("*Pichia* fermentation process guidelines"). The fermentation process was stopped after 68 h. Afterwards, cells were separated from the medium by centrifugation at 6000×g and 4° C. for 20 min.

Histidine was added to a final concentration of 1 mM and the supernatant was applied in upward flow direction with a flow of 12 ml/min onto an expanded bed absorption column (Streamline column 25 [2.5×22 cm—settled] with Streamline Chelating Sepharose, GE Healthcare, Sweden) saturated with $Ni^{2+}$ ions and equilibrated with 50 mM phosphate buffer, pH 6.8, 300 mM sodium chloride. Bound enzyme was washed with 1.5 L 50 mM phosphate buffer, pH 6.8, 300 mM sodium chloride. Enzyme was eluted in downward flow direction at a flow rate of 8 ml/min using 50 mM phosphate buffer, pH 6.8, 300 mM sodium chloride containing 100 mM histidine. QC-containing fractions were pooled and ammonium sulfate was added to a final concentration of 700 mM. After centrifugation at 100000×g (4° C.) for 1 h the resulting solution was applied onto a Butyl Sepharose fast flow column (1.6×13 cm, GE Healthcare, Sweden) at a flow rate of 2 ml/min. Bound enzyme was washed for 3 column volumes applying 50 mM phosphate buffer, pH 6.8, 700 mM ammonium sulfate and eluted in reversed flow direction with 5 mM phosphate buffer, pH 6.8. Fractions containing QC-activity were pooled and dialysed over night at 4° C. against a 100 fold excess v/v of 30 mM Bis-Tris, pH 6.8. The solution was centrifuged at 100000×g (4° C.) for 1 h and applied onto a Uno Q6 column (12×53 mm, Bio-Rad, Germany) at a flow rate of 4 ml/min. Bound enzyme was washed for 3 column volumes applying 30 mM Bis-Tris, pH 6.8. Enzyme was eluted with 30 mM Bis-Tris, pH 6.8 containing 100 mM sodium chloride. QC-containing fractions were pooled and purity was analysed by SDS-PAGE. The purified enzyme was stored at −20° C. after addition of 50% glycerol or without glycerol at −80° C.

(B) Characterization of Human Glutaminyl Cyclase

Detection of Disulfide Bond Applying SDS-PAGE

For detection of a disulfide bond of hQC WT (wild type) and the C139A/C164A mutant SDS-PAGE was applied. Therefore enzyme was deglycosylated using Endoglycosidase $H_f$ (1000 units per 0.2 mg QC for 1 h at room temperature; NEB, Germany) and mixed with loading buffer:

TABLE 2

| Buffer conditions for reducing and non-reducing SDS-PAGE | |
|---|---|
| Non-reducing conditions | Reducing conditions |
| 45 mM Tris-HCl, pH 6.8 | 45 mM Tris-HCl, pH 6.8 |
| 10% glycerol | 10% glycerol |
| 0.01% bromine phenol blue | 0.01% bromine phenol blue |
| | 5% β-mercaptoethanol |

Samples were boiled for 5 min and a 15% Tris-Glycine SDS gel (6 cm×8 cm) was run with 5 µg protein per lane at 200 V for 2 h. Protein was visualised by Coomassie staining (FIG. 5).

While migration shifts for the hQC WT between reducing (shaded grey lanes, disulfide bond is broken) and non-reducing (white lanes, disulfide bridge) conditions; due to diffusion of the reducing agent the band pattern of lanes 3 and 6 is a mixed type; no difference in migration appears between both conditions for the C139A/C164A mutant. No reducing events/breaking of a disulfide bond occurs which influences migration on SDS-PAGE for the mutant.

Conformational Stability—CD-Spectra hQC and the C139A/C164A mutant were desalted by size exclusion chromatography using a Sephadex G-25 fast desalting column (1.0×10 cm; GE Healthcare, Sweden), which was equilibrated in 10 mM phosphate buffer, pH 6.8. Protein concentration was adjusted to 40 µM (WT) and 37 µM (C139A/C164A).

CD-spectra were acquired with a Jasco J-715 spectrapolarimeter (Jasco, Germany) using quartz cuvettes of 0.1 cm pathlength and an external thermostat (Julabo F25, Julabo, Germany). For wavelength scans (general settings: sensitivity 100 mdeg, data pitch 1 nm, scanning mode continuous, scanning speed 50 nm/min, response time 1 s, band with 1 nm) the mean of 10 scans between 190 and 260 nm (far UV/amide region) was calculated and corrected by subtraction of the buffer spectrum (FIG. 6). The percentage of secondary structure elements at 20° C. was calculated using the Jasco secondary structure estimation program based on the method of Yang (Yang, J. T., Wu, C. S., and Martinez, H. M. [1986] *Methods Enzymol* 130, 208-269).

Both enzymes show a typical CD spectrum for proteins with a high α-helical content characterized by minima at wavelength of 208 nm and 222 nm. The tertiary structure was calculated to WT: 54% α-helix, 25.8% β-sheet, 18.5% random; C139A/C164A: 55.6% α-helix, 25.8% β-sheet, 20.2% random. These values are very similar, leading to the conclusion that the loss of the disulfide bond does not evoke changes in tertiary structure.

Figure 7:
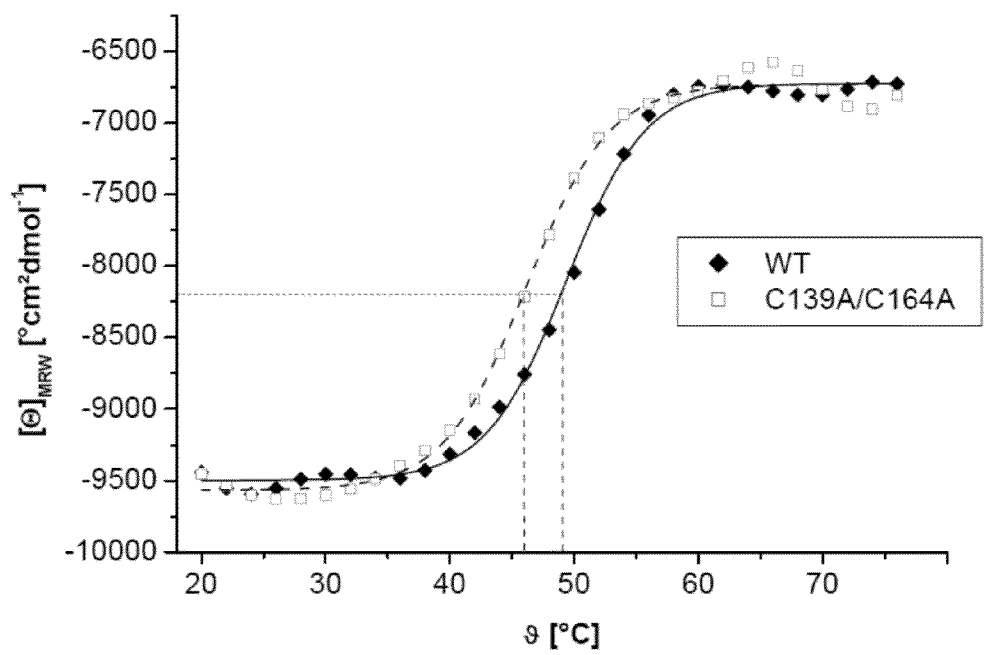

To study the conformational stability, temperature was increased from 20 to 80° C. with a velocity of 30° C./h and a delay of 60 s. Wavelength scans were done every 10 K whereas the ellipticity at a wavelength of 227 nm was measured every 2 K (FIG. 7). At this wavelength, a major change of the spectrum could be observed. A sigmoid fit revealed a temperature of 49° C. where half of the WT enzyme is unfolded. For the C139A/C164A variant, this value is decreased to 46° C. A conformation stabilizing effect can be attributed to the disulfide bond of hQC.

Figure 8:
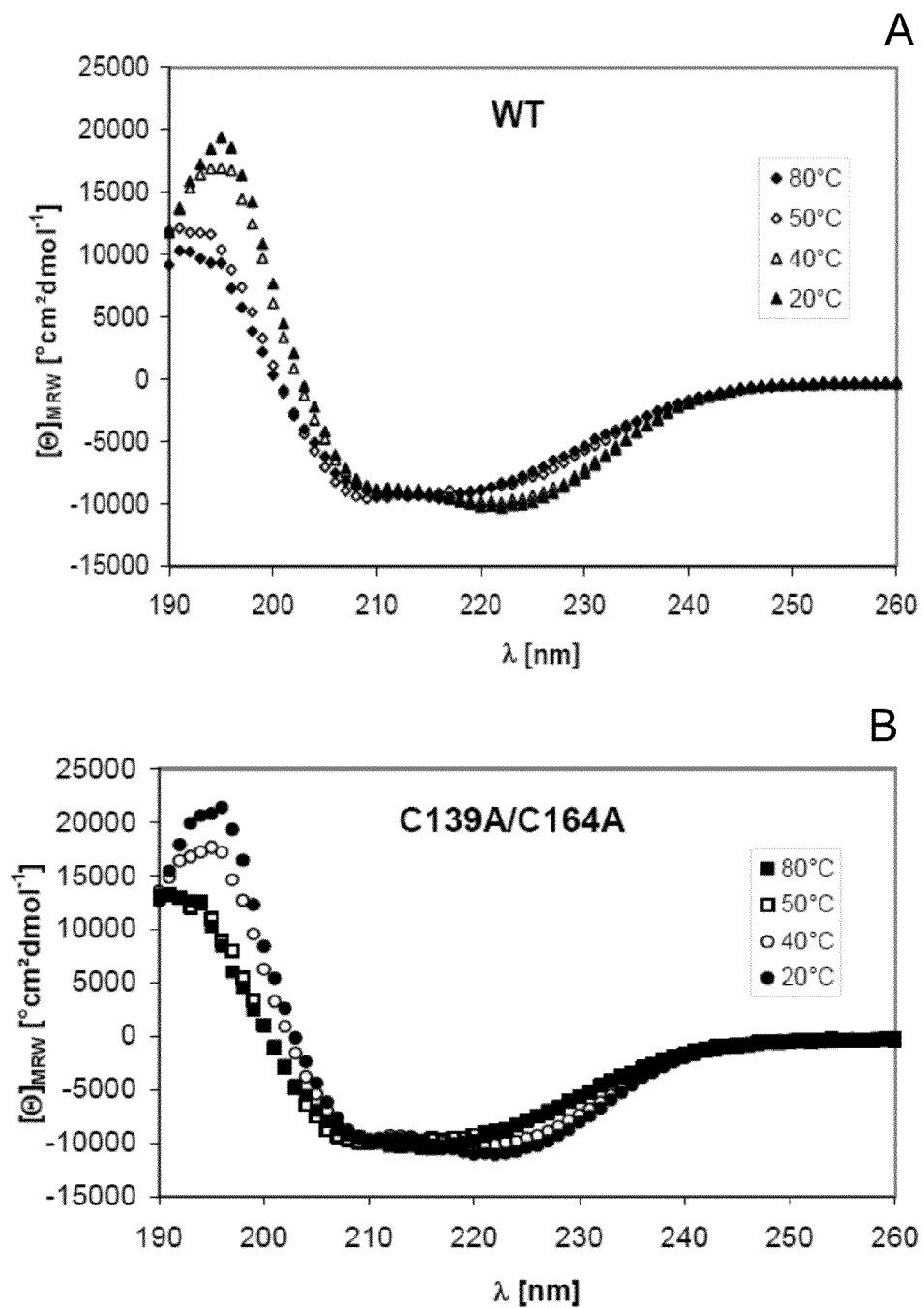

Because of the wide-meshed recording, this difference can not be detected in the wavelength scans (FIG. 8). Refolding does not occur upon cooling.

Conformational Stability—Fluorescence Emission Spectra

Figure 9:
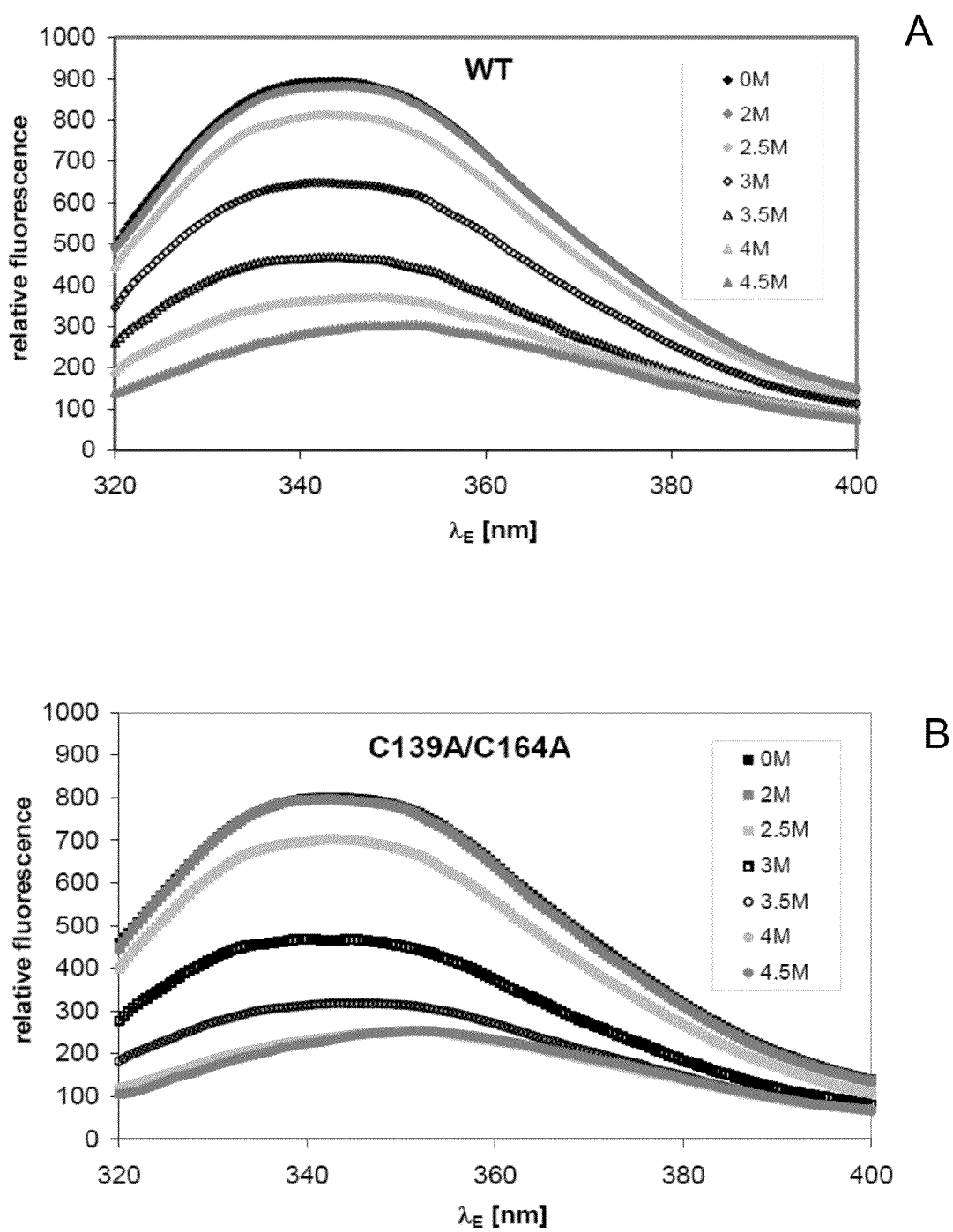

Fluorescence emission spectra were recorded in the wavelength range between 320 and 400 nm (major emission caused by tryptophan residues) at 22° C. using the luminescence spectrometer LS 50 B (Perkin-Elmer, USA). The excitation wavelength was 295 nm (only excitation of tryptophan residues) at a scanning speed of 100 nm/min using a slit width of 3 nm for excitation and 6 nm for emission. To study conformational stability hQC WT and the C139A/C164A mutant were diluted with 50 mM phosphate buffer, pH 6.8 containing diverse concentrations of guanidine hydrochloride (GdmCl) to a concentration of 0.24 µM (WT) respectively 0.31 µM (C139A/C164A mutant). Spectra were acquired and the spectrum of the corresponding buffer was subtracted (FIG. 9).

Usually, upon denaturation the emission maximum of proteins exhibits a tryptophan-mediated shift from a shorter wavelength to about 350 nm which corresponds to the fluorescence maximum of tryptophan in aqueous solutions (Schmid, F. X. [1989] *Protein Structure: A Practical Approach* [Creighton, T. E:, Ed.] pp 251-285, IRL Press, oxford). The native enzymes (hQC WT and C139A/C164A mutant) exhibit a fluorescence emission maximum at 344 nm which shifts upon unfolding to a wavelength of 354 nm, indicating a more hydrophilic environment of the tryptophan residues compared to the folded state.

The conformation of both enzymes is stable up to a GdmCl concentration of 2M. At a concentration of 2.5 M unfolding can be detected indicated by a reduction of fluorescence emission. In comparison to hQC WT the unfolding is increased for the C139A/C164A mutant. While there is still a folded fraction at 4 M GdmCl for hQC WT the C139A/C164A mutant is completely unfolded.

Figure 10:
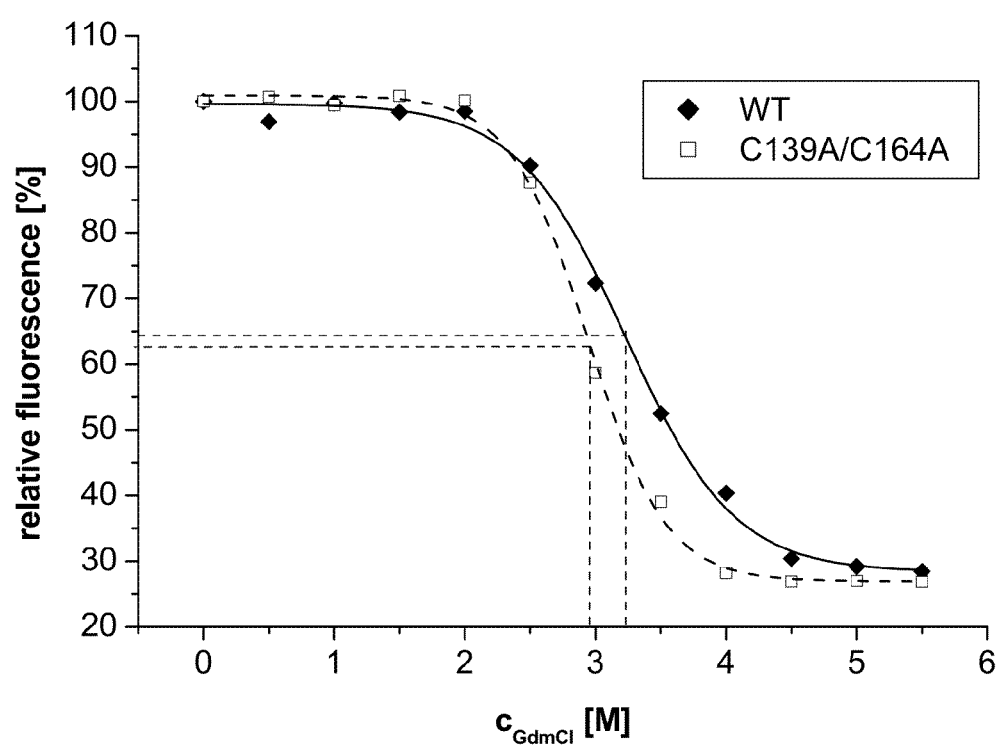

At an emission wavelength of 337 nm major changes in relative fluorescence could be observed. The GdmCl concentrations where half of the protein is unfolded could be determined as 3.2 M for hQC WT and 2.9 M for the C139A/C164A mutant (FIG. 10). This confirms the conformation stabilizing effect of the disulfide bond.

(C) Crystallization of Human Glutaminyl Cyclase

Crystallisation was conducted by applying the hanging drop vapour diffusion method. First screening for crystallisation conditions was carried out with several commercial available basic screening kits at 13° C. (protein concentration 5 mg/ml, 0.5 mM Inhibitor A) and 21° C. (protein concentration 7.5 mg/ml, 0.5 mM Inhibitor A). The most promising crystals grew in buffer C5 of the JBScreen Classic 7 kit by Jena Bioscience (JBS, Germany) [30% (w/v) 2-methyl-2,4-pentanediol; 10% (w/v) PEG 4000; 100 mM imidazole-HCl, pH 8] at a temperature of 21° C. and a protein concentration of 7.5 mg/ml. For further optimization the concentration of PEG 4000 was varied revealing a concentration of 11% (w/v) PEG 4000 as ideal. By X-ray structure analysis a resolution of 2.1 Å was achieved.

Crystal Growth

Crystals were grown using the hanging drop vapor diffusion technique at room temperature (21° C.) in Easyxtal 24-well plates (Qiagen). The mother liquor buffer consisted of 0.1M imidazol pH 8, 30% (v/v) 2-methyl 2,4-pentanediol and 11% (w/v) 4000PEG. Protein solution concentrated up to a 10 mg/ml was recombinant human glutaminyl cyclase in the presence of 25 mM Bis-Tris pH6.8/100 mM NaCl buffer. A mixture of 1 µl mother liquor buffer and 1 µl protein solution was set. Crystals appeared usually ten to fifteen days after the experiment was initiated and they displayed a macroscopic plate shape (FIG. 11).

Cryosolution

Before x-ray measurements, crystals were rapidly soaked into a new cryo-buffer solution where mother liquor buffer solution was saturated with 15% (v/v) glycerol. Immediately crystals were collected from the cryo-buffer solution using a pin nylon loop and they were mounted onto the goniometer and flash frozen at −180° C. under a nitrogen stream.

Data Collection

Data collection from a single crystal was undertaken by means of Cu Kα radiation ($\lambda$=1.5418 Å) by using a rotating-anode source (RA Micro 007; Rigaku/MSC, Tokyo, Japan) and CCD detector device (CCD Saturn 944+, Rigaku) with Varimax™ Optics (Rigaku) and an AFC-11 goniometer.

Finally, the crystal was demounted and stored in liquid nitrogen for an additional measurement in the beam line BL14.1 of the synchrotron in Berlin (Bessy).

Data Processing

Data processing was carried out using the programs included in the crystallographic suite CCP4. The image reflection intensities were indexed and integrated using the program Mosflm. Afterwards the integrated intensities were scaled and merged using the program Scala. Moreover, initial phases were obtained with a molecular replacement approach using Phaser and taking the crystal structure with PDBid 2AFO as searching model. Thus, initial electron densities were obtained. Subsequent manual building of the missing fragments and maximum-likelihood refinement cycles were performed by using the programs COOT and REFMAC5 as well as from the CCP4 suite.

Results

Table 3 summarizes the statistics of the data set obtained in Berlin synchrotron Bessy with a crystal of the human glutaminyl cyclase and their corresponding statistics for the data processing and model building. Programs used were for data processing MOSFLM and SCALA, for molecular replacement PHASER, for refinement REFMAC5 and for Model Building: Coot (all of them included in the CCP4 suite). Numbers between brackets belong to the outer shell resolution limit.

TABLE 3

Summary of Statistics for Human Glutaminyl Cyclase Crystal

| Data collection | |
| --- | --- |
| Data set collected at | BESSY |
| Space group | C121 |
| Cell dimensions? | |
| a, b, c (Å) | 82.6 63.9 77.5 |
| α, β, γ (°) | 90.0 105.7 90.0 |
| Resolution (Å) | 11.98-2.08 |
| Rmerge | 8.0 (51.3) |
| I/SigmaI | 8.6 (2.0) |
| Completeness (%) | 94.4 |
| Redundancy | 2.9 |
| Refinement | |
| Resolution (Å) | 11.98-2.08 |
| No. reflections (work/test) | 22217/1073 |
| $R_{work}/R_{free}$ | 20.5/26.3 |

TABLE 3-continued

Summary of Statistics for Human Glutaminyl Cyclase Crystal

Data collection

No. atoms

| | |
|---|---|
| Protein | 2556 |
| Water | 167 |
| B-factors (Mean value) | 29.64 |
| R.m.s deviations | |
| Bond lengths (Å) | 0.022 |
| Bond angles (°) | 1.915 |

Overall three dimensional structure. The model built from the obtained experimental electron density includes the human glutaminyl cyclase residues from $A^{35}$ to $L^{361}$, a zinc ion and an imidazole molecule. The protein shows a globular α/β hydrolase fold (FIG. 12). A central β-sheet is formed with six β-strands all in parallel fashion but not the second. This β-sheet is surrounded by α-helices in a sandwich manner with two helices in one side and six more α-helices in the opposite face. The protein's structure is completed with a rather large amount of random coiled loops which are building the active site of the enzyme. This active site is accommodating a zinc ion which is coordinated by three protein residues, $E^{202}$, $D^{159}$ and $H^{330}$ and an imidazol molecule (FIG. 13). Moreover the protein shows the presence of a disulfide bridge between residues $C^{139}$ and $C^{164}$. Additionally four cis-peptide bonds are present between the pair of residues: $D^{159}$-$S^{160}$, $H^{228}$—$P^{229}$, $G^{301}$-$V^{302}$ and $S^{323}$—P324. Finally two segments of the polypeptide chain are not visible in the electron density. The gaps include residues between $K^{182}$ and $D^{190}$ and between $F^{146}$ and $N^{150}$.

Example 2

Isolation, Purification and Crystallisation of Murine Glutaminyl Cyclase (A) Isolation and Purification of Murine Glutaminyl Cyclase
Cloning Procedures The primers for isolation of the open reading frame of mQC were designed using PubMed nucleotide entry AK017598, encoding the putative mQC. The primer sequences were as follows: sense 5'-ATATGCATGCATG-GCAGGCAGCGAAGACAAGC-3' (SEQ ID NO: 9); anti-sense 5'-ATATAAGCTTTTACAAGTGAAGATATTC-CAACACAAAGAC-3' (SEQ ID NO: 10). Total RNA was isolated from murine insulinoma cell line β-TC 3 cells using the RNeasy Mini Kit (Qiagen, Germany) and reversely transcribed by SuperScriptII (Invitrogen, Germany). Subsequently, mQC cDNA was amplified on a 1:12.5 dilution of generated product in a 50 µl reaction with Herculase Enhanced DNA-Polymerase (Stratagene, USA), inserted into the PCR Script CAM Cloning vector (Stratagene, USA) and verified by sequencing. The cDNA fragment encoding the mature mQC was amplified using the primers 5'-ATACTC-GAGAAAAGAGCCTGGACGCAGGAGAAG-3' (XhoI, sense) (SEQ ID NO: 11) and 5'-ATATCTAGATTACAAGT-GAAGATATTCCAAC-3' (XbaI, antisense) (SEQ ID NO: 12). The digested fragment was ligated into the vector pPIC-ZαB, propagated in *E. coli* and verified by sequencing of the sense and antisense strand. Finally, the expression plasmid was linearized using PmeI, precipitated, and stored at −20° C.

Transformation of *P. pastoris* and Mini-Scale Expression 1-2 µg of plasmid DNA were used for transformation of competent *P. pastoris* cells by electroporation according to the manufacturer's instructions (BioRad, Germany). Selection was conducted on plates containing 100 µg/ml Zeocin. In order to test the recombinant yeast clones upon mQC expression, recombinants were grown for 24 h in 10 ml conical tubes containing 2 ml BMGY. Subsequently, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and fermentation.

Large-Scale Expression and Purification of murine QC (mQC)

The large-scale expression of mQC was performed in a 5 L reactor (Biostad B; B. Braun Biotech, Germany). Fermentation was carried out in basal salt medium supplemented with trace salts at pH 5.5. Initially, biomass was accumulated in batch phase with glycerol as sole carbon source for about 28 h. The expression of mQC was initiated by methanol feeding according to a three-step profile recommended by Invitrogen for an entire fermentation time of approximately 65 h.

Subsequently, cells and turbidity were removed by two sequential centrifugation steps at 6000×g and 38000×g for 20 min and 3.5 h. For purification, the fermentation broth was diluted with cold water to a conductivity of about 4 mS/cm and applied in reversed flow direction (12 ml/min) onto a Streamline SP XL column (2.5×100 cm), equilibrated with 0.05 M phosphate buffer, pH 6.4. After a washing step in reversed flow direction with equilibration buffer for 2 column volumes, proteins were eluted at a flow rate of 8 ml/min using 0.15 M Tris-HCl buffer, pH 7.6, containing 1.5 M NaCl in forward direction. The QC containing fractions were pooled, and ammonium sulfate was added to a final concentration of 1 M. The resulting solution was centrifuged at 75000×g for 20 min and applied onto a butyl-Sepharose FF column (1.6×13 cm) at a flow rate of 4 ml/min, equilibrated with 0.05 M phosphate buffer pH 6.8, containing 1 M ammonium sulfate. Bound mQC was washed with 0.05 M phosphate buffer, pH 6.8, containing 1 M ammonium sulfate for 5 column volumes and eluted in reversed flow direction with 0.05 M phosphate buffer, pH 6.8. The fractions containing mQC were pooled and diluted with water to a conductivity lower than 10 mS/cm and applied onto an Uno S column (BioRad, Germany), equilibrated with 0.05 M phosphate buffer, pH 6. After a washing step using equilibration buffer containing 0.09 M NaCl, mQC was eluted using the same buffer containing 1.5 M NaCl. The fractions exhibiting QC activity were pooled and applied to a HiPrep desalting column (2.6×10 cm), which was equilibrated with 0.015 M BisTris, pH 6.8, containing 0.1 M NaCl. After purification the mQC was concentrated to 10 mg/ml and stored at −80° C.

(B) Crystallization of Murine Glutaminyl Cyclase
Crystal Growth

Crystals were grown using the hanging drop vapor diffusion technique at room temperature (21° C.) in Easyxtal 24-well plates (Qiagen). The mother liquor buffer consisted of 0.1M sodium acetate pH 5.3, 0.2M ammonium sulphate and 12% (w/v) 2000 MME-PEG. The protein solution of recombinant mouse glutaminyl cyclase (mQC) was concentrated up to 10 mg/ml in the presence of 15 mM Bis-Tris pH6.8/100 mM NaCl buffer. A mixture of 1 µl mother liquor buffer and 1 µl protein solution was set. Crystals appeared usually in the course of one week after experiment was initiated and they displayed a macroscopic rod/needle shape (FIG. 14).

Cryosolution

Before x-ray measurements, crystals were rapidly soaked into a new cryo-buffer solution where mother liquor buffer solution was saturated with 20% (v/v) glycerol. Immediately crystals were collected from the cryo-buffer solution using a pin nylon loop and they were mounted onto the goniometer and flash frozen at −180° C. under a nitrogen stream.

Data Collection

Data collection from a single crystal was undertaken by means of Cu Kα radiation (λ=1.5418 Å) by using a rotating-anode source (RA Micro 007; Rigaku/MSC, Tokyo, Japan) and CCD detector device (CCD Saturn 944+, Rigaku) with Varimax™ Optics (Rigaku) and an AFC-11 goniometer.

Finally the crystal was demounted and stored in liquid nitrogen for an additional measurement in the beam line Bessy-MX BL14.1 of the synchrotron in Berlin (Bessy) with a wave length radiation (λ=0.91841 Å)

Data Processing

Data processing was carried out as described for Example 1.

Results

Figure 17:
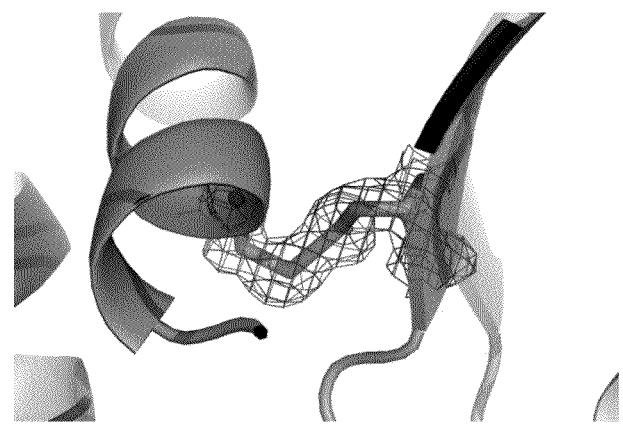
Figure 18:
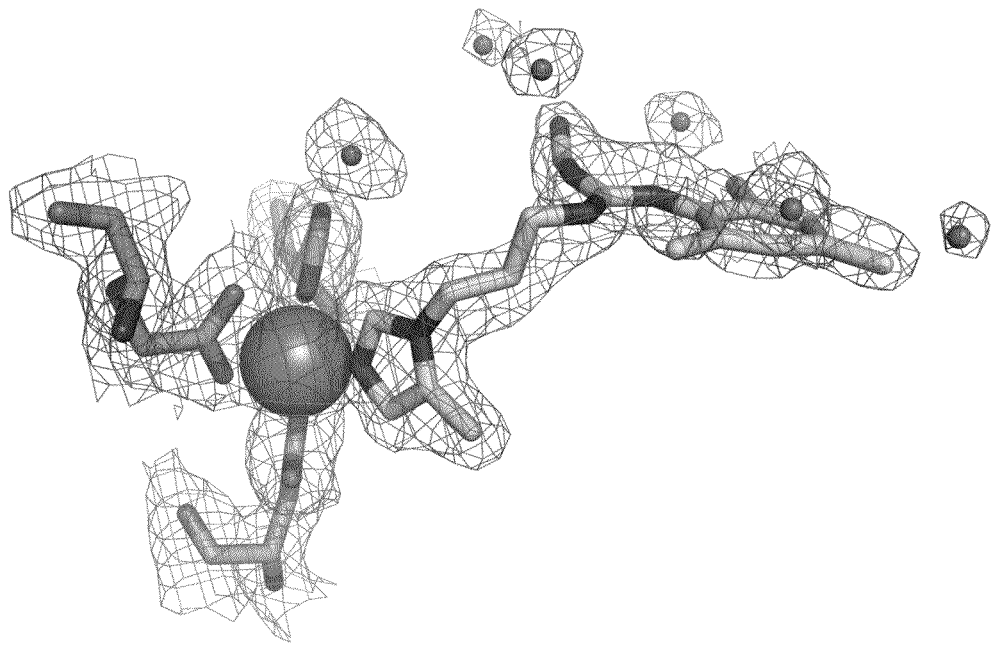
Figure 19:
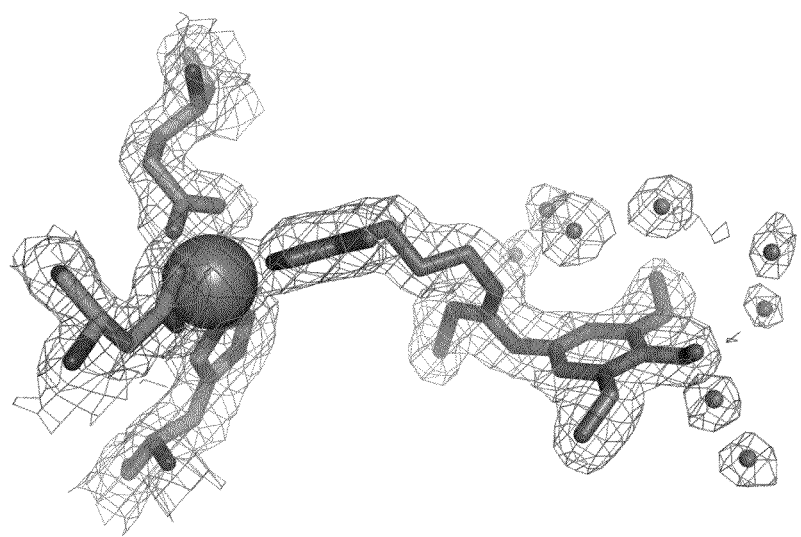

Overall three dimensional structure. Three different protein-inhibitor complexes were obtained. The models built from the obtained experimental electron density include the mouse glutaminyl cyclase residues from $A^{36}$ to $L^{362}$, a zinc ion and an inhibitory molecule. The protein shows a globular α/β hydrolase fold (FIG. 15). A central β-sheet is formed with six β-strands all in parallel fashion but not the second. This β-sheet is surrounded by α-helices in a sandwich manner with two helices in one side and six more α-helices in the opposite face. The protein's structure is completed with a rather large amount of random coiled loops which are building the active site of the enzyme (FIGS. 16, 18 and 19). This active site is accommodating a zinc ion which is coordinated by three protein residues $D^{160}$, $E^{203}$ and $H^{331}$ and an inhibitor molecule. Three different compounds were crystallized in different crystallization set ups, Inhibitor A, Inhibitor C and Inhibitor B, respectively FIGS. 16, 18 and 19. These three different molecules displayed the same localization and overall interaction patterns. Moreover the protein shows the presence of a disulfide bridge between residues $C^{140}$ and $C^{165}$ (FIG. 17).

Table 4 summarizes the statistics of the data set obtained with the crystals of mouse glutaminyl cyclase and their corresponding data processing and model building. The programs used were for data processing MOSFLM and SCALA, for molecular replacement PHASER for refinement REFMAC5 and for Model Building Coot. All programs belong to the CCP4 suite. Numbers between brackets belong to the outer shell resolution limit. On the table header are indicated the co-crystallized inhibitor for their respective summary of statistics of each data set.

TABLE 4

Summary of Statistics for Murine Glutaminyl Cyclase Crystals

| Data collection | Inhibitor A | Inhibitor B | Inhibitor C |
|---|---|---|---|
| Data ser collected at | BESSY | BESSY | BESSY |
| Space group | P212121 | P212121 | P212121 |
| Cell dimensions? | | | |
| a, b, c (Å) | 42.7 83.0 95.7 | 42.7 84.6 96.5 | 42.7 84.6 97.2 |
| α, β, γ (°) | 90.0 90.0 90.0 | 90.0 90.0 90.0 | 90.0 90.0 90.0 |
| Resolution (Å) | 19.81-1.80 | 32.0-1.98 | 30.7-1.9 |
| Rmerge | | 14.3 (73.1) | 7.3 (59.0) |
| I/SigmaI | | 14.3 (2.4) | 17.5 (2.4) |
| Completeness (%) | 100.0 | 100.0 | 100.0 |
| Redundancy | | 4.0 (3.4) | 3.1 (1.6) |
| Refinement | | | |
| Resolution (Å) | 19.81-1.80 | 32.0-1.98 | 30.7-1.9 |
| No. reflections (work/test) | 29995/1580 | 23586/1242 | 20392/1074 |
| $R_{work}/R_{free}$ | 18.98/25.44 | 18.0/23.8 | 17.6/22.8 |
| No. atoms | | | |
| Protein | 2622 | 2622 | 2622 |
| Water | 340 | 318 | 285 |
| B-factors (Mean value) | 21.00 | 24.99 | 24.99 |
| R.m.s deviations | | | |
| Bond lengths (Å) | 0.015 | 0.018 | 0.015 |
| Bond angles (°) | 1.637 | 2.175 | 1.747 |

What is claimed is:

1. A co-crystal comprising murine glutaminyl cyclase and a glutaminyl cyclase inhibitor selected from the group consisting of inhibitor A, inhibitor B, and inhibitor C, the co-crystal having a characterised space group of P2₁2₁2₁ and having unit cell dimensions of +/−5% of a=42.7 Å, b=84.0 Å, c=96.5 Å, α=90.0°, β=90.0° and γ=90.0°;

wherein, the murine glutaminyl cyclase comprises amino acid residues A36 to L362 of SEQ ID NO: 13;

inhibitor A has a structure of

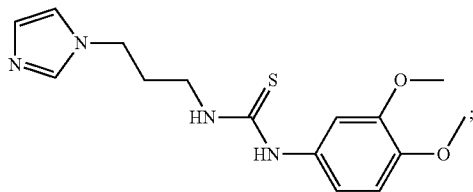 [SMILES: COc1ccc(NC(=S)NCCCn2ccnc2)cc1OC]

inhibitor B has a structure of

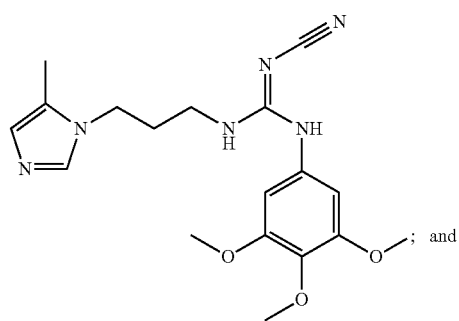

inhibitor C has a structure of

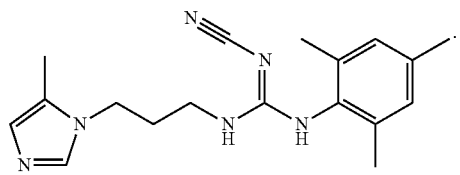 [SMILES: Cc1cc(C)c(N/C(=N/C#N)NCCCn2cncc2C)c(C)c1]

2. A co-crystal as defined in claim 1, having unit cell dimensions of a=42.7 Å, b=83.0 Å, c=95.7 Å, α=90.0°, β=90.0° and γ=90.0°, wherein the glutaminyl cyclase inhibitor is inhibitor A.

3. A co-crystal as defined in claim 1, having unit cell dimensions of a=42.7 Å, b=84.6 Å, c=96.5 Å, α=90.0°, β=90.0° and γ=90.0°, wherein the glutaminyl cyclase inhibitor is inhibitor B.

4. A co-crystal as defined in claim 1, having unit cell dimensions of a=42.7 Å, b=84.6 Å, c=97.2 Å, α=90.0°, β=90.0° and γ=90.0°, wherein the glutaminyl cyclase inhibitor is inhibitor C.

5. A co-crystal as defined in claim 1, which diffracts x-rays for determination of atomic co-ordinates of the crystal to a resolution of between 1.9 Å and 32.0 Å.

6. A co-crystal as defined in claim 1, wherein the murine glutaminyl cyclase consists of amino acid residues A36 to L362 of SEQ ID NO:13.

7. A co-crystal as defined claim 1, which comprises a binding pocket provided by residues D160, E203 and H331 of SEQ ID NO: 13 according to the coordinates of FIGS. 2 to 4.

8. A co-crystal as defined in claim 6, which comprises a disulfide bridge between residues C140 and C165 of SEQ ID NO: 13.

9. A co-crystal as defined in claim 7, which comprises a disulfide bridge between residues C140 and C165 of SEQ ID NO: 13.

10. A co-crystal as defined in claim 1, which comprises a zinc ion coordination site provided by residues D160, E203, and H331.

11. A co-crystal as defined in claim 1, wherein the co-crystal comprises a zinc ion coordinated by residues D160, E203, and H331.

12. A method of preparing the co-crystal of murine glutaminyl cyclase and a glutaminyl cyclase inhibtor as described in claim 1, which comprises the steps of:

(a) providing a solution of murine glutaminyl cyclase, in the presence of a glutaminyl cyclase inhibitor selected from the group consisting of inhibitor A, inhibitor B, and inhibitor C, in a suitable buffer such as 15 mM Bis-Tris pH6.8/100 mM NaCl buffer;

(b) mixing the solution with a crystallization solution comprising 0.1M sodium acetate pH 5.3, 0.2M ammonium sulphate and 12% (w/v) 2000 MME-PEG; and (c) incubating the mixture under conditions to promote hanging drop vapor diffusion for a time sufficient to produce the co-crystal of murine glutaminyl cyclase and the glutaminyl cyclase inhibitor.

13. A co-crystal comprising murine glutaminyl cyclase and a glutaminyl cyclase inhibitor obtainable by the crystallisation method as defined in claim 12.

* * * * *